United States Patent
Dorsey et al.

(10) Patent No.: US 7,601,716 B2
(45) Date of Patent: Oct. 13, 2009

(54) PYRIDOPYRAZINES AND DERIVATIVES THEREOF AS ALK AND C-MET INHIBITORS

(75) Inventors: Bruce D. Dorsey, Ambler, PA (US);
Karen L. Milkiewicz, Exton, PA (US);
Douglas A. Pippin, Chester Springs, PA (US); Jay P. Theroff, West Chester, PA (US); Ted Underiner, Malvern, PA (US); Linda Weinberg, Villanova, PA (US); Craig A. Zificsak, Downingtown, PA (US)

(73) Assignee: Cephalon, Inc., Frazer, PA (US)

( * ) Notice: Subject to any disclaimer, the term of this patent is extended or adjusted under 35 U.S.C. 154(b) by 30 days.

(21) Appl. No.: 11/799,066

(22) Filed: Apr. 30, 2007

(65) Prior Publication Data

US 2008/0032972 A1 Feb. 7, 2008

Related U.S. Application Data

(60) Provisional application No. 60/796,465, filed on May 1, 2006.

(51) Int. Cl.
*A61K 31/4985* (2006.01)

(52) U.S. Cl. .................. 514/249; 544/350; 544/405; 544/117; 546/268.1; 548/518

(58) Field of Classification Search .................. 544/350
See application file for complete search history.

(56) References Cited

U.S. PATENT DOCUMENTS

| | | | |
|---|---|---|---|
| 4,296,114 | A | 10/1981 | Appleton et al. |
| 5,283,244 | A | 2/1994 | Sakamoto et al. |
| 5,393,771 | A | 2/1995 | Atwal |
| 5,424,311 | A | 6/1995 | Billhardt-Troughton et al. |
| 5,521,170 | A | 5/1996 | Setoi et al. |
| 6,150,356 | A | 11/2000 | Lloyd et al. |
| 6,166,031 | A | 12/2000 | Eggler et al. |
| 6,492,389 | B1 | 12/2002 | Huang et al. |
| 6,809,097 | B1 | 10/2004 | Thomas et al. |
| 6,809,113 | B2 | 10/2004 | Laborde et al. |
| 2003/0232818 | A1 | 12/2003 | Anderson et al. |
| 2004/0019058 | A1 | 1/2004 | Bridger et al. |
| 2004/0121996 | A1 | 6/2004 | Barvarian et al. |
| 2004/0138199 | A1 | 7/2004 | Gogliotti et al. |

FOREIGN PATENT DOCUMENTS

| | | |
|---|---|---|
| CA | 2 475 320 | 8/2003 |
| JP | 11292877 | 10/1999 |
| WO | WO 00/00478 | 1/2000 |
| WO | WO 2004/076412 | 9/2004 |
| WO | WO 2005009967 | 2/2005 |
| WO | WO 2005/019236 | 3/2005 |
| WO | WO2005/021547 | 3/2005 |
| WO | WO 2005/028451 | 3/2005 |
| WO | WO-2007/024949 | * 1/2007 |
| WO | WO 2007002949 | 3/2007 |

OTHER PUBLICATIONS

PCT Written Opinion for PCT/US2007/010656.
PCT International Search Report for PCT/US2007/010656.
Chemical Abstracts Registry Database XP002456370.
Chemical Abstracts Registry Database XP002456371.
Chemical Abstracts Registry Database XP002456372.
Chemical Abstracts Registry Database XP002456373.
Chemical Abstracts Registry Database XP002456374.
Chemical Abstracts Registry Database XP002456375.
Chemical Abstracts Registry Database XP002456376.
Chemical Abstracts Registry Database XP002456377.
Chemical Abstracts Registry Database XP002456378.
Chemical Abstracts Registry Database XP002456379.
Chemical Abstracts Registry Database XP002456380.
Sako, M., "Product class 20: pyridopyrazines," *Science of Synthesis*, 2004, 16, 1269-1290.
Vinot, N. et al., "Study of the reaction of organomagnesium compounds with pyrido[2,3-b]pyrazines," *Bulletin de la Societe Chimique de France*, 1976, 1-2, Pt. 2, 251-254.
Vinot, N. et al., "Reduction of pyrido[2,3-b]pyrazines by lithium aluminum hydride," *Bulletin de la Societe Chimique de France*, 1973, 11, Pt. 2, 3100-3102.
Settimo, A. et al., "Synthesis of some 11H-indolo[3,2-c][1,8]naphthyridines," *Il Farmaco* —Ed. Sc., 1978, 33, 770-780.
Dragoli, Dean R., *J. Amer. Chem. Soc.*, 2001, 123(41), 10127-10128.
Sundberg, Richard J., *J. Org. Chem.*, 1988, 53(21), 5097-107.
Cheon, Hyae-Gyeong, et al., *Bioorg. Med. Chem. Lett.*, 2004, 14, 2661-2664.
Zhang, XueJun, et al., *J. Org. Chem.*, 2006, 71, 4170-4177.
Krompiec, Stanislaw, et al., *Tetrahedron Lett.*, 2001, 42, 7095-7098.
Hamashima, Yoshitaka, et al., *J. Am. Chem. Soc.*, 2005, 127, 10164-10165.

* cited by examiner

*Primary Examiner*—James O Wilson
*Assistant Examiner*—Brian McDowell

(57) ABSTRACT

The present invention provides a compound of Formula I

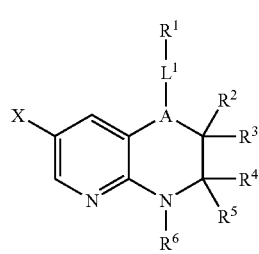

or a pharmaceutically acceptable salt form thereof, wherein A, $L^1$, $R^1$, $R^2$, $R^3$, $R^4$, $R^5$, $R^6$, and X are as defined herein. The compounds of Formula I have ALK and/or c-Met inhibitory activity, and may be used to treat ALK- or c-Met-mediated disorders or conditions.

19 Claims, No Drawings

PYRIDOPYRAZINES AND DERIVATIVES THEREOF AS ALK AND C-MET INHIBITORS

BACKGROUND OF THE INVENTION

Anaplastic Lymphoma Kinase (ALK) is a cell membrane-spanning receptor tyrosine kinase, which belongs to the insulin receptor subfamily. The most abundant expression of ALK occurs in the neonatal brain, suggesting a possible role for ALK in brain development (Duyster, J. et al., *Oncogene*, 2001, 20, 5623-5637).

ALK is also implicated in the progression of certain tumors. For example, approximately sixty percent of anaplastic large cell lymphomas (ALCL) are associated with a chromosome mutation that generates a fusion protein consisting of nucleophosmin (NMP) and the intracellular domain of ALK. (Armitage, J. O. et al., *Cancer: Principle and Practice of Oncology*, 6$^{th}$ edition, 2001, 2256-2316; Kutok J. L. & Aster J. C., *J. Clin. Oncol.*, 2002, 20, 3691-3702). This mutant protein, NMP-ALK, possesses a constitutively active tyrosine kinase domain that is responsible for its oncogenic property through activation of downstream effectors. (Falini, B. et al., *Blood*, 1999, 94, 3509-3515; Morris, S. W. et al., *Brit. J. Haematol.*, 2001, 113, 275-295; Duyster et al.; Kutok & Aster). Experimental data have demonstrated that the aberrant expression of constitutively active ALK is directly implicated in the pathogenesis of ALCL and that inhibition of ALK can markedly impair the growth of ALK+ lymphoma cells (Kuefer, Mu et al. *Blood*, 1997, 90, 2901-2910; Bai, R. Y. et al., *Mol. Cell. Biol.*, 1998, 18, 6951-6961; Bai, R. Y. et al., *Blood*, 2000, 96, 4319-4327; Ergin, M. et al., *Exp. Hematol.*, 2001, 29, 1082-1090; Slupianek, A. et al., *Cancer Res.*, 2001, 61, 2194-2199; Turturro, F. et al., *Clin. Cancer Res.*, 2002, 8, 240-245). The constitutively activated chimeric ALK has also been demonstrated in about 60% of inflammatory myofibroblastic tumors (IMTs), a slow-growing sarcoma that mainly affects children and young adults. (Lawrence, B. et al., *Am. J. Pathol.*, 2000, 157, 377-384; Duyster et al.).

In addition, ALK and its putative ligand, pleiotrophin, are overexpressed in human glioblastomas (Stoica, G. et al., *J. Biol. Chem.*, 2001, 276, 16772-16779). In mouse studies, depletion of ALK reduced glioblastoma tumor growth and prolonged animal survival (Powers, C. et al., *J. Biol. Chem.*, 2002, 277, 14153-14158; Mentlein, R. et al, *J. Neurochem.*, 2002, 83, 747-753).

It is possible that an ALK inhibitor would either permit durable cures when combined with current chemotherapy for ALCL, IMT, or glioblastoma, or be used as a single therapeutic agent in a maintenance role to prevent cancer recurrence in those patients. Various ALK inhibitors have been reported, including indazoloisoquinolines (WO 2005/009389), thiazole amides and oxazole amides (WO 2005/097765), pyrrolopyrimidines (WO 2005080393), and pyrimidinediamines (WO 2005/016894).

c-Met is a member of the tyrosine kinase growth factor receptor family. c-Met expression occurs in endothelial, epithelial, and mesenchymal cells. c-Met binding to the endogenous ligand, hepatocyte growth factor (HGF), promotes cell migration, proliferation, and invasion.

c-Met is implicated in the progression of certain tumors. c-Met overexpression has been shown in numerous tumor types including colon, breast, renal, lung, hemangiomas, squamous cell myeloid leukemia, melanomas, glioblastomas, and astrocytomas. (Maulik et al., *Cytokine & Growth Factor Reviews*, 2002, 13, 41-59; Funakoshi et al., *Clinica Chimica Acta*, 2003, 1-23; Longati et al., *Curr. Drug Targets*, 2001, 2, 41-55). Activation of tumor cell c-Met receptors enhances tumor cell proliferation, invasion/metastasis, and resistance to apoptosis and cytotoxic therapies.

It is possible that a c-Met inhibitor would have potent anti-tumor effects in many cancers. Various c-Met inhibitors have been reported, including aminoheteroaryl compounds (WO 2004/076412; WO 2005/082411; US 2005/0009840), 5-6 bicyclic heterocycles (WO 2005/028475), monocyclic heterocycles (US 2005/0245530), bicyclic heterocycles (US 2005/0239820), triazolotriazine compounds (WO 2005/010005; US 2005/0075340), triarylimidazoles (US 2005/0085473), indolinone hydrazides (WO 2005/005378), tetracyclic compounds (WO 2005/004808), imidazole derivatives (WO 2005/040154), quinolines and quinazolines (WO 2005/030140), and quinolinoxynaphthalenes (WO 2005/070891). (See also Sattler, M., et al., *Cancer Res.*, 2003, 63, 5462-5469; Christensen, J. G., et al., *Cancer Res.*, 2003, 63, 7345-7355).

A need exists for ALK and c-Met inhibitors for use as pharmaceutical agents.

SUMMARY OF THE INVENTION

The present invention provides a compound of Formula I

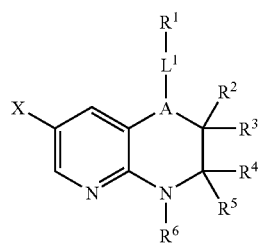

or a pharmaceutically acceptable salt form thereof, wherein A, $L^1$, $R^1$, $R^2$, $R^3$, $R^4$, $R^5$, $R^6$, and X are as defined herein.

The compounds of Formula I have ALK and/or c-Met inhibitory activity, and may be used to treat ALK- or c-Met-mediated disorders or conditions.

The present invention further provides a pharmaceutical composition comprising at least one compound of the present invention together with at least one pharmaceutically acceptable carrier, diluent, or excipient therefor.

In another aspect, the present invention provides a method of treating a subject suffering from an ALK- or c-Met-mediated disorder or condition comprising: administering to the subject the pharmaceutical composition of the present invention.

DETAILED DESCRIPTION OF THE INVENTION

I. Definitions

As used herein, the following terms have the meanings ascribed to them unless specified otherwise.

"Alkyl" or "alkyl group" includes both straight and branched chain aliphatic hydrocarbon groups. Examples of straight-chain alkyl groups include, but are not limited to, methyl, ethyl, n-propyl, n-butyl, n-pentyl, n-hexyl, n-heptyl, n-octyl, n-nonyl, n-decyl, etc. Examples of branched-chain alkyl groups include, but are not limited to, isopropyl, tert-butyl, isobutyl, etc.

The term "$C_{x-y}$" indicates the number of carbon atoms in a group. For example, a "$C_{1-6}$-alkyl" is an alkyl group having from one (1) to six (6) carbon atoms. In some instances, x=0, i.e., "$C_{0-y}$". The term "$C_{0-y}$" indicates that the group may be absent or present, and if present, defines the number of carbon atoms in the group. For example, "$C_{0-6}$-alkyl" indicates that an alkyl group may be absent (x=0) or present (x=1-6), and if present contains from one (1) to six (6). carbon atoms. For example, "—$C_{0-6}$-alkyl-C(=O)—$C_{0-6}$-alkyl-" includes —C(=O)—, —$C_{1-6}$-alkyl-C(=O)—, and —$C_{1-6}$-alkyl-C(=O)—$C_{1-6}$-alkyl-. Examples of —$C_{0-6}$-alkyl-C(=O)—$C_{0-6}$-alkyl- include, but are not limited to, —C(=O), —CH$_2$CH$_2$—C(=O), and —CH(CH$_3$)CH$_2$CH$_2$—C(=O)—CH$_2$—.

"Alkenyl" or "alkenyl group" includes straight and branched chain unsaturated alkyl groups which have two (2) or more carbon atoms and at least one double bond. Examples include, but are not limited to, ethenyl, 3-buten-1-yl, 2-ethenylbutyl, and 3-hexen-1-yl.

"Alkynyl" or "alkynyl group" includes straight and branched chain unsaturated alkyl groups which have two (2) or more carbon atoms and at least one triple bond. Examples include, but are not limited to, ethynyl, 3-butyn-1-yl, propynyl, 2-butyn-1-yl, and 3-pentyn-1-yl.

"Haloalkyl" or "haloalkyl group" refers to alkyl groups in which one or more hydrogen atoms are replaced by halogen atoms. Haloalkyl includes both saturated alkyl groups and unsaturated alkenyl and alkynyl groups, such as for example —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —CI=CH$_2$, —C≡C—CF$_3$, —CHFCH$_2$CH$_3$ and —CHFCH$_2$CF$_3$.

"Halogen" includes fluorine, chlorine, bromine and iodine atoms.

"Pseudohalogen" refers to —OCN, —SCN, —CF$_3$, and —CN.

"Cycloalkyl" or "cycloalkyl group" includes monocyclic, bicyclic, and tricyclic non-aromatic carbocyclic rings, which may be saturated or unsaturated. Examples include, but are not limited to, cyclopropyl, cyclopropenyl, cyclobutyl, cyclobutenyl, cyclopentyl, cyclopentenyl, cyclohexyl, cyclohexenyl, norbornyl, and norbornenyl.

A cycloalkyl group can also include ring systems substituted on ring carbons with one or more —OH functional groups (which may further tautomerize to give a ring C=O group).

"Heterocycloalkyl" or "heterocycloalkyl group" includes 3-15 membered monocyclic, bicyclic, and tricyclic non-aromatic rings, which may be saturated or unsaturated, and which contain, in addition to carbon atoms, at least one heteroatom, such as nitrogen, oxygen or sulfur. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane.

Unless otherwise indicated, the foregoing heterocycloalkyl groups can be C— attached or N-attached where such is possible and results in the creation of a stable structure. For example, piperidinyl can be piperidin-1-yl (N-attached) or piperidin-4-yl (C-attached).

A heterocycloalkyl group can also include ring systems substituted on ring carbons with one or more —OH functional groups (which may further tautomerize to give a ring C=O group) and/or substituted on a ring sulfur atom by one (1) or two (2) oxygen atoms to give S=O or SO$_2$ groups, respectively.

"Aryl" or "aryl group" includes phenyl and 9-15 membered bicyclic or tricyclic hydrocarbon ring systems in which at least one of the rings is aromatic. Examples include, but are not limited to, naphthyl, indanyl, 1,2,3,4-tetrahydronaphthalenyl, and 6,7,8,9-tetrahydro-5H-benzocycloheptenyl.

An aryl group can also include ring systems substituted on ring carbons with one or more —OH functional groups (which may further tautomerize to give a ring C=O group).

"Heteroaryl" or "heteroaryl group" includes (a) 5 and 6 membered monocyclic aromatic rings, which contain, in addition to carbon atom(s), at least one heteroatom, such as nitrogen, oxygen or sulfur, and (b) 8-15 membered bicyclic and tricyclic rings, which contain, in addition to carbon atoms, at least one heteroatom, such as nitrogen, oxygen or sulfur, and in which at least one of the rings is aromatic. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl.

A heteroaryl group can also include ring systems substituted on ring carbons with one or more —OH functional groups (which may further tautomerize to give a ring C=O group) and/or substituted on a ring sulfur atom by one (1) or two (2) oxygen atoms to give S=O or SO$_2$ groups, respectively.

"Linker" or "linker group" refers to a bond, atom, or group of atoms that connects other atoms or groups of atoms within a molecule. For example, $L^1$ is a linker group that connects the groups A and $R^1$ in a compound of Formula I (A-$L^1$-$R^1$). Linker groups are identified herein as an atom or group of atoms between two dashed lines (—). For example, an oxygen atom linker is identified herein as —O—. As used herein, no directionality is intended in the representation of asymmetrical linkers. Therefore, "—$C_{1-6}$-alkyl-C(=O)—" is equivalent to "—C(=O)—$C_{1-6}$-alkyl-" and "—$C_{1-6}$-alkyl-C(=O)O—" is equivalent to "—OC(=O)—$C_{1-6}$-alkyl-." For example, the A and $R^1$ groups may be connected by the asymmetrical linker, —$C_{1-6}$-alkyl-C(=O)—, in either of the following manners: A-$C_{1-6}$-alkyl-C(=O)—$R^1$ or A-C(=O)—$C_{1-6}$-alkyl-$R^1$.

"Chemically stable" or "stable" refers to a compound that is sufficiently robust to be isolated to a useful degree of purity from a reaction mixture, and then incorporated into a pharmaceutical composition. The present invention is directed only to stable compounds.

"Pharmaceutical composition" refers to a composition suitable for administration in medical or veterinary use.

When lists of alternative substituents include members which, owing to valency requirements, chemical stability, or other reasons, cannot be used to substitute a particular group, the list is intended to be read in context to include those members of the list that are suitable for substituting the particular group. For example, those of ordinary skill in the art will appreciate that if $G^1$ is a bond, then $L^2$ and $L^3$ should not both be —O—, since peroxides are not chemically stable.

"Pharmaceutically acceptable" refers to physiologically tolerable materials, which do not typically produce an allergic or other untoward reaction, such as gastric upset, dizziness and the like, when administered to a mammal.

"Therapeutically effective amount" refers to an amount of a compound, or a pharmaceutically acceptable salt thereof, sufficient to inhibit, halt, or cause an improvement in a disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

It should be appreciated that determination of proper dosage forms, dosage amounts, and routes of administration is within the level of ordinary skill in the pharmaceutical and medical arts, and is described below.

"Subject" refers to a member of the class Mammalia. Examples of mammals include, without limitation, humans, primates, chimpanzees, rodents, mice, rats, rabbits, horses, livestock, dogs, cats, sheep, and cows.

"Treatment" refers to the acute or prophylactic diminishment or alleviation of at least one symptom or characteristic associated or caused by a disorder being treated. For example, treatment can include diminishment of several symptoms of a disorder or complete eradication of a disorder.

"Administering" refers to the method of contacting a compound with a subject. Modes of "administering" include, but are not limited to, methods that involve contacting the compound intravenously, intraperitoneally, intranasally, transdermally, topically, via implantation, subcutaneously, parentally, intramuscularly, orally, systemically, and via adsorption.

II. Compounds

In one embodiment, the present invention provides a compound of Formula I

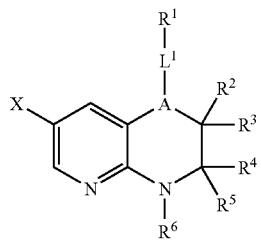

I or a pharmaceutically acceptable salt form thereof, wherein:

A is chosen from N and CH;

X is chosen from -$L^2G^1L^3G^2L^4R^7$ and $R^8$;

$L^1$ is a bond, —$C_{0-3}$-alkyl-C(=O)—$C_{0-3}$-alkyl-, —$C_{0-3}$-alkyl-S(=O)$_n$—$C_{0-3}$-alkyl-, —$C_{0-3}$-alkyl-C(=O)NR$^{10}$—$C_{0-3}$-alkyl-, —$C_{0-3}$-alkyl-S(=O)$_2$NR$^{10}$—$C_{0-3}$-alkyl-, —$C_{0-3}$-alkyl-C(=O)O—$C_{0-3}$-alkyl-, —$C_{0-3}$-alkyl-OC(=O)NR$^{10}$—$C_{0-3}$-alkyl-, —$C_{0-3}$-alkyl-NR$^{10}$—$C_{0-3}$-alkyl-, —$C_{0-3}$-alkyl-O—$C_{0-3}$-alkyl-, —$C_{1-6}$-alkyl-, —$C_{2-6}$-alkenyl-, or —$C_{2-6}$-alkynyl-;

$R^1$ is an optionally mono- or polysubstituted group chosen from aryl, $C_{3-10}$-cycloalkyl, heterocycloalkyl, and heteroaryl, wherein the substituents may be identical or different and are chosen from halogen, —NO$_2$, —OR$^{20}$, —C(=O)R$^{20}$, —C(=O)OR$^{20}$, —C(=O)NR$^{20}$R$^{21}$, —NR$^{20}$R$^{21}$, $C_{1-3}$-alkyl, $C_{1-3}$-haloalkyl, aryl, heteroaryl, $C_{3-10}$-cycloalkyl, heterocycloalkyl, pseudohalogen, —S(=O)$_n$R$^{20}$, —S(=O)$_2$NR$^{20}$R$^{21}$, —OCH$_2$F, —OCHF$_2$, —OCF$_3$, —NHOH, —OC(=O)R$^{20}$, —OC(=O)NR$^{20}$R$^{21}$, —NR$^{20}$C(=O)R$^{21}$, —NR$^{20}$C(=O)OR$^{21}$, and —SCF$_3$;

$R^2$ and $R^3$ are independently chosen from H, OH, and $C_{1-6}$-alkyl, or $R^2$ and $R^3$ together form a carbonyl group;

$R^4$ and $R^5$ are independently chosen from H and $C_{1-6}$-alkyl, or $R^4$ and $R^5$ together form a carbonyl group, or one of $R^4$ and $R^5$ forms a double bond with $R^6$;

$R^6$ is chosen from H and $C_{1-6}$-alkyl, or $R^6$ forms a double bond with $R^4$ or $R^5$;

$L^2$ is a bond, —$C_{0-3}$-alkyl-C(=O)—$C_{0-3}$-alkyl-, —$C_{0-3}$-alkyl-S(=O)$_n$—$C_{0-3}$-alkyl-, —$C_{0-3}$-alkyl-C(=O)NR$^{30}$—$C_{0-3}$-alkyl-, —$C_{0-3}$-alkyl-S(=O)$_2$NR$^{30}$—$C_{0-3}$-alkyl-, —$C_{0-3}$-alkyl-C(=O)O—$C_{0-3}$-alkyl-, —$C_{0-3}$-alkyl-OC(=O)NR$^{30}$—$C_{0-3}$-alkyl-, —$C_{0-3}$-alkyl-NR$^{30}$—$C_{0-3}$-alkyl-, —$C_{0-3}$-alkyl-O—$C_{0-3}$-alkyl-, —$C_{1-3}$-alkyl-, —$C_{2-3}$-alkenyl-, or —$C_{2-3}$-alkynyl-;

$G^1$ is a bond, or an optionally mono- or polysubstituted group chosen from aryl, $C_{3-10}$-cycloalkyl, heterocycloalkyl, and heteroaryl, wherein the substituents may be identical or different and are chosen from halogen, —NO$_2$, —OR$^{40}$, —C(=O)R$^{40}$, —C(=O)OR$^{40}$, —C(=O)NR$^{40}$R$^{41}$, —NR$^{40}$R$^{41}$, $C_{1-3}$-alkyl, $C_{1-3}$-haloalkyl, aryl, heteroaryl, $C_{3-10}$-cycloalkyl, heterocycloalkyl, pseudohalogen, —S(=O)$_n$R$^{40}$, —S(=O)$_2$NR$^{40}$R$^{41}$, —OCH$_2$F, —OCHF$_2$, —OCF$_3$, —NHOH, —OC(=O)R$^{40}$, —OC(=O)NR$^{40}$R$^{41}$, —NR$^{40}$C(=O)R$^{41}$, —NR$^{40}$C(=O)OR$^{41}$, and —SCF$_3$;

$L^3$ is a bond, —$C_{0-3}$-alkyl-C(=O)—$C_{0-3}$-alkyl-, —$C_{0-3}$-alkyl-S(=O), —$C_{0-3}$-alkyl-, —$C_{0-3}$-alkyl-C(=O)NR$^{50}$—$C_{0-3}$-alkyl-, —$C_{0-3}$-alkyl-S(=O)$_2$NR$^{50}$—$C_{0-3}$-alkyl-, —$C_{0-3}$-alkyl-C(=O)O—$C_{0-3}$-alkyl-, —$C_{0-3}$-alkyl-OC(=O)NR$^{50}$—$C_{0-3}$-alkyl-, —$C_{0-3}$-alkyl-NR$^{10}$—$C_{0-3}$-alkyl-, —$C_{0-3}$-alkyl-O—$C_{0-3}$-alkyl-, —$C_{1-3}$-alkyl-, —$C_{2-3}$-alkenyl-, or —$C_{2-3}$-alkynyl-;

$G^2$ is a bond, or an optionally mono- or polysubstituted group chosen from aryl, $C_{3-10}$-cycloalkyl, heterocycloalkyl, and heteroaryl, wherein the substituents may be identical or different and are chosen from halogen, —NO$_2$, —OR$^{60}$, —C(=O)R$^{60}$, —C(=O)OR$^{60}$, —C(=O)NR$^{60}$R$^{61}$, —NR$^{60}$R$^{61}$, $C_{1-3}$-alkyl, $C_{1-3}$-haloalkyl, aryl, heteroaryl, $C_{3-10}$-cycloalkyl, heterocycloalkyl, pseudohalogen, —S(=O)$_n$R$^{60}$, —S(=O)$_2$NR$^{60}$R$^{61}$, —OCH$_2$F, —OCHF$_2$, —OCF$_3$, —NHOH, —OC(=O)R$^{60}$, —OC(=O)NR$^{60}$R$^{61}$, —NR$^{60}$C(=O)OR$^{61}$, —NR$^{60}$C(=O)OR$^{61}$, and —SCF$_3$;

$L^4$ is a bond, —$C_{0-3}$-alkyl-C(=O)—$C_{0-3}$-alkyl-, —$C_{0-3}$-alkyl-S(=O)$_n$—$C_{0-3}$-alkyl-, —$C_{0-3}$-alkyl-C(=O)NR$^{70}$—$C_{0-3}$-alkyl-, —$C_{0-3}$-alkyl-S(=O)$_2$NR$^{70}$—$C_{0-3}$-alkyl-, —$C_{0-3}$-alkyl-C(=O)O—$C_{0-3}$-alkyl-, —$C_{0-3}$-alkyl-OC(=O)NR$^{70}$—$C_{0-3}$-alkyl-, —$C_{0-3}$-alkyl-NR$^{70}$—$C_{0-3}$-alkyl-, —$C_{0-3}$-alkyl-O—$C_{0-3}$-alkyl-, —$C_{1-3}$-alkyl-, —$C_{2-3}$-alkenyl-, or —$C_{2-3}$-alkynyl-;

$R^7$ is an optionally mono- or polysubstituted group chosen from $C_{1-6}$-alkyl, $C_{2-6}$-alkenyl, $C_{2-6}$-alkynyl, aryl, $C_{3-10}$-cycloalkyl, heterocycloalkyl, and heteroaryl, wherein the substituents may be identical or different and are chosen from halogen, $-NO_2$, $-OR^{80}$, $-C(=O)R^{80}$, $-C(=O)OR^{80}$, $-C(=O)NR^{80}R^{81}$, $-NR^{80}R^{81}$, $C_{1-6}$-alkyl, $C_{1-6}$-haloalkyl, aryl, heteroaryl, $C_{3-10}$-cycloalkyl, heterocycloalkyl, pseudohalogen, $-S(=O)_nR^{80}$, $-S(=O)_2NR^{80}R^{81}$, $-OCH_2F$, $-OCHF_2$, $-OCF_3$, $-NHOH$, $-OC(=O)R^{80}$, $-C(=O)NR^{80}R^{81}$, $-NR^{80}C(=O)R^{81}$, $-NR^{80}C(=O)OR^{81}$, $-SiR^{80}R^{81}R^{82}$ and $-SCF_3$;

$R^8$ is chosen from H, halogen, CN, and $C(=O)OH$;

$R^{10}$, $R^{20}$, $R^{21}$, $R^{30}$, $R^{40}$, $R^{41}$, $R^{50}$, $R^{60}$, $R^{61}$, $R^{70}$, $R^{80}$, $R^{81}$, and $R^{82}$ at each occurrence are independently chosen from H, $C_{1-6}$-alkyl, $C_{1-6}$-haloalkyl, aryl, heteroaryl, $C_{3-10}$-cycloalkyl, and heterocycloalkyl; and n is 0, 1, or 2;

provided that when $L^1$ is $-C(=O)-$ and $R^1$ is phenyl, $R^8$ is not H or Br.

In certain embodiments, A is N, i.e., a compound of Formula I(a):

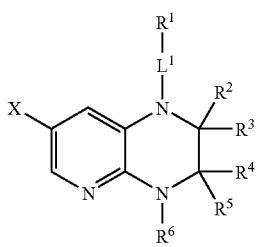

I(a)

Preferably, when A is N, $L^1$ is $-C_{0-3}$-alkyl-$C(=O)-C_{0-3}$-alkyl-, $-C_{0-3}$-alkyl-$S(=O)_n-C_{0-3}$-alkyl-, $-C_{0-3}$-alkyl-$C(=O)NR^{10}-C_{0-3}$-alkyl-, $-C_{0-3}$-alkyl-$S(=O)_2NR^{10}-C_{0-3}$-alkyl-, $-C_{0-3}$-alkyl-$C(=O)O-C_{0-3}$-alkyl-, or $-C_{1-6}$-alkyl-. More preferably, when A is N, $L^1$ is $-C(=O)-C_{0-3}$-alkyl-, $-S(=O)_2-C_{0-3}$-alkyl-, $-C(=O)NR^{10}-C_{0-3}$-alkyl-, $-S(=O)_2NR^{10}-C_{0-3}$-alkyl-, $-C(=O)O-C_{0-3}$-alkyl-, or $-C_{1-6}$-alkyl-. More preferably, when A is N, $L^1$ is $-C_{0-3}$-alkyl-$C(=O)-C_{0-3}$-alkyl-, $-C_{0-3}$-alkyl-$S(=O)_2-C_{0-3}$-alkyl-, or $-C_{1-6}$-alkyl-. More preferably, when A is N, $L^1$ is $-C(=O)-C_{0-3}$-alkyl-, $-S(=O)_2-C_{0-3}$-alkyl-, or $-C_{1-6}$-alkyl-. More preferably, when A is N, $L^1$ is $-C(=O)-C_{0-3}$-alkyl-, $-S(=O)_2-$, or $-C_{1-6}$-alkyl-. More preferably, when A is N, $L^1$ is $-C(=O)-$, $-C(=O)CH_2-$, $-S(=O)_2-$, or $-C_{1-6}$-alkyl-. More preferably, when A is N, $L^1$ is $-C(=O)-$, $-C(=O)CH_2-$, $-S(=O)_2-$, $-CH_2-$, or $-CH(CH_3)-$. More preferably, when A is N, $L^1$ is $-C(=O)-$, $-C(=O)CH_2-$, $-S(=O)_2-$, or $-CH_2-$.

In certain embodiments, A is CH, i.e., a compound of Formula I(b):

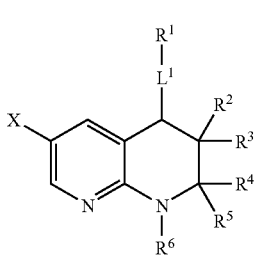

I(b)

Preferably, when A is CH, $L^1$ is $-C_{0-3}$-alkyl-$C(=O)-C_{0-3}$-alkyl-, $-C_{0-3}$-alkyl-$S(=O)$, $-C_{0-3}$-alkyl-, $-C_{0-3}$-alkyl-$C(=O)NR^{10}-C_{0-3}$-alkyl-, $-C_{0-3}$-alkyl-$S(=O)_2NR^{10}-C_{0-3}$-alkyl-, $-C_{0-3}$-alkyl-$C(=O)O-C_{0-3}$-alkyl-, $-C_{0-3}$-alkyl-$NR^{10}-C_{0-3}$-alkyl-, $-C_{0-3}$-alkyl-$O-C_{0-3}$-alkyl-, or $-C_{1-6}$-alkyl-. More preferably, when A is CH, $L^1$ is $-C_{1-3}$-alkyl-$C(=O)-C_{0-3}$-alkyl-, $-S(=O)_n-C_{0-3}$-alkyl-, $-C_{1-3}$-alkyl-$C(=O)NR^{10}-C_{0-3}$-alkyl-, $-C_{1-3}$-alkyl-$C(=O)O-C_{0-3}$-alkyl-, $-C_{0-3}$-alkyl-$NR^{10}-C_{0-3}$-alkyl-, $-C_{0-3}$-alkyl-$O-C_{0-3}$-alkyl-, or $-C_{1-6}$-alkyl-. More preferably, when A is CH, $L^1$ is $-CH_2-C(=O)-C_{0-3}$-alkyl-, $-S(=O)_n-C_{0-3}$-alkyl-, $-CH_2-C(=O)NR^{10}-C_{0-3}$-alkyl-, $-CH_2-C(=O)O-C_{0-3}$-alkyl-, $-C_{0-3}$-alkyl-$NR^{10}-C_{0-3}$-alkyl-, $-C_{0-3}$-alkyl-$O-C_{0-3}$-alkyl-, or $-C_{1-6}$-alkyl-. More preferably, when A is CH, $L^1$ is $-CH_2-C(=O)-C_{0-3}$-alkyl-, $-S(=O)_n-C_{0-3}$-alkyl-, $-CH_2-C(=O)NR^{10}-C_{0-3}$-alkyl-, $-CH_2-C(=O)O-C_{0-3}$-alkyl-, $-C_{0-3}$-alkyl-$NR^{10}-C_{0-3}$-alkyl-, $-C_{0-3}$-alkyl-$O-C_{0-3}$-alkyl-, or $-CH_2-$. More preferably, when A is CH, $L^1$ is $-C_{0-3}$-alkyl-$NR^{10}-C_{0-3}$-alkyl-, $-C_{0-3}$-alkyl-$O-C_{0-3}$-alkyl-, or $-C_{1-6}$-alkyl-. More preferably, when A is CH, $L^1$ is $-NR^{10}-C_{0-3}$-alkyl-, $-O-C_{0-3}$-alkyl-, or $-CH_2-$. More preferably, when A is CH, $L^1$ is $-NR^{10}-$, $-O-C_{0-3}$-alkyl-, or $-CH_2-$. More preferably, when A is CH, $L^1$ is $-C_{0-3}$-alkyl-$O-C_{0-3}$-alkyl- or $-C_{1-6}$-alkyl-. More preferably, when A is CH, $L^1$ is $-C_{0-3}$-alkyl-$O-C_{0-3}$-alkyl- or $-CH_2-$. More preferably, when A is CH, $L^1$ is $-O-C_{0-3}$-alkyl-, or $-CH_2-$. More preferably, when A is CH, $L^1$ is $-O-$ or $-CH_2-$.

Preferably, when A is CH, $L^1$-$R^1$ is $-C_{1-3}$-alkyl-$C(=O)-C_{0-3}$-alkyl-$R^1$, $-C_{0-3}$-alkyl-$S(=O)$, $-C_{0-3}$-alkyl-$R^1$, $-C_{1-3}$-alkyl-$C(=O)NR^{10}-C_{0-3}$-alkyl-$R^1$, $R^1-C_{0-3}$-alkyl-$C(=O)NR^{10}-C_{0-3}$-alkyl-, $-C_{0-3}$-alkyl-$S(=O)_2NR^{10}-C_{0-3}$-alkyl-$R^1$, $R^1-C_{0-3}$-alkyl-$S(=O)_2NR^{10}-C_{0-3}$-alkyl-, $-C_{1-3}$-alkyl-$C(=O)O-C_{0-3}$-alkyl-$R^1$, $R^1-C_{0-3}$-alkyl-$C(=O)O-C_{0-3}$-alkyl-, $-C_{0-3}$-alkyl-$OC(=O)NR^{10}-C_{0-3}$-alkyl-$R^1$, $R^1-C_{0-3}$-alkyl-$OC(=O)NR^{10}-C_{0-3}$-alkyl-, $-C_{0-3}$-alkyl-$NR^{10}-C_{0-3}$-alkyl-$R^1$, $-C_{0-3}$-alkyl-$O-C_{0-3}$-alkyl-$R^1$, $-C_{1-6}$-alkyl-$R^1$, $-C_{2-6}$-alkenyl-$R^1$, or $-C_{2-6}$-alkynyl-$R^1$. More preferably, when A is CH, $L^1$-$R^1$ is $-C_{1-3}$-alkyl-$C(=O)-C_{0-3}$-alkyl-$R^1$, $-S(=O)_n-C_{0-3}$-alkyl-$R^1$, $-C_{1-3}$-alkyl-$C(=O)NR^{10}-C_{0-3}$-alkyl-$R^1$, $R^1-C_{0-3}$-alkyl-$C(=O)NR^{10}-C_{0-3}$-alkyl-, $-C_{0-3}$-alkyl-$S(=O)_2NR^{10}-C_{0-3}$-alkyl-$R^1$, $R^1-C_{0-3}$-alkyl-$S(=O)_2NR^{10}-C_{0-3}$-alkyl-, $-C_{1-3}$-alkyl-$C(=O)O-C_{0-3}$-alkyl-$R^1$, $R^1-C_{0-3}$-alkyl-$C(=O)O-C_{0-3}$-alkyl-, $-C_{0-3}$-alkyl-$OC(=O)NR^{10}-C_{0-3}$-alkyl-$R^1$, $R^1-C_{0-3}$-alkyl-$OC(=O)NR^{10}-C_{0-3}$-alkyl-, $-C_{0-3}$-alkyl-$NR^{10}-C_{0-3}$-alkyl-$R^1$, $-C_{0-3}$-alkyl-$O-C_{0-3}$-alkyl-$R^1$, or $-C_{1-6}$-alkyl-$R^1$.

Preferably, $R^{10}$ at each occurrence is independently chosen from H, $C_{1-6}$-alkyl, and $C_{1-6}$-haloalkyl. More preferably, $R^{10}$ at each occurrence is independently chosen from H and $C_{1-6}$-alkyl. More preferably, $R^{10}$ at each occurrence is H.

Preferably, $L^1$ is $-C_{0-3}$-alkyl-$C(=O)-C_{0-3}$-alkyl-, $-C_{0-3}$-alkyl-$S(=O)_n-C_{0-3}$-alkyl-, $-C_{0-3}$-alkyl-$C(=O)NR^{10}-C_{0-3}$-alkyl-, $-C_{0-3}$-alkyl-$S(=O)_2NR^{10}-C_{0-3}$-alkyl-, $-C_{0-3}$-alkyl-$C(=O)O-C_{0-3}$-alkyl-, $-C_{0-3}$-alkyl-$OC(=O)NR^{10}-C_{0-3}$-alkyl-, $-C_{0-3}$-alkyl-$NR^{10}-C_{0-3}$-alkyl-, $-C_{0-3}$-alkyl-$O-C_{0-3}$-alkyl-, $-C_{1-6}$-alkyl-, $-C_{2-6}$-alkenyl-, or $-C_{2-6}$-alkynyl-.

Preferably, $R^1$ is an optionally mono- or polysubstituted group chosen from aryl and heteroaryl. More preferably, $R^1$ is an optionally mono- or polysubstituted aryl group. More preferably, $R^1$ is an optionally mono- or polysubstituted group chosen from phenyl, pyridinyl, and furanyl. More preferably, $R^1$ is an optionally mono- or polysubstituted group chosen from phenyl, pyridin-3-yl, and furan-2-yl.

Preferably, each $R^1$ substituent is independently chosen from halogen, $-NO_2$, $-OR^{20}$, $-C(=O)OR^{20}$, $-NR^{20}R^{21}$, $C_{1-3}$-alkyl, $C_{1-3}$-haloalkyl, aryl, heteroaryl, $C_{3-10}$-cycloalkyl, heterocycloalkyl, pseudohalogen, $-S(=O)_nR^{20}$, $-S(=O)_2NR^{20}R^{21}$, $-OCH_2F$, $-OCHF_2$, $-OCF_3$, $-NHOH$, $-OC$ (=O)R$^{20}$, —OC(=O)NR$^{20}$R$^{21}$, —NR$^{20}$C(=O)R$^{21}$, and —SCF$_3$. More preferably, each R$^1$ substituent is independently chosen from halogen, —OR$^{20}$, —(=O)R$^{20}$, —C(=O)OR$^{20}$, —C(=O)NR$^{20}$R$^{21}$, —NR$^{20}$R$^{21}$, C$_{1-3}$-alkyl, C$_{1-3}$-haloalkyl, pseudohalogen, —S(=O)$_n$R$^{20}$, —S(=O)$_2$NR$^{20}$R$^{21}$, —OCH$_2$F, —OCHF$_2$, —OCF$_3$, —NHOH, —OC(=O)R$^{20}$, —OC(=O)NR$^{20}$R$^{21}$, —NR$^{20}$C(=O)R$^{21}$, —NR$^{20}$C(=O)OR$^{21}$, and —SCF$_3$. More preferably, each R$^1$ substituent is independently chosen from halogen, —OR$^{20}$, —C(=O)R$^{20}$, —C(=O)OR$^{20}$, —C(=O)NR$^{20}$R$^{21}$, —NR$^{20}$R$^{21}$, C$_{1-3}$-alkyl, C$_{1-3}$-haloalkyl, pseudohalogen, —OCF$_3$, —OC(=O)R$^{20}$, —OC(=O)NR$^{20}$R$^{21}$, —NR$^{20}$C(=O)R$^{21}$, —NR$^{20}$C(=O)OR$^{21}$, and —SCF$_3$. More preferably, each R$^1$ substituent is independently chosen from halogen, —OR$^{20}$, —C(=O)R$^{20}$, —C(=O)OR$^{20}$, —C(=O)NR$^{20}$R$^{21}$, —NR$^{20}$R$^{21}$, C$_{1-3}$-alkyl, C$_{1-3}$-haloalkyl, pseudohalogen, —OCF$_3$, —NR$^{20}$C(=O)R$^{21}$, and —NR$^{20}$C(=O)OR$^{21}$. More preferably, each R$^1$ substituent is independently chosen from halogen, —OR$^{20}$, —C(=O)R$^{20}$, —C(=O)OR$^{20}$, —C(=O)NR$^{20}$R$^{21}$, —NR$^{20}$R$^{21}$, C$_{1-3}$-haloalkyl, —CN, and —OCF$_3$. More preferably, each R$^1$ substituent is independently chosen from halogen, —C(=O)R$^{20}$, C$_{1-3}$-haloalkyl, pseudohalogen, and —OCF$_3$. More preferably, each R$^1$ substituent is independently chosen from halogen, —C(=O)R$^{20}$, C$_{1-3}$-haloalkyl, —CN, and —OCF$_3$. More preferably, each R$^1$ substituent is independently chosen from halogen, —C(=O)—C$_{1-6}$-alkyl, C$_{1-3}$-haloalkyl, pseudohalogen, and —OCF$_3$. More preferably, each R$^1$ substituent is independently chosen from halogen, —C(=O)—C$_{1-6}$-alkyl, C$_{1-3}$-haloalkyl, —CN, and —OCF$_3$. More preferably, each R$^1$ substituent is independently chosen from chloro, fluoro, —CF$_3$, —C(=O)CH$_3$, —CN, and —OCF$_3$.

Preferably, R$^1$ is chosen from 2-chloro-3,6-difluorophenyl, phenyl, 2,5-difluorophenyl, 2,4,5-trifluorophenyl, 5-chloro-2-(trifluoromethyl)phenyl, 2-chloro-5-(trifluoromethyl)phenyl, 2-chlorophenyl, 2,5-dichlorophenyl, 5-fluoro-2-(trifluoromethyl)phenyl, 2,6-dichlorophenyl, 3-fluoro-2-(trifluoromethyl)phenyl, 3-chlorophenyl, 3,5-dichlorophenyl, pyridin-3-yl, 2-acetyl-5-fluorophenyl, 2-cyano-3,6-difluorophenyl, 5-(trifluoromethyl)furan-2-yl, 2-(trifluoromethoxy)phenyl, and 2-chloropyridin-3-yl.

Preferably, R$^{20}$ and R$^{21}$ at each occurrence are independently chosen from H, C$_{1-6}$-alkyl, and C$_{1-6}$-haloalkyl. More preferably, R$^{20}$ and R$^{21}$ at each occurrence are independently chosen from H and C$_{1-6}$-alkyl. More preferably, R$^{20}$ and R$^{21}$ at each occurrence are H.

Preferably, R$^2$ and R$^3$ are independently chosen from H and C$_{1-6}$-alkyl, or R$^2$ and R$^3$ together form a carbonyl group. More preferably, R$^2$ and R$^3$ are H, or R$^2$ and R$^3$ together form a carbonyl group. More preferably, R$^2$ and R$^3$ together form a carbonyl group. More preferably, R$^2$ and R$^3$ are H.

Preferably, R$^2$ and R$^3$ together form a carbonyl group, and R$^4$ and R$^5$ are independently chosen from H and C$_{1-6}$-alkyl, or one of R$^4$ and R$^5$ forms a double bond with R$^6$.

Preferably, R$^4$ and R$^5$ are H, or one of R$^4$ and R$^5$ forms a double bond with R$^6$. More preferably, R$^4$ and R$^5$ are H.

Preferably, R$^6$ is H, or R$^6$ forms a double bond with R$^4$ or R$^5$. More preferably, R$^6$ is H.

In certain embodiments, X is -L$^2$G$^1$L$^3$G$^2$L$^4$R$^7$, i.e., a compound of Formula I(c):

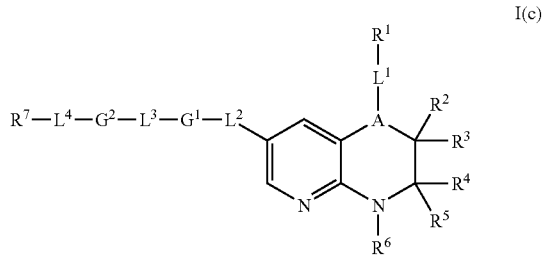

Preferably, L$^2$ is a bond, —C$_{0-3}$-alkyl-C(=O)—C$_{0-3}$-alkyl-, —S(=O)$_n$—C$_{0-3}$-alkyl-, —C(=O)NR$^{30}$—C$_{0-3}$-alkyl-, —S(=O)$_2$NR$^{30}$—C$_{0-3}$-alkyl-, —C(=O)O—C$_{0-3}$-alkyl-, —CH$_2$—OC(=O)NR$^{31}$—C$_{0-3}$-alkyl-, —C$_{0-3}$-alkyl-OC(=O)NR$^{31}$—CH$_2$—, —CH$_2$—NR$^{30}$—C$_{0-3}$-alkyl-, —CH$_2$—O—C$_{0-3}$-alkyl-, —CH$_2$—OC(=O)—C$_{0-3}$alkyl-, —CH$_2$—NR$^{10}$C(=O)—C$_{0-3}$-alkyl-, —CH$_2$—NR$^{10}$S(=O)$_2$—C$_{0-3}$-alkyl-, —C$_{1-3}$-alkyl-, —C$_{2-3}$-alkenyl-, or —C$_{2-3}$-alkynyl-. More preferably, L$^2$ is a bond, —C$_{0-3}$-alkyl-C(=O)—C$_{0-3}$-alkyl-, —S(=O)$_n$—C$_{0-3}$-alkyl-, —C(=O)NR$^{30}$—C$_{0-3}$-alkyl-, —S(=O)$_2$NR$^{30}$—C$_{0-3}$-alkyl-, —C(=O)O—C$_{0-3}$-alkyl-, —CH$_2$—OC(=O)NR$^{30}$—C$_{0-3}$-alkyl-, —C$_{0-3}$-alkyl-OC(=O)NR$^{30}$—CH$_2$—, —CH$_2$—NR$^{30}$—C$_{0-3}$-alkyl-, —CH$_2$—O—C$_{0-3}$-alkyl-, —C$_{1-3}$-alkyl-, —C$_{2-3}$-alkenyl-, or —C$_{2-3}$-alkynyl-. More preferably, L$^2$ is a bond, —C$_{0-3}$-alkyl-C(=O)—C$_{0-3}$-alkyl-, —S(=O)$_n$—C$_{0-3}$-alkyl-, —C(=O)NR$^{30}$—C$_{0-3}$-alkyl-, —S(=O)$_2$NR$^{30}$—C$_{0-3}$-alkyl-, —C(=O)O—C$_{0-3}$-alkyl-, —CH$_2$—OC(=O)NR$^{30}$—C$_{0-3}$-alkyl-, —C$_{0-3}$-alkyl-OC(=O)NR$^{10}$—CH$_2$—, —CH$_2$—NR$^{30}$—C$_{0-3}$-alkyl-, —CH$_2$—O—C$_{0-3}$-alkyl-, or —C$_{2-3}$-alkynyl-. More preferably, L$^2$ is a bond, —C$_{0-3}$-alkyl-C(=O—C$_{0-3}$-alkyl-, —C$_{0-3}$-alkyl-C(=O)NR$^{10}$—C$_{0-3}$-alkyl-, —C$_{0-3}$-alkyl-C(=O)O—C$_{0-3}$-alkyl-, or —C$_{2-3}$-alkynyl-. More preferably, L$^2$ is a bond, —C$_{0-3}$-alkyl-C(=O)—C$_{0-3}$-alkyl-, —C(=O)NR$^{30}$—C$_{0-3}$-alkyl-, —C(=O)O—C$_{0-3}$-alkyl-, or —C$_{2-3}$-alkynyl-. More preferably, L$^2$ is a bond, —C(=O)—C$_{0-3}$-alkyl-, —C(=O)NR$^{30}$—C$_{0-3}$-alkyl-, —C(=O)O—C$_{0-3}$-alkyl-, or —C$_{2-3}$-alkynyl-. More preferably, L$^2$ is a bond, —C(=O), —C(=O)O—, —C(=O)O—C$_{1-3}$-alkyl-, —C(=O)NR$^{30}$—C$_{0-3}$-alkyl-, or —C$_{2-3}$-alkynyl-. More preferably, L$^2$ is a bond, —C(=O)—, —C(=O)NR$^{30}$—, or —C$_{2-3}$-alkynyl-. More preferably, L$^2$ is a bond, —C(=O), —C(=O)O—, —C(=O)O—CH$_2$—, —C(=O)NH—(CH$_2$)$_3$—, —C(=O)NH—(CH$_2$)$_2$—, —C(=O)NH—CH$_2$—, —C(=O)NH—, —C≡C—, or —C≡C-CH$_2$—.

Preferably, R$^{30}$ at each occurrence is independently chosen from H, C$_{1-6}$-alkyl, and C$_{1-6}$-haloalkyl. More preferably R$^{30}$ at each occurrence is independently chosen from H and C$_{1-6}$-alkyl. More preferably, R$^{30}$ at each occurrence is H.

Preferably, G$^1$ is a bond, or an optionally mono- or polysubstituted group chosen from aryl, heterocycloalkyl, and heteroaryl. More preferably, G$^1$ is a bond, or an optionally mono- or polysubstituted group chosen from aryl and heteroaryl. More preferably, G$^1$ is a bond or an optionally mono- or polysubstituted aryl group. More preferably, G$^1$ is a bond, or an optionally mono- or polysubstituted group chosen from phenyl, pyridinyl, piperazinyl, pyrimidinyl, tetrahydropyridinyl, pyrazolyl, pyrrolyl, piperidinyl, 4-carbonyl-1,3,8-triazaspiro[4.5]decanyl, pyrrolidinyl, and thiazolyl.

Preferably, each G$^1$ substituent is independently chosen from halogen, —NO$_2$, —OR$^{40}$, —C(=O)R$^{40}$, —C(=O)OR$^{40}$, —C(=O)NR$^{40}$R$^{41}$, —NR$^{40}$R$^{41}$, C$_{1-3}$-alkyl, C$_{1-3}$-haloalkyl, pseudohalogen, —S(=O)$_n$R$^{40}$, —S(=O)$_2$NR$^{40}$R$^{41}$, —OCH$_2$F, —OCHF$_2$, —OCF$_3$, —NHOH, —OC(=O)R$^{40}$, —OC(=O)NR$^{40}$R$^{41}$, —NR$^{40}$C(=O)R$^{41}$, —NR$^{40}$C(=O)OR$^{41}$, and —SCF$_3$. More preferably, each G$^1$ substituent is independently chosen from halogen, —OR$^{40}$, —C(=O)R$^{40}$, —C(=O)OR$^{40}$, —C(=O)NR$^{40}$R$^{41}$, —NR$^{40}$R$^{41}$, C$_{1-3}$-alkyl, C$_{1-3}$-haloalkyl, —CN, —S(=O)OR$^{40}$, —S(=O)$_2$NR$^{40}$R$^{41}$, —OCF$_3$, —OC(=O)R$^{40}$, —NR$^{40}$C(=O)R$^{41}$, and —SCF$_3$. More preferably, each G$^1$ substituent is independently chosen from halogen, —OR$^{40}$, —C(=O)R$^{40}$, —C(=O)OR$^{40}$, —C(=O)NR$^{40}$R$^{41}$, —NR$^{40}$R$^{41}$, C$_{1-3}$-alkyl, C$_{1-3}$-haloalkyl, —CN, and —OCF$_3$. More preferably, each G$^1$ substituent is independently chosen from halogen, —OR$^{40}$, C$_{1-3}$-alkyl, and C$_{1-3}$-haloalkyl. More preferably, each G$^1$ substituent is independently chosen from halogen, —OR$^{40}$, and C$_{1-3}$-haloalkyl. More preferably, each G$^1$ substituent is independently chosen from halogen and —OR$^{40}$. More preferably, each G$^1$ substituent is independently chosen from halogen and hydroxyl. More preferably, each G$^1$ substituent is independently chosen from chloro, fluoro, and hydroxyl. More preferably, G$^1$ is unsubstituted.

Preferably, R$^{40}$ and R$^{41}$ at each occurrence are independently chosen from H, C$_{1-6}$-alkyl, and C$_{1-6}$-haloalkyl. More preferably, R$^{40}$ and R$^{41}$ at each occurrence are independently chosen from H and C$_{1-6}$-alkyl. More preferably, R$^{40}$ and R$^{41}$ at each occurrence are H.

Preferably, L$^3$ is a bond, —C$_{0-3}$-alkyl-C(=O)—C$_{0-3}$-alkyl-, —C$_{0-3}$-alkyl-S(=O), —C$_{0-3}$-alkyl-, —C$_{0-3}$-alkyl-C(=O)NR$^{50}$—C$_{0-3}$-alkyl-, —C$_{0-3}$-alkyl-S(=O)$_2$NR$^{50}$—C$_{0-3}$-alkyl-, —C$_{0-3}$-alkyl-C(=O)O—C$_{0-3}$-alkyl-, —C$_{0-3}$-alkyl-NR$^{10}$—C$_{0-3}$-alkyl-, —C$_{0-3}$-alkyl-O—C$_{0-3}$-alkyl-, —C$_{1-3}$-alkyl-, —C$_{2-3}$-alkenyl-, or —C$_{2-3}$-alkynyl-. More preferably, L$^3$ is a bond, —C$_{0-3}$-alkyl-C(=O)—C$_{0-3}$-alkyl-, —C$_{0-3}$-alkyl-S(=O)$_n$—C$_{0-3}$-alkyl-, —C$_{0-3}$-alkyl-C(=O)NR$^{50}$—C$_{0-3}$-alkyl-, —C$_{0-3}$-alkyl-S(=O)$_2$NR$^{50}$—C$_{0-3}$-alkyl-, —C$_{0-3}$-alkyl-C(=O)O—C$_{0-3}$-alkyl-, —C$_{0-3}$-alkyl-OC(=O)NR$^{50}$—C$_{0-3}$-alkyl-, —C$_{0-3}$-alkyl-NR$^{50}$—C$_{0-3}$-alkyl-, —C$_{0-3}$-alkyl-O—C$_{0-3}$-alkyl-, or —C$_{1-3}$-alkyl-. More preferably, L$^3$ is a bond, —C$_{0-3}$-alkyl-C(=O)—C$_{0-3}$-alkyl-, —C$_{0-3}$-alkyl-S(=O)$_n$—C$_{0-3}$-alkyl-, —C$_{0-3}$-alkyl-C(=O)NR$^{50}$—C$_{0-3}$-alkyl-, —C$_{0-3}$-alkyl-S(=O)$_2$NR$^{50}$—C$_{0-3}$-alkyl-, —C$_{0-3}$-alkyl-C(=O)O—C$_{0-3}$-alkyl-, —C$_{0-3}$-alkyl-NR$^{50}$—C$_{0-3}$-alkyl-, —C$_{0-3}$-alkyl-O—C$_{0-3}$-alkyl-, or —C$_{1-3}$-alkyl-. More preferably, L$^3$ is a bond, —C(=O)—C$_{0-3}$-alkyl-, —S(=O)$_2$—C$_{0-3}$-alkyl-, —C$_{0-3}$-alkyl-C(=O)NR$^{50}$—C$_{0-3}$-alkyl-, —C$_{0-3}$-alkyl-S(=O)$_2$NR$^{50}$—, —C(=O)O—C$_{0-3}$-alkyl-, —OC(=O)NR$^{10}$—C$_{0-3}$-alkyl-, —NR$^{50}$—C$_{0-3}$-alkyl-, —O—C$_{0-3}$-alkyl-, or —C$_{1-3}$-alkyl-. More preferably, L$^3$ is a bond, —C$_{0-3}$-alkyl-C(=O)—C$_{0-3}$-alkyl-, —C$_{0-3}$-alkyl-C(=O)NR$^{50}$—C$_{0-3}$-alkyl-, —C$_{0-3}$-alkyl-S(=O)$_2$NR$^{50}$—C$_{0-3}$-alkyl-, —C$_{0-3}$-alkyl-C(=O)O—C$_{0-3}$-alkyl-, —C$_{0-3}$-alkyl-OC(=O)NR$^{50}$—C$_{0-3}$-alkyl-, —C$_{0-3}$-alkyl-NR$^{50}$—C$_{0-3}$-alkyl-, —C$_{0-3}$-alkyl-O—C$_{0-3}$-alkyl-, or —C$_{1-3}$-alkyl-. More preferably, L$^3$ is a bond, —C(=O)—C$_{0-3}$-alkyl-, —C$_{0-3}$-alkyl-C(=O)NR$^{50}$—C$_{0-3}$-alkyl-, —C$_{0-3}$-alkyl-S(=O)$_2$NR$^{50}$—, —C(=O)O—C$_{0-3}$-alkyl-, —OC(=O)NR$^{50}$—C$_{0-3}$-alkyl-, —NR$^{50}$—C$_{0-3}$-alkyl-, —O—C$_{0-3}$-alkyl-, or —C$_{1-3}$-alkyl-. More preferably, L$^3$ is a bond, —C(=O)—, —C(=O)O—C$_{0-3}$-alkyl-, —C(=O)NR$^{50}$—C$_{0-3}$-alkyl-, —C$_{0-3}$-alkyl-S(=O)$_2$NR$^{50}$—, —O—C$_{0-3}$-alkyl-, —C$_{1-3}$-alkyl-, —NR$^{50}$—C$_{0-3}$-alkyl-, —OC(=O)NR$^{50}$—C$_{0-3}$-alkyl-, or —C$_{1-13}$-alkyl-C(=O)NR$^{50}$—. More preferably, L$^3$ is a bond, —C(=O)—C$_{0-3}$-alkyl-, —S(=O)$_2$—, —C(=O)NR$^{50}$—, or —S(=O)$_2$NR$^{10}$—. More preferably, L$^3$ is a bond, —C(=O)—, —C(=O)O—C$_{0-3}$-alkyl-, —C(=O)N(C$_{1-3}$-alkyl)-C$_{0-3}$-alkyl-, —C(=O)NH—C$_{0-3}$-alkyl-, —C$_{0-3}$-alkyl-S(=O)$_2$NH—, —O—C$_{0-3}$-alkyl-, —C$_{1-3}$-alkyl-, —NH—C$_{0-3}$-alkyl-, —OC(=O)NH—C$_{0-3}$-alkyl-, or —C$_{1-3}$-alkyl-C(=O)NH—. More preferably, L$^3$ is a bond, —C(=O)—, —C(=O)O—, —C(=O)O—CH$_2$—, —C(=O)NH—(CH$_2$)$_5$—, —C(=O)NH—(CH$_2$)$_3$—, —C(=O)NH—(CH$_2$)$_2$—, —C(=O)NH—CH$_2$—, —C(=O)NH—, —C(=O)N(CH$_3$)—CH$_2$—, —C(=O)N(CH$_3$)—, —(CH$_2$)$_2$S(=O)$_2$NH—, —CH$_2$—S(=O)$_2$NH—, —S(=O)$_2$NH—, —O—(CH$_2$)$_2$—, —O—CH$_2$—, —O—, —(CH$_2$)$_2$—, —CH$_2$—, —NH—(CH$_2$)$_2$—, —NH—CH$_2$—, —NH—, —OC(=O)NH—CH$_2$—, —OC(=O)NH—, or —CH$_2$—C(=O)NH—.

Preferably, R$^{50}$ at each occurrence is independently chosen from H, C$_{1-6}$-alkyl, and C$_{1-6}$-haloalkyl. More preferably, R$^{50}$ at each occurrence is independently chosen from H and C$_{1-6}$-alkyl. More preferably, R$^{50}$ at each occurrence is H.

Preferably, G$^2$ is a bond, or an optionally mono- or polysubstituted group chosen from aryl, heterocycloalkyl, and heteroaryl. More preferably, G$^2$ is a bond, or an optionally mono- or polysubstituted group chosen from aryl and heteroaryl. More preferably, G$^2$ is a bond, or an optionally mono- or polysubstituted group chosen from aryl and heterocycloalkyl. More preferably, G$^2$ is a bond or an optionally mono- or polysubstituted aryl group. More preferably, G$^2$ is a bond or an optionally mono- or polysubstituted heterocycloalkyl group. More preferably, G$^2$ is a bond or an optionally mono- or polysubstituted heteroaryl group. More preferably, G$^2$ is a bond, or an optionally mono- or polysubstituted group chosen from piperazinyl, pyrrolidinyl, piperidinyl, phenyl, 4-carbonyl-1,3,8-triazaspiro[4.5]decanyl, and thiazolyl.

Preferably, each G$^2$ substituent is independently chosen from halogen, —NO$_2$, —OR$^{60}$, —C(=O)R$^{60}$, —C(=O)OR$^{60}$, —C(=O)NR$^{60}$R$^{61}$, —NR$^{60}$R$^{61}$, C$_{1-3}$-alkyl, C$_{1-3}$-haloalkyl, pseudohalogen, —S(=O)$_n$R$^{60}$, —S(=O)$_2$NR$^{60}$R$^{61}$, —OCH$_2$F, —OCHF$_2$, —OCF$_3$, —NHOH, —OC(=O)R$^{60}$, —OC(=O)NR$^{60}$R$^{61}$, —NR$^{60}$C(=O)R$^{61}$, —NR$^{60}$C(=O)OR$^{61}$, and —SCF$_3$. More preferably, each G$^2$ substituent is independently chosen from halogen, —OR$^{60}$, —C(=O)R$^{60}$, —C(=O)OR$^{60}$, —C(=O)NR$^{60}$R$^{61}$, —NR$^{60}$R$^{61}$, C$_{1-3}$-alkyl, C$_{1-3}$-haloalkyl, —CN, —S(=O)$_n$R$^{60}$, —S(=O)$_2$NR$^{60}$R$^{61}$, —OCF$_3$, —OC(=O)R$^{60}$, —NR$^{60}$C(=O)R$^{61}$, and —SCF$_3$. More preferably, each G$^2$ substituent is independently chosen from halogen, —OR$^{60}$, —C(=O)R$^{60}$, —C(=O)OR$^{60}$, —C(=O)NR$^{60}$R$^{61}$, —NR$^{60}$R$^{61}$, C$_{1-3}$-alkyl, C$_{1-3}$-haloalkyl, —CN, and —OCF$_3$. More preferably, each G$^2$ substituent is independently chosen from halogen, —OR$^{60}$, C$_{1-3}$-alkyl, and C$_{1-3}$-haloalkyl. More preferably, each G$^2$ substituent is independently chosen from halogen, —OR$^{60}$, and C$_{1-3}$-haloalkyl. More preferably, each G$^2$ substituent is independently chosen from halogen and —OR$^{60}$. More preferably, each G$^2$ substituent is independently chosen from halogen and hydroxyl. More preferably, each G$^2$ substituent is independently chosen from chloro, fluoro, and hydroxyl. More preferably, each G$^2$ substituent is hydroxyl. More preferably, G$^2$ is unsubstituted.

Preferably, R$^{60}$ and R$^{61}$ at each occurrence are independently chosen from H, C$_{1-6}$-alkyl, and C$_{1-6}$-haloalkyl. More preferably, R$^{60}$ and R$^{61}$ at each occurrence are independently chosen from H and C$_{1-6}$-alkyl. More preferably, R$^{60}$ and R$^{61}$ at each occurrence are H.

Preferably, L$^4$ is a bond, —C$_{0-3}$-alkyl-C(=O)—C$_{0-3}$-alkyl-, —C$_{0-3}$-alkyl-S(=O)$_n$—C$_{0-3}$-alkyl-, —C$_{0-3}$-alkyl-C(=O)NR$^{70}$—C$_{0-3}$-alkyl-, —C$_{0-3}$-alkyl-S(=O)$_2$NR$^{70}$—C$_{0-3}$-alkyl-, —C$_{0-3}$-alkyl-C(=O)O—C$_{0-3}$-alkyl-, —C$_{0-3}$-alkyl-NR$^{70}$—C$_{0-3}$-alkyl-, —C$_{0-3}$-alkyl-O—C$_{0-3}$-alkyl-, —C$_{1-3}$-alkyl-, —C$_{2-3}$-alkenyl-, or —C$_{2-3}$-alkynyl-. More preferably, L$^4$ is a bond, —C$_{0-3}$-alkyl-C(=O)—C$_{0-3}$-alkyl-, —C$_{0-3}$-alkyl-S(=O)$_n$—C$_{0-3}$-alkyl-, —C$_{0-3}$-alkyl-C(=O)NR$^{70}$—C$_{0-3}$-alkyl-, —C$_{0-3}$-alkyl-S(=O)$_2$NR$^{70}$—C$_{0-3}$-alkyl-, —C$_{0-3}$-alkyl-C(=O)O—C$_{0-3}$-alkyl-, —C$_{0-3}$-alkyl- NR$^{70}$—C$_{0-3}$-alkyl-, —C$_{0-3}$-alkyl-O—C$_{0-3}$-alkyl-, or —C$_{1-3}$-alkyl-. More preferably, L$^4$ is a bond, —C$_{0-3}$-alkyl-C(=O)—C$_{0-3}$-alkyl-, —S(=O)$_n$—C$_{0-3}$-alkyl-, —C$_{0-3}$-alkyl-C(=O)NR$^{70}$—C$_{0-3}$-alkyl-, —S(=O)$_2$NR$^{70}$—C$_{0-3}$-alkyl-, —C$_{0-3}$-alkyl-C(=O)O—C$_{0-3}$-alkyl-, —NR$^{70}$—C$_{0-3}$-alkyl-, —O—C$_{0-3}$-alkyl-, or —C$_{1-3}$-alkyl-. More preferably, L$^4$ is a bond, —C(=O)—C$_{0-3}$-alkyl-, —S(=O)$_n$—C$_{0-3}$-alkyl-, —C$_{0-3}$-alkyl-C(=O)NR$^{70}$—, —S(=O)$_2$NR$^{70}$—, —C(=O)O—C$_{0-3}$-alkyl-, —NR$^{10}$—C$_{0-3}$-alkyl-, —O—C$_{0-3}$-alkyl-, or —C$_{1-3}$-alkyl-. More preferably, L$^4$ is a bond, —C(=O)—C$_{0-3}$-alkyl-, —S(=O)$_2$—C$_{0-3}$-alkyl-, —C$_{0-3}$-alkyl-C(=O)NR$^{70}$—, —S(=O)$_2$NR$^{70}$—, —C(=O)O—C$_{0-3}$-alkyl-, —NR$^{70}$—, or —C$_{1-3}$-alkyl-. More preferably, L$^4$ is a bond, —C$_{0-3}$-alkyl-C(=O)—C$_{0-3}$-alkyl-, —C$_{0-3}$-alkyl-C(=O)NR$^{70}$—C$_{0-3}$-alkyl-, —C$_{0-3}$-alkyl-C(=O)O—C$_{0-3}$-alkyl-, or —C$_{1-3}$-alkyl-. More preferably, L$^4$ is a bond, —C(=O)—C$_{0-3}$-alkyl-, —C$_{0-3}$-alkyl-C(=O)NR$^{70}$—, —C(=O)O—C$_{0-3}$-alkyl-, or —C$_{1-3}$-alkyl-. More preferably, L$^4$ is a bond, —C(=O), —C$_{1-3}$-alkyl-, —C(=O)O—C$_{0-3}$-alkyl-, or —C$_{1-3}$-alkyl-C(=O)NH—. More preferably, L$^4$ is a bond, —C(=O)—, —(CH$_2$)$_2$—, —CH$_2$—, —C(=O)O—, —C(=O)O—CH$_2$—, or —CH$_2$—C(=O)NH.

Preferably, R$^{70}$ at each occurrence is independently chosen from H, C$_{1-6}$-alkyl, and C$_{1-6}$-haloalkyl. More preferably, R$^{70}$ at each occurrence is independently chosen from H and C$_{1-6}$-alkyl. More preferably, R$^{70}$ at each occurrence is H.

Preferably, R$^{70}$ is an optionally mono- or polysubstituted group chosen from C$_{1-6}$-alkyl, aryl, C$_{3-10}$-cycloalkyl, heterocycloalkyl, and heteroaryl. More preferably, R$^7$ is an optionally mono- or polysubstituted group chosen from C$_{1-6}$-alkyl, aryl, heterocycloalkyl, and heteroaryl. More preferably, R$^7$ is an optionally mono- or polysubstituted group chosen from aryl, C$_{3-10}$-cycloalkyl, heterocycloalkyl, and heteroaryl. More preferably, R$^7$ is an optionally mono- or polysubstituted group chosen from aryl, heterocycloalkyl, and heteroaryl. More preferably, R$^7$ is an optionally mono- or polysubstituted group chosen from pyridinyl, phenyl, methyl, ethyl, propyl, isopropyl, butyl, tert-butyl, isobutyl, pentyl, isopentyl, hexyl, piperazinyl, pyrrolidinyl, morpholinyl, pyrimidinyl, dihydropyridinyl, tetrahydropyridinyl, propynyl, pyrazolyl, pyrrolyl, piperidinyl, 1,3-dihydro-2-carbonylbenzoimidazolyl, 4-carbonyl-1,3,8-triazaspiro[4.5]decanyl, thieno[3,2-d]pyrimidinyl, furo[3,2-c]pyridinyl, benzo[d]isoxazolyl, thienyl, quinolinyl, pyrazinyl, thiazolyl, naphthalenyl, indanyl, cyclohexyl, tetrahydrofuranyl, indolyl, and isoindolyl. More preferably, R$^7$ is an optionally mono- or polysubstituted group chosen from pyridin-3-yl, piperazin-1-yl, phenyl, pyrrolidin-1-yl, morpholin-4-yl, methyl, ethyl, propyl, butyl, pentyl, hexyl, piperidin-1-yl, pyridin-4-yl, isoxazol-4-yl, pyrimidin-5-yl, propyn-1-yl, 1,1-dioxo-1λ$^6$-thiomorpholin-4-yl, pyrazol-4-yl, pyrrol-3-yl, pyrimidin-2-yl, isopropyl, isobutyl, isopentyl, tert-butyl, 1,3-dihydro-2-carbonylbenzoimidazol-1-yl, 4-carbonyl-1,3,8-triazaspiro[4.5]decan-8-yl, thieno[3,2-d]pyrimidin-4-yl, furo[3,2-c]pyridin-4-yl, benzo[d]isoxazol-3-yl, pyridin-2-yl, piperidin-4-yl, thien-2-yl, quinolin-4-yl, pyrazin-2-yl, thiazol-4-yl, naphthalen-1-yl, indan-1-yl, cyclohexyl, 4-biphenyl, tetrahydrofuran-2-yl, indan-2-yl, thiazol-2-yl, indol-3-yl, and isoindol-2-yl.

Preferably, at least one of G$^1$ and R$^7$ is an optionally mono- or polysubstituted group chosen from aryl, C$_{3-10}$-cycloalkyl, heterocycloalkyl, and heteroaryl.

Preferably, each R$^7$ substituent is independently chosen from halogen, —OR$^{80}$, —C(=O)R$^{80}$, —C(=O)OR$^{80}$, —C(=O)NR$^{80}$R$^{81}$, —NR$^{80}$R$^{81}$, C$_{1-6}$-alkyl, C$_{1-6}$-haloalkyl, aryl, heteroaryl, C$_{3-10}$-cycloalkyl, heterocycloalkyl, pseudohalogen, —S(=O)$_n$R$^{80}$, —S(=O)$_2$NR$^{80}$R$^{81}$, —OCH$_2$F, —OCHF$_2$, —OCF$_3$, —NHOH, —OC(=O)R$^{80}$, —OC(=O)NR$^{80}$R$^{81}$, —NR$^{80}$C(=O)R$^{81}$, —NR$^{80}$C(=O)OR$^{81}$, —SiR$^{80}$R$^{81}$R$^{82}$ and —SCF$_3$. More preferably, each R$^7$ substituent is independently chosen from halogen, OR$^{80}$, —C(=O)R$^{80}$, —C(=O)OR$^{80}$, —C(=O)NR$^{80}$R$^{81}$, —NR$^{80}$R$^{81}$, C$_{1-6}$-alkyl, C$_{1-6}$-haloalkyl, aryl, heteroaryl, C$_{3-10}$-cycloalkyl, heterocycloalkyl, pseudohalogen, —S(=O)$_n$R$^{80}$, —S(=O)$_2$NR$^{80}$R$^{81}$, —OCF$_3$, —OC(=O)R$^{80}$, —NR$^{80}$C(=O)R$^{81}$, —SiR$^{80}$R$^{81}$R$^{82}$ and —SCF$_3$. More preferably, each R$^7$ substituent is independently chosen from halogen, —OR$^{80}$, —C(=O)R$^{80}$, —C(=O)OR$^{80}$, —C(=O)NR$^{80}$R$^{81}$, —NR$^{80}$R$^{81}$, C$_{1-6}$-alkyl, C$_{1-6}$-haloalkyl, aryl, heteroaryl, C$_{3-10}$-cycloalkyl, heterocycloalkyl, pseudohalogen, —S(=O)$_n$R$^{80}$, —S(=O)$_2$NR$^{80}$R$^{81}$, —OCF$_3$, —OC(=O)R$^{80}$, and —NR$^{80}$C(=O)R$^{81}$. More preferably, each R$^7$ substituent is independently chosen from halogen, —OR$^{80}$, —C(=O)R$^{80}$, —C(=O)OR$^{80}$, —C(=O)NR$^{80}$R$^{81}$, —NR$^{80}$R$^{81}$, C$_{1-6}$-alkyl, C$_{1-6}$-haloalkyl, aryl, heteroaryl, C$_{3-10}$-cycloalkyl, heterocycloalkyl, pseudohalogen, —S(=O)$_n$R$^{80}$, —S(=O)$_2$NR$^{80}$R$^{81}$, —OCF$_3$, and —SiR$^{80}$R$^{81}$R$^{82}$. More preferably, each R$^7$ substituent is independently chosen from halogen, —OR$^{80}$, —C(=O)R$^{80}$, —C(=O)OR$^{80}$, —C(=O)NR$^{80}$R$^{81}$, —NR$^{80}$R$^{81}$, C$_{1-6}$-alkyl, C$_{1-6}$-haloalkyl, aryl, heteroaryl, C$_{3-10}$-cycloalkyl, heterocycloalkyl, cyano, —S(=O)$_2$R$^{80}$, —S(=O)$_2$NR$^{80}$R$^{81}$, —OCF$_3$, and —SiR$^{80}$R$^{81}$R$^{82}$. More preferably, each R$^7$ substituent is independently chosen from methyl, carboxy, N,N-dimethylamino, acetyl, methanesulfonyl, aminocarbonyl, ethylaminocarbonyl, cyano, ethoxycarbonyl, methoxycarbonyl, pyrrolidin-1-yl, chloro, morpholin-4-yl, fluoro, methoxy, tert-butoxycarbonyl, pyrrolidin-1-yl, tert-butoxycarbonylamino, amino, 1,1-dioxo-1λ$^6$-thiomorpholin-4-yl, isopentyl, triisopropylsilyl, phenyl, pyrimidin-2-yl, 1,3-dihydro-2-carbonylbenzoimidazol-1-yl, trifluoromethyl, thieno[3,2-d]pyrimidin-4-yl, furo[3,2-c]pyridin-4-yl, fluoro, pyridin-2-yl, trifluoromethoxy, thien-2-yl, pyridin-4-yl, pyridin-3-yl, pyrrolidin-1-yl, sulfamoyl, pyrazin-2-yl, naphthalen-1-yl, phenoxy, tetrahydrofuran-2-ylcarbonyl, tetrahydrofuran-2-yl, indan-2-ylaminocarbonyl, cyclohexyl, pyridin-3-yl, thiazol-2-yl, acetamindo, indol-3-yl, benzoyl, isopropylaminocarbonyl, morpholin-4-ylcarbonyl, cyclohexylaminocarbonyl, indan-1-ylaminocarbonyl, indan-2-ylaminocarbonyl, and isoindol-2-ylcarbonyl.

Preferably, R$^{80}$, R$^{81}$, and R$^{82}$ at each occurrence are independently chosen from H, C$_{1-6}$-alkyl, and C$_{1-6}$-haloalkyl. More preferably, R$^{80}$, R$^{81}$, and R$^{82}$ at each occurrence are independently chosen from H and C$_{1-6}$-alkyl. More preferably, R$^{80}$, R$^{81}$, and R$^{82}$ at each occurrence are H.

Preferably, R$^{80}$ at each occurrence is independently chosen from H, C$_{1-6}$-alkyl, C$_{1-6}$-haloalkyl, aryl, heteroaryl, and heterocycloalkyl. More preferably, R$^{80}$ at each occurrence is independently chosen from H, C$_{1-6}$-alkyl, C$_{1-6}$-haloalkyl, aryl, and heteroaryl. More preferably, R$^{80}$ at each occurrence is independently chosen from H, C$_{1-6}$-alkyl, C$_{1-6}$-haloalkyl, and aryl.

Preferably, when R$^7$ is C$_{1-6}$-alkyl, at least one of L$^2$, G$^1$, L$^3$, G$^2$, or L$^4$ is not a bond.

Preferably, R$^7$ is chosen from pyridin-3-yl, 4-methylpiperazin-1-yl, 4-carboxyphenyl, pyrrolidin-1-yl, morpholin-4-yl, N,N-dimethylaminomethyl, N,N-dimethylaminoethyl, N,N-dimethylaminopropyl, N,N-dimethylaminobutyl, N,N-dimethylaminopentyl, N,N-dimethylaminohexyl, 4-acetylphenyl, methyl, ethyl, 4-methanesulfonylphenyl, benzamidyl, N-ethylbenzamidyl, 2-cyanopyridin-5-yl, 2-ethoxycarbonylpyridin-5-yl, 4-ethoxycarbonylphenyl, 3-ethoxycarbonylphenyl, 3-carboxyphenyl, 3-methoxycarbonylphenyl, 4-(1-pyrrolidinyl)piperidin-1-yl, 2-carboxypyridin-5-yl, 3-ethoxycarbonylpyridin-5-yl, 3-carboxypyridin-5-yl, 3-chloro-2-morpholin-4-ylpyridin-4-yl, 3-fluoro-2-morpholin-4-ylpyridin-4-yl, 3,5-dimethylisoxazol-4-yl, 2-(4-morpholinyl)pyrimidin-5-yl, 2-methoxypyrimidin-5-yl, 1-tert-butoxycarbonyl-3,6-dihydro-2H-pyridin-4-yl, 1,2,3,6-tetrahydropyridin-4-yl, 2-chloropyridin-5-yl, 2-(1-pyrrolidinyl)pyridin-5-yl, 2-chloropyridin-4-yl, 3-tert-butoxycarbonylaminopropyn-1-yl, 3-aminopropyn-1-yl, 3-dimethylaminopropyn-1-yl, 3-(1,1-dioxo-1$\lambda^6$-thiomorpholin-4-yl)propyn-1-yl, 1,1-dioxo-1$\lambda^6$-thiomorpholin-4-yl, 2-aminopyridin-5-yl, 2-(1-pyrrolidinyl)pyridin-4-yl, 2-(4-morpholinyl)pyridin-4-yl, 3-(4-morpholinyl)phenyl, 1-isopentylpyrazol-4-yl, 2-(1-piperazinyl)pyridin-4-yl, 4-acetylpiperazin-1-yl, pyrazol-4-yl, pyrrol-3-yl, 1-(triisopropylsilyl)pyrrol-3-yl, 1-methylpyrazol-4-yl, piperidin-1-yl, 4-methoxypiperidin-1-yl, 4-phenylpiperazin-1-yl, pyrimidin-2-yl, phenyl, methyl, ethyl, isopropyl, isobutyl, isopentyl, tert-butyl, piperazin-1-yl, 4-(2-pyrimidinyl)piperazin-1-yl, 4-chlorophenyl, 1,3-dihydro-2-carbonylbenzoimidazol-1-yl, 4-(1,3-dihydro-2-carbonylbenzoimidazol-1-yl)piperidin-1-yl, 2-methoxyphenyl, 3-(trifluoromethyl)phenyl, 4-phenylpiperidin-1-yl, 3,4-dichlorophenyl, benzhydryl, benzyl, 4-carbonyl-1-phenyl-1,3,8-triazaspiro[4.5]decan-8-yl, 4-carbonyl-1,3,8-triazaspiro[4.5]decan-8-yl, thieno[3,2-d]pyrimidin-4-yl, 4-thieno[3,2-d]pyrimidin-4-ylpiperazin-1-yl, 4-methoxyphenyl, furo[3,2-c]pyridin-4-yl, 4-furo[3,2-c]pyridin-4-ylpiperazin-1-yl, 6-fluorobenzo[d]isoxazol-3-yl, 3-chlorophenyl, pyridin-2-yl, 2-pyridinylmethyl, 2-(2-pyridinyl)ethyl, 1-ethoxycarbonylpiperidin-4-yl, 4-(trifluoromethoxy)phenyl, 4-(4-morpholinyl)piperidin-1-yl, thien-2-yl, 2-thienylmethyl, 2-(2-thienyl)ethyl, pyridin-4-yl, 4-pyridinylmethyl, 3-pyridinylmethyl, quinolin-4-yl, 2-methylquinolin-4-yl, 1-pyrrolidinylmethyl, 3,5-bis(trifluoromethyl)phenyl, 4-sulfamoylphenyl, pyrazin-2-yl, 4-(2-pyrazinyl)piperazin-1-yl, thiazol-4-yl, 2-phenylthiazol-4-yl, naphthalene-1-yl, 1-naphthalenylmethyl, indan-1-yl, cyclohexyl, 4-biphenyl, 2-phenoxyethyl, phenoxymethyl, tetrahydrofuran-2-yl, 4-(2-tetrahydrofuranylcarbonyl)piperazin-1-yl, phenethyl, 2-tetrahydrofuranylmethyl, 2-chlorophenyl, 2-(trifluoromethyl)phenyl, indan-2-yl, 3-(2-indanylaminocarbonyl)phenyl, cyclohexylmethyl, 2-(3-pyridinyl)pyrrolidin-1-yl, 4-(4-morpholinyl)phenyl, thiazol-2-yl, 4-(2-thiazolyl)piperazin-1-yl, 2-(4-morpholinyl)pyridin-5-yl, 4-acetamidophenyl, indol-3-yl, 4-(3-indolyl)piperidin-1-yl, 4-benzoylpiperazin-1-yl, 1-methylpiperidin-4-yl, isopropylaminocarbonylmethyl, 3-(4-morpholinylcarbonyl)phenyl, 3-methoxyphenyl, 3-(cyclohexylaminocarbonyl)phenyl, 4-(trifluoromethyl)phenyl, methoxymethyl, methoxyethyl, 4-(4-morpholinylcarbonyl)phenyl, 4-(1-indanylaminocarbonyl)phenyl, 4-(2-indanylaminocarbonylphenyl, isoindol-2-yl, and 4-(2-isoindolylcarbonyl)phenyl.

In certain embodiments, X is $R^8$, i.e., a compound of Formula I(d):

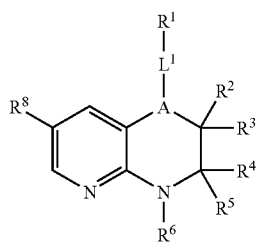

I(d)

Preferably, $R^8$ is H, Br, I, CN, or C(=O)OH. More preferably, $R^8$ is Br, I, CN, or C(=O)OH. More preferably, $R^8$ is I, CN, or C(=O)OH. More preferably, $R^8$ is I.

In addition to having ALK and c-Met inhibitory activity, the compounds of Formula I(d) are useful as intermediates for the preparation of other compounds of Formula I (e.g., compounds of Formula I(c)).

Preferably, n is 0 or 2. More preferably, n is 0. More preferably, n is 2.

The present invention provides a compound of Formula I in which A, $L^1$, $R^1$, $R^2$, $R^3$, $R^4$, $R^5$, $R^6$, $L^2$, $G^1$, $L^3$, $G^2$, $L^4$, $R^7$, $R^8$, $R^{10}$, $R^{20}$, $R^{21}$, $R^{30}$, $R^{40}$, $R^{41}$, $R^{50}$, $R^{60}$, $R^{61}$, $R^{70}$, $R^{80}$, $R^{81}$, $R^{82}$, and n are independently chosen as set forth in any of the above-recited definitions. Thus, the present invention includes a compound of Formula I having A, $L^1$, $R^1$, $R^2$, $R^3$, $R^4$, $R^5$, $R^6$, $L^2$, $G^1$, $L^3$, $G^2$, $L^4$, $R^7$, $R^8$, $R^{10}$, $R^{20}$, $R^{21}$, $R^{30}$, $R^{40}$, $R^{41}$, $R^{50}$, $R^{60}$, $R^{61}$, $R^{70}$, $R^{80}$, $R^{81}$, $R^{82}$, and n defined by any combination of the broader and narrower definitions of these substituents as set forth above. For example, included within the scope of the present invention are compounds of Formula I in which $R^{10}$, $R^{20}$, $R^{21}$, $R^{30}$, $R^{40}$, $R^{41}$, $R^{50}$, $R^{51}$, $R^{60}$, $R^{61}$, $R^{70}$, $R^{80}$, $R^{81}$, and $R^{82}$ at each occurrence are independently chosen from H and $C_{1-6}$-alkyl. As another example, also included within the scope of the present invention are compounds of Formula I in which $R^{10}$, $R^{20}$, $R^{21}$, $R^{30}$, $R^{40}$, $R^{41}$, $R^{50}$, $R^{51}$, $R^{60}$, $R^{61}$, $R^{70}$, $R^{80}$, $R^{81}$, and $R^{82}$ at each occurrence are H. As another example, also included within the scope of the present invention are compounds of Formula I in which $G^1$ is a bond, or an optionally mono- or polysubstituted group chosen from aryl, heterocycloalkyl, and heteroaryl, and each $G^1$ substituent is independently chosen from halogen and —$OR^{40}$. As another example, also included within the scope of the present invention are compounds of Formula I in which $G^2$ is a bond, or an optionally mono- or polysubstituted group chosen from aryl, heterocycloalkyl, and heteroaryl, and each $G^2$ substituent is independently chosen from halogen and —$OR^{60}$. As another example, also included within the scope of the present invention are compounds of Formula I in which $R^7$ is an optionally mono- or polysubstituted group chosen from $C_{1-6}$-alkyl, aryl, $C_{3-10}$-cycloalkyl, heterocycloalkyl, and heteroaryl, and each $R^7$ substituent is independently chosen from halogen, —$OR^{80}$, —C(=O)$R^{80}$, —C(=O)O$R^{80}$, —C(=O)N$R^{80}R^{81}$, —N$R^{80}R^{81}$, $C_{1-6}$-alkyl, $C_{1-6}$-haloalkyl, aryl, heteroaryl, $C_{3-10}$-cycloalkyl, heterocycloalkyl, cyano, —S(=O)$_n R^{80}$, —S(=O)$_2$N$R^{80}R^{81}$, —OCF$_3$, and —SiR$^{80}R^{81}R^{82}$. As another example, also included within the scope of the present invention are compounds of Formula I in which at least one of $G^1$ and $R^7$ is an optionally mono- or polysubstituted group chosen from aryl, $C_{3-10}$-cycloalkyl, heterocycloalkyl, and heteroaryl, each $G^1$ substituent is independently chosen from halogen and —$OR^{40}$, and each $R^7$ substituent is independently chosen from halogen, —$OR^{80}$, —C(=O)$R^{80}$, —C(=O)O$R^{80}$, —C(=O)N$R^{80}R^{81}$, —N$R^{80}R^{81}$, $C_{1-6}$-alkyl, $C_{1-6}$-haloalkyl, aryl, heteroaryl, $C_{3-10}$-cycloalkyl, heterocycloalkyl, cyano, —S(=O)$_n R^{80}$, —S(=O)$_2$N$R^{80}R^{81}$, —OCF$_3$, and —SiR$^{80}R^{81}R^{82}$. As another example, also included within the scope of the present invention are compounds of Formula I in which A is N;

$L^1$ is —$C_{0-3}$-alkyl-C(=O)—$C_{0-3}$-alkyl-, —$C_{0-3}$-alkyl-S(=O), —$C_{0-3}$-alkyl-, —$C_{0-3}$-alkyl-C(=O)N$R^{10}$—$C_{0-3}$-alkyl-, —$C_{0-3}$-alkyl-S(=O)$_2$N$R^{10}$—$C_{0-3}$-alkyl-, —$C_{0-3}$-alkyl-C(=O)O—$C_{0-3}$-alkyl-, or —$C_{1-6}$-alkyl-;

$R^1$ is an optionally mono- or polysubstituted group chosen from aryl, $C_{3-10}$-cycloalkyl, heterocycloalkyl, and heteroaryl, wherein the substituents may be the same or different and are chosen from halogen, $-OR^{20}$, $-C(=O)R^{20}$, $-C(=O)OR^{20}$, $-C(=O)NR^{20}R^{21}$, $-NR^{20}R^{21}$, $C_{1-3}$-haloalkyl, $-CN$, and $-OCF_3$;

$R^2$ and $R^3$ are independently chosen from H, OH, and $C_{1-6}$-alkyl, or $R^2$ and $R^3$ together form a carbonyl group;

$R^4$ and $R^5$ are independently chosen from H and $C_{1-6}$-alkyl, or $R^4$ and $R^5$ together form a carbonyl group, or one of $R^4$ and $R^5$ forms a double bond with $R^6$;

$R^6$ is chosen from H and $C_{1-6}$-alkyl, or $R^6$ forms a double bond with $R^4$ or $R^5$;

X is $-L^2G^1L^3G^2L^4R^7$;

$L^2$ is a bond, $-C_{0-3}$-alkyl-C(=O)—$C_{0-3}$-alkyl-, $-S(=O)_n-C_{0-3}$-alkyl-, $-C(=O)NR^{30}-C_{0-3}$-alkyl-, $-S(=O)_2NR^{30}-C_{0-3}$-alkyl-, $-C(=O)O-C_{0-3}$-alkyl-, $-CH_2-OC(=O)NR^{30}-C_{0-3}$-alkyl-, $-C_{0-3}$-alkyl-OC(=O)NR^{30}-CH_2-, $-CH_2-NR^{30}-C_{0-3}$-alkyl-, $-CH_2-O-C_{0-3}$-alkyl-, $-C_{1-3}$-alkyl-, $-C_{2-3}$-alkenyl-, or $-C_{2-3}$-alkynyl-;

$G^1$ is a bond, or an optionally mono- or polysubstituted group chosen from aryl, $C_{3-10}$-cycloalkyl, heterocycloalkyl, and heteroaryl, wherein the substituents may be identical or different and are chosen from halogen, $-OR^{40}$, and $C_{1-3}$-haloalkyl;

$L^3$ is a bond, $-C(=O)-C_{0-3}$-alkyl-, $-S(=O)_2-C_{0-3}$-alkyl-, $-C_{0-3}$-alkyl-C(=O)NR^{50}—$C_{0-3}$-alkyl-, $-C_{0-3}$-alkyl-S(=O)_2NR^{50}-, $-C(=O)O-C_{0-3}$-alkyl-, $-OC(=O)NR^{50}-C_{0-3}$-alkyl-, $-NR^{50}-C_{0-3}$-alkyl-, $-O-C_{0-3}$-alkyl-, or $-C_{1-3}$-alkyl-;

$G^2$ is a bond, or an optionally mono- or polysubstituted group chosen from aryl, $C_{3-10}$-cycloalkyl, heterocycloalkyl, and heteroaryl, wherein the substituents may be identical or different and are chosen from halogen, $-OR^{60}$, and $C_{1-3}$-haloalkyl;

$L^4$ is a bond, $-C(=O)-C_{0-3}$-alkyl-, $-S(=O)_2-C_{0-3}$-alkyl-, $-C_{0-3}$-alkyl-C(=O)NR^{70}—, $-S(=O)_2NR^{10}—$, $-C(=O)O-C_{0-3}$-alkyl-, $-NR^{70}—$, or $-C_{1-3}$-alkyl-;

$R^7$ is an optionally mono- or polysubstituted group chosen from $C_{1-6}$-alkyl, aryl, $C_{3-10}$-cycloalkyl, heterocycloalkyl, and heteroaryl, wherein the substituents may be identical or different and are chosen from halogen, $-OR^{80}$, $-C(=O)R^{80}$, $-C(=O)OR^{80}$, $-C(=O)NR^{80}R^{81}$, $-NR^{80}R^{81}$, $C_{1-6}$-alkyl, $C_{1-6}$-haloalkyl, aryl, heteroaryl, $C_{3-10}$-cycloalkyl, heterocycloalkyl, pseudohalogen, $-S(=O)_nR^{80}$, $-S(=O)_2NR^{80}R^{81}$, $-OCF_3$, $-OC(=O)R^{80}$, and $-NR^{80}C(=O)R^{81}$;

$R^{10}$, $R^{20}$, $R^{21}$, $R^{30}$, $R^{40}$, $R^{50}$, $R^{60}$, $R^{70}$, and $R^{81}$ at each occurrence are independently chosen from H, $C_{1-6}$-alkyl, and $C_{1-6}$-haloalkyl;

$R^{80}$ at each occurrence is independently chosen from H, $C_{1-6}$-alkyl, and $C_{1-6}$-haloalkyl, aryl, and heteroaryl; and n is 0 or 2. As another example, also included within the scope of the present invention are compounds of Formula I in which A is N;

$L^1$ is $-C_{0-3}$-alkyl-C(=O)—$C_{0-3}$-alkyl-, $-C_{0-3}$-alkyl-S(=O)_2-C_{0-3}$-alkyl-, or $-C_{1-6}$-alkyl-;

$R^1$ is an optionally mono- or polysubstituted group chosen from aryl and heteroaryl, wherein the substituents may be identical or different and are chosen from halogen, $-C(=O)R^{20}$, $C_{1-3}$-haloalkyl, $-CN$, and $-OCF_3$;

$R^2$ and $R^3$ are independently chosen from H and $C_{1-6}$-alkyl, or $R^2$ and $R^3$ together form a carbonyl group;

$R^4$ and $R^5$ are H, or one of $R^4$ and $R^5$ forms a double bond with $R^6$;

$R^6$ is H, or $R^6$ forms a double bond with $R^4$ or $R^5$;

X is $-L^2G^1L^3G^2L^4R^7$;

$L^2$ is a bond, $-C_{0-3}$-alkyl-C(=O)—$C_{0-3}$-alkyl-, $-C_{0-3}$-alkyl-C(=O)NR^{30}—$C_{0-3}$-alkyl-, $-C_{0-3}$-alkyl-C(=O)O—$C_{0-3}$-alkyl-, or $-C_{2-3}$-alkynyl-;

$G^1$ is a bond, or an optionally mono- or polysubstituted group chosen from aryl, heterocycloalkyl, and heteroaryl, wherein the substituents may be identical or different and are chosen from halogen and $-OR^{40}$;

$L^3$ is a bond, $-C_{0-3}$-alkyl-C(=O)—$C_{0-3}$-alkyl-, $-C_{0-3}$-alkyl-C(=O)NR^{50}—$C_{0-3}$-alkyl-, $-C_{0-3}$-alkyl-S(=O)_2NR^{50}—$C_{0-3}$-alkyl-, $-C_{0-3}$-alkyl-C(=O)O—$C_{0-3}$-alkyl-, $-C_{0-3}$-alkyl-OC(=O)NR^{50}—$C_{0-3}$-alkyl-, $-C_{0-3}$-alkyl-NR^{50}—$C_{0-3}$-alkyl-, $-C_{0-3}$-alkyl-O—$C_{0-3}$-alkyl-, or $-C_{1-3}$-alkyl-;

$G^2$ is a bond, or an optionally mono- or polysubstituted group chosen from aryl, heterocycloalkyl, and heteroaryl, wherein the substituents may be identical or different and are chosen from halogen and $-OR^{60}$.

$L^4$ is a bond, $-C_{0-3}$-alkyl-C(=O)—$C_{0-3}$-alkyl-, $-C_{0-3}$-alkyl-C(=O)NR^{70}—$C_{0-3}$-alkyl-, $-C_{0-3}$-alkyl-C(=O)O—$C_{0-3}$-alkyl-, or $-C_{1-3}$-alkyl-;

$R^7$ is an optionally mono- or polysubstituted group chosen from $C_{1-6}$-alkyl, aryl, heterocycloalkyl, and heteroaryl, wherein the substituents may be identical or different and are chosen from halogen, $-OR^{80}$, $-C(=O)R^{80}$, $-C(=O)OR^{80}$, $-C(=O)NR^{80}R^{81}$, $-NR^{80}R^{81}$, $C_{1-6}$-alkyl, $C_{1-6}$-haloalkyl, aryl, heteroaryl, $C_{3-10}$-cycloalkyl, heterocycloalkyl, pseudohalogen, $-S(=O)_nR^{80}$, $-S(=O)_2NR^{80}R^{81}$, $-OCF_3$, and $-SiR^{80}R^{81}R^{82}$;

$R^{20}$, $R^{30}$, $R^{40}$, $R^{50}$, $R^{60}$, $R^{70}$, $R^{80}$, $R^{81}$, and $R^{82}$ at each occurrence are independently chosen from H, $C_{1-6}$-alkyl, and $C_{1-6}$-haloalkyl; and n is 2. As another example, also included within the scope of the present invention are compounds of Formula I in which A is CH;

$L^1$ is $-C_{0-3}$-alkyl-O—$C_{0-3}$-alkyl-, or $-C_{1-6}$-alkyl-;

$R^1$ is an optionally mono- or polysubstituted group chosen from aryl and heteroaryl, wherein the substituents may be identical or different and are chosen from halogen, $-C(=O)R^{20}$, $C_{1-3}$-haloalkyl, $-CN$, and $-OCF_3$;

$R^2$ and $R^3$ are independently chosen from H and $C_{1-6}$-alkyl, or $R^2$ and $R^3$ together form a carbonyl group;

$R^4$ and $R^5$ are H, or one of $R^4$ and $R^5$ forms a double bond with $R^6$;

$R^6$ is H, or $R^6$ forms a double bond with $R^4$ or $R^5$;

X is $-L^2G^1L^3G^2L^4R^7$;

$L^2$ is a bond, $-C_{0-3}$-alkyl-C(=O)—$C_{0-3}$-alkyl-, $-C_{0-3}$-alkyl-C(=O)NR^{30}—$C_{0-3}$-alkyl-, $-C_{0-3}$-alkyl-C(=O)O—$C_{0-3}$-alkyl-, or $-C_{2-3}$-alkynyl-;

$G^1$ is a bond, or an optionally mono- or polysubstituted group chosen from aryl, heterocycloalkyl, and heteroaryl, wherein the substituents may be identical or different and are chosen from halogen and $-OR^{40}$;

$L^3$ is a bond, $-C_{0-3}$-alkyl-C(=O)—$C_{0-3}$-alkyl-, $-C_{0-3}$-alkyl-C(=O)NR^{50}—$C_{0-3}$-alkyl-, $-C_{0-3}$-alkyl-S(=O)_2NR^{50}—$C_{0-3}$-alkyl-, $-C_{0-3}$-alkyl-C(=O)O—$C_{0-3}$-alkyl-, $-C_{0-3}$-alkyl-OC(=O)NR^{50}—$C_{0-3}$-alkyl-, $-C_{0-3}$-alkyl-NR^{50}—$C_{0-3}$-alkyl-, $-C_{0-3}$-alkyl-O—$C_{0-3}$-alkyl-, or $-C_{1-3}$-alkyl-;

$G^2$ is a bond, or an optionally mono- or polysubstituted group chosen from aryl, heterocycloalkyl, and heteroaryl, wherein the substituents may be identical or different and are chosen from halogen and $-OR^{60}$.

$L^4$ is a bond, $-C_{0-3}$-alkyl-C(=O)—$C_{0-3}$-alkyl-, $-C_{0-3}$-alkyl-C(=O)NR^{70}—$C_{0-3}$-alkyl-, $-C_{0-3}$-alkyl-C(=O)O—$C_{0-3}$-alkyl-, or $-C_{1-3}$-alkyl-;

$R^7$ is an optionally mono- or polysubstituted group chosen from $C_{1-6}$-alkyl, aryl, heterocycloalkyl, and heteroaryl, wherein the substituents may be identical or different and are chosen from halogen, —OR$^{80}$, —C(=O)R$^{10}$, —C(=O)OR$^{80}$, —C(=O)NR$^{80}$R$^{81}$, —NR$^{80}$R$^{81}$, C$_{1-6}$-alkyl C$_{1-6}$-haloalkyl, aryl, heteroaryl, C$_{3-10}$-cycloalkyl, heterocycloalkyl, pseudohalogen, —S(=O)$_n$R$^{80}$, —S(=O)$_2$NR$^{80}$R$^{81}$, —OCF$_3$, and —SiR$^{80}$R$^{81}$R$^{82}$;

R$^{20}$, R$^{30}$, R$^{40}$, R$^{50}$, R$^{60}$, R$^{70}$, R$^{80}$, R$^{81}$, and R$^{82}$ at each occurrence are independently chosen from H, C$_{1-6}$-alkyl, and C$_{1-6}$-haloalkyl; and n is 2.

In one embodiment, the present invention provides a compound of Formula I(c) chosen from:

1-(2-Chloro-3,6-difluorobenzyl)-7-pyridin-3-yl-3,4-dihydro-1H-pyrido[2,3-b]pyrazin-2-one;
4-[1-(2-Chloro-3,6-difluorobenzyl)-2-oxo-1,2,3,4-tetrahydropyrido[2,3-b]pyrazin-7-yl]benzoic acid ethyl ester;
4-[1-(2-Chloro-3,6-difluorobenzyl)-2-oxo-1,2,3,4-tetrahydropyrido[2,3-b]pyrazin-7-yl]benzoic acid;
1-(2-Chloro-3,6-difluorobenzyl)-7-[4-(4-methylpiperazine-1-carbonyl)phenyl]-3,4-dihydro-1H-pyrido[2,3-b]pyrazin-2-one;
4-(1-Benzyl-2-oxo-1,2,3,4-tetrahydropyrido[2,3-b]pyrazin-7-yl)benzoic acid ethyl ester;
4-(1-Benzyl-2-oxo-1,2,3,4-tetrahydropyrido[2,3-b]pyrazin-7-yl)benzoic acid;
1-Benzyl-7-pyridin-3-yl-3,4-dihydro-1H-pyrido[2,3-b]pyrazin-2-one;
4-(1-Benzyl-2-oxo-1,2,3,4-tetrahydropyrido[2,3-b]pyrazin-7-yl)-N-(2-pyrrolidin-1-yl-ethyl)benzamide;
S-1-Benzyl-7-[4-(2-[(pyrrolidin-1-yl)methyl]pyrrolidine-1-carbonyl)phenyl]-3,4-dihydro-1H-pyrido[2,3-b]pyrazin-2-one;
4-(1-Benzyl-2-oxo-1,2,3,4-tetrahydropyrido[2,3-b]pyrazin-7-yl)-N-(3-morpholin-4-yl-propyl)benzamide;
4-(1-Benzyl-2-oxo-1,2,3,4-tetrahydropyrido[2,3-b]pyrazin-7-yl)-N-(4-dimethylaminobutyl)benzamide;
4-(1-benzyl-2-oxo-1,2,3,4-tetrahydropyrido[2,3-b]pyrazin-7-yl)-N-(6-dimethylaminohexyl)benzamide;
1-Benzyl-7-[4-(4-(pyrrolidin-1-yl)piperidine-1-carbonyl)phenyl]-1H-pyrido[2,3-b]pyrazin-2-one;
S-1-Benzyl-7-[3-(2-[(pyrrolidin-1-yl)methyl]pyrrolidine-1-carbonyl)phenyl]-3,4-dihydro-1H-pyrido[2,3-b]pyrazin-2-one;
3-(1-Benzyl-2-oxo-1,2,3,4-tetrahydropyrido[2,3-b]pyrazin-7-yl)-N-(2-dimethylamino-ethyl)benzamide;
1-Benzyl-7-[3-(pyrrolidine-1-carbonyl)phenyl]-3,4-dihydro-1H-pyrido[2,3-b]pyrazin-2-one;
7-(4-Acetylphenyl)-1-benzyl-3,4-dihydro-1H-pyrido[2,3-b]pyrazin-2-one;
3-(1-Benzyl-2-oxo-1,2,3,4-tetrahydropyrido[2,3-b]pyrazin-7-yl)-N-ethyl-benzamide;
4-(1-Benzyl-2-oxo-1,2,3,4-tetrahydropyrido[2,3-b]pyrazin-7-yl)benzamide;
1-Benzyl-7-(4-methanesulfonyl-phenyl)-3,4-dihydro-1H-pyrido[2,3-b]pyrazin-2-one;
1-Benzyl-7-[4-(4-methylpiperazine-1-carbonyl)phenyl]-3,4-dihydro-1H-pyrido[2,3-b]pyrazin-2-one;
1-Benzyl-7-[4-(4-(pyrrolidin-1-yl)piperidine-1-carbonyl)phenyl]-3,4-dihydro-1H-pyrido[2,3-b]pyrazin-2-one;
4-(1-Benzyl-2-oxo-1,2,3,4-tetrahydropyrido[2,3-b]pyrazin-7-yl)-N-ethyl-benzamide;
5-(1-Benzyl-2-oxo-1,2,3,4-tetrahydropyrido[2,3-b]pyrazin-7-yl)pyridine-2-carbonitrile;
5-(1-Benzyl-2-oxo-1,2,3,4-tetrahydropyrido[2,3-b]pyrazin-7-yl)pyridine-2-carboxylic acid ethyl ester;
3-(1-Benzyl-2-oxo-1,2,3,4-tetrahydropyrido[2,3-b]pyrazin-7-yl)benzoic acid methyl ester;
3-(1-Benzyl-2-oxo-1,2,3,4-tetrahydropyrido[2,3-b]pyrazin-7-yl)benzoic acid;
1-Benzyl-7-pyridin-3-yl-1,2,3,4-tetrahydropyrido[2,3-b]pyrazine;
4-(1-Benzyl-1,2,3,4-tetrahydropyrido[2,3-b]pyrazin-7-yl)benzoic acid ethyl ester;
4-(1-Benzyl-1,2,3,4-tetrahydropyrido[2,3-b]pyrazin-7-yl)benzoic acid;
[4-(1-Benzyl-1,2,3,4-tetrahydropyrido[2,3-b]pyrazin-7-yl)phenyl]-(4-methylpiperazin-1-yl)methanone;
[4-(1-Benzyl-1,2,3,4-tetrahydropyrido[2,3-b]pyrazin-7-yl)phenyl]-((S)-2-pyrrolidinylmethylpyrrolidin-1-yl)methanone;
[4-(1-Benzyl-1,2,3,4-tetrahydropyrido[2,3-b]pyrazin-7-yl)phenyl]-(4-(pyrrolidin-1-yl)piperidin-1-yl)methanone;
Phenyl-(7-pyridin-3-yl-3,4-dihydro-2H-pyrido[2,3-b]pyrazin-1-yl)methanone;
4-(1-Benzoyl-1,2,3,4-tetrahydropyrido[2,3-b]pyrazin-7-yl)benzoic acid ethyl ester;
2-Pyrrolidin-1-yl-ethanesulfonic acid[4-(1-benzyl-2-oxo-1,2,3,4-tetrahydropyrido[2,3-b]pyrazin-7-yl)phenyl]amide;
2-Pyrrolidin-1-yl-ethanesulfonic acid[4-(1-benzoyl-1,2,3,4-tetrahydropyrido[2,3-b]pyrazin-7-yl)phenyl]amide;
2-(4-Methylpiperazin-1-yl)-ethanesulfonic acid[4-(1-benzoyl-1,2,3,4-tetrahydropyrido[2,3-b]pyrazin-7-yl)phenyl]amide;
2-Pyrrolidin-1-yl-ethanesulfonic acid{4-[1-(2,5-difluorobenzyl)-2-oxo-1,2,3,4-tetrahydropyrido[2,3-b]pyrazin-7-yl]phenyl}-amide;
2-[Ethyl-((S)-1-pyrrolidin-1-ylmethyl-propyl)-amino]-ethanesulfonic acid{4-[1-(2,5-difluorobenzyl)-2-oxo-1,2,3,4-tetrahydropyrido[2,3-b]pyrazin-7-yl]phenyl}-amide;
2-Morpholin-4-yl-ethanesulfonic acid{4-[1-(2,5-difluorobenzyl)-2-oxo-1,2,3,4-tetrahydropyrido[2,3-b]pyrazin-7-yl]phenyl}-amide;
2-Pyrrolidin-1-yl-ethanesulfonic acid{4-[1-(2,5-difluorobenzyl)-1,2,3,4-tetrahydropyrido[2,3-b]pyrazin-7-yl]phenyl}-amide;
4-(1-Benzoyl-1,2,3,4-tetrahydropyrido[2,3-b]pyrazin-7-yl)-N-(2-dimethylamino-ethyl)benzamide;
4-(1-Benzoyl-1,2,3,4-tetrahydropyrido[2,3-b]pyrazin-7-yl)-N-(3-dimethylamino-propyl)benzamide;
{7-[4-(4-Methylpiperazine-1-carbonyl)phenyl]-3,4-dihydro-2H-pyrido[2,3-b]pyrazin-1-yl}phenylmethanone;
4-[1-(2,5-Difluorobenzyl)-2-oxo-1,2,3,4-tetrahydropyrido[2,3-b]pyrazin-7-yl]benzoic acid ethyl ester;
4-[1-(2,5-Difluorobenzyl)-2-oxo-1,2,3,4-tetrahydropyrido[2,3-b]pyrazin-7-yl]benzoic acid;
1-(2,5-Difluorobenzyl)-7-[4-((S)-2-[(pyrrolidin-1-yl)methyl]pyrrolidine-1-carbonyl)phenyl]-3,4-dihydro-1H-pyrido[2,3-b]pyrazin-2-one;
4-[1-(2,5-Difluorobenzyl)-2-oxo-1,2,3,4-tetrahydropyrido[2,3-b]pyrazin-7-yl]-N-(2-pyrrolidin-1-yl-ethyl)benzamide;
1-(2,5-Difluorobenzyl)-7-[4-(4-methylpiperazine-1-carbonyl)phenyl]-3,4-dihydro-1H-pyrido[2,3-b]pyrazin-2-one;
1-(2,5-Difluorobenzyl)-7-[4-(4-(pyrrolidin-1-yl)piperidine-1-carbonyl)phenyl]-3,4-dihydro-1H-pyrido[2,3-b]pyrazin-2-one;
(S)-2-[(pyrrolidin-1-yl)methyl]pyrrolidine-1-carboxylic acid{4-[1-(2,5-difluorobenzyl)-2-oxo-1,2,3,4-tetrahydropyrido[2,3-b]pyrazin-7-yl]phenyl}-amide;
4-[1-(2,5-Difluorobenzyl)-1,2,3,4-tetrahydropyrido[2,3-b]pyrazin-7-yl]benzoic acid ethyl ester;
4-[1-(2,5-Difluorobenzyl)-1,2,3,4-tetrahydropyrido[2,3-b]pyrazin-7-yl]benzoic acid;

{4-[1-(2,5-Difluorobenzyl)-1,2,3,4-tetrahydropyrido[2,3-b]pyrazin-7-yl]phenyl}-((S)-2-((pyrrolidin-1-yl)methyl)pyrrolidin-1-yl)methanone;
{4-[1-(2,5-Difluorobenzyl)-1,2,3,4-tetrahydropyrido[2,3-b]pyrazin-7-yl]phenyl}-(4-(pyrrolidin-1-yl)piperidin-1-yl)methanone;
{4-[1-(2,5-Difluorobenzyl)-1,2,3,4-tetrahydropyrido[2,3-b]pyrazin-7-yl]phenyl}-(4-methylpiperazin-1-yl)methanone;
{4-[1-(2,5-Difluorobenzyl)-1,2,3,4-tetrahydropyrido[2,3-b]pyrazin-7-yl]phenyl}-morpholin-4-yl-methanone;
1-(2,5-Difluorobenzyl)-7-[6-(4-methylpiperazin-1-yl)pyridin-3-yl]-1,2,3,4-tetrahydropyrido[2,3-b]pyrazine;
1-(2,5-Difluorobenzyl)-7-(6-morpholin-4-yl-pyridin-3-yl)-1,2,3,4-tetrahydropyrido[2,3-b]pyrazine;
5-[1-(2,5-Difluorobenzyl)-1,2,3,4-tetrahydropyrido[2,3-b]pyrazin-7-yl]-pyridine-2-carbonitrile;
5-[1-(2,5-Difluorobenzyl)-1,2,3,4-tetrahydropyrido[2,3-b]pyrazin-7-yl]-pyridine-2-carboxylic acid;
5-[1-(2,5-Difluorobenzyl)-1,2,3,4-tetrahydropyrido[2,3-b]pyrazin-7-yl]-nicotinic acid ethyl ester;
5-[1-(2,5-Difluorobenzyl)-1,2,3,4-tetrahydropyrido[2,3-b]pyrazin-7-yl]-nicotinic acid;
1-(2,5-Difluorobenzyl)-1,2,3,4-tetrahydropyrido[2,3-b]pyrazine-7-carboxylic acid ethyl ester;
{5-[1-(2,5-Difluorobenzyl)-1,2,3,4-tetrahydropyrido[2,3-b]pyrazin-7-yl]-pyridin-2-yl}morpholin-4-yl-methanone;
[1-(2,5-Difluorobenzyl)-1,2,3,4-tetrahydropyrido[2,3-b]pyrazin-7-yl]-(4-methylpiperazin-1-yl)methanone;
1-(2,5-Difluorobenzyl)-1,2,3,4-tetrahydropyrido[2,3-b]pyrazine-7-carboxylic acid[2(4-methylpiperazin-1-yl)ethyl]amide;
7-[4-((S)-2-[(pyrrolidin-1-yl)methyl]pyrrolidine-1-carbonyl)phenyl]-1-(2,4,5-trifluorobenzyl)-3,4-dihydro-1H-pyrido[2,3-b]pyrazin-2-one;
((S)-2-((pyrrolidin-1-yl)methyl)pyrrolidin-1-yl)-{4-[1-(2,4,5-trifluorobenzyl)-1,2,3,4-tetrahydropyrido[2,3-b]pyrazin-7-yl]phenyl}-methanone;
7-[4-(4-Methylpiperazine-1-carbonyl)phenyl]-1-(2,4,5-trifluorobenzyl)-3,4-dihydro-1H-pyrido[2,3-b]pyrazin-2-one;
(4-Methylpiperazin-1-yl)-{4-[1-(2,4,5-trifluorobenzyl)-1,2,3,4-tetrahydropyrido[2,3-b]pyrazin-7-yl]phenyl}-methanone;
(2,5-Difluorophenyl)-{7-[4-(4-methylpiperazine-1-carbonyl)phenyl]-3,4-dihydro-2H-pyrido[2,3-b]pyrazin-1-yl}-methanone;
(2,5-Difluorophenyl)-{7-[4-((S)-2-[(pyrrolidin-1-yl)methyl]pyrrolidine-1-carbonyl)phenyl]-3,4-dihydro-2H-pyrido[2,3-b]pyrazin-1-yl}-methanone;
1-(2,5-Difluorobenzyl)-3,3-dimethyl-7-[4-((S)-2-[(pyrrolidin-1-yl)methyl]pyrrolidine-1-carbonyl)phenyl]-3,4-dihydro-1H-pyrido[2,3-b]pyrazin-2-one;
1-(2,5-Difluorobenzyl)-3,3-dimethyl-7-[4-(4-methylpiperazine-1-carbonyl)phenyl]-3,4-dihydro-1H-pyrido[2,3-b]pyrazin-2-one;
{4-[1-(2,5-Difluorobenzyl)-3,3-dimethyl-1,2,3,4-tetrahydropyrido[2,3-b]pyrazin-7-yl]phenyl}-((S)-2-((pyrrolidin-1-yl)methyl)pyrrolidin-1-yl)methanone;
{4-[1-(2,5-Difluorobenzyl)-3,3-dimethyl-1,2,3,4-tetrahydropyrido[2,3-b]pyrazin-7-yl]phenyl}-(4-methylpiperazin-1-yl)methanone;
{4-[1-(2-Chloro-3,6-difluorobenzyl)-1,2,3,4-tetrahydropyrido[2,3-b]pyrazin-7-yl]phenyl}-(4-(pyrrolidin-1-yl)piperidin-1-yl)methanone;
{4-[1-(2-Chloro-3,6-difluorobenzyl)-1,2,3,4-tetrahydropyrido[2,3-b]pyrazin-7-yl]phenyl}-((S)-2-((pyrrolidin-1-yl)methyl)pyrrolidin-1-yl)methanone;
1-(2-Chloro-3,6-difluorobenzyl)-7-(3-chloro-2-morpholin-4-yl-pyridin-4-yl)-1,2,3,4-tetrahydropyrido[2,3-b]pyrazine;
1-(2-Chloro-3,6-difluorobenzyl)-7-(3-fluoro-2-morpholin-4-yl-pyridin-4-yl)-1,2,3,4-tetrahydropyrido[2,3-b]pyrazine;
1-(2-Chloro-3,6-difluorobenzyl)-7-(3,5-dimethyl-isoxazol-4-yl)-1,2,3,4-tetrahydropyrido[2,3-b]pyrazine;
{4-[1-(2-Chloro-3,6-difluorobenzyl)-1,2,3,4-tetrahydropyrido[2,3-b]pyrazin-7-yl]phenyl}-(4-methylpiperazin-1-yl)methanone;
1-(2-Chloro-3,6-difluorobenzyl)-7-(6-morpholin-4-yl-pyridin-3-yl)-1,2,3,4-tetrahydropyrido[2,3-b]pyrazine;
1-(2-Chloro-3,6-difluorobenzyl)-7-[2-(4-methylpiperazin-1-yl)-pyrimidin-5-yl]-1,2,3,4-tetrahydropyrido[2,3-b]pyrazine;
1-(2-Chloro-3,6-difluorobenzyl)-7-(2-morpholin-4-yl-pyrimidin-5-yl)-1,2,3,4-tetrahydropyrido[2,3-b]pyrazine;
1-(2-Chloro-3,6-difluorobenzyl)-7-(4-morpholin-4-yl-phenyl)-1,2,3,4-tetrahydropyrido[2,3-b]pyrazine;
7-[6-(4-Methylpiperazin-1-yl)pyridin-3-yl]-1,2,3,4-tetrahydropyrido[2,3-b]pyrazine;
2-Phenyl-1-{7-[4-(4-(pyrrolidin-1-yl)piperidine-1-carbonyl)phenyl]-3,4-dihydro-2H-pyrido[2,3-b]pyrazin-1-yl}-ethanone;
2-(2,5-Difluorophenyl)-1-{7-[2-(4-methylpiperazin-1-yl)pyridin-4-yl]-3,4-dihydro-2H-pyrido[2,3-b]pyrazin-1-yl}ethanone;
2-(2,5-Difluorophenyl)-1-{7-[4-(4-(pyrrolidin-1-yl)piperidine-1-carbonyl)phenyl]-3,4-dihydro-2H-pyrido[2,3-b]pyrazin-1-yl}ethanone;
{4-[1-(5-Chloro-2-trifluoromethylbenzyl)-1,2,3,4-tetrahydropyrido[2,3-b]pyrazin-7-yl]phenyl}-(4-(pyrrolidin-1-yl)piperidin-1-yl)methanone;
1-(5-Chloro-2-trifluoromethylbenzyl)-7-[6-(4-methylpiperazin-1-yl)pyridin-3-yl]-1,2,3,4-tetrahydropyrido[2,3-b]pyrazine;
1-(2-Chloro-5-trifluoromethylbenzyl)-7-[6-(4-methylpiperazin-1-yl)pyridin-3-yl]-1,2,3,4-tetrahydropyrido[2,3-b]pyrazine;
1-(2,5-Difluorobenzenesulfonyl)-7-[6-(4-methylpiperazin-1-yl)pyridin-3-yl]-1,2,3,4-tetrahydropyrido[2,3-b]pyrazine;
1-Benzenesulfonyl-7-[6-(4-methylpiperazin-1-yl)pyridin-3-yl]-1,2,3,4-tetrahydropyrido[2,3-b]pyrazine;
1-(2-Chlorobenzenesulfonyl)-7-[6-(4-methylpiperazin-1-yl)pyridin-3-yl]-1,2,3,4-tetrahydropyrido[2,3-b]pyrazine;
1-(2,5-Dichlorobenzyl)-7-(2-methoxypyrimidin-5-yl)-1,2,3,4-tetrahydropyrido[2,3-b]pyrazine;
4-[1-(2,5-Dichlorobenzyl)-1,2,3,4-tetrahydropyrido[2,3-b]pyrazin-7-yl]-3,6-dihydro-2H-pyridine-1-carboxylic acid tert-butyl ester;
1-(2,5-Dichlorobenzyl)-7-(1,2,3,6-tetrahydropyridin-4-yl)-1,2,3,4-tetrahydropyrido[2,3-b]pyrazine;
{4-[1-(2,5-Dichlorobenzyl)-1,2,3,4-tetrahydropyrido[2,3-b]pyrazin-7-yl]phenyl}-(4-methylpiperazin-1-yl)methanone;
1-(2,6-Dichlorobenzyl)-7-pyridin-3-yl-3,4-dihydro-1H-pyrido[2,3-b]pyrazin-2-one;
1-(2,6-Dichlorobenzyl)-7-pyridin-3-yl-1,2,3,4-tetrahydropyrido[2,3-b]pyrazine;
4-[1-(2,6-Dichlorobenzyl)-2-oxo-1,2,3,4-tetrahydropyrido[2,3-b]pyrazin-7-yl]benzoic acid ethyl ester;

4-[1-(2,6-Dichlorobenzyl)-2-oxo-1,2,3,4-tetrahydropyrido[2,3-b]pyrazin-7-yl]benzoic acid;

S-1-(2,6-Dichlorobenzyl)-7-[4-((2-pyrrolidin-1-yl)methylpyrrolidine-1-carbonyl)phenyl]-3,4-dihydro-1H-pyrido[2,3-b]pyrazin-2-one;

4-[1-(2,6-Dichlorobenzyl)-2-oxo-1,2,3,4-tetrahydropyrido[2,3-b]pyrazin-7-yl]-N-(2-pyrrolidin-1-yl-ethyl)benzamide;

4-[1-(2,6-Dichlorobenzyl)-2-oxo-1,2,3,4-tetrahydropyrido[2,3-b]pyrazin-7-yl]-N-(6-dimethylaminohexyl)benzamide;

4-[1-(2,6-Dichlorobenzyl)-2-oxo-1,2,3,4-tetrahydropyrido[2,3-b]pyrazin-7-yl]-N-(4-dimethylaminobutyl)benzamide;

7-[4-(4-Methylpiperazine-1-carbonyl)phenyl]-1-[1-(2,4,5-trifluorophenyl)ethyl]-3,4-dihydro-1H-pyrido[2,3-b]pyrazin-2-one;

S-{2-[(pyrrolidin-1-yl)methyl]pyrrolidin-1-yl}-(4-{1-[1-(2,4,5-trifluorophenyl)ethyl]-1,2,3,4-tetrahydropyrido[2,3-b]pyrazin-7-yl}phenyl)methanone;

(4-Methylpiperazin-1-yl)-(4-{1-[1-(2,4,5-trifluorophenyl)ethyl]-1,2,3,4-tetrahydropyrido[2,3-b]pyrazin-7-yl}phenyl)methanone;

S-(4-{1-[1-(2,5-Difluorophenyl)ethyl]-1,2,3,4-tetrahydropyrido[2,3-b]pyrazin-7-yl}phenyl)-{2-[(pyrrolidin-1-yl)methyl]pyrrolidin-1-yl}methanone;

1-[1-(2,5-Difluorophenyl)ethyl]-7-[4-(4-methylpiperazine-1-carbonyl)phenyl]-3,4-dihydro-1H-pyrido[2,3-b]pyrazin-2-one;

S-(4-{1-[1-(2,5-Difluorophenyl)ethyl]-1,2,3,4-tetrahydropyrido[2,3-b]pyrazin-7-yl}phenyl)-{2-[(pyrrolidin-1-yl)methyl]pyrrolidin-1-yl}methanone;

1-(2,5-Dichlorobenzyl)-7-[4-(4-(pyrrolidin-1-yl)piperidine-1-carbonyl)phenyl]-3,4-dihydro-1H-pyrido[2,3-b]pyrazin-2-one;

S-1-(2,5-Dichlorobenzyl)-7-[4-(2-[(pyrrolidin-1-yl)methyl]pyrrolidine-1-carbonyl)phenyl]-3,4-dihydro-1H-pyrido[2,3-b]pyrazin-2-one;

S-{4-[1-(2,5-Dichlorobenzyl)-1,2,3,4-tetrahydropyrido[2,3-b]pyrazin-7-yl]phenyl}-{2-[(pyrrolidin-1-yl)methyl]pyrrolidin-1-yl}methanone;

{4-[1-(2,5-Dichlorobenzyl)-1,2,3,4-tetrahydropyrido[2,3-b]pyrazin-7-yl]phenyl}-(4-(pyrrolidin-1-yl)piperidin-1-yl)methanone;

1-(2,6-Dichlorobenzyl)-7-[4-(4-(pyrrolidin-1-yl)piperidine-1-carbonyl)phenyl]-3,4-dihydro-1H-pyrido[2,3-b]pyrazin-2-one;

{4-[1-(2,6-Dichlorobenzyl)-1,2,3,4-tetrahydropyrido[2,3-b]pyrazin-7-yl]phenyl}-(4-(pyrrolidin-1-yl)piperidin-1-yl)methanone;

{4-[1-(2,6-Dichlorobenzyl)-1,2,3,4-tetrahydropyrido[2,3-b]pyrazin-7-yl]phenyl}-{2-[(pyrrolidin-1-yl)methyl]pyrrolidin-1-yl}methanone;

7-(6-Chloropyridin-3-yl)-1-(2,5-dichlorobenzyl)-1,2,3,4-tetrahydropyrido[2,3-b]pyrazine;

1-(2,5-Dichlorobenzyl)-7-(6-pyrrolidin-1-yl-pyridin-3-yl)-1,2,3,4-tetrahydropyrido[2,3-b]pyrazine;

7-(2-Chloropyridin-4-yl)-1-(2,6-dichlorobenzyl)-1,2,3,4-tetrahydropyrido[2,3-b]pyrazine;

{3-[1-(2,5-Dichlorobenzyl)-1,2,3,4-tetrahydropyrido[2,3-b]pyrazin-7-yl]prop-2-ynyl}carbamic acid tert-butyl ester;

3-[1-(2,5-Dichlorobenzyl)-1,2,3,4-tetrahydropyrido[2,3-b]pyrazin-7-yl]prop-2-ynylamine;

{3-[1-(2,6-Dichlorobenzyl)-1,2,3,4-tetrahydropyrido[2,3-b]pyrazin-7-yl]prop-2-ynyl}carbamic acid tert-butyl ester;

3-[1-(2,6-Dichlorobenzyl)-1,2,3,4-tetrahydropyrido[2,3-b]pyrazin-7-yl]prop-2-ynylamine;

N-{3-[1-(2,6-Dichlorobenzyl)-1,2,3,4-tetrahydropyrido[2,3-b]pyrazin-7-yl]prop-2-ynyl}-2-dimethylamino-acetamide;

{3-[1-(2,5-Dichlorobenzyl)-1,2,3,4-tetrahydropyrido[2,3-b]pyrazin-7-yl]prop-2-ynyl}-dimethylamine;

1-(2,5-Dichlorobenzyl)-7-[3-(1,1-dioxo-1$\lambda^6$-thiomorpholin-4-yl)prop-1-ynyl]-1,2,3,4-tetrahydropyrido[2,3-b]pyrazine;

1-[1-(2-Chloro-3,6-difluorophenyl)ethyl]-7-[6-(4-methylpiperazin-1-yl)pyridin-3-yl]-1,2,3,4-tetrahydropyrido[2,3-b]pyrazine;

1-(2,5-Dichlorobenzyl)-7-[6-(4-methylpiperazin-1-yl)pyridin-3-yl]-1,2,3,4-tetrahydropyrido[2,3-b]pyrazine;

1-[3-Fluoro-2-(trifluoromethyl)benzyl]-7-[6-(4-methylpiperazin-1-yl)pyridin-3-yl]-1,2,3,4-tetrahydropyrido[2,3-b]pyrazine;

1-(2-Chloro-3,6-difluorobenzyl)-7-(2-chloropyridin-4-yl)-1,2,3,4-tetrahydropyrido[2,3-b]pyrazine;

1-(2-Chloro-3,6-difluorobenzyl)-7-(2-pyrrolidin-1-yl-pyridin-4-yl)-1,2,3,4-tetrahydropyrido[2,3-b]pyrazine;

5-[1-(2-Chloro-3,6-difluorobenzyl)-1,2,3,4-tetrahydropyrido[2,3-b]pyrazin-7-yl]-pyridin-2-ylamine;

1-(2-Chloro-3,6-difluorobenzyl)-7-[6-(4-methylpiperazin-1-yl)pyridin-3-yl]-1,2,3,4-tetrahydropyrido[2,3-b]pyrazine;

1-(2-Chloro-3,6-difluorobenzyl)-7-(2-morpholin-4-yl-pyridin-4-yl)-1,2,3,4-tetrahydropyrido[2,3-b]pyrazine;

1-(2,5-Dichlorobenzyl)-4-methyl-7-[6-(4-methylpiperazin-1-yl)pyridin-3-yl]-1,2,3,4-tetrahydropyrido[2,3-b]pyrazine;

1-(2-Chloro-3,6-difluorobenzyl)-7-(3-morpholin-4-yl-phenyl)-1,2,3,4-tetrahydropyrido[2,3-b]pyrazine;

1-(2-Chloro-3,6-difluorobenzyl)-7-[2-(4-methylpiperazin-1-yl)pyridin-4-yl]-1,2,3,4-tetrahydropyrido[2,3-b]pyrazine;

1-(2-Chloro-3,6-difluorobenzyl)-7-[1-(3-methylbutyl)-1H-pyrazol-4-yl]-1,2,3,4-tetrahydropyrido[2,3-b]pyrazine;

1-(2-Chloro-3,6-difluorobenzyl)-7-(1H-pyrazol-4-yl)-1,2,3,4-tetrahydropyrido[2,3-b]pyrazine;

4-{1-[5-Chloro-2-(trifluoromethyl)benzyl]-1,2,3,4-tetrahydropyrido[2,3-b]pyrazin-7-yl}benzoic acid ethyl ester;

3-{1-[5-Chloro-2-(trifluoromethyl)benzyl]-1,2,3,4-tetrahydropyrido[2,3-b]pyrazin-7-yl}benzoic acid ethyl ester;

4-{1-[5-Chloro-2-(trifluoromethyl)benzyl]-1,2,3,4-tetrahydropyrido[2,3-b]pyrazin-7-yl}benzoic acid;

3-{1-[5-Chloro-2-(trifluoromethyl)benzyl]-1,2,3,4-tetrahydropyrido[2,3-b]pyrazin-7-yl}benzoic acid;

(2-{4-[1-(2-Chloro-3,6-difluorobenzyl)-1,2,3,4-tetrahydropyrido[2,3-b]pyrazin-7-yl]-pyrazol-1-yl}ethyl)dimethylamine;

1-[5-Chloro-2-(trifluoromethyl)benzyl]-7-(2-piperazin-1-yl-pyridin-4-yl)-1,2,3,4-tetrahydro-pyrido[2,3-b]pyrazine;

1-[4-(4-{1-[5-Chloro-2-(trifluoromethyl)benzyl]-1,2,3,4-tetrahydro-pyrido[2,3-b]pyrazin-7-yl}pyridin-2-yl)piperazin-1-yl]ethanone;

1-[5-Chloro-2-(trifluoromethyl)benzyl]-7-(1H-pyrazol-4-yl)-1,2,3,4-tetrahydro-pyrido[2,3-b]pyrazine;

1-[5-Chloro-2-(trifluoromethyl)benzyl]-7-(1-triisopropylsilanyl-1H-pyrrol-3-yl)-1,2,3,4-tetrahydropyrido[2,3-b]pyrazine;

1-[5-Chloro-2-(trifluoromethyl)benzyl]-7-(1H-pyrrol-3-yl)-1,2,3,4-tetrahydro-pyrido[2,3-b]pyrazine;

1-[5-Chloro-2-(trifluoromethyl)benzyl]-7-(1-methyl-1H-pyrazol-4-yl)-1,2,3,4-tetrahydropyrido[2,3-b]pyrazine;

{1-[(5-Chloro-2-trifluoromethyl)benzyl]-1,2,3,4-tetrahydro-pyrido[2,3-b]pyrazin-7-yl}piperidin-1-yl-methanone;

{1-[(5-Chloro-2-trifluoromethyl)benzyl]-1,2,3,4-tetrahydropyrido[2,3-b]pyrazin-7-yl}-(4-methoxy-piperidin-1-yl)methanone;
[1-(2,5-Dichlorobenzyl)-1,2,3,4-tetrahydropyrido[2,3-b]pyrazin-7-yl]-(4-phenylpiperazin-1-yl)-methanone;
[1-(2,5-Dichlorobenzyl)-1,2,3,4-tetrahydropyrido[2,3-b]pyrazin-7-yl]-(4-pyrimidin-2-yl-piperazin-1-yl)-methanone;
[4-(4-Chlorophenyl)-4-hydroxypiperidin-1-yl]-[1-(2,5-dichlorobenzyl)-1,2,3,4-tetrahydropyrido[2,3-b]pyrazin-7-yl]methanone;
1-{1-[1-(2,5-Dichlorobenzyl)-1,2,3,4-tetrahydropyrido[2,3-b]pyrazine-7-carbonyl]piperidin-4-yl)}-1,3-dihydrobenzoimidazol-2-one;
[1-(2,5-Dichlorobenzyl)-1,2,3,4-tetrahydropyrido[2,3-b]pyrazin-7-yl]-[4-(2-methoxyphenyl)piperazin-1-yl]methanone;
[1-(2,5-Dichlorobenzyl)-1,2,3,4-tetrahydropyrido[2,3-b]pyrazin-7-yl]-{4-[3-(trifluoromethyl)phenyl]piperazin-1-yl}methanone;
[1-(2,5-Dichlorobenzyl)-1,2,3,4-tetrahydropyrido[2,3-b]pyrazin-7-yl]-(4-phenylpiperidin-1-yl)methanone;
[1-(2,5-Dichlorobenzyl)-1,2,3,4-tetrahydropyrido[2,3-b]pyrazin-7-yl]-[4-(3,4-dichlorophenyl)-piperazin-1-yl]methanone;
(4-Benzhydrylpiperazin-1-yl)-[1-(2,5-dichlorobenzyl)-1,2,3,4-tetrahydropyrido[2,3-b]pyrazin-7-yl]methanone;
(4-Benzylpiperidin-1-yl)-[1-(2,5-dichlorobenzyl)-1,2,3,4-tetrahydropyrido[2,3-b]pyrazin-7-yl]methanone;
8-[1-(2,5-Dichlorobenzyl)-1,2,3,4-tetrahydropyrido[2,3-b]pyrazine-7-carbonyl]-1-phenyl-1,3,8-triaza-spiro[4.5]decan-4-one;
[1-(2,5-Dichlorobenzyl)-1,2,3,4-tetrahydropyrido[2,3-b]pyrazin-7-yl]-(4-thieno[3,2-d]pyrimidin-4-yl-piperazin-1-yl)methanone;
[1-(2,5-Dichlorobenzyl)-1,2,3,4-tetrahydropyrido[2,3-b]pyrazin-7-yl]-[4-(4-methoxybenzyl)piperazin-1-yl]methanone;
(4-Benzoylpiperazin-1-yl)-[1-(2,5-dichlorobenzyl)-1,2,3,4-tetrahydropyrido[2,3-b]pyrazin-7-yl]methanone;
[1-(2,5-Dichlorobenzyl)-1,2,3,4-tetrahydropyrido[2,3-b]pyrazin-7-yl]-(4-furo[3,2-c]pyridin-4-yl-piperazin-1-yl)methanone;
[1-(2,5-Dichlorobenzyl)-1,2,3,4-tetrahydropyrido[2,3-b]pyrazin-7-yl]-[4-(6-fluorobenzo[d]isoxazol-3-yl)piperidin-1-yl]methanone;
[4-(3-Chlorophenyl)piperazin-1-yl]-[1-(2,5-dichlorobenzyl)-1,2,3,4-tetrahydropyrido[2,3-b]pyrazin-7-yl]methanone;
1-(2,5-Dichlorobenzyl)-1,2,3,4-tetrahydropyrido[2,3-b]pyrazine-7-carboxylic acid (2-pyridin-2-yl-ethyl)amide;
4-{[1-(2,5-Dichlorobenzyl)-1,2,3,4-tetrahydropyrido[2,3-b]pyrazine-7-carbonyl]amino}piperidine-1-carboxylic acid ethyl ester;
1-(2,5-Dichlorobenzyl)-1,2,3,4-tetrahydropyrido[2,3-b]pyrazine-7-carboxylic acid (1-benzyl-piperidin-4-yl)amide;
1-(2,5-Dichlorobenzyl)-1,2,3,4-tetrahydropyrido[2,3-b]pyrazine-7-carboxylic acid (2,2-diphenylethyl)amide;
1-{4-[1-(2,5-Dichlorobenzyl)-1,2,3,4-tetrahydropyrido[2,3-b]pyrazine-7-carbonyl]piperazin-1-yl}ethanone;
1-(2,5-Dichlorobenzyl)-1,2,3,4-tetrahydropyrido[2,3-b]pyrazine-7-carboxylic acid 3-chlorobenzylamide;
[1-(2,5-Dichlorobenzyl)-1,2,3,4-tetrahydropyrido[2,3-b]pyrazin-7-yl]-[4-(2-pyridin-2-yl-ethyl)piperazin-1-yl]methanone;
1-(2,5-Dichlorobenzyl)-1,2,3,4-tetrahydropyrido[2,3-b]pyrazine-7-carboxylic acid 4-(trifluoromethoxy)benzylamide;
[1-(2,5-Dichlorobenzyl)-1,2,3,4-tetrahydropyrido[2,3-b]pyrazin-7-yl]-(4-morpholin-4-yl-piperidin-1-yl)methanone;
1-(2,5-Dichlorobenzyl)-1,2,3,4-tetrahydropyrido[2,3-b]pyrazine-7-carboxylic acid (2-thiophen-2-yl-ethyl)amide;
1-(2,5-Dichlorobenzyl)-1,2,3,4-tetrahydropyrido[2,3-b]pyrazine-7-carboxylic acid benzhydrylamide;
1-(2,5-Dichlorobenzyl)-1,2,3,4-tetrahydropyrido[2,3-b]pyrazine-7-carboxylic acid (pyridin-4-ylmethyl)amide;
1-(2,5-Dichlorobenzyl)-1,2,3,4-tetrahydropyrido[2,3-b]pyrazine-7-carboxylic acid (pyridin-3-ylmethyl)amide;
2-{4-[1-(2,5-Dichlorobenzyl)-1,2,3,4-tetrahydropyrido[2,3-b]pyrazine-7-carbonyl]piperazin-1-yl}-N-isopropylacetamide;
[1-(2,5-Dichlorobenzyl)-1,2,3,4-tetrahydropyrido[2,3-b]pyrazin-7-yl]-[4-(2-methylquinolin-4-yl)piperazin-1-yl]methanone;
[1-(2,5-Dichlorobenzyl)-1,2,3,4-tetrahydropyrido[2,3-b]pyrazin-7-yl]-((S)-2-pyrrolidin-1-ylmethyl-pyrrolidin-1-yl)methanone;
1-(2,5-Dichlorobenzyl)-1,2,3,4-tetrahydropyrido[2,3-b]pyrazine-7-carboxylic acid 3,5-bis-(trifluoromethyl)benzylamide;
1-(2,5-Dichlorobenzyl)-1,2,3,4-tetrahydropyrido[2,3-b]pyrazine-7-carboxylic acid[2-(4-sulfamoylphenyl)ethyl]amide;
[1-(2,5-Dichlorobenzyl)-1,2,3,4-tetrahydropyrido[2,3-b]pyrazin-7-yl]-(2,3,5,6-tetrahydro-[1,2']bipyrazinyl-4-yl)methanone;
1-(2,5-Dichlorobenzyl)-1,2,3,4-tetrahydropyrido[2,3-b]pyrazine-7-carboxylic acid (2-phenylthiazol-4-yl-methyl)amide;
[1-(2,5-Dichlorobenzyl)-1,2,3,4-tetrahydropyrido[2,3-b]pyrazin-7-yl]morpholin-4-yl-methanone;
1-(2,5-Dichlorobenzyl)-1,2,3,4-tetrahydropyrido[2,3-b]pyrazine-7-carboxylic acid (naphthalen-1-yl-methyl)amide;
1-(2,5-Dichlorobenzyl)-1,2,3,4-tetrahydropyrido[2,3-b]pyrazine-7-carboxylic acid indan-1-ylamide;
1-(2,5-Dichlorobenzyl)-1,2,3,4-tetrahydropyrido[2,3-b]pyrazine-7-carboxylic acid benzylamide;
[1-(2,5-Dichlorobenzyl)-1,2,3,4-tetrahydropyrido[2,3-b]pyrazin-7-yl]-[4-(4-methoxyphenyl)piperazin-1-yl]methanone;
1-(2,5-Dichlorobenzyl)-1,2,3,4-tetrahydropyrido[2,3-b]pyrazine-7-carboxylic acid cyclohexylamide;
1-(2,5-Dichlorobenzyl)-1,2,3,4-tetrahydropyrido[2,3-b]pyrazine-7-carboxylic acid (biphenyl-4-ylmethyl)amide;
[4-(4-Chlorophenyl)piperazin-1-yl]-[1-(2,5-dichlorobenzyl)-1,2,3,4-tetrahydropyrido[2,3-b]pyrazin-7-yl]methanone;
1-(2,5-Dichlorobenzyl)-1,2,3,4-tetrahydropyrido[2,3-b]pyrazine-7-carboxylic acid (2-phenoxyethyl)amide;
[1-(2,5-Dichlorobenzyl)-1,2,3,4-tetrahydropyrido[2,3-b]pyrazin-7-yl]-[4-(tetrahydrofuran-2-carbonyl)piperazin-1-yl]methanone;
1-(2,5-Dichlorobenzyl)-1,2,3,4-tetrahydropyrido[2,3-b]pyrazine-7-carboxylic acid phenethyl-amide;
1-(2,5-Dichlorobenzyl)-1,2,3,4-tetrahydropyrido[2,3-b]pyrazine-7-carboxylic acid (tetrahydrofuran-2-yl-methyl)amide;
[4-(4-Chlorobenzyl)piperazin-1-yl]-[1-(2,5-dichlorobenzyl)-1,2,3,4-tetrahydropyrido[2,3-b]pyrazin-7-yl]methanone;

1-(2,5-Dichlorobenzyl)-1,2,3,4-tetrahydropyrido[2,3-b]
pyrazine-7-carboxylic acid 2-chloro-benzylamide;
[1-(2,5-Dichlorobenzyl)-1,2,3,4-tetrahydropyrido[2,3-b]
pyrazin-7-yl]-[4-(2-(trifluoromethyl)phenyl)piperazin-1-
yl]methanone;
1-(2,5-Dichlorobenzyl)-1,2,3,4-tetrahydropyrido[2,3-b]
pyrazine-7-carboxylic acid 4-methoxybenzylamide;
1-(2,5-Dichlorobenzyl)-1,2,3,4-tetrahydropyrido[2,3-b]
pyrazine-7-carboxylic acid indan-2-ylamide;
[1-(2,5-Dichlorobenzyl)-1,2,3,4-tetrahydropyrido[2,3-b]
pyrazin-7-yl]-(4-phenethyl-piperazin-1-yl)methanone;
[4-(2-Chlorophenyl)piperazin-1-yl]-[1-(2,5-dichlorobenzyl)-1,2,3,4-tetrahydropyrido[2,3-b]pyrazin-7-yl]methanone;
[(4-Cyclohexylmethyl)piperazin-1-yl]-[1-(2,5-dichlorobenzyl)-1,2,3,4-tetrahydropyrido[2,3-b]pyrazin-7-yl]methanone;
1-(2,5-Dichlorobenzyl)-1,2,3,4-tetrahydropyrido[2,3-b]
pyrazine-7-carboxylic acid 4-sulfamoyl-benzylamide;
[1-(2,5-Dichlorobenzyl)-1,2,3,4-tetrahydropyrido[2,3-b]
pyrazin-7-yl]-(2-pyridin-3-yl-pyrrolidin-1-yl)methanone;
{4-[5-(2,5-Dichlorophenoxy)-5,6,7,8-tetrahydro-[1,8]naphthyridin-3-yl]phenyl}-4-methyl-piperazin-1-yl)methanone;
4-(2-Chloro-3,6-difluorophenoxy)-6-[6-(4-methylpiperazin-1-yl)pyridin-3-yl]-1,2,3,4-tetrahydro-[1,8]naphthyridine;
{4-[5-(3-Chlorophenoxy)-5,6,7,8-tetrahydro-[1,8]naphthyridin-3-yl]-phenyl}-(4-methylpiperazin-1-yl)methanone;
{4-[5-(3,5-Dichlorophenoxy)-5,6,7,8-tetrahydro-[1,8]naphthyridin-3-yl]phenyl}-(4-methylpiperazin-1-yl)methanone;
(4-Methylpiperazin-1-yl)-{4-[5-(pyridine-3-yloxy)-5,6,7,8-tetrahydro-[1,8]naphthyridin-3-yl]phenyl}methanone;
1-(4-Fluoro-2-{6-[4-(4-methylpiperazine-1-carbonyl)phenyl]-1,2,3,4-tetrahydro-[1,8]naphthyridin-4-yloxy}phenyl)ethanone;
4-(3-Chlorophenoxy)-6-[2-(4-methylpiperazin-1-yl)pyridin-4-yl]-1,2,3,4-tetrahydro-[1,8]naphthyridine;
4-(3-Chlorophenoxy)-6-(3-morpholin-4-yl-phenyl)-1,2,3,4-tetrahydro-[1,8]naphthyridine;
4-(3-Chlorophenoxy)-6-(4-morpholin-4-yl-phenyl)-1,2,3,4-tetrahydro-[1,8]naphthyridine;
4-(3-Chlorophenoxy)-6-[6-(4-methylpiperazin-1-yl)pyridin-3-yl]-1,2,3,4-tetrahydro-[1,8]naphthyridine;
4-(2,5-Difluorobenzyl)-6-[6-(4-methylpiperazin-1-yl)pyridin-3-yl]-1,2,3,4-tetrahydro-[1,8]naphthyridine;
(4-{1-[5-Chloro-2-(trifluoromethyl)benzyl]-1,2,3,4-tetrahydropyrido[2,3-b]pyrazin-7-yl}phenyl)-(4-morpholin-4-yl-piperidin-1-yl)methanone;
(4-{1-[5-Chloro-2-(trifluoromethyl)benzyl]-1,2,3,4-tetrahydropyrido[2,3-b]pyrazin-7-yl}phenyl)-(4-thiazol-2-yl-piperazin-1-yl)methanone;
3,6-Difluoro-2-[7-(6-morpholin-4-yl-pyridin-3-yl)-3,4-dihydro-2H-pyrido[2,3-b]pyrazin-1-ylmethyl]benzonitrile;
7-(6-Morpholin-4-yl-pyridin-3-yl)-1-[5-(trifluoromethyl)furan-2-ylmethyl]-1,2,3,4-tetrahydropyrido[2,3-b]pyrazine;
7-[2-(4-Methylpiperazin-1-yl)pyridin-4-yl]-1-[5-(trifluoromethyl)furan-2-ylmethyl]-1,2,3,4-tetrahydropyrido[2,3-b]pyrazine;
1-[5-Chloro-2-(trifluoromethyl)benzyl]-1,2,3,4-tetrahydropyrido[2,3-b]pyrazine-7-carboxylic acid[4-(dimethylamino)butyl]amide;
4-{1-[2-(Trifluoromethoxy)benzyl]-1,2,3,4-tetrahydropyrido[2,3-b]pyrazin-7-yl}benzoic acid ethyl ester;
4-{1-[2-(Trifluoromethoxy)benzyl]-1,2,3,4-tetrahydropyrido[2,3-b]pyrazin-7-yl}benzoic acid;
4-[1-(2-Chloropyridin-3-ylmethyl)-1,2,3,4-tetrahydropyrido[2,3-b]pyrazin-7-yl]benzoic acid ethyl ester;
4-[1-(2-Chloropyridin-3-ylmethyl)-1,2,3,4-tetrahydropyrido[2,3-b]pyrazin-7-yl]benzoic acid;
{4-[1-(2-Chloropyridin-3-ylmethyl)-1,2,3,4-tetrahydropyrido[2,3-b]pyrazin-7-yl]phenyl}-(4-pyrrolidin-1-yl-piperidin-1-yl)methanone;
N-(4-{1-[5-Chloro-2-(trifluoromethyl)benzyl]-1,2,3,4-tetrahydropyrido[2,3-b]pyrazin-7-yl}phenyl)acetamide;
(4-Pyrrolidin-1-yl-piperidin-1-yl)-(4-{1-[2-(trifluoromethoxy)benzyl]-1,2,3,4-tetrahydropyrido[2,3-b]pyrazin-7-yl}phenyl)methanone;
(3-{1-[5-Chloro-2-(trifluoromethyl)benzyl]-1,2,3,4-tetrahydropyrido[2,3-b]pyrazin-7-yl}phenyl)-(4-phenylpiperazin-1-yl)methanone;
(3-{1-[5-Chloro-2-(trifluoromethyl)benzyl]-1,2,3,4-tetrahydropyrido[2,3-b]pyrazin-7-yl}phenyl)-(4-pyrimidin-2-ylpiperazin-1-yl)methanone;
[4-(4-Chlorophenyl)-piperazin-1-yl]-(3-{1-[5-Chloro-2-(trifluoromethyl)benzyl]-1,2,3,4-tetrahydropyrido[2,3-b]pyrazin-7-yl}phenyl)methanone;
[4-(4-Chlorophenyl)-4-hydroxypiperidin-1-yl]-(3-{1-[5-Chloro-2-(trifluoromethyl)benzyl]-1,2,3,4-tetrahydropyrido[2,3-b]pyrazin-7-yl}phenyl)methanone;
1-[1-(3-{1-[5-Chloro-2-(trifluoromethyl)benzyl]-1,2,3,4-tetrahydropyrido[2,3-b]pyrazin-7-yl}benzoyl)piperidin-4-yl]-1,3-dihydrobenzoimidazol-2-one;
(3-{1-[5-Chloro-2-(trifluoromethyl)benzyl]-1,2,3,4-tetrahydropyrido[2,3-b]pyrazin-7-yl}phenyl)-[4-(2-methoxyphenyl)piperazin-1-yl]methanone;
(3-{1-[5-Chloro-2-(trifluoromethyl)benzyl]-1,2,3,4-tetrahydropyrido[2,3-b]pyrazin-7-yl}phenyl)-{4-[3-(trifluoromethyl)phenyl]piperazin-1-yl}methanone;
(3-{1-[5-Chloro-2-(trifluoromethyl)benzyl]-1,2,3,4-tetrahydropyrido[2,3-b]pyrazin-7-yl}phenyl)-(4-phenylpiperidin-1-yl)methanone;
(3-{1-[5-Chloro-2-(trifluoromethyl)benzyl]-1,2,3,4-tetrahydropyrido[2,3-b]pyrazin-7-yl}phenyl)-[4-(1H-indol-3-yl)piperidin-1-yl]methanone;
(4-Benzhydrylpiperazin-1-yl)-(3-{1-[5-Chloro-2-(trifluoromethyl)benzyl]-1,2,3,4-tetrahydropyrido[2,3-b]pyrazin-7-yl}phenyl)methanone;
(4-Benzylpiperidin-1-yl)-(3-{1-[5-Chloro-2-(trifluoromethyl)benzyl]-1,2,3,4-tetrahydropyrido[2,3-b]pyrazin-7-yl}phenyl)methanone;
(3-{1-[5-Chloro-2-(trifluoromethyl)benzyl]-1,2,3,4-tetrahydropyrido[2,3-b]pyrazin-7-yl}phenyl)-[4-(3,4-dichlorophenyl)piperazin-1-yl]methanone;
8-(3-{1-[5-Chloro-2-(trifluoromethyl)benzyl]-1,2,3,4-tetrahydropyrido[2,3-b]pyrazin-7-yl}benzoyl)-1-phenyl-1,3,8-triaza-spiro[4.5]decan-4-one;
(3-{1-[5-Chloro-2-(trifluoromethyl)benzyl]-1,2,3,4-tetrahydropyrido[2,3-b]pyrazin-7-yl}phenyl)-{4-[2-(trifluoromethyl)phenyl]piperazin-1-yl}methanone;
(3-{1-[5-Chloro-2-(trifluoromethyl)benzyl]-1,2,3,4-tetrahydropyrido[2,3-b]pyrazin-7-yl}phenyl)-(4-thieno[3,2-d]pyrimidin-4-ylpiperazin-1-yl)methanone;
[4-(4-Chlorobenzyl)piperazin-1-yl]-(3-{1-[5-Chloro-2-(trifluoromethyl)benzyl]-1,2,3,4-tetrahydropyrido[2,3-b]pyrazin-7-yl}phenyl)methanone;
(3-{1-[5-Chloro-2-(trifluoromethyl)benzyl]-1,2,3,4-tetrahydropyrido[2,3-b]pyrazin-7-yl}phenyl)-[4-(4-methoxybenzyl)piperazin-1-yl]methanone;
(4-Benzoylpiperazin-1-yl)-(3-{1-[5-Chloro-2-(trifluoromethyl)benzyl]-1,2,3,4-tetrahydropyrido[2,3-b]pyrazin-7-yl}phenyl)methanone;

(3-{1-[5-Chloro-2-(trifluoromethyl)benzyl]-1,2,3,4-tetrahydropyrido[2,3-b]pyrazin-7-yl}phenyl)-(4-furo[3,2-c]pyridin-4-ylpiperazin-1-yl)methanone;
(3-{1-[5-Chloro-2-(trifluoromethyl)benzyl]-1,2,3,4-tetrahydropyrido[2,3-b]pyrazin-7-yl}phenyl)-[4-(6-fluorobenzo[d]isoxazol-3-yl)piperidin-1-yl]methanone;
4-(3-{1-[5-Chloro-2-(trifluoromethyl)benzyl]-1,2,3,4-tetrahydropyrido[2,3-b]pyrazin-7-yl}benzoylamino)piperidine-1-carboxylic acid ethyl ester;
N-(1-Benzylpiperidin-4-yl)-3-{1-[5-chloro-2-(trifluoromethyl)benzyl]-1,2,3,4-tetrahydropyrido[2,3-b]pyrazin-7-yl}benzamide;
3-{1-[5-Chloro-2-(trifluoromethyl)benzyl]-1,2,3,4-tetrahydropyrido[2,3-b]pyrazin-7-yl}-N-(2,2-diphenylethyl)benzamide;
3-{1-[5-Chloro-2-(trifluoromethyl)benzyl]-1,2,3,4-tetrahydropyrido[2,3-b]pyrazin-7-yl}-N-(1-methylpiperidin-4-yl)benzamide;
(3-{1-[5-Chloro-2-(trifluoromethyl)benzyl]-1,2,3,4-tetrahydropyrido[2,3-b]pyrazin-7-yl}phenyl)-[4-(2-pyridin-2-ylethyl)piperazin-1-yl]methanone;
3-{1-[5-Chloro-2-(trifluoromethyl)benzyl]-1,2,3,4-tetrahydropyrido[2,3-b]pyrazin-7-yl}-N-[4-(trifluoromethoxy)benzyl]benzamide;
N-[3,5-Bis(trifluoromethyl)benzyl]-3-{1-[5-chloro-2-(trifluoromethyl)benzyl]-1,2,3,4-tetrahydropyrido[2,3-b]pyrazin-7-yl}benzamide;
N-Benzhydryl-3-{1-[5-chloro-2-(trifluoromethyl)benzyl]-1,2,3,4-tetrahydropyrido[2,3-b]pyrazin-7-yl}benzamide;
3-{1-[5-Chloro-2-(trifluoromethyl)benzyl]-1,2,3,4-tetrahydropyrido[2,3-b]pyrazin-7-yl}-N-pyridin-4-ylmethylbenzamide;
3-{1-[5-Chloro-2-(trifluoromethyl)benzyl]-1,2,3,4-tetrahydropyrido[2,3-b]pyrazin-7-yl}-N-pyridin-3-ylmethylbenzamide;
2-[4-(3-{1-[5-Chloro-2-(trifluoromethyl)benzyl]-1,2,3,4-tetrahydropyrido[2,3-b]pyrazin-7-yl}benzoyl)piperazin-1-yl]-N-isopropylacetamide;
(3-{1-[5-Chloro-2-(trifluoromethyl)benzyl]-1,2,3,4-tetrahydropyrido[2,3-b]pyrazin-7-yl}phenyl)-[4-(2-methylquinolin-4-yl)piperazin-1-yl]methanone;
3-{1-[5-Chloro-2-(trifluoromethyl)benzyl]-1,2,3,4-tetrahydropyrido[2,3-b]pyrazin-7-yl}-N-[2-(4-sulfamoylphenyl)ethyl]benzamide;
(3-{1-[5-Chloro-2-(trifluoromethyl)benzyl]-1,2,3,4-tetrahydropyrido[2,3-b]pyrazin-7-yl}phenyl)-(2,3,5,6-tetrahydro-[1,2']bipyrazinyl-4-yl)methanone;
3-{1-[5-Chloro-2-(trifluoromethyl)benzyl]-1,2,3,4-tetrahydropyrido[2,3-b]pyrazin-7-yl}-N-(2-phenylthiazol-4-ylmethyl)benzamide;
(3-{1-[5-Chloro-2-(trifluoromethyl)benzyl]-1,2,3,4-tetrahydropyrido[2,3-b]pyrazin-7-yl}phenyl)morpholin-4-ylmethanone;
3-{1-[5-Chloro-2-(trifluoromethyl)benzyl]-1,2,3,4-tetrahydropyrido[2,3-b]pyrazin-7-yl}-N-naphthalen-1-ylmethylbenzamide;
3-{1-[5-Chloro-2-(trifluoromethyl)benzyl]-1,2,3,4-tetrahydropyrido[2,3-b]pyrazin-7-yl}-N-indan-1-ylbenzamide;
(3-{1-[5-Chloro-2-(trifluoromethyl)benzyl]-1,2,3,4-tetrahydropyrido[2,3-b]pyrazin-7-yl}phenyl)-[4-(3-methoxyphenyl)piperazin-1-yl]methanone;
(3-{1-[5-Chloro-2-(trifluoromethyl)benzyl]-1,2,3,4-tetrahydropyrido[2,3-b]pyrazin-7-yl}phenyl)-[4-(4-methoxyphenyl)piperazin-1-yl]methanone;
3-{1-[5-Chloro-2-(trifluoromethyl)benzyl]-1,2,3,4-tetrahydropyrido[2,3-b]pyrazin-7-yl}-N-cyclohexylbenzamide;
3-{1-[5-Chloro-2-(trifluoromethyl)benzyl]-1,2,3,4-tetrahydropyrido[2,3-b]pyrazin-7-yl}-N-(4-methanesulfonylbenzyl)benzamide;
N-(2-Chlorobenzyl)-3-{1-[5-Chloro-2-(trifluoromethyl)benzyl]-1,2,3,4-tetrahydropyrido[2,3-b]pyrazin-7-yl}benzamide;
N-(4-Chlorobenzyl)-3-{1-[5-Chloro-2-(trifluoromethyl)benzyl]-1,2,3,4-tetrahydropyrido[2,3-b]pyrazin-7-yl}benzamide;
N-(3-Chlorobenzyl)-3-{1-[5-Chloro-2-(trifluoromethyl)benzyl]-1,2,3,4-tetrahydropyrido[2,3-b]pyrazin-7-yl}benzamide;
(3-{1-[5-Chloro-2-(trifluoromethyl)benzyl]-1,2,3,4-tetrahydropyrido[2,3-b]pyrazin-7-yl}phenyl)-[4-(tetrahydrofuran-2-carbonyl)piperazin-1-yl]methanone;
3-{1-[5-Chloro-2-(trifluoromethyl)benzyl]-1,2,3,4-tetrahydropyrido[2,3-b]pyrazin-7-yl}-N-(tetrahydrofuran-2-ylmethyl)benzamide;
3-{1-[5-Chloro-2-(trifluoromethyl)benzyl]-1,2,3,4-tetrahydropyrido[2,3-b]pyrazin-7-yl}-N-(3-methoxybenzyl)benzamide;
3-{1-[5-Chloro-2-(trifluoromethyl)benzyl]-1,2,3,4-tetrahydropyrido[2,3-b]pyrazin-7-yl}-N-(4-methoxybenzyl)benzamide;
3-{1-[5-Chloro-2-(trifluoromethyl)benzyl]-1,2,3,4-tetrahydropyrido[2,3-b]pyrazin-7-yl}-N-(2-phenoxyethyl)benzamide;
N-Benzyl-3-{1-[5-Chloro-2-(trifluoromethyl)benzyl]-1,2,3,4-tetrahydropyrido[2,3-b]pyrazin-7-yl}benzamide;
[4-(3-Chlorophenyl)piperazin-1-yl]-(3-{1-[5-chloro-2-(trifluoromethyl)benzyl]-1,2,3,4-tetrahydropyrido[2,3-b]pyrazin-7-yl}phenyl)methanone;
3-{1-[5-Chloro-2-(trifluoromethyl)benzyl]-1,2,3,4-tetrahydropyrido[2,3-b]pyrazin-7-yl}-N-indan-2-ylbenzamide;
(3-{1-[5-Chloro-2-(trifluoromethyl)benzyl]-1,2,3,4-tetrahydropyrido[2,3-b]pyrazin-7-yl}phenyl)-(4-phenethylpiperazin-1-yl)methanone;
[4-(2-Chlorophenyl)piperazin-1-yl]-(3-{1-[5-chloro-2-(trifluoromethyl)benzyl]-1,2,3,4-tetrahydropyrido[2,3-b]pyrazin-7-yl}phenyl)methanone;
N-(1-Benzylpyrrolidin-3-yl)-3-{1-[5-chloro-2-(trifluoromethyl)benzyl]-1,2,3,4-tetrahydropyrido[2,3-b]pyrazin-7-yl}benzamide;
(3-{1-[5-Chloro-2-(trifluoromethyl)benzyl]-1,2,3,4-tetrahydropyrido[2,3-b]pyrazin-7-yl}phenyl)-[4-(cyclohexylmethyl)piperazin-1-yl]methanone;
3-{1-[5-Chloro-2-(trifluoromethyl)benzyl]-1,2,3,4-tetrahydropyrido[2,3-b]pyrazin-7-yl}-N-(4-sulfamoylbenzyl)benzamide;
(3-{1-[5-Chloro-2-(trifluoromethyl)benzyl]-1,2,3,4-tetrahydropyrido[2,3-b]pyrazin-7-yl}phenyl)-(4-morpholin-4-ylpiperidin-1-yl)methanone;
(3-{1-[5-Chloro-2-(trifluoromethyl)benzyl]-1,2,3,4-tetrahydropyrido[2,3-b]pyrazin-7-yl}phenyl)-((S)-2-pyrrolidin-1-ylmethylpyrrolidin-1-yl)methanone;
(3-{1-[5-Chloro-2-(trifluoromethyl)benzyl]-1,2,3,4-tetrahydropyrido[2,3-b]pyrazin-7-yl}phenyl)-(2-pyridin-3-ylpyrrolidin-1-yl)methanone;
3-{1-[5-Chloro-2-(trifluoromethyl)benzyl]-1,2,3,4-tetrahydropyrido[2,3-b]pyrazin-7-yl}-N-(2-methoxybenzyl)-N-methylbenzamide;
(4-{1-[5-Chloro-2-(trifluoromethyl)benzyl]-1,2,3,4-tetrahydropyrido[2,3-b]pyrazin-7-yl}phenyl)-(4-phenylpiperazin-1-yl)methanone;
(4-{1-[5-Chloro-2-(trifluoromethyl)benzyl]-1,2,3,4-tetrahydropyrido[2,3-b]pyrazin-7-yl}phenyl)-(4-pyrimidin-2-ylpiperazin-1-yl)methanone;

[4-(4-Chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone;

[4-(4-Chlorophenyl)-4-hydroxypiperidin-1-yl]-(4-{1-[5-chloro-2-(trifluoromethyl)benzyl]-1,2,3,4-tetrahydropyrido[2,3-b]pyrazin-7-yl}phenyl)methanone;

1-[1-(4-{1-[5-Chloro-2-(trifluoromethyl)benzyl]-1,2,3,4-tetrahydropyrido[2,3-b]pyrazin-7-yl}benzoyl)piperidin-4-yl]-1,3-dihydrobenzoimidazol-2-one;

(4-{1-[5-Chloro-2-(trifluoromethyl)benzyl]-1,2,3,4-tetrahydropyrido[2,3-b]pyrazin-7-yl}phenyl)-[4-(2-methoxyphenyl)piperazin-1-yl]methanone;

(4-{1-[5-Chloro-2-(trifluoromethyl)benzyl]-1,2,3,4-tetrahydropyrido[2,3-b]pyrazin-7-yl}phenyl)-{4-[3-(trifluoromethyl)phenyl]piperazin-1-yl}methanone;

(4-{1-[5-Chloro-2-(trifluoromethyl)benzyl]-1,2,3,4-tetrahydropyrido[2,3-b]pyrazin-7-yl}phenyl)-(4-phenylpiperidin-1-yl)methanone;

(4-{1-[5-Chloro-2-(trifluoromethyl)benzyl]-1,2,3,4-tetrahydropyrido[2,3-b]pyrazin-7-yl}phenyl)-[4-(1H-indol-3-yl)piperidin-1-yl]methanone;

(4-Benzhydrylpiperazin-1-yl)-(4-{1-[5-chloro-2-(trifluoromethyl)benzyl]-1,2,3,4-tetrahydropyrido[2,3-b]pyrazin-7-yl}phenyl)methanone;

(4-Benzylpiperidin-1-yl)-(4-{1-[5-chloro-2-(trifluoromethyl)benzyl]-1,2,3,4-tetrahydropyrido[2,3-b]pyrazin-7-yl}phenyl)methanone;

(4-{1-[5-Chloro-2-(trifluoromethyl)benzyl]-1,2,3,4-tetrahydropyrido[2,3-b]pyrazin-7-yl}phenyl)-[4-(3,4-dichlorophenyl)piperazin-1-yl]methanone;

8-(4-{1-[5-Chloro-2-(trifluoromethyl)benzyl]-1,2,3,4-tetrahydropyrido[2,3-b]pyrazin-7-yl}benzoyl)-1-phenyl-1,3,8-triaza-spiro[4.5]decan-4-one;

(4-{1-[5-Chloro-2-(trifluoromethyl)benzyl]-1,2,3,4-tetrahydropyrido[2,3-b]pyrazin-7-yl}phenyl)-{4-[2-(trifluoromethyl)phenyl]piperazin-1-yl}methanone;

(4-{1-[5-Chloro-2-(trifluoromethyl)benzyl]-1,2,3,4-tetrahydropyrido[2,3-b]pyrazin-7-yl}phenyl)-(4-thieno[3,2-d]pyrimidin-4-yl-piperazin-1-yl)methanone;

[4-(4-Chlorobenzyl)piperazin-1-yl]-(4-{1-[5-chloro-2-(trifluoromethyl)benzyl]-1,2,3,4-tetrahydropyrido[2,3-b]pyrazin-7-yl}phenyl)methanone;

(4-{1-[5-Chloro-2-(trifluoromethyl)benzyl]-1,2,3,4-tetrahydropyrido[2,3-b]pyrazin-7-yl}phenyl)-[4-(4-methoxybenzyl)piperazin-1-yl]methanone;

(4-Benzoylpiperazin-1-yl)-(4-{1-[5-chloro-2-(trifluoromethyl)benzyl]-1,2,3,4-tetrahydropyrido[2,3-b]pyrazin-7-yl}phenyl)methanone;

(4-{1-[5-Chloro-2-(trifluoromethyl)benzyl]-1,2,3,4-tetrahydropyrido[2,3-b]pyrazin-7-yl}phenyl)-(4-furo[3,2-c]pyridin-4-ylpiperazin-1-yl)methanone;

(4-{1-[5-Chloro-2-(trifluoromethyl)benzyl]-1,2,3,4-tetrahydropyrido[2,3-b]pyrazin-7-yl}phenyl)-[4-(6-fluorobenzo[d]isoxazol-3-yl)-piperidin-1-yl]methanone;

4-{1-[5-Chloro-2-(trifluoromethyl)benzyl]-1,2,3,4-tetrahydropyrido[2,3-b]pyrazin-7-yl}-N-(2-pyridin-2-yl-ethyl)benzamide;

4-(4-{1-[5-Chloro-2-(trifluoromethyl)benzyl]-1,2,3,4-tetrahydropyrido[2,3-b]pyrazin-7-yl}benzoylamino)piperidine-1-carboxylic acid ethyl ester;

N-(1-Benzylpiperidin-4-yl)-4-{1-[5-chloro-2-(trifluoromethyl)benzyl]-1,2,3,4-tetrahydropyrido[2,3-b]pyrazin-7-yl}benzamide;

4-{1-[5-Chloro-2-(trifluoromethyl)benzyl]-1,2,3,4-tetrahydropyrido[2,3-b]pyrazin-7-yl}-N-(2,2-diphenylethyl)benzamide;

1-[4-(4-{1-[5-Chloro-2-(trifluoromethyl)benzyl]-1,2,3,4-tetrahydropyrido[2,3-b]pyrazin-7-yl}benzoyl)piperazin-1-yl]ethanone;

4-{1-[5-Chloro-2-(trifluoromethyl)benzyl]-1,2,3,4-tetrahydropyrido[2,3-b]pyrazin-7-yl}-N-(1-methylpiperidin-4-yl)benzamide;

(4-{1-[5-Chloro-2-(trifluoromethyl)benzyl]-1,2,3,4-tetrahydropyrido[2,3-b]pyrazin-7-yl}phenyl)-[4-(2-pyridin-2-yl-ethyl)piperazin-1-yl]methanone;

4-{1-[5-Chloro-2-(trifluoromethyl)benzyl]-1,2,3,4-tetrahydropyrido[2,3-b]pyrazin-7-yl}-N-[4-(trifluoromethoxy)benzyl]benzamide;

4-{1-[5-Chloro-2-(trifluoromethyl)benzyl]-1,2,3,4-tetrahydropyrido[2,3-b]pyrazin-7-yl}-N-[4-(trifluoromethyl)benzyl]benzamide;

N-[3,5-Bis(trifluoromethyl)benzyl]-4-{1-[5-Chloro-2-(trifluoromethyl)benzyl]-1,2,3,4-tetrahydropyrido[2,3-b]pyrazin-7-yl}benzamide;

4-{1-[5-Chloro-2-(trifluoromethyl)benzyl]-1,2,3,4-tetrahydropyrido[2,3-b]pyrazin-7-yl}-N-(2-thiophen-2-yl-ethyl)benzamide;

N-Benzhydryl-4-{1-[5-chloro-2-(trifluoromethyl)benzyl]-1,2,3,4-tetrahydropyrido[2,3-b]pyrazin-7-yl}benzamide;

4-{1-[5-Chloro-2-(trifluoromethyl)benzyl]-1,2,3,4-tetrahydropyrido[2,3-b]pyrazin-7-yl}-N-pyridin-4-ylmethylbenzamide;

4-{1-[5-Chloro-2-(trifluoromethyl)benzyl]-1,2,3,4-tetrahydropyrido[2,3-b]pyrazin-7-yl}-N-pyridin-3-ylmethylbenzamide;

2-[4-(4-{1-[5-Chloro-2-(trifluoromethyl)benzyl]-1,2,3,4-tetrahydropyrido[2,3-b]pyrazin-7-yl}benzoyl)piperazin-1-yl]-N-isopropylacetamide;

(4-{1-[5-Chloro-2-(trifluoromethyl)benzyl]-1,2,3,4-tetrahydropyrido[2,3-b]pyrazin-7-yl}phenyl)-[4-(2-methylquinolin-4-yl)piperazin-1-yl]methanone;

4-{1-[5-Chloro-2-(trifluoromethyl)benzyl]-1,2,3,4-tetrahydropyrido[2,3-b]pyrazin-7-yl}-N-(2-methoxyethyl)benzamide;

4-{1-[5-Chloro-2-(trifluoromethyl)benzyl]-1,2,3,4-tetrahydropyrido[2,3-b]pyrazin-7-yl}-N-[2-(4-sulfamoylphenyl)ethyl]benzamide;

(4-{1-[5-Chloro-2-(trifluoromethyl)benzyl]-1,2,3,4-tetrahydropyrido[2,3-b]pyrazin-7-yl}phenyl)-(2,3,5,6-tetrahydro[1,2']bipyrazinyl-4-yl)methanone;

4-{1-[5-Chloro-2-(trifluoromethyl)benzyl]-1,2,3,4-tetrahydropyrido[2,3-b]pyrazin-7-yl}-N-(2-phenylthiazol-4-ylmethyl)benzamide;

(4-{1-[5-Chloro-2-(trifluoromethyl)benzyl]-1,2,3,4-tetrahydropyrido[2,3-b]pyrazin-7-yl}phenyl)morpholin-4-ylmethanone;

4-{1-[5-Chloro-2-(trifluoromethyl)benzyl]-1,2,3,4-tetrahydropyrido[2,3-b]pyrazin-7-yl}-N-naphthalen-1-ylmethylbenzamide;

4-{1-[5-Chloro-2-(trifluoromethyl)benzyl]-1,2,3,4-tetrahydropyrido[2,3-b]pyrazin-7-yl}-N-indan-1-ylbenzamide;

(4-{1-[5-Chloro-2-(trifluoromethyl)benzyl]-1,2,3,4-tetrahydropyrido[2,3-b]pyrazin-7-yl}phenyl)-[4-(4-methoxyphenyl)piperazin-1-yl]methanone;

N-(2-Chlorobenzyl)-4-{1-[5-chloro-2-(trifluoromethyl)benzyl]-1,2,3,4-tetrahydropyrido[2,3-b]pyrazin-7-yl}benzamide;

N-(4-Chlorobenzyl)-4-{1-[5-chloro-2-(trifluoromethyl)benzyl]-1,2,3,4-tetrahydropyrido[2,3-b]pyrazin-7-yl}benzamide;

N-(3-Chloro-benzyl)-4-{1-[5-chloro-2-(trifluoromethyl)benzyl]-1,2,3,4-tetrahydropyrido[2,3-b]pyrazin-7-yl}benzamide;

(4-{1-[5-Chloro-2-(trifluoromethyl)benzyl]-1,2,3,4-tetrahydropyrido[2,3-b]pyrazin-7-yl}phenyl)-[4-(tetrahydrofuran-2-carbonyl)piperazin-1-yl]methanone;
4-{1-[5-Chloro-2-(trifluoromethyl)benzyl]-1,2,3,4-tetrahydropyrido[2,3-b]pyrazin-7-yl}-N-phenethylbenzamide;
4-{1-[5-Chloro-2-(trifluoromethyl)benzyl]-1,2,3,4-tetrahydropyrido[2,3-b]pyrazin-7-yl}-N-(tetrahydrofuran-2-ylmethyl)benzamide;
4-{1-[5-Chloro-2-(trifluoromethyl)benzyl]-1,2,3,4-tetrahydropyrido[2,3-b]pyrazin-7-yl}-N-(3-methoxybenzyl)benzamide;
4-{1-[5-Chloro-2-(trifluoromethyl)benzyl]-1,2,3,4-tetrahydropyrido[2,3-b]pyrazin-7-yl}-N-(4-methoxybenzyl)benzamide;
4-{1-[5-Chloro-2-(trifluoromethyl)benzyl]-1,2,3,4-tetrahydropyrido[2,3-b]pyrazin-7-yl}-N-(2-phenoxyethyl)benzamide;
N-Benzyl-4-{1-[5-chloro-2-(trifluoromethyl)benzyl]-1,2,3,4-tetrahydropyrido[2,3-b]pyrazin-7-yl}benzamide;
[4-(3-Chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone;
4-{1-[5-Chloro-2-(trifluoromethyl)benzyl]-1,2,3,4-tetrahydropyrido[2,3-b]pyrazin-7-yl}-N-indan-2-ylbenzamide;
(4-{1-[5-Chloro-2-(trifluoromethyl)benzyl]-1,2,3,4-tetrahydropyrido[2,3-b]pyrazin-7-yl}phenyl)-(4-phenethylpiperazin-1-yl)methanone;
N-Biphenyl-4-ylmethyl-4-{1-[5-Chloro-2-(trifluoromethyl)benzyl]-1,2,3,4-tetrahydropyrido[2,3-b]pyrazin-7-yl}benzamide;
[4-(2-Chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone;
N-(1-Benzylpyrrolidin-3-yl)-4-{1-[5-chloro-2-(trifluoromethyl)benzyl]-1,2,3,4-tetrahydropyrido[2,3-b]pyrazin-7-yl}benzamide;
(4-{1-[5-Chloro-2-(trifluoromethyl)benzyl]-1,2,3,4-tetrahydropyrido[2,3-b]pyrazin-7-yl}phenyl)-[4-(cyclohexylmethyl)piperazin-1-yl]methanone;
4-{1-[5-Chloro-2-(trifluoromethyl)benzyl]-1,2,3,4-tetrahydropyrido[2,3-b]pyrazin-7-yl}-N-(4-sulfamoylbenzyl)benzamide;
(4-{1-[5-Chloro-2-(trifluoromethyl)benzyl]-1,2,3,4-tetrahydropyrido[2,3-b]pyrazin-7-yl}phenyl)-((S)-2-pyrrolidin-1-ylmethylpyrrolidin-1-yl)methanone;
(4-{1-[5-Chloro-2-(trifluoromethyl)benzyl]-1,2,3,4-tetrahydropyrido[2,3-b]pyrazin-7-yl}phenyl)-(2-pyridin-3-ylpyrrolidin-1-yl)methanone;
4-{1-[5-Chloro-2-(trifluoromethyl)benzyl]-1,2,3,4-tetrahydropyrido[2,3-b]pyrazin-7-yl}-N-(2-methoxybenzyl)-N-methylbenzamide;
(4-{1-[5-Chloro-2-(trifluoromethyl)benzyl]-1,2,3,4-tetrahydropyrido[2,3-b]pyrazin-7-yl}phenyl)-(1,3-dihydroisoindol-2-yl)methanone;
{4-[1-(5-Chloro-2-trifluoromethyl-benzyl)-1,2,3,4-tetrahydropyrido[2,3-b]pyrazin-7-yl]-phenyl}-(spiro[isobenzofuran-1(3H), 4'-piperidine]-1-yl)methanone; and
1-(2-Chloro-3,6-difluorobenzyl)-7-[6-(4-methylpiperazin-1-yl)pyridin-3-yl]-1,4-dihydro-2H-pyrido[2,3-b]pyrazin-3-one;

or a pharmaceutically acceptable salt form thereof.

In one embodiment, the present invention provides a compound of Formula I(d) chosen from:
1-(2-Chloro-3,6-difluorobenzyl)-7-iodo-3,4-dihydro-1H-pyrido[2,3-b]pyrazin-2-one;
1-Benzyl-7-iodo-3,4-dihydro-1H-pyrido[2,3-b]pyrazin-2-one;
1-Benzyl-1,2,3,4-tetrahydropyrido[2,3-b]pyrazine;
1-Benzyl-7-iodo-1,2,3,4-tetrahydropyrido[2,3-b]pyrazine;
(3,4-Dihydro-2H-pyrido[2,3-b]pyrazin-1-yl)phenylmethanone;
(7-Iodo-3,4-dihydro-2H-pyrido[2,3-b]pyrazin-1-yl)phenylmethanone;
1-(2,5-Difluorobenzyl)-7-iodo-1,2,3,4-tetrahydropyrido[2,3-b]pyrazine;
1-(2,5-Difluorobenzyl)-1,2,3,4-tetrahydropyrido[2,3-b]pyrazine-7-carbonitrile;
1-(2,5-Difluorobenzyl)-1,2,3,4-tetrahydropyrido[2,3-b]pyrazine-7-carboxylic acid;
7-Iodo-1-(2,4,5-trifluorobenzyl)-3,4-dihydro-1H-pyrido[2,3-b]pyrazin-2-one;
7-Iodo-1-(2,4,5-trifluorobenzyl)-1,2,3,4-tetrahydropyrido[2,3-b]pyrazine;
(2,5-Difluorophenyl)-(7-iodo-3,4-dihydro-2H-pyrido[2,3-b]pyrazin-1-yl)methanone;
1-(2,5-Difluorobenzyl)-7-iodo-3,3-dimethyl-3,4-dihydro-1H-pyrido[2,3-b]pyrazin-2-one;
1-(2,5-Difluorobenzyl)-7-iodo-3,3-dimethyl-1,2,3,4-tetrahydropyrido[2,3-b]pyrazine;
1-(2-Chloro-3,6-difluorobenzyl)-7-iodo-1,2,3,4-tetrahydropyrido[2,3-b]pyrazine;
1-(7-Iodo-3,4-dihydro-2H-pyrido[2,3-b]pyrazin-1-yl)-2-phenylethanone;
2-(2,5-Difluorophenyl)-1-(7-iodo-3,4-dihydro-2H-pyrido[2,3-b]pyrazin-1-yl)ethanone;
1-(5-Chloro-2-trifluoromethylbenzyl)-7-iodo-1,2,3,4-tetrahydropyrido[2,3-b]pyrazine;
1-(2-Chloro-5-trifluoromethylbenzyl)-7-iodo-3,4-dihydro-1H-pyrido[2,3-b]pyrazin-2-one;
1-(2-Chloro-5-trifluoromethylbenzyl)-7-iodo-1,2,3,4-tetrahydropyrido[2,3-b]pyrazine;
1-(2,5-Difluorobenzenesulfonyl)-7-iodo-1,2,3,4-tetrahydropyrido[2,3-b]pyrazine;
1-Benzenesulfonyl-7-iodo-1,2,3,4-tetrahydropyrido[2,3-b]pyrazine;
1-(2-Chlorobenzenesulfonyl)-7-iodo-1,2,3,4-tetrahydropyrido[2,3-b]pyrazine;
1-(2,5-Dichlorobenzyl)-1,2,3,4-tetrahydropyrido[2,3-b]pyrazine-7-carbonitrile;
1-(2,5-Dichlorobenzyl)-1,2,3,4-tetrahydropyrido[2,3-b]pyrazine-7-carboxylic acid;
1-(5-Fluoro-2-trifluoromethylbenzyl)-7-iodo-3,4-dihydro-1H-pyrido[2,3-b]pyrazin-2-one;
1-(5-Fluoro-2-trifluoromethylbenzyl)-7-iodo-1,2,3,4-tetrahydropyrido[2,3-b]pyrazin-2-one;
1-(2,6-Dichlorobenzyl)-7-iodo-3,4-dihydro-1H-pyrido[2,3-b]pyrazin-2-one;
7-Iodo-1-[1-(2,4,5-trifluorophenyl)ethyl]-3,4-dihydro-1H-pyrido[2,3-b]pyrazin-2-one;
7-Iodo-1-[1-(2,4,5-trifluorophenyl)ethyl]-1,2,3,4-tetrahydropyrido[2,3-b]pyrazine;
1-[1-(2,5-Difluorophenyl)ethyl]-7-iodo-3,4-dihydro-1H-pyrido[2,3-b]pyrazin-2-one;
1-[1-(2,5-Difluorophenyl)ethyl]-7-iodo-1,2,3,4-tetrahydropyrido[2,3-b]pyrazine;
1-(2,5-Dichlorobenzyl)-7-iodo-3,4-dihydro-1H-pyrido[2,3-b]pyrazin-2-one;
1-(2,5-Dichlorobenzyl)-7-iodo-1,2,3,4-tetrahydropyrido[2,3-b]pyrazine;
1-(2,6-Dichlorobenzyl)-7-iodo-1,2,3,4-tetrahydropyrido[2,3-b]pyrazine;

1-[1-(2-Chloro-3,6-difluorophenyl)ethyl]-7-iodo-3,4-dihydro-1H-pyrido[2,3-b]pyrazin-2-one;
1-[1-(2-Chloro-3,6-difluorophenyl)ethyl]-7-iodo-1,2,3,4-tetrahydropyrido[2,3-b]pyrazine;
1-[3-Fluoro-2-(trifluoromethyl)benzyl]-7-iodo-3,4-dihydro-1H-pyrido[2,3-b]pyrazin-2-one;
1-[3-Fluoro-2-(trifluoromethyl)benzyl]-7-iodo-1,2,3,4-tetrahydropyrido[2,3-b]pyrazine;
1-(2,5-Dichlorobenzyl)-7-iodo-4-methyl-1,2,3,4-tetrahydropyrido[2,3-b]pyrazine;
6-Bromo-4-(3-chlorophenoxy)-1,2,3,4-tetrahydro-[1,8]naphthyridine;
4-(2,5-Difluorobenzyl)-1,2,3,4-tetrahydro-[1,8]naphthyridine;
6-Bromo-4-(2,5-difluorobenzyl)-1,2,3,4-tetrahydro-[1,8]naphthyridine;
7-Iodo-1-[5-(trifluoromethyl)furan-2-ylmethyl]-3,4-dihydro-1H-pyrido[2,3-b]pyrazin-2-one;
7-Iodo-1-[5-(trifluoromethyl)furan-2-ylmethyl]-1,2,3,4-tetrahydropyrido[2,3-b]pyrazine;
7-Iodo-1-[2-(trifluoromethoxy)benzyl]-3,4-dihydro-1H-pyrido[2,3-b]pyrazin-2-one;
7-Iodo-1-[2-(trifluoromethoxy)benzyl]-1,2,3,4-tetrahydropyrido[2,3-b]pyrazine;
1-(2-Chloropyridin-3-ylmethyl)-7-iodo-3,4-dihydro-1H-pyrido[2,3-b]pyrazin-2-one; and
1-(2-Chloropyridin-3-ylmethyl)-7-iodo-1,2,3,4-tetrahydropyrido[2,3-b]pyrazine;

or a pharmaceutically acceptable salt form thereof.

The present invention provides pharmaceutically acceptable salts of compounds of Formula I. Pharmaceutically acceptable acid addition salts of basic compounds of Formula I include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic-acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. Also contemplated are the salts of amino acids such as arginate, gluconate, galacturonate, and the like; see, for example, Berge et al., "Pharmaceutical Salts," J. of Pharmaceutical Science, 1977; 66:1-19.

The acid addition salts of basic compounds of Formula I may be prepared by contacting the free base form with a sufficient amount of the desired acid to produce the salt in the conventional manner. The free base form may be regenerated by contacting the salt form with a base and isolating the free base in the conventional manner. The free base forms can differ from their respective salt forms somewhat in certain physical properties such as solubility in polar solvents, but it is expected that the salts are generally similar to their respective free bases for purposes of the present invention.

Pharmaceutically acceptable base addition salts of acidic compounds of Formula I are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine; see, for example, Berge et al., supra., 1977.

The base addition salts of acidic compounds of Formula I may be prepared by contacting the free acid form with a sufficient amount of the desired base to produce the salt in the conventional manner. The free acid form may be regenerated by contacting the salt form with an acid and isolating the free acid in a conventional manner. The free acid forms can differ from their respective salt forms somewhat in certain physical properties such as solubility in polar solvents, but it is expected that the salts are generally similar to their respective free acids for purposes of the present invention.

Some of the compounds in the present invention may exist as stereoisomers, including enantiomers, diastereomers, and geometric isomers. Geometric isomers include compounds of the present invention that have alkenyl groups, which may exist as entgegen or zusammen conformations, in which case all geometric forms thereof, both entgegen and zusammen, cis and trans, and mixtures thereof, are within the scope of the present invention. Some compounds of the present invention have cycloalkyl groups, which may be substituted at more than one carbon atom, in which case all geometric forms thereof, both cis and trans, and mixtures thereof, are within the scope of the present invention. All of these forms, including (R), (S), epimers, diastereomers, cis, trans, syn, anti, (E), (Z), tautomers, and mixtures thereof, are contemplated in the compounds of the present invention.

The compounds to be used in the present invention can exist in unsolvated crystalline forms as well as solvated crystalline forms, including hydrated crystalline forms. In general, the solvated forms, including hydrated forms, are similar to unsolvated forms and are intended to be encompassed within the scope of the present invention.

III. Pharmaceutical Compositions

The present invention further provides pharmaceutical compositions comprising a compound of the present invention (e.g., a compound of Formula I or a pharmaceutically acceptable salt thereof), together with a pharmaceutically acceptable carrier, diluent, or excipient therefor. Preferably, the pharmaceutical composition contains a therapeutically effective amount of a compound of the present invention. In certain embodiments, these compositions are useful in the treatment of an ALK- or c-Met-mediated disorder or condition. The compounds of the invention can also be combined in a pharmaceutical composition that also comprises compounds that are useful for the treatment of cancer or another ALK- or c-Met-mediated disorder.

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Preferably, a compound of the present invention will cause a decrease in symptoms or a disease indicia associated with an ALK- or c-Met-mediated disorder as measured quantitatively or qualitatively.

For preparing a pharmaceutical composition from a compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component (i.e., compound of the present invention). In tablets, the active component is mixed with the carrier having the necessary binding properties in suitable proportions and compacted in the shape and size desired.

The powders and tablets contain from 1% to 95% (w/w) of the active compound (i.e., compound of the present invention). In certain embodiments, the active compound ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg, or from 1% to 95% (w/w) of a unit dose, according to the particular application and the potency of the active component. The composition can, if desired, also contain other compatible therapeutic agents.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

The dose administered to a subject, in the context of the present invention should be sufficient to effect a beneficial therapeutic response in the subject over time. The dose will be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 10 mg/kg for a typical subject. Many different administration methods are known to those of skill in the art.

For administration, compounds of the present invention can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

IV. Methods of Treatment

In another aspect, the present invention provides a method of treating a subject suffering from an ALK- or c-Met-mediated disorder or condition comprising the step of administering to the subject a therapeutically effective amount of a compound of Formula I or a pharmaceutically acceptable salt form thereof. Preferably, the compound of Formula I or a pharmaceutically acceptable salt form thereof is administered to the subject in a pharmaceutical composition comprising a pharmaceutically acceptable carrier. In certain embodiments, the ALK- or c-Met-mediated condition or disorder is cancer.

In certain embodiments, the ALK- or c-Met-mediated condition is selected from anaplastic large cell lymphoma, inflammatory myofibroblastic tumor, glioblastoma, and other solid tumors. In certain embodiments, the ALK- or c-Met-mediated condition is selected from colon cancer, breast cancer, renal cancer, lung cancer, hemangioma, squamous cell myeloid leukemia, melanoma, glioblastoma, and astrocytoma.

The ALK- or c-Met-mediated disorder or condition can be treated prophylactically, acutely, and chronically using compounds of the present invention, depending on the nature of the disorder or condition. Typically, the host or subject in each of these methods is human, although other mammals can also benefit from the administration of a compound of the present invention.

In therapeutic applications, the compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. In certain embodiments, the compounds of the present invention are delivered orally. The compounds can also be delivered rectally, bucally or by insufflation.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

V. Chemistry

All reagents and solvents were obtained from commercial sources and used as received. $^1$H NMRs were obtained on a Bruker Avance at 400 MHz in the solvent indicated with tetramethylsilane as an internal standard. Analytical HPLC was run using a Zorbax RX-C8, 5×150 mm column eluting with a mixture of acetonitrile and water containing 0.1% trifluoroacetic acid with a gradient of 10-100%. LCMS results were obtained on either of two instruments. First, in Examples that indicate LCMS retention times, analysis was performed on a Waters Aquity Ultra Performance LC with a 2.1 mm×50 mm Waters Aquity HPLC BEH C18 1.7 μm column. The target column temperature was 45° C., with a run time of two (2) minutes, a flow rate of 0.600 mL/min, and a solvent mixture of 5% (0.1% formic acid/water):95% (acetonitrile/0.1% formic acid). The mass spectrometry data was acquired on a Micromass LC-ZQ 2000 quadrupole mass spectrometer. Second, in Examples that do not indicate LCMS retention times, analysis was performed on a Bruker Esquire 200 ion trap. Automated column chromatography was performed on a CombiFlash Companion (ISCO, Inc.). Melting points were taken on a Mel-Temp apparatus and are uncorrected.

The overall synthesis for compounds of Formula I in which A is nitrogen (i.e., compounds of Formula I(a)) is generically set forth in Scheme 1.

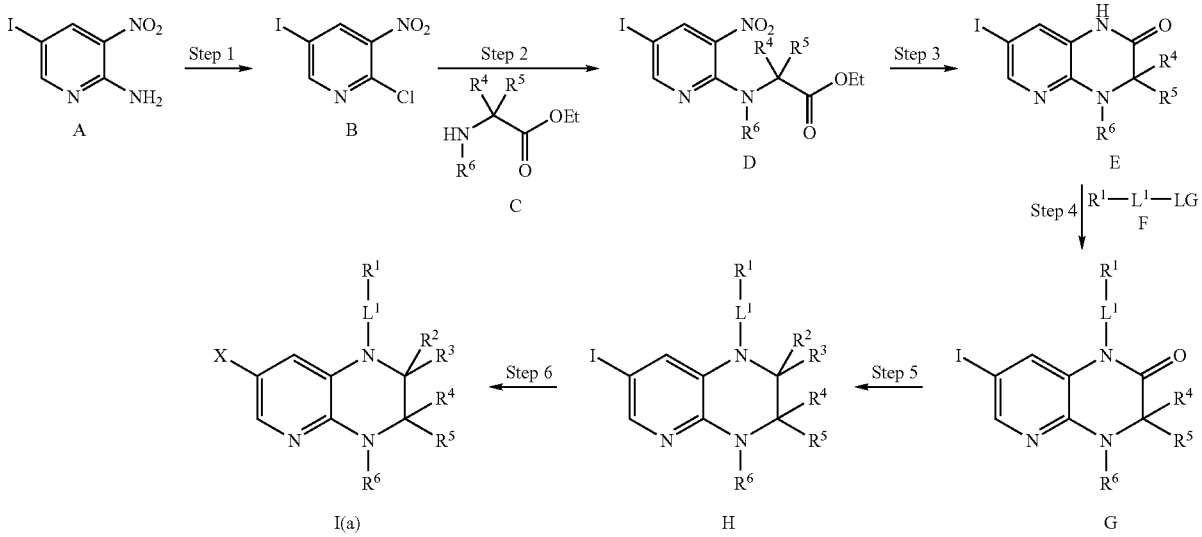

In Step 1, 2-amino-5-iodo-3-nitropyridine (A) is converted into its corresponding diazonium salt (NaNO$_2$/HCl) in the presence of cuprous chloride to form 2-chloro-5-iodo-3-nitropyridine (B). This process is described in Carroll, F. I. et al., *J. Med. Chem.*, 2002, 45, 4755-4761, which is incorporated herein by reference in its entirety. 2-amino-5-iodo-3-nitropyridine is commercially available from Sigma-Aldrich Corp. (St. Louis, Mo.). 2-amino-5-iodo-3-nitropyridine may be prepared by reacting 2-amino-3-nitropyridine with iodine and hydroiodic acid (See Carroll et al.).

In Step 2, the 2-chloropyridine B obtained in Step 1 is reacted with an alpha-amino ester C containing suitable $R^4$ and $R^5$ groups to form the 2-aminopyridine D. An $R^6$ group may be introduced in this step (e.g., $R^6$=H, $C_{1-6}$-alkyl) or in a subsequent step.

In Step 3, compound D is reduced ($SnCl_2$) and cyclized to form compound E, which contains the bicyclic pyrido[2,3-b]pyrazinone core.

In Step 4, an $R^1$-$L^1$ group is introduced at the amido nitrogen of compound E by displacement of the leaving group (LG) from compound F. The product is compound G. Alkylation and acylation reactions useful in Step 4 are described in General Procedures 1 and 2 (below). Examples 121, 123, and 124 describe suitable sulfonylation reactions for preparing compound G in which compound F ($R^1$-$L^1$-LG) is $R^1$—$C_{0-3}$-alkyl-S(=O)$_2$—Cl. For compounds in which $R^1$ is aryl or heteroaryl, and $L^1$ is a bond, a Buchwald-Hartwig coupling may be used to prepare compound G.

In Step 5, the carbonyl group of compound G is optionally reduced. A reduction reaction useful in Step (5) is described in General Procedure 3 (below).

In Step 6, an X group is introduced. Transition metal mediated coupling reactions useful in Step 6 are described in General Procedures 4-6 (below). Reactions useful for modifying the introduced X side chain are described in General Procedures 7-10 (below). Compounds of Formula I in which X is —$C_{1-3}$—C(=O)—$C_{0-3}$-alkyl-$G^1L^3G^2L^4R^7$ (i.e., $L^2$=—$C_{1-3}$—C(=O)—$C_{0-3}$-alkyl-) can be synthesized by reacting compound H with the appropriately substituted ketone and strong base. Compounds of Formula I in which X is —S(=O), —$C_{0-3}$-alkyl-$G^1L^3G^2L^4R^7$ (i.e., $L^2$=—S(=O), —$C_{0-3}$-alkyl-) or —S(=O)$_2$$NR^{30}$—$C_{0-3}$-alkyl-$G^1L^3G^2L^4R^7$ (i.e., $L^2$=—S(=O)$_2$$NR^{30}$—$C_{0-3}$-alkyl-) can be synthesized by reacting compound H with an appropriately substituted sulfinic acid. Alternatively, compounds of Formula I in which X is —S(=O), —$C_{0-3}$-alkyl-$G^1L^3G^2L^4R^7$ or —S(=O)$_2$$NR^{30}$—$C_{0-3}$-alkyl-$G^1L^3G^2L^4R^7$ can be synthesized by introducing a sulfonyl moiety at the outset of the synthesis, as shown in Scheme 2, optionally followed by reduction of the sulfonyl moiety to form the corresponding sulfoxide or sulfide.

Scheme 2. Alternative Synthesis of $L^2$ =
—S(=O)$_n$—$C_{0-3}$-alkyl- or
—S(=O)$_n$$NR^{30}$—$C_{0-3}$-alkyl-

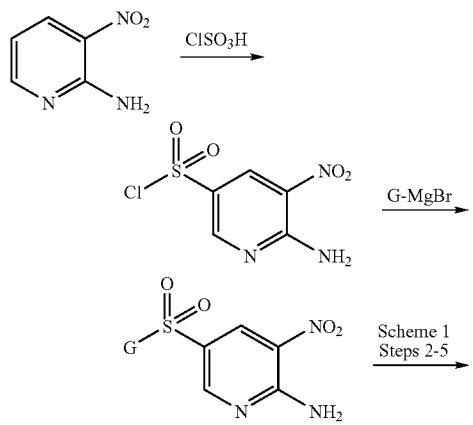

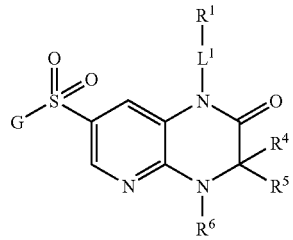

$G$ = —$C_{0-3}$-alkyl-$G^1L^3G^2L^4R^7$ or
—$NR^{30}C_{0-3}$-alkyl-$G^1L^3G^2L^4R^7$ General Procedure 1—Alkylation

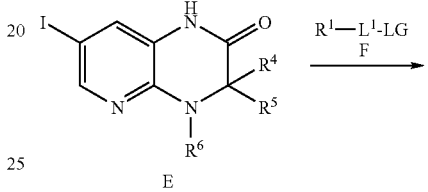

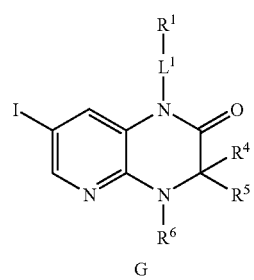

Compound E is suspended in anhydrous N,N-dimethylformamide. NaH (1 eq) is added, forming a solution. A suitable $R^1$-$L^1$-LG compound (1 eq) is added and the resulting reaction stirred at room temperature for 1-4 hours. The resulting product (G) is purified by silica gel chromatography. Alkylation selectivity is determined by $^1$H NMR Nuclear Overhauser Effect (NOE) analysis.

Suitable $R^1$-$L^1$-LG compounds for use in this reaction include, but are not limited to, $R^1$—$C_{0-3}$-alkyl-C(=O)—$C_{1-3}$-alkyl-Br, $R^1$—$C_{0-3}$-alkyl-S(=O)$_n$—$C_{1-3}$-alkyl-Br, $R^1$—$C_{0-3}$-alkyl-C(=O)$NR^{10}$—$C_{1-3}$-alkyl-Br, $R^1$—$C_{0-3}$-alkyl-S(=O)$_2$$NR^{10}$$C_{1-3}$-alkyl-Br, $R^1$—$C_{0-3}$-alkyl-C(=O)O—$C_{1-3}$-alkyl-Br, $R^1$—$C_{1-3}$-alkyl-OC(=O)$NR^{10}$—$C_{1-3}$-alkyl-Br, $R^1$—$C_{0-3}$-alkyl-$NR^{10}$—$C_{1-3}$-alkyl-Br, $R^1$—$C_{0-3}$-alkyl-O—$C_{1-3}$-alkyl-Br, $R^1$—$C_{1-3}$-alkyl-Br, $C_{3-10}$-cycloalkyl-Br, heterocycloalkyl-Br, and heteroaryl-Br.

General Procedure 2—Acylation

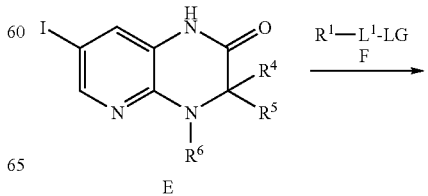

-continued

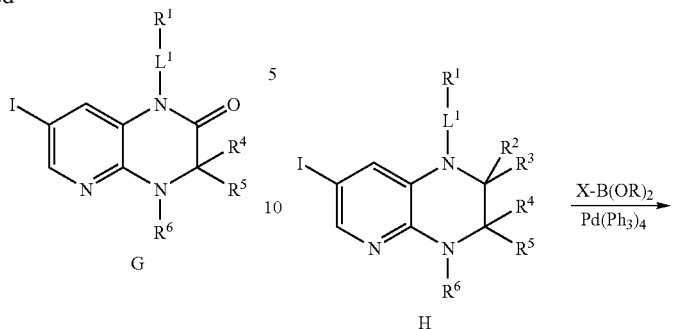

Compound E is dissolved in anhydrous tetrahydrofuran. Pyridine (1.0 eq) is added, and the solution is cooled to 0° C. A suitable $R^1$-$L^1$-LG compound (1.0 eq) is added dropwise, forming a white precipitate. The reaction is stirred at 0° C. for 15 minutes, allowed to warm to room temperature, and stirred at room temperature for 2-16 hours. The reaction is diluted with ethyl acetate, washed with $NaHCO_3$, dried over $MgSO_4$, filtered, concentrated, and purified by silica gel chromatography to provide compound G.

Suitable $R^1$-$L^1$-LG compounds for use in this reaction include, but are not limited to, the following $R^1$-$L^1$-LG compounds: $R^1$—$C_{0-3}$-alkyl-C(=O)—Cl, $R^1$—$C_{0-3}$-alkyl-S(=O)$_2$—Cl, $R^1$—$C_{0-3}$-alkyl-OC(=O)—Cl, $R^1$—$C_{0-3}$-alkyl-$NR^{10}$—C(=O)—Cl, and $R^1$—$C_{0-3}$-alkyl-$NR^{10}$—S(=O)$_2$—Cl.

General Procedure 3—Reduction

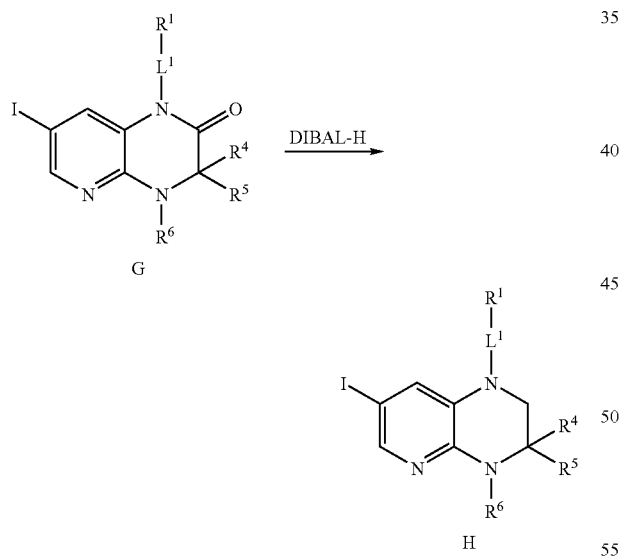

Compound G is suspended in anhydrous $CH_2Cl_2$ and cooled to 0° C. DIBAL (8.0 eq) is added and the resulting solution is allowed to warm to room temperature over 16 hours. The reaction mixture is quenched with methanol and a saturated solution of potassium sodium tartrate is added. The resulting mixture is stirred at room temperature until the phases separated (about two (2) hours). The organic phase is isolated, dried over $MgSO_4$, filtered, and concentrated. The product (H; $R^2$,$R^3$=H) is purified via silica gel chromatography.

General Procedure 4—Suzuki Coupling

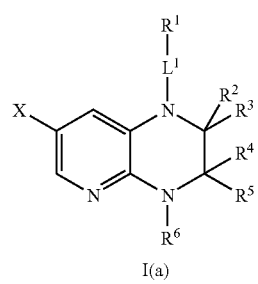

A. The iodo starting material (H), a suitable boronic acid (R=H) or boronate ester (R=alkyl) (1.2-2.0 eq), $Pd(PPh_3)_4$ (0.02-0.05 eq), and 2 M $Na_2CO_3$ (2.5 eq) are combined in a mixture of toluene/ethanol (6:1, v/v). The reaction mixture is heated to 80° C. for 1-16 hours. The reaction mixture is then diluted with $CH_2Cl_2$, dried over $MgSO_4$, filtered, and concentrated. The product (I(a)) is then purified via silica gel chromatography; or B. The iodo starting material (H), a suitable boronic acid or boronate ester (1.5 eq-2.0 eq), and $PdCl_2(PPh_3)_2$ (0.1 eq) are dissolved in tetrahydrofuran (6 mL). Potassium carbonate powder (5.0 eq.) is dissolved in water (6 mL) in a separate flask. The potassium carbonate solution is added to the boronic acid solution, and the resulting mixture is purged with nitrogen and stirred at 70° C. for one (1) hour. The reaction mixture is concentrated, and methylene chloride and water are added. The organic phase is isolated, washed with saturated sodium bicarbonate solution and brine, dried with magnesium sulfate, filtered and concentrated. The product of Formula I(a) is then purified by normal phase column chromatography.

Suitable boronic acids or boronate esters include, but are not limited to, those in which the X group of the X—B(OR)$_2$ reagent is linked to the boron atom of the X—B(OR)$_2$ reagent via an alkyl, aryl, heteroaryl, or alkenyl C—B bond.

Alternative reaction conditions include, but are not limited to, the following:

(a) Reaction of a heteroaryl boronic acid with compound H in dioxane/water (2:1) at 100° C. for 18 hours in the presence of $Pd_2$(dibenzylideneacetone)$_3$ (1 mol-%), P(cyclohexyl)$_3$ (2.4 mol-%) and $K_3PO_4$ (1.7 eq). (See Kudo, N. et al., *Angew. Chem. Int. Ed.*, 2006, 45, 1282-1284); and (b) Reaction of a vinyl or alkenyl boronic acid with compound H in tert-amyl alcohol at room temperature for 24 hours in the presence of Pd(acetate)$_2$ (5 mol-%), P(tert-butyl)$_2$CH$_3$ or [HP(tert-butyl)$_2$CH$_3$]BF$_4$ (0.1 eq) and KOtert-butyl (3 eq). (See Kirchhoff, J. H. et al., *J. Am. Chem. Soc.*, 2002, 124, 13662-13663).

General Procedure 5—Sonogashira Coupling

General Procedure 6—Rosenmund-von Braun Coupling

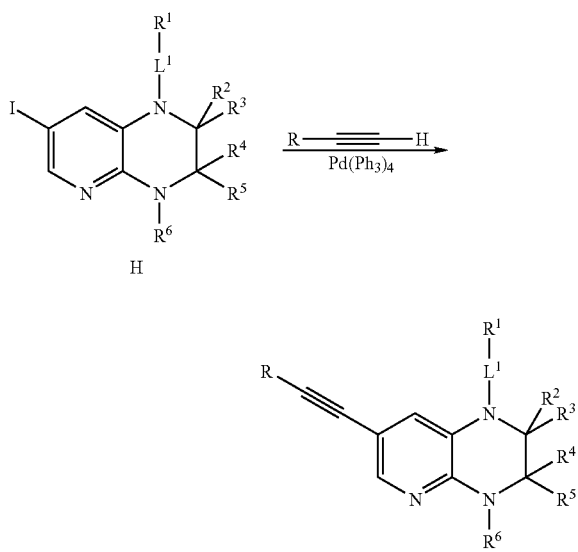

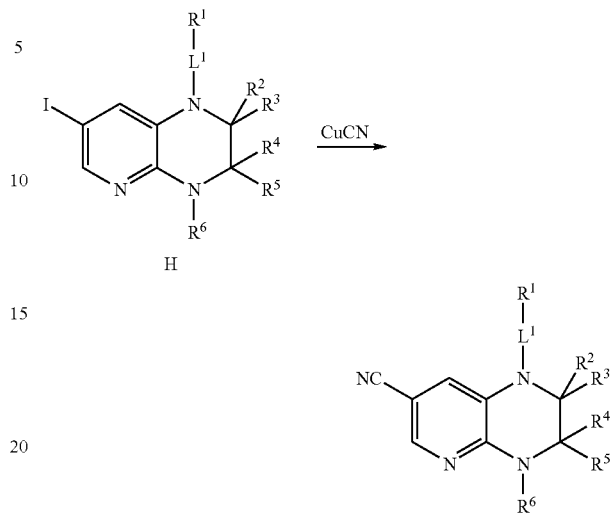

The iodo starting material (H), a suitable terminal alkyne (20 mg), tetrakis(triphenylphosphine) palladium (0.045 eq.), copper (I) iodide (9 mg), triethylamine (0.5 mL) and anhydrous tetrahydrofuran (1 mL) are combined in a Schlenk flask. The solution is purged with nitrogen, evacuated, stirred under nitrogen for 16 hours. The reaction mixture is concentrated, diluted with CH$_2$Cl$_2$, washed with H$_2$O, dried with magnesium sulfate, filtered and concentrated. The product is then purified by normal phase column chromatography.

The product may be converted to the corresponding alkenyl and alkyl compounds of Formula I(a) by reduction of the triple bond (e.g., catalytic hydrogenation or Na/NH$_3$).

The iodo starting material H is dissolved in anhydrous N,N-dimethylformamide. CuCN (2.0 eq) is added and the reaction mixture is heated to 120° C. in a microwave oven for 15 minutes. The reaction mixture is concentrated, diluted with CH$_2$Cl$_2$, and washed with H$_2$O/NH$_4$OH (10:1, v/v) to remove copper. The mixture is then filtered. The organic phase is dried over MgSO$_4$, filtered, and concentrated. The product is purified by silica gel chromatography.

As shown in Scheme 3, the —CN group of the product is a useful building block, which can be converted by standard chemical processes into a variety of linker groups (L$^2$). Examples include, but are not limited to, —C(=O)—C$_{0-3}$-alkyl-, —C(=O)NR$^{10}$—C$_{0-3}$-alkyl-, —C(=O)O—C$_{0-3}$-alkyl-, —CH$_2$—OC(=O)NR$^{10}$—C$_{0-3}$alkyl-, —CH$_2$—NR$^{10}$C(=O)O—C$_{0-3}$-alkyl-, —CH$_2$—NR$^{10}$—C$_{0-3}$-alkyl-, —CH$_2$—O—C$_{0-3}$-alkyl-, —CH$_2$—OC(=O)—C$_{0-3}$alkyl-, —CH$_2$—NR$^{10}$C(=O)—C$_{0-3}$-alkyl-, and —CH$_2$—NR$^{10}$S(=O)$_2$—C$_{0-3}$-alkyl-. (See Fleming, F. F. et al., *Tetrahedron*, 2005, 61, 747).

Scheme 3. Transformation of Cyano Group

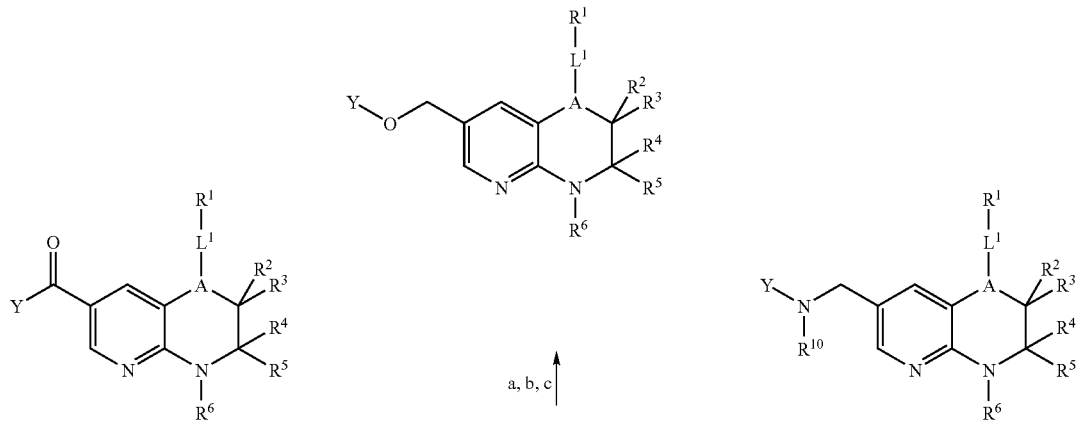

-continued

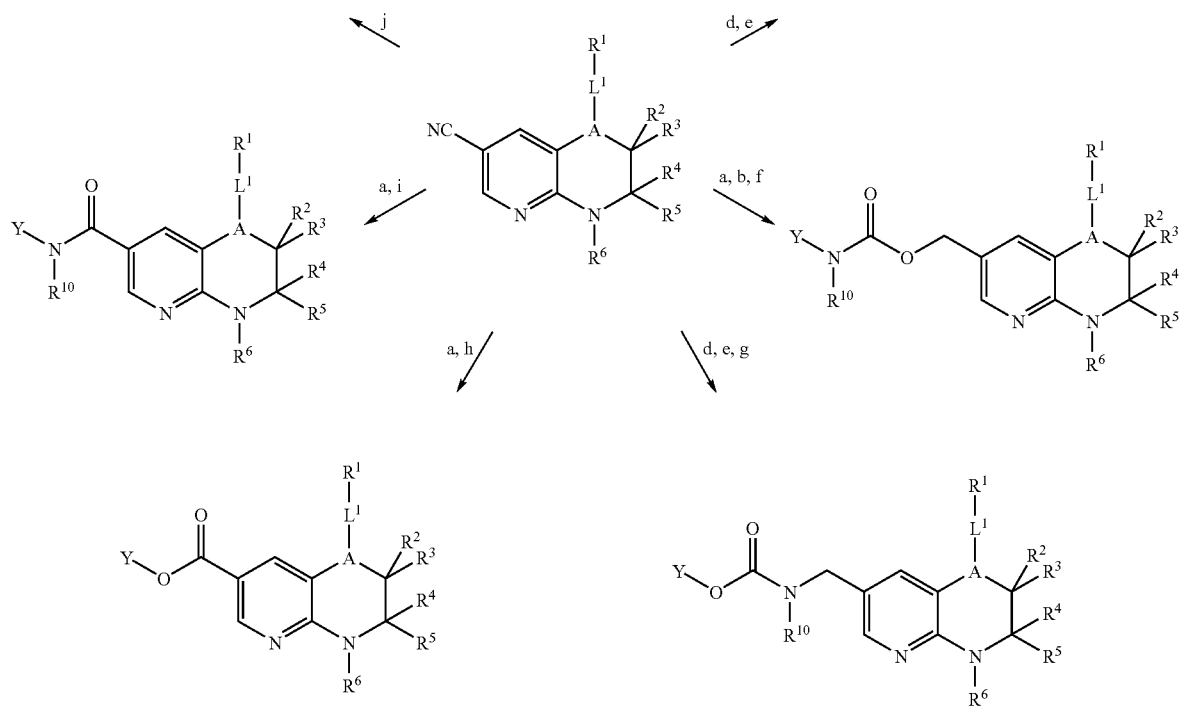

Y = ——C$_{0-3}$-alkyl-G$^1$L$^3$G$^2$L$^4$R$^7$

Conditions: a) basic hydrolysis (aqueous OH⁻ heat), b) NaBH$_4$, c) alkylation (Y—Br, base), d) DIBAL reduction,
e) reductive amination (NaCNBH$_3$, amine), f) reaction with Y—N=C=O, g) carbamate formation (YOC(=O)Cl or YOC(=O)OC(=O)Y, base) h) ester formation (acid, (Y—OH), i) amide coupling (e.g. EDCI, HOBT, TEA, DMF, (Y—NHR$^{10}$), j) Grignard reaction (Y—MgBr, CuI).

General Procedure 7—Saponification

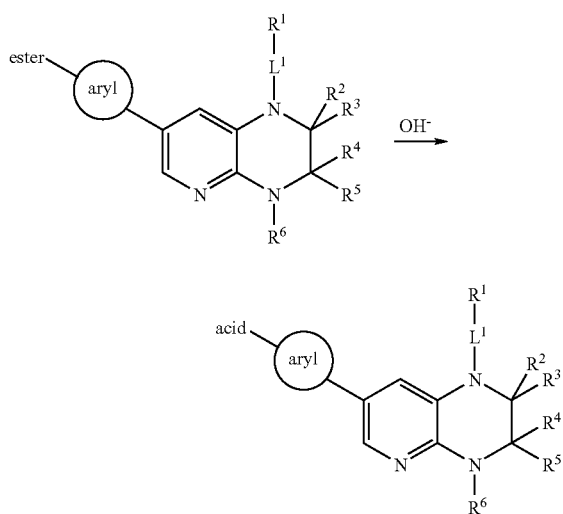

A suitable aryl ester starting material is heated with LiOH·H$_2$O (5 eq) in a mixture of tetrahydrofuran and H$_2$O (1:1, v/v) at 70° C. for 2 to 16 hours. The resulting solution is concentrated and neutralized with 1 N HCl. The resulting precipitate is filtered to obtain the product aryl carboxylic acid.

General Procedure 8—Amidation

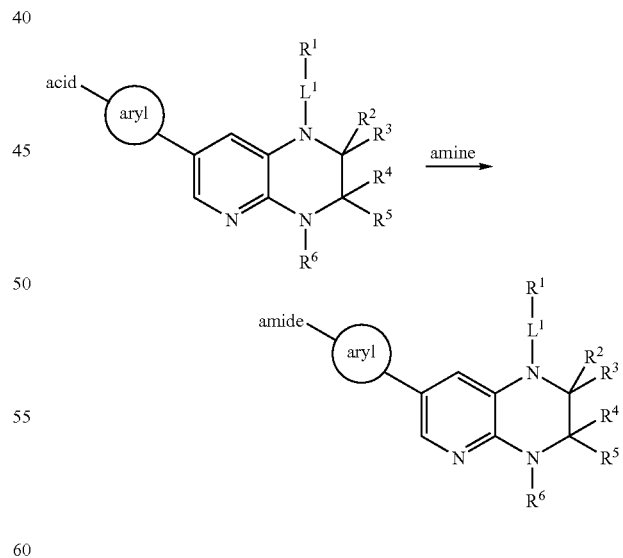

A suitable aryl carboxylic acid starting material is combined with N-(3-dimethylaminopropyl)-N'-ethylcarbodiimide hydrochloride (2.0 eq), 1-hydroxybenzotriazole (1.7 eq), and triethylamine (1.4 eq) in anhydrous N,N-dimethylformamide. The resulting mixture is stirred at room temperature for 30 minutes, a suitable amine is added, and the mixture is stirred for 3-16 hours. The reaction mixture is then concentrated, diluted with CH$_2$Cl$_2$, washed with H$_2$O, and dried over MgSO$_4$. The product amide is purified via silica gel chromatography or reversed-phase preparative HPLC.

The amidation reaction of General Procedure 8 may also be used to prepare amide boronates for use in the Suzuki coupling reaction (General Procedure 4). For example, Scheme 4 shows the amidation of 4-(4,4,5,5-tetramethyl-[1,3,2]dioxaborolan-2-yl)benzoic acid, which is commercially available from Sigma-Aldrich Corp. (St. Louis, Mo.), by reaction with 4-(pyrrolidin-1-yl)piperidine using the reaction conditions of General Procedure 8.

Scheme 4. Synthesis of Amide Boronates

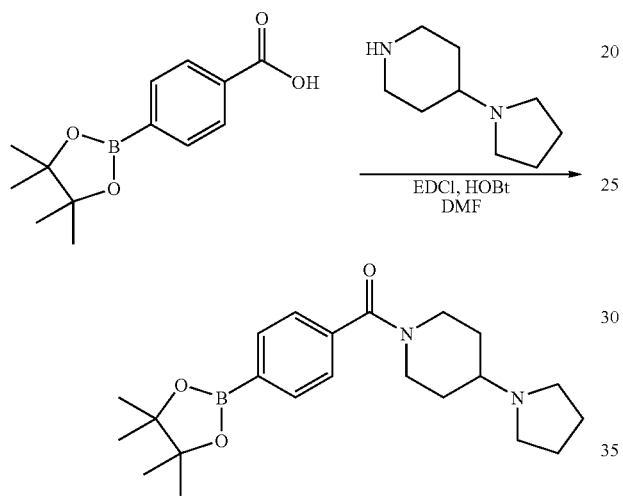

General Procedure 9—Hydrolysis

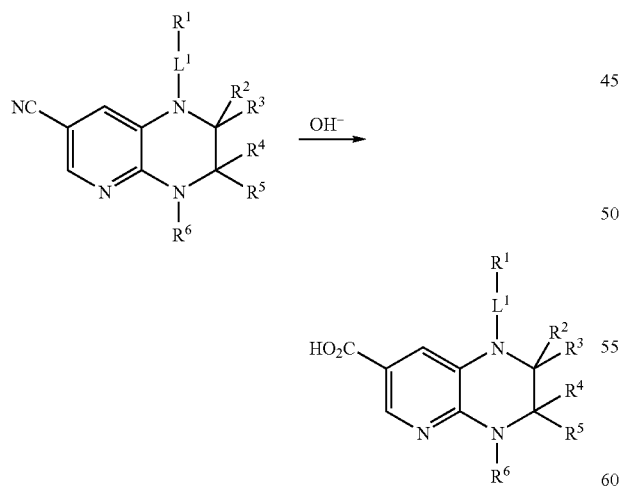

A suitable cyano starting material is suspended in a mixture of NaOH (10 N), H$_2$O, and ethanol (1:1:1, v/v/v) and heated to 80° C. for 16 hours. The reaction mixture is diluted with H$_2$O and neutralized with HCl. The resulting carboxylic is isolated (e.g., by filtration).

General Procedure 10—Amidation

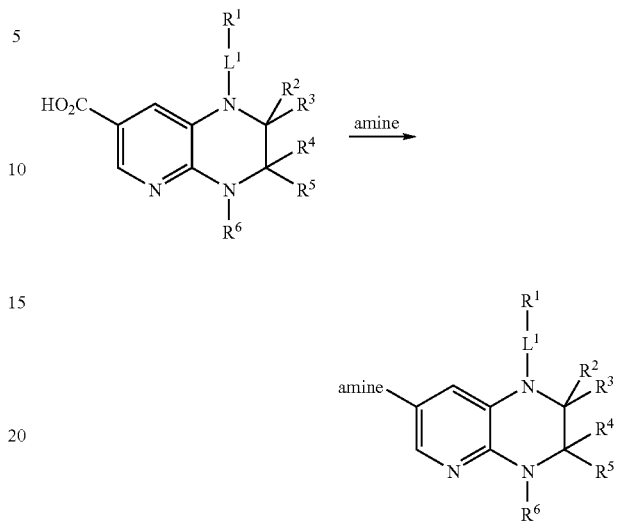

To a mixture of a suitable carboxylic acid starting material (1.3 eq) in anhydrous dimethylacetamide (DMA, 0.3 mL) is added polystyrene-supported dicyclohexylcarbodiimide (DCC, 6.0 eq) followed by a solution of N-hydroxybenzotriazole in DMA (300 mM, 1.5 eq). The reaction mixture is thoroughly mixed and allowed to stand at room temperature for 15 minutes. The reaction mixture is then treated with a 0.10 M solution of a suitable amine (1.0 eq) and heated with 250 W microwave pulses to 60° C. The reaction mixture is then cooled to room temperature and treated with resin bound macroporous carbonate (acid scavenger) overnight. The reaction mixture is filtered, the solid is washed twice with DMA (200 µL) followed by acetonitrile (200 µL). The combined washes are evaporated under reduced pressure to afford the amide product.

General Procedure 11—Sulfonamide Boronate Synthesis

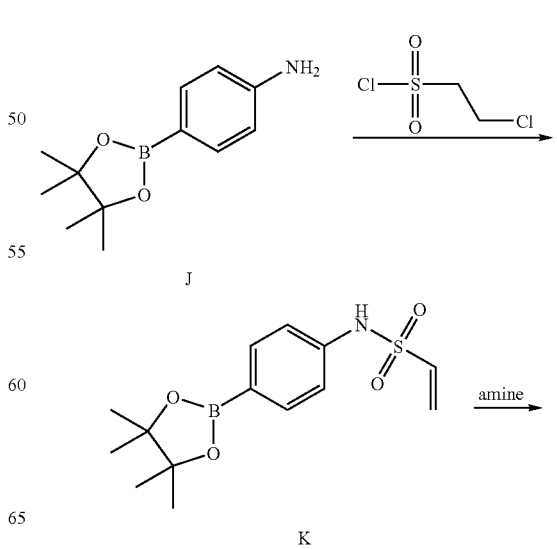

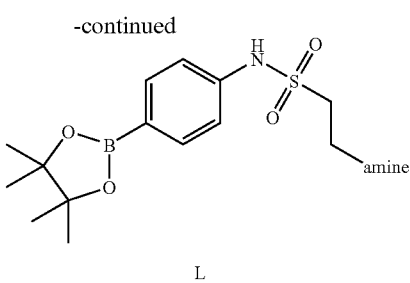

L 4-(4,4,5,5-tetramethyl-[1,3,2]dioxaborolan-2-yl)phenylamine (J) is dissolved in CH$_2$Cl$_2$ and N-methyl morpholine (3 eq) is added. The reaction mixture is cooled to 0° C. and 2-chloroethanesulfonyl chloride (1.1 eq) is added dropwise. The reaction mixture is allowed to warm to room temperature and stirred for four (4) hours. The reaction mixture is then concentrated, diluted with ethyl acetate, washed with brine, dried over MgSO$_4$, concentrated, and purified through silica gel chromatography. The resulting ethenesulfonic acid [4-(4,4,5,5-tetramethyl-[1,3,2]dioxaborolan-2-yl)phenyl]amide (K) is dissolved in methanol and a suitable amine (2.5 eq) is added in methanol. The reaction mixture is stirred at room temperature for four (4) hours. Isocyanate resin is added to each vial to consume excess amine. After stirring overnight, the resin is filtered and the reaction solution concentrated to afford the desired sulfonamide boronate (L).

The overall scheme used to prepare compounds of Formula I in which A is carbon (i.e., compounds of Formula I(b)) is generically set forth in Schemes 5-12.

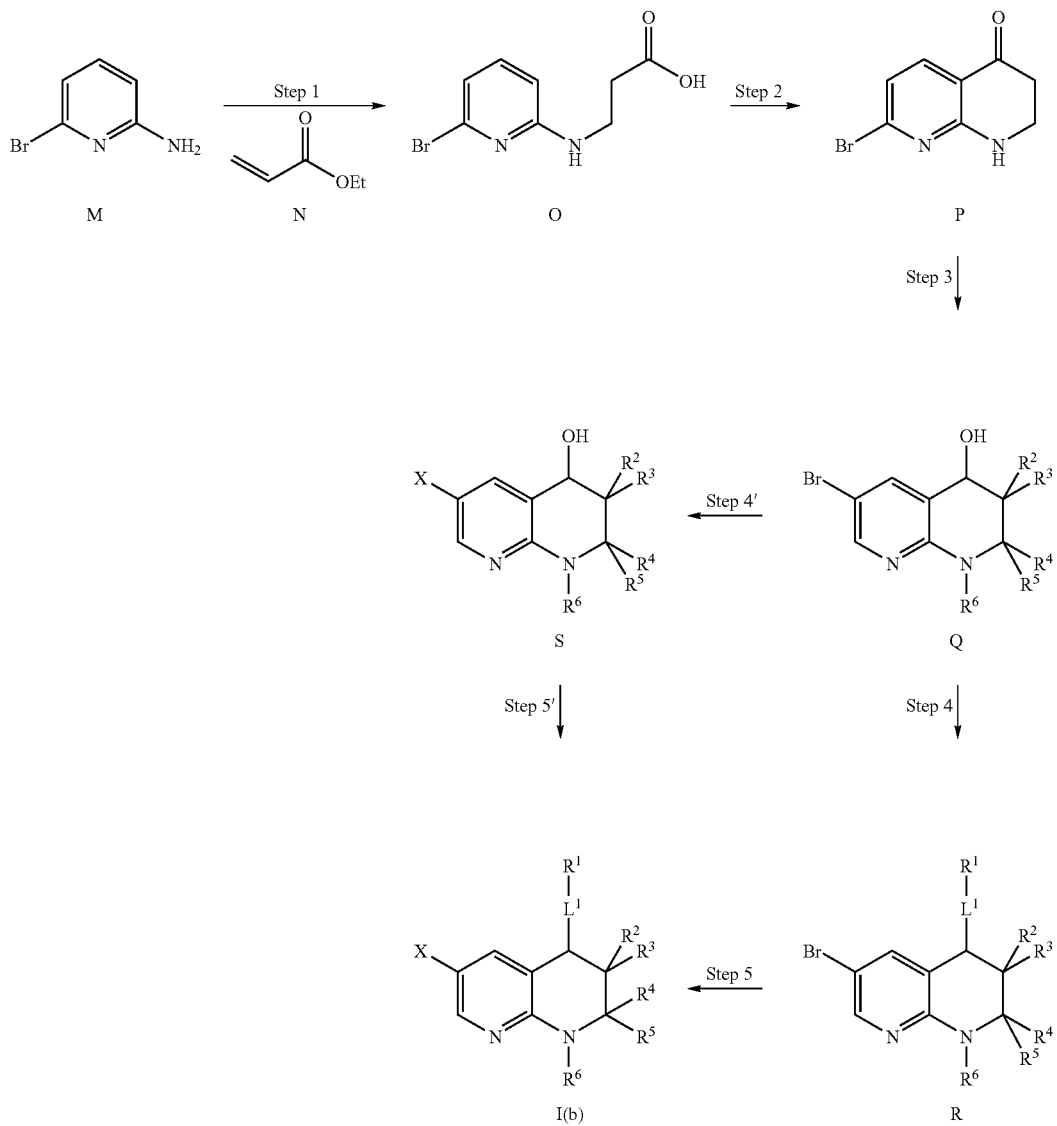

Scheme 5. Overall Synthesis: A = Carbon

In Step 1, 2-amino-5-bromopyridine (M) is converted to 3-(6-bromo-pyridin-2-ylamino)propionic acid (O) by reaction with ethyl acrylate (N). This process is described in Settimo, D. A. et al., *Il Farmaco—Ed. Sc.*, 1978, 33(10), 770-80, which is incorporated herein by reference in its entirety. 2-amino-5-bromopyridine is commercially available from Sigma-Aldrich Corp. (St. Louis, Mo.).

In Step 2, the aryl carboxylic acid O is treated with Eaton's reagent to afford 7-bromo-2,3-dihydro-1H-[1,8]naphthyridin-4-one (P).

In Step 3, compound P is reduced (NaBH$_4$), debrominated (n-BuLi), and rebrominated (N-bromosuccinimide) to form compound Q. Optionally, the carbonyl group of compound P can be converted to an enolate and then substituted with R$^2$/R$^3$ groups prior to the reduction reaction. Optionally, compound P can be transformed into the corresponding α,β-unsaturated ketone (e.g., by conversion to an α-selenoxide or α-sulfoxide intermediate followed by elimination) and then substituted at the β-position with R$^4$/R$^5$ groups (e.g., via a Michael addition reaction) prior to the reduction reaction. Optionally, an R$^6$ group can be introduced (e.g., by N-alkylation) prior to the reduction reaction. Compound Q may be converted to a compound of Formula I(b) by steps 4 and 5 or 4' and 5'.

In Step 4, compound Q is converted to compound R by introduction of an R$^1$-L$^1$ group. The conversion may be accomplished by a variety of methods known to those of ordinary skill in the art. For example, the benzylic hydroxyl group of compound Q may be activated by conversion to the corresponding tosylate, mesylate, triflate, or halide intermediate and then displaced with a nucleophilic R$^1$-L$^1$ group or a nucleophilic derivative of a R$^1$-L$^1$ group, such as an organolithium or organometallic derivative (e.g., Grignard, lithium, lithium dialkylcopper, aluminum, or boron derivatives) (See March, J., "Advanced Organic Chemistry," 3d ed., John Wiley & Sons, Inc., 1985, pp. 400-404, 407; Luh, T-Y et al., *Chem. Rev.*, 2000, 100, 3187-3204) (See Scheme 6). A displacement reaction useful in Step 4 is described in General Procedure 12 (below).

In addition, Step 4 may be performed by coupling the hydroxyl group of compound Q to a suitable carbonyl chloride reagent. Suitable carbonyl chloride reagents include, but are not limited to, Cl—C(=O)—C$_{0-3}$-alkyl-R$^1$ and Cl—C(=O)NR$^{10}$—C$_{0-3}$-alkyl-R$^1$, which result in products of Formula R in which L$^1$-R$^1$ is —OC(=O)—C$_{0-3}$-alkyl-R$^1$ and —OC(=O)NR$^{10}$—C$_{0-3}$-alkyl-R$^1$, respectively.

In Step 5, compound R is converted to a compound of Formula I (A=carbon) by introduction of an X group. The conversion may be performed using a transition metal mediated coupling reaction (met=Pd, Cu, etc.). A coupling reaction useful in Step 4' is described in General Procedure 13 (below). The coupling reactions in General Procedures 4, 5, and 6 (above) are also useful for preparing the corresponding compounds of Formula I(b).

Steps 4' and 5' are the same as Steps 5 and 4, respectively.

Scheme 6. Overall Synthesis: A = Carbon, R$^1$L$^1$ = Nucleophile

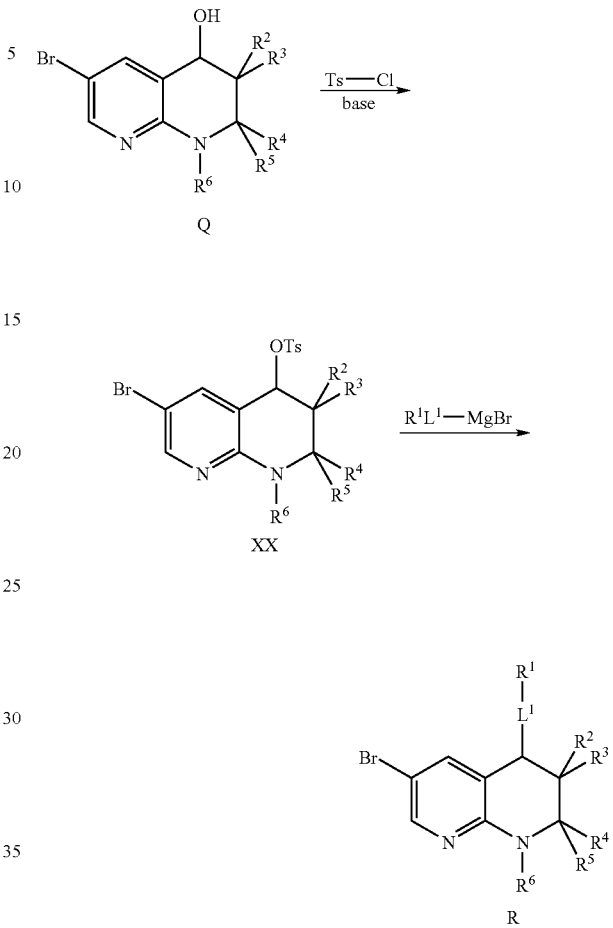

In the first step, compound Q is reacted with p-toluenesulfonyl chloride (tosyl chloride) to form the activated tosylate XX. Other activating groups that can be used instead of tosylate include, but are not limited to, mesylate, triflate, and halide.

In the second step, compound XX is reacted with a suitable Grignard reagent (R$^1$L$^1$-MgBr) or another suitable organometallic reagent to form compound R. Suitable organometallic reagents include, but are not limited to, R$^1$-L$^1$-Li, R$^1$-L$^1$-MgBr, and (R$^1$-L$^1$)$_2$CuLi, wherein R$^1$-L$^1$- is —C$_{1-3}$-alkyl-C(=O)—C$_{0-3}$-alkyl-R$^1$, —C$_{1-3}$-alkyl-S(=O)$_n$—C$_{0-3}$-alkyl-R$^1$, —C$_{1-3}$-alkyl-C(=O)NR$^{10}$—C$_{0-3}$-alkyl-R$^1$, R$^1$—C$_{0-3}$-alkyl-C(=O)NR$^{10}$—C$_{1-3}$-alkyl-, —C$_{1-3}$-alkyl-S(=O)$_2$NR$^{10}$—C$_{0-3}$-alkyl-R$^1$, R$^1$—C$_{0-3}$-alkyl-S(=O)$_2$NR$^{10}$—C$_{1-3}$-alkyl-, —C$_{1-3}$-alkyl-C(=O)O—C$_{0-3}$-alkyl-R$^1$, R$^1$—C$_{0-3}$-alkyl-C(=O)O—C$_{1-3}$-alkyl-, —C$_{1-3}$-alkyl-OC(=O)NR$^{10}$—C$_{0-3}$-alkyl-R$^1$, R$^1$—C$_{0-3}$-alkyl-OC(=O)NR$^{10}$—C$_{1-3}$-alkyl-, —C$_{1-3}$-alkyl-NR$^{10}$—C$_{0-3}$-alkyl-R$^1$, —C$_{1-3}$-alkyl-O—C$_{0-3}$-alkyl-R$^1$, —C$_{1-6}$-alkyl-R$^1$, —C$_{2-6}$-alkenyl-R$^1$, or —C$_{2-6}$-alkynyl-R$^1$.

Scheme 7. Overall Synthesis: A = Carbon, $L^1 = $ —CH$_2$—

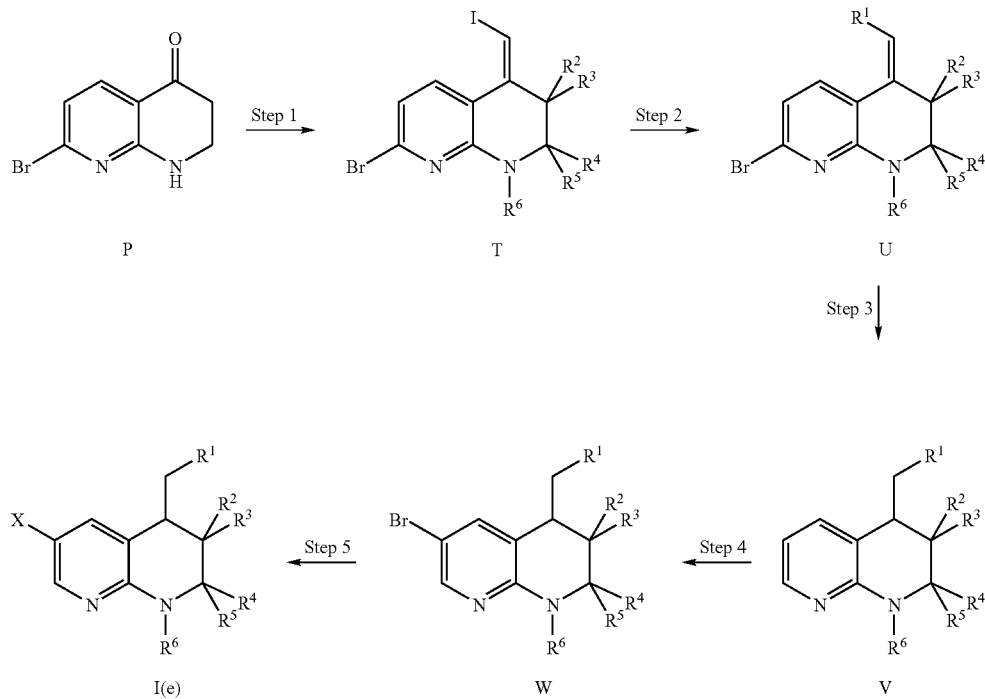

In Step 1, compound P (Scheme 5) is converted to compound T by means of a Takai reaction. Optionally, the carbonyl group of compound P can be converted to an enolate and then substituted with $R^2/R^3$ groups prior to the Takai reaction. Optionally, compound P can be transformed into the corresponding α,β-unsaturated ketone (e.g., by conversion to an α-selenoxide or α-sulfoxide intermediate followed by elimination) and then substituted at the β-position with $R^4/R^5$ groups (e.g., via a Michael addition reaction) prior to the Takai reaction. Optionally, an $R^6$ group can be introduced (e.g., by N-alkylation) prior to the Takai reaction.

In Step 2, compound T is converted to compound U via a transition metal catalyzed coupling reaction (e.g., a Suzuki reaction).

In Step 3, compound U is hydrogenated and debrominated by hydrogenolysis to form compound V.

In Step 4, compound V is brominated to form compound W.

In Step 5, compound W is converted to compound I(e) via a transition metal catalyzed coupling reaction (See General Procedures 4-6 and 13).

Scheme 8. Overall Synthesis: A = Carbon, $L^1 = $ —NR$^{10}$—C$_{0-3}$-alkyl-R$^1$

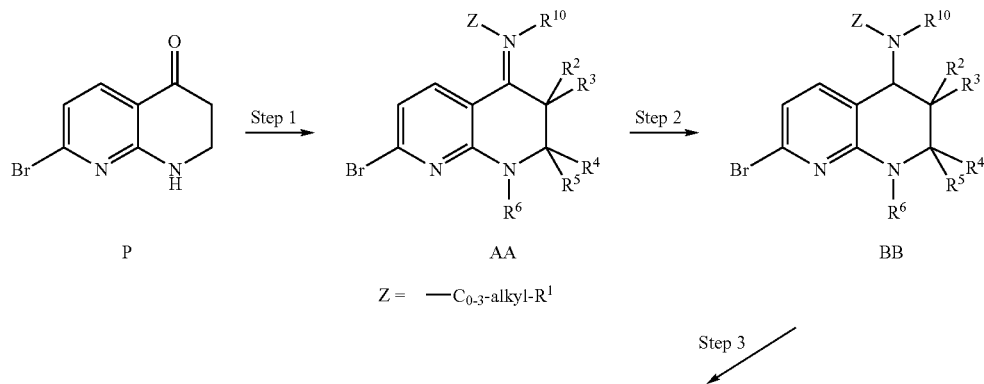

$Z = $ —C$_{0-3}$-alkyl-R$^1$

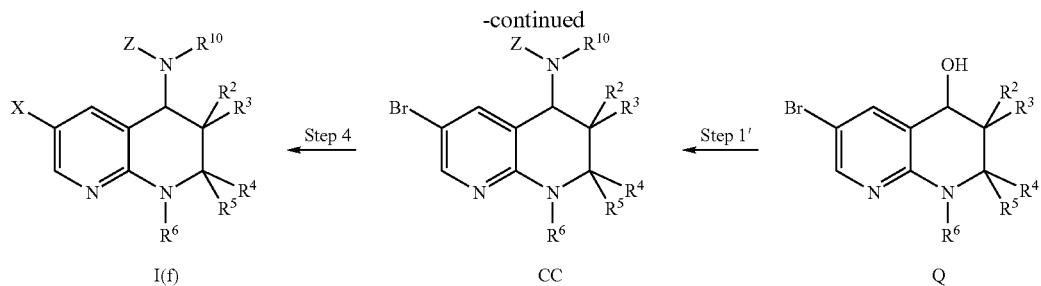

In Step 1, compound P (Scheme 5) is converted to an imine or iminium of Formula AA by means of a condensation reaction with an amine of formula Z-NH—$R^{10}$. Optionally, the carbonyl group of compound P can be converted to an α-enolate and then substituted at the α-position with $R^2/R^3$ groups prior to the condensation reaction. Optionally, compound P can be transformed into the corresponding α,β-unsaturated ketone (e.g., by conversion to an α-selenoxide or α-sulfoxide intermediate followed by elimination) and then substituted at the β-position with $R^4/R^5$ groups (e.g., via a Michael addition reaction) prior to the condensation reaction. Optionally, an $R^6$ group can be introduced (e.g., by N-alkylation) prior to the condensation reaction.

In Step 2, compound AA is converted to compound BB by means of a reduction. Steps 1 and 2 may be combined into a single step (i.e. a reductive amination).

In Step 3, compound BB is converted to compound CC by means of debromination/rebromination (e.g., as in Scheme 5, Step 3).

In addition, when Z=H the —$NHR^{10}$ group of compound BB may be coupled to a suitable carbonyl or sulfonyl chloride reagent to form additional compounds of Formula CC. Suitable carbonyl or sulfonyl chloride reagents include, but are not limited to, $R^1$—$C_{0-3}$-alkyl-C(=O)—Cl, $R^1$—$C_{0-3}$-alkyl-S(=O)$_2$—Cl, or $R^1$—$C_{0-3}$-alkyl-OC(=O)—Cl, which result in products of Formula CC in which $L^1$-$R^1$ is $R^1$—$C_{0-3}$-alkyl-C(=O)$NR^{10}$—, $R^1$—$C_{0-3}$-alkyl-S(=O)$_2$$NR^{10}$—, or $R^1$—$C_{0-3}$-alkyl-OC(=O)$NR^{10}$—, respectively.

In Step 4, compound CC is converted to compound I(f) (e.g., as in Scheme 5, Step 5).

Alternatively, in Step 1′, compound CC may be prepared from compound Q by activation of compound Q (e.g., by transformation to the corresponding benzylic halide, alkyl sulfonate or aryl sulfonate as in Scheme 5, Step 4) prior to treatment with an amine of formula Z-NH—$R^{10}$.

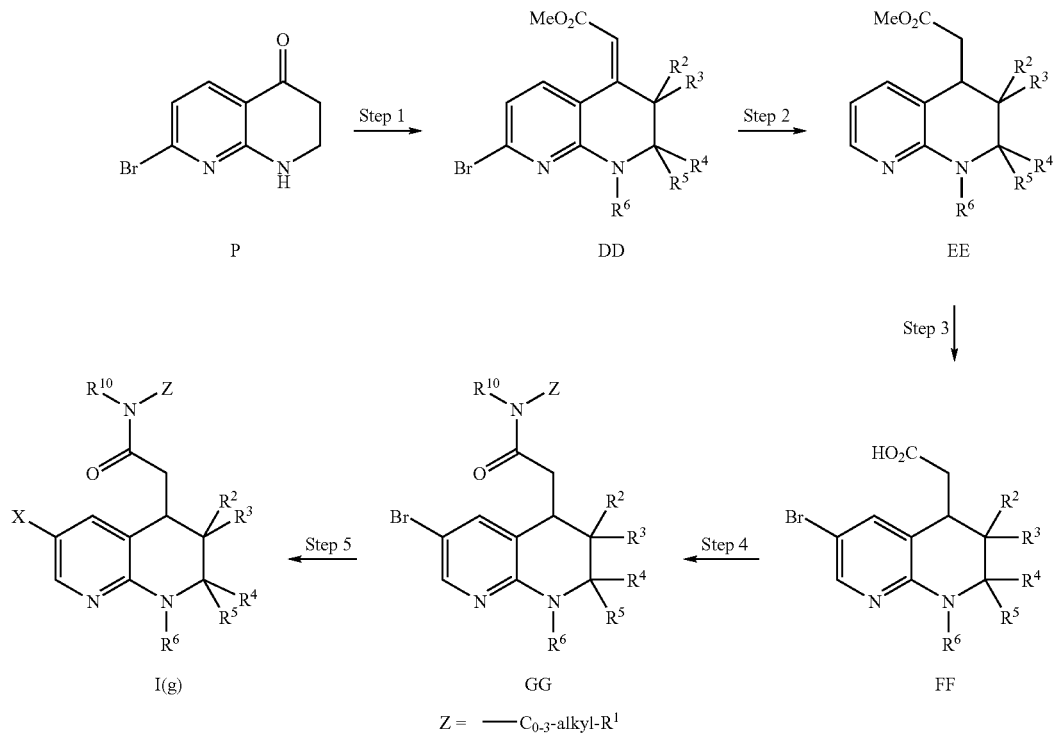

In Step 1, compound P (Scheme 5) is converted to compound DD by means of a Horner-Emmons reaction. Optionally, $R^2$, $R^3$, $R^4$, $R^5$ and/or $R^6$ groups may be introduced prior to the Horner-Emmons reaction as in Scheme 8.

In Step 2, compound DD is converted to compound EE by means of hydrogenation of the double bond and debromination by hydrogenolysis or metallation/protonation (Scheme 5, Step 3).

In Step 3, compound EE is brominated and hydrolyzed to form compound FF. Optionally, compound FF may be alkylated α to the carbonyl group prior to the coupling step with one or two methyl groups or an ethyl group (e.g., by treatment with base and then methyl bromide).

In Step 4, compound FF is coupled with an amine of formula Z-NH-$R^{10}$ to form compound GG.

In Step 5, compound GG is converted to compound I(g) (e.g., as in Scheme 5, Step 5).

Scheme 10. Overall Synthesis:

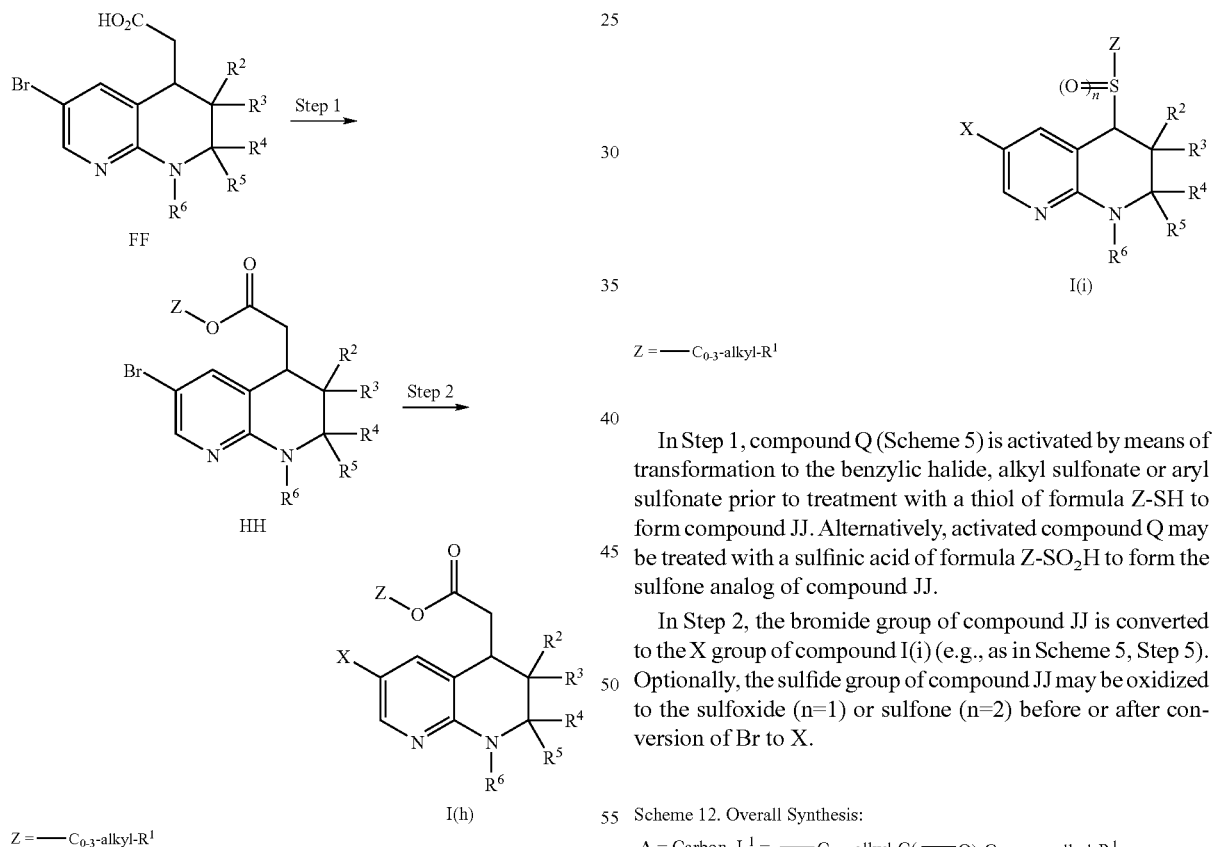

In Step 1, compound FF (Scheme 9) is esterified with Z-OH to form compound HH.

In Step 2, compound HH is converted to compound I(h) (e.g., as in Scheme 5, Step 5).

Optionally, compound FF or HH may be alkylated α to the carbonyl group prior to Steps 1 or 2 with one or two methyl groups or an ethyl group (e.g., by treatment with base and then methyl bromide).

Scheme 11. Overall Synthesis:

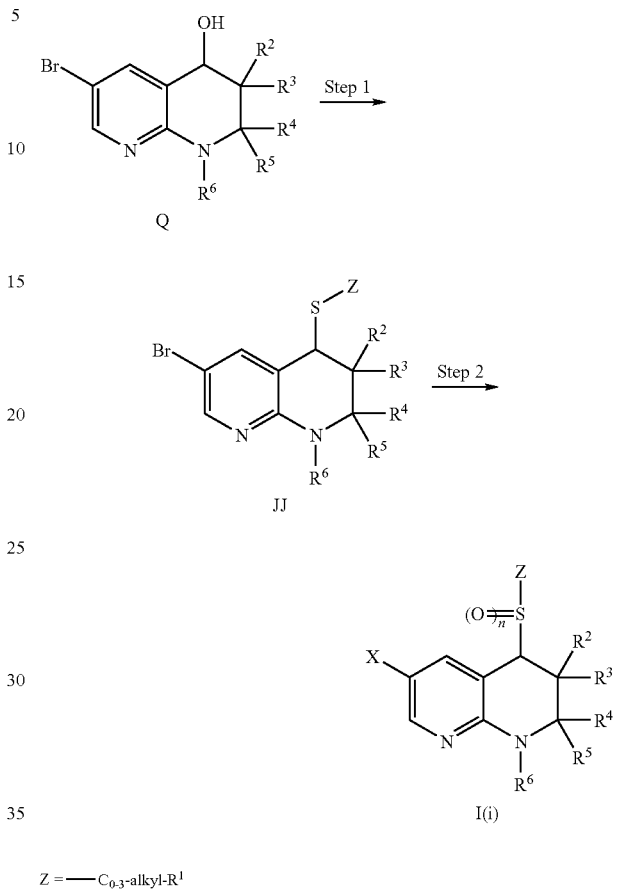

In Step 1, compound Q (Scheme 5) is activated by means of transformation to the benzylic halide, alkyl sulfonate or aryl sulfonate prior to treatment with a thiol of formula Z-SH to form compound JJ. Alternatively, activated compound Q may be treated with a sulfinic acid of formula Z-SO$_2$H to form the sulfone analog of compound JJ.

In Step 2, the bromide group of compound JJ is converted to the X group of compound I(i) (e.g., as in Scheme 5, Step 5). Optionally, the sulfide group of compound JJ may be oxidized to the sulfoxide (n=1) or sulfone (n=2) before or after conversion of Br to X.

Scheme 12. Overall Synthesis:

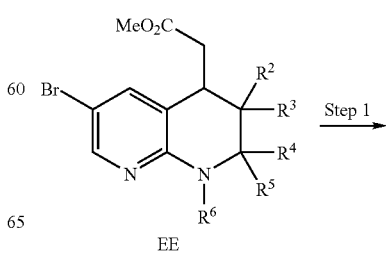

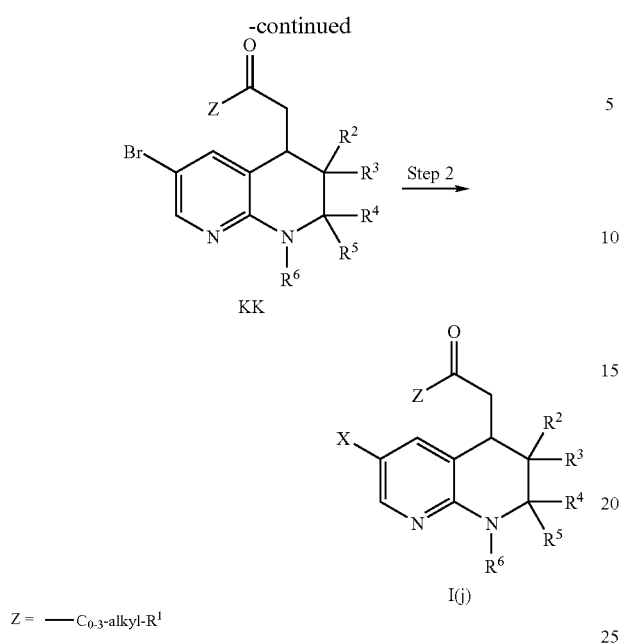

Z = —— $C_{0-3}$-alkyl-$R^1$

In Step 1, compound EE (Scheme 9) is converted to compound KK by reaction with an organometallic reagent such as a Grignard or organolithium reagent (e.g., Z-MgBr or Z-Li).

In Step 2, compound KK is converted to compound I(j) (e.g., as in Scheme 5, Step 5).

Optionally, compound EE or KK may be alkylated α to the carbonyl group prior to Steps 1 or 2 with one or two methyl groups or an ethyl group (e.g., by treatment with base and then methyl bromide).

General Procedure 12—Mitsunobu Reaction

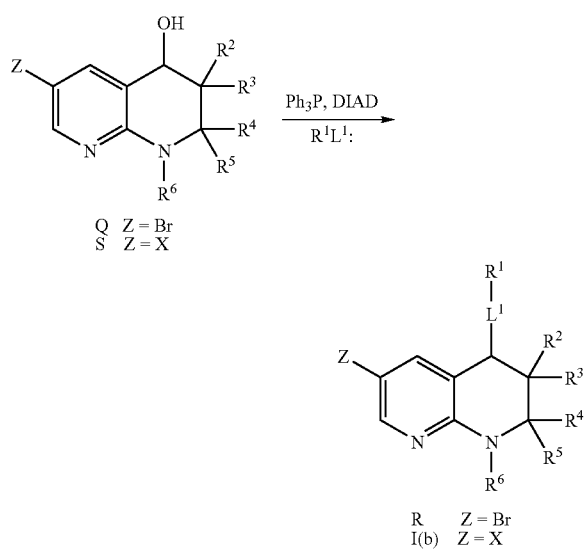

The starting benzyl alcohol (Q or S) (1 eq) is combined with a suitable nucleophile ($R^1L^1$:) (1-3.0 eq) and triphenylphosphine (1-3.0 eq) in anhydrous tetrahydrofuran. Diisopropylazodicarboxylate (3.0 eq) is added and the reaction mixture stirred at room temperature for 15 minutes. The mixture is then concentrated under reduced pressure and purified by silica gel chromatography to afford the desired product (R or I(b)).

General Procedure 13—Suzuki Coupling

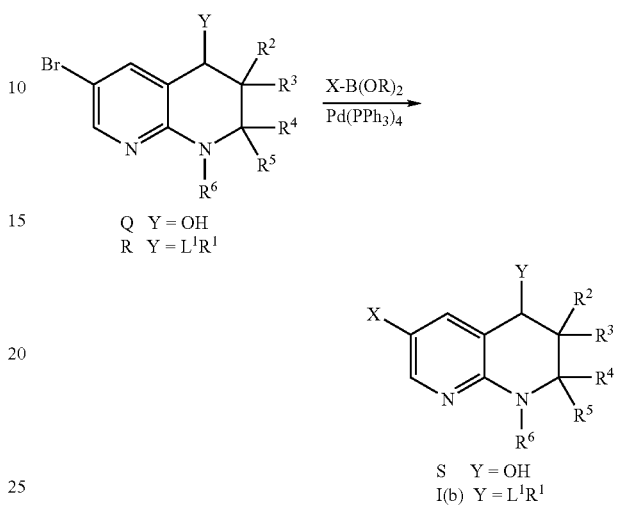

The starting bromide (Q or R) (1.0 eq) is combined with a suitable boronic acid or boronic ester (1.4 eq) and Pd(PPh$_3$)$_4$ (0.05 eq) in a mixture of toluene and ethanol (1-5:1, v/v). Sodium carbonate Na$_2$CO$_3$ (2N, 4.0 eq) is added and the reaction mixture is heated at 80-100° C. for 0.5 to 24 hours. Two purification procedures may be followed. In the first procedure, the mixture is concentrated under reduced pressure, and the residue is taken up in methylene chloride and washed with water. The organic phase is dried over sodium sulfate, filtered, and concentrated under reduced pressure, and purified by silica gel chromatography to afford the desired product (S or I(b)). In the second procedure, the crude reaction mixture is cooled, directly concentrated onto silica gel, and purified by silica gel chromatography to afford the desired product (S or I(b)).

VI. Biology

ALK Kinase Assay

Example compounds were tested for their ability to inhibit the kinase activity of baculovirus-expressed ALK using a modification of the ELISA protocol reported for trkA in Angeles, T. S. et al., *Anal. Biochem.* 1996, 236, 49-55, which is incorporated herein by reference in its entirety. Phosphorylation of the substrate, phospholipase C-gamma (PLC-γ) generated as a fusion protein with glutathione S-transferase (GST) as reported in Rotin, D. et al., *EMBO J.* 1992, 11, 559-567, which is incorporated herein by reference in its entirety, was detected with a europium-labeled anti-phosphotyrosine antibody and measured by time-resolved fluorescence (TRF). Briefly, each 96-well plate was coated with 100 μL/well of 10 μg/mL substrate (phospholipase C-γ) in Tris-buffered saline (TBS). The assay mixture (total volume=100 μL/well) consisting of 20 mM HEPES (pH 7.2), 1 μM ATP ($K_m$ level), 5 mM MnCl$_2$, 0.1% BSA, 2.5% DMSO, and various concentrations of test compound was then added to the assay plate. The reaction was initiated by adding enzyme (30 ng/ml ALK) and was allowed to proceed at 37° C. for 15 minutes. Detection of the phosphorylated product was performed by adding 100 μl/well of Eu-N1 labeled PT66 antibody (Perkin Elmer # AD0041). Incubation at 37° C. then proceeded for one (1) hour, followed by addition of 100 μL enhancement solution (Wallac #1244-105). The plate was gently agitated and after thirty minutes, the fluorescence of the resulting solution was measured using the EnVision 2100 (or 2102) multilabel plate reader (Perkin Elmer).

Data analysis was performed using ActivityBase (IDBS, Guilford, UK). $IC_{50}$ values were calculated by plotting percent inhibition versus $log_{10}$ of the concentration of compound and fitting to the nonlinear regression sigmoidal dose-response (variable slope) equation in XLFit (IDBS, Guilford, UK).

c-Met Kinase Assay

The kinase activity of c-Met was evaluated using the same methods as for ALK, with the following modifications: Plates were coated with 20 μg/mL phospholipase C-γ and the assay mixture consisted of 50 mM HEPES (pH 7.2), 50 mM NaCl, 3 μM ATP ($K_m$ level), 4 mM $MnCl_2$, 0.01% TritonX-100, 0.02% BSA, 2.5% DMSO. Reactions were initiated with 30 ng/mL c-Met (cytoplasmic domain, Invitrogen Corporation #PV3143).

ALK Cellular Assay

Immunoblotting of phospho-NPM-ALK and total NPM-ALK from cell lysates was carried out according to the protocols provided by the antibody suppliers. In brief, after treatment of Example compounds, cells were lysed in Frak lysis buffer [10 mM Tris, pH 7.5, 1% Triton X-100, 50 mM sodium chloride, 20 mM sodium fluoride, 2 mM sodium pyrophosphate, 0.1% BSA, plus freshly prepared 1 mM activated sodium vanadate, 1 mM dithiothreitol (#165680050, ARCOS Organics, Geel, Belgium), and 1 mM PMSF (#837091, Boehringer Mannheim Biochemicals, Indianapolis, Ind.), protease inhibitors cocktail III (#539134-1Set, Calbiochem, 1:100 dilution)]. After brief sonication, the lysates were cleared by centrifugation, mixed with sample buffer and subjected to SDS-PAGE. Following transfer to membranes, the membranes were blotted with either rabbit phospho-NPM-ALK(Y664) (Cat#3341) or ALK antibody (Cat#3342) from Cell Signaling Technology (Beverly, Mass.), and then the HRP-conjugated goat anti-rabbit antibodies (Santa Cruz, Calif.) after washed in TBS/0.2% Tween-20. The protein bands were visualized with ECL Western Blotting detection reagents (RPN2106, Amersham Biosciences, Buckinghamshire, UK) and quantitated with gel-pro analyzer 3.1 software.

To measure ALK tyrosine phosphorylation in cells with an ELISA assay, fluoronunc plates (Cat#437796, Nalge Nunc, Rochester, N.Y.) were pre-coated with goat anti-mouse IgG, and incubated with the capture mouse ALK antibody (Cat#35-4300, Zymed, Seattle, Wash.) diluted 1:1000 in Superblock (Pierce, Rockford, Ill.). Following blocking, cell lysates were added to plates and incubated overnight at 4° C. Plates were incubated with the detecting antibody, anti-phospho-ALK (Y664) (Cell Signaling Technology), diluted at 1:2000, followed by incubation with goat anti-rabbit-IgG alkaline phosphatase to amplify the detection. Wells were exposed to the fluorogenic substrate 4-MeUP (#3368-04-5, Calbiochem) and the signal quantified using a CytoFluor® (series 4000) Fluorescence Multi-Well Plate Reader (Applied Biosystems, Foster City, Calif.).

c-Met Cellular Assay

HT29 and GTL-16 cells were serum starved for one hour in media containing 0.05% BSA and varying concentrations of Example compounds (1-10 μM). A549 cells were serum starved overnight in media containing 0.05% BSA then treated for one hour with Example compounds followed by a 15 minute stimulation with 50 ng/mL HGF (Peprotech, Rocky Hill, N.J.), respectively. Samples were resolved by electrophoresis on a 3-8% Tris-Acetate gel (40 ma/gel) and then transferred to a nitrocellulose membrane. Membranes were blocked for one hour at room temperature in Odyssey Blocking Buffer (Licor #927-40000) diluted 1:1 with 1×TBS. Membranes were then co-incubated overnight at 4° C. with primary antibodies [total Met (Cell Signaling, #3127) and Phospho-Met (Biosource, #44-888G) 1:1000 each in Odyssey Blocking Buffer diluted 1:1 with 1×TBS-T 0.05%]. The next day, membranes were washed and co-incubated with secondary antibodies [Goat anti mouse IRDye800 (Rockland, #610-132-121) and Goat anti rabbit Alexa fluor 700 (Molecular Probes, #A21038) 1:10,000] in Odyssey Blocking Buffer diluted 1:1 with 1×TBS-T 0.05% for one hour at room temperature protected from light. Blots were then washed and read on the Odyssey Infrared Imager. Total c-Met signal was visualized at 800 nm detection and phospho-c-Met signal was visualized at 700 nm detection.

Results

Biological data for the Example compounds is presented in the following Tables 1-3.

| | |
|---|---|
| $IC_{50}$ > 100 μM | − |
| $IC_{50}$ 100 μM-10 μM | + |
| $IC_{50}$ 10 μM-1 μM | ++ |
| $IC_{50}$ 1 μM-0.1 μM | +++ |
| $IC_{50}$ < 0.1 μM | ++++ |
| Not tested | NT |

TABLE 1

ALK, c-Met Kinase Inhibition

| Example | c-Met | ALK |
|---|---|---|
| 1 | + | + |
| 2 | − | − |
| 3 | − | + |
| 4 | + | ++ |
| 5 | − | ++ |
| 6 | + | +++ |
| 7 | + | ++ |
| 8 | − | + |
| 9 | − | + |
| 10 | − | + |
| 11 | + | + |
| 12 | + | ++ |
| 13 | − | + |
| 14 | − | + |
| 15 | + | ++ |
| 16 | + | ++ |
| 17 | + | + |
| 18 | + | ++ |
| 19 | + | ++ |
| 20 | + | ++ |
| 21 | − | + |
| 22 | − | − |
| 23 | + | ++ |
| 24 | − | ++ |
| 25 | + | ++ |
| 26 | + | ++ |
| 27 | + | + |
| 28 | − | − |
| 29 | + | +++ |
| 30 | + | ++ |
| 31 | + | − |
| 32 | − | − |
| 33 | − | + |
| 34 | + | ++ |
| 35 | − | ++ |
| 36 | ++ | +++ |
| 37 | + | ++ |
| 38 | +++ | +++ |

TABLE 1-continued

ALK, c-Met Kinase Inhibition

| Example | c-Met | ALK |
|---|---|---|
| 39 | + | ++ |
| 40 | − | − |
| 41 | − | − |
| 42 | − | − |
| 43 | + | − |
| 44 | + | − |
| 45 | − | ++ |
| 46 | + | + |
| 47 | + | + |
| 48 | ++ | +++ |
| 49 | + | +++ |
| 50 | − | +++ |
| 51 | + | +++ |
| 52 | + | + |
| 53 | + | − |
| 54 | + | − |
| 55 | − | + |
| 56 | + | ++ |
| 57 | +++ | +++ |
| 58 | + | +++ |
| 59 | + | +++ |
| 60 | ++ | +++ |
| 61 | ++ | +++ |
| 62 | + | ++ |
| 63 | − | +++ |
| 64 | + | +++ |
| 65 | ++ | ++++ |
| 66 | ++ | ++++ |
| 67 | ++ | +++ |
| 68 | ++ | +++ |
| 69 | ++ | ++++ |
| 70 | + | +++ |
| 71 | − | +++ |
| 72 | ++ | +++ |
| 73 | + | +++ |
| 74 | + | + |
| 75 | + | +++ |
| 76 | ++ | +++ |
| 77 | − | ++ |
| 78 | − | − |
| 79 | − | + |
| 80 | − | + |
| 81 | − | − |
| 82 | + | − |
| 83 | + | ++ |
| 84 | ++ | +++ |
| 85 | + | + |
| 86 | ++ | ++ |
| 87 | − | − |
| 88 | ++ | + |
| 89 | + | + |
| 90 | − | − |
| 91 | + | − |
| 92 | − | − |
| 93 | − | − |
| 94 | + | ++ |
| 95 | + | ++ |
| 96 | + | ++ |
| 97 | − | + |
| 98 | − | ++ |
| 99 | +++ | ++++ |
| 100 | +++ | ++++ |
| 101 | ++ | +++ |
| 102 | ++ | +++ |
| 103 | + | +++ |
| 104 | +++ | ++++ |
| 105 | ++ | ++++ |
| 106 | ++ | ++++ |
| 107 | + | ++++ |
| 108 | + | ++++ |
| 109 | − | + |
| 110 | + | − |
| 111 | + | − |
| 112 | + | + |
| 113 | + | ++ |
| 114 | + | ++ |
| 115 | − | ++ |
| 116 | − | + |
| 117 | ++ | ++++ |
| 118 | ++ | ++++ |
| 119 | − | − |
| 120 | ++ | +++ |
| 121 | + | ++ |
| 122 | ++ | +++ |
| 123 | + | + |
| 124 | + | ++ |
| 125 | + | +++ |
| 126 | ++ | +++ |
| 127 | − | ++ |
| 128 | + | − |
| 129 | + | +++ |
| 130 | + | ++ |
| 131 | ++ | ++ |
| 132 | ++ | ++++ |
| 133 | − | − |
| 134 | + | + |
| 135 | − | − |
| 136 | − | − |
| 137 | − | + |
| 138 | + | ++ |
| 139 | + | + |
| 140 | ++ | ++ |
| 141 | ++ | +++ |
| 142 | ++ | +++ |
| 143 | ++ | +++ |
| 144 | ++ | +++ |
| 145 | − | − |
| 146 | + | − |
| 147 | − | + |
| 148 | + | +++ |
| 149 | − | − |
| 150 | − | − |
| 151 | + | +++ |
| 152 | + | ++ |
| 153 | − | − |
| 154 | + | ++++ |
| 155 | − | + |
| 156 | +++ | ++++ |
| 157 | +++ | ++++ |
| 158 | − | ++ |
| 159 | ++ | ++++ |
| 160 | +++ | ++++ |
| 161 | +++ | +++ |
| 162 | + | ++ |
| 163 | +++ | ++++ |
| 164 | ++ | ++++ |
| 165 | − | +++ |
| 166 | − | +++ |
| 167 | + | +++ |
| 168 | + | ++ |
| 169 | + | +++ |
| 170 | − | ++ |
| 171 | − | + |
| 172 | + | +++ |
| 173 | ++ | ++ |
| 174 | + | +++ |
| 175 | − | − |
| 176 | + | ++ |
| 177 | ++ | ++++ |
| 178 | + | − |
| 179 | − | − |
| 180 | ++ | ++++ |
| 181 | ++ | +++ |
| 182 | NT | NT |
| 183 | ++ | +++ |
| 184 | ++ | ++++ |
| 185 | +++ | ++++ |
| 186 | ++ | ++++ |
| 187 | − | − |
| 188 | − | ++ |

TABLE 1-continued

ALK, c-Met Kinase Inhibition

| Example | c-Met | ALK |
|---|---|---|
| 189 | +++ | ++++ |
| 190 | +++ | ++++ |
| 191 | +++ | +++ |
| 192 | +++ | ++++ |
| 193 | − | − |
| 194 | − | +++ |
| 195 | ++ | ++ |
| 196 | + | ++ |
| 197 | ++ | +++ |
| 198 | +++ | ++++ |
| 199 | ++ | ++++ |
| 200 | ++ | +++ |
| 201 | NT | NT |
| 202 | + | +++ |
| 203 | ++ | +++ |
| 204 | + | +++ |
| 205 | ++ | ++++ |
| 206 | − | + |
| 207 | − | ++ |
| 208 | − | ++ |
| 209 | + | ++ |
| 210 | + | ++ |
| 211 | + | + |
| 212 | ++ | ++ |
| 213 | + | ++ |
| 214 | + | + |
| 215 | + | + |
| 216 | − | ++ |
| 217 | − | ++ |
| 218 | + | + |
| 219 | + | ++ |
| 220 | ++ | ++ |
| 221 | − | + |
| 222 | + | + |
| 223 | − | ++ |
| 224 | + | ++ |
| 225 | + | ++ |
| 226 | + | + |
| 227 | + | + |
| 228 | + | ++ |
| 229 | ++ | ++ |
| 230 | − | ++ |
| 231 | + | ++ |
| 232 | − | +++ |
| 233 | + | ++ |
| 234 | − | ++ |
| 235 | + | ++ |
| 236 | + | ++ |
| 237 | ++ | ++ |
| 238 | − | ++ |
| 239 | − | ++ |
| 240 | − | +++ |
| 241 | − | +++ |
| 242 | − | ++ |
| 243 | + | + |
| 244 | − | ++ |
| 245 | + | +++ |
| 246 | − | +++ |
| 247 | − | ++ |
| 248 | − | ++ |
| 249 | − | + |
| 250 | − | +++ |
| 251 | + | + |
| 252 | − | + |
| 253 | − | +++ |
| 254 | − | ++ |
| 255 | − | ++ |
| 256 | − | ++ |
| 257 | − | + |
| 258 | − | ++ |
| 259 | − | ++ |
| 260 | − | ++ |
| 261 | − | ++ |
| 262 | − | + |
| 263 | − | ++ |
| 264 | − | ++ |
| 265 | − | − |
| 266 | − | − |
| 267 | − | + |
| 268 | − | − |
| 269 | + | − |
| 270 | − | − |
| 271 | + | − |
| 272 | ++ | +++ |
| 273 | + | + |
| 274 | ++ | ++ |
| 275 | ++ | + |
| 276 | + | + |
| 277 | + | + |
| 278 | ++ | ++ |
| 279 | + | ++ |
| 280 | + | ++ |
| 281 | ++ | +++ |
| 282 | NT | NT |
| 283 | − | − |
| 284 | NT | NT |
| 285 | NT | NT |
| 286 | − | ++ |
| 287 | +++ | ++++ |
| 288 | + | +++ |
| 289 | +++ | ++++ |
| 290 | − | + |
| 291 | − | + |
| 292 | − | ++ |
| 293 | ++ | ++ |
| 294 | + | + |
| 295 | ++ | ++++ |
| 296 | NT | NT |
| 297 | − | ++ |
| 298 | − | ++ |
| 299 | − | ++ |
| 300 | NT | NT |
| 301 | NT | NT |
| 302 | − | − |
| 303 | − | − |
| 304 | − | ++ |
| 305 | ++ | ++++ |
| 306 | NT | +++ |
| 307 | NT | +++ |
| 308 | NT | +++ |
| 309 | NT | +++ |
| 310 | NT | +++ |
| 311 | NT | +++ |
| 312 | NT | +++ |
| 313 | NT | +++ |
| 314 | NT | +++ |
| 315 | NT | ++ |
| 316 | NT | +++ |
| 317 | NT | +++ |
| 318 | NT | +++ |
| 319 | NT | +++ |
| 320 | NT | +++ |
| 321 | NT | +++ |
| 322 | NT | +++ |
| 323 | NT | +++ |
| 324 | NT | +++ |
| 325 | NT | +++ |
| 326 | NT | +++ |
| 327 | NT | ++++ |
| 328 | NT | +++ |
| 329 | NT | ++++ |
| 330 | NT | +++ |
| 331 | NT | ++ |
| 332 | NT | +++ |
| 333 | NT | +++ |
| 334 | NT | ++++ |
| 335 | NT | +++ |
| 336 | NT | +++ |
| 337 | NT | +++ |
| 338 | NT | +++ |

TABLE 1-continued

ALK, c-Met Kinase Inhibition

| Example | c-Met | ALK |
|---|---|---|
| 339 | NT | +++ |
| 340 | NT | +++ |
| 341 | NT | +++ |
| 342 | NT | +++ |
| 343 | NT | +++ |
| 344 | NT | +++ |
| 345 | NT | +++ |
| 346 | NT | +++ |
| 347 | NT | +++ |
| 348 | NT | +++ |
| 349 | NT | +++ |
| 350 | NT | ++ |
| 351 | NT | +++ |
| 352 | NT | +++ |
| 353 | NT | ++ |
| 354 | NT | +++ |
| 355 | NT | +++ |
| 356 | NT | +++ |
| 357 | NT | +++ |
| 358 | NT | +++ |
| 359 | NT | +++ |
| 360 | NT | +++ |
| 361 | NT | ++++ |
| 362 | NT | +++ |
| 363 | NT | +++ |
| 364 | NT | +++ |
| 365 | NT | ++++ |
| 366 | NT | +++ |
| 367 | NT | +++ |
| 368 | NT | +++ |
| 369 | NT | +++ |
| 370 | NT | +++ |
| 371 | NT | +++ |
| 372 | NT | +++ |
| 373 | NT | +++ |
| 374 | NT | +++ |
| 375 | NT | +++ |
| 376 | NT | +++ |
| 377 | NT | ++ |
| 378 | NT | ++ |
| 379 | NT | +++ |
| 380 | NT | +++ |
| 381 | NT | +++ |
| 382 | NT | +++ |
| 383 | NT | +++ |
| 384 | NT | +++ |
| 385 | NT | ++++ |
| 386 | NT | +++ |
| 387 | NT | +++ |
| 388 | NT | +++ |
| 389 | NT | +++ |
| 390 | NT | +++ |
| 391 | NT | +++ |
| 392 | NT | ++++ |
| 393 | NT | ++++ |
| 394 | NT | ++++ |
| 395 | NT | +++ |
| 396 | NT | +++ |
| 397 | NT | +++ |
| 398 | NT | +++ |
| 399 | NT | ++ |
| 400 | NT | +++ |
| 401 | NT | +++ |
| 402 | NT | ++++ |
| 403 | NT | ++++ |
| 404 | NT | ++++ |
| 405 | NT | +++ |
| 406 | NT | ++++ |
| 407 | NT | +++ |
| 408 | NT | +++ |
| 409 | NT | ++ |
| 410 | NT | +++ |
| 411 | NT | +++ |
| 412 | NT | +++ |
| 413 | NT | +++ |
| 414 | NT | +++ |
| 415 | NT | ++++ |
| 416 | NT | +++ |
| 417 | NT | +++ |
| 418 | NT | +++ |
| 419 | NT | +++ |
| 420 | NT | +++ |
| 421 | NT | +++ |
| 422 | NT | +++ |
| 423 | NT | +++ |
| 424 | NT | +++ |
| 425 | NT | ++ |
| 426 | NT | +++ |
| 427 | NT | +++ |
| 428 | NT | ++ |
| 429 | NT | +++ |
| 430 | NT | ++++ |
| 431 | NT | +++ |
| 432 | NT | +++ |
| 433 | NT | +++ |
| 434 | NT | +++ |
| 437 | ++ | +++ |

Preferably, the compounds of the present invention exhibit an $IC_{50}$ in the ALK kinase assay of 100 μM-10 μM. More preferably, the compounds of the present invention exhibit an $IC_{50}$ in the ALK kinase assay of 10 μM-1 μM. More preferably, the compounds of the present invention exhibit an $IC_{50}$ in the ALK kinase assay of 1 μM-0.1 μM. More preferably, the compounds of the present invention exhibit an $IC_{50}$ in the ALK kinase assay of <0.1 μM.

Preferably, the compounds of the present invention exhibit an $IC_{50}$ in the c-Met kinase assay of 100 μM-10 μM. More preferably, the compounds of the present invention exhibit an $IC_{50}$ in the e-Met kinase assay of 10 μM-1 μM. More preferably, the compounds of the present invention exhibit an $IC_{50}$ in the c-Met kinase assay of 1 μM-0.1 μM. More preferably, the compounds of the present invention exhibit an $IC_{50}$ in the c-Met kinase assay of <0.1 μM.

TABLE 2 c-Met Cellular Activity/Autophosphorylation Assay*

| Example | HT29 Cells (1 μM) | HT29 Cells (3 μM) | A549 Cells (1 μM) | A549 Cells (3 μM) | GTL-16 Cells (1 μM) | GTL-16 Cells (3 μM) |
|---|---|---|---|---|---|---|
| 69 | 1 | 1 | 1 | 1 | | |
| 72 | 2 | 2 | 1 | 1 | | |
| 76 | 1 | 2 | 1 | 1 | | |
| 99 | 1 | 1 | 1 | 1 | | |
| 100 | 1 | 1 | 1 | 1 | | |
| 102 | 2 | 3 | 1 | 2 | | |
| 104 | 1 | 3 | | | | |
| 117 | 1 | 1 | | | | |
| 118 | 2 | 3 | 1 | 2 | | |
| 120 | 2 | 2 | 1 | 2 | | |
| 122 | 2 | 2 | 1 | 2 | | |
| 157 | 1 | 2 | 1 | 1 | | |
| 159 | 1 | 1 | 1 | 1 | | |
| 160 | 2 | 2 | 1 | 1 | | |
| 163 | 1 | 2 | 1 | 1 | | |
| 164 | 1 | 1 | 1 | 1 | | |
| 168 | 1 | 2 | 1 | 1 | | |
| 177 | 2 | 2 | 1 | 1 | | |
| 184 | 3 | 4 | | | | |
| 185 | 3 | 4 | | | 1 | 1 |
| 186 | 2 | 2 | | | 1 | 1 |

TABLE 2-continued c-Met Cellular Activity/Autophosphorylation Assay*

| Example | HT29 Cells (1 μM) | HT29 Cells (3 μM) | A549 Cells (1 μM) | A549 Cells (3 μM) | GTL-16 Cells (1 μM) | GTL-16 Cells (3 μM) |
|---|---|---|---|---|---|---|
| 190 |  |  | 1 | 1 |  |  |
| 287 | 1 | 2 | 1 | 1 |  |  |

*Inhibition scores: 1, 0-25%; 2, 26-50%; 3, 51-75%; 4, 76-100%

Preferably, the compounds of the present invention exhibit an inhibition score in the c-Met Cellular Assay of 26-50%. More preferably, the compounds of the present invention exhibit an inhibition score in the c-Met Cellular Assay of 51-75%. More preferably, the compounds of the present invention exhibit an inhibition score in the c-Met Cellular Assay of 76-100%.

TABLE 3

ALK Cellular Activity

| Example | ALK Cellular Activity Inhibition Score at 1 μM* | ALK Cellular Activity** |
|---|---|---|
| 6 | 1 |  |
| 38 |  | ++ |
| 48 | 2 |  |
| 51 | 2 |  |
| 57 | 1 |  |
| 58 | 1 |  |
| 65 |  | ++++ |
| 66 |  | ++++ |
| 69 |  | + |
| 99 |  | ++++ |
| 100 |  | ++++ |
| 105 |  | + |
| 106 |  | ++++ |
| 117 |  | ++++ |
| 118 |  | ++++ |
| 132 |  | +++ |
| 141 | 3 |  |
| 144 | 1 |  |
| 154 |  | +++ |
| 156 |  | +++ |
| 157 |  | +++ |
| 159 |  | +++ |
| 160 |  | ++++ |
| 163 |  | + |
| 164 |  | +++ |
| 177 |  | +++ |
| 180 |  | +++ |
| 186 |  | ++++ |
| 189 |  | ++++ |
| 190 |  | ++ |
| 198 |  | ++++ |
| 199 |  | ++++ |
| 200 |  | + |
| 205 |  | +++ |
| 295 |  | +++ |

*Inhibition scores: 1, 0-25%; 2, 26-50%; 3, 51-75%; 4, 76-100%
**$IC_{50}$ > 1000 nM −
$IC_{50}$ 751 nM-1000 nM +
$IC_{50}$ 501 nM-750 nM ++
$IC_{50}$ 251 nM-500 nM +++
$IC_{50}$ ≤ 250 nM ++++

Preferably, the compounds of the present invention exhibit an inhibition score in the ALK Cellular Assay of 26-50%. More preferably, the compounds of the present invention exhibit an inhibition score in the ALK Cellular Assay of 51-75%. More preferably, the compounds of the present invention exhibit an inhibition score in the ALK Cellular Assay of 76-100%.

EXAMPLES

Preparation 1. (S)-2-[(pyrrolidin-1-yl)methyl]pyrrolidine-1-carboxyl-[4-(4,4,5,5-tetramethyl[1,3,2]dioxaborolan-2-yl)phenyl]amide

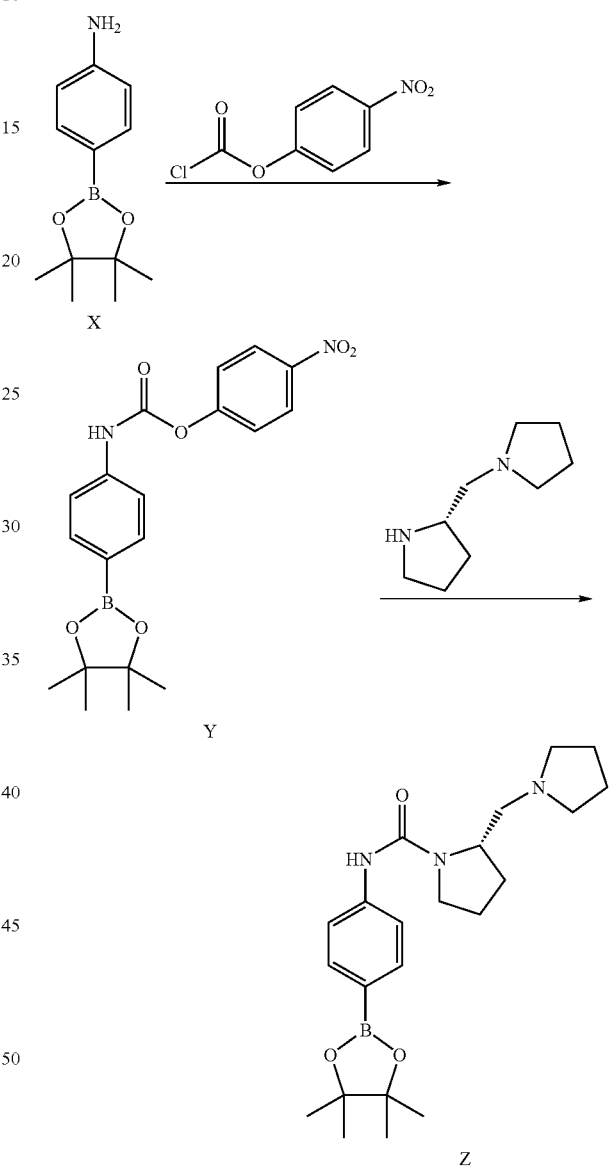

A solution of 4-(4,4,5,5-tetramethyl-[1,3,2]dioxaborolan-2-yl)phenylamine (X) (15.12 g, 69 mmol) in $CH_2Cl_2$ (600 mL) was treated with pyridine (5.46 g, 69 mmol) and cooled in an ice bath. p-Nitrophenylchloroformate (14.00 g, 69.5 mmol) was added, the ice bath was removed, and the reaction was stirred overnight. The mixture was poured into a separatory funnel and successively washed with aqueous, saturated $NaHCO_3$ solution (3×), $H_2O$, aqueous, saturated $Cu_2SO_4$, $H_2O$, and brine. The organic phase was passed through a Buchner funnel containing $Na_2SO_4$, and the filtrate was evaporated to afford the carbamate product (Y) (24.84 g, 96% yield), which was used directly in the next step.

To a mixture of the carbamate (Y) (621 mg, 1.62 mmol) in dichloromethane (2 mL) was added triethylamine (227 µL, 1.63 mmol) and (S)-2-pyrrolidin-1-yl-methylpyrrolidine. After 1.5 hours, the reaction was extracted into ethyl acetate and washed with aqueous, saturated NaHCO₃ solution (3×), H₂O, and brine. The organic phase was passed through a Buchner funnel containing MgSO₄, and the filtrate was evaporated to afford a residue that was dissolved in CHCl₃ and treated with macroporous-carbamate resin (to remove residual p-nitrophenol). After gentle agitation overnight, the mixture was filtered and the filtrate evaporated to give the title compound (Z).

Preparation 2.
1-(1-Bromoethyl)-2,4,5-trifluorobenzene

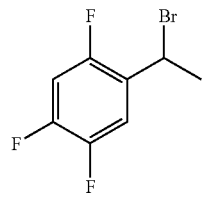

Phosphorus tribromide (0.275 mL) and anhydrous methylene chloride (12 mL) were combined and the solution cooled over ice water for 15 minutes. The solution was added to a mixture of 1-(2,4,5-trifluorophenyl)ethanol (0.506 g) and methylene chloride (8 mL), and the reaction was stirred at room temperature for 1.5 hours. The reaction mixture was then poured into H₂O and extracted into methylene chloride. The organic phase was isolated, dried with magnesium sulfate, filtered and concentrated (without heat) to give the title compound. $^1$H-NMR (CD₃OD, 400 MHz) δ 2.00 (3H, d, J=7.1 Hz), 5.37 (1H, m), 6.92 (1H, m), 7.36 (1H, m).

Preparation 3.
2-(1-Bromoethyl)-3-chloro-1,4-difluorobenzene

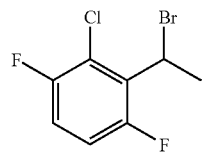

Phosphorus tribromide (1.3 mL) and anhydrous CH₂Cl₂ (50 mL) were combined and then cooled over ice water for 20 minutes. The cooled solution was then added to a mixture of 1-(2-chloro-3,6-difluorophenyl)ethanol (2.71 g) and methylene chloride (50 mL), and the resulting mixture was stirred at room temperature for two (2) hours. The mixture was then poured into H₂O and extracted into CH₂Cl₂. The organic phase was isolated, dried with magnesium sulfate, filtered, and concentrated to give the title compound (78% yield).

Example 1

(5-Iodo-3-nitro-pyridin-2-ylamino)-acetic acid ethyl ester

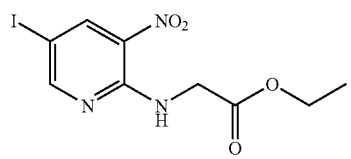

2-Chloro-5-iodo-3-nitro-pyridine (13 g) was dissolved in ethanol. Glycine ethyl ester HCl was added (5.0 eq) followed by triethylamine (5.0 eq). The reaction mixture was heated to 80° C. for four (4) hours. The reaction mixture was concentrated to dryness and triturated with H₂O to give the title compound as a white solid (82-94% yield). M.p. 200° C. (dec), LCMS: m/z=352.08 (M+H⁺), $^1$H-NMR (CDCl₃, 400 MHz) δ 1.30 (t, J=7.1 Hz, 3H), 4.25 (q, J=7.1 Hz, 2H), 4.33 (d, J=5.6 Hz, 2H), 8.44 (bs, 1H), 8.52 (d, J=2.0 Hz, 1H), 8.69 (d, J=2.0 Hz, 1H).

Example 2

7-Iodo-3,4-dihydro-1H-pyrido[2,3-b]pyrazin-2-one

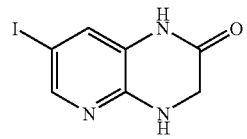

(5-Iodo-3-nitro-pyridin-2-ylamino)-acetic acid ethyl ester (17 g) was dissolved in ethanol. SnCl₂2H₂O was added and the reaction mixture was heated to 80° C. for two (2) hours. The resulting precipitate was filtered and washed with ethanol to give the title compound as a rust colored solid (59-77% yield). M.p. 81° C., LCMS: m/z=275.91 (M+H⁺), $^1$H-NMR (DMSO-d₆, 400 MHz) δ 3.94 (s, 2H), 6.94 (bs, 1H), 7.12 (d, J=1.8 Hz, 1H), 7.74 (s, J=1.8 Hz, 1H), 10.40 (bs, 1H).

Example 3

1-(2-Chloro-3,6-difluorobenzyl)-7-iodo-3,4-dihydro-1H-pyrido[2,3-b]pyrazin-2-one

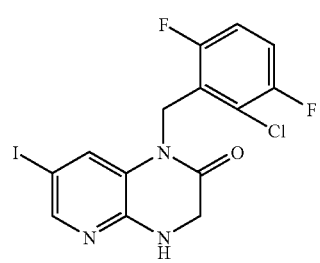

7-Iodo-3,4-dihydro-1H-pyrido[2,3-b]pyrazin-2-one (300 mg) was reacted with 2-chloro-3,6-difluorobenzyl bromide as in General Procedure 1. The title compound was obtained as an off white solid (63% yield). M.p. 237° C., LCMS: m/z=436.17 (M+H⁺), $^1$H-NMR (DMSO-d₆, 400 MHz) δ 4.01 (s, 2H), 5.24 (s, 2H), 7.05 (d, J=1.5 Hz, 1H), 7.23-7.32 (m, 1H), 7.41-7.48 (m, 1H), 7.79 (d, J=1.5 Hz, 1H).

Example 4

1-(2-Chloro-3,6-difluorobenzyl)-7-pyridin-3-yl-3,4-dihydro-1H-pyrido[2,3-b]pyrazin-2-one, trifluoroacetic acid salt

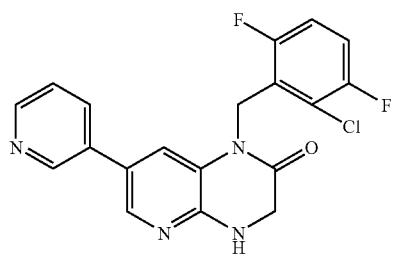

1-(2-Chloro-3,6-difluorobenzyl)-7-iodo-3,4-dihydro-1H-pyrido[2,3-b]pyrazin-2-one (21 mg) was reacted with pyridine 3-boronic acid as in General Procedure 4A, with the modification that the mixture was heated to 130° C. in a microwave oven for 10 minutes. The reaction mixture was purified via reversed phase preparative HPLC to give the title compound as a pale yellow foam (48% yield). M.p. (foam), LCMS: m/z=387.24 (M+H$^+$), $^1$H-NMR (CDCl$_3$, 400 MHz) δ 4.53 (s, 2H), 5.51 (s, 2H), 7.13-7.19 (m, 2H), 7.34 (s, 1H), 7.73 (s, 2H), 7.98-8.02 (m, 1H), 8.70-8.79 (m, 2H), 10.9 (bs, 1H).

Example 5

4-[1-(2-Chloro-3,6-difluorobenzyl)-2-oxo-1,2,3,4-tetrahydropyrido[2,3-b]pyrazin-7-yl]benzoic acid ethyl ester

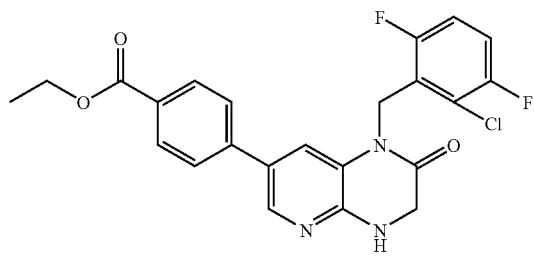

1-(2-Chloro-3,6-difluorobenzyl)-7-iodo-3,4-dihydro-1H-pyrido[2,3-b]pyrazin-2-one (280 mg) was reacted with 4-ethoxycarbonyl phenyl boronic acid as in General Procedure 4A, with the modification that the mixture was heated to 130° C. in a microwave oven for 5 minutes. The title compound was obtained as a white solid after silica gel chromatography (19% yield). M.p. 180-182° C., LCMS: m/z=458.37 (M+H$^+$), $^1$H-NMR (DMSO-d$_6$, 400 MHz) δ 1.34 (t, J=7.1 Hz, 3H), 4.08 (s, 2H), 4.33 (q, J=7.1 Hz, 2H), 5.39 (s, 2H), 7.18 (bs, 1H), 7.29-7.33 (m, 1H), 7.39-7.47 (m, 1H), 7.42 (s, 1H), 7.46 (d, J=8.3 Hz, 2H), 7.66 (d, J=8.3 Hz, 2H), 7.97 (s, 1H).

Example 6

4-[1-(2-Chloro-3,6-difluorobenzyl)-2-oxo-1,2,3,4-tetrahydropyrido[2,3-b]pyrazin-7-yl]benzoic acid

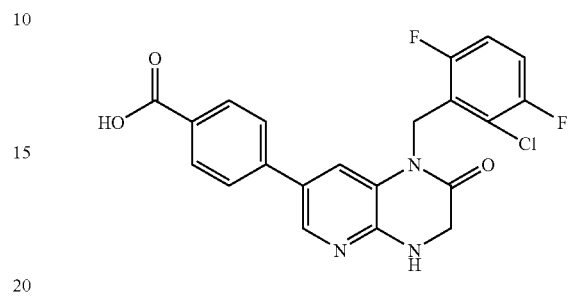

4-[1-(2-Chloro-3,6-difluorobenzyl)-2-oxo-1,2,3,4-tetrahydropyrido[2,3-b]pyrazin-7-yl]benzoic acid ethyl ester (43 mg) was saponified as described in General Procedure 7 to give the title compound as a white solid (52% yield). M.p.>300° C., LCMS: m/z=430.31 (M+H$^+$), $^1$H-NMR (DMSO-d$_6$, 400 MHz) δ 4.15 (s, 2H), 5.41 (s, 2H), 7.28-7.33 (m, 1H), 7.41-7.46 (m, 1H), 7.59 (s, 1H), 7.67 (d, J=8.3 Hz, 2H), 7.98 (d, J=8.3 Hz, 2H), 8.09 (s, 1H).

Example 7

1-(2-Chloro-3,6-difluorobenzyl)-7-[4-(4-methylpiperazine-1-carbonyl)phenyl]-3,4-dihydro-1H-pyrido[2,3-b]pyrazin-2-one

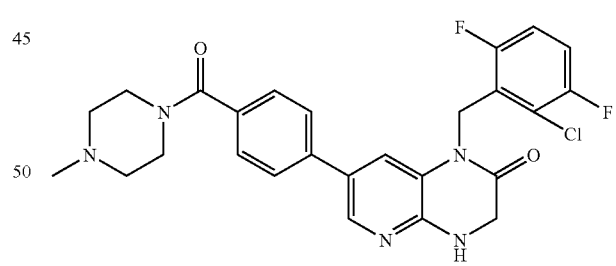

4-[1-(2-Chloro-3,6-difluorobenzyl)-2-oxo-1,2,3,4-tetrahydropyrido[2,3-b]pyrazin-7-yl]benzoic acid (13 mg) was reacted with 1-methyl piperazine as in General Procedure 8 to give the title compound as an off-white foam (45% yield). M.p. (foam), LCMS: m/z=512.07 (M+H$^+$), $^1$H-NMR (DMSO-d$_6$, 400 MHz) δ 2.30-2.43 (m, 2H), 2.83 (s, 3H), 3.06-3.18 (m, 2H), 3.21-3.33 (m, 2H), 3.40-3.48 (m, 2H), 4.08 (s, 2H), 5.39 (s, 2H), 7.28 (bs, 1H), 7.22-7.32 (m, 1H), 7.46 (s, 1H), 7.50 (d, J=8.3 Hz, 2H), 7.62 (d, J=8.3 Hz, 2H), 8.05 (s, 1H).

Example 8

1-Benzyl-7-iodo-3,4-dihydro-1H-pyrido[2,3-b]pyrazin-2-one

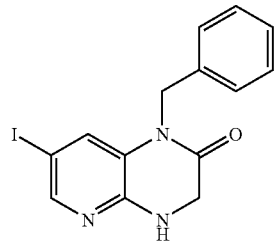

7-Iodo-3,4-dihydro-1H-pyrido[2,3-b]pyrazin-2-one (1.623 g) was reacted with benzyl bromide as in General Procedure 1 to give the title compound as a light yellow solid (38% yield). M.p. 225° C., LCMS: m/z=366.03 (M+H+), $^1$H-NMR (DMSO-$d_6$, 400 MHz) δ 4.14 (s, 2H), 5.10 (s, 2H), 7.13 (s, 1H), 7.7.22-7.29 (m, 4H), 7.31-7.38 (m, 2H), 7.78 (s, 1H).

Example 9

4-(1-Benzyl-2-oxo-1,2,3,4-tetrahydropyrido[2,3-b]pyrazin-7-yl)benzoic acid ethyl ester

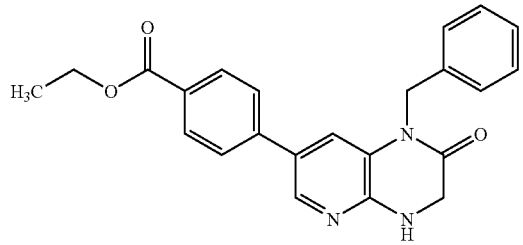

1-Benzyl-7-iodo-3,4-dihydro-1H-pyrido[2,3-b]pyrazin-2-one (509 mg) was reacted with 4-ethoxycarbonyl phenyl boronic acid as in General Procedure 4B to give the title compound as a brown solid (72% yield). M.p.=178° C., LCMS: m/z=388.23 (M+H+), $^1$H-NMR (DMSO-$d_6$, 400 MHz) δ 1.32 (3H, t, J=7.1 Hz), 4.20 (2H, d, J=1.5 Hz), 4.31 (2H, q, J=7.1 Hz), 5.26 (2H, s), 7.23 (2H, m), 7.32 (2H, s), 7.34 (2H, m), 7.39 (1H, d, J=1.8 Hz), 7.63 (2H, d, J=8.6 Hz), 7.94 (2H, d, J=8.3 Hz), 8.06 (1H, d, J=2.0 Hz).

Example 10

4-(1-Benzyl-2-oxo-1,2,3,4-tetrahydropyrido[2,3-b]pyrazin-7-yl)benzoic acid

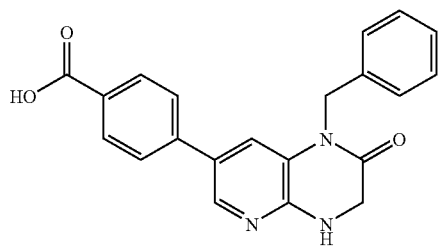

4-(1-Benzyl-2-oxo-1,2,3,4-tetrahydropyrido[2,3-b]pyrazin-7-yl)benzoic acid ethyl ester (390 mg) was saponified under the conditions of General Procedure 7 to give the title compound as a light brown solid (99% yield). M.p.>200° C., LCMS: m/z=360.17 (M+H+), $^1$H-NMR (DMSO-$d_6$, 400 MHz) δ 4.19 (2H, s), 5.26 (2H, s), 7.23 (2H, s), 7.32 (4H, m), 7.39 (1H, s), 7.60 (2H, d, J=8.3 Hz), 7.92 (2H, d, J=8.3 Hz), 8.05 (1H, s).

Example 11

1-Benzyl-7-pyridin-3-yl-3,4-dihydro-1H-pyrido[2,3-b]pyrazin-2-one

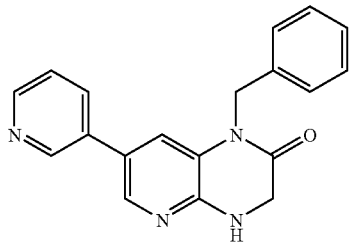

1-Benzyl-7-iodo-3,4-dihydro-1H-pyrido[2,3-b]pyrazin-2-one (100 mg) was reacted with 3-pyridine boronic acid as in General Procedure 4A to give the title compound as a light yellow solid (60% yield). M.p. 58° C., LCMS: m/z=317.16 (M+H+), $^1$H-NMR (CD$_3$OD, 400 MHz) δ 4.42 (s, 2H), 7.22-7.31 (m, 2H), 7.32-7.38 (m, 4H), 7.50 (s, 1H), 7.85-7.92 (m, 1H), 8.02 (s, 1H), 8.39 (d, J=8.1 Hz, 1H), 8.65-8.75 (m, 1H), 8.75-8.90 (m, 1H).

Example 12

4-(1-Benzyl-2-oxo-1,2,3,4-tetrahydropyrido[2,3-b]pyrazin-7-yl)-N-(2-pyrrolidin-1-yl-ethyl)benzamide, trifluoroacetic acid salt

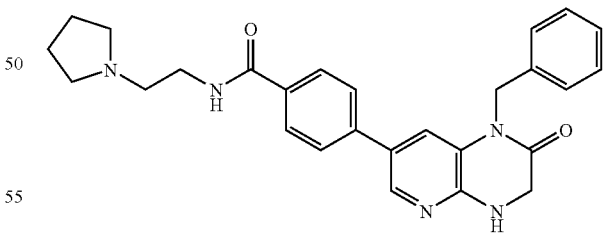

4-(1-Benzyl-2-oxo-1,2,3,4-tetrahydropyrido[2,3-b]pyrazin-7-yl)benzoic acid (23 mg) was coupled to 2-pyrrolidin-1-yl-ethylamine as in General Procedure 8 to give the title compound as a brown solid after preparative reversed-phase HPLC purification (29% yield). M.p.=107° C., LCMS: m/z=456.15 (M+H+), $^1$H-NMR (CDCl$_3$, 400 MHz) δ 2.13 (4H, m), 3.40 (6H, m), 3.81 (4H, m), 4.54 (2H, s), 5.27 (2H, s), 7.38 (4H, m), 7.75 (1H, s), 7.92 (2H, d, J=8.3 Hz).

Example 13

S-1-Benzyl-7-[4-(2-[(pyrrolidin-1-yl)methyl]pyrrolidine-1-carbonyl)phenyl]-3,4-dihydro-1H-pyrido[2,3-b]pyrazin-2-one, trifluoroacetic acid salt

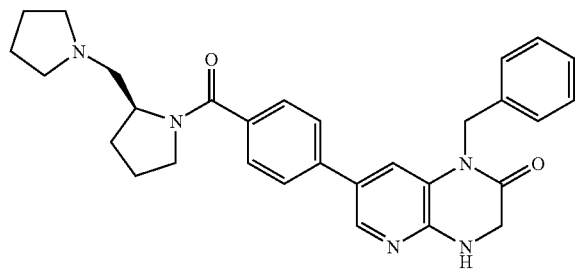

4-(1-Benzyl-2-oxo-1,2,3,4-tetrahydropyrido[2,3-b]pyrazin-7-yl)benzoic acid (48 mg) was coupled to (S)-(+)-1-(2-pyrrolidinylmethyl)pyrrolidine as in General Procedure 8 to give the title compound as a pink solid after preparative reversed-phase HPLC purification (43% yield). LCMS: m/z=496.24 (M+H$^+$), $^1$H-NMR (CDCl$_3$, 400 MHz) δ 1.94 (3H, m), 2.13 (4H, bs), 2.29 (1H, m), 3.05 (1H, bs), 3.24 (2H, m), 3.38 (1H, m), 3.49 (1H, m), 3.64 (3H, m), 3.86 (1H, bs), 4.05 (1H, bs), 4.57 (3H, s), 5.29 (2H, s), 7.35 (8H, m), 7.61 (2H, d, J=8.1 Hz), 7.74 (1H, s).

Example 14

4-(1-Benzyl-2-oxo-1,2,3,4-tetrahydropyrido[2,3-b]pyrazin-7-yl)-N-(3-morpholin-4-yl-propyl)benzamide, trifluoroacetic acid salt

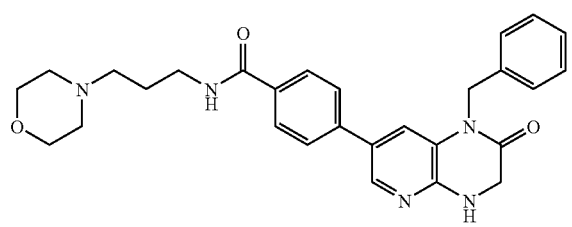

4-(1-Benzyl-2-oxo-1,2,3,4-tetrahydropyrido[2,3-b]pyrazin-7-yl)benzoic acid (43 mg) was coupled to 3-morpholin-4-yl-propylamine as in General Procedure 8 to give the title compound as an orange solid after preparative reversed-phase HPLC purification (12% yield). LCMS: m/z=486.24 (M+H$^+$), $^1$H-NMR (CDCl$_3$, 400 MHz) δ 2.13 (3H, m), 3.18 (4H, m), 3.40 (1H, m), 3.53 (5H, m), 4.00 (6H, m), 4.57 (2H, s), 5.28 (2H, s), 7.36 (8H, m), 7.71 (1H, s), 7.93 (2H, d, J=8.3 Hz)

Example 15

4-(1-Benzyl-2-oxo-1,2,3,4-tetrahydropyrido[2,3-b]pyrazin-7-yl)-N-(4-dimethylaminobutyl)benzamide, trifluoroacetic acid salt

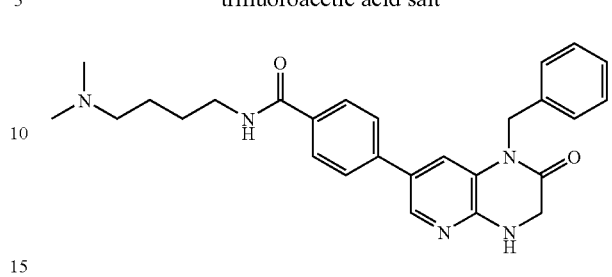

4-(1-Benzyl-2-oxo-1,2,3,4-tetrahydropyrido[2,3-b]pyrazin-7-yl)benzoic acid (40 mg) was coupled to 3-dimethylaminobutylamine as in General Procedure 8 to give the title compound as a yellow solid after preparative reversed-phase HPLC purification (17% yield). LCMS: m/z=458.19 (M+H$^+$), $^1$H-NMR (CD$_3$OD, 400 MHz) δ 1.70 (2H, m), 1.79 (2H, m), 2.89 (6H, s), 3.19 (2H, t, J=8.0 Hz), 3.45 (2H, t, J=6.7 Hz), 4.50 (2H, s), 5.36 (2H, s), 7.30 (1H, m), 7.37 (4H, m), 7.49 (2H, d, J=8.3 Hz), 7.54 (1H, d, J=1.5 Hz), 7.88 (3H, m).

Example 16

4-(1-benzyl-2-oxo-1,2,3,4-tetrahydropyrido[2,3-b]pyrazin-7-yl)-N-(6-dimethylaminohexyl)benzamide

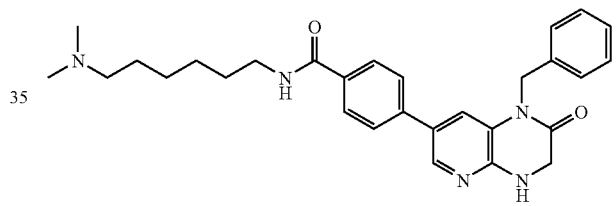

4-(1-Benzyl-2-oxo-1,2,3,4-tetrahydropyrido[2,3-b]pyrazin-7-yl)benzoic acid (47 mg) was coupled to 3-dimethylaminohexylamine as in General Procedure 8 to give the title compound as a light brown solid (19% yield). M.p.>200° C., LCMS: m/z=486.19 (M+H$^+$), $^1$H-NMR (CDCl$_3$, 400 MHz) δ 2.28 (9H, m), 3.47 (3H, m), 4.35 (2H, s), 4.96 (1H, bs), 5.21 (2H, s), 7.20 (2H, m), 7.35 (5H, m), 7.52 (1H, s), 7.77 (2H, d, J=8.3 Hz), 7.99 (1H, d, J=2.0 Hz).

Example 17

1-Benzyl-7-[4-(4-(pyrrolidin-1-yl)piperidine-1-carbonyl)phenyl]-1H-pyrido[2,3-b]pyrazin-2-one, trifluoroacetic acid salt

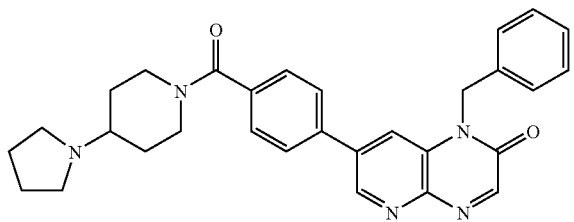

4-(1-Benzyl-2-oxo-1,2,3,4-tetrahydropyrido[2,3-b]pyrazin-7-yl)benzoic acid (22 mg) was coupled to 4-(1 pyrrolidinyl)piperidine as in General Procedure 8 to give the title compound as a tan solid after preparative reversed-phase HPLC purification (16% yield). LCMS: m/z=494.27 (M+H+), 1H-NMR (CD3OD, 400 MHz) δ 1.67 (2H, bs), 2.10 (8H, m), 3.19 (3H, m), 3.45 (1H, m), 3.67 (2H, bs), 3.91 (1H, bs), 5.57 (2H, s), 7.28 (1H, m), 7.36 (4H, m), 7.51 (2H, d, J=8.1 Hz), 7.61 (2H, d, J=8.1 Hz), 7.78 (1H, d, J=1.5 Hz), 8.44 (1H, d, J=1.0 Hz).

Example 18

S-1-Benzyl-7-[3-(2-[(pyrrolidin-1-yl)methyl]pyrrolidine-1-carbonyl)phenyl]-3,4-dihydro-1H-pyrido[2,3-b]pyrazin-2-one, trifluoroacetic acid salt

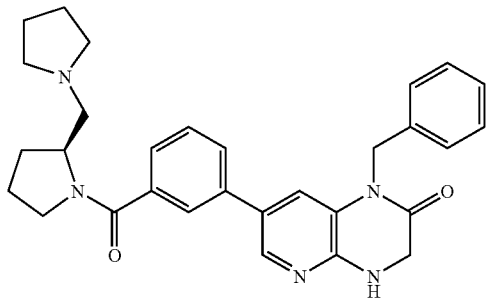

4-(1-Benzyl-2-oxo-1,2,3,4-tetrahydropyrido[2,3-b]pyrazin-7-yl)benzoic acid (33 mg) was coupled to (S)-(+)-1-(2-pyrrolidinylmethyl)pyrrolidine as in General Procedure 8 to give the title compound as a yellow solid after preparative reversed-phase HPLC purification (32% yield). LCMS: m/z=496.24 (M+H+), 1H-NMR (CD3OD, 400 MHz) δ 1.85 (2H, m), 2.00 (1H, m), 2.09 (2H, m), 2.23 (2H, m), 2.37 (2H, m), 3.21 (3H, m), 3.57 (5H, m), 3.76 (1H, m), 4.08 (1H, m), 4.38 (2H, s), 4.59 (1H, m), 5.34 (2H, s), 7.30 (1H, m), 7.38 (4H, m), 7.42 (1H, d, J=1.5 Hz), 7.55 (3H, s), 7.60 (1H, s), 7.92 (1H, s), 8.09 (1H, s).

Example 19

3-(1-Benzyl-2-oxo-1,2,3,4-tetrahydropyrido[2,3-b]pyrazin-7-yl)-N-(2-dimethylamino-ethyl)benzamide, trifluoroacetic acid salt

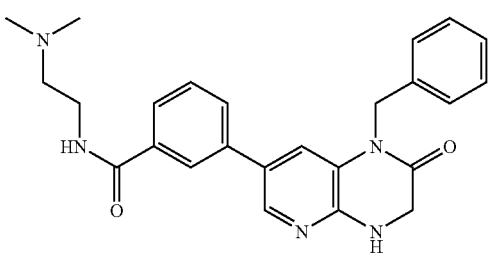

4-(1-Benzyl-2-oxo-1,2,3,4-tetrahydropyrido[2,3-b]pyrazin-7-yl)benzoic acid (33 mg) was coupled to 3-dimethylaminoethylamine as in General Procedure 8 to give the title compound as a yellow solid after preparative reversed-phase HPLC purification (34% yield). LCMS: m/z=430.22 (M+H+), 1H-NMR (CDCl3, 400 MHz) δ 2.92 (6H, s), 3.67 (3H, m), 3.82 (2H, t, J=5.6 Hz), 4.00 (1H, s), 4.55 (2H, s), 5.30 (2H, s), 7.34 (7H, m), 7.49 (2H, m), 7.73 (1H, s), 7.87 (2H, m).

Example 20

1-Benzyl-7-[3-(pyrrolidine-1-carbonyl)phenyl]-3,4-dihydro-1H-pyrido[2,3-b]pyrazin-2-one

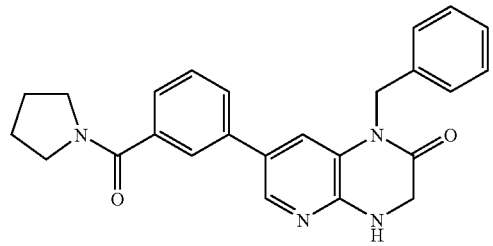

3-(1-Benzyl-2-oxo-1,2,3,4-tetrahydropyrido[2,3-b]pyrazin-7-yl)benzoic acid (31 mg) was coupled to pyrrolidine as in General Procedure 8 to give the title compound as a yellow solid (47% yield). LCMS: m/z=413.30 (M+H+), 1H-NMR (CD3OD, 400 MHz) δ 1.92 (2H, m), 2.02 (2H, m), 3.36 (1H, m), 3.40 (2H, t, J=6.6 Hz), 3.62 (2H, t, J=6.9 Hz), 4.49 (2H, s), 4.91 (1H, s), 5.36 (2H, s), 7.29 (1H, m), 7.37 (2H, d, J=1.8 Hz), 7.39 (2H, s), 7.49 (1H, s), 7.52 (3H, s), 7.53 (1H, d, J=1.5 Hz), 7.84 (1H, d, J=1.5 Hz).

Example 21

7-(4-Acetylphenyl)-1-benzyl-3,4-dihydro-1H-pyrido[2,3-b]pyrazin-2-one

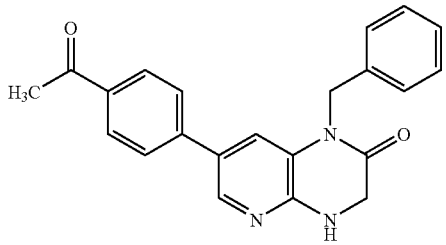

1-Benzyl-7-iodo-3,4-dihydro-1H-pyrido[2,3-b]pyrazin-2-one (35 mg) was reacted with 4-acetylphenyl boronic acid as in General Procedure 4B to give the title compound as a yellow solid (20% yield). M.p.=200° C., LCMS: m/z=358.24 (M+H+), 1H-NMR (CDCl3, 400 MHz) δ 2.61 (3H, s), 4.36 (2H, s), 5.22 (2H, s), 7.21 (1H, d, J=2.0 Hz), 7.28 (4H, m), 7.37 (4H, m), 7.96 (2H, d, J=8.3 Hz), 8.01 (1H, d, J=1.8 Hz).

Example 22

3-(1-Benzyl-2-oxo-1,2,3,4-tetrahydropyrido[2,3-b]pyrazin-7-yl)-N-ethyl-benzamide

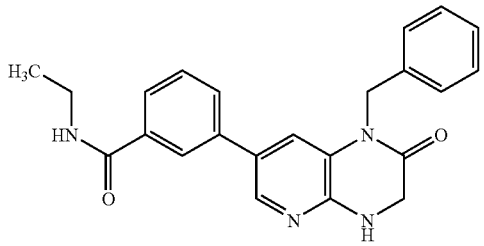

3-(1-Benzyl-2-oxo-1,2,3,4-tetrahydropyrido[2,3-b]pyrazin-7-yl)benzoic acid (35 mg) was coupled with ethylamine as in General Procedure 8 to give the title compound as a yellow solid (3% yield). LCMS: m/z=387.26 (M+H$^+$), $^1$H-NMR (CDCl$_3$, 400 MHz) δ 1.27 (3H, t, J=7.2 Hz), 3.47 (2H, quartet, J=7.2 Hz), 4.50 (2H, s), 5.28 (2H, s), 7.36 (8H, m), 7.48 (1H, t, J=7.6 Hz), 7.79 (2H, m), 7.84 (1H, s).

Example 23

4-(1-Benzyl-2-oxo-1,2,3,4-tetrahydropyrido[2,3-b]pyrazin-7-yl)benzamide

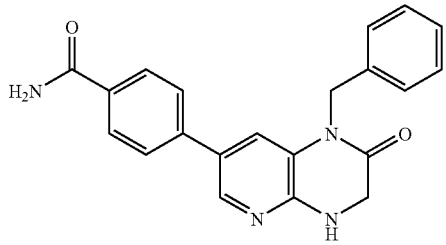

1-Benzyl-7-iodo-3,4-dihydro-1H-pyrido[2,3-b]pyrazin-2-one (50 mg) was reacted with 4-carbamoylphenyl boronic acid as in General Procedure 4B to give the title compound as a white solid (24% yield). M.p.>200° C., LCMS: m/z=359.22 (M+H$^+$), $^1$H-NMR (DMSO-d$_6$, 400 MHz) δ 4.22 (2H, s), 5.28 (2H, s), 7.24 (1H, m), 7.33 (5H, m), 7.41 (1H, s), 7.56 (2H, d, J=8.6 Hz), 7.88 (2H, d, J=8.3 Hz), 7.96 (1H, bs), 8.04 (1H, d, J=1.8 Hz).

Example 24

1-Benzyl-7-(4-methanesulfonyl-phenyl)-3,4-dihydro-1H-pyrido[2,3-b]pyrazin-2-one

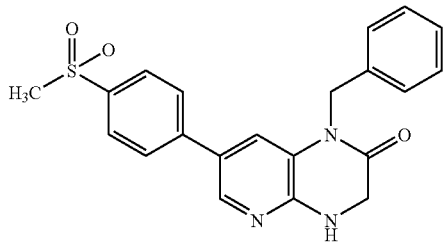

1-Benzyl-7-iodo-3,4-dihydro-1H-pyrido[2,3-b]pyrazin-2-one (46 mg) was reacted with 4-(methanesulfonyl)phenyl boronic acid as in General Procedure 4B to give the title compound as a yellow solid (43% yield). LCMS: m/z=394.22 (M+H$^+$), $^1$H-NMR (CDCl$_3$, 400 MHz) δ 3.08 (3H, s), 4.54 (2H, s), 5.28 (2H, s), 7.30 (3H, m), 7.39 (3H, m), 7.45 (2H, d, J=8.3 Hz), 7.78 (1H, d, J=1.5 Hz), 7.94 (2H, d, J=8.3 Hz).

Example 25

1-Benzyl-7-[4-(4-methylpiperazine-1-carbonyl)phenyl]-3,4-dihydro-1H-pyrido[2,3-b]pyrazin-2-one, trifluoroacetic acid salt

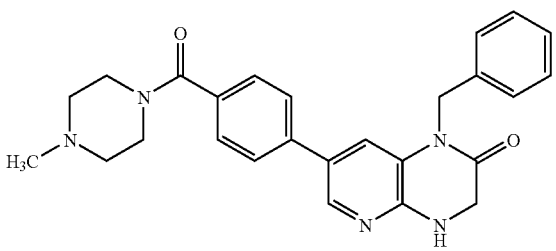

1-Benzyl-7-iodo-3,4-dihydro-1H-pyrido[2,3-b]pyrazin-2-one (43 mg) was reacted with (4-methylpiperazin-1-yl)-[4-(4,4,5,5-tetramethyl-[1,3,2]dioxaborolan-2-yl)phenyl]methanone as in General Procedure 4B to give the title compound as a white solid after preparative reversed-phase HPLC purification (38% yield). LCMS: m/z=442.23 (M+H$^+$), $^1$H-NMR (CD$_3$OD, 400 MHz) δ 2.95 (3H, s), 3.19 (3H, m), 3.31 (4H, m), 3.48 (2H, m), 4.52 (2H, s), 5.36 (2H, s), 7.29 (1H, m), 7.37 (4H, m), 7.53 (5H, m), 7.85 (1H, d, J=1.8 Hz).

Example 26

1-Benzyl-7-[4-(4-(pyrrolidin-1-yl)piperidine-1-carbonyl)phenyl]-3,4-dihydro-1H-pyrido[2,3-b]pyrazin-2-one, trifluoroacetic acid salt

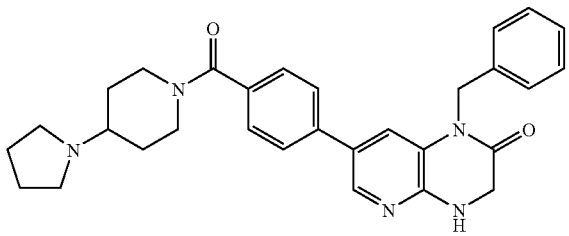

4-(1-Benzyl-2-oxo-1,2,3,4-tetrahydropyrido[2,3-b]pyrazin-7-yl)benzoic acid (45 mg) was coupled with 4-(1 pyrrolidinyl)piperidine as in General Procedure 8 to give the title compound as a yellow solid after preparative reversed-phase HPLC purification (28% yield). LCMS: m/z=496.15 (M+H$^+$), $^1$H-NMR (CD$_3$OD, 400 MHz) δ 1.67 (2H, m), 2.09 (7H, m), 3.17 (3H, m), 3.41 (2H, m), 3.66 (2H, m), 3.86 (2H, bs), 4.51 (2H, s), 5.36 (2H, s), 7.29 (1H, m), 7.38 (4H, s), 7.50 (1H, d, J=1.5 Hz), 7.53 (2H, m), 7.85 (1H, d, J=1.5 Hz).

Example 27

4-(1-Benzyl-2-oxo-1,2,3,4-tetrahydropyrido[2,3-b] pyrazin-7-yl)-N-ethyl-benzamide

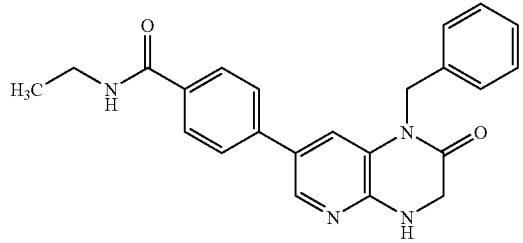

4-(1-Benzyl-2-oxo-1,2,3,4-tetrahydropyrido[2,3-b]pyrazin-7-yl)benzoic acid (43 mg) was coupled with ethylamine as in General Procedure 8 to give the title compound as a tan solid (15% yield). M.p.=195° C., LCMS: m/z=387.31 (M+H$^+$), $^1$H-NMR (CDCl$_3$, 400 MHz) δ 1.24 (3H, t, J=7.3 Hz), 3.44 (2H, quartet, J=7.3 Hz), 4.51 (2H, s), 5.26 (2H, s), 7.33 (8H, m), 7.76 (1H, d, J=8.6 Hz), 7.81 (2H, d, J=8.1 Hz), 8.05 (1H, d, J=8.3 Hz).

Example 28

5-(1-Benzyl-2-oxo-1,2,3,4-tetrahydropyrido[2,3-b] pyrazin-7-yl)pyridine-2-carbonitrile

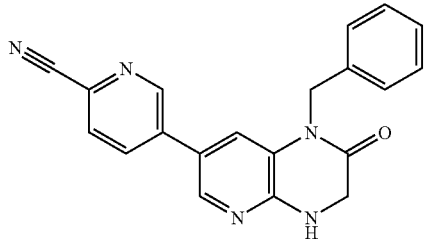

1-Benzyl-7-iodo-3,4-dihydro-1H-pyrido[2,3-b]pyrazin-2-one (196 mg) was reacted with 2-cyanopyridine-5-boronic acid pinacol ester as in General Procedure 4B to give the title compound as a yellow solid (46% yield). M.p.>200° C., LCMS: m/z=342.20 (M+H$^+$), $^1$H-NMR (DMSO-d$_6$, 400 MHz) δ 4.23 (2H, s), 5.27 (2H, s), 7.23 (1H, m), 7.32 (4H, m), 7.49 (2H, m), 8.03 (1H, d, J=8.3 Hz), 8.18 (2H, m), 8.95 (1H, d, J=2.0 Hz).

Example 29

5-(1-Benzyl-2-oxo-1,2,3,4-tetrahydropyrido[2,3-b] pyrazin-7-yl)pyridine-2-carboxylic acid ethyl ester

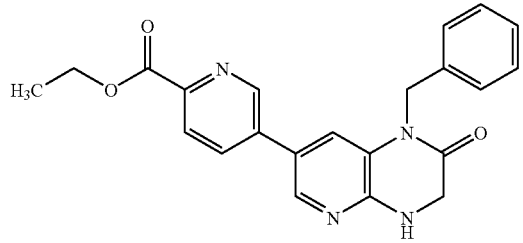

5-(1-Benzyl-2-oxo-1,2,3,4-tetrahydropyrido[2,3-b]pyrazin-7-yl)pyridine-2-carbonitrile (32 mg) was mixed with ethanol (1.5 mL) and 4 N HCl (2.0 mL) in dioxane and then heated in a microwave oven at 150° C. for 80 minutes. The reaction mixture was concentrated and purified with preparative reversed-phase HPLC to give the title compound as an orange solid. LCMS: m/z=389.22 (M+H$^+$), $^1$H-NMR (CD$_3$OD, 400 MHz) δ 1.42 (3H, t, J=7.1 Hz), 4.44 (4H, m), 5.35 (2H, s), 7.28 (1H, m), 7.37 (5H, m), 7.55 (1H, d, J=1.8 Hz), 8.00 (1H, d, J=1.8 Hz), 8.03 (1H, dd, J=8.1, 2.3 Hz), 8.17 (1H, d, J=8.3 Hz), 8.69 (1H, d, J=2.0 Hz).

Example 30

3-(1-Benzyl-2-oxo-1,2,3,4-tetrahydropyrido[2,3-b] pyrazin-7-yl)benzoic acid methyl ester

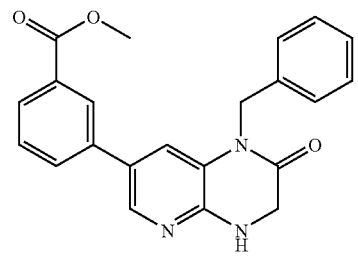

1-Benzyl-7-iodo-3,4-dihydro-1H-pyrido[2,3-b]pyrazin-2-one (370 mg) was reacted with 3-methoxycarbonyl phenyl boronic acid as in General Procedure 4A to give the title compound as a white solid (70% yield). M.p. 211° C., LCMS: m/z=374.17 (M+H$^+$), $^1$H-NMR (CD$_3$OD, 400 MHz) δ 3.95 (s, 3H), 4.48 (s, 2H), 5.35 (s, 2H), 7.23-7.35 (m, 2H), 7.38-7.40 (m, 2H), 7.50-7.58 (m, 2H), 7.60-7.66 (m, 2H), 7.84 (s, 1H), 7.9-8.1 (m, 2H).

Example 31

3-(1-Benzyl-2-oxo-1,2,3,4-tetrahydropyrido[2,3-b] pyrazin-7-yl)benzoic acid

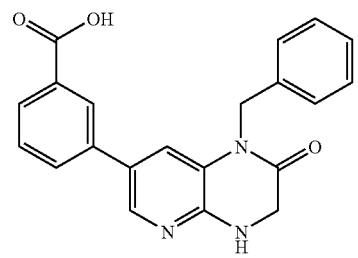

3-(1-Benzyl-2-oxo-1,2,3,4-tetrahydropyrido[2,3-b]pyrazin-7-yl)benzoic acid methyl ester (245 mg) was saponified as in General Procedure 7 to give the title compound as a tan film (73% yield). M.p. (film), LCMS: m/z=360.18 (M+H$^+$), $^1$H-NMR (CD$_3$OD, 400 MHz) δ 4.53 (s, 2H), 5.37 (s, 2H), 7.28-7.35 (m, 1H), 7.37-7.45 (m, 4H), 7.52-7.58 (m, 1H), 7.62-7.65 (m, 2H), 7.82 (d, J=1.8 Hz, 1H), 8.03 (s, 1H), 8.04 (d, J=8.8 Hz, 1H).

Example 32

1-Benzyl-1,2,3,4-tetrahydropyrido[2,3-b]pyrazine

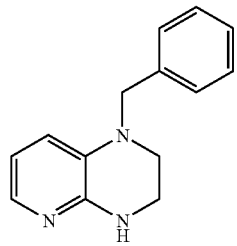

1-Benzyl-7-iodo-3,4-dihydro-1H-pyrido[2,3-b]pyrazin-2-one (50 mg) was dissolved in anhydrous tetrahydrofuran and added to LiAlH$_4$ (1 M in tetrahydrofuran, 9.0 eq) over 2 minutes. After stirring for 35 minutes at room temperature, the reaction mixture was quenched with wet ether, diluted with ethyl acetate and H$_2$O, and filtered. The organic phase was isolated, dried, filtered, and concentrated. Silica gel chromatography (0-10% methanol in CH$_2$Cl$_2$) gave the title compound as a pale yellow film (10% yield). M.p. (film), LCMS: m/z=226.19 (M+H$^+$), $^1$H-NMR (CDCl$_3$, 400 MHz) δ 3.35-3.40 (m, 2H), 3.52-3.57 (m, 2H), 4.40 (s, 2H), 4.83 (bs, 1H), 6.41-6.50 (m, 1H), 6.56-6.63 (m, 1H), 7.20-7.38 (m, 5H), 7.43 (d, J=1.2H).

Example 33

1-Benzyl-7-iodo-1,2,3,4-tetrahydropyrido[2,3-b]pyrazine

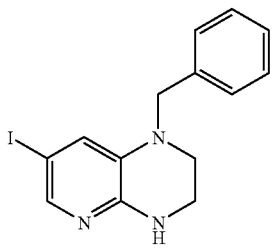

1-Benzyl-7-iodo-3,4-dihydro-1H-pyrido[2,3-b]pyrazin-2-one (50 mg) was reduced as in General Procedure 3 to give the title compound as a light brown solid (25% yield). M.p. 147-148° C., LCMS: m/z=352.02 (M+H$^+$), $^1$H-NMR (CDCl$_3$, 400 MHz) δ 3.09-3.32 (m, 2H), 3.51-3.54 (m, 2H), 4.36 (s, 2H), 6.84 (s, 1H), 7.23-7.30 (m, 1H), 7.31-7.39 (m, 4H), 7.58 (d, J=1.5 Hz, 1H).

Example 34

1-Benzyl-7-pyridin-3-yl-1,2,3,4-tetrahydropyrido[2,3-b]pyrazine

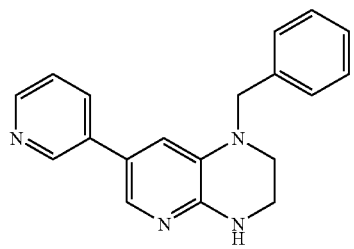

1-Benzyl-7-iodo-1,2,3,4-tetrahydropyrido[2,3-b]pyrazine (30 mg) was reacted with pyridine 3-boronic acid as in General Procedure 4A to give the title compound as a light yellow film (23% yield). M.p. (film), LCMS: m/z=303.40 (M+H$^+$), $^1$H-NMR (CDCl$_3$, 400 MHz) δ 3.41-3.44 m, 2H), 3.60-3.63 (m, 2H), 4.49 (s, 2H), 6.80 (s, 1H), 5.40 (bs, 1H), 6.80 (s, 1H), 7.27-7.42 (m, 5H), 7.64 (s, 1H), 7.65 (d, J=7.8 Hz, 1H), 8.48 (d, J=4.8 Hz, 1H), 8.63 (s, 1H).

Example 35

4-(1-Benzyl-1,2,3,4-tetrahydropyrido[2,3-b]pyrazin-7-yl)benzoic acid ethyl ester

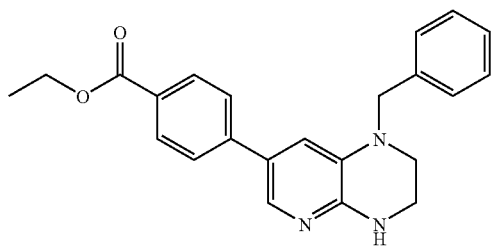

(7-Iodo-3,4-dihydro-2H-pyrido[2,3-b]pyrazin-1-yl)phenyl-methanone (293 mg) was reacted with 4-ethoxycarbonyl phenyl boronic acid as in General Procedure 4A to give the title compound as a pale yellow solid (42% yield). M.p. 178-179° C., LCMS: m/z=374.30 (M+H$^+$), $^1$H-NMR (CDCl$_3$, 400 MHz) δ 1.38 (t, J=7.1) Hz, 3H), 3.40 (t, J=5.1 Hz, 2H), 3.60-3.63 (m, 2H), 4.35 (q, J=7.1 Hz, 2H), 4.48 (s, 2H), 6.85 (s, 1H), 7.27-7.49 (m, 5H), 7.43 (d, J=8.3 Hz, 2H), 7.73 (d, J=2.0 Hz, 2H), 8.00 (d, J=8.3 Hz, 2H).

Example 36

4-(1-Benzyl-1,2,3,4-tetrahydropyrido[2,3-b]pyrazin-7-yl)benzoic acid

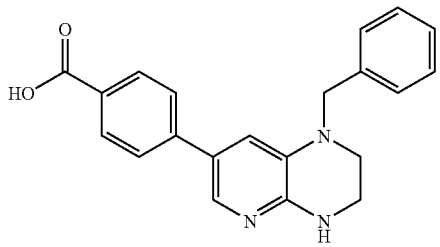

4-(1-Benzyl-1,2,3,4-tetrahydropyrido[2,3-b]pyrazin-7-yl)benzoic acid ethyl ester (118 mg) was saponified as in General Procedure 7 to give the title compound as a pale yellow solid (90% yield). M.p.>300° C., LCMS: m/z=346.30 (M+H$^+$), $^1$H-NMR (DMSO-d$_6$, 400 MHz) δ 3.35-3.38 (m, 2H), 3.52-3.54 (m, 2H), 4.62 (s, 2H), 7.08 (s, 1H), 7.25-7.27 (m, 1H), 7.29-7.32 (m, 4H), 7.62 (d, J=8.4 Hz, 2H), 7.69 (d, J=1.8 Hz, 1H), 7.92 (d, J=8.4 Hz, 2H), 12.86 (bs, 1H).

Example 37

[4-(1-Benzyl-1,2,3,4-tetrahydropyrido[2,3-b]pyrazin-7-yl)phenyl]-(4-methylpiperazin-1-yl)methanone

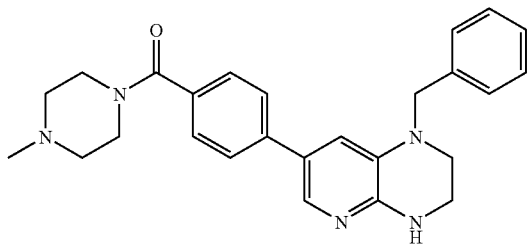

4-(1-Benzyl-1,2,3,4-tetrahydropyrido[2,3-b]pyrazin-7-yl)benzoic acid (20 mg) was reacted with 1-methyl piperazine as in General Procedure 8 to give the title compound as a yellow solid (32% yield). M.p. 180-181° C., LCMS: m/z=428.30 (M+H$^+$), $^1$H-NMR (CDCl$_3$, 400 MHz) δ 2.31 (s, 3H), 2.33-2.52 (m, 4H), 3.38-3.43 (m, 2H), 3.45-3.55 (m, 2H), 3.46-3.50 (m, 2H), 3.58-3.62 (m, 2H), 3.64-3.82 (m, 2H), 4.48 (s, 2H), 5.29 (s, 1H), 6.83 (s, 1H), 7.27-7.39 (m, 9H), 7.69 (s, 1H).

Example 38

[4-(1-Benzyl-1,2,3,4-tetrahydropyrido[2,3-b]pyrazin-7-yl)phenyl]-((S)-2-pyrrolidinylmethylpyrrolidin-1-yl)methanone, trifluoroacetic acid salt

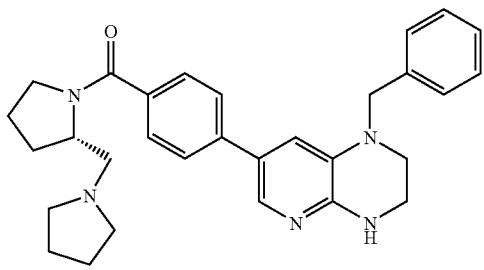

4-(1-Benzyl-1,2,3,4-tetrahydropyrido[2,3-b]pyrazin-7-yl)benzoic acid (20 mg) was reacted with (S)-(+)-1-(2-pyrrolidinylmethyl)pyrrolidine as in General Procedure 8 to give the title compound as a yellow foam after reversed phase preparative HPLC (43% yield). M.p. foam, LCMS: m/z 482.30, $^1$H-NMR (CDCl$_3$, 400 MHz) δ 1.82-1.84 (m, 1H), 1.92-2.05 (m, 2H), 2.06-2.20 (m, 4H), 2.92-3.08 (m, 1H), 3.18-3.25 (m, 1H), 3.25-3.35 (m, 1H), 3.39-48 (m, 2H), 3.50-3.5 (m, 1H), 3.55-3.63 (m, 1H), 3.65-3.71 (m, 1H), 3.72-3.77 (m, 2H), 3.82-3.94 (m, 1H), 4.01-4.11 (m, 1H), 4.48-4.59 (m, 3H), 6.92 (s, 1H), 7.26-7.42 (m, 8H), 7.56 (d, J=8.1 Hz, 2H), 11.06 (bs, 1H).

Example 39

[4-(1-Benzyl-1,2,3,4-tetrahydropyrido[2,3-b]pyrazin-7-yl)phenyl]-(4-(pyrrolidin-1-yl)piperidin-1-yl)methanone

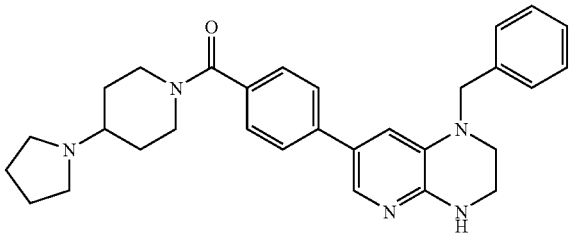

4-(1-Benzyl-1,2,3,4-tetrahydropyrido[2,3-b]pyrazin-7-yl)benzoic acid (20 mg) was reacted with 4-(1 pyrrolidinyl)piperidine as in General Procedure 8 to give the title compound as a yellow solid (22% yield). M.p. 120° C., LCMS: m/z=482.26 (M+H$^+$), $^1$H-NMR (CDCl$_3$, 400 MHz) δ 1.53-1.65 (m, 7H), 1.90-2.04 (m, 3H), 2.25-2.35 (m, 1H), 2.53-2.63 (m, 4H), 2.91-3.06 (m, 2H), 3.38-3.44 (m, 2H), 3.59-3.62 (m, 2H), 4.48 (s, 2H), 5.01 (bs, 1H), 6.84 (s, 1H), 7.28-7.40 (m, 9H), 7.70 (s, 1H).

Example 40

7-Iodo-1,2,3,4-tetrahydropyrido[2,3-b]pyrazine

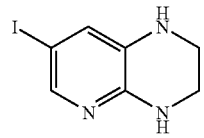

7-Iodo-3,4-dihydro-1H-pyrido[2,3-b]pyrazin-2-one (200 mg) was reduced as in General Procedure 3 using 4 eq DIBAL-H to give the title compound as a white solid (31% yield). M.p. 126-128° C., LCMS: m/z=262.30 (M+H$^+$), $^1$H-NMR (DMSO-d$_6$, 400 MHz) δ 3.13-3.17 (m, 2H), 3.27-3.29 (m, 2H), 5.78 (s, 1H), 6.37 (s, 1H), 6.78 (d, J=2.0 Hz, 1H), 7.33 (d, J=2.0 Hz, 1H).

Example 41

(3,4-Dihydro-2H-pyrido[2,3-b]pyrazin-1-yl)phenylmethanone

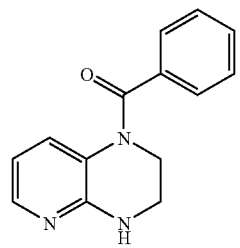

1,2,3,4-tetrahydropyrido[2,3-b]pyrazine was reacted with benzoyl chloride as in General Procedure 2 to give the title compound as a beige solid (<10% yield). M.p. 166-168° C., LCMS: m/z=240.12 (M+H⁺), ¹H-NMR (DMSO-d$_6$, 400 MHz) δ 3.45-3.49 (m, 2H), 3.84-3.87 (m, 2H), 6.40 (s, 1H), 6.77 (dd, J=4.8 Hz, 4.5 Hz, 1H), 6.92 (dd, J=1.5 Hz, 7.8 Hz, 1H), 7.10 (dd, J=1.5 Hz, 4.6 Hz, 1H), 7.25-7.34 (m, 5H).

Example 42

(7-Iodo-3,4-dihydro-2H-pyrido[2,3-b]pyrazin-1-yl) phenylmethanone

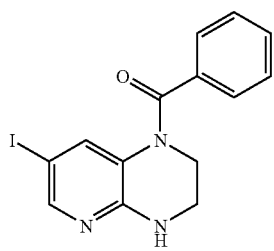

7-Iodo-1,2,3,4-tetrahydropyrido[2,3-b]pyrazine (50 mg) was reacted with benzoyl chloride as in General Procedure 2 to give the title compound as a pale yellow solid (61% yield). M.p. 164-166° C., LCMS: m/z=366.00 (M+H⁺), ¹H-NMR (CDCl$_3$, 400 MHz) δ 3.45-3.50 (m, 2H), 3.90 (t, J=4.8 Hz, 2H), 7.37-7.47 (m, 6H), 7.95 (s, 1H).

Example 43

Phenyl-(7-pyridin-3-yl-3,4-dihydro-2H-pyrido[2,3-b]pyrazin-1-yl)methanone

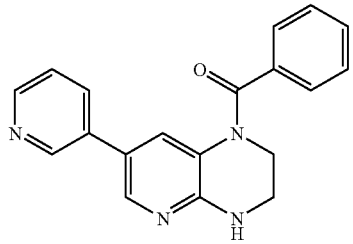

(7-Iodo-3,4-dihydro-2H-pyrido[2,3-b]pyrazin-1-yl)phenyl-methanone (50 mg) was reacted with pyridine 3-boronic acid as in General Procedure 4A to give the title compound as a yellow solid (25% yield). M.p. 219-220° C., LCMS: m/z=317.40 (M+H⁺), ¹H-NMR (CDCl$_3$, 400 MHz) δ 3.45-3.50 (m, 2H), 4.02 (t, J=4.8 Hz, 2H), 5.39 (s, 1H), 7.20-7.22 (m, 2H), 7.40-7.44 (m, 3H), 7.47-7.51 (m, 3H), 8.03 (s, 1H), 8.30 (s, 1H), 8.47 (d, J=4.3 Hz, 1H).

Example 44

4-(1-Benzoyl-1,2,3,4-tetrahydropyrido[2,3-b] pyrazin-7-yl)benzoic acid ethyl ester

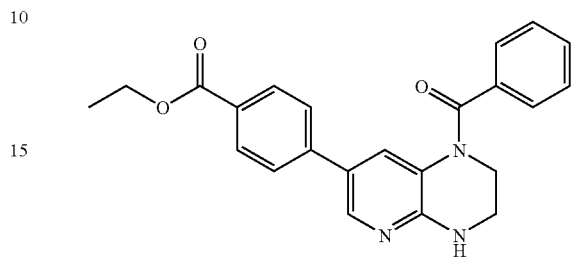

(7-Iodo-3,4-dihydro-2H-pyrido[2,3-b]pyrazin-1-yl)phenyl-methanone (215 mg) was reacted with 4-ethoxycarbonyl phenyl boronic acid as in General Procedure 4A to give the title compound as an off-white solid (32% yield). M.p. 177-178° C., LCMS: m/z=388.23 (M+H⁺), ¹H-NMR (CDCl$_3$, 400 MHz) δ 1.38 t, (J=7.1 Hz, 3H), 3.67-3.72 (m, 2H), 4.01-4.08 (m, 2H), 4.36 (q, J=7.1 Hz, 2H), 5.21 (bs, 1H), 7.12-7.16 (m, 2H), 7.40-7.53 (m, 5H), 7.95 (d, J=8.3 Hz, 2H), 8.08 (s, 1H).

Example 45

2-Pyrrolidin-1-yl-ethanesulfonic acid[4-(1-benzyl-2-oxo-1,2,3,4-tetrahydropyrido[2,3-b]pyrazin-7-yl)phenyl]amide, trifluoroacetic acid salt

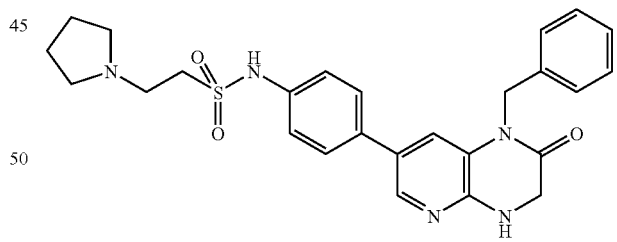

2-pyrrolidin-1-yl-ethanesulfonic acid[4-(4,4,5,5-tetramethyl-[1,3,2]dioxaborolan-2-yl)phenyl]amide was prepared as in General Procedure 11 and then reacted with 1-benzyl-7-iodo-3,4-dihydro-1H-pyrido[2,3-b]pyrazin-2-one (31 mg) as in General Procedure 4B to give the title compound as a yellow solid after purification by preparative reversed-phase HPLC (38% yield). LCMS: m/z=492.09 (M+H⁺), ¹H-NMR (CD$_3$OD, 400 MHz) δ 2.08 (4H, bs), 3.13 (2H, m), 3.63 (6H, m), 4.51 (2H, s), 5.34 (2H, s), 7.30 (3H, m), 7.37 (6H, m), 7.51 (1H, s), 7.75 (1H, s).

Example 46

2-Pyrrolidin-1-yl-ethanesulfonic acid[4-(1-benzoyl-1,2,3,4-tetrahydropyrido[2,3-b]pyrazin-7-yl)phenyl]amide

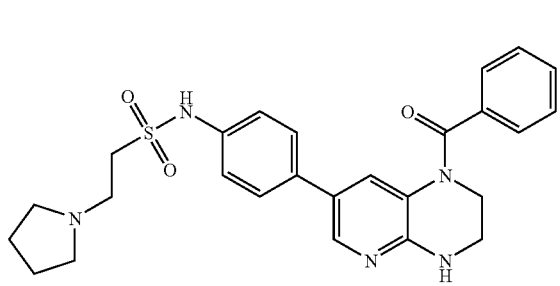

2-Pyrrolidin-1-yl-ethanesulfonic acid[4-(4,4,5,5-tetramethyl-[1,3,2]dioxaborolan-2-yl)phenyl]amide (50 mg) was prepared as in General Procedure 11 and then reacted with (7-Iodo-3,4-dihydro-2H-pyrido[2,3-b]pyrazin-1-yl)phenylmethanone as in General Procedure 4A to give the title compound as an off-white foam (18% yield). M.p. foam, LCMS: m/z=492.10 (M+H$^+$), $^1$H-NMR (CDCl$_3$, 400 MHz) δ 1.33 (s, 1H), 1.76-1.82 (m, 4H), 2.45-2.55 (m, 4H), 3.02 (t, J=6.3 Hz, 2H), 3.22 (t, J=6.0 Hz, 2H), 3.63-3.68 (m, 2H), 4.02 (t, J=4.6 Hz, 2H), 5.33 (bs, 1H), 6.98-7.-4 (m, 2H), 7.11 (d, J=8.3 Hz, 2H), 7.26 (s, 1H), 7.47 (d, J=8.3 Hz, 2H), 7.48-7.54 (m, 3H), 7.98 (d, J=2.0 Hz, 1H).

Example 47

2-(4-Methylpiperazin-1-yl)-ethanesulfonic acid[4-(1-benzoyl-1,2,3,4-tetrahydropyrido[2,3-b]pyrazin-7-yl)phenyl]amide

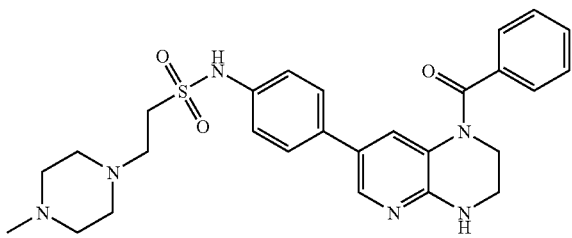

2-(4-Methylpiperazin-1-yl)-ethanesulfonic acid[4-(4,4,5,5-tetramethyl[1,3,2]dioxaborolan-2-yl)phenyl]amide (50 mg) was prepared as in General Procedure 11 and then reacted with (7-Iodo-3,4-dihydro-2H-pyrido[2,3-b]pyrazin-1-yl)phenylmethanone as in General Procedure 4A to give the title compound as a yellow foam (45% yield). M.p. foam, LCMS: m/z=521.20 (M+H$^+$), $^1$H-NMR (CDCl$_3$, 400 MHz) δ 3.68 (s, 3H), 2.35-2.58 (m, 8H), 2.90 (t, J=6.6 Hz, 2H), 3.23 (t, J=6.3 Hz, 2H), 3.65-3.69 (m, 2H), 3.97-4.05 (m, 2H), 5.45 (bs, 1H), 6.99-7.06 (m, 2H), 7.16 (d, J=8.3 Hz, 2H), 7.27 (s, 1H), 7.39-7.53 (m, 5H), 7.99 (d, J=1.8 Hz, 1H).

Example 48

2-Pyrrolidin-1-yl-ethanesulfonic acid{4-[1-(2,5-difluorobenzyl)-2-oxo-1,2,3,4-tetrahydropyrido[2,3-b]pyrazin-7-yl]phenyl}-amide

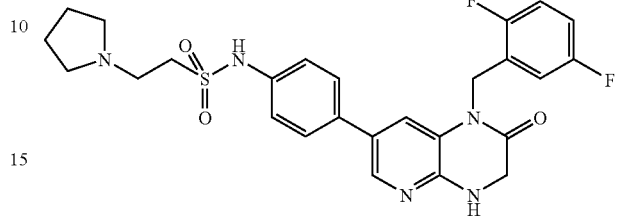

2-Pyrrolidin-1-yl-ethanesulfonic acid[4-(4,4,5,5-tetramethyl-[1,3,2]dioxaborolan-2-yl)phenyl]amide (40 mg) was prepared as in General Procedure 11 and then reacted with 1-(2,5-Difluorobenzyl)-7-iodo-3,4-dihydro-1H-pyrido[2,3-b]pyrazin-2-one as in General Procedure 4A with the modification that the reaction was heated to 130° C. in a microwave oven for 10 minutes. The title compound was isolated as an off-white solid (36% yield). M.p.>300° C., LCMS: m/z=528.03 (M+H$^+$), $^1$H-NMR (CDCl$_3$, 400 MHz) δ 1.83-1.86 (m, 4H), 2.52-2.64 (m, 4H), 3.06 (t, J=6.3 Hz, 2H), 3.25 (t, J=6.3 Hz, 2H), 4.32 (s, 2H), 4.97 (bs, 1H), 5.21 (s, 2H), 6.89-6.98 (m, 2H), 7.05-7.11 (m, 1H), 7.16 (d, J=1.8 Hz, 1H), 7.21 (d, J=8.6 Hz, 2H), 7.26 (s, 1H), 7.33 (d, J=8.6 Hz, 2H), 7.92 (s, 1H).

Example 49

2-[Ethyl-((S)-1-pyrrolidin-1-ylmethyl-propyl)-amino]-ethanesulfonic acid{4-[1-(2,5-difluorobenzyl)-2-oxo-1,2,3,4-tetrahydropyrido[2,3-b]pyrazin-7-yl]phenyl}-amide

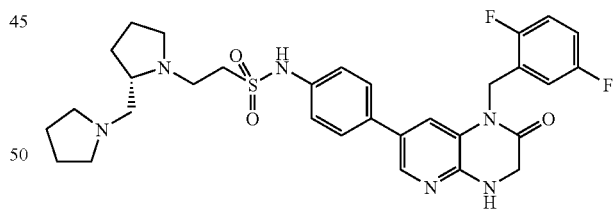

2-[Ethyl-((S)-1-pyrrolidin-1-ylmethyl-propyl)-amino]-ethanesulfonic acid[4-(4,4,5,5-tetramethyl-[1,3,2]dioxaborolan-2-yl)phenyl]amide (40 mg) was prepared as in General Procedure 11 and then reacted with 1-(2,5-difluorobenzyl)-7-iodo-3,4-dihydro-1H-pyrido[2,3-b]pyrazin-2-one as in General Procedure 4A with the modification that the reaction was heated to 130° C. in a microwave oven for 10 minutes. The title compound was obtained as a light yellow foam (10% yield). M.p. foam, LCMS: m/z=611.07 (M+H$^+$), $^1$H-NMR (CDCl$_3$, 400 MHz) δ 1.44-1.53 (m, 1H), 1.82-1.99 (m, 5H), 2.22-2.25 (m, 1H), 2.26-2.33 (m, 2H), 2.45-2.55 (m, 2H), 2.70-2.92 (m, 7H), 2.90-3.12 (m, 2H), 3.44-3.60 (m, 2H), 4.32 (s, 2H), 4.96 (s, 1H), 5.21 (s, 2H), 6.88-6.98 (m, 2H), 7.04-7.12 (m, 1H), 7.18 (s, 1H), 7.29 (d, J=8.6 Hz, 2H), 7.36 (d, J=8.6 Hz, 2H), 7.98 (d, J=1.89 Hz, 1H).

Example 50

2-Morpholin-4-yl-ethanesulfonic acid{4-[1-(2,5-difluorobenzyl)-2-oxo-1,2,3,4-tetrahydropyrido[2,3-b]pyrazin-7-yl]phenyl}-amide

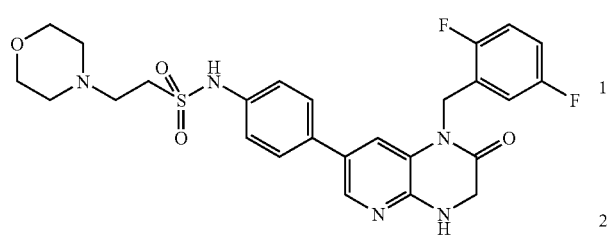

2-Morpholin-4-yl-ethanesulfonic acid[4-(4,4,5,5-tetramethyl-[1,3,2]dioxaborolan-2-yl)phenyl]amide (40 mg) was prepared as in General Procedure 11 and then reacted with 1-(2,5-difluorobenzyl)-7-iodo-3,4-dihydro-1H-pyrido[2,3-b]pyrazin-2-one as in General Procedure 4A to give the title compound as a white solid (11% yield). m.p. 225° C., LCMS: m/Z=544.20 (M+H⁺), ¹H-NMR (CDCl₃, 400 MHz) δ 2.51 (t, J=4.5 Hz, 4H), 2.92 (t, J=6.3 Hz, 2H), 3.28 (t, J=6.3 Hz, 2H), 4.31 (s, 2H), 4.95 (s, 1H), 5.22 (s, 2H), 6.91-6.99 (m, 2H), 7.05-7.10 (m, 1H), 7.14 (s, 1H), 7.25 (d, J=8.6 Hz, 2H), 7.34 (d, J=8.6 Hz, 2H), 7.92 (s, 1H).

Example 51

2-Pyrrolidin-1-yl-ethanesulfonic acid{4-[1-(2,5-difluorobenzyl)-1,2,3,4-tetrahydropyrido[2,3-b]pyrazin-7-yl]phenyl}-amide

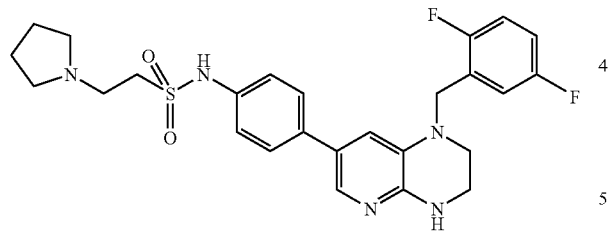

2-Pyrrolidin-1-yl-ethanesulfonic acid[4-(4,4,5,5-tetramethyl-[1,3,2]dioxaborolan-2-yl)phenyl]amide (39 mg) was prepared as in General Procedure 11 and then reacted with 1-(2,5-difluorobenzyl)-7-iodo-1,2,3,4-tetrahydropyrido[2,3-b]pyrazine as in General Procedure 4A with the modification that the reaction was heated to 130° C. in a microwave oven for 10 minutes. The title compound was obtained as a light yellow solid (15% yield). M.p. slow decomp, LCMS: m/z= (M+H⁺), ¹H-NMR (CDCl₃, 400 MHz) δ 1.80-1.84 (m, 4H), 2.54-2.58 (m, 4H), 3.03 (t, J=6.1 Hz, 2H), 3.23 (t, J=6.1 Hz, 2H), 3.45 (t, J=5.3 Hz, 2H), 3.60-3.64 (m, 2H), 4.49 (s, 2H), 5.03 (bs, 1H), 6.73 (s, 1H), 6.92-7.08 (m, 3H), 7.17 (d, J=8.3 Hz, 2H), 7.33 (d, J=8.5 Hz, 2H), 7.66 (d, J=1.8 Hz, 1H), 8.08 (s, 1H).

Example 52

4-(1-Benzoyl-1,2,3,4-tetrahydropyrido[2,3-b]pyrazin-7-yl)-N-(2-dimethylamino-ethyl)benzamide

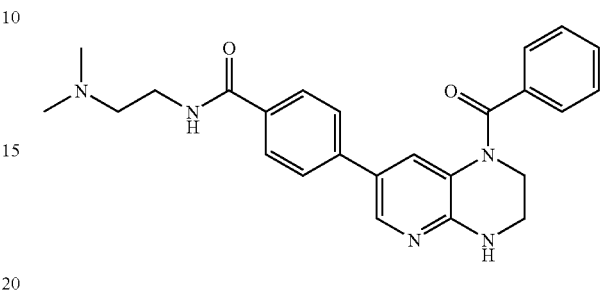

(7-Iodo-3,4-dihydro-2H-pyrido[2,3-b]pyrazin-1-yl)phenyl-methanone (50 mg) was reacted with N-(2-dimethylamino-ethyl)-4-(4,4,5,5-tetramethyl-[1,3,2]dioxaborolan-2-yl)benzamide as in General Procedure 4A to give the title compound as a light yellow solid (24% yield). M.p. 145-147° C., LCMS: m/z=430.26 (M+H⁺), ¹H-NMR (CDCl₃, 400 MHz) δ 2.28 (s, 6H), 2.48-2.53 (m, 2H), 3.48-3.54 (m, 2H), 3.66-3.71 (m, 2H0, 4.01 (t, J=4.8 Hz, 2H), 5.55 (bs, 1H), 6.84-6.87 (m, 1H), 7.09-7.15 (m, 2H), 7.38-7.52 (m, 6H), 7.71 (d, J=8.1 Hz, 2H), 8.05 (d, J=2.0 Hz, 1H).

Example 53

4-(1-Benzoyl-1,2,3,4-tetrahydropyrido[2,3-b]pyrazin-7-yl)-N-(3-dimethylamino-propyl)benzamide

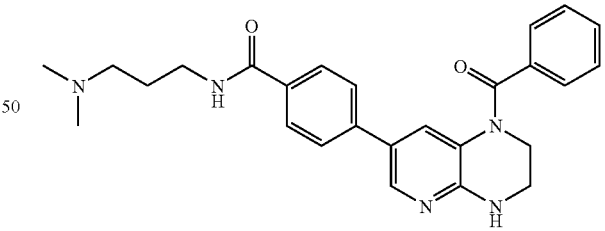

(7-Iodo-3,4-dihydro-2H-pyrido[2,3-b]pyrazin-1-yl)phenyl-methanone (50 mg) was reacted with N-(3-dimethylamino-propyl)-4-(4,4,5,5-tetramethyl-[1,3,2]dioxaborolan-2-yl) benzamide as in General Procedure 4A to give the title compound as a light yellow solid (44% yield). M.p. 94° C., LCMS: m/z=444.20 (M+H⁺), ¹H-NMR (CDCl₃, 400 MHz) δ 1.72-1.80 (m, 2H), 2.27 (s, 6H), 2.48-2.53 (t, J=5.8 Hz, 2H), 3.48-3.54 (m, 2H), 3.67-3.73 (m, 2h), 3.98-4.04 (m, 2H), 5.44 (bs, 1H), 7.10-7.18 (m, 2H), 7.36-7.48 (m, 6H), 7.69 (d, J=8.1 Hz, 2H), 8.07 (s, 1H), 8.42 (bs, 1H).

Example 54

{7-[4-(4-Methylpiperazine-1-carbonyl)phenyl]-3,4-dihydro-2H-pyrido[2,3-b]pyrazin-1-yl}phenylmethanone

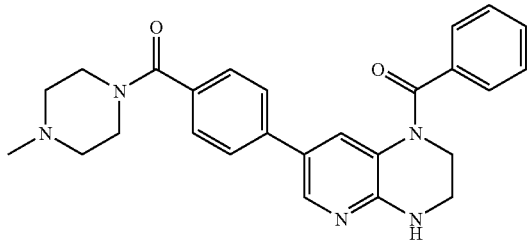

(7-Iodo-3,4-dihydro-2H-pyrido[2,3-b]pyrazin-1-yl)phenylmethanone (50 mg) was reacted with (4-methylpiperazin-1-yl)-[4-(4,4,5,5-tetramethyl-[1,3,2]doxaborolan-2-yl)phenyl]methanone as in General Procedure 4A to give the title compound as a light green foam (53% yield). M.p. foam, LCMS: m/z=442.30 (M+H$^+$), $^1$H-NMR (CDCl$_3$, 400 MHz) δ 2.32 (s, 3H), 2.35-2.48 (m, 4H), 3.40-3.50 (m, 2H), 3.62-3.69 (M, 2h), 3.70-3.80 (m, 2h), 3.97-4.03 (m, 2H), 5.42 (bs, 1H), 7.06-7.15 (m, 2H), 7.34 (d, J=8.1 Hz, 2H), 7.40-7.52 (m, 6H), 8.05 (s, 1H).

Example 55

4-[1-(2,5-Difluorobenzyl)-2-oxo-1,2,3,4-tetrahydropyrido[2,3-b]pyrazin-7-yl]benzoic acid ethyl ester

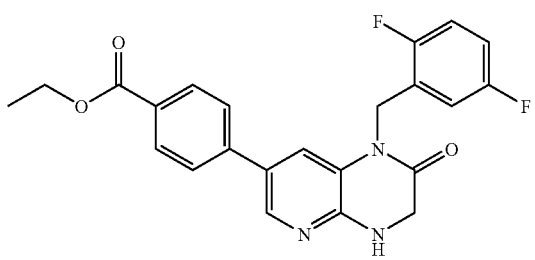

1-(2,5-Difluorobenzyl)-7-iodo-3,4-dihydro-1H-pyrido[2,3-b]pyrazin-2-one (600 mg) was reacted with 4-ethoxycarbonyl phenyl boronic acid as in General Procedure 4A to give the title compound as an off-white solid (62% yield). M.p. 201-203° C., LCMS: m/z=424.20 (M+H$^+$), $^1$H-NMR (DMSO-d$_6$, 400 MHz) δ 1.32 (t, J=7.0 Hz, 3H), 3.99 (s, 2H), 4.32 (q, J=7.0 Hz, 2H), 5.26 (s, 2H), 7.03-7.09 (m, 1H), 7.11-7.19 (m, 1H), 7.33 (s, 1H), 7.34-7.38 (m, 1H), 7.39 (s, 1H), 7.67 (d, J=7.0 Hz, 2H), 6.8 Hz, 2H), 8.10 (s, 1H).

Example 56

4-[1-(2,5-Difluorobenzyl)-2-oxo-1,2,3,4-tetrahydropyrido[2,3-b]pyrazin-7-yl]benzoic acid

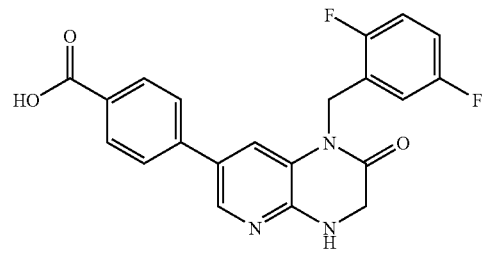

4-[1-(2,5-Difluorobenzyl)-2-oxo-1,2,3,4-tetrahydropyrido[2,3-b]pyrazin-7-yl]benzoic acid ethyl ester (385 mg) was saponified as in General Procedure 7 to give the title compound as an off-white solid (85% yield). M.p.>300° C., LCMS: m/z=396.13 (M+H$^+$), $^1$H-NMR (DMSO-d$_6$, 400 MHz) δ 4.21 (s, 2H), 5.26 (s, 2H), 7.05-7.11 (m, 1H), 7.12-7.18 (m, 1H), 7.27-7.38 (m, 1H), 7.66 (d, J=7.3 Hz, 2H), 7.94 (d, J=7.1 Hz, 2H), 8.10 (s, 1H).

Example 57

1-(2,5-Difluorobenzyl)-7-[4-((S)-2-[(pyrrolidin-1-yl)methyl]pyrrolidine-1-carbonyl)phenyl]-3,4-dihydro-1H-pyrido[2,3-b]pyrazin-2-one

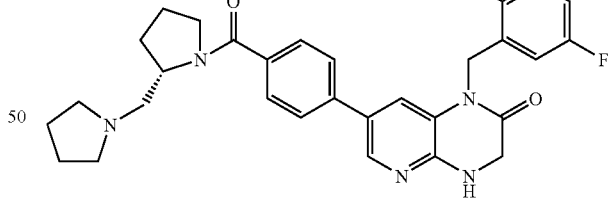

4-[1-(2,5-Difluorobenzyl)-2-oxo-1,2,3,4-tetrahydropyrido[2,3-b]pyrazin-7-yl]benzoic acid (35 mg) was reacted with (S)-(+)-1-(2-pyrrolidinylmethyl)pyrrolidine as in General Procedure 8 to give the title compound as a white solid (32% yield). M.p. 125° C., LCMS: m/z=532.10 (M+H$^+$), $^1$H-NMR (CDCl$_3$, 400 MHz) δ 1.22-1.26 (m, 2H), 1.68-1.82 (m, 4H), 1.89-2.15 (m, 4H), 2.56-2.70 (m, 3H), 2.80-2.90 (m, 1H), 3.42-3.52 (m, 1H), 4.33 (s, 2H), 4.43-4.50 (m, 1H), 5.02 (bs, 1H), 5.22 (s, 2H), 6.91-6.98 (m, 2H), 7.04-7.10 (m, 1H), 7.21 (d, J=1.5 Hz, 1H), 7.39 (d, J=8.1 Hz, 2H), 7.54 (bd, J=7.6 Hz, 2H), 8.01 (d, J=1.5 Hz, 2H).

Example 58

4-[1-(2,5-Difluorobenzyl)-2-oxo-1,2,3,4-tetrahydro-pyrido[2,3-b]pyrazin-7-yl]-N-(2-pyrrolidin-1-yl-ethyl)benzamide

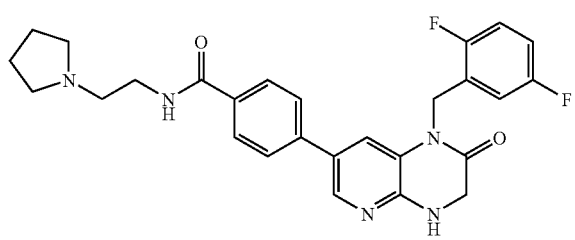

4-[1-(2,5-Difluorobenzyl)-2-oxo-1,2,3,4-tetrahydropyrido[2,3-b]pyrazin-7-yl]benzoic acid (35 mg) was reacted with N-(2-aminoethyl)pyrrolidine as in General Procedure 8 to give the title compound as a white solid (25% yield). M.p. 235° C. (dec), LCMS: m/z=492.20 (M+H$^+$), $^1$H-NMR (CDCl$_3$, 400 MHz) δ 1.81-18.5 (m, 4H), 2.55-2.65 (m, 4H), 2.72-2.80 (m, 2H), 3.58-3.62 (m, 2H), 4.68 (s, 2H), 4.99 (s, 1H), 5.23 (s, 2H), 6.85-6.95 (m, 2H), 7.02-7.08 (m, 1H), 7.07 (s, 1H), 7.44 (d, J=8.3 Hz, 2H), 7.83 (d, J=8.1 Hz, 2H), 8.03 (s, 1H), 8.08 (s, 1H).

Example 59

1-(2,5-Difluorobenzyl)-7-[4-(4-methylpiperazine-1-carbonyl)phenyl]-3,4-dihydro-1H-pyrido[2,3-b]pyrazin-2-one

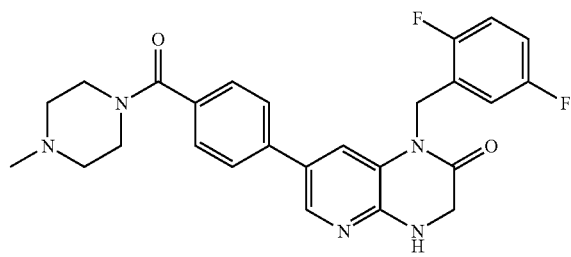

4-[1-(2,5-Difluorobenzyl)-2-oxo-1,2,3,4-tetrahydropyrido[2,3-b]pyrazin-7-yl]benzoic acid (35 mg) was reacted with 1-methyl piperazine as in General Procedure 8 to give the title compound as a light yellow solid (38% yield). m.p. 223° C. (dec), LCMS: m/z=478.20 (M+H$^+$), $^1$H-NMR (CDCl$_3$, 400 MHz) δ 2.32 (s, 3H), 2.35-2.48 (m, 4H), 3.48-3.54 (m, 2H), 3.70-3.80 (m, 2H), 4.34 (s, 2H), 5.11 (s, 1H), 5.22 (s, 2H), 6.90-6.98 (m, 2H), 7.06-7.13 (m, 1H), 7.20 (d, J=1.8 Hz, 1H), 7.41 (d, J=8.1 Hz, 1H), 7.45 (d, J=8.3 Hz, 1H), 8.01 (d, J=1.8 Hz, 1H).

Example 60

1-(2,5-Difluorobenzyl)-7-[4-(4-(pyrrolidin-1-yl)piperidine-1-carbonyl)phenyl]-3,4-dihydro-1H-pyrido[2,3-b]pyrazin-2-one

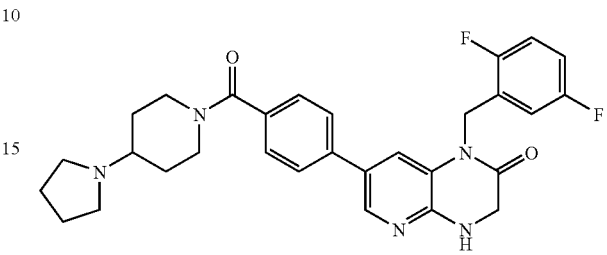

4-[1-(2,5-Difluorobenzyl)-2-oxo-1,2,3,4-tetrahydropyrido[2,3-b]pyrazin-7-yl]benzoic acid (35 mg) was reacted with 4-(1 pyrrolidinyl)piperidine as in General Procedure 8 to give the title compound as a pale yellow solid (30% yield). M.p. 186° C. (dec) m/z=532.30 (M+H$^+$), $^1$H-NMR (CDCl$_3$, 400 MHz) δ 1.44-1.58 (m, 4H), 1.90-2.06 (m, 2H), 2.28-2.32 (m, 1H), 2.52-2.64 (m, 4H), 2.85-3.11 (m, 3H), 3.70-3.82 (m, 2H), 4.34 (s, 2H), 4.50-4.62 (m, 2H), 5.06 (s, 1H), 5.22 (s, 2H), 6.6.88-6.96 (m, 2H), 7.10-7.22 (m, 1H), 7.20 (s, 1H), 7.40 (dd, J=8.3 Hz, 2H), 8.01 (s, 1H).

Example 61

(S)-2-[(pyrrolidin-1-yl)methyl]pyrrolidine-1-carboxylic acid{4-[1-(2,5-difluorobenzyl)-2-oxo-1,2,3,4-tetrahydropyrido[2,3-b]pyrazin-7-yl]phenyl}-amide

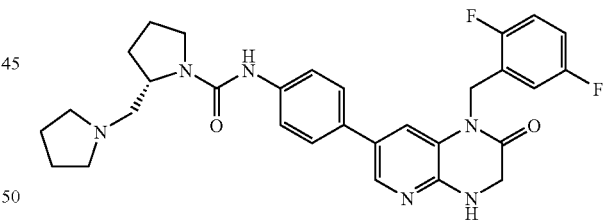

1-(2,5-Difluorobenzyl)-7-iodo-3,4-dihydro-1H-pyrido[2,3-b]pyrazin-2-one (35 mg) was reacted with the product of Preparation 1 (i.e., (S)-2-[(pyrrolidin-1-yl)methyl]pyrrolidine-1-carboxyl-[4-(4,4,5,5-tetramethyl-[1,3,2]dioxaborolan-2-yl)phenyl]amide (N)) as in General Procedure 4A to give the title compound as an orange foam (29% yield). M.p. foam, LCMS: m/z=547.10 (M+H$^+$), $^1$H-NMR (CDCl$_3$, 400 MHz) δ 1.65-1.73 (m, 2H), 1.89-1.95 (m, 4H), 2.45-2.50 (m, 1H), 2.55-2.68 (m, 2H), 2.79-2.89 (m, 2H), 2.91-2.99 (m, 1H), 3.30-3.38 (m, 1H), 3.42-3.52 (m, 1H), 3.79-3.92 (m, 2H), 4.30 (s, 1H), 4.88 (bs, 1H), 5.20 (s, 2H), 6.87-7.09 (m, 4H), 7.15 (s, 1H), 7.23-7.27 (m, 2H), 7.35 (d, J=8.3 Hz, 2H), 7.98 (s, 1H).n 11.09 (bs, 1H).

Example 62

1-(2,5-Difluorobenzyl)-7-iodo-1,2,3,4-tetrahydropyrido[2,3-b]pyrazine

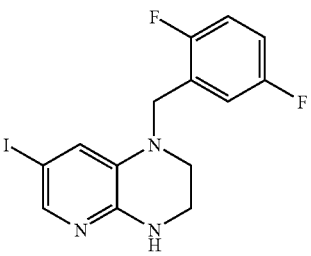

7-Iodo-3,4-dihydro-1H-pyrido[2,3-b]pyrazin-2-one (525 mg) was reacted with 2,5-difluorobenzyl bromide as in General Procedure 1 to give 1-(2,5-Difluorobenzyl)-7-iodo-3,4-dihydro-1H-pyrido[2,3-b]pyrazin-2-one as a tan solid (70% yield). This amide was then reduced as in General Procedure 3 to give the title compound as a white solid (42% yield). M.p. 175° C., LCMS: m/z=388.10 (M+H$^+$), $^1$H-NMR (DMSO-d$_6$, 400 MHz) δ 3.26-3.30 (m, 2H), 3.36-3.42 (m, 2H), 4.44 (s, 2H), 6.63 (bs, 1H), 6.77 (s, 1H), 7.05-7.10 (m, 1H), 7.15-7.19 (m, 1H), 7.20-7.27 (m, 1H), 7.41 (s, 1H).

Example 63

4-[1-(2,5-Difluorobenzyl)-1,2,3,4-tetrahydropyrido[2,3-b]pyrazin-7-yl]benzoic acid ethyl ester

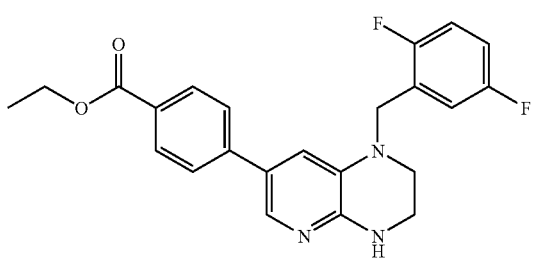

1-(2,5-Difluorobenzyl)-7-iodo-1,2,3,4-tetrahydropyrido[2,3-b]pyrazine (500 mg) was reacted with 4-ethoxycarbonyl phenyl boronic acid as in General Procedure 4A to give the title compound as an off-white solid (63% yield). M.p. 173-174° C., LCMS: m/z=410.30 (M+H$^+$), $^1$H-NMR (CDCl$_3$, 400 MHz) δ 1.39 (t, J=7.1 Hz, 3H), 3.45 (t, J=5.0 Hz, 2H), 3.61-3.66 (m, 2H), 4.37 (q, J=7.1 Hz, 2H), 4.49 (s, 2H), 5.32 (bs, 1H), 6.78 (d, J=1.5 Hz, 1H), 6.89-6.96 (m, 1H), 6.99-7.08 (m, 2H), 7.45 (d, J=8.4 Hz, 2H), 7.76 (d, J=1.8 Hz, 2H), 8.02 (d, J=8.6 Hz, 2H).

Example 64

4-[1-(2,5-Difluorobenzyl)-1,2,3,4-tetrahydropyrido[2,3-b]pyrazin-7-yl]benzoic acid

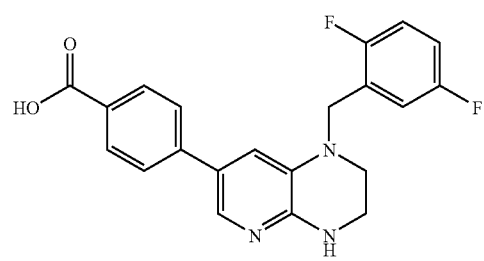

4-[1-(2,5-Difluorobenzyl)-1,2,3,4-tetrahydropyrido[2,3-b]pyrazin-7-yl]benzoic acid ethyl ester (300 mg) was saponified as in General Procedure 7 to give the title compound as a beige solid (91% yield). M.p.>300° C., LCMS: m/z=382.20 (M+H$^+$), $^1$H-NMR (DMSO-d$_6$, 400 MHz) δ 3.28-3.33 (m, 2H), 3.40-3.49 (m, 2H), 4.58 (s, 2H), 6.58 (s, 1H), 6.77 (s, 1H), 7.10-7.20 (m, 2H), 7.26-7.34 (m, 1H), 7.59 (d, J=8.3 Hz, 2H), 7.73 (s, 1H), 7.89 (d, J=8.3 Hz, 2H), 12.92 (bs, 1H).

Example 65

{4-[1-(2,5-Difluorobenzyl)-1,2,3,4-tetrahydropyrido[2,3-b]pyrazin-7-yl]phenyl}-((S)-2-((pyrrolidin-1-yl)methyl)pyrrolidin-1-yl)methanone

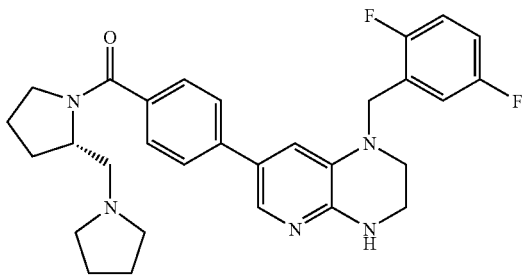

4-[1-(2,5-Difluorobenzyl)-1,2,3,4-tetrahydropyrido[2,3-b]pyrazin-7-yl]benzoic acid (50 mg) was reacted with (S)-(+)-1-(2-pyrrolidinylmethyl)pyrrolidine as in General Procedure 8 to give the title compound as a pale yellow solid (53% yield). M.p. 143-144° C., LCMS: m/z=518.30 (M+H$^+$), $^1$H-NMR (CDCl$_3$, 400 MHz) δ 1.48-1.58 (m, 1H), 1.87-2.15 (m, 4H), 2.17-2.22 (m, 3H), 2.55-2.64 (m, 4H), 2.83-2.89 (m, 1H), 3.12-3.23 (m, 1H), 3.42-3.50 (m, 2H), 3.60-3.64 (m, 2H), 4.40-4.49 (m, 3H), 5.07 (bs, 1H), 6.76 (s, 1H), 6.86-7.09 (m, 3H), 7.41 (d, J=8.1 Hz, 2H), 7.45-7.52 (m, 2H), 7.73 (s, 1H).

Example 66

{4-[1-(2,5-Difluorobenzyl)-1,2,3,4-tetrahydropyrido[2,3-b]pyrazin-7-yl]phenyl}-(4-(pyrrolidin-1-yl)piperidin-1-yl)methanone

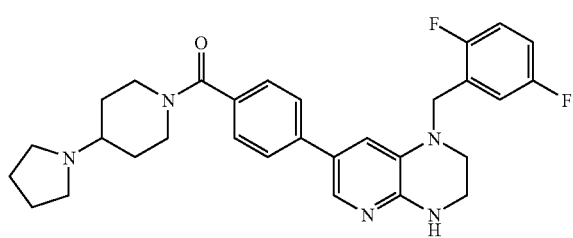

4-[1-(2,5-Difluorobenzyl)-1,2,3,4-tetrahydropyrido[2,3-b]pyrazin-7-yl]benzoic acid (34 mg) was reacted with 4-(1-pyrrolidinyl)piperidine as in General Procedure 8 to give the title compound as a pale yellow solid (47% yield). M.p. 202-204° C., LCMS: m/z=518.10 (M+H$^+$), $^1$H-NMR (CDCl$_3$, 400 MHz) δ 1.55-1.58 (m, 2H), 1.77-1.84 (m, 4H), 1.88-2.02 (m, 2H), 2.2402.30 (m, 1H), 2.56-2.62 (M, 4H), 2.90-3.12 (m, 2H), 3.44-3.48 (m, 2H), 3.64-3.68 (m, 2H), 3.77-3.87 (m, 1H), 4.49 (s, 2H), 4.55-4.63 (m, 1H), 4.95 (bs, 1H), 6.76 (s, 1H), 6.93-7.09 (m, 3H), 7.39 (dd, J=8.3 Hz, 4H), 7.72 (s, 1H), 8.08 (s, 1H).

Example 67

{4-[1-(2,5-Difluorobenzyl)-1,2,3,4-tetrahydropyrido[2,3-b]pyrazin-7-yl]phenyl}-(4-methylpiperazin-1-yl)methanone

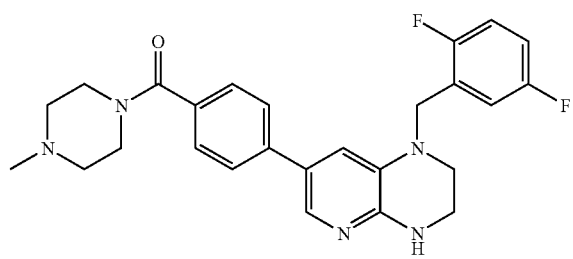

4-[1-(2,5-Difluorobenzyl)-1,2,3,4-tetrahydropyrido[2,3-b]pyrazin-7-yl]benzoic acid (34 mg) was reacted with 1-methylpiperazine as in General Procedure 8 to give the title compound as a pale yellow solid (25% yield). M.p. 180° C., LCMS: m/z=464.10 (M+H$^+$), $^1$H-NMR (CDCl$_3$, 400 MHz) δ 2.32 (s, 3H), 2.30-2.49 (m, 4H), 3.46 (t, J=5.0 Hz, 2H), 3.50-3.55 (m, 2H), 3.62-3.66 (m, 2H), 3.67-3.83 (m, 2H), 4.50 (s, 2H), 5.02 (bs, 1H), 6.75 (s, 1H), 6.86-7.08 (m, 3H), 7.40 (dd, J=8.3 Hz, 4H), 7.72 (s, 1H).

Example 68

{4-[1-(2,5-Difluorobenzyl)-1,2,3,4-tetrahydropyrido[2,3-b]pyrazin-7-yl]phenyl}-morpholin-4-yl-methanone

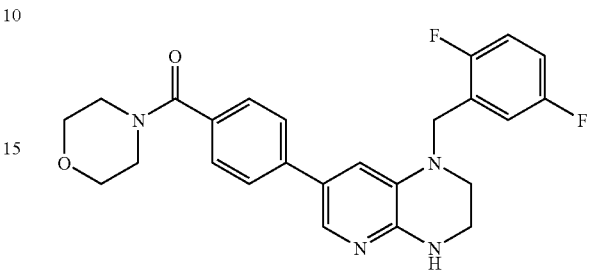

4-[1-(2,5-Difluorobenzyl)-1,2,3,4-tetrahydropyrido[2,3-b]pyrazin-7-yl]benzoic acid (60 mg) was reacted with morpholine as in General Procedure 8 to give the title compound as a light yellow foam (59% yield). M.p. (foam), LCMS: m/z=451.21 (M+H$^+$), $^1$H-NMR (CDCl$_3$, 400 MHz) δ 3.444-3.48 (m, 2H), 3.62-3.66 (m, 2H), 3.64-3.76 (m, 8H), 4.50 (s, 2H), 5.00 (s, 1H), 6.75 (s, 1H), 6.84-7.15 (m, 3H) 7.43 (dd, J=8.3 Hz, 4H), 7.71 (d, J=1.8 Hz, 1H).

Example 69

1-(2,5-Difluorobenzyl)-7-[6-(4-methylpiperazin-1-yl)pyridin-3-yl]-1,2,3,4-tetrahydropyrido[2,3-b]pyrazine

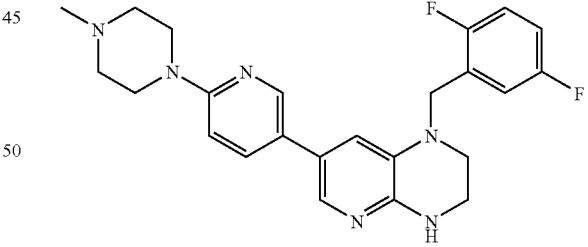

1-(2,5-Difluorobenzyl)-7-iodo-1,2,3,4-tetrahydropyrido[2,3-b]pyrazine (50 mg) was reacted with 1-methyl-4-[5-(4,4,5,5-tetramethyl-[1,3,2]dioxaborolan-2-yl)pyridin-2-yl]piperazine as in General Procedure 4A to give the title compound as a beige solid (53% yield). M.p. 192-193° C., LCMS: m/z=437.07 (M+H$^+$), $^1$H-NMR (CDCl$_3$, 400 MHz) δ 2.34 (s, 3H), 2.52-2.58 (m, 4H, 3.43-3.50 (m, 2H), 3.52-3.59 (m, 4H), 3.60-3.65 (m, 2H), 4.47 (s, 2H), 4.90 (s, 1H), 6.62 (m, 2H), 6.91-7.09 (m, 3H), 7.52 (dd, J=8.8 Hz, 2.5 Hz, 1H), 7.62 (d, J=1.8 Hz, 1H), 8.2 (d, J=2.5 Hz, 1H).

Example 70

1-(2,5-Difluorobenzyl)-7-(6-morpholin-4-yl-pyridin-3-yl)-1,2,3,4-tetrahydropyrido[2,3-b]pyrazine

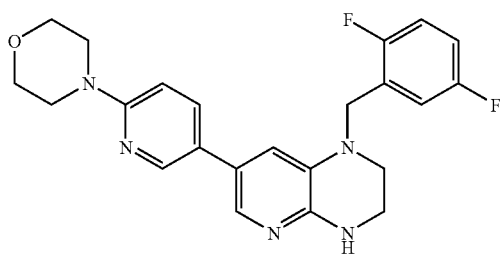

1-(2,5-Difluorobenzyl)-7-iodo-1,2,3,4-tetrahydropyrido[2,3-b]pyrazine (50 mg) was reacted with 4-[5-(4,4,5,5-Tetramethyl-[1,3,2]dioxaborolan-2-yl)pyridin-2-yl]-morpholine as in General Procedure 4A to give the title compound as an off-white solid (48% yield). M.p. 206-207° C., LCMS: m/z=423.99 (M+H$^+$), $^1$H-NMR (CDCl$_3$, 400 MHz) δ 3.45-3.53 (m, 6H), 3.60-3.67 (m, 2H), 3.80-3.87 (m, 4H), 4.48 (s, 2H), 4.86 (s, 1H), 6.64 (d, J=8.6 Hz, 1H), 6.66 (s, 1H), 6.89-7.06 (m, 3H), 7.55 (dd, J=8.8 Hz, 2.5 Hz, 1H), 7.62 (d, J=1.8 Hz, 1H), 8.24 (d, J=2.3 Hz, 1H).

Example 71

5-[1-(2,5-Difluorobenzyl)-1,2,3,4-tetrahydropyrido[2,3-b]pyrazin-7-yl]-pyridine-2-carbonitrile

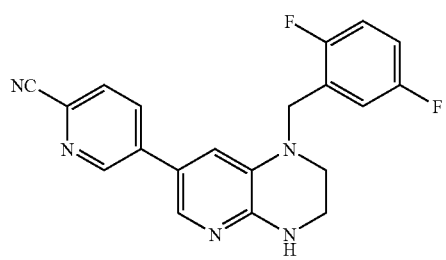

1-(2,5-Difluorobenzyl)-7-iodo-1,2,3,4-tetrahydropyrido[2,3-b]pyrazine (1.0 g) was reacted with 5-(4,4,5,5-Tetramethyl-[1,3,2]dioxaborolan-2-yl)pyridine-2-carbonitrile as in General Procedure 4A to give the title compound as a bright yellow solid (24% yield). M.p. 200° C. (dec), LCMS: m/z=364.53 (M+H$^+$), $^1$H-NMR (CDCl$_3$, 400 MHz) δ 3.46-3.52 (m, 2H), 3.62-3.72 (m, 2H), 4.50 (s, 2H), 5.12 (s, 1H), 6.70 (s, 1H), 6.92-7.00 (m, 2H), 7.03-7.12 (m, 1H), 7.62-7.69 (m, 2H), 7.67 (s, J=3.0 Hz, 1H), 7.75 (m, 1H), 8.73 (d, J=1.5 Hz, 1H).

Example 72

5-[1-(2,5-Difluorobenzyl)-1,2,3,4-tetrahydropyrido[2,3-b]pyrazin-7-yl]-pyridine-2-carboxylic acid

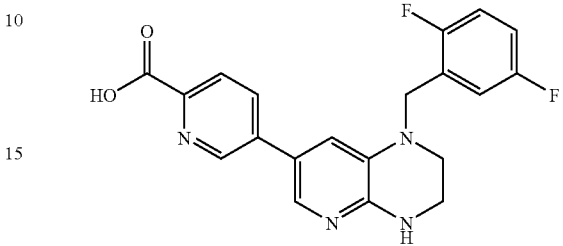

5-[1-(2,5-Difluorobenzyl)-1,2,3,4-tetrahydropyrido[2,3-b]pyrazin-7-yl]-pyridine-2-carbonitrile (45 mg) was hydrolyzed as in General Procedure 9, with the exception that the reaction mixture was heated to 70° C. for three (3) hours. Filtration gave the title compound as a yellowish brown precipitate (63% yield). M.p. 240° C. (dec), LCMS: m/z=383.00 (M+H$^+$), $^1$H-NMR (DMSO-d$_6$, 400 MHz) δ 3.29-3.38 (m, 2H), 3.42-3.49 (m, 2H), 4.60 (s, 2H), 6.95 (s, 1H), 7.03 (s, 1H), 7.12-7.19 (m, 2H), 7.28-7.35 (m, 1H), 7.81 (s, 1H), 8.00 (d, J=8.1 Hz, 1H), 8.07 (dd, J=8.1 Hz, 2.0 Hz, 1H), 8.84 (s, 1H).

Example 73

5-[1-(2,5-Difluorobenzyl)-1,2,3,4-tetrahydropyrido[2,3-b]pyrazin-7-yl]-nicotinic acid ethyl ester

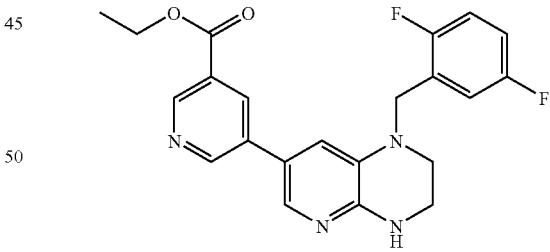

1-(2,5-Difluorobenzyl)-7-iodo-1,2,3,4-tetrahydropyrido[2,3-b]pyrazine (350 mg) was reacted with 5-(4,4,5-trimethyl-[1,3,2]dioxaborolan-2-yl)-nicotinic acid ethyl ester as in General Procedure 4A to give the title compound as a tan solid (29% yield). M.p. 169-172° C., LCMS: m/z=411.03 (M+H$^+$), $^1$H-NMR (CDCl$_3$, 400 MHz) δ 1.42 (t, J=7.1 Hz, 3H), 3.47-3.52 (m, 2H), 3.62-3.71 (m, 2H), 4.42 (q, J=7.1 Hz, 2H), 4.51 (s, 2H), 4.99 (s, 1H), 6.75 (s, 1H), 6.91-7.02 (m, 2H), 7.03-7.11 (m, 1H), 7.74 (d, J=2.0 Hz, 1H), 8.28 (d, J=2.3 Hz, 1H), 8.79 (d, J=2.3 Hz, 1H), 9.08 (d, J=2.0 Hz, 1H).

Example 74

5-[1-(2,5-Difluorobenzyl)-1,2,3,4-tetrahydropyrido[2,3-b]pyrazin-7-yl]-nicotinic acid

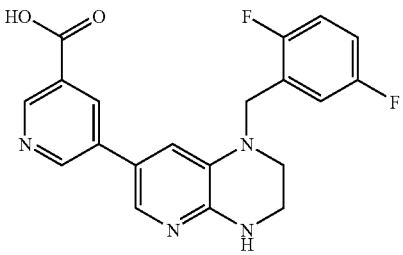

5-[1-(2,5-Difluorobenzyl)-1,2,3,4-tetrahydropyrido[2,3-b]pyrazin-7-yl]-nicotinic acid ethyl ester (75 mg) was saponified as in General Procedure 7 to give the title compound as a tan solid (22% yield). M.p. 255-260° C., LCMS: m/z=382.94 (M+H$^+$), $^1$H-NMR (DMSO-d$_6$, 400 MHz) δ 3.28-3.36 (m, 2H), 3.42-3.50 (m, 2H), 4.60 (s, 2H), 6.84 (s, 1H), 7.02 (s, 1H), 7.12-7.20 (m, 2H), 7.26-7.33 (m, 1H), 7.74 (d, J=1.8 Hz, 1H), 8.27 (d, J=2.0 Hz, 1H), 8.89-8.93 (m, 2H).

Example 75

1-(2,5-Difluorobenzyl)-1,2,3,4-tetrahydropyrido[2,3-b]pyrazine-7-carboxylic acid ethyl ester

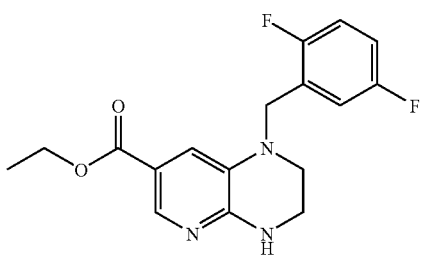

1-(2,5-Difluorobenzyl)-7-iodo-1,2,3,4-tetrahydropyrido[2,3-b]pyrazine (100 mg) was combined with Mo(CO)$_6$ (0.5 eq), DMAP (2.0 eq), and DIEA (2.0 eq) in a mixture of dioxane and ethanol (1:1, v/v) and heated to 150° C. in a microwave oven for 15 minutes as described in *J. Comb. Chem.*, 2003, 5, 350-352. The reaction mixture was diluted with ethanol and the black precipitate was filtered. Silica gel chromatography gave the title compound as a yellow solid (16% yield). M.p. 124-125° C., LCMS: m/z=334.02 (M+H$^+$), $^1$H-NMR (CDCl$_3$, 400 MHz) δ 1.33 (t, J=7.0 Hz, 3H), 3.32-3.38 (m, 2H), 3.61-3.68 (m, 2H), 4.28 (q, J=7.1 Hz, 2H), 4.45 (s, 2H), 5.68 (bs, 1H), 6.90-6.99 (m, 2H), 7.01-7.09 (m, 1H), 7.16 (d, J=1.5 Hz, 1H), 8.18 (d, J=1.8 Hz, 1H).

Example 76

{5-[1-(2,5-Difluorobenzyl)-1,2,3,4-tetrahydropyrido[2,3-b]pyrazin-7-yl]-pyridin-2-yl}morpholin-4-yl-methanone

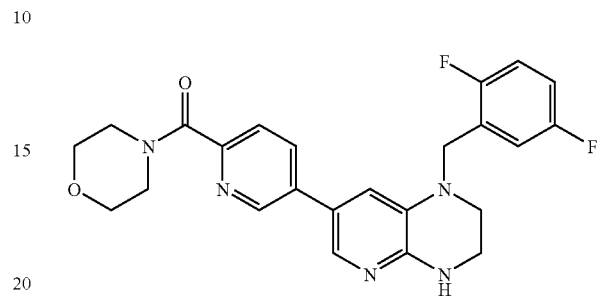

5-[1-(2,5-Difluorobenzyl)-1,2,3,4-tetrahydropyrido[2,3-b]pyrazin-7-yl]-pyridine-2-carboxylic acid (32 mg) was reacted with morpholine as in General Procedure 8 to give the title compound as a yellow solid (26% yield). M.p. 111-113° C., LCMS: m/z=451.92 (M+H$^+$), $^1$H-NMR (CDCl$_3$, 400 MHz) δ 3.47-3.53 (m, 2H), 3.67-3.76 (m, 8H), 3.77-3.85 (m, 2H), 4.50 (s, 2H), 5.09 (s, 1H), 6.71 (d J=1.5 Hz, 1H), 6.92-7.04 (m, 2H), 7.05-7.12 (m, 1H), 7.69-7.74 (m, 2H), 7.78-7.83 (m, 2H), 8.60 (d, J=2.3 Hz, 1H).

Example 77

1-(2,5-Difluorobenzyl)-1,2,3,4-tetrahydropyrido[2,3-b]pyrazine-7-carbonitrile

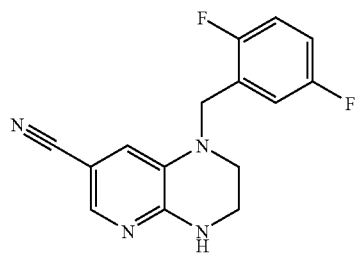

1-(2,5-Difluorobenzyl)-7-iodo-1,2,3,4-tetrahydropyrido[2,3-b]pyrazine (394 mg) was reacted with CuCN as in General Procedure 6 to give the title compound as a brown solid (86% yield). M.p. 204-206° C., LCMS: m/z=287.07 (M+H$^+$), $^1$H-NMR (DMSO-d$_6$, 400 MHz) δ 3.23-3.37 (m, 2H), 3.44-3.50 (m, 2H), 4.49 (s, 2H), 6.82 (s, 1H), 7.09-7.22 (m, 2H), 7.25-7.33 (m, 1H), 7.62 (bs, 1H), 7.73 (d, J=1.8 Hz, 1H).

Example 78

1-(2,5-Difluorobenzyl)-1,2,3,4-tetrahydropyrido[2,3-b]pyrazine-7-carboxylic acid

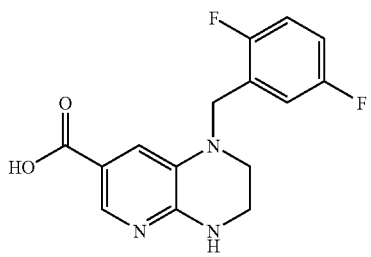

1-(2,5-Difluorobenzyl)-1,2,3,4-tetrahydropyrido[2,3-b]pyrazine-7-carbonitrile (239 mg) was hydrolyzed as in General Procedure 9. Filtration gave the title compound as a brown solid (58% yield). M.p. 231° C. (dec), LCMS: m/z=306.00 (M+H+), 1H-NMR (DMSO-d6, 400 MHz) δ 3.37-3.42 (m, 2H), 3.55-3.60 (m, 2H), 4.55 (s, 2H), 6.94 (d, J=1.0 Hz, 1H), 7.22-7.33 (m, 2H), 7.40-7.48 (m, 1H), 7.91 (d, J=1.3 Hz, 1 h), 8.31 (bs, 1H).

Example 79

[1-(2,5-Difluorobenzyl)-1,2,3,4-tetrahydropyrido[2,3-b]pyrazin-7-yl]-(4-methylpiperazin-1-yl)methanone

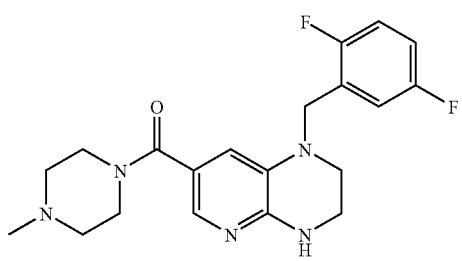

1-(2,5-Difluorobenzyl)-1,2,3,4-tetrahydropyrido[2,3-b]pyrazine-7-carboxylic acid (40 mg) was reacted with 1-methyl piperazine as in General Procedure 8 to give the title compound as an orange foam (65% yield). M.p. (foam), LCMS: m/z=388.08 (M+H+), 1H-NMR (CDCl3, 400 MHz) δ 2.28 (s, 3H), 2.32-2.38 (m, 4H), 3.41 (t, J=5.0 Hz, 2H), 3.53-3.61 (m, 4H), 3.62-3.65 (m, 2H), 4.44 (s, 2H), 5.07 (bs, 1H), 6.61 (s, 1H), 6.89-6.94 (m, 2H), 6.98-7.04 (m, 1H), 7.59 (d, J=1.5 Hz, 1H).

Example 80

1-(2,5-Difluorobenzyl)-1,2,3,4-tetrahydropyrido[2,3-b]pyrazine-7-carboxylic acid[2(4-methylpiperazin-1-yl)ethyl]amide

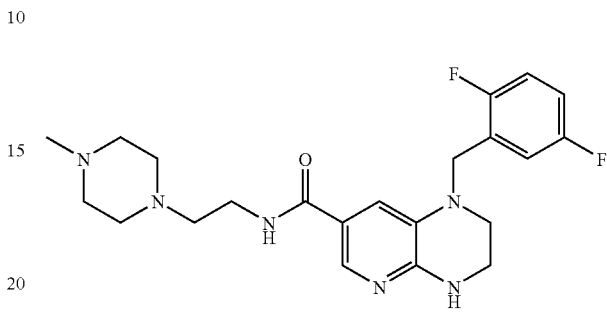

1-(2,5-Difluorobenzyl)-1,2,3,4-tetrahydropyrido[2,3-b]pyrazine-7-carboxylic acid (40 mg) was reacted with 2(4-methylpiperazin-1-yl)ethylamine as in General Procedure 8 to give the title compound as an orange foam (82% yield). M.p. (foam), LCMS: m/z=431.09 (M+H+), 1H-NMR (CDCl3, 400 MHz) δ 2.28 (s, 3H), 2.41-2.58 (m, 6H), 3.12-3.23 (m, 4H), 3.53-3.39 (m, 2H), 3.42-3.51 (m, 2H), 3.58-3.67 (m, 2H), 4.49 (s, 2H), 5.33 s, 1H), 6.72 (s, 1H), 6.84-6.91 (m, 2H), 6.93-7.04 (m, 1H), 7.10 (s, 1H), 7.85 (d, J=1.5 Hz, 1H).

Example 81

7-Iodo-1-(2,4,5-trifluorobenzyl)-3,4-dihydro-1H-pyrido[2,3-b]pyrazin-2-one

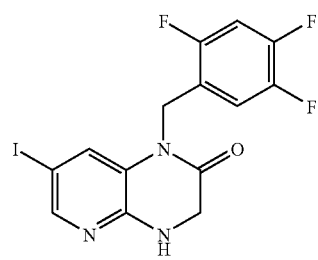

7-Iodo-3,4-dihydro-1H-pyrido[2,3-b]pyrazin-2-one (1.0 g) was reacted with 2,4,5 trifluorobenzyl bromide as in General Procedure 1 to give the title compound as a pale yellow solid (55% yield). M.p. 227-228° C., LCMS: m/z=420.00 (M+H+), 1H-NMR (CDCl3, 400 MHz) δ 4.26 (s, 2H), 4.89 (bs, 1H), 5.06 (s, 2H), 6.91-7.00 (m, 2H), 7.16 (s, 1H), 7.91 (s, 1H).

Example 82

7-Iodo-1-(2,4,5-trifluorobenzyl)-1,2,3,4-tetrahydropyrido[2,3-b]pyrazine

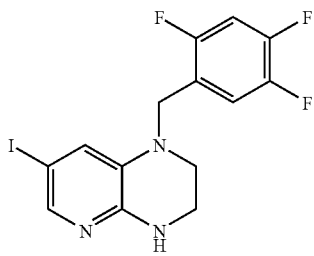

7-Iodo-1-(2,4,5-trifluorobenzyl)-3,4-dihydro-1H-pyrido[2,3-b]pyrazin-2-one (600 mg) was reduced as in General Procedure 3 to give the title compound as a white solid (63% yield). M.p. 154-156° C., LCMS: m/z=405.92 (M+H$^+$), $^1$H-NMR (CDCl$_3$, 400 MHz) δ 4.27 (s, 2h), 4.91 (bs, 1H), 5.06 (s, 2H), 6.93-7.02 (m, 2H), 7.19 (s, 1H), 7.94 (d, J=1.8 Hz, 1H).

Example 83

7-[4-((S)-2-[(pyrrolidin-1-yl)methyl]pyrrolidine-1-carbonyl)phenyl]-1-(2,4,5-trifluorobenzyl)-3,4-dihydro-1H-pyrido[2,3-b]pyrazin-2-one

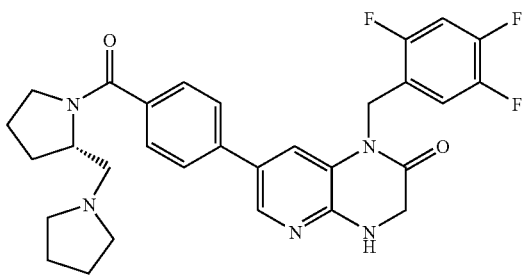

7-Iodo-1-(2,4,5-trifluorobenzyl)-3,4-dihydro-1H-pyrido[2,3-b]pyrazin-2-one (42 mg) was reacted with S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4A to give the title compound as a white solid (31% yield). M.p. 117-118 LCMS: m/z=550.20 (M+H$^+$), $^1$H-NMR (CDCl$_3$, 400 MHz) δ 1.48-1.69 (m, 4H), 1.88-2.15 (m, 5H), 2.57-2.70 (m, 3H), 2.80-2.92 (m, 1H), 3.42-3.53 (m, 2H), 4.33 (s, 2H), 5.12 (bs, 1H), 5.18 (s, 2H), 6.95-7.04 (m, 1H), 7.08-7.14 (m, 1H), 7.22 (s, 1H), 7.41 (d, J=8.1 Hz, 2H), 7.52-7.60 (m, 2H), 8.03 (s, 1H).

Example 84

((S)-2-((pyrrolidin-1-yl)methyl)pyrrolidin-1-yl)-{4-[1-(2,4,5-trifluorobenzyl)-1,2,3,4-tetrahydropyrido[2,3-b]pyrazin-7-yl]phenyl}-methanone

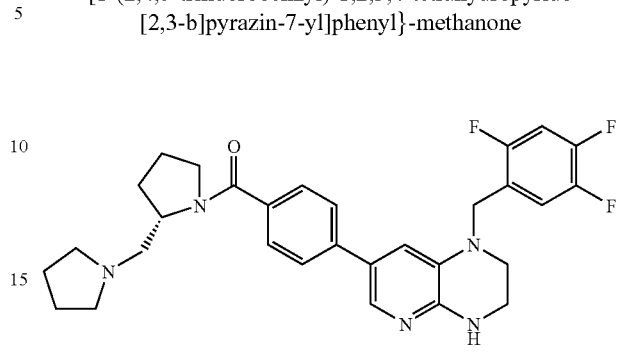

7-Iodo-1-(2,4,5-trifluorobenzyl)-1,2,3,4-tetrahydropyrido[2,3-b]pyrazine (40 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4A to give the title compound as a light orange foam (28% yield). M.p. foam, LCMS: m/z=536.13 (M+H$^+$), $^1$H-NMR (CDCl$_3$, 400 MHz) δ 1.47-1.60 (m, 1H), 1.61-1.69 (m, 4H), 1.72-2.12 (m, 5H), 2.53-2.71 (m, 3H), 2.80-3.01 (m, 1H), 3.38-3.43 (m, 2H), 3.45-3.51 (m, 2H), 3.63 (s, 2H), 4.46 (s, 2H), 4.96 (bs, 1H).6.75 (s, 1 h), 6.94-7.02 (m, 1H), 6.91-7.16 (m, 1H), 7.41 (d, J=8.3 Hz, 2H), 7.46-7.54 (m, 2H), 7.74 (s, 1H).

Example 85

7-[4-(4-Methylpiperazine-1-carbonyl)phenyl]-1-(2,4,5-trifluorobenzyl)-3,4-dihydro-1H-pyrido[2,3-b]pyrazin-2-one

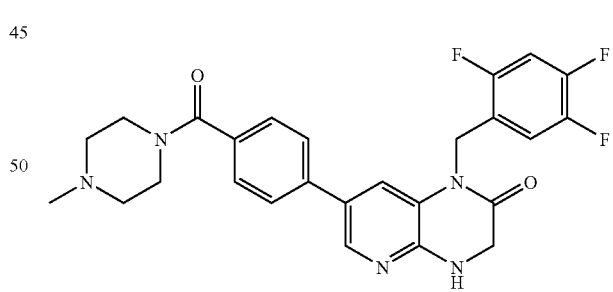

7-Iodo-1-(2,4,5-trifluorobenzyl)-3,4-dihydro-1H-pyrido[2,3-b]pyrazin-2-one (42 mg) was reacted with (4-methylpiperazin-1-yl)-[4-(4,4,5,5-tetramethyl-[1,3,2]dioxaborolan-2-yl)phenyl]methanone as in General Procedure 4A to give the title compound as a white solid (32% yield). M.p. 238° C., LCMS: m/z=496.00 (M+H$^+$), $^1$H-NMR (CDCl$_3$, 400 MHz) δ 2.33 (s, 3H), 2.35-2.53 (m, 4H), 3.43-3.58 (m, 2H), 3.72-3.84 (m, 2H), 4.33 (s, 2H), 5.11 (s, 1H), 5.30 (s, 2H), 6.97-7.03 (m, 1H), 7.05-7.14 (m, 1H), 7.21 (s, 1H), 7.45 (dd, J=8.1 Hz, 4H), 8.02 (s, 1H).

Example 86

(4-Methylpiperazin-1-yl)-{4-[1-(2,4,5-trifluorobenzyl)-1,2,3,4-tetrahydropyrido[2,3-b]pyrazin-7-yl]phenyl}-methanone

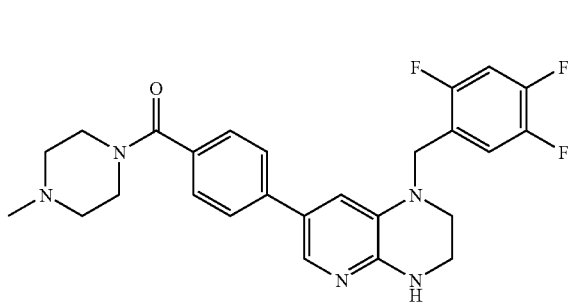

7-Iodo-1-(2,4,5-trifluorobenzyl)-1,2,3,4-tetrahydropyrido[2,3-b]pyrazine (40 mg) was reacted with (4-methylpiperazin-1-yl)-[4-(4,4,5,5-tetramethyl-[1,3,2]dioxaborolan-2-yl)phenyl]methanone as in General Procedure 4A to give the title compound as a pale yellow foam (30% yield). M.p. (foam), LCMS: m/z=482.10 (M+H$^+$), $^1$H-NMR (CDCl$_3$, 400 MHz) δ 2.33 (s, 3H), 2.35-2.52 (m, 4H), 3.39-3.42 (m, 2H), 3.42-3.56 (m, 2H), 3.58-3.66 (m, 2H), 3.68-3.88 (m, 2H), 4.45 (s, 2H), 4.98 (s, 1H), 6.72 (s, 1H), 6.89-7.02 (m, 1H), 7.08-7.15 (m, 1H), 7.35-7.44 (m, 4H), 7.70 (s, 1H).

Example 87

(2,5-Difluorophenyl)-(7-iodo-3,4-dihydro-2H-pyrido[2,3-b]pyrazin-1-yl)methanone

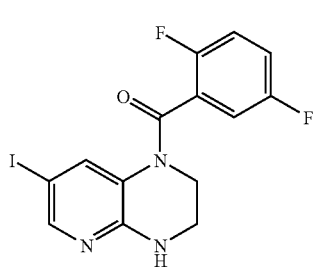

7-Iodo-1,2,3,4-tetrahydropyrido[2,3-b]pyrazine (614 mg) was reacted with 2,5-difluorobenzoyl chloride as in General Procedure 2 to give the title compound as an off-white foam (47% yield). M.p. foam, LCMS: m/z=402.20 (M+H$^+$), $^1$H-NMR (CDCl$_3$, 400 MHz) δ 1.70-1.90 (m, 2H), 3.50-3.65 (m, 2H), 5.29 (bs, 1H), 6.99 (s, 1H), 7.10-7.18 (m, 2H), 7.20-7.25 (m, 1H), 7.99 (s, 1H).

Example 88

(2,5-Difluorophenyl)-{7-[4-(4-methylpiperazine-1-carbonyl)phenyl]-3,4-dihydro-2H-pyrido[2,3-b]pyrazin-1-yl}-methanone

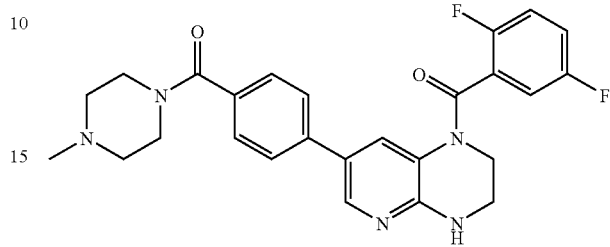

(2,5-Difluorophenyl)-(7-iodo-3,4-dihydro-2H-pyrido[2,3-b]pyrazin-1-yl)methanone (35 mg) was reacted with (4-methylpiperazin-1-yl)-[4-(4,4,5,5-tetramethyl-[1,3,2]dioxaborolan-2-yl)phenyl]methanone as in General Procedure 4A to give the title compound as a light yellow solid (36% yield). M.p. 201-203° C., LCMS: m/z=478.10 (M+H$^+$), $^1$H-NMR (CDCl$_3$, 400 MHz) δ 2.32 (s, 3H), 2.33-2.52 (m, 4H), 3.40-3.85 (m, 8H), 5.31 (s, 1H), 6.70-7.05 (m, 3H), 7.15 (s, 1H), 7.24-7.45 (m, 4H), 8.09 (s, 1H).

Example 89

(2,5-Difluorophenyl)-{7-[4-((S)-2-[(pyrrolidin-1-yl)methyl]pyrrolidine-1-carbonyl)phenyl]-3,4-dihydro-2H-pyrido[2,3-b]pyrazin-1-yl}-methanone

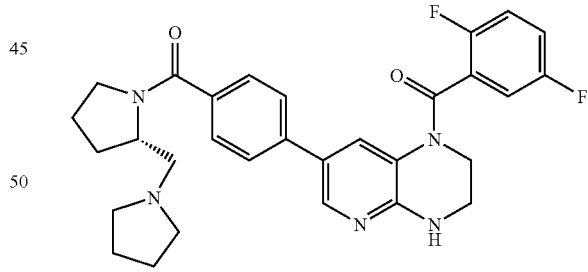

(2,5-Difluorophenyl)-(7-iodo-3,4-dihydro-2H-pyrido[2,3-b]pyrazin-1-yl)methanone (30 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4A to give the title compound as tan film (13% yield). M.p. (film), LCMS: m/z=532.10 (M+H$^+$), $^1$H-NMR (CDCl$_3$, 400 MHz) δ 1.76-1.88 (m, 4H), 1.90-2.15 (m, 5H), 2.62-2.73 (m, 4H), 2.90-2.99 (m, 1H), 3.38-3.75 (m, 5H), 4.40-4.45 (m, 1H), 5.35 (s, 1H), 6.72-6.98 (m, 3H), 7.15 (s, 1H), 7.27-7.53 (m, 4H), 8.09 (s, 1H).

Example 90

2-(5-Iodo-3-nitro-pyridin-2-ylamino)-2-methyl-propionic acid methyl ester

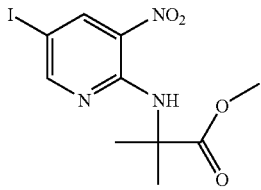

2-Chloro-5-iodo-3-nitro-pyridine (1.61 g) was dissolved in ethanol. Methyl α-aminoisobutyrate HCl was added (2.4 eq) followed by triethylamine (2.4 eq). The reaction mixture was heated to 150° C. in a microwave oven for 30 minutes. The reaction mixture was concentrated to dryness and triturated with H$_2$O. Silica gel chromatography of the resulting brown solid afforded the title compound as a bright yellow crystalline solid (78% yield based on recovered starting material). M.p. 121-122° C., $^1$H-NMR (CDCl$_3$, 400 MHz) δ 1.56 (s, 3H), 1.66 (s, 3H), 3.67 (s, 3H), 8.53 (s, 1H), 8.47 (d, J=2.0 Hz, 1H), 8.68 (d, J=2.3 Hz, 1H).

Example 91

7-Iodo-3,3-dimethyl-3,4-dihydro-1H-pyrido[2,3-b]pyrazin-2-one

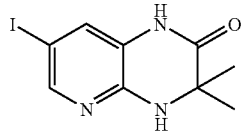

2-(5-Iodo-3-nitro-pyridin-2-ylamino)-2-methyl-propionic acid methyl ester (618 mg) was dissolved in ethanol. SnCl$_2$2H$_2$O (5 eq) was added and the reaction mixture was heated to 80° C. for three (3) hours. The resulting precipitate was filtered and washed with ethanol to give the title compound as an off-white solid (46% yield). M.p.>300° C., LCMS: m/z=304.30 (M+H$^+$), $^1$H-NMR (DMSO-d$_6$, 400 MHz) δ 1.29 (s, 6H), 7.11 (bs, 1H), 7.16 (d, J=1.8 Hz, 1H), 7.80 (d, J=2.0 Hz, 1H), 10.38 (bs, 1H).

Example 92

1-(2,5-Difluorobenzyl)-7-iodo-3,3-dimethyl-3,4-dihydro-1H-pyrido[2,3-b]pyrazin-2-one

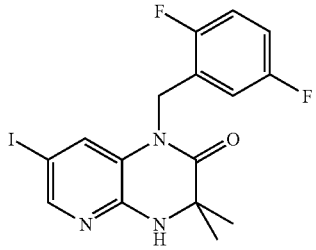

7-Iodo-3,3-dimethyl-3,4-dihydro-1H-pyrido[2,3-b]pyrazin-2-one (237 mg) was reacted with 2,5-difluorobenzyl bromide as in General Procedure 1 to give the title compound as a white solid (98% yield). M.p. 198-201° C., LCMS: m/z=430.00 (M+H$^+$), $^1$H-NMR (DMSO-d$_6$, 400 MHz) δ 1.36 (s, 6H), 5.12 (s, 2H), 6.79-6.83 (m, 1H), 7.15-7.22 (m, 1H), 7.28-7.32 (m, 1H), 7.31 (s, 1H), 7.40 (s, 1H), 7.90 (s, 1H).

Example 93

1-(2,5-Difluorobenzyl)-7-iodo-3,3-dimethyl-1,2,3,4-tetrahydropyrido[2,3-b]pyrazine

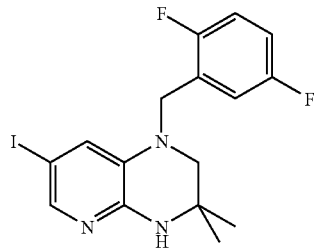

1-(2,5-Difluorobenzyl)-7-iodo-3,3-dimethyl-3,4-dihydro-1H-pyrido[2,3-b]pyrazin-2-one (60 mg) was reduced as in General Procedure 3 to give the title compound as a white solid (53% yield). M.p. 168-169° C., LCMS: m/z=415.98 (M+H$^+$), $^1$H-NMR (CDCl$_3$, 400 MHz) δ 1.27 (s, 6H), 3.05 (s, 2H), 4.41 (s, 2H), 4.64 (s, 1H), 6.79 (s, 1H), 6.92-6.98 (m, 2H), 7.02-7.10 (m, 1H), 7.63 (d, J=1.0 Hz, 1H).

Example 94

1-(2,5-Difluorobenzyl)-3,3-dimethyl-7-[4-((S)-2-[(pyrrolidin-1-yl)methyl]pyrrolidine-1-carbonyl)phenyl]-3,4-dihydro-1H-pyrido[2,3-b]pyrazin-2-one

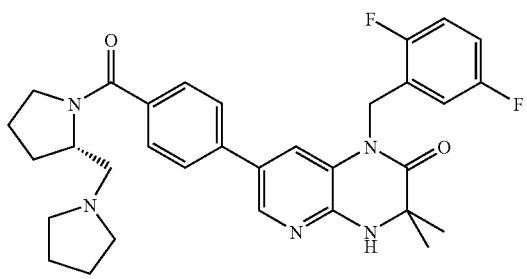

1-(2,5-Difluorobenzyl)-7-iodo-3,3-dimethyl-3,4-dihydro-1H-pyrido[2,3-b]pyrazin-2-one (45 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4A to give the title compound as a white solid (31% yield). M.p. 171-172° C., LCMS: m/z=560.16 (M+H$^+$), $^1$H-NMR (CDCl$_3$, 400 MHz) δ 1.56 (s, 6H), 1.72-1.83 (m, 4H), 1.90-2.02 (m, 3H), 2.08-2.30 (m, 2H), 2.58-2.68 (m, 4H), 2.85-2.92 (m, 1H), 3.36-3.56 (m, 2H), 4.43-4.48 (m, 1H), 5.01 (s, 1H), 5.21 (s, 2H), 6.84-6.88 (m, 1H), 6.91-6.97 (m, 1H), 7.04-7.11 (m, 1H), 7.20 (1.5 Hz, 1H), 7.41 (d, J=8.4 Hz, 2H), 7.52-7.58 (m, 2H), 8.04 (d, J=1.5 Hz, 1H).

Example 95

1-(2,5-Difluorobenzyl)-3,3-dimethyl-7-[4-(4-methylpiperazine-1-carbonyl)phenyl]-3,4-dihydro-1H-pyrido[2,3-b]pyrazin-2-one

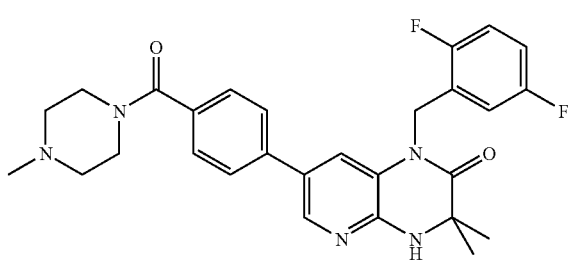

1-(2,5-Difluorobenzyl)-7-iodo-3,3-dimethyl-3,4-dihydro-1H-pyrido[2,3-b]pyrazin-2-one (45 mg) was reacted with (4-methylpiperazin-1-yl)-[4-(4,4,5,5-tetramethyl-[1,3,2]dioxaborolan-2-yl)phenyl]methanone as in General Procedure 4A to give the title compound as a white solid (55% yield). M.p. 204-206° C., LCMS: m/z=506.16 (M+H$^+$), $^1$H-NMR (CDCl$_3$, 400 MHz) δ 1.56 (s, 6H), 2.33 (s, 3H), 2.36-2.54 (m, 4H), 3.36-3.54 (m, 2H), 3.73-3.83 (m, 2H), 5.14 (s, 1H), 5.21 (s, 2H), 6.84-6.88 (m, 1H), 6.93-6.98 (m, 1H), 7.07-7.13 (m, 1H), 7.19 (d, J=1.5 Hz, 1H), 7.43 (m, 4H), 8.03 (d, J=2.0 Hz, 1H).

Example 96

{4-[1-(2,5-Difluorobenzyl)-3,3-dimethyl-1,2,3,4-tetrahydropyrido[2,3-b]pyrazin-7-yl]phenyl}-((S)-2-((pyrrolidin-1-yl)methyl)pyrrolidin-1-yl)methanone

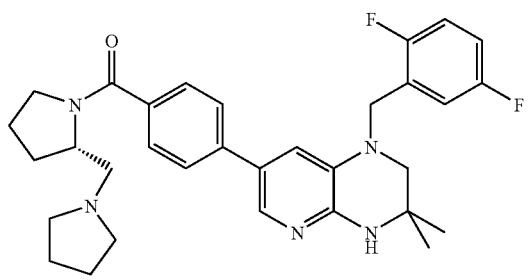

1-(2,5-Difluorobenzyl)-7-iodo-3,3-dimethyl-1,2,3,4-tetrahydropyrido[2,3-b]pyrazine (44 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4A to give the title compound as a light yellow solid (11% yield). M.p. 74-77° C., LCMS: m/z=546.15 (M+H$^+$), $^1$H-NMR (CDCl$_3$, 400 MHz) δ 1.26 (s, 6H), 1.70-1.83 (m, 4H), 1.85-1.99 (m, 4H), 2.00-2.16 (m, 2H), 2.58-2.69 (m, 4H), 2.82-2.94 (m, 1H), 3.13 (s, 2H), 3.46-3.54 (m, 2H), 4.52 (s, 2H), 4.77 (bs, 1H), 6.80 (s, 1H), 6.94-6.96 (m, 1H), 7.03-7.07 (m, 2H), 7.42 (d, J=8.1 Hz, 2H), 7.42-7.53 (m, 2H), 7.74 (s, 1H).

Example 97

{4-[1-(2,5-Difluorobenzyl)-3,3-dimethyl-1,2,3,4-tetrahydropyrido[2,3-b]pyrazin-7-yl]phenyl}-(4-methylpiperazin-1-yl)methanone

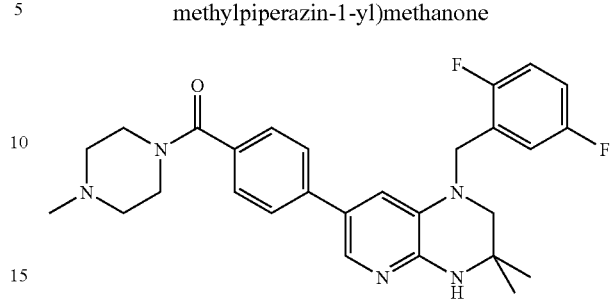

1-(2,5-Difluorobenzyl)-7-iodo-3,3-dimethyl-1,2,3,4-tetrahydropyrido[2,3-b]pyrazine (44 mg) was reacted with (4-methylpiperazin-1-yl)-[4-(4,4,5,5-tetramethyl-[1,3,2]dioxaborolan-2-yl)phenyl]methanone as in General Procedure 4A to give the title compound as an off-white solid (55% yield). M.p. 191-192° C., LCMS: m/z=492.10 (M+H$^+$), $^1$H-NMR (CDCl$_3$, 400 MHz) δ 1.34 (s, 6H), 2.32 (s, 3H), 2.38-2.50 (m, 4H), 3.13 (s, 2H), 3.45-3.58 (m, 2H), 3.65-3.85 (m, 2H), 4.52 (s, 2H), 4.90 (bs, 1H), 6.79 (d, J=1.3 Hz, 1H), 6.90-6.97 (m, 1H), 6.99-7.08 (m, 2H), 7.42 (dd, J=8.6 Hz, 4H), 7.74 (d, J=1.5 Hz, 1H).

Example 98

1-(2-Chloro-3,6-difluorobenzyl)-7-iodo-1,2,3,4-tetrahydropyrido[2,3-b]pyrazine

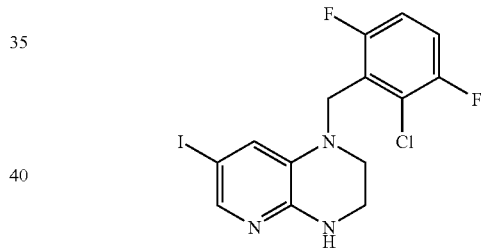

1-(2-Chloro-3,6-difluorobenzyl)-7-iodo-3,4-dihydro-1H-pyrido[2,3-b]pyrazin-2-one (348 mg) was reduced as in General Procedure 3 to give the title compound as an off-white solid (42% yield). M.p. 156-157° C., LCMS: m/z=422.00 (M+H$^+$), $^1$H-NMR (CDCl$_3$, 400 MHz) δ 3.12-3.20 (m, 2H), 3.42-3.50 (m, 2H), 4.41 (s, 2H), 4.89 (bs, 1H), 6.98-7.05 (m, 1H), 7.08 (s, 1H), 7.10-7.18 (m, 1H), 7.62 (d, J=1.5 Hz, 1H).

Example 99

{4-[1-(2-Chloro-3,6-difluorobenzyl)-1,2,3,4-tetrahydropyrido[2,3-b]pyrazin-7-yl]phenyl}-(4-(pyrrolidin-1-yl)piperidin-1-yl)methanone

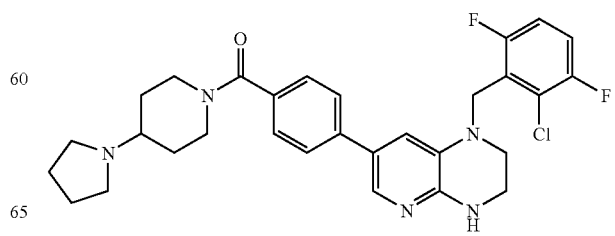

1-(2-Chloro-3,6-difluorobenzyl)-7-iodo-1,2,3,4-tetrahydropyrido[2,3-b]pyrazine (42 mg) was reacted with (4-(pyrrolidin-1-yl)piperidin-1-yl)-[4-(4,4,5,5-tetramethyl-[1,3,2]dioxaborolan-2-yl)phenyl]methanone as in General Procedure 4A to give the title compound as a pale yellow foam (36% yield). M.p. 93-95° C., LCMS: m/z=553.00 (M+H$^+$), $^1$H-NMR (CDCl$_3$, 400 MHz) δ 1.75-1.85 (m, 5H), 1.87-2.04 (m, 2H), 2.22-2.33 (m, 1H), 2.88-3.08 (m, 2H), 3.28-3.33 (m, 2H), 3.52-3.58 (m, 2H), 3.82-3.90 (m, 1H), 4.53 (s, 1H), 4.90 (bs, 1H), 6.96-7.02 (m, 1H), 7.17 (s, 1H), 7.18-7.20 (m, 1H), 7.42 (d, J=8.3 Hz, 2H), 7.51 (d, J=8.3 Hz, 2H), 7.75 (s, 1H).

Example 100

{4-[1-(2-Chloro-3,6-difluorobenzyl)-1,2,3,4-tetrahydropyrido[2,3-b]pyrazin-7-yl]phenyl}-((S)-2-((pyrrolidin-1-yl)methyl)pyrrolidin-1-yl)methanone

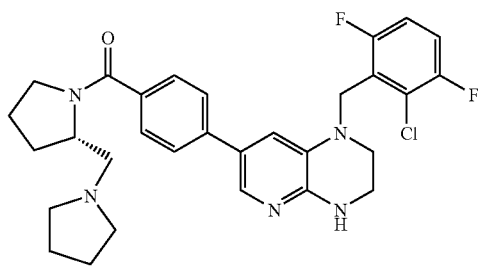

1-(2-Chloro-3,6-difluorobenzyl)-7-iodo-1,2,3,4-tetrahydropyrido[2,3-b]pyrazine (42 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4A to give the title compound as a pale yellow foam (33% yield). M.p. (foam), LCMS: m/z=553.00 (M+H$^+$), $^1$H-NMR (CDCl$_3$, 400 MHz) δ 1.73-1.80 (m, 4H), 1.90-2.04 (m, 3H), 2.10-2.29 (m, 2H), 2.58-2.70 (m, 4H), 2.85-2.95 (m, 1H), 3.26-3.33 (m, 2H), 3.48-3.58 (m, 2H), 4.42-4.50 (m, 1H), 4.53 (s, 2H), 4.95 (s, 1H), 6.96-7.04 (m, 1H), 7.11 (s, 1H), 7.10-7.18 (m, 1H), 7.47-7.56 (m, 4H), 7.74 (s, 1H).

Example 101

1-(2-Chloro-3,6-difluorobenzyl)-7-(3-chloro-2-morpholin-4-yl-pyridin-4-yl)-1,2,3,4-tetrahydropyrido[2,3-b]pyrazine

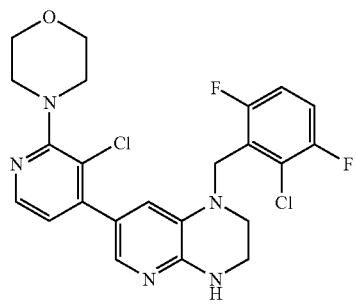

1-(2-Chloro-3,6-difluorobenzyl)-7-iodo-1,2,3,4-tetrahydropyrido[2,3-b]pyrazine (100 mg) was reacted with 4-[3-chloro-4-(4,4,5,5-tetramethyl-[1,3,2]dioxaborolan-2-yl)pyridin-2-yl]morpholine as in General Procedure 4A to give the title compound as a tan foam (49% yield). M.p. (foam), LCMS: m/z=493.59 (M+H$^+$), $^1$H-NMR (CDCl$_3$, 400 MHz) δ 3.28 (t, J=5.3 Hz, 2H), 3.38 (t, J=4.8 Hz, 4H), 3.52-3.58 (m, 2H), 3.89 (t, J=4.3 Hz, 4H), 4.47 (d, J=1.3 Hz, 2H), 5.16 (bs, 1H), 6.89 (d, J=5.0 Hz, 1H), 6.97-7.06 (m, 2H), 7.08-7.15 (m, 1H), 7.56 (d, J=1.8 Hz, 1H), 8.17 (d, J=5.0 Hz, 1H).

Example 102

1-(2-Chloro-3,6-difluorobenzyl)-7-(3-fluoro-2-morpholin-4-yl-pyridin-4-yl)-1,2,3,4-tetrahydropyrido[2,3-b]pyrazine

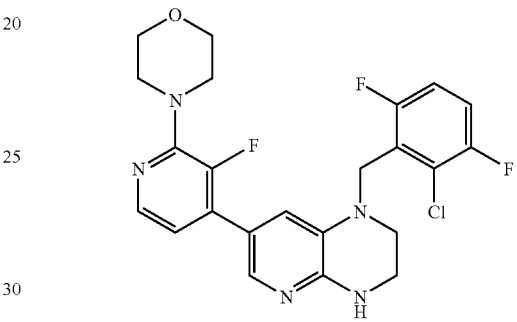

1-(2-Chloro-3,6-difluorobenzyl)-7-iodo-1,2,3,4-tetrahydropyrido[2,3-b]pyrazine (100 mg) was reacted with 4-[3-fluoro-4-(4,4,5,5-tetramethyl-[1,3,2]dioxaborolan-2-yl)pyridin-2-yl]morpholine as in General Procedure 4A to give the title compound as a tan foam (35% yield). M.p. (foam), LCMS: m/z=476.02 (M+H$^+$), $^1$H-NMR (CDCl$_3$, 400 MHz) δ 3.28 (t, J=4.8 Hz, 2H), 3.48 (t, J=4.8 Hz, 4H), 3.52-3.65 (m, 2H), 3.87 (t, J=4.6 Hz, 4H), 4.50 (s, 2H), 5.38 (bs, 1H), 6.82-6.86 (m, 1H), 6.97-7.04 (m, 1H), 7.08 (s, 1H), 7.04-7.15 (m, 1H), 7.70 (s, 1H), 8.00 (d, J=5.0 Hz, 1H).

Example 103

1-(2-Chloro-3,6-difluorobenzyl)-7-(3,5-dimethylisoxazol-4-yl)-1,2,3,4-tetrahydropyrido[2,3-b]pyrazine

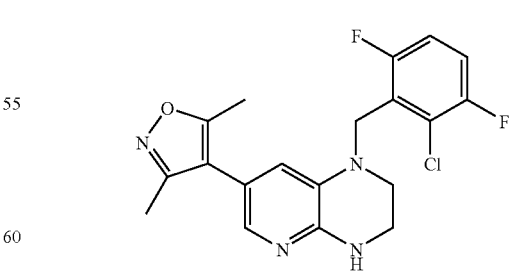

1-(2-Chloro-3,6-difluorobenzyl)-7-iodo-1,2,3,4-tetrahydropyrido[2,3-b]pyrazine (75 mg) was reacted with 3,5-dimethylisoxazole-4 boronic acid as in General Procedure 4A to give the title compound as a pale yellow solid (45% yield). M.p.

215-216° C., LCMS: m/z=393.42 (M+H⁺), ¹H-NMR (CDCl₃, 400 MHz) δ 2.22 (s, 3H), 2.36 (s, 3H), 3.31 (t, J=5.0 Hz, 2H), 3.52-3.58 (m, 2H), 4.47 (s, 2H), 4.98 (bs, 1H), 6.71 (s, 1H), 6.98-7.05 (m, 1H), 7.09-7.17 (m, 1H), 7.36 (d, J=1.3 Hz, 1H).

Example 104

{4-[1-(2-Chloro-3,6-difluorobenzyl)-1,2,3,4-tetrahydropyrido[2,3-b]pyrazin-7-yl]phenyl}-(4-methylpiperazin-1-yl)methanone

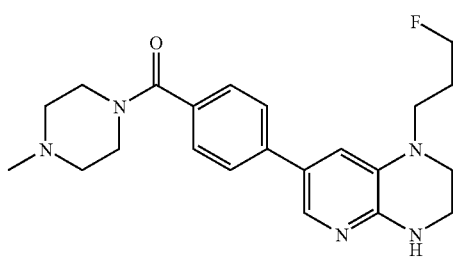

1-(2-Chloro-3,6-difluorobenzyl)-7-iodo-1,2,3,4-tetrahydropyrido[2,3-b]pyrazine (100 mg) was reacted with (4-methylpiperazin-1-yl)-[4-(4,4,5,5-tetramethyl-[1,3,2]dioxaborolan-2-yl)phenyl]methanone as in General Procedure 4A to give the title compound as a pale yellow foam (17% yield). M.p. (foam), LCMS: m/z=499.43 (M+H⁺), ¹H-NMR (CDCl₃, 400 MHz) δ 2.33 (s, 3H), 2.36-2.52 (m, 4H), 3.26-3.33 (m, 2H), 3.52-3.56 (m, 2H), 3.52-3.86 (m, 4H), 4.53 (s, 2H), 5.00 (bs, 1H), 6.97-7.04 (m, 1H), 7.10 (s, 1H), 7.11-7.17 (m, 1H), 7.44 (dd, J=8.4 Hz, 1.8 Hz, 2H), 7.52 (dd, J=8.3 Hz, 1.8 Hz, 2H), 7.74 (d, J=1.8 Hz, 1H).

Example 105

1-(2-Chloro-3,6-difluorobenzyl)-7-(6-morpholin-4-yl-pyridin-3-yl)-1,2,3,4-tetrahydropyrido[2,3-b]pyrazine

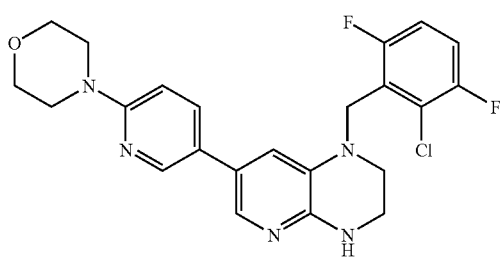

1-(2-Chloro-3,6-difluorobenzyl)-7-iodo-1,2,3,4-tetrahydropyrido[2,3-b]pyrazine (100 mg) was reacted with 2-(4-morpholino)pyridine-5-boronic acid pinacol ester as in General Procedure 4A to give the title compound as a beige foam (52% yield). M.p. (foam), LCMS: m/z=458.04 (M+H⁺), ¹H-NMR (CDCl₃, 400 MHz) δ 3.28-3.34 (m, 2H), 3.51-3.59 (m, 6H), 3.81-3.88 (m, 4H), 4.54 (s, 2H), 5.30 (s, 1H), 6.69 (d, J=8.8 Hz, 1H), 7.00-7.08 (m, 2H), 7.11-7.18 (m, 1H), 7.53 (s, 1H), 7.61 (dd, J=8.8 Hz, 2.5 Hz, 1H), 8.33 (s, J=2.2 Hz, 1H).

Example 106

1-(2-Chloro-3,6-difluorobenzyl)-7-[2-(4-methylpiperazin-1-yl)-pyrimidin-5-yl]-1,2,3,4-tetrahydropyrido[2,3-b]pyrazine

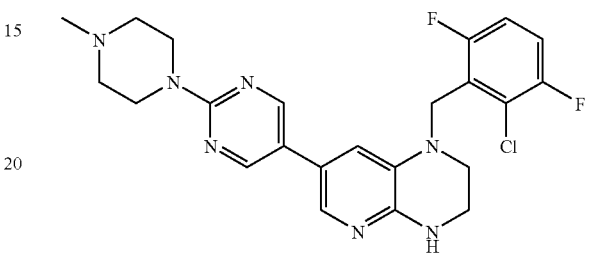

1-(2-Chloro-3,6-difluorobenzyl)-7-iodo-1,2,3,4-tetrahydropyrido[2,3-b]pyrazine (100 mg) was reacted with 2-(4-methylpiperazin-1-yl)pyrimidine-5-boronic acid pinacol ester as in General Procedure 4A to give the title compound as a pale orange solid (27% yield). M.p. 194-195° C., LCMS: m/z=472.09 (M+H⁺), ¹H-NMR (CDCl₃, 400 MHz) δ 2.38 (s, 3H), 2.51-2.58 (m, 4H), 3.31 (t, J=4.8 Hz, 2H), 3.49-3.58 (m, 2H), 3.89-3.97 (m, 4H), 4.51 (s, 2H), 4.95 (bs, 1H), 6.96 (s, 1H), 6.99-7.08 (m, 1H), 7.10-7.18 (m, 1H), 7.57 (s, 1H), 8.45 (s, 1H).

Example 107

1-(2-Chloro-3,6-difluorobenzyl)-7-(2-morpholin-4-yl-pyrimidin-5-yl)-1,2,3,4-tetrahydropyrido[2,3-b]pyrazine

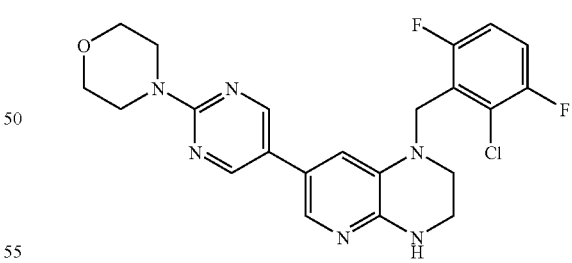

1-(2-Chloro-3,6-difluorobenzyl)-7-iodo-1,2,3,4-tetrahydropyrido[2,3-b]pyrazine (100 mg) was reacted with 2-(4-morpholino)pyrimidine-5-boronic acid pinacol ester as in General Procedure 4A to give the title compound as an off-white solid (27% yield). M.p. 250-251° C., LCMS: m/z=459.17 (M+H⁺), ¹H-NMR (CDCl₃, 400 MHz) δ 3.29-3.35 (m, 2H), 3.52-3.56 (m, 2H), 3.78-3.84 (m, 8H), 4.51 (s, 2H), 4.86 (bs, 1H), 6.96 (s, 1H), 7.00-7.08 (m, 1H), 7.10-7.17 (m, 1H), 7.59 (d, J=1.8 Hz, 1H), 8.46 (s, 1H).

Example 108

1-(2-Chloro-3,6-difluorobenzyl)-7-(4-morpholin-4-yl-phenyl)-1,2,3,4-tetrahydropyrido[2,3-b]pyrazine

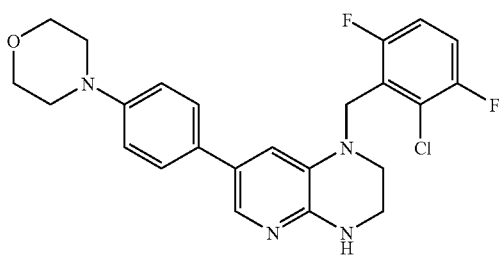

1-(2-Chloro-3,6-difluorobenzyl)-7-iodo-1,2,3,4-tetrahydropyrido[2,3-b]pyrazine (100 mg) was reacted with 4-morpholine phenyl-boronic acid pinacol ester as in General Procedure 4A to give the title compound as a pale yellow solid (49% yield). M.p. 217-219° C., LCMS: m/z=456.56 (M+H$^+$), $^1$H-NMR (CDCl$_3$, 400 MHz) δ 3.19 (t, J=4.8 Hz, 4H), 3.27 (t, J=4.8 Hz, 2H), 3.49-3.55 (m, 2H), 3.88 (t, J=4.6 Hz, 4H), 4.52 (s, 2H), 4.78 (bs, 1H), 6.96 (d, J=8.8 Hz, 2H), 6.98-7.05 (m, 1H), 7.09 (s, 1H), 7.10-7.15 (m, 1H), 7.42 (d, J=8.6 Hz, 2H), 7.70 (d, J=1.5 Hz, 1H).

Example 109

7-[6-(4-Methylpiperazin-1-yl)pyridin-3-yl]-1,2,3,4-tetrahydropyrido[2,3-b]pyrazine

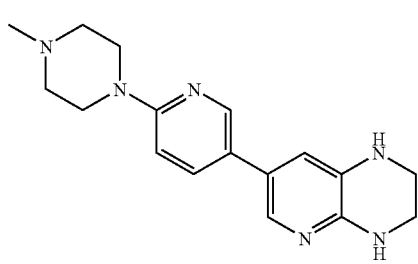

7-Iodo-1,2,3,4-tetrahydropyrido[2,3-b]pyrazine (704 mg) was reacted with 1-methyl-4-[5-(4,4,5,5-tetramethyl-[1,3,2]dioxaborolan-2-yl)pyridin-2-yl]piperazine as in General Procedure 4A to give the title compound as a yellow solid (20% yield). M.p. 225° C. (dec), LCMS: m/z=311.13 (M+H$^+$), $^1$H-NMR (CDCl$_3$, 400 MHz) δ 2.35 (s, 3H), 2.49-2.56 (m, 4H), 3.36-3.42 (m, 2H), 3.53-3.63 (m, 6H), 4.90 (bs, 1H), 6.68 (d, J=8.8 Hz, 1H), 6.77 (d, J=1.5 Hz, 1H), 7.58 (dd, J=8.8 Hz, 2.3 Hz, 1H), 7.63 (d, J=1.3 Hz, 1H), 8.31 (d, J=2.0 Hz, 1H).

Example 110

1-(7-Iodo-3,4-dihydro-2H-pyrido[2,3-b]pyrazin-1-yl)-2-phenylethanone

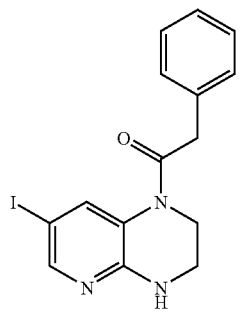

7-Iodo-1,2,3,4-tetrahydropyrido[2,3-b]pyrazine (300 mg) was reacted with phenyl acetyl chloride as in General Procedure 2 to give the title compound as a pale yellow foam (31% yield). M.p. (foam), LCMS: m/z=379.86 (M+H$^+$), $^1$H-NMR (CDCl$_3$, 400 MHz) δ 3.32-3.45 (m, 2H), 3.75-3.85 (m, 2H), 3.87 (s, 2H), 5.25 (bs, 1H), 7.21-7.38 (m, 5H), 8.01 (s, 1H).

Example 111

2-Phenyl-1-{7-[4-(4-(pyrrolidin-1-yl)piperidine-1-carbonyl)phenyl]-3,4-dihydro-2H-pyrido[2,3-b]pyrazin-1-yl}-ethanone

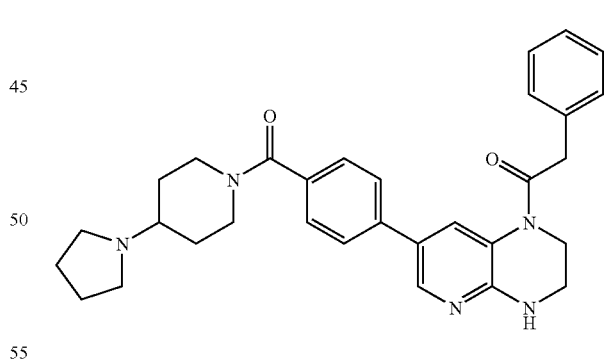

1-(7-Iodo-3,4-dihydro-2H-pyrido[2,3-b]pyrazin-1-yl)-2-phenylethanone (30 mg) was reacted with (4-(pyrrolidin-1-yl)piperidin-1-yl)-[4-(4,4,5,5-tetramethyl-[1,3,2]dioxaborolan-2-yl)phenyl]methanone as in General Procedure 4A to give the title compound as a white foam (52% yield). M.p. (foam), LCMS: m/z=510.13 (M+H$^+$), $^1$H-NMR (CDCl$_3$, 400 MHz) δ 1.47-1.62 (m, 2H), 1.75-2.05 (m, 3H), 2.22-2.29 (m, 1H), 2.53-2.62 (m, 5H), 2.82-3.10 (m, 3H), 3.33-3.52 (m, 2H), 3.71-3.88 (m, 3H), 3.95 (s, 2H), 4.51-4.63 (m, 1H), 5.25 (bs, 1H), 7.12-7.34 (m, 5H), 7.35-7.48 (m, 4H), 8.16 (s, 1H).

Example 112

2-(2,5-Difluorophenyl)-1-(7-iodo-3,4-dihydro-2H-pyrido[2,3-b]pyrazin-1-yl)ethanone

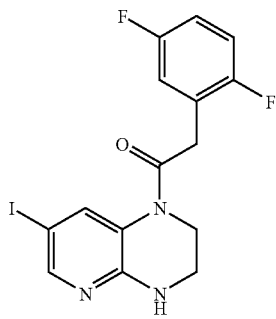

7-Iodo-1,2,3,4-tetrahydropyrido[2,3-b]pyrazine (300 mg) was reacted with 2,5-difluorophenyl acetyl chloride as in General Procedure 2 to give the title compound as an off-white solid (14% yield). M.p. 152-153° C., LCMS: m/z=415.90 (M+H$^+$), $^1$H-NMR (CDCl$_3$, 400 MHz) δ 3.47-3.54 (m, 2H), 3.80-3.87 (m, 4H), 5.44 (bs, 1H), 6.90-7.04 (m, 3H), 8.03 (s, 1H).

Example 113

2-(2,5-Difluorophenyl)-1-{7-[2-(4-methylpiperazin-1-yl)pyridin-4-yl]-3,4-dihydro-2H-pyrido[2,3-b]pyrazin-1-yl}ethanone

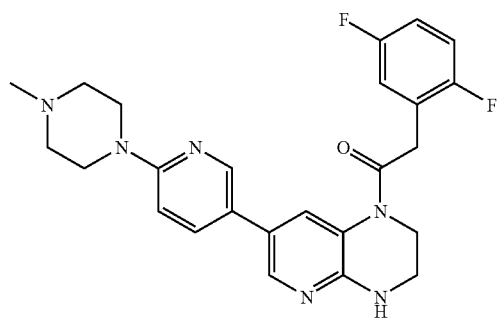

2-(2,5-Difluorophenyl)-1-(7-iodo-3,4-dihydro-2H-pyrido[2,3-b]pyrazin-1-yl)-ethanone (30 mg) was reacted with 1-methyl-4-[5-(4,4,5,5-tetramethyl-[1,3,2]dioxaborolan-2-yl)pyridin-2-yl]piperazine as in General Procedure 4A to give the title compound as a light yellow solid (15% yield). M.p.>300° C., LCMS: m/z=465.02 (M+H$^+$), $^1$H-NMR (CDCl$_3$, 400 MHz) δ 2.36 (s, 3H), 2.52-2.57 (m, 2H), 3.52-3.62 (m, 6H), 3.90-3.96 (m, 4H), 5.11 (bs, 1H), 6.70 (d, J=8.8 Hz, 1H), 6.90-7.04 (m, 3H), 7.41-7.58 (m, 2H), 8.07 (s, 1H), 8.32 (s, 1H).

Example 114

2-(2,5-Difluorophenyl)-1-{7-[4-(4-(pyrrolidin-1-yl)piperidine-1-carbonyl)phenyl]-3,4-dihydro-2H-pyrido[2,3-b]pyrazin-1-yl}ethanone

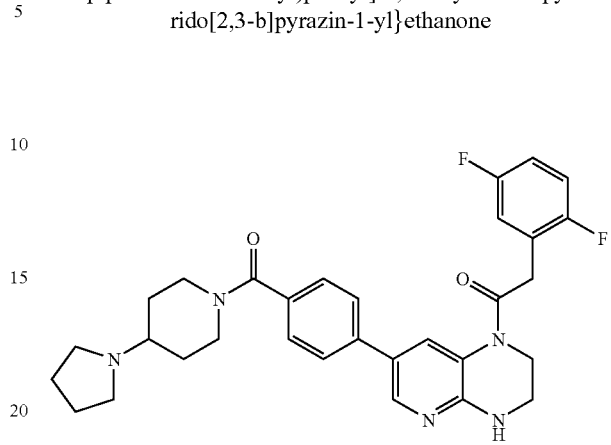

2-(2,5-Difluorophenyl)-1-(7-iodo-3,4-dihydro-2H-pyrido[2,3-b]pyrazin-1-yl)ethanone (30 mg) was reacted with (4-(pyrrolidin-1-yl)piperidin-1-yl)-[4-(4,4,5,5-tetramethyl-[1,3,2]dioxaborolan-2-yl)phenyl]methanone as in General Procedure 4A to give the title compound as a white foam (20% yield). M.p. (foam), LCMS: m/z=546.09 (M+H$^+$), $^1$H-NMR (CDCl$_3$, 400 MHz) δ 1.42-1.72 (m, 6H), 2.22-2.42 (m, 2H), 2.54-2.64 (m, 5H), 2.85-3.11 (m, 3H), 3.56-3.62 (m, 2H), 3.88-3.92 (m, 4H), 4.55-4.66 (m, 1H), 5.23 (s, 1H), 6.91-7.07 (m, 3H), 7.41-7.49 (m, 4H), 8.16 (s, 1H).

Example 115

1-(5-Chloro-2-trifluoromethylbenzyl)-7-iodo-1,2,3,4-tetrahydropyrido[2,3-b]pyrazine

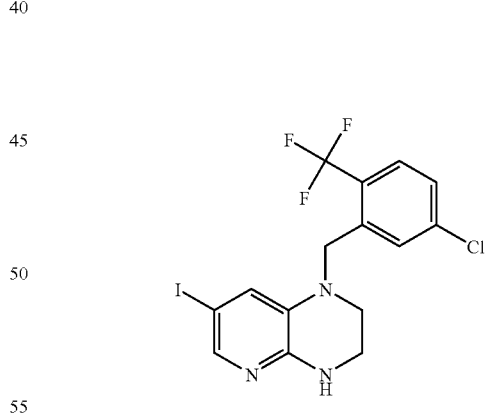

7-Iodo-3,4-dihydro-1H-pyrido[2,3-b]pyrazin-2-one (968 mg) was reacted with 5-chloro-2-(trifluoromethyl)benzyl bromide as in General Procedure 1. The resulting 1-(2-chloro-5-trifluoromethylbenzyl)-7-iodo-3,4-dihydro-1H-pyrido[2,3-b]pyrazin-2-one was reduced as in General Procedure 2 to give the title compound as an orange solid (17% yield). M.p. 189-191° C., LCMS: m/z=454.08 (M+H$^+$), $^1$H-NMR (DMSO-d$_6$, 400 MHz) δ 3.28-3.34 (m, 2H), 3.41-3.46 (m, 2H), 4.53 (s, 2H), 6.52 (s, 1H), 6.75 (s, 1H), 7.44 (s, 2H), 7.59 (d, J=8.4 Hz, 1H), 7.82 (d, J=8.6 Hz, 1H).

Example 116

1-(2-Chloro-5-trifluoromethylbenzyl)-7-iodo-3,4-dihydro-1H-pyrido[2,3-b]pyrazin-2-one

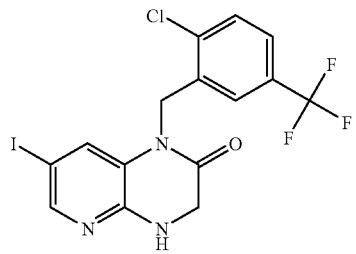

7-Iodo-3,4-dihydro-1H-pyrido[2,3-b]pyrazin-2-one (924 mg) was reacted with 2-chloro-5-(trifluoromethyl)benzyl bromide as in General Procedure 1 to give the title compound as a white solid (39% yield). M.p. 252-253° C., LCMS: m/z=468.02 (M+H$^+$), $^1$H-NMR (DMSO-d$_6$, 400 MHz) δ 4.16 (d, J=1.2 Hz, 2H), 5.16 (s, 2H), 7.20 (s, 1H), 7.26 (d, J=1.3 Hz, 1H), 7.42 (s, 1H), 7.71 (dd, J=8.3 Hz, 1.5 Hz, 1H), 7.77 (d, J=8.6 Hz, 1H), 7.83 (d, J=1.5 Hz, 1H).

Example 117

{4-[1-(5-Chloro-2-trifluoromethylbenzyl)-1,2,3,4-tetrahydropyrido[2,3-b]pyrazin-7-yl]phenyl}-(4-(pyrrolidin-1-yl)piperidin-1-yl)methanone

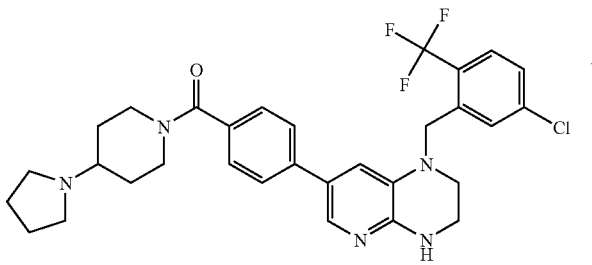

1-(5-Chloro-2-trifluoromethylbenzyl)-7-iodo-1,2,3,4-tetrahydropyrido[2,3-b]pyrazine (40 mg) was reacted with (4-(pyrrolidin-1-yl)piperidin-1-yl)-[4-(4,4,5,5-tetramethyl[1,3,2]dioxaborolan-2-yl)phenyl]methanone as in General Procedure 4A to give the title compound as an orange foam (19% yield). M.p. (foam), LCMS: m/z=487.19, $^1$H-NMR (CDCl$_3$, 400 MHz) δ 1.43-1.62 (m, 3H), 1.65-1.99 (m, 3H), 2.21-2.30 (m, 2H), 2.52-2.61 (m, 6H), 2.87-3.08 (m, 3H), 3.47-3.51 (m, 2H), 3.65-3.71 (m, 2H), 4.62 (s, 2H), 5.02 (s, 1H), 6.59 (d, J=1.5 Hz, 1H), 7.31-7.39 (m, 5H), 7.50 (s, 1H), 7.65 (d, J=8.4 Hz, 1H), 7.74 (s, 1H).

Example 118

1-(5-Chloro-2-trifluoromethylbenzyl)-7-[6-(4-methylpiperazin-1-yl)pyridin-3-yl]-1,2,3,4-tetrahydropyrido[2,3-b]pyrazine

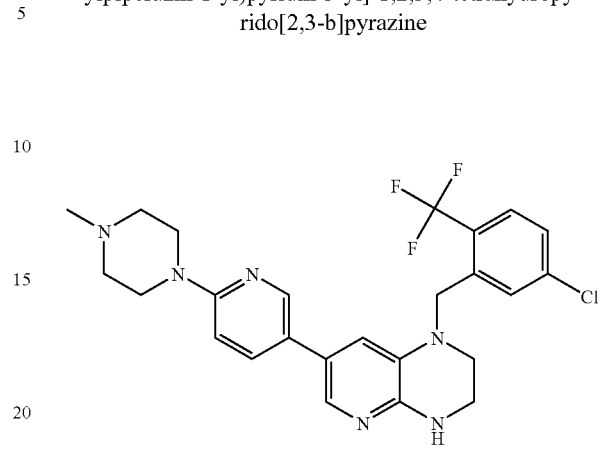

1-(5-Chloro-2-trifluoromethylbenzyl)-7-iodo-1,2,3,4-tetrahydropyrido[2,3-b]pyrazine (40 mg) was reacted with 1-methyl-4-[5-(4,4,5,5-tetramethyl-[1,3,2]dioxaborolan-2-yl)pyridin-2-yl]piperazine as in General Procedure 4A to give the title compound as a pale orange solid (28% yield). M.p. 226-227° C., LCMS: m/z=503.90 (M+H$^+$), $^1$H-NMR (CDCl$_3$, 400 MHz) δ 2.34 (s, 3H), 2.51 (t, J=5.0 Hz, 4H), 3.47-3.56 (m, 6H), 3.62-3.69 (m, 2H), 4.61 (s, 2H), 4.92 (bs, 1H), 6.49 (d, J=1.0 Hz, 1H), 6.64 (d, J=8.8 Hz, 1H), 7.34 (d, J=8.3 Hz, 1H), 7.52-7.58 (m, 2H), 7.61-7.65 (m, 2H), 8.18 (d, J=2.3 Hz, 1H).

Example 119

1-(2-Chloro-5-trifluoromethylbenzyl)-7-iodo-1,2,3,4-tetrahydropyrido[2,3-b]pyrazine

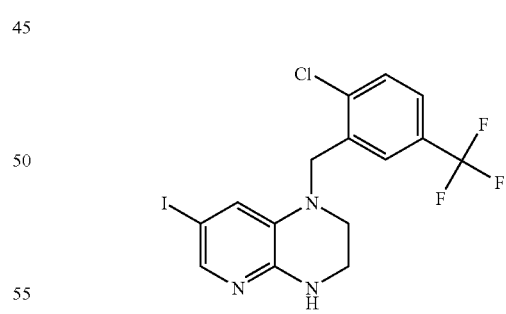

1-(2-Chloro-5-trifluoromethylbenzyl)-7-iodo-3,4-dihydro-1H-pyrido[2,3-b]pyrazin-2-one (590 mg) was reduced as in General Procedure 2 to give the title compound as a yellow solid (28% yield). M.p. 120-125° C., LCMS: m/z=454.01 (M+H$^+$), $^1$H-NMR (CDCl$_3$, 400 MHz) δ 3.38 (t, J=5.0 Hz, 2H), 3.55-3.61 (m, 2H), 4.45 (s, 2H), 5.11 (s, 1H), 6.66 (s, 1H), 7.47 (s, 1H), 7.53 (dd, J=8.3 Hz, 2H), 7.62 (d, J=1.8 Hz, 1H).

Example 120

1-(2-Chloro-5-trifluoromethylbenzyl)-7-[6-(4-methylpiperazin-1-yl)pyridin-3-yl]-1,2,3,4-tetrahydropyrido[2,3-b]pyrazine

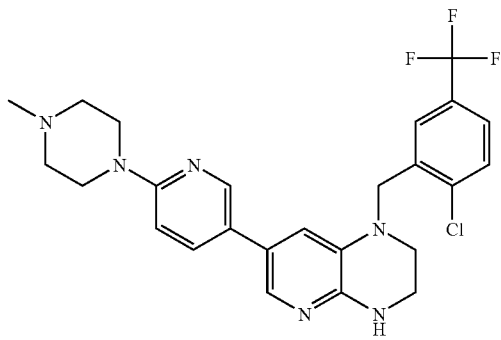

1-(2-Chloro-5-trifluoromethylbenzyl)-7-iodo-1,2,3,4-tetrahydropyrido[2,3-b]pyrazine (40 mg) was reacted with 1-methyl-4-[5-(4,4,5,5-tetramethyl-[1,3,2]dioxaborolan-2-yl)pyridin-2-yl]piperazine as in General Procedure 4A to give the title compound as a yellow film (13% yield). M.p. (film), LCMS: m/z=502.98 (M+H$^+$), $^1$H-NMR (CDCl$_3$, 400 MHz) δ 2.34 (s, 3H), 2.51 (t, J=5.3 Hz, 4H), 3.28 (t, J=5.3 Hz, 2H), 3.54 (t, J=5.0 Hz, 4H), 3.66-3.72 (m, 2H), 4.53 (s, 2H), 4.89 (bs, 1H), 6.53 (s, 1H), 6.64 (d, J=8.8 Hz, 1H), 7.46-7.54 (m, 4H), 7.63 (d, J=1.8 Hz, 1H), 8.18 (d, J=2.3 Hz, 1H).

Example 121

1-(2,5-Difluorobenzenesulfonyl)-7-iodo-1,2,3,4-tetrahydropyrido[2,3-b]pyrazine

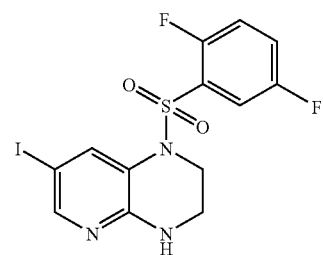

7-Iodo-1,2,3,4-tetrahydropyrido[2,3-b]pyrazine (100 mg) was dissolved in anhydrous pyridine. 2,5-difluorobenzene sulfonyl chloride (1.0 eq) was added and the mixture stirred at room temperature for 16 hours. The reaction mixture was concentrated and purified by column chromatography to give the title compound as a pale yellow solid (13% yield). M.p. 187-188° C., LCMS: m/z=437.73 (M+H$^+$), $^1$H-NMR (CDCl$_3$, 400 MHz) δ 3.29-3.33 (m, 2H), 3.83 (t, J=4.8 Hz, 2H), 5.08 (bs, 1H), 7.11-7.19 (m, 1H), 7.26-7.33 (m, 1H), 7.58-7.63 (m, 1H), 7.96 (d, J=1.5 Hz, 1H), 8.03 (d, J=1.8 Hz, 1H).

Example 122

1-(2,5-Difluorobenzenesulfonyl)-7-[6-(4-methylpiperazin-1-yl)pyridin-3-yl]-1,2,3,4-tetrahydropyrido[2,3-b]pyrazine

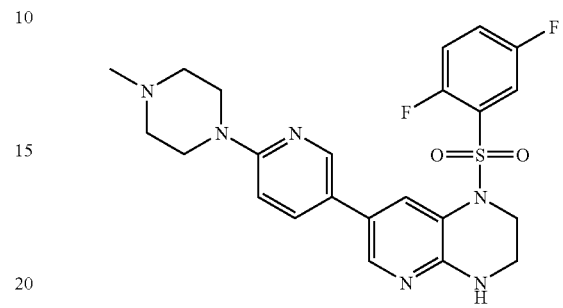

1-(2,5-Difluorobenzenesulfonyl)-7-iodo-1,2,3,4-tetrahydropyrido[2,3-b]pyrazine (50 mg) was reacted with 1-methyl-4-[5-(4,4,5,5-tetramethyl-[1,3,2]dioxaborolan-2-yl)pyridin-2-yl]piperazine as in General Procedure 4A to methylpiperazine as a yellow foam (35% yield). M.p. (foam), LCMS: m/z=487.04 (M+H$^+$), $^1$H-NMR (CDCl$_3$, 400 MHz) δ 2.34 (s, 3H), 2.54 (t, J=5.3 Hz, 4H), 3.35-3.38 (m, 2H), 3.60 (t, J=5.0 Hz, 4H), 3.91 (t, J=4.8 Hz, 2H), 5.05 (bs, 1H), 6.71 (d, J=8.8 Hz, 1H), 7.11-7.17 (m, 1H), 7.24-7.29 (m, 1H), 7.58-7.63 (m, 2H), 7.90 (d, J=2.0 Hz, 1H), 8.05 (d, J=2.3 Hz, 1H), 8.34 (d, J=2.6 Hz, 1H).

Example 123

1-Benzenesulfonyl-7-iodo-1,2,3,4-tetrahydropyrido[2,3-b]pyrazine

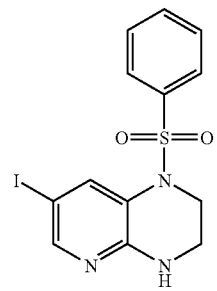

7-Iodo-1,2,3,4-tetrahydropyrido[2,3-b]pyrazine (300 mg) was dissolved in anhydrous pyridine. Phenylsulfonyl chloride (1.0 eq) was added and the reaction mixture was heated to 100° C. in a microwave oven for 10 minutes. Silica gel chromatography gave the title compound as a pale orange solid (23% yield). M.p. 145-146° C., LCMS: m/z=407.71 (M+H$^+$), $^1$H-NMR (CDCl$_3$, 400 MHz) δ 2.94-2.99 (m, 2H), 3.74 (t, J=5.0 Hz, 2H), 4.83 (bs, 1H), 7.45-7.49 (m, 2H), 7.58-7.65 (m, 3H), 8.06 (d, J=2.0 Hz, 1H), 8.17 (d, J=2.0 Hz, 1H).

Example 124

1-(2-Chlorobenzenesulfonyl)-7-iodo-1,2,3,4-tetrahydropyrido[2,3-b]pyrazine

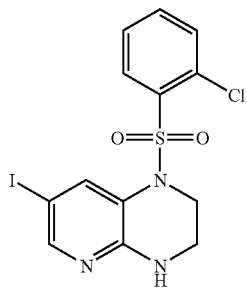

7-Iodo-1,2,3,4-tetrahydropyrido[2,3-b]pyrazine (300 mg) was dissolved in anhydrous pyridine. 2-chlorobenzene sulfonyl chloride (1.0 eq) was added and the reaction mixture was heated to 100° C. in a microwave oven for 10 minutes. Silica gel chromatography gave the title compound as a pale orange solid (10% yield). M.p. 146-147° C., LCMS: m/z=435.94 (M+H$^+$), $^1$H-NMR (CDCl$_3$, 400 MHz) δ 3.30-3.35 (m, 2H), 3.80 (t, J=5.0 Hz, 2H), 5.02 (bs, 1H), 7.42-4.57 (m, 3H), 7.81 (d, J=1.8 Hz, 1H), 8.00 (d, J=1.8 Hz, 1H), 8.10 (dd, J=8.6 Hz, 1.5 Hz, 1H).

Example 125

1-Benzenesulfonyl-7-[6-(4-methylpiperazin-1-yl)pyridin-3-yl]-1,2,3,4-tetrahydropyrido[2,3-b]pyrazine

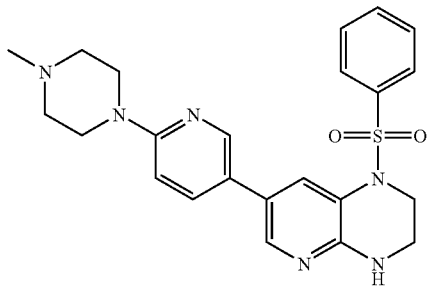

1-Benzenesulfonyl-7-iodo-1,2,3,4-tetrahydropyrido[2,3-b]pyrazine (88 mg) was reacted with 1-Methyl-4-[5-(4,4,5,5-tetramethyl-[1,3,2]dioxaborolan-2-yl)pyridin-2-yl]piperazine as in General Procedure 4A to give the title compound as a yellow foam (72% yield). M.p. (foam), LCMS: m/z=450-98 (M+H$^+$), $^1$H-NMR (CDCl$_3$, 400 MHz) δ 2.39 (s, 3H), 2.60 (t, J=5.0 Hz, 4H), 2.98-3.03 (m, 2H), 3.64 (t, J=5.0 Hz, 4H), 3.80 (t, J=5.0 Hz, 2H), 5.16 (bs, 1H), 6.73 (d, J=8.8 Hz, 1H), 7.40-7.45 (m, 2H), 7.51-7.54 (m, 1H), 7.62 (d, J=8.6 Hz, 2H), 7.67 (dd, J=8.8 Hz, 2,5 Hz, 1H), 8.08 (s, 1H), 8.40 (d, J=2.0 Hz, 1H).

Example 126

1-(2-Chlorobenzenesulfonyl)-7-[6-(4-methylpiperazin-1-yl)pyridin-3-yl]-1,2,3,4 tetrahydropyrido[2,3-b]pyrazine

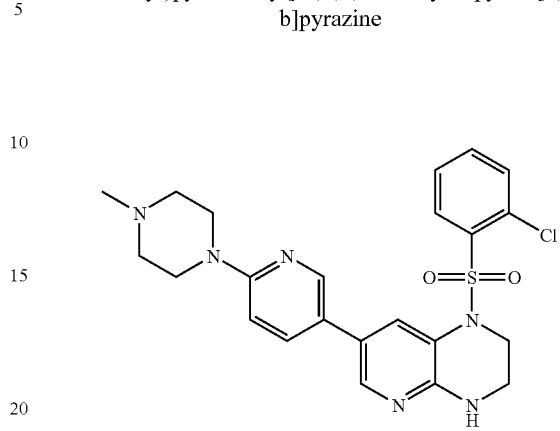

1-(2-Chlorobenzenesulfonyl)-7-iodo-1,2,3,4-tetrahydropyrido[2,3-b]pyrazine (44 mg) was reacted with 1-methyl-4-[5-(4,4,5,5-tetramethyl-[1,3,2]dioxaborolan-2-yl)pyridin-2-yl]piperazine as in General Procedure 4A to give the title compound as a yellow solid (41% yield). M.p. 164-165° C., LCMS: m/z=486.79 (M+H$^+$), $^1$H-NMR (CDCl$_3$, 400 MHz) δ 2.36 (s, 3H), 2.54 (t, J=5.1 Hz, 4H), 3.39-3.42 (m, 2H), 3.60 (t, J=4.5 Hz, 4H), 3.88 (t, J=4.5 Hz, 2H), 5.17 (bs, 1H), 6.69 (d, J=8.8 Hz, 1H), 7.39-7.45 (m, 1H), 7.51-7.56 (m, 3H), 7.73 (s, 1H), 8.01 (d, J=1.0 Hz, 1H), 8.13 (dd, J=8.6 Hz, 1.0 Hz, 1H), 8.27 (d, J=2.6 Hz, 1H).

Example 127

1-(2,5-Dichlorobenzyl)-1,2,3,4-tetrahydropyrido[2,3-b]pyrazine-7-carbonitrile

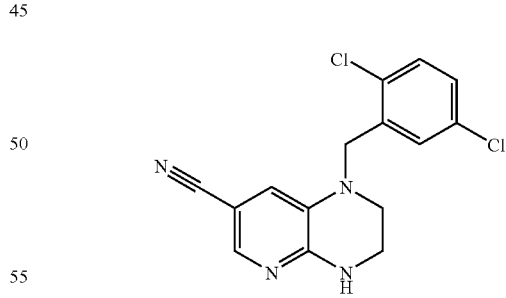

1-(2,5-Dichlorobenzyl)-7-iodo-1,2,3,4-tetrahydropyrido[2,3-b]pyrazine (2.0 g) was reacted with CuCN as in General Procedure 6 to give the title compound as an off-white solid (46% yield). M.p. 221-222° C., LCMS: m/z=320.77 (M+H$^+$), $^1$H-NMR (DMSO-d$_6$, 400 MHz) δ 3.28 (t, J=4.6 Hz, 2H), 3.45-3.54 (m, 2H), 4.48 (s, 2H), 6.69 (s, 1H), 7.29 (d, J=2.5 Hz, 1H), 7.41 (dd, J=8.6 Hz, 2.5 Hz, 1H), 7.54 (d, J=8.6 Hz, 1H), 7.67 (bs, 1H), 7.75 (d, J=1.8 Hz, 1H).

Example 128

1-(2,5-Dichlorobenzyl)-1,2,3,4-tetrahydropyrido[2,3-b]pyrazine-7-carboxylic acid

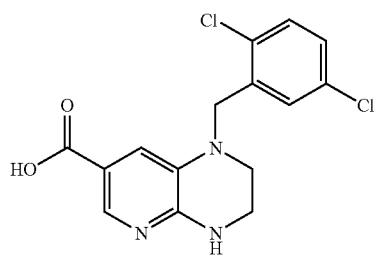

1-(2,5-Dichlorobenzyl)-1,2,3,4-tetrahydropyrido[2,3-b]pyrazine-7-carbonitrile (680 mg) was hydrolyzed as in General Procedure 9. Filtration gave the title compound as an orange solid (quantitative yield). M.p. 273° C. (dec), LCMS: m/z=340.23 (M+H$^+$), $^1$H-NMR (DMSO-d$_6$, 400 MHz) δ 3.48-3.53 (m, 2H), 3.61-3.71 (m, 2H), 4.62 (s, 2H), 6.87 (s, 1H), 7.42 (d, J=7.6 Hz, 1H), 7.43 (s, 1H), 7.57 (d, J=7.8 Hz, 1H), 7.88 (s, 1H), 9.33 (bs, 1H), 13.20 (bs, 1H).

Example 129

1-(2,5-Dichlorobenzyl)-7-(2-methoxypyrimidin-5-yl)-1,2,3,4-tetrahydropyrido[2,3-b]pyrazine

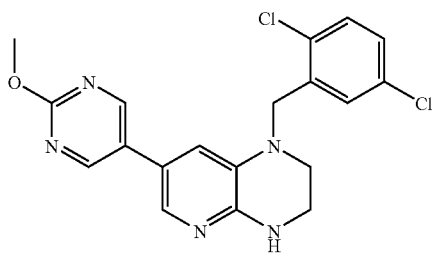

1-(2,5-dichlorobenzyl)-7-iodo-1,2,3,4-tetrahydropyrido[2,3-b]pyrazine (500 mg) was reacted with 2-methoxypyrimidine-5-boronic acid as in General Procedure 4A to give the title compound as a pale orange foam in 42% yield. M.p. (foam), LCMS: m/z=404.36 (M+H$^+$), $^1$H-NMR (CDCl$_3$, 400 MHz) δ 3.51 (t, J=5.3 Hz, 2H), 3.66-3.70 (m, 2H), 4.01 (s, 3H), 4.49 (s, 2H), 4.99 (bs, 1H), 6.46 (d, J=1.5 Hz, 1H), 7.18-7.26 (m, 2H), 7.35 (d, J=8.3 Hz, 1H), 7.62 (d, J=2.0 Hz, 1H), 8.50 (s, 1H).

Example 130

4-[1-(2,5-Dichlorobenzyl)-1,2,3,4-tetrahydropyrido[2,3-b]pyrazin-7-yl]-3,6-dihydro-2H-pyridine-1-carboxylic acid tert-butyl ester

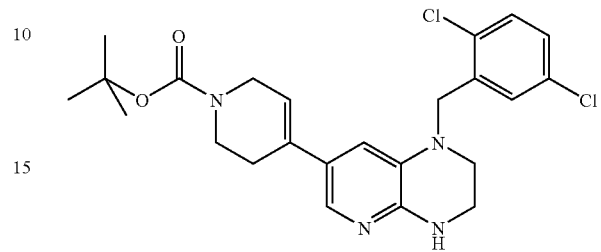

1-(2,5-dichlorobenzyl)-7-iodo-1,2,3,4-tetrahydropyrido[2,3-b]pyrazine (300 mg) was reacted with 4-(4,4,5,5-tetramethyl-[1,3,2]dioxaborolan-2-yl)-3,6-dihydro-2H-pyridine-1-carboxylic acid tert-butyl ester as in General Procedure 4A to give the title compound as a beige solid (35% yield). M.p. 92-95° C., LCMS: m/z=477.28 (M+H$^+$), $^1$H-NMR (CDCl$_3$, 400 MHz) δ 1.47 (s, 9H), 2.32-2.38 (m, 2H), 3.39-3.46 (m, 2H), 3.52-3.59 (m, 2H), 3.60-3.65 (m, 2H), 3.95-3.99 (m, 2H), 4.43 (s, 2H), 5.18 (s, 1H), 5.69-5.72 (m, 1H); 6.43 (s, 1H), 7.17-7.20 (m, 1H), 7.23 (s, 1H), 7.34 (d, J=8.3 Hz, 1H), 7.50 (s, 1H).

Example 131

1-(2,5-Dichlorobenzyl)-7-(1,2,3,6-tetrahydropyridin-4-yl)-1,2,3,4-tetrahydropyrido[2,3-b]pyrazine

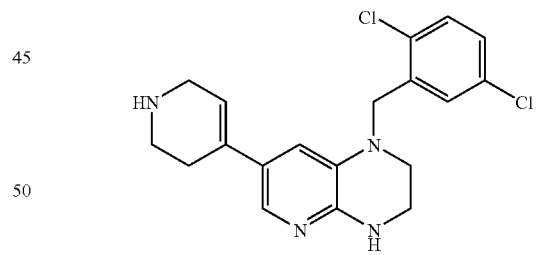

4-[1-(2,5-Dichlorobenzyl)-1,2,3,4-tetrahydropyrido[2,3-b]pyrazin-7-yl]-3,6-dihydro-2H-pyridine-1-carboxylic acid tert-butyl ester (105 mg) was dissolved in CH$_2$Cl$_2$/trifluoroacetic acid (3:1, v/v) and stirred at room temperature for two (2) hours. The reaction mixture was concentrated, diluted with CH$_2$Cl$_2$, washed with NaHCO$_3$ (×2), dried, filtered, and concentrated to give the title compound as a pale orange solid (84% yield). M.p. 133-136° C., LCMS: m/z=375.13 (M+H$^+$), $^1$H-NMR (DMSO-d$_6$, 400 MHz) δ 2.30-2.38 (m, 2H), 3.00-3.06 (m, 1H), 3.28-3.34 (m, 2H), 3.52-3.58 (m, 2H), 4.49 (s, 2H), 5.80 (s, 1H), 6.47 (s, 1H), 6.59 (s, 1H), 7.29 (d, J=2.5 Hz, 1H), 7.37-7.42 (m, 2H), 7.54 (d, J=8.6 Hz, 1H).

Example 132

{4-[1-(2,5-Dichlorobenzyl)-1,2,3,4-tetrahydropyrido[2,3-b]pyrazin-7-yl]phenyl}-(4-methylpiperazin-1-yl)methanone

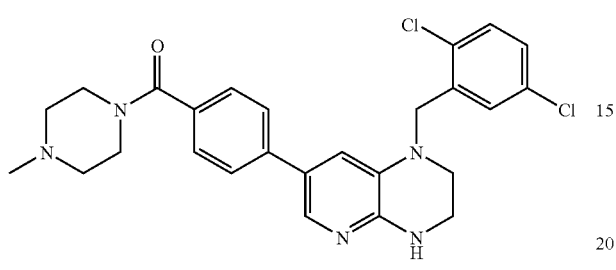

1-(2,5-dichlorobenzyl)-7-iodo-1,2,3,4-tetrahydropyrido[2,3-b]pyrazine (100 mg) was reacted with (4-methylpiperazin-1-yl)-[4-(4,4,5,5-tetramethyl-[1,3,2]dioxaborolan-2-yl)phenyl]methanone as in General Procedure 4A to give the title compound as a pale yellow foam (49% yield). M.p. (foam), LCMS: m/z=498.07 (M+H$^+$), $^1$H-NMR (CDCl$_3$, 400 MHz) δ 2.31 (s, 3H), 2.32-2.50 (m, 4H), 3.44-3.51 (m, 2H), 3.45-3.84 (m, 4H), 3.63-3.68 (m, 2H), 4.49 (s, 2H), 5.21 (s, 1H), 6.62 (d, J=1.5 Hz, 1H), 7.18-7.21 (m, 1H), 7.24-7.29 (m, 1H), 7.34 (d, J=8.6 Hz, 1H), 7.39-7.42 (m, 4H), 7.72 (d, J=1.8 Hz, 1H).

Example 133

1-(5-Fluoro-2-trifluoromethylbenzyl)-7-iodo-3,4-dihydro-1H-pyrido[2,3-b]pyrazin-2-one

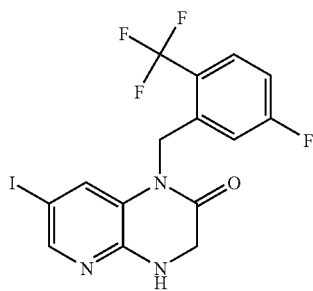

7-Iodo-3,4-dihydro-1H-pyrido[2,3-b]pyrazin-2-one (1.07 g) was reacted with 5-fluoro-2-trifluoromethylbenzyl bromide as in General Procedure 1 to give the title compound as an off-white solid (51% yield). M.p. 244-245° C., LCMS: m/z=453.03 (M+H$^+$), $^1$H-NMR (DMSO-d$_6$, 400 MHz) δ 4.21 (s, 2H), 5.15 (s, 2H), 6.97 (s, 1H0, 7.12 (d, J=9.8 Hz, 1H), 7.25 (s, 1H), 7.36 (dd, J=8.3 Hz, 1H), 7.84 (s, 1H), 7.88-7.94 (m, 1H).

Example 134

1-(5-Fluoro-2-trifluoromethylbenzyl)-7-iodo-1,2,3,4-tetrahydropyrido[2,3-b]pyrazin-2-ol

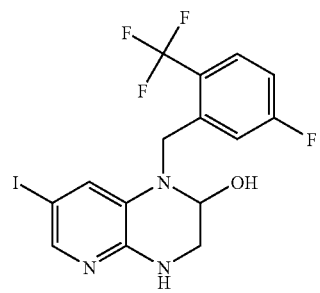

1-(5-Fluoro-2-trifluoromethylbenzyl)-7-iodo-3,4-dihydro-1H-pyrido[2,3-b]pyrazin-2-one (870 mg) was reduced as in General Procedure 3 to give the title compound as an off-white solid (30% yield). M.p. 142° C. (dec), LCMS: m/z=455.10 (M+H$^+$), $^1$H-NMR (CDCl$_3$, 400 MHz) δ 3.51 (d, J=11.4 Hz, 1H), 3.61 (dd, J=11.4 Hz, 1.5 Hz, 1H), 4.57 (d, J=18.2 Hz, 1H), 4.87 (d, J=18.2 Hz, 1H), 4.95 (s, 1H), 5.32 (bs, 1H), 6.49 (d, J=1.6 Hz, 1H), 7.01-7.11 (m, 2H), 7.56 (d, J=1.5 Hz, 1H), 7.73 (dd, J=8.6 Hz, 3.3 Hz, 1H).

Example 135

4-(2-Oxo-1,2,3,4-tetrahydropyrido[2,3-b]pyrazin-7-yl)benzoic acid ethyl ester

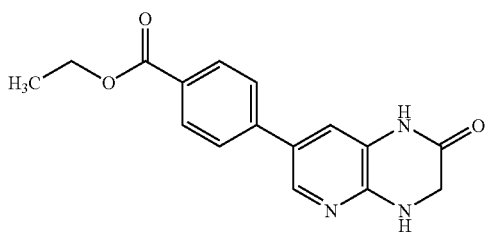

7-Iodo-3,4-dihydro-1H-pyrido[2,3-b]pyrazin-2-one (520 mg) was reacted with 4-ethoxycarbonylphenyl boronic acid as in General Procedure 4B to give the title compound as a light yellow solid in 79% yield. M.p.>200° C., LCMS: m/z=298.14 (M+H$^+$), $^1$H-NMR (DMSO-d$_6$, 400 MHz) δ 1.33 (3H, t, J=7.1 Hz), 4.32 (2H, q, J=7.1 Hz), 7.26 (1H, d, J=2.0 Hz), 7.67 (2H, d, J=8.3 Hz), 7.99 (2H, d, J=8.1 Hz), 8.04 (1H, d, J=2.3 Hz).

Example 136

1-(2,6-Dichlorobenzyl)-7-iodo-3,4-dihydro-1H-pyrido[2,3-b]pyrazin-2-one

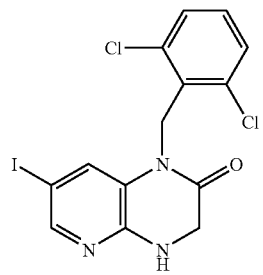

7-Iodo-3,4-dihydro-1H-pyrido[2,3-b]pyrazin-2-one (500 mg) was treated with 2,6-dichlorobenzyl bromide as in General Procedure 1 to give the title compound as an off-white solid. M.p.>200° C., LCMS: m/z=434.37 (M+H$^+$), $^1$H-NMR (DMSO-d$_6$, 400 MHz) δ 3.30 (2H, s), 5.29 (2H, s), 7.31 (1H, d, J=8.6 Hz), 7.34 (1H, d, J=7.6 Hz), 7.45 (1H, s), 7.47 (1H, s), 7.76 (1H, d, J=1.0 Hz).

Example 137

1-(2,6-Dichlorobenzyl)-7-pyridin-3-yl-3,4-dihydro-1H-pyrido[2,3-b]pyrazin-2-one

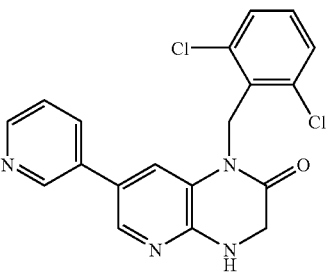

1-(2,6-Dichlorobenzyl)-7-iodo-3,4-dihydro-1H-pyrido[2,3-b]pyrazin-2-one (150 mg) was reacted with pyridine-3-boronic acid as in General Procedure 4B to give the title compound as a brown solid. M.p.>200° C., LCMS: m/z=385.48 (M+H$^+$), $^1$H-NMR (DMSO-d$_6$, 400 MHz) δ 4.06 (2H, s), 5.45 (2H, s), 7.07 (1H, s), 7.45 (5H, m), 7.85 (1H, d, J=7.8 Hz), 8.01 (1H, s), 8.49 (1H, d, J=4.8 Hz), 8.67 (1H, s) (NMR and LCMS indicate presence of triphenylphosphine impurity)

Example 138

1-(2,6-Dichlorobenzyl)-7-pyridin-3-yl-1,2,3,4-tetrahydropyrido[2,3-b]pyrazine, trifluoroacetic acid salt

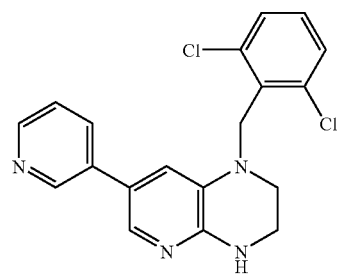

1-(2,6-Dichlorobenzyl)-7-pyridin-3-yl-3,4-dihydro-1H-pyrido[2,3-b]pyrazin-2-one (83 mg) was reduced as in General Procedure 3 to give the title compound as a green solid after preparative reversed-phase HPLC purification (3% yield). LCMS: m/z=371.35 (M+H$^+$), $^1$H-NMR (CDCl$_3$, 400 MHz) δ 3.24 (2H, t, J=4.9 Hz), 3.62 (2H, t, J=4.9 Hz), 4.72 (2H, s), 7.19 (1H, s), 7.43 (2H, d, J=8.1 Hz), 7.47 (1H, d, J=1.5 Hz), 7.54 (1H, m), 7.96 (1H, m), 8.65 (1H, d, J=4.3 Hz), 8.80 (1H, s).

Example 139

4-[1-(2,6-Dichlorobenzyl)-2-oxo-1,2,3,4-tetrahydropyrido[2,3-b]pyrazin-7-yl]benzoic acid ethyl ester

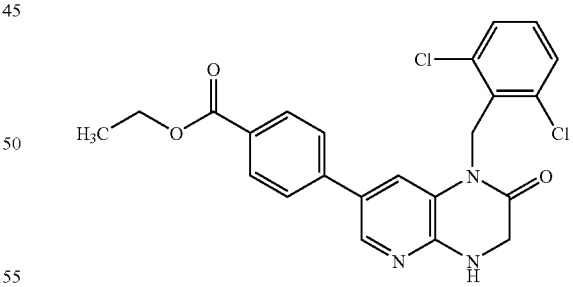

1-(2,6-Dichlorobenzyl)-7-iodo-3,4-dihydro-1H-pyrido[2,3-b]pyrazin-2-one (231 mg) was reacted with 4-ethoxycarbonyl phenyl boronic acid as in General Procedure 4B to give the title compound as a yellow solid. M.p.=226° C., LCMS: m/z=456.52 (M+H$^+$), $^1$H-NMR (DMSO-d$_6$, 400 MHz) δ 1.35 (3H, t, J=6.9 Hz), 4.09 (3H, s), 4.33 (3H, q, J=7.1 Hz), 5.47 (2H, s), 7.32 (2H, m), 7.48 (2H, d, J=8.1 Hz), 7.57 (3H, m), 7.63 (1H, m), 7.90 (1H, m), 7.98 (2H, d, J=8.2 Hz), 8.03 (1H, d, J=2.0 Hz).

Example 140

4-[1-(2,6-Dichlorobenzyl)-2-oxo-1,2,3,4-tetrahydro-pyrido[2,3-b]pyrazin-7-yl]benzoic acid

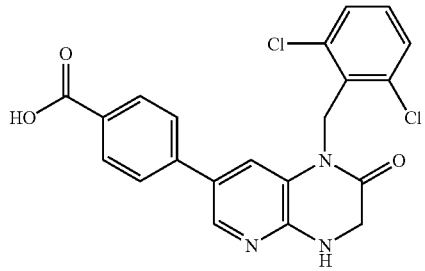

4-[1-(2,6-Dichlorobenzyl)-2-oxo-1,2,3,4-tetrahydropyrido[2,3-b]pyrazin-7-yl]benzoic acid ethyl ester (243 mg) was saponified as in General Procedure 7 to give the title compound as an off-white solid (87% yield). M.p.>200° C., LCMS: m/z=428.47 (M+H$^+$), $^1$H-NMR (DMSO-d$_6$, 400 MHz) δ 4.07 (2H, d, J=1.3 Hz), 5.44 (2H, s), 7.10 (1H, bs), 7.32 (2H, m), 7.48 (2H, d, J=8.1 Hz), 7.54 (2H, d, J=8.3 Hz), 7.95 (2H, d, J=8.3 Hz), 8.03 (1H, d, J=2.0 Hz).

Example 141

S-1-(2,6-Dichlorobenzyl)-7-[4-((2-pyrrolidin-1-yl)methylpyrrolidine-1-carbonyl)phenyl]-3,4-dihydro-1H-pyrido[2,3-b]pyrazin-2-one

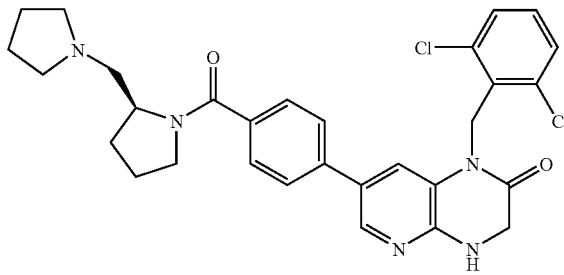

4-[1-(2,6-Dichlorobenzyl)-2-oxo-1,2,3,4-tetrahydropyrido[2,3-b]pyrazin-7-yl]benzoic acid (43 mg) was coupled to (S)-(+)-1-(2-pyrrolidinylmethyl)pyrrolidine as in General Procedure 8 to give the title compound as a brown solid (41% yield). M.p.=188° C., LCMS: m/z=564.07 (M+H$^+$), $^1$H-NMR (CDCl$_3$, 400 MHz) δ 0.88 (1H, m), 1.26 (2H, m), 1.76 (5H, m), 2.04 (6H, m), 2.23 (1H, m), 2.64 (4H, m), 2.89 (1H, m), 3.49 (3H, m), 4.25 (2H, s), 4.45 (1H, bs), 4.84 (1H, bs), 5.56 (2H, s), 7.16 (1H, m), 7.33 (4H, m), 7.52 (2H, d, J=8.3 Hz), 7.94 (1H, d, J=1.5 Hz).

Example 142

4-[1-(2,6-Dichlorobenzyl)-2-oxo-1,2,3,4-tetrahydro-pyrido[2,3-b]pyrazin-7-yl]-N-(2-pyrrolidin-1-yl-ethyl)benzamide

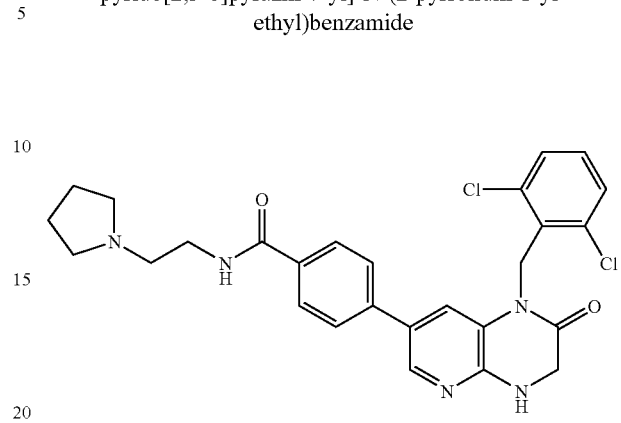

4-[1-(2,6-Dichlorobenzyl)-2-oxo-1,2,3,4-tetrahydropyrido[2,3-b]pyrazin-7-yl]benzoic acid (40 mg) was coupled to 2-pyrrolidin-1-yl-ethylamine as in General Procedure 8 to give the title compound as an off-white solid (26% yield). M.p.>200° C., LCMS: m/z=524.11 (M+H$^+$), $^1$H-NMR (CDCl$_3$, 400 MHz) δ 1.82 (4H, m), 2.60 (4H, m), 2.74 (2H, m), 3.59 (2H, m), 4.26 (2H, s), 4.85 (1H, bs), 5.56 (2H, s), 7.16 (1H, m), 7.32 (2H, d, J=8.1 Hz), 7.39 (2H, d, J=8.3 Hz), 7.82 (2H, d, J=8.3 Hz), 7.96 (1H, d, J=1.8 Hz).

Example 143

4-[1-(2,6-Dichlorobenzyl)-2-oxo-1,2,3,4-tetrahydro-pyrido[2,3-b]pyrazin-7-yl]-N-(6-dimethylamino-hexyl)benzamide, trifluoroacetic acid salt

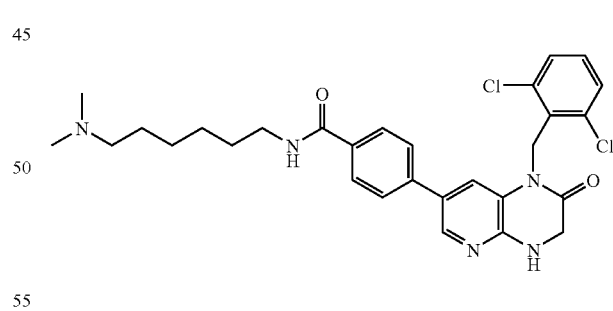

4-[1-(2,6-Dichlorobenzyl)-2-oxo-1,2,3,4-tetrahydropyrido[2,3-b]pyrazin-7-yl]benzoic acid (43 mg) was coupled to 3-dimethylaminohexylamine as in General Procedure 8 to give the title compound as an off-white solid after preparative reversed-phase HPLC purification (33% yield). M.p.=150° C., LCMS: m/z=554.28 (M+H$^+$), $^1$H-NMR (CD$_3$OD, 400 MHz) δ 1.47 (4H, m), 1.71 (4H, m), 2.88 (6H, s), 3.13 (2H, t, J=8.1 Hz), 3.41 (2H, t, J=7.1 Hz), 4.30 (2H, s), 5.63 (2H, s), 7.28 (1H, m), 7.42 (3H, m), 7.48 (2H, d, J=8.3 Hz), 7.88 (3H, m).

Example 144

4-[1-(2,6-Dichlorobenzyl)-2-oxo-1,2,3,4-tetrahydro-pyrido[2,3-b]pyrazin-7-yl]-N-(4-dimethylaminobutyl)benzamide, trifluoroacetic acid salt

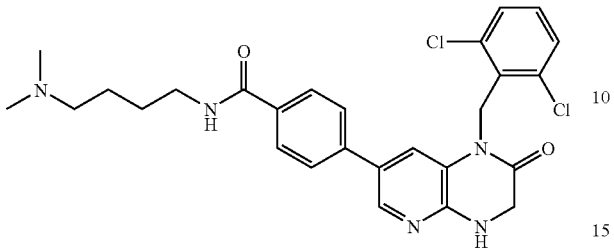

4-[1-(2,6-Dichlorobenzyl)-2-oxo-1,2,3,4-tetrahydropyrido[2,3-b]pyrazin-7-yl]benzoic acid (36 mg) was coupled to 3-Dimethylaminobutylamine as in General Procedure 8 to give the title compound as a tan solid after preparative reversed-phase HPLC purification (50% yield). M.p.=147° C., LCMS: m/z=526.11 (M+H$^+$), $^1$H-NMR (CD$_3$OD, 400 MHz) δ 1.71 (2H, m), 1.80 (2H, m), 2.90 (6H, s), 3.20 (2H, t, J=7.8 Hz), 3.46 (2H, t, J=6.7 Hz), 4.35 (2H, s), 5.64 (2H, s), 7.29 (1H, t, J=8.1 Hz), 7.43 (2H, d, J=8.1 Hz), 7.48 (2H, d, J=6.1 Hz), 7.51 (1H, s), 7.89 (2H, s), 7.90 (1H, s).

Example 145

7-Iodo-1-[1-(2,4,5-trifluorophenyl)ethyl]-3,4-dihydro-1H-pyrido[2,3-b]pyrazin-2-one

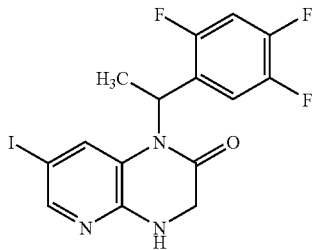

7-Iodo-3,4-dihydro-1H-pyrido[2,3-b]pyrazin-2-one (297 mg) was alkylated with 1-(1-bromoethyl)-2,4,5-trifluorobenzene as in General Procedure 1 to give the title compound.

Example 146

7-[4-(4-Methylpiperazine-1-carbonyl)phenyl]-1-[1-(2,4,5-trifluorophenyl)ethyl]-3,4-dihydro-1H-pyrido[2,3-b]pyrazin-2-one, trifluoroacetic acid salt

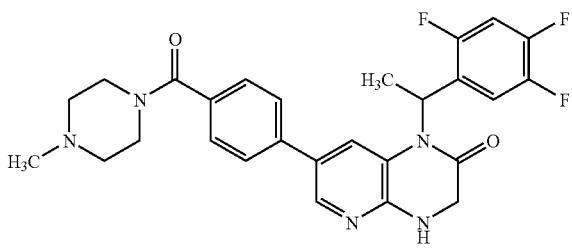

7-Iodo-1-[1-(2,4,5-trifluorophenyl)ethyl]-3,4-dihydro-1H-pyrido[2,3-b]pyrazin-2-one (45 mg) was reacted with (4-methylpiperazin-1-yl)-[4-(4,4,5,5-tetramethyl-[1,3,2]dioxaborolan-2-yl)phenyl]methanone as in General Procedure 4B to give the title compound as a colorless solid after preparative reversed-phase HPLC purification (15% yield). LCMS: m/z=510.11 (M+H$^+$), $^1$H-NMR (CD$_3$OD, 400 MHz) δ 1.91 (3H, d, J=7.1 Hz), 2.96 (3H, s), 3.22 (2H, m), 3.52 (3H, m), 4.28 (2H, d), 6.22 (1H, m), 7.17 (1H, m), 7.64 (5H, m), 7.82 (1H, s), 7.93 (1H, s).

Example 147

7-Iodo-1-[1-(2,4,5-trifluorophenyl)ethyl]-1,2,3,4-tetrahydropyrido[2,3-b]pyrazine

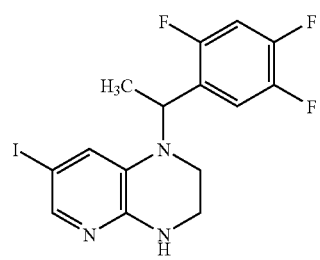

7-Iodo-1-[1-(2,4,5-trifluorophenyl)ethyl]-3,4-dihydro-1H-pyrido[2,3-b]pyrazin-2-one (551 mg) was reduced as in General Procedure 3 to give the title compound as a yellow foam (52% yield). LCMS: m/z=419.94 (M+H$^+$), $^1$H-NMR (CDCl$_3$, 400 MHz) δ 1.54 (3H, d, J=6.8 Hz), 3.15 (1H, m), 3.30 (1H, m), 3.43 (2H, t, J=4.7 Hz), 5.02 (1H, quartet, J=6.9 Hz), 5.47 (1H, bs), 6.86 (1H, s), 6.96 (1H, m), 7.11 (1H, m), 7.55 (1H, d, J=1.5 Hz).

Example 148

S-{2-[(pyrrolidin-1-yl)methyl]pyrrolidin-1-yl}-(4-{1-[1-(2,4,5-trifluorophenyl)ethyl]-1,2,3,4-tetrahydropyrido[2,3-b]pyrazin-7-yl}phenyl)methanone, trifluoroacetic acid salt

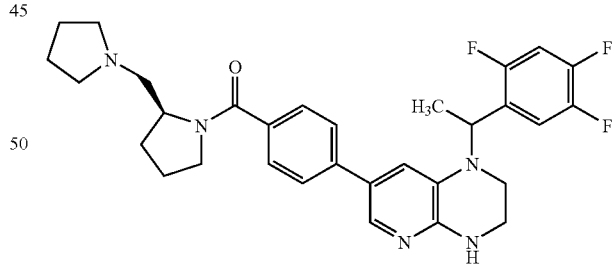

7-Iodo-1-[1-(2,4,5-trifluorophenyl)ethyl]-1,2,3,4-tetrahydropyrido[2,3-b]pyrazine (44 mg) was reacted with (S)-2-pyrrolidin-1-yl-methylpyrrolidine-1-carboxyl-[4-(4,4,5,5-tetramethyl-[1,3,2]dioxaborolan-2-yl)phenyl]amide as in General Procedure 4B to give the title compound as a yellow solid after reversed-phase HPLC purification (45% yield). LCMS: m/z=550.09 (M+H$^+$), $^1$H-NMR (CD$_3$OD, 400 MHz) δ 3.31 (3H, d, J=6.8 Hz), 2.06 (8H, m), 3.21 (3H, m), 3.49 (6H, m), 3.74 (1H, m), 4.05 (1H, m), 4.58 (1H, m), 5.50 (1H, quartet, J=6.8 Hz), 7.24 (1H, m), 7.41 (1H, s), 7.53 (2H, m), 7.69 (4H, m).

Example 149

(4-Methylpiperazin-1-yl)-(4-{1-[1-(2,4,5-trifluorophenyl)ethyl]-1,2,3,4-tetrahydropyrido[2,3-b]pyrazin-7-yl}phenyl)methanone

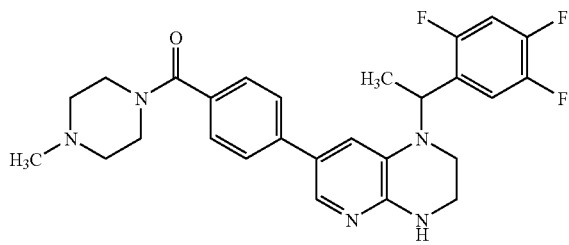

7-Iodo-1-[1-(2,4,5-trifluorophenyl)ethyl]-1,2,3,4-tetrahydropyrido[2,3-b]pyrazine (30 mg) was reacted with (4-methylpiperazin-1-yl)-[4-(4,4,5,5-tetramethyl-[1,3,2]dioxaborolan-2-yl)phenyl]methanone as in General Procedure 4B to give the title compound as a yellow solid (2% yield). LCMS: m/z=560.73 (M+H$^+$), $^1$H-NMR (CDCl$_3$, 400 MHz) δ 1.26 (8H, m), 2.44 (7H, m), 3.64 (4H, m), 7.38 (1H, m), 7.47 (4H, m), 7.61 (4H, m).

Example 150

1-[1-(2,5-Difluorophenyl)ethyl]-7-iodo-3,4-dihydro-1H-pyrido[2,3-b]pyrazin-2-one

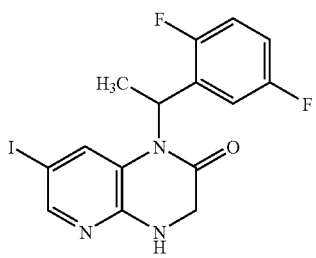

7-Iodo-3,4-dihydro-1H-pyrido[2,3-b]pyrazin-2-one (1.030 g) was alkylated with 2,5-difluoro-alpha-bromoethylbenzene as in General Procedure 1 to give the title compound as a yellow solid. LCMS: m/z=415.93 (M+H$^+$)

Example 151

S-(4-{1-[1-(2,5-Difluorophenyl)ethyl]-1,2,3,4-tetrahydropyrido[2,3-b]pyrazin-7-yl}phenyl)-{2-[(pyrrolidin-1-yl)methyl]pyrrolidin-1-yl}methanone

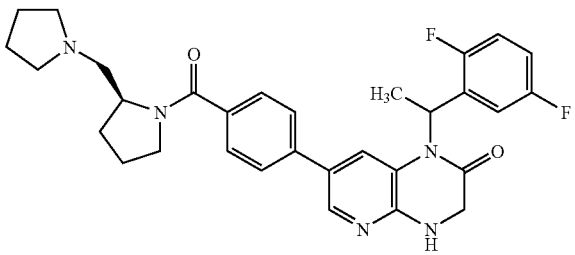

1-[1-(2,5-Difluorophenyl)ethyl]-7-iodo-3,4-dihydro-1H-pyrido[2,3-b]pyrazin-2-one (59 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4B to give the title compound as a yellow solid (4% yield). LCMS: m/z=546.15 (M+H$^+$), $^1$H-NMR (CD$_3$OD, 400 MHz) δ 1.57 (1H, m), 1.84 (4H, m), 1.89 (3H, d, J=7.1 Hz), 1.98 (3H, m), 2.15 (2H, s), 2.71 (4H, m), 2.93 (1H, m), 3.44 (1H, m), 3.61 (1H, m), 4.07 (2H, d, J=4.3 Hz), 4.43 (1H, bs), 6.23 (1H, m), 7.05 (2H, m), 7.49 (6H, m), 7.95 (1H, s).

Example 152

1-[1-(2,5-Difluorophenyl)ethyl]-7-[4-(4-methylpiperazine-1-carbonyl)phenyl]-3,4-dihydro-1H-pyrido[2,3-b]pyrazin-2-one, trifluoroacetic acid salt

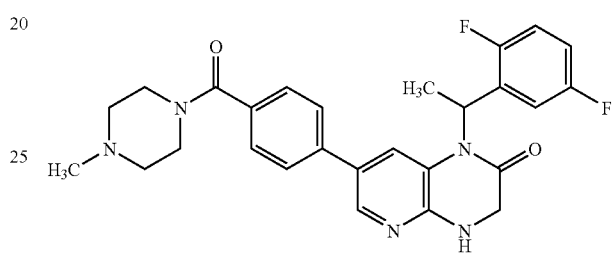

1-[1-(2,5-Difluorophenyl)ethyl]-7-iodo-3,4-dihydro-1H-pyrido[2,3-b]pyrazin-2-one (55 mg) was reacted with (4-methylpiperazin-1-yl)-[4-(4,4,5,5-tetramethyl-[1,3,2]dioxaborolan-2-yl)phenyl]methanone as in General Procedure 4B to give the title compound as a yellow solid after preparative reversed-phase HPLC purification (7% yield). LCMS: m/z=492.13 (M+H$^+$), $^1$H-NMR (CD$_3$OD, 400 MHz) δ 1.91 (3H, d, J=7.1 Hz), 2.96 (3H, s), 3.22 (5H, m), 3.52 (3H, m), 4.31 (2H, m), 6.32 (1H, quartet, J=6.8 Hz), 7.09 (2H, m), 7.51 (1H, m), 7.58 (4H, m), 7.74 (1H, s), 7.90 (1H, d, J=1.5 Hz).

Example 153

1-[1-(2,5-Difluorophenyl)ethyl]-7-iodo-1,2,3,4-tetrahydropyrido[2,3-b]pyrazine

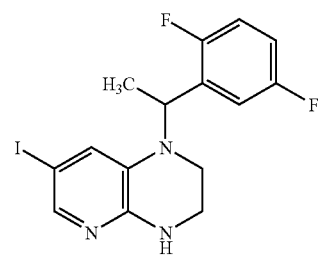

1-[1-(2,5-Difluorophenyl)ethyl]-7-iodo-3,4-dihydro-1H-pyrido[2,3-b]pyrazin-2-one (438 mg) was reduced as in General Procedure 3 to give the title compound as a yellow solid. LCMS: m/z=402.01 (M+H$^+$), $^1$H-NMR (CDCl$_3$, 400 MHz) δ 1.55 (3H, d, J=6.8 Hz), 3.34 (2H, m), 3.44 (2H, m), 4.81 (1H, s), 5.05 (1H, m), 7.00 (4H, m), 7.58 (1H, d, J=1.5 Hz).

Example 154

S-(4-{1-[1-(2,5-Difluorophenyl)ethyl]-1,2,3,4-tetrahydropyrido[2,3-b]pyrazin-7-yl}phenyl)-{2-[(pyrrolidin-1-yl)methyl]pyrrolidin-1-yl}methanone

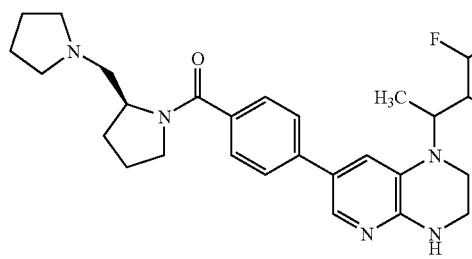

1-[1-(2,5-Difluorophenyl)ethyl]-7-iodo-1,2,3,4-tetrahydropyrido[2,3-b]pyrazine (73 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4B to give the title compound as an orange foam (6% yield). LCMS: m/z=532.12 (M+H$^+$), $^1$H-NMR (CD$_3$OD, 400 MHz) δ 1.61 (3H, m), 1.84 (4H, m), 2.03 (3H, m), 2.24 (2H, m), 2.73 (2H, m), 2.94 (1H, m), 3.44 (3H, m), 3.58 (1H, m), 4.15 (4H, m), 4.43 (1H, bs), 5.28 (1H, m), 7.04 (2H, m), 7.14 (1H, m), 7.22 (1H, m), 7.54 (5H, m).

Example 155

1-(2,5-Dichlorobenzyl)-7-iodo-3,4-dihydro-1H-pyrido[2,3-b]pyrazin-2-one

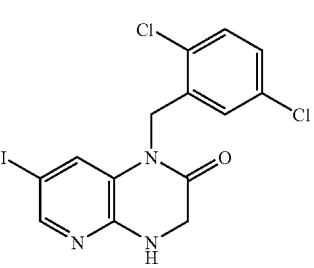

7-Iodo-3,4-dihydro-1H-pyrido[2,3-b]pyrazin-2-one (1.012 g) was reacted with 2,5-dichlorobenzyl bromide as in General Procedure 1 to give the title compound as a brown solid (69% yield). M.p.>200° C., LCMS: m/z=434.36 (M+H$^+$), $^1$H-NMR (DMSO-d$_6$, 400 MHz) δ 4.18 (2H, s), 5.07 (2H, s), 4.18 (2H, s), 7.14 (1H, d, J=1.8 Hz), 7.15 (1H, d, J=2.3 Hz), 7.40 (1H, dd, J=8.6, 2.5 Hz), 7.56 (1H, d, J=8.6 Hz), 7.85 (1H, d, J=1.8 Hz).

Example 156

1-(2,5-Dichlorobenzyl)-7-[4-(4-(pyrrolidin-1-yl)piperidine-1-carbonyl)phenyl]-3,4-dihydro-1H-pyrido[2,3-b]pyrazin-2-one

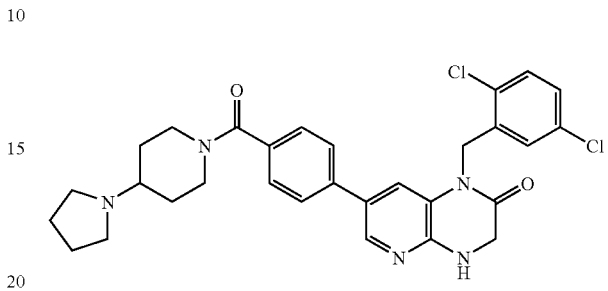

1-(2,5-Dichlorobenzyl)-7-iodo-3,4-dihydro-1H-pyrido[2,3-b]pyrazin-2-one (62 mg) was reacted with (4-(pyrrolidin-1-yl)piperidin-1-yl)-[4-(4,4,5,5-tetramethyl-[1,3,2]dioxaborolan-2-yl)phenyl]methanone as in General Procedure 4B to give the title compound as a brown solid (42% yield). M.p.>200° C., LCMS: m/z=564.14 (M+H$^+$), $^1$H-NMR (DMSO-d$_6$, 400 MHz) δ 1.37 (2H, m), 1.67 (4H, m), 1.81 (2H, m), 3.22 (6H, m), 3.51 (3H, m), 4.22 (2H, s), 5.23 (2H, s), 7.22 (3H, m), 7.38 (3H, m), 7.55 (3H, m), 8.06 (1H, s).

Example 157

S-1-(2,5-Dichlorobenzyl)-7-[4-(2-[(pyrrolidin-1-yl)methyl]pyrrolidine-1-carbonyl)phenyl]-3,4-dihydro-1H-pyrido[2,3-b]pyrazin-2-one

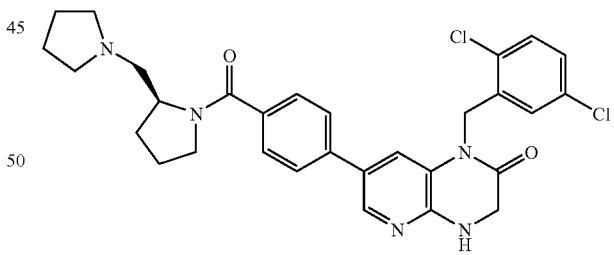

1-(2,5-Dichlorobenzyl)-7-iodo-3,4-dihydro-1H-pyrido[2,3-b]pyrazin-2-one (47 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4B to give the title compound as a brown solid (47% yield). M.p.=180° C., LCMS: m/z=564.09 (M+H$^+$), $^1$H-NMR (CDCl$_3$, 400 MHz) δ 1.99 (11H, m), 2.64 (3H, m), 2.87 (1H, m), 3.48 (2H, m), 4.38 (2H, s), 4.44 (1H, bs), 5.26 (2H, s), 5.44 (1H, s), 7.05 (2H, m), 7.21 (1H, dd, J=8.6, 2.3 Hz), 7.37 (3H, m), 7.54 (2H, m), 8.02 (1H, s).

Example 158

1-(2,5-Dichlorobenzyl)-7-iodo-1,2,3,4-tetrahydropyrido[2,3-b]pyrazine

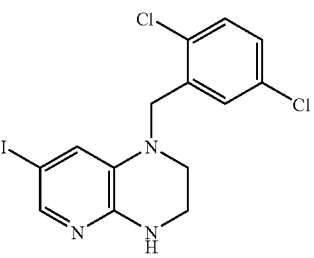

1-(2,5-Dichlorobenzyl)-7-iodo-3,4-dihydro-1H-pyrido[2,3-b]pyrazin-2-one (991 mg) was reduced as in General Procedure 3 to give the title compound as a brown solid (85% yield). M.p.=169° C., LCMS: m/z=421.39 (M+H⁺), ¹H-NMR (CDCl₃, 400 MHz) δ 3.40 (3H, m), 3.59 (2H, m), 4.39 (2H, s), 4.85 (1H, bs), 6.64 (1H, s), 7.18 (1H, d, J=2.8 Hz), 7.22 (1H, dd, J=8.6, 2.8 Hz), 7.35 (1H, d, J=8.6 Hz), 7.63 (1H, d, J=1.5 Hz).

Example 159

S-{4-[1-(2,5-Dichlorobenzyl)-1,2,3,4-tetrahydropyrido[2,3-b]pyrazin-7-yl]phenyl}-{2-[(pyrrolidin-1-yl)methyl]pyrrolidin-1-yl}methanone

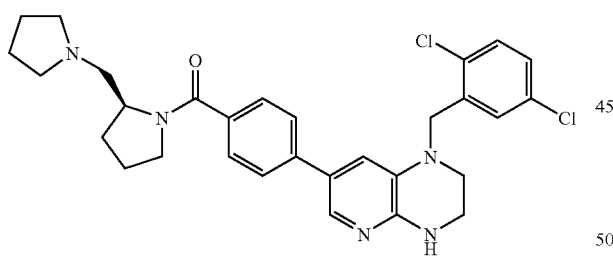

1-(2,5-Dichlorobenzyl)-7-iodo-3,4-dihydro-1H-pyrido[2,3-b]pyrazine (106 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4B to give the title compound as a brown solid (1% yield). LCMS: m/z=550.03 (M+H⁺), ¹H-NMR (CDCl₃, 400 MHz) δ 1.78 (4H, m), 1.99 (1H, m), 2.17 (2H, s), 2.64 (3H, m), 2.87 (1H, m), 3.48 (4H, m), 3.66 (2H, m), 4.44 (1H, m), 4.50 (2H, s), 4.92 (1H, bs), 6.64 (1H, s), 7.21 (1H, dd, J=8.5, 2.4 Hz), 7.30 (1H, d, J=2.3 Hz), 7.35 (1H, d, J=8.6 Hz), 7.39 (2H, d, J=8.3 Hz), 7.50 (2H, m), 7.61 (1H, m), 7.73 (1H, d, J=1.8 Hz).

Example 160

{4-[1-(2,5-Dichlorobenzyl)-1,2,3,4-tetrahydropyrido[2,3-b]pyrazin-7-yl]phenyl}-(4-(pyrrolidin-1-yl)piperidin-1-yl)methanone

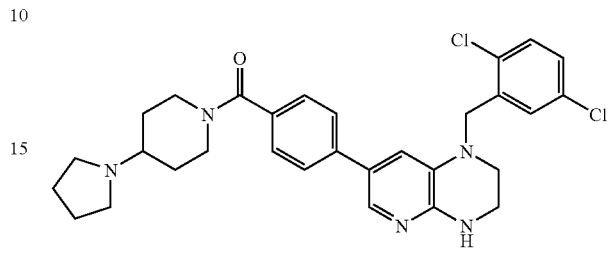

1-(2,5-Dichlorobenzyl)-7-iodo-3,4-dihydro-1H-pyrido[2,3-b]pyrazine (64 mg) was reacted with (4-(pyrrolidin-1-yl)piperidin-1-yl)-[4-(4,4,5,5-tetramethyl-[1,3,2]dioxaborolan-2-yl)phenyl]methanone as in General Procedure 4B to give the title compound as a yellow solid (10% yield). LCMS: m/z=550.11 (M+H⁺), ¹H-NMR (CDCl₃, 400 MHz) δ 1.53 (2H, m), 1.80 (7H, m), 2.25 (1H, m), 2.57 (4H, m), 2.98 (2H, m), 3.48 (2H, t, J=4.7 Hz), 3.65 (2H, m), 3.82 (1H, bs), 4.49 (2H, s), 4.59 (1H, m), 5.00 (1H, bs), 6.63 (1H, d, J=1.3 Hz), 7.21 (1H, dd, J=8.6, 2.5 Hz), 7.29 (1H, d, J=2.5 Hz), 37.38 (5H, m), 7.73 (1H, d, J=1.8 Hz).

Example 161

1-(2,6-Dichlorobenzyl)-7-[4-(4-(pyrrolidin-1-yl)piperidine-1-carbonyl)phenyl]-3,4-dihydro-1H-pyrido[2,3-b]pyrazin-2-one

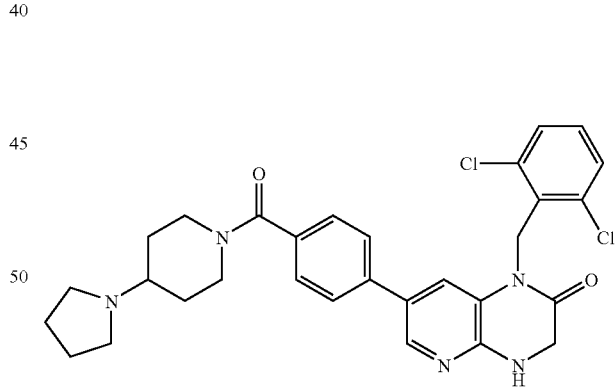

1-(2,6-Dichlorobenzyl)-7-iodo-3,4-dihydro-1H-pyrido[2,3-b]pyrazin-2-one (60 mg) was reacted with (4-(pyrrolidin-1-yl)piperidin-1-yl)-[4-(4,4,5,5-tetramethyl-[1,3,2]dioxaborolan-2-yl)phenyl]methanone as in General Procedure 4B to give the title compound as a brown solid (35% yield). M.p.=199° C., LCMS: m/z=564.03 (M+H⁺), ¹H-NMR (CDCl₃, 400 MHz) δ 1.89 (6H, m), 2.25 (1H, m), 2.59 (5H, s), 2.99 (3H, m), 3.80 (1H, bs), 4.26 (2H, d, J=1.3 Hz), 4.60 (1H, bs), 4.84 (1H, bs), 5.56 (2H, s), 7.17 (1H, m), 7.33 (5H, m), 7.41 (2H, d, J=8.1 Hz), 7.94 (1H, d, J=1.8 Hz),

Example 162

1-(2,6-Dichlorobenzyl)-7-iodo-1,2,3,4-tetrahydropyrido[2,3-b]pyrazine

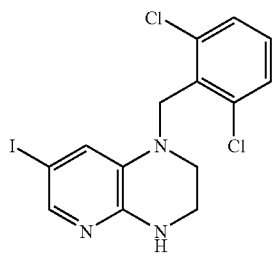

1-(2,6-Dichlorobenzyl)-7-iodo-3,4-dihydro-1H-pyrido[2,3-b]pyrazin-2-one was reduced as in General Procedure 3 to give the title compound as a light yellow solid. M.p.>200° C., LCMS: m/z=420.31 (M+H$^+$), $^1$H-NMR (CDCl$_3$, 400 MHz) δ 3.03 (2H, t, J=4.8 Hz), 3.42 (2H, m), 4.48 (2H, s), 4.81 (1H, s), 7.09 (1H, s), 7.24 (1H, m), 7.36 (2H, d, J=8.2 Hz), 7.63 (1H, d, J=1.6 Hz).

Example 163

{4-[1-(2,6-Dichlorobenzyl)-1,2,3,4-tetrahydropyrido[2,3-b]pyrazin-7-yl]phenyl}-(4-(pyrrolidin-1-yl)piperidin-1-yl)methanone

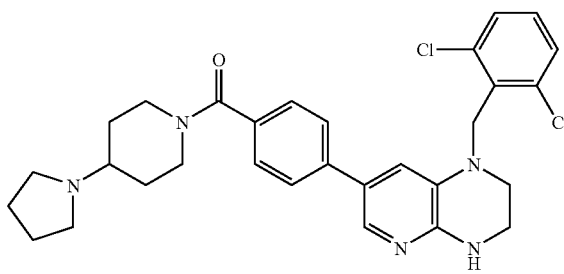

1-(2,6-Dichlorobenzyl)-7-iodo-1,2,3,4-tetrahydropyrido[2,3-b]pyrazine (56 mg) was reacted with (4-(pyrrolidin-1-yl)piperidin-1-yl)-[4-(4,4,5,5-tetramethyl-[1,3,2]dioxaborolan-2-yl)phenyl]methanone as in General Procedure 4B to give the title compound as a yellow solid (10% yield). LCMS: m/z=470.05 (M+H$^+$), $^1$H-NMR (CDCl$_3$, 400 MHz) δ 1.56 (3H, m), 1.90 (11H, m), 2.17 (1H, s), 2.28 (1H, m), 2.59 (5H, m), 2.98 (3H, m), 3.14 (2H, t, J=4.7 Hz), 3.50 (2H, m), 3.85 (1H, bs), 4.61 (3H, s), 4.92 (1H, bs), 7.12 (1H, s), 7.23 (1H, m), 7.48 (6H, m), 7.75 (1H, d, J=1.5 Hz).

Example 164

{4-[1-(2,6-Dichlorobenzyl)-1,2,3,4-tetrahydropyrido[2,3-b]pyrazin-7-yl]phenyl}-{2-[(pyrrolidin-1-yl)methyl]pyrrolidin-1-yl}methanone

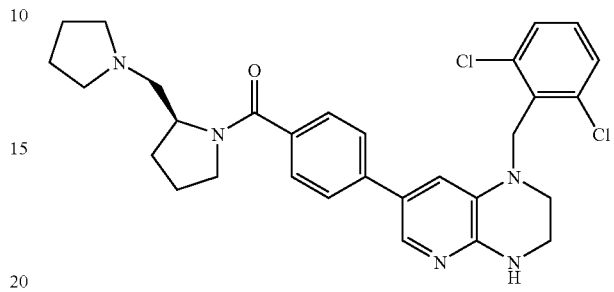

1-(2,6-Dichlorobenzyl)-7-iodo-1,2,3,4-tetrahydropyrido[2,3-b]pyrazine (72 mg) was reacted with (S)-2-[(pyrrolidin-1-yl)methyl]pyrrolidine-1-carboxyl-[4-(4,4,5,5-tetramethyl-[1,3,2]dioxaborolan-2-yl)phenyl]amide as in General Procedure 4B to give the title compound as a yellow solid (22% yield). LCMS: m/z=549.94 (M+H$^+$), $^1$H-NMR (CDCl$_3$, 400 MHz) δ 1.83 (7H, m), 2.26 (2H, m), 3.01 (5H, m), 3.57 (4H, m), 4.46 (1H, bs), 4.61 (2H, s), 5.17 (1H, bs), 7.11 (1H, d, J=1.5 Hz), 7.25 (1H, m), 7.37 (2H, d, J=8.1 Hz), 7.56 (4H, m), 7.74 (1H, s).

Example 165

7-(6-Chloropyridin-3-yl)-1-(2,5-dichlorobenzyl)-1,2,3,4-tetrahydropyrido[2,3-b]pyrazine

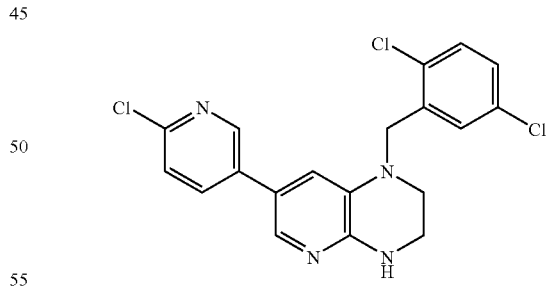

1-(2,5-Dichlorobenzyl)-7-iodo-1,2,3,4-tetrahydropyrido[2,3-b]pyrazine (115 mg) was reacted with 2-chloro-5-(4,4,5,5-tetramethyl-1,3,2-dioxaborolan-2-yl)pyridine as in General Procedure 4B to give the title compound as a yellow solid (54% yield). M.p.=205° C., LCMS: m/z=405.57 (M+H$^+$), $^1$H-NMR (CDCl$_3$, 400 MHz) δ 3.50 (2H, t, J=4.8 Hz), 3.67 (2H, m), 4.49 (2H, s), 5.10 (1H, bs), 6.52 (1H, s), 7.21 (1H, dd, J=8.3, 2.3 Hz), 7.29 (2H, m), 7.35 (1H, d, J=8.3 Hz), 7.55 (2H, m), 8.36 (1H, d, J=2.5 Hz).

Example 166

1-(2,5-Dichlorobenzyl)-7-(6-pyrrolidin-1-yl-pyridin-3-yl)-1,2,3,4-tetrahydropyrido[2,3-b]pyrazine

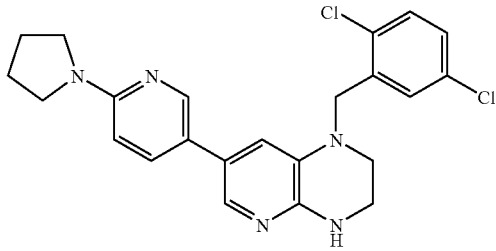

Pyrrolidine (1 mL) was added to 7-(6-chloropyridin-3-yl)-1-(2,5-dichlorobenzyl)-1,2,3,4-tetrahydropyrido[2,3-b]pyrazine (49 mg), and the mixture was stirred at 87° C. for 16 hours. The reaction mixture was then concentrated, and $CH_2Cl_2$ and $H_2O$ were added. The organic phase was isolated, dried with magnesium sulfate, filtered and then purified by normal phase column chromatography eluting with 3% methanol in $CH_2Cl_2$ to give the title compound as a yellow solid (36% yield). M.p.>200° C., LCMS: m/z=440.19 (M+H$^+$), $^1$H-NMR (CDCl$_3$, 400 MHz) δ 1.99 (4H, m), 3.47 (6H, m), 3.64 (2H, t, J=4.0 Hz), 4.47 (2H, s), 4.98 (1H, bs), 6.35 (1H, d, J=8.8 Hz), 6.52 (1H, d, J=1.8 Hz), 7.18 (1H, dd, J=8.3, 2.5 Hz), 7.26 (1H, m), 7.32 (1H, d, J=8.6 Hz), 7.48 (1H, dd, J=8.7, 2.4 Hz), 7.62 (1H, d, J=1.8 Hz), 8.17 (1H, d, J=2.3 Hz).

Example 167

7-(2-Chloropyridin-4-yl)-1-(2,6-dichlorobenzyl)-1,2,3,4-tetrahydropyrido[2,3-b]pyrazine

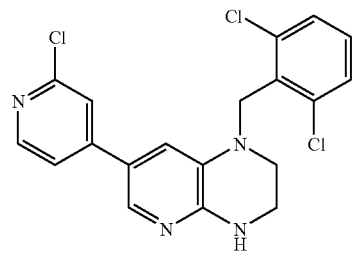

1-(2,6-Dichlorobenzyl)-7-iodo-1,2,3,4-tetrahydropyrido[2,3-b]pyrazine (511 mg) was reacted with 2-chloropyridine-4-boronic acid as in General Procedure 4B to give the title compound as a yellow solid (31% yield). M.p.=194° C., LCMS: m/z=405.56 (M+H$^+$), $^1$H-NMR (CDCl$_3$, 400 MHz) δ 3.17 (2H, t, J=4.8 Hz), 3.53 (2H, m), 4.62 (2H, s), 5.12 (1H, bs), 7.06 (1H, s), 7.42 (4H, m), 7.68 (1H, m), 7.81 (1H, d, J=1.8 Hz), 8.35 (1H, d, J=5.1 Hz).

Example 168

{3-[1-(2,5-Dichlorobenzyl)-1,2,3,4-tetrahydropyrido[2,3-b]pyrazin-7-yl]prop-2-ynyl}carbamic acid tert-butyl ester

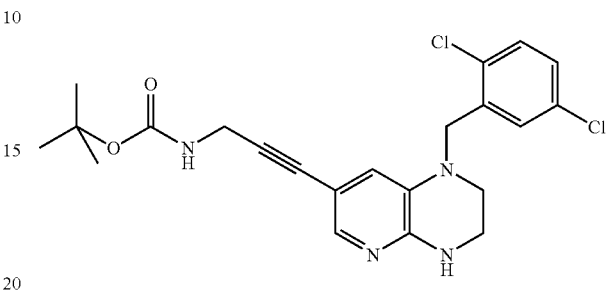

1-(2,5-Dichlorobenzyl)-7-iodo-1,2,3,4-tetrahydropyrido[2,3-b]pyrazine (40 mg) was coupled with N-boc propargylamine as in General Procedure 5 to give the title compound as a yellow solid (63% yield). LCMS: m/z=447.49 (M+H$^+$), $^1$H-NMR (CDCl$_3$, 400 MHz) δ 1.45 (9H, s), 3.41 (2H, t, J=4.8 Hz), 3.62 (2H, s), 4.05 (2H, m), 4.40 (2H, s), 4.81 (1H, m), 5.41 (1H, bs), 6.41 (1H, s), 7.21 (2H, m), 7.34 (1H, d, J=8.3 Hz), 7.61 (1H, s).

Example 169

3-[1-(2,5-Dichlorobenzyl)-1,2,3,4-tetrahydropyrido[2,3-b]pyrazin-7-yl]prop-2-ynylamine

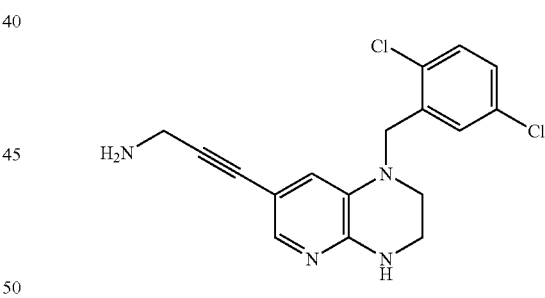

{3-[1-(2,5-Dichlorobenzyl)-1,2,3,4-tetrahydropyrido[2,3-b]pyrazin-7-yl]prop-2-ynyl}carbamic acid tert-butyl ester (19 mg), trifluoroacetic acid (250 μL) and $CH_2Cl_2$ (1 mL) were stirred under nitrogen at room temperature for 1.5 hours. 2 N NaOH (2 mL) and $CH_2Cl_2$ (approx. 10 mL) were added. The organic phase was isolated, washed twice with $H_2O$, washed once with brine, dried over sodium sulfate, filtered and then purified by normal phase column chromatography, eluting with 5% methanol in methylene chloride, to give the title compound as an off-white solid (37% yield). M.p.=183° C., LCMS: m/z=347.35 (M+H$^+$), $^1$H-NMR (CDCl$_3$, 400 MHz) δ 3.42 (2H, t, J=4.8 Hz), 3.61 (4H, m), 4.41 (2H, s), 5.04 (1H, bs), 6.42 (1H, s), 7.21 (2H, m), 7.34 (1H, d, J=8.3 Hz), 7.59 (1H, s, J=1.0 Hz).

Example 170

{3-[1-(2,6-Dichlorobenzyl)-1,2,3,4-tetrahydropyrido[2,3-b]pyrazin-7-yl]prop-2-ynyl}carbamic acid tert-butyl ester

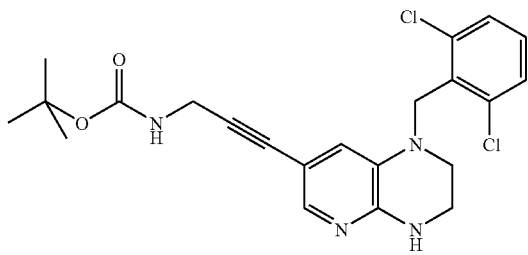

1-(2,6-Dichlorobenzyl)-7-iodo-1,2,3,4-tetrahydropyrido[2,3-b]pyrazine (1.951 g) was coupled with N-boc propargylamine as in General Procedure 5 to give the title compound as an orange solid. LCMS: m/z=447.53 (M+H$^+$), $^1$H-NMR (DMSO-d$_6$, 400 MHz) δ 1.40 (9H, s), 2.86 (2H, m), 3.27 (2H, m), 3.95 (2H, d, J=5.6 Hz), 4.46 (2H, s), 6.86 (1H, s), 6.89 (1H, s), 7.29 (1H, m), 7.42 (2H, m), 7.54 (2H, d, J=8.3 Hz).

Example 171

3-[1-(2,6-Dichlorobenzyl)-1,2,3,4-tetrahydropyrido[2,3-b]pyrazin-7-yl]prop-2-ynylamine, trifluoroacetic acid salt

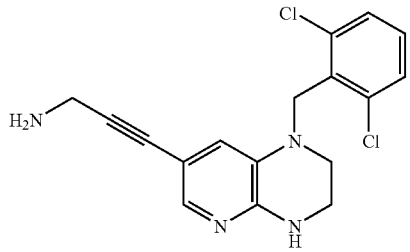

{3-[1-(2,6-Dichlorobenzyl)-1,2,3,4-tetrahydropyrido[2,3-b]pyrazin-7-yl]prop-2-ynyl}carbamic acid tert-butyl ester (641 mg), trifluoroacetic acid (3.1 mL) and CH$_2$Cl$_2$ (31 mL) were stirred overnight under nitrogen at room temperature, then concentrated to give the title compound.

Example 172

N-{3-[1-(2,6-Dichlorobenzyl)-1,2,3,4-tetrahydropyrido[2,3-b]pyrazin-7-yl]prop-2-ynyl}-2-dimethylamino-acetamide

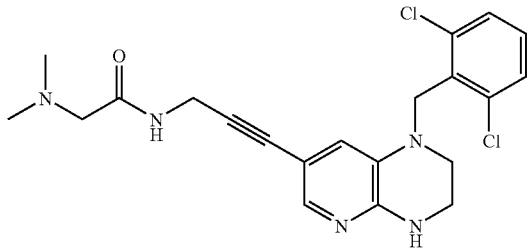

3-[1-(2,6-Dichlorobenzyl)-1,2,3,4-tetrahydropyrido[2,3-b]pyrazin-7-yl]prop-2-ynylamine, trifluoroacetic acid salt(s) (99 mg) and 1 N NaOH (4 mL) were stirred at room temperature for two (2) hours. The reaction mixture was then concentrated, anhydrous CH$_2$Cl$_2$ (4 mL), dimethylaminoacetyl chloride HCl (48 mg) and triethylamine (45 μL) were added, and the reaction was stirred at room temperature for 16 hours. The reaction mixture was then concentrated and purified with normal phase column chromatography, eluting with 9/1 CH$_2$Cl$_2$/methanol to 97/3/1 CH$_2$Cl$_2$/methanol/NH$_4$OH to give the title compound as a yellow solid. M.p.>200° C., LCMS: m/z=432.04 (M+H$^+$), $^1$H-NMR (CDCl$_3$, 400 MHz) δ 2.31 (6H, s), 3.00 (4H, m), 3.44 (2H, m), 4.31 (2H, d, J=5.6 Hz), 4.50 (2H, s), 5.11 (1H, bs), 6.93 (1H, d, J=1.0 Hz), 7.23 (1H, m), 7.37 (2H, m), 7.63 (1H, d, J=1.5 Hz).

Example 173

{3-[1-(2,5-Dichlorobenzyl)-1,2,3,4-tetrahydropyrido[2,3-b]pyrazin-7-yl]prop-2-ynyl}-dimethylamine

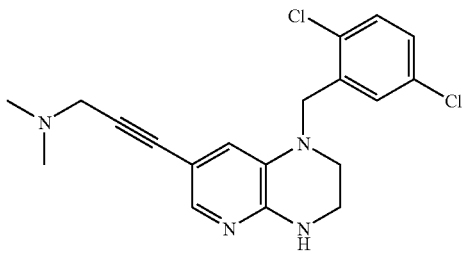

1-(2,5-Dichlorobenzyl)-7-iodo-1,2,3,4-tetrahydropyrido[2,3-b]pyrazine (113 mg) was coupled with 1-dimethylamino-2-propyne as in General Procedure 5 to give the title compound as a yellow solid (49% yield). M.p.=168° C., LCMS: m/z=375.08 (M+H$^+$), $^1$H-NMR (CDCl$_3$, 400 MHz) δ 2.31 (6H, s), 3.38 (4H, m), 3.61 (2H, t, J=4.0 Hz), 4.40 (2H, s), 5.54 (1H, bs), 6.45 (1H, d, J=1.5 Hz), 7.21 (2H, m), 7.33 (1H, m), 7.61 (1H, d, J=1.5 Hz).

Example 174

1-(2,5-Dichlorobenzyl)-7-[3-(1,1-dioxo-1λ$^6$-thiomorpholin-4-yl)prop-1-ynyl]-1,2,3,4-tetrahydropyrido[2,3-b]pyrazine

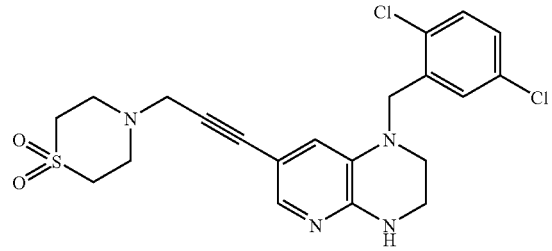

1-(2,5-Dichlorobenzyl)-7-iodo-1,2,3,4-tetrahydropyrido[2,3-b]pyrazine (108 mg) was coupled with 4-prop-2-ynyl-thiomorpholine 1,1-dioxide as in General Procedure 5 to give the title compound as an off-white solid (34% yield). M.p.>200° C., LCMS: m/z=467.33 (M+H$^+$), $^1$H-NMR (CDCl$_3$, 400 MHz) δ 3.11 (8H, s), 3.40 (2H, t, J=4.8 Hz), 3.56 (2H, s), 3.61 (2H, t, J=4.7 Hz), 4.41 (2H, s), 6.42 (1H, dt, J=1.5 Hz), 7.22 (2H, m), 7.35 (1H, d, J=8.3 Hz), 7.58 (1H, d, J=1.5 Hz).

Example 175

1-[1-(2-Chloro-3,6-difluorophenyl)ethyl]-7-iodo-3,4-dihydro-1H-pyrido[2,3-b]pyrazin-2-one

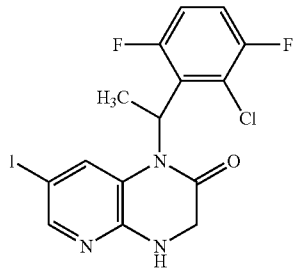

7-Iodo-3,4-dihydro-1H-pyrido[2,3-b]pyrazin-2-one (2.935 g) was treated with 2-(1-bromoethyl)-3-chloro-1,4-difluorobenzene (Preparation 3) as in General Procedure 1 to give the title compound as an orange solid (11% yield). LCMS: m/z=449.86 (M+H$^+$), $^1$H-NMR (DMSO-d$_6$, 400 MHz) δ 1.79 (3H, m), 2.73 (1H, s), 2.89 (1H, s), 5.76 (1H, m), 6.96 (1H, s), 7.29 (1H, m), 7.43 (1H, m), 7.62 (1H, s), 7.83 (1H, m).

Example 176

1-[1-(2-Chloro-3,6-difluorophenyl)ethyl]-7-iodo-1,2,3,4-tetrahydropyrido[2,3-b]pyrazine

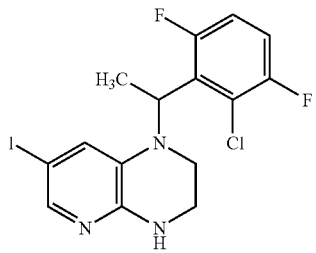

1-[1-(2-Chloro-3,6-difluorophenyl)ethyl]-7-iodo-3,4-dihydro-1H-pyrido[2,3-b]pyrazin-2-one (514 mg) was reduced as in General Procedure 3 to give the title compound as an orange solid (59% yield). M.p.=166° C., LCMS: m/z=436.07 (M+H$^+$), $^1$H-NMR (CDCl$_3$, 400 MHz) δ 1.63 (3H, m), 3.46 (4H, m), 4.75 (1H, bs), 5.16 (1H, quartet, J=7.2 Hz), 6.81 (1H, s), 6.97 (1H, m), 7.08 (1H, m), 7.54 (1H, d, J=1.5 Hz).

Example 177

1-[1-(2-Chloro-3,6-difluorophenyl)ethyl]-7-[6-(4-methylpiperazin-1-yl)pyridin-3-yl]-1,2,3,4-tetrahydropyrido[2,3-b]pyrazine

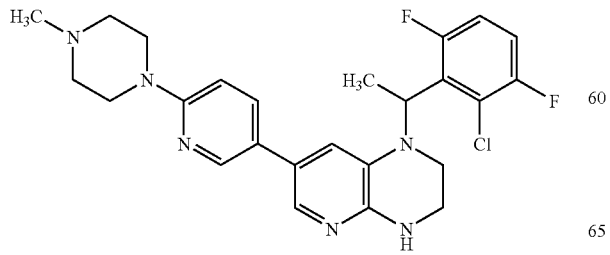

1-[1-(2-Chloro-3,6-difluorophenyl)ethyl]-7-iodo-1,2,3,4-tetrahydropyrido[2,3-b]pyrazine (53 mg) was coupled to 1-methyl-4-[5-(4,4,5,5-tetramethyl-[1,3,2]dioxaborolan-2-yl)pyridin-2-yl]piperazine as in General Procedure 4B to give the title compound as an orange solid (15% yield). LCMS: m/z=435.02 (M+H$^+$), $^1$H-NMR (CDCl$_3$, 400 MHz) δ 1.66 (3H, d, J=7.1 Hz), 2.35 (3H, s), 2.54 (4H, t, J=4.9 Hz), 3.54 (8H, m), 4.89 (1H, bs), 5.31 (1H, m), 6.68 (1H, d, J=8.9 Hz), 6.72 (1H, s), 6.96 (1H, m), 7.05 (1H, m), 7.52 (1H, dd, J=8.8, 2.5 Hz), 7.57 (1H, s), 8.29 (1H, d, J=2.3 Hz).

Example 178

1-[3-Fluoro-2-(trifluoromethyl)benzyl]-7-iodo-3,4-dihydro-1H-pyrido[2,3-b]pyrazin-2-one

7-Iodo-3,4-dihydro-1H-pyrido[2,3-b]pyrazin-2-one (1.051 g) was alkylated with 3-fluoro-2-(trifluoromethyl)benzyl bromide as in General Procedure 1 to give the title compound as a light brown solid (54% yield). M.p.>200° C., LCMS: m/z=451.79 (M+H$^+$), $^1$H-NMR (DMSO-d$_6$, 400 MHz) δ 4.17 (2H, s), 5.20 (2H, bs), 7.01 (1H, d, J=7.6 Hz), 7.17 (1H, s), 7.23 (1H, s), 7.42 (1H, m), 7.63 (1H, m), 7.86 (1H, m).

Example 179

1-[3-Fluoro-2-(trifluoromethyl)benzyl]-7-iodo-1,2,3,4-tetrahydropyrido[2,3-b]pyrazine

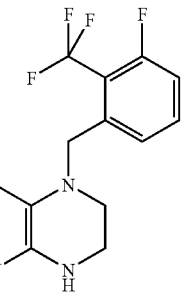

1-[3-Fluoro-2-(trifluoromethyl)benzyl]-7-iodo-3,4-dihydro-1H-pyrido[2,3-b]pyrazin-2-one (922 mg) was reduced as in General Procedure 3 to give the title compound as a brown solid (64% yield). LCMS: m/z=437.80 (M+H$^+$), $^1$H-NMR (DMSO-d$_6$, 400 MHz) δ 3.28 (2H, m), 3.40 (2H, m), 4.60

(2H, s), 4.68 (1H, m), 6.59 (1H, d, J=1.3 Hz), 6.70 (1H, s), 7.22 (1H, d, J=7.8 Hz), 7.43 (1H, d, J=1.5 Hz), 7.69 (1H, m).

Example 180

1-(2,5-Dichlorobenzyl)-7-[6-(4-methylpiperazin-1-yl)pyridin-3-yl]-1,2,3,4-tetrahydropyrido[2,3-b]pyrazine

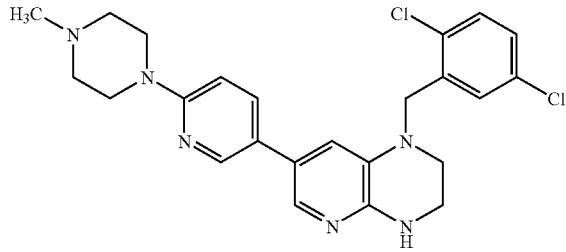

1-(2,5-Dichlorobenzyl)-7-iodo-1,2,3,4-tetrahydropyrido[2,3-b]pyrazine (94 mg) was coupled to 1-methyl-4-[5-(4,4,5,5-tetramethyl-[1,3,2]dioxaborolan-2-yl)pyridin-2-yl]piperazine as in General Procedure 4B to give the title compound as a brown solid (50% yield). LCMS: m/z=468.97 (M+H+), ¹H-NMR (CDCl₃, 400 MHz) δ 2.33 (3H, s), 2.51 (4H, t, J=5.1 Hz), 3.48 (2H, m), 3.55 (4H, t, J=5.1 Hz), 3.64 (2H, t, J=4.7 Hz), 4.46 (2H, s), 5.20 (1H, bs), 6.52 (1H, d, J=1.5 Hz), 6.65 (1H, d, J=8.8 Hz), 7.19 (1H, dd, J=8.5, 2.4 Hz), 7.26 (1H, d, J=2.3 Hz), 7.33 (1H, d, J=8.3 Hz), 7.52 (1H, dd, J=8.6, 2.5 Hz), 7.62 (1H, d, J=1.5 Hz), 8.20 (1H, d, J=2.5 Hz).

Example 181

1-[3-Fluoro-2-(trifluoromethyl)benzyl]-7-[6-(4-methylpiperazin-1-yl)pyridin-3-yl]-1,2,3,4-tetrahydropyrido[2,3-b]pyrazine

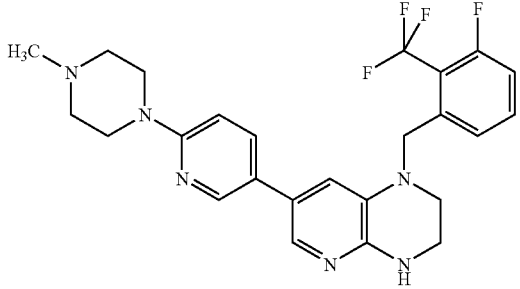

1-[3-Fluoro-2-(trifluoromethyl)benzyl]-7-iodo-1,2,3,4-tetrahydropyrido[2,3-b]pyrazine (101 mg) was coupled to 1-methyl-4-[5-(4,4,5,5-tetramethyl-[1,3,2]dioxaborolan-2-yl)pyridin-2-yl]piperazine as in General Procedure 4B to give the title compound as a yellow solid (31% yield). LCMS: m/z=487.09 (M+H+), ¹H-NMR (CDCl₃, 400 MHz) δ 2.33 (3H, s), 2.51 (4H, t, J=4.9 Hz), 3.49 (2H, m), 3.55 (4H, t, J=4.9 Hz), 3.63 (2H, m), 4.65 (2H, s), 5.08 (1H, bs), 6.48 (1H, d, J=1.8 Hz), 6.64 (1H, d, J=8.8 Hz), 7.09 (1H, m), 7.26 (1H, m), 7.45 (2H, m), 7.62 (1H, d, J=1.8 Hz), 8.18 (1H, d, J=2.5 Hz).

Example 182

1-(2-Chloro-3,6-difluorobenzyl)-7-(2-chloropyridin-4-yl)-1,2,3,4-tetrahydropyrido[2,3-b]pyrazine

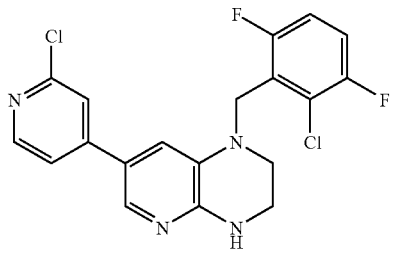

1-(2-Chloro-3,6-difluorobenzyl)-7-iodo-1,2,3,4-tetrahydropyrido[2,3-b]pyrazine (308 mg) was coupled to 2-chloro-5-(4,4,5,5-tetramethyl-1,3,2-dioxaborolan-2-yl)pyridine as in General Procedure 4B to give the title compound (50% yield). LCMS: m/z=407.32 (M+H+), ¹H-NMR (CDCl₃, 400 MHz) δ 3.30 (2H, t, J=4.8 Hz), 3.56 (2H, m), 4.34 (2H, s), 5.35 (1H, bs), 7.06 (2H, m), 7.15 (1H, m), 7.33 (1H, dd, J=5.3, 1.5 Hz), 5.46 (1H, m), 7.80 (1H, d, J=1.5 Hz), 8.34 (1H, d, J=5.3 Hz).

Example 183

1-(2-Chloro-3,6-difluorobenzyl)-7-(2-pyrrolidin-1-yl-pyridin-4-yl)-1,2,3,4-tetrahydropyrido[2,3-b]pyrazine

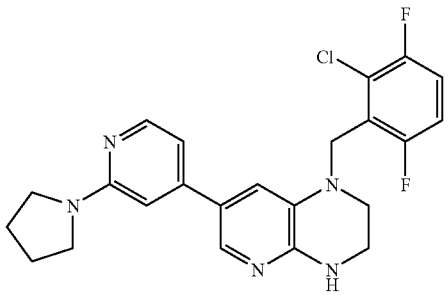

Pyrrolidine (1 mL) was added to 1-(2-chloro-3,6-difluorobenzyl)-7-(2-chloropyridin-4-yl)-1,2,3,4-tetrahydropyrido[2,3-b]pyrazine (32 mg). The reaction mixture was stirred at 87° C. for 72 hours and then concentrated. The residue was purified by normal phase column chromatography eluting with 5% methanol in CH₂Cl₂ to give the title compound as a yellow solid (35% yield). LCMS: m/z=442.21 (M+H+), ¹H-NMR (CDCl₃, 400 MHz) δ 2.03 (4H, m), 3.33 (2H, m), 3.53 (6H, m), 4.53 (2H, d, J=1.3 Hz), 5.06 (1H, bs), 6.43 (1H, d, J=0.8 Hz), 6.68 (1H, dd, J=5.4, 1.4 Hz), 7.02 (1H, m), 7.12 (2H, m), 7.79 (1H, d, J=1.8 Hz), 8.15 (1H, d, J=5.6 Hz).

Example 184

5-[1-(2-Chloro-3,6-difluorobenzyl)-1,2,3,4-tetrahydropyrido[2,3-b]pyrazin-7-yl]-pyridin-2-ylamine

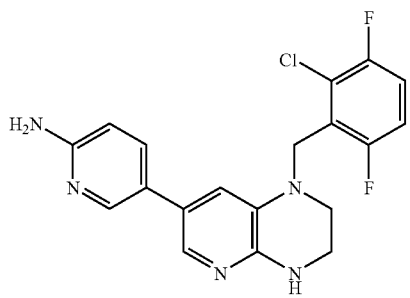

1-(2-Chloro-3,6-difluorobenzyl)-7-iodo-1,2,3,4-tetrahydropyrido[2,3-b]pyrazine (87 mg) was coupled to 5-(4,4,5,5-Tetramethyl-[1,3,2]dioxaborolan-2-yl)pyridin-2-ylamine as in General Procedure 4B to give the title compound as a light brown solid (52% yield). M.p.>200° C., LCMS: m/z=388.10 (M+H$^+$), $^1$H-NMR (CDCl$_3$, 400 MHz) δ 3.28 (2H, m), 3.51 (2H, m), 4.52 (2H, d, J=1.3 Hz), 6.58 (1H, dd, J=8.6, 0.8 Hz), 7.00 (1H, d, J=2.0 Hz), 7.05 (1H, m), 7.14 (1H, m), 7.30 (2H, s), 7.54 (1H, d, J=2.0 Hz), 7.58 (1H, dd, J=8.6, 2.5 Hz), 8.13 (1H, dd, J=2.4, 0.6 Hz).

Example 185

1-(2-Chloro-3,6-difluorobenzyl)-7-[6-(4-methylpiperazin-1-yl)pyridin-3-yl]-1,2,3,4-tetrahydropyrido[2,3-b]pyrazine

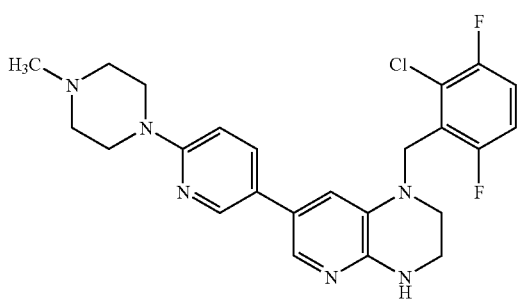

1-(2-Chloro-3,6-difluorobenzyl)-7-iodo-1,2,3,4-tetrahydropyrido[2,3-b]pyrazine (88 mg) was coupled to 1-Methyl-4-[5-(4,4,5,5-tetramethyl-[1,3,2]dioxaborolan-2-yl)pyridin-2-yl]piperazine as in General Procedure 4B to give the title compound as a light brown solid (16% yield). M.p.=219° C., LCMS: m/z=471.12 (M+H$^+$), $^1$H-NMR (CDCl$_3$, 400 MHz) δ 2.36 (3H, s), 2.54 (4H, t, J=5.1 Hz), 3.27 (2H, t, J=4.8 Hz), 3.51 (2H, t, J=4.7 Hz), 3.59 (4H, t, J=5.1 Hz), 4.50 (2H, d, J=1.0 Hz), 5.01 (1H, bs), 6.70 (1H, d, J=8.8 Hz), 7.03 (2H, m), 7.11 (1H, m), 7.61 (1H, dd, J=8.8, 2.5 Hz), 7.64 (1H, d, J=1.8 Hz), 8.35 (1H, d, J=2.3 Hz).

Example 186

1-(2-Chloro-3,6-difluorobenzyl)-7-(2-morpholin-4-yl-pyridin-4-yl)-1,2,3,4-tetrahydropyrido[2,3-b]pyrazine

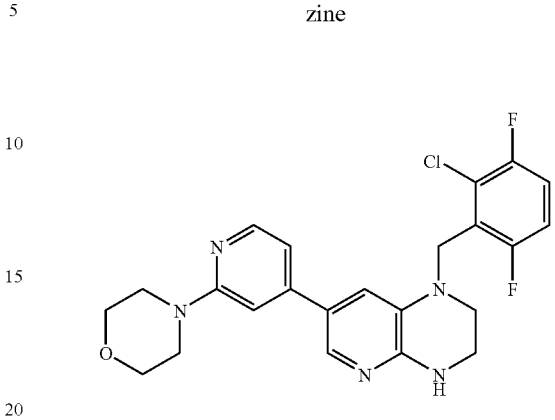

Morpholine (2 mL) was added to 1-(2-chloro-3,6-difluorobenzyl)-7-(2-chloropyridin-4-yl)-1,2,3,4-tetrahydropyrido[2,3-b]pyrazine (61 mg), and the mixture was heated in a microwave oven for two (2) hours at 180° C. The mixture was then concentrated, and the residue was purified through silica gel chromatography followed by preparative reversed-phase HPLC. The trifluoroacetic acid salt was neutralized with saturated sodium bicarbonate, and the free base extracted into methylene chloride, washed with brine and dried with magnesium sulfate. The solution was concentrated to give the title compound as a yellow solid (21% yield). M.p.=157° C., LCMS: m/z=458.07 (M+H$^+$), $^1$H-NMR (CDCl$_3$, 400 MHz) δ 3.38 (2H, t, J=4.7 Hz), 3.56 (4H, t, J=4.8 Hz), 3.62 (2H, t, J=4.5 Hz), 3.86 (4H, t, J=4.8 Hz), 4.58 (2H, s), 6.65 (1H, s), 6.76 (1H, d, J=5.1 Hz), 7.06 (2H, m), 7.16 (1H, m), 7.59 (2H, m), 8.22 (1H, d, J=5.1 Hz).

Example 187

1-(2,5-Dichlorobenzyl)-7-iodo-4-methyl-1,2,3,4-tetrahydropyrido[2,3-b]pyrazine

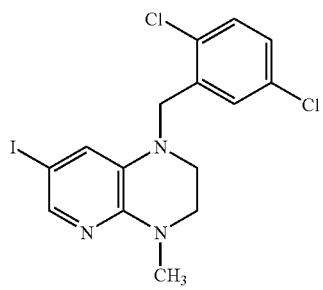

To a solution of 1-(2,5-dichlorobenzyl)-7-iodo-1,2,3,4-tetrahydropyrido[2,3-b]pyrazine (305 mg) in anhydrous N,N-dimethylformamide was added NaH (1.6 eq) followed by iodomethane (1.4 eq). The reaction mixture was stirred at room temperature for 48 hours and then concentrated. Column chromatography gave the title compound as a yellow solid (56% yield). LCMS: m/z=434.17 (M+H$^+$), $^1$H-NMR (CDCl$_3$, 400 MHz) δ 3.09 (3H, s), 3.42 (2H, m), 3.48 (2H, m), 4.36 (2H, s), 6.54 (1H, d, J=1.8 Hz), 7.17 (1H, d, J=2.3 Hz), 7.21 (1H, dd, J=8.6, 2.5 Hz), 7.34 (1H, d, J=4.3 Hz), 7.72 (1H, d, J=1.8 Hz).

Example 188

1-(2,5-Dichlorobenzyl)-4-methyl-7-[6-(4-methylpiperazin-1-yl)pyridin-3-yl]-1,2,3,4-tetrahydropyrido[2,3-b]pyrazine

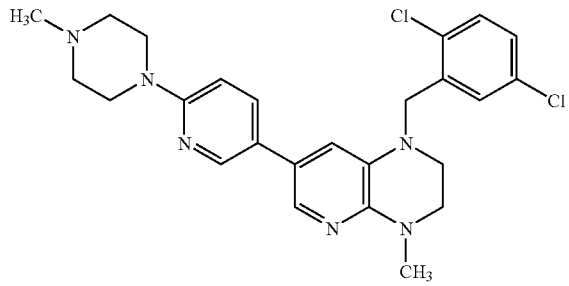

1-(2,5-Dichlorobenzyl)-7-iodo-4-methyl-1,2,3,4-tetrahydropyrido[2,3-b]pyrazine (83 mg) was coupled to 1-methyl-4-[5-(4,4,5,5-tetramethyl-[1,3,2]dioxaborolan-2-yl)pyridin-2-yl]piperazine as in General Procedure 4B to give the title compound as a brown solid (43% yield). LCMS: m/z=483.33 (M+H$^+$), $^1$H-NMR (CDCl$_3$, 400 MHz) δ 2.33 (3H, s), 2.52 (4H, t, J=5.1 Hz), 3.16 (3H, s), 3.53 (8H, m), 4.45 (2H, s), 6.45 (1H, d, J=1.8 Hz), 6.65 (1H, d, J=8.8 Hz), 7.18 (1H, dd, J=8.5, 4.8 Hz), 7.25 (1H, d, J=2.3 Hz), 7.32 (1H, d, J=8.3 Hz), 7.52 (1H, dd, J=8.6, 2.5 Hz), 7.75 (1H, d, J=1.8 Hz), 8.22 (1H, d, J=2.5 Hz).

Example 189

1-(2-Chloro-3,6-difluorobenzyl)-7-(3-morpholin-4-yl-phenyl)-1,2,3,4-tetrahydropyrido[2,3-b]pyrazine

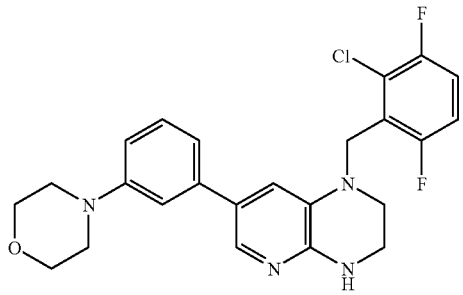

1-(2-Chloro-3,6-difluorobenzyl)-7-(2-chloropyridin-4-yl)-1,2,3,4-tetrahydropyrido[2,3-b]pyrazine (100 mg) was coupled to 4-[3-(4,4,5,5-Tetramethyl-[1,3,2]dioxaborolan-2-yl)phenyl]-morpholine as in General Procedure 4B to give the title compound as a yellow solid. LCMS: m/z=457.05 (M+H$^+$), $^1$H-NMR (CDCl$_3$, 400 MHz) δ 3.21 (4H, t, J=4.8 Hz), 3.29 (2H, t, J=4.7 Hz), 3.52 (2H, t, J=4.2 Hz), 3.89 (4H, t, J=4.8 Hz), 4.52 (2H, s), 5.09 (1H, bs), 6.84 (1H, dd, J=8.0, 1.9 Hz), 7.00 (3H, m), 7.10 (2H, m), 7.29 (1H, m), 7.72 (1H, d, J=1.8 Hz).

Example 190

1-(2-Chloro-3,6-difluorobenzyl)-7-[2-(4-methylpiperazin-1-yl)pyridin-4-yl]-1,2,3,4-tetrahydropyrido[2,3-b]pyrazine

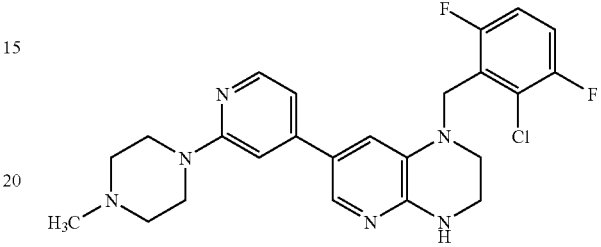

1-(2-Chloro-3,6-difluorobenzyl)-7-(2-chloropyridin-4-yl)-1,2,3,4-tetrahydropyrido[2,3-b]pyrazine (88 mg) was coupled to 1-methyl-4-[4-(4,4,5,5-tetramethyl-[1,3,2]dioxaborolan-2-yl)pyridin-2-yl]piperazine as in General Procedure 4B to give the title compound as a light yellow solid (15% yield). LCMS: m/z=471.07 (M+H$^+$), $^1$H-NMR (CDCl$_3$, 400 MHz) δ 2.36 (3H, s), 2.56 (4H, t, J=4.9 Hz), 3.33 (2H, t, J=4.7 Hz), 3.55 (2H, m), 3.62 (4H, t, J=4.9 Hz), 4.53 (2H, s), 5.23 (1H, bs), 6.72 (1H, s), 6.78 (1H, dd, J=5.3, 1.3 Hz), 7.03 (2H, m), 7.12 (1H, m), 7.77 (1H, d, J=1.8 Hz), 8.18 (1H, d, J=5.1 Hz).

Example 191

1-(2-Chloro-3,6-difluorobenzyl)-7-[1-(3-methylbutyl)-1H-pyrazol-4-yl]-1,2,3,4-tetrahydropyrido[2,3-b]pyrazine

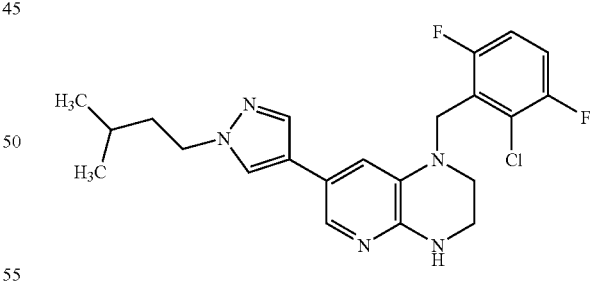

1-(2-Chloro-3,6-difluorobenzyl)-7-iodo-1,2,3,4-tetrahydropyrido[2,3-b]pyrazine (99 mg) was reacted with 1-(3-methylbutyl)-1H-pyrazole-4-boronic acid, pinacol ester as in General Procedure 4B to give the title compound as a brown solid (21% yield). M.p.=134° C., LCMS: m/z=431.92 (M+H$^+$), $^1$H-NMR (CDCl$_3$, 400 MHz) δ 0.96 (6H, d, J=6.6 Hz), 1.61 (1H, m), 1.80 (2H, m), 3.28 (2H, t, J=4.8 Hz), 3.51 (2H, m), 4.15 (2H, t, J=7.5 Hz), 4.50 (2H, s), 4.90 (1H, bs), 6.96 (1H, d, J=1.5 Hz), 7.02 (1H, m), 7.12 (1H, m), 7.51 (1H, s), 7.63 (2H, m).

Example 192

1-(2-Chloro-3,6-difluorobenzyl)-7-(1H-pyrazol-4-yl)-1,2,3,4-tetrahydropyrido[2,3-b]pyrazine

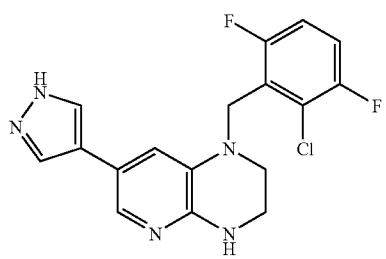

1-[(2-Chloro-3,6-difluoro)benzyl]-7-iodo-1,2,3,4-tetrahydropyrido[2,3-b]pyrazine (224 mg) was reacted with 4-(4,4,5,5-tetramethyl-1,3,2-dioxaborolan-2-yl)pyrazole-1-carboxylic acid-tert-butyl ester as in General Procedure 4B to give the title compound as an off-white solid. m.p.=272° C., LCMS: m/z=361.78 (M+H$^+$), $^1$H-NMR (CDCl$_3$, 400 MHz) δ 3.30 (2H, t, J=4.7 Hz), 3.41 (1H, m), 3.50 (2H, m), 4.51 (2H, s), 7.00 (1H, d, J=1.5 Hz), 7.04 (1H, m), 7.13 (1H, m), 7.59 (1H, d, J=1.5 Hz), 7.72 (2H, s).

Example 193

4-{1-[5-Chloro-2-(trifluoromethyl)benzyl]-1,2,3,4-tetrahydropyrido[2,3-b]pyrazin-7-yl}benzoic acid ethyl ester

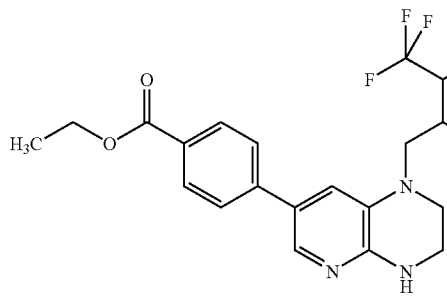

1-[5-Chloro-2-(trifluoromethyl)benzyl]-7-iodo-1,2,3,4-tetrahydropyrido[2,3-b]pyrazine (7.0 g) was reacted with 4-ethoxycarbonyl phenyl boronic acid as in General Procedure 4A. The title compound was obtained as a yellow solid (71% yield). M.p.=154° C., LCMS: m/z=476.04 (M+H$^+$), $^1$H-NMR (CDCl$_3$, 400 MHz) δ 1.40, (t, 3H), 3.49 (m, 2H), 3.71 (m, 2H), 4.35 (q, 2H), 4.61 (s, 2H), 5.72 (bs, 1H), 6.62 (s, 1H), 7.44 (m, 3H), 7.50 (s, 1H), 7.63 (d, 1H), 7.72 (s, 1H), 8.07 (d, 2H).

Example 194

3-{1-[5-Chloro-2-(trifluoromethyl)benzyl]-1,2,3,4-tetrahydropyrido[2,3-b]pyrazin-7-yl}benzoic acid ethyl ester

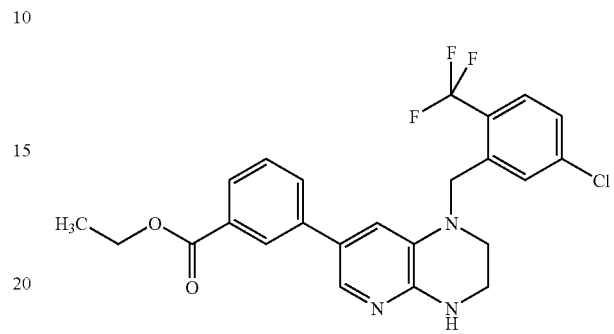

1-[5-Chloro-2-(trifluoromethyl)benzyl]-7-iodo-1,2,3,4-tetrahydropyrido[2,3-b]pyrazine (7.5 g) was reacted with 3-ethoxycarbonyl phenyl boronic acid as in General Procedure 4A. The title compound was obtained as a white solid (72% yield). m.p.=174° C., LCMS: m/z=475.95 (M+H$^+$), $^1$H-NMR (CDCl$_3$, 400 MHz) δ 1.40 (t, 3H), 3.48 (m, 2H), 3.69 (m, 2H), 4.32 (q, 2H), 4.63 (s, 2H), 5.51 (bs, 1H), 6.52 (s, 1H), 7.35 (m, 1H), 7.42 (m, 1H), 7.48 (s, 1H), 7.54 (m, 1H), 7.65 (d, 1H), 7.70 (s, 1H), 7.90 (d, 1H), 8.03 (s, 1H).

Example 195

4-{1-[5-Chloro-2-(trifluoromethyl)benzyl]-1,2,3,4-tetrahydropyrido[2,3-b]pyrazin-7-yl}benzoic acid

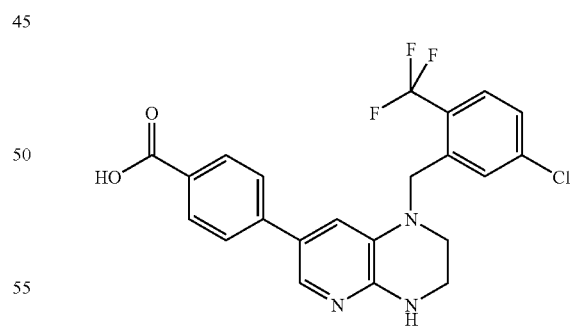

4-{1-[5-Chloro-2-(trifluoromethyl)benzyl]-1,2,3,4-tetrahydropyrido[2,3-b]pyrazin-7-yl}benzoic acid ethyl ester (5.1 g) was saponified as in General Procedure 7 to give the title compound as a light orange solid (88% yield). LCMS: m/z=447.88 (M+H$^+$), $^1$H-NMR (DMSO-d$_6$, 400 MHz) δ 3.41 (m, 2H), 3.60 (m, 2H), 4.80 (s, 2H), 7.07 (s, 1H), 7.63 (m, 3H), 7.74 (s, 1H), 7.82 (d, 1H), 7.95 (m, 2H), 8.81 (s, 1H), 13.01 (bs, 1H).

Example 196

3-{1-[5-Chloro-2-(trifluoromethyl)benzyl]-1,2,3,4-tetrahydropyrido[2,3-b]pyrazin-7-yl}benzoic acid

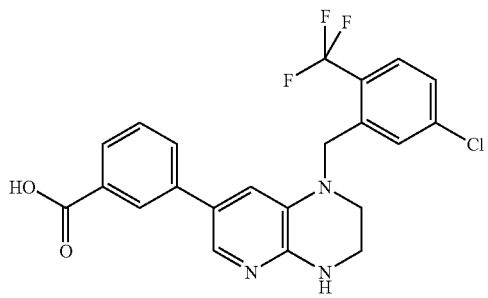

3-{1-[5-Chloro-2-(trifluoromethyl)benzyl]-1,2,3,4-tetrahydropyrido[2,3-b]pyrazin-7-yl}benzoic acid ethyl ester (5.5 g) was saponified as in General Procedure 7 to give the title compound as a tan solid (97% yield). LCMS: m/z=448.07 (M+H$^+$), $^1$H-NMR (DMSO-d$_6$, 400 MHz) δ 3.42 (m, 2H), 3.51 (m, 2H), 4.62 (s, 2H), 6.61 (s, 1H), 6.75 (s, 1H), 7.35 (m, 2H), 7.52 (m, 3H), 7.62 (s, 1H), 7.74 (d, 1H), 7.82 (d, 1H), 7.88 (s, 1H).

Example 197

(2-{4-[1-(2-Chloro-3,6-difluorobenzyl)-1,2,3,4-tetrahydropyrido[2,3-b]pyrazin-7-yl]-pyrazol-1-yl}ethyl)dimethylamine

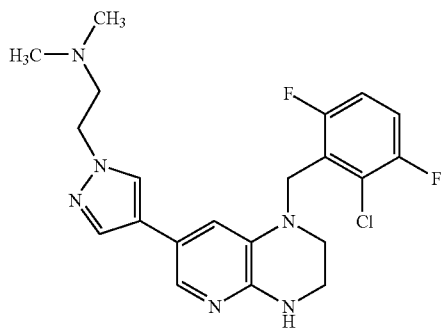

Anhydrous DMF (2 mL) was added to a mixture of 1-(2-chloro-3,6-difluorobenzyl)-7-(1H-pyrazol-4-yl)-1,2,3,4-tetrahydropyrido[2,3-b]pyrazine (57 mg, 0.000158 mol), cesium carbonate (0.110 g) and 2-dimethylaminoethyl chloride HCl (0.025 g). The reaction mixture was stirred at room temperature under nitrogen for 13 days and then concentrated and dissolved in methylene chloride. The organic phase was washed with water, dried with magnesium sulfate, filtered, and concentrated. The residue was purified on normal phase silica gel chromatography to give the title compound as an off-white solid (9% yield). LCMS: m/z=433.13 (M+H$^+$), $^1$H-NMR (CDCl$_3$, 400 MHz) δ 2.30 (6H, s), 2.79 (2H, t, J=6.8 Hz), 3.29 (2H, t, J=4.7 Hz), 3.51 (2H, m), 4.24 (2H, t, J=6.8 Hz), 4.50 (2H, s), 4.77 (1H, bs), 6.97 (1H, s), 7.02 (1H, m), 7.12 (1H, m), 7.60 (1H, s), 7.63 (1H, d, J=1.5 Hz), 7.66 (1H, s).

Example 198

1-[5-Chloro-2-(trifluoromethyl)benzyl]-7-(2-piperazin-1-yl-pyridin-4-yl)-1,2,3,4-tetrahydro-pyrido[2,3-b]pyrazine

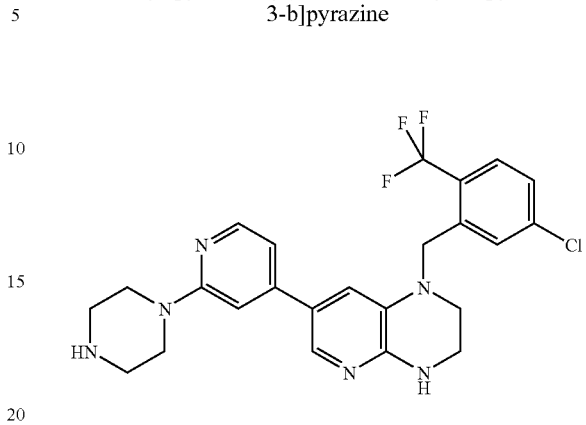

1-[5-Chloro-2-(trifluoromethyl)benzyl]-7-iodo-1,2,3,4-tetrahydro-pyrido[2,3-b]pyrazine (293 mg) was reacted with 2-(piperazin-1-yl)pyridine-4-boronic acid, pinacol ester as in General Procedure 4B to give the title compound as an off-white solid. m.p.=189° C., LCMS: m/z=489.08 (M+H$^+$), $^1$H-NMR (CDCl$_3$, 400 MHz) δ 2.98 (4H, m), 3.49 (6H, m), 3.71 (2H, m), 4.61 (2H, s), 5.29 (1H, s), 5.34 (1H, bs), 6.55 (2H, m), 6.64 (1H, dd, J=5.2, 1.4 Hz), 7.36 (1H, d, J=8.1 Hz), 7.52 (1H, s), 7.64 (1H, d, J=8.3 Hz), 7.77 (1H, d, J=2.0 Hz), 8.12 (1H, d, J=5.3 Hz).

Example 199

1-[4-(4-{1-[5-Chloro-2-(trifluoromethyl)benzyl]-1,2,3,4-tetrahydro-pyrido[2,3-b]pyrazin-7-yl}pyridin-2-yl)piperazin-1-yl]ethanone

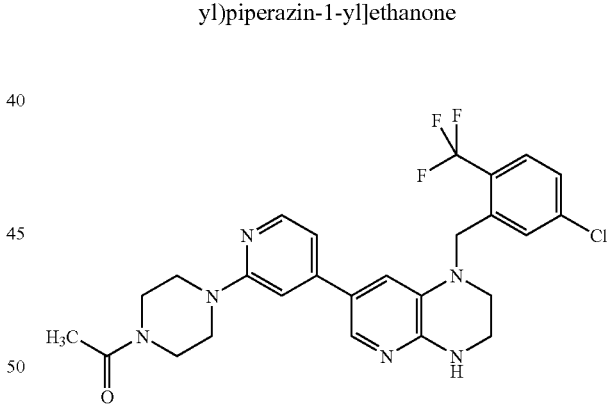

To a solution of 1-[5-chloro-2-(trifluoromethyl)benzyl]-7-(2-piperazin-1-yl-pyridin-4-yl)-1,2,3,4-tetrahydro-pyrido[2,3-b]pyrazine (63 mg, 0.000129 mol) in anhydrous DMF (1 mL) was added acetyl chloride (0.012 mL) and triethylamine (0.020 mL). The mixture was stirred at room temperature under nitrogen overnight and then concentrated. The residue was purified on normal phase silica gel chromatography to give the title compound as a yellow solid (56% yield). m.p.=241° C., LCMS: m/z=531.31 (M+H$^+$), $^1$H-NMR (CDCl$_3$, 400 MHz) δ 2.15 (3H, s), 3.47 (2H, m), 3.52 (2H, m), 3.57 (2H, m), 3.62 (2H, m), 3.73 (4H, m), 4.61 (2H, s), 5.25 (1H, bs), 6.55 (2H, m), 6.69 (1H, d, J=5.3 Hz), 7.37 (1H, d, J=8.3 Hz), 7.52 (1H, s), 7.65 (1H, d, J=8.3 Hz), 7.78 (1H, bs), 8.12 (1H, d, J=5.3 Hz).

Example 200

1-[5-Chloro-2-(trifluoromethyl)benzyl]-7-(1H-pyrazol-4-yl)-1,2,3,4-tetrahydro-pyrido[2,3-b]pyrazine

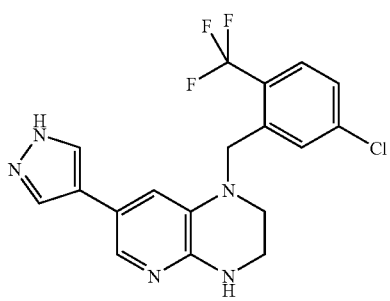

1-[5-Chloro-2-(trifluoromethyl)benzyl]-7-iodo-1,2,3,4-tetrahydro-pyrido[2,3-b]pyrazine (109 mg) was reacted with 4-(4,4,5,5-tetramethyl-1,3,2-dioxaborolan-2-yl)pyrazole-1-carboxylic acid-tert-butyl ester as in General Procedure 4B, then added 6 mL $CH_2Cl_2$ and TFA (0.6 mL), and purified on normal phase silica gel chromatography to give the title compound as an off-white solid (44% yield). m.p.=271° C., LCMS: m/z=394.24 (M+H$^+$), $^1$H-NMR (CDCl$_3$, 400 MHz) δ 3.50 (2H, m), 3.66 (2H, m), 4.05 (3H, s), 4.61 (2H, s), 6.50 (1H, d, J=1.5 Hz), 7.40 (1H, s), 7.50 (1H, s), 7.56 (3H, m), 7.68 (1H, d, J=8.6 Hz).

Example 201

1-[5-Chloro-2-(trifluoromethyl)benzyl]-7-(1-triisopropylsilanyl-1H-pyrrol-3-yl)-1,2,3,4-tetrahydropyrido[2,3-b]pyrazine

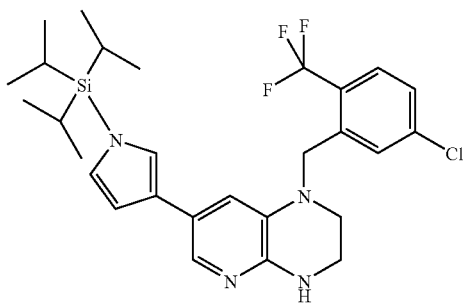

1-[5-Chloro-2-(trifluoromethyl)benzyl]-7-iodo-1,2,3,4-tetrahydro-pyrido[2,3-b]pyrazine (111 mg) was reacted with 1-(triisopropylsilyl)-1H-pyrrole-3-boronic acid as in General Procedure 4B to give the title compound as an off-white solid (80% yield). LCMS: m/z=349.34 (M+H$^+$), $^1$H-NMR (CDCl$_3$, 400 MHz) δ 1.08 (18H, d, J=7.6 Hz), 1.41 (3H, m), 3.49 (2H, m), 3.65 (2H, m), 4.58 (2H, s), 4.92 (1H, bs), 6.37 (1H, m), 6.54 (1H, d, J=1.8 Hz), 6.72 (1H, m), 6.76 (1H, m), 7.32 (1H, d, J=8.6 Hz), 7.54 (1H, s), 7.61 (1H, d, J=8.6 Hz), 7.70 (1H, m).

Example 202

1-[5-Chloro-2-(trifluoromethyl)benzyl]-7-(1H-pyrrol-3-yl)-1,2,3,4-tetrahydro-pyrido[2,3-b]pyrazine

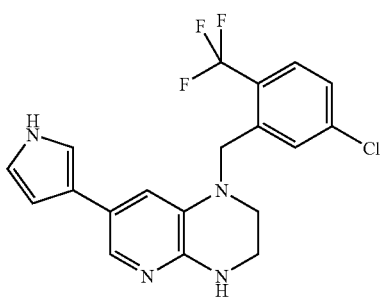

Anhydrous tetrahydrofuran (1 mL) and tetrabutylammonium fluoride, 1 M solution in tetrahydrofuran (0.761 mL) were added to 1-[5-chloro-2-(trifluoromethyl)benzyl]-7-(1-triisopropylsilanyl-1H-pyrrol-3-yl)-1,2,3,4-tetrahydro-pyrido[2,3-b]pyrazine (107 mg, 0.000195 mol). The reaction was stirred at room temperature under nitrogen for two (2) hours and then concentrated. The residue was purified on normal phase silica gel chromatography to give the title compound as an off-white solid. LCMS: m/z=393.24 (M+H$^+$), $^1$H-NMR (CDCl$_3$, 400 MHz) δ 3.35 (2H, bs), 3.48 (2H, m), 3.63 (2H, m), 4.59 (2H, s), 6.26 (1H, s), 6.56 (1H, d, J=1.3 Hz), 6.74 (1H, t, J=2.0 Hz), 6.82 (1H, s), 7.34 (1H, d, J=8.3 Hz), 7.50 (1H, s), 7.60 (1H, s), 7.64 (1H, d, J=8.3 Hz).

Example 203

1-[5-Chloro-2-(trifluoromethyl)benzyl]-7-(1-methyl-1H-pyrazol-4-yl)-1,2,3,4-tetrahydropyrido[2,3-b]pyrazine

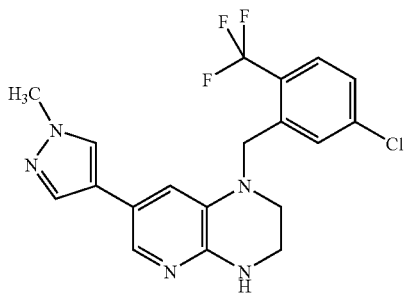

1-[5-Chloro-2-(trifluoromethyl)benzyl]-7-iodo-1,2,3,4-tetrahydropyrido[2,3-b]pyrazine (112 mg) was reacted with 1-methyl-4-(4,4,5,5-tetramethyl-1,3,2-dioxaborolan-2-yl)-1H-pyrazole as in General Procedure 4B to give the title compound as a brown solid (74% yield). m.p.=156° C., LCMS: m/z=408.25 (M+H$^+$), $^1$H-NMR (CDCl$_3$, 400 MHz) δ 3.48 (2H, m), 3.65 (2H, m), 3.87 (3H, s), 4.58 (2H, s), 5.06 (1H, s), 6.45 (1H, s), 7.36 (2H, m), 7.49 (2H, m), 7.63 (2H, m).

Example 204

{1-[(5-Chloro-2-trifluoromethyl)benzyl]-1,2,3,4-tetrahydro-pyrido[2,3-b]pyrazin-7-yl}piperidin-1-yl-methanone

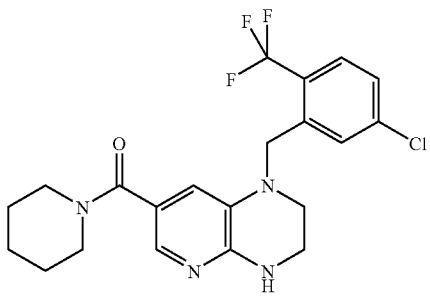

4-{1-[5-Chloro-2-(trifluoromethyl)benzyl]-1,2,3,4-tetrahydropyrido[2,3-b]pyrazin-7-yl}benzoic acid (89 mg) was reacted with piperidine as in General Procedure 8 to give the title compound as an orange solid (64% yield). m.p.=216° C., LCMS: m/z=515.27 (M+H$^+$), $^1$H-NMR (CDCl$_3$, 400 MHz) δ 1.61 (6H, m), 2.88 (1H, s), 2.95 (1H, s), 3.38 (2H, s), 3.49 (2H, m), 3.69 (2H, m), 4.62 (2H, s), 5.26 (1H, s), 6.60 (1H, s), 7.37 (5H, m), 7.51 (1H, s), 7.64 (1H, d, J=8.3 Hz), 7.75 (1H, d, J=1.5 Hz).

Example 205

{1-[(5-Chloro-2-trifluoromethyl)benzyl]-1,2,3,4-tetrahydropyrido[2,3-b]pyrazin-7-yl}-(4-methoxy-piperidin-1-yl)methanone

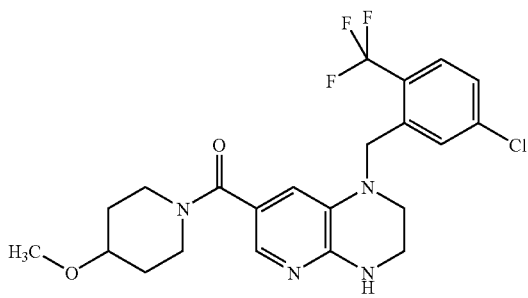

4-{1-[5-Chloro-2-(trifluoromethyl)benzyl]-1,2,3,4-tetrahydropyrido[2,3-b]pyrazin-7-yl}benzoic acid (80 mg) was reacted with 4-methoxypiperidine HCl as in General Procedure 8 to give the title compound as an orange solid (58% yield). LCMS: m/z=545.26 (M+H$^+$), $^1$H-NMR (CDCl$_3$, 400 MHz) δ 1.73 (4H, m), 2.88 (1H, s), 2.95 (1H, s), 3.36 (3H, s), 3.47 (4H, m), 3.68 (3H, m), 4.62 (2H, s), 5.35 (1H, bs), 6.59 (1H, d, J=1.3 Hz), 7.38 (5H, m), 7.51 (1H, s), 7.64 (1H, d, J=8.3 Hz), 7.75 (1H, s).

Example 206

[1-(2,5-Dichlorobenzyl)-1,2,3,4-tetrahydropyrido[2,3-b]pyrazin-7-yl]-(4-phenylpiperazin-1-yl)-methanone

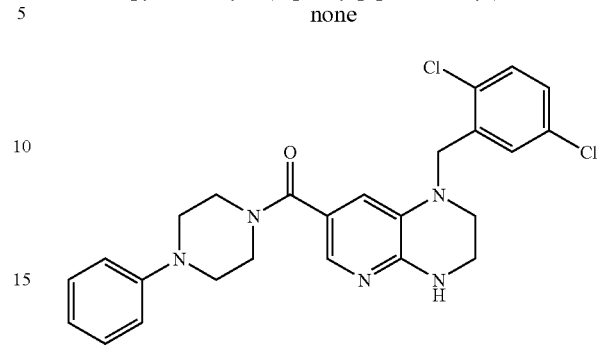

[1-(2,5-Dichlorobenzyl)-1,2,3,4-tetrahydropyrido[2,3-b]pyrazin-7-yl]benzoic acid was reacted with 1-phenylpiperazine as in General Procedure 10 to give the title compound. LCMS: m/z=481.97 (M+H$^+$); retention time=1.12 minutes.

Example 207

[1-(2,5-Dichlorobenzyl)-1,2,3,4-tetrahydropyrido[2,3-b]pyrazin-7-yl]-(4-pyrimidin-2-yl-piperazin-1-yl)-methanone

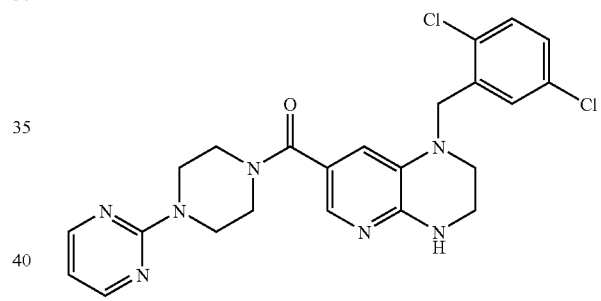

[1-(2,5-Dichlorobenzyl)-1,2,3,4-tetrahydropyrido[2,3-b]pyrazin-7-yl]benzoic acid was reacted with 1-(2-pyrimidyl)piperazine as in General Procedure 10 to give the title compound. LCMS: m/z=483.93 (M+H$^+$); retention time=0.99 minutes.

Example 208

[4-(4-Chlorophenyl)-4-hydroxypiperidin-1-yl]-[1-(2,5-dichlorobenzyl)-1,2,3,4-tetrahydropyrido[2,3-b]pyrazin-7-yl]methanone

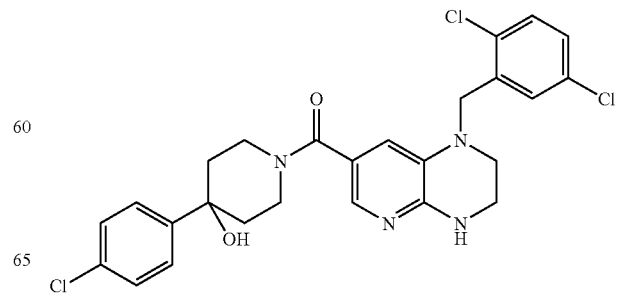

[1-(2,5-Dichlorobenzyl)-1,2,3,4-tetrahydropyrido[2,3-b]pyrazin-7-yl]benzoic acid was reacted with 4-(4-chlorophenyl)-4-hydroxypiperidine as in General Procedure 10 to give the title compound. LCMS: m/z=530.89 (M+H$^+$); retention time=1.1 minutes.

Example 209

1-{1-[1-(2,5-Dichlorobenzyl)-1,2,3,4-tetrahydropyrido[2,3-b]pyrazine-7-carbonyl]piperidin-4-yl}-1,3-dihydrobenzoimidazol-2-one

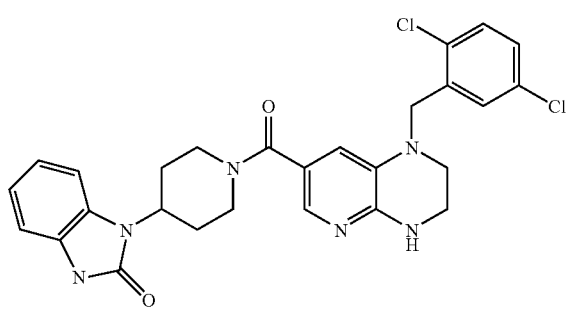

[1-(2,5-Dichlorobenzyl)-1,2,3,4-tetrahydropyrido[2,3-b]pyrazin-7-yl]benzoic acid was reacted with 1,3-dihydrobenzoimidazol-2-one as in General Procedure 10 to give the title compound. LCMS: m/z=536.96 (M+H$^+$); retention time=0.97 minutes.

Example 210

[1-(2,5-Dichlorobenzyl)-1,2,3,4-tetrahydropyrido[2,3-b]pyrazin-7-yl]-[4-(2-methoxyphenyl)piperazin-1-yl]methanone

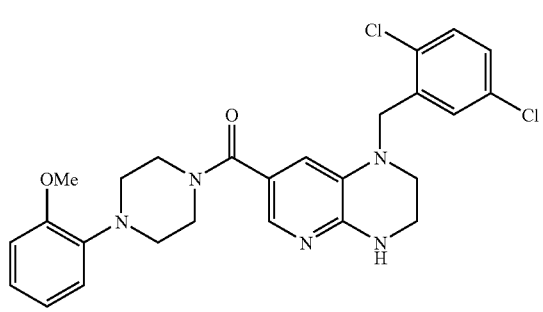

[1-(2,5-Dichlorobenzyl)-1,2,3,4-tetrahydropyrido[2,3-b]pyrazin-7-yl]benzoic acid was reacted with 1-(2-methoxyphenyl)piperazine as in General Procedure 10 to give the title compound. LCMS: m/z=511.94 (M+H$^+$); retention time=1.09 minutes.

Example 211

[1-(2,5-Dichlorobenzyl)-1,2,3,4-tetrahydropyrido[2,3-b]pyrazin-7-yl]-{4-[3-(trifluoromethyl)phenyl]piperazin-1-yl}methanone

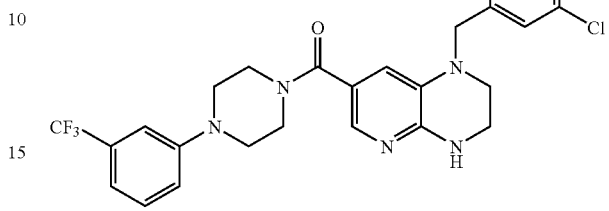

[1-(2,5-Dichlorobenzyl)-1,2,3,4-tetrahydropyrido[2,3-b]pyrazin-7-yl]benzoic acid was reacted with 1-[3-(trifluoromethyl)phenyl]piperazine as in General Procedure 10 to give the title compound. LCMS: m/z=549.92 (M+H$^+$); retention time=1.24 minutes.

Example 212

[1-(2,5-Dichlorobenzyl)-1,2,3,4-tetrahydropyrido[2,3-b]pyrazin-7-yl]-(4-phenylpiperidin-1-yl)methanone

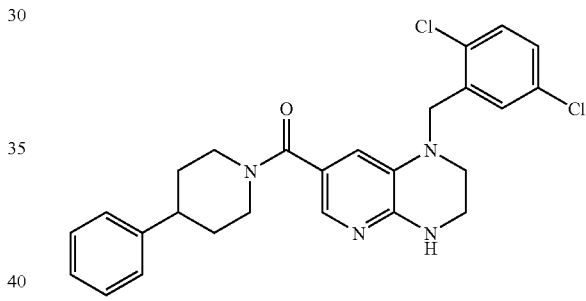

[1-(2,5-Dichlorobenzyl)-1,2,3,4-tetrahydropyrido[2,3-b]pyrazin-7-yl]benzoic acid was reacted with 4-phenylpiperidine as in General Procedure 10 to give the title compound. LCMS: m/z=480.99 (M+H$^+$); retention time=1.17 minutes.

Example 213

[1-(2,5-Dichlorobenzyl)-1,2,3,4-tetrahydropyrido[2,3-b]pyrazin-7-yl]-[4-(3,4-dichlorophenyl)-piperazin-1-yl]methanone

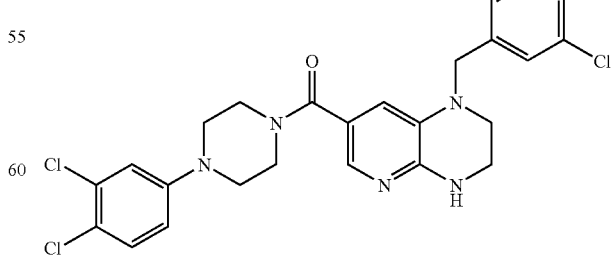

[1-(2,5-Dichlorobenzyl)-1,2,3,4-tetrahydropyrido[2,3-b]pyrazin-7-yl]benzoic acid was reacted with 1-(3,4-dichlorophenyl)piperazine as in General Procedure 10 to give the title compound. LCMS: m/z=549.85 (M+H⁺); retention time=1.31 minutes.

Example 214

(4-Benzhydrylpiperazin-1-yl)-[1-(2,5-dichlorobenzyl)-1,2,3,4-tetrahydropyrido[2,3-b]pyrazin-7-yl]methanone

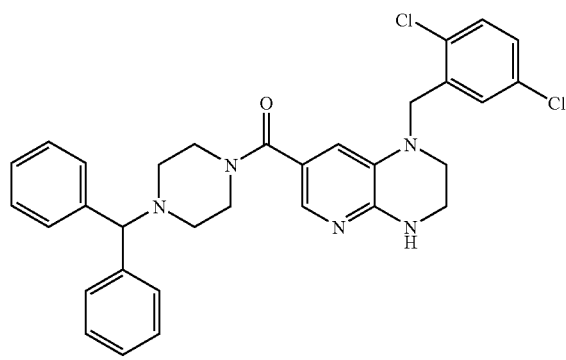

[1-(2,5-Dichlorobenzyl)-1,2,3,4-tetrahydropyrido[2,3-b]pyrazin-7-yl]benzoic acid was reacted with 1-benzhydrylpiperazine as in General Procedure 10 to give the title compound. LCMS: m/z=571.95 (M+H⁺); retention time=1.2 minutes.

Example 215

(4-Benzylpiperidin-1-yl)-[1-(2,5-dichlorobenzyl)-1,2,3,4-tetrahydropyrido[2,3-b]pyrazin-7-yl]methanone

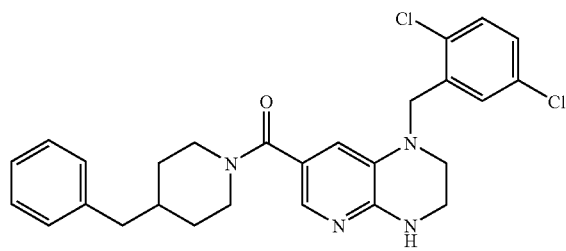

[1-(2,5-Dichlorobenzyl)-1,2,3,4-tetrahydropyrido[2,3-b]pyrazin-7-yl]benzoic acid was reacted with 1-benzylpiperidine as in General Procedure 10 to give the title compound. LCMS: m/z=495.02 (M+H⁺); retention time=1.25 minutes.

Example 216

8-[1-(2,5-Dichlorobenzyl)-1,2,3,4-tetrahydropyrido[2,3-b]pyrazine-7-carbonyl]-1-phenyl-1,3,8-triaza-spiro[4.5]decan-4-one

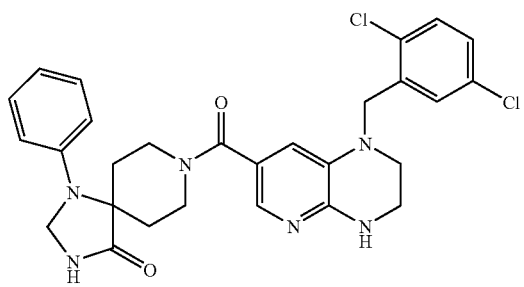

[1-(2,5-Dichlorobenzyl)-1,2,3,4-tetrahydropyrido[2,3-b]pyrazin-7-yl]benzoic acid was reacted with 1-phenyl-1,3,8-triaza-spiro[4.5]decan-4-one as in General Procedure 10 to give the title compound. LCMS: m/z=550.97 (M+H⁺); retention time=1.02 minutes.

Example 217

[1-(2,5-Dichlorobenzyl)-1,2,3,4-tetrahydropyrido[2,3-b]pyrazin-7-yl]-(4-thieno[3,2-d]pyrimidin-4-yl-piperazin-1-yl)methanone

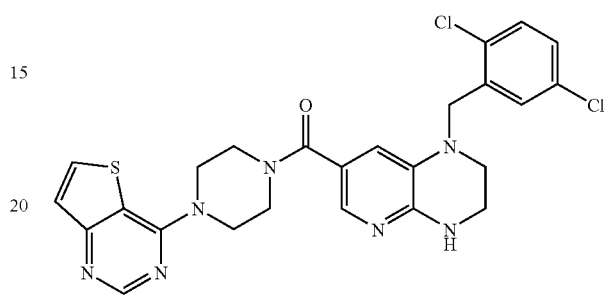

[1-(2,5-Dichlorobenzyl)-1,2,3,4-tetrahydropyrido[2,3-b]pyrazin-7-yl]benzoic acid was reacted with 1-(thieno[3,2-d]pyrimidin-4-yl)piperazine as in General Procedure 10 to give the title compound. LCMS: m/z=539.89 (M+H⁺); retention time=0.81 minutes.

Example 218

[1-(2,5-Dichlorobenzyl)-1,2,3,4-tetrahydropyrido[2,3-b]pyrazin-7-yl]-[4-(4-methoxybenzyl)piperazin-1-yl]methanone

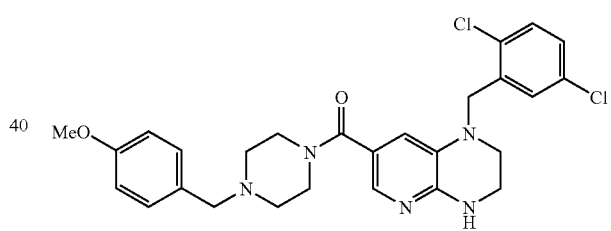

[1-(2,5-Dichlorobenzyl)-1,2,3,4-tetrahydropyrido[2,3-b]pyrazin-7-yl]benzoic acid was reacted with 1-(4-methoxybenzyl)piperazine as in General Procedure 10 to give the title compound. LCMS: m/z=525.95 (M+H⁺); retention time=0.81 minutes.

Example 219

(4-Benzoylpiperazin-1-yl)-[1-(2,5-dichlorobenzyl)-1,2,3,4-tetrahydropyrido[2,3-b]pyrazin-7-yl]methanone

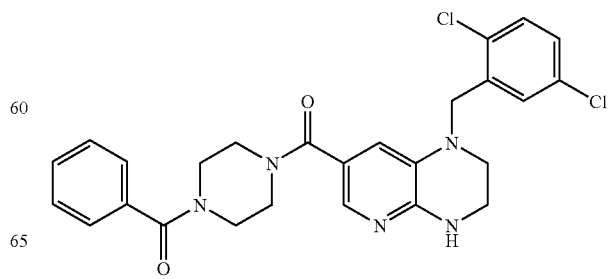

[1-(2,5-Dichlorobenzyl)-1,2,3,4-tetrahydropyrido[2,3-b]pyrazin-7-yl]benzoic acid was reacted with 1-benzoylpiperazine as in General Procedure 10 to give the title compound. LCMS: m/z=509.83 (M+H⁺); retention time=0.97 minutes.

Example 220

[1-(2,5-Dichlorobenzyl)-1,2,3,4-tetrahydropyrido[2,3-b]pyrazin-7-yl]-(4-furo[3,2-c]pyridin-4-yl-piperazin-1-yl)methanone

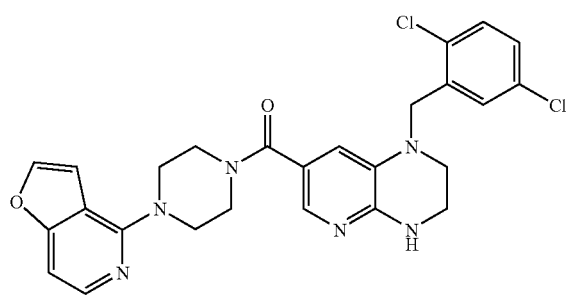

[1-(2,5-Dichlorobenzyl)-1,2,3,4-tetrahydropyrido[2,3-b]pyrazin-7-yl]benzoic acid was reacted with 1-(fiuro[3,2-c]pyridin-4-yl)piperazine as in General Procedure 10 to give the title compound. LCMS: m/z=522.95 (M+H⁺); retention time=0.82 minutes.

Example 221

[1-(2,5-Dichlorobenzyl)-1,2,3,4-tetrahydropyrido[2,3-b]pyrazin-7-yl]-[4-(6-fluorobenzo[d]isoxazol-3-yl)piperidin-1-yl]methanone

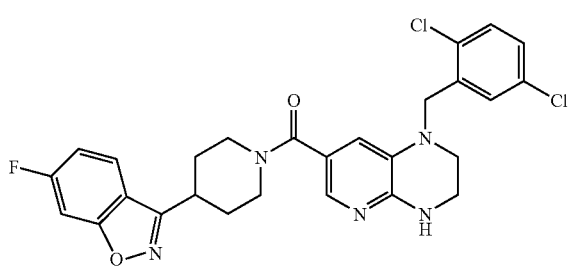

[1-(2,5-Dichlorobenzyl)-1,2,3,4-tetrahydropyrido[2,3-b]pyrazin-7-yl]benzoic acid was reacted with 4-(6-fluorobenzo[d]isoxazol-3-yl)piperidine as in General Procedure 10 to give the title compound. LCMS: fi/z=539.95 (M+H⁺); retention time=1.15 minutes.

Example 222

[4-(3-Chlorophenyl)piperazin-1-yl]-[1-(2,5-dichlorobenzyl)-1,2,3,4-tetrahydropyrido[2,3-b]pyrazin-7-yl]methanone

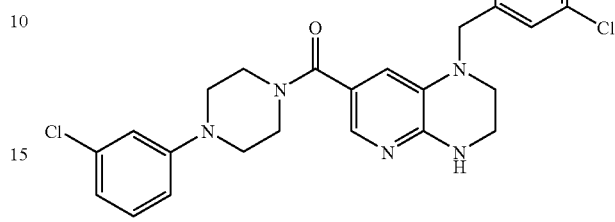

[1-(2,5-Dichlorobenzyl)-1,2,3,4-tetrahydropyrido[2,3-b]pyrazin-7-yl]benzoic acid was reacted with 1-(3-chlorophenyl)piperazine as in General Procedure 10 to give the title compound. LCMS: m/z=515.91 (M+H⁺); retention time=1.21 minutes.

Example 223

1-(2,5-Dichlorobenzyl)-1,2,3,4-tetrahydropyrido[2,3-b]pyrazine-7-carboxylic acid (2-pyridin-2-yl-ethyl)amide

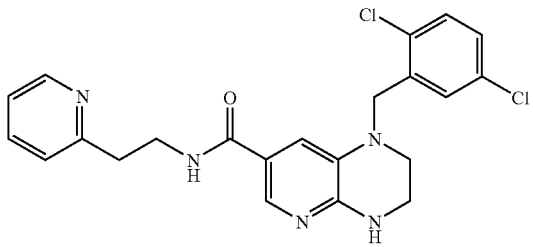

[1-(2,5-Dichlorobenzyl)-1,2,3,4-tetrahydropyrido[2,3-b]pyrazin-7-yl]benzoic acid was reacted with 2-(2-pyridyl)ethylamine as in General Procedure 10 to give the title compound. LCMS: m/z=441.87 (M+H⁺); retention time=0.77 minutes.

Example 224

4-{[1-(2,5-Dichlorobenzyl)-1,2,3,4-tetrahydropyrido[2,3-b]pyrazine-7-carbonyl]amino}piperidine-1-carboxylic acid ethyl ester

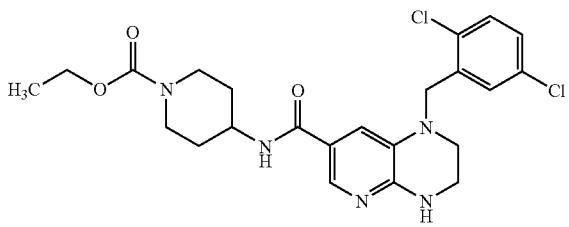

[1-(2,5-Dichlorobenzyl)-1,2,3,4-tetrahydropyrido[2,3-b]pyrazin-7-yl]benzoic acid was reacted with ethyl 4-amino-1- piperidinecarboxylate as in General Procedure 10 to give the title compound. LCMS: m/z=491.94 (M+H$^+$); retention time=1.02 minutes.

Example 225

1-(2,5-Dichlorobenzyl)-1,2,3,4-tetrahydropyrido[2,3-b]pyrazine-7-carboxylic acid (1-benzyl-piperidin-4-yl)amide

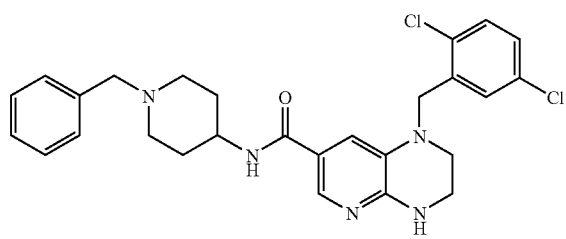

[1-(2,5-Dichlorobenzyl)-1,2,3,4-tetrahydropyrido[2,3-b]pyrazin-7-yl]benzoic acid was reacted with 4-amino-1-benzylpiperidine as in General Procedure 10 to give the title compound. LCMS: m/z=509.99 (M+H$^+$); retention time=0.82 minutes.

Example 226

1-(2,5-Dichlorobenzyl)-1,2,3,4-tetrahydropyrido[2,3-b]pyrazine-7-carboxylic acid (2,2-diphenylethyl)amide

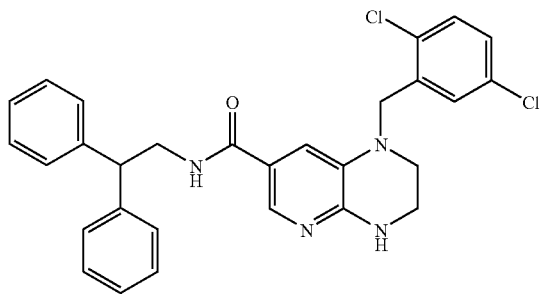

[1-(2,5-Dichlorobenzyl)-1,2,3,4-tetrahydropyrido[2,3-b]pyrazin-7-yl]benzoic acid was reacted with 2,2-diphenylethylamine as in General Procedure 10 to give the title compound. LCMS: m/z=516.96 (M+H$^+$); retention time=1.23 minutes.

Example 227

1-{4-[1-(2,5-Dichlorobenzyl)-1,2,3,4-tetrahydropyrido[2,3-b]pyrazine-7-carbonyl]piperazin-1-yl}ethanone

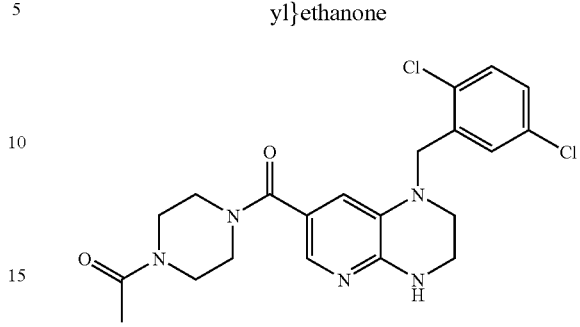

[1-(2,5-Dichlorobenzyl)-1,2,3,4-tetrahydropyrido[2,3-b]pyrazin-7-yl]benzoic acid was reacted with 1-acetylpiperazine as in General Procedure 10 to give the title compound. LCMS: m/z=447.97 (M+H$^+$); retention time=0.84 minutes.

Example 228

1-(2,5-Dichlorobenzyl)-1,2,3,4-tetrahydropyrido[2,3-b]pyrazine-7-carboxylic acid 3-chlorobenzylamide

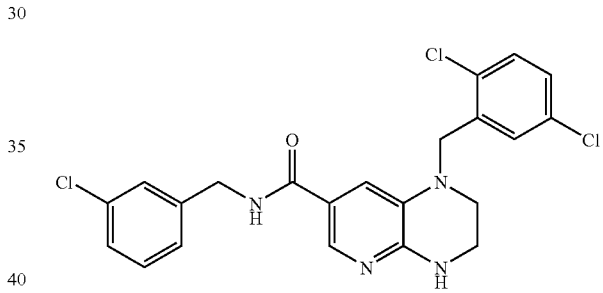

[1-(2,5-Dichlorobenzyl)-1,2,3,4-tetrahydropyrido[2,3-b]pyrazin-7-yl]benzoic acid was reacted with 3-chlorobenzylamine as in General Procedure 10 to give the title compound. LCMS: m/z=460.9 (M+H$^+$); retention time=1.14 minutes.

Example 229

[1-(2,5-Dichlorobenzyl)-1,2,3,4-tetrahydropyrido[2,3-b]pyrazin-7-yl]-[4-(2-pyridin-2-yl-ethyl)piperazin-1-yl]methanone

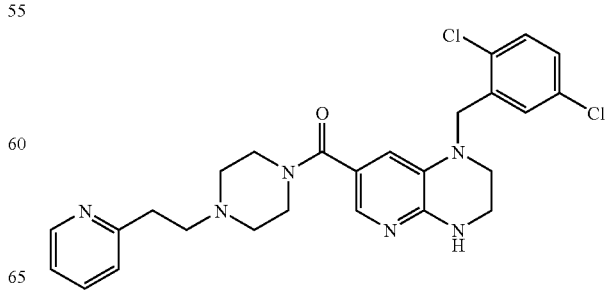

[1-(2,5-Dichlorobenzyl)-1,2,3,4-tetrahydropyrido[2,3-b]pyrazin-7-yl]benzoic acid was reacted with 1-(2-(2-pyridyl)ethyl)piperazine as in General Procedure 10 to give the title compound. LCMS: m/z=510.96 (M+H$^+$); retention time=0.72 minutes.

Example 230

1-(2,5-Dichlorobenzyl)-1,2,3,4-tetrahydropyrido[2,3-b]pyrazine-7-carboxylic acid 4-(trifluoromethoxy)benzylamide

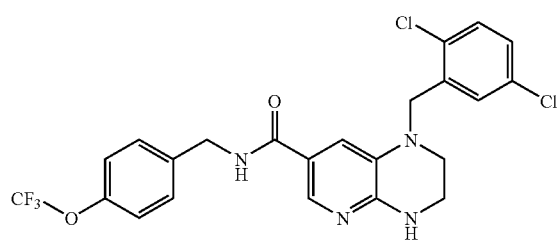

[1-(2,5-Dichlorobenzyl)-1,2,3,4-tetrahydropyrido[2,3-b]pyrazin-7-yl]benzoic acid was reacted with 4-(trifluoromethoxy)benzylamine as in General Procedure 10 to give the title compound. LCMS: m/z=510.89 (M+H$^+$); retention time=1.21 minutes.

Example 231

[1-(2,5-Dichlorobenzyl)-1,2,3,4-tetrahydropyrido[2,3-b]pyrazin-7-yl]-(4-morpholin-4-yl-piperidin-1-yl)methanone

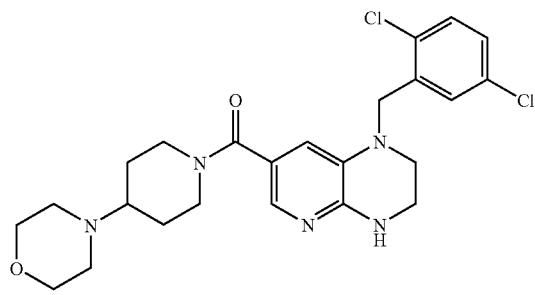

[1-(2,5-Dichlorobenzyl)-1,2,3,4-tetrahydropyrido[2,3-b]pyrazin-7-yl]benzoic acid was reacted with 4-morpholin-4-yl-piperidine as in General Procedure 10 to give the title compound. LCMS: m/z=489.99 (M+H$^+$); retention time=0.68 minutes.

Example 232

1-(2,5-Dichlorobenzyl)-1,2,3,4-tetrahydropyrido[2,3-b]pyrazine-7-carboxylic acid (2-thiophen-2-yl-ethyl)amide

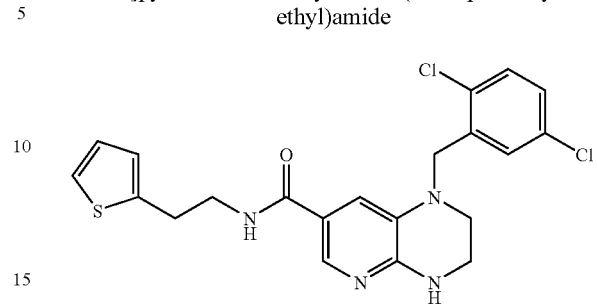

[1-(2,5-Dichlorobenzyl)-1,2,3,4-tetrahydropyrido[2,3-b]pyrazin-7-yl]benzoic acid was reacted with 2-(2-thiophenyl)ethylamine as in General Procedure 10 to give the title compound. LCMS: m/z=446.92 (M+H$^+$); retention time=1.08 minutes.

Example 233

1-(2,5-Dichlorobenzyl)-1,2,3,4-tetrahydropyrido[2,3-b]pyrazine-7-carboxylic acid benzhydrylamide

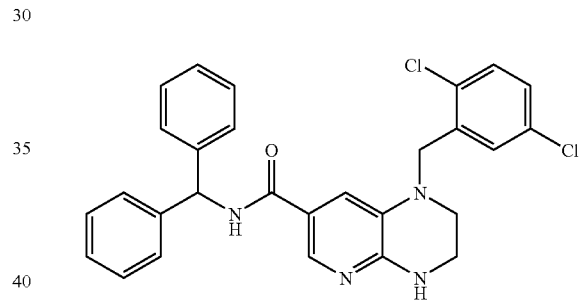

[1-(2,5-Dichlorobenzyl)-1,2,3,4-tetrahydropyrido[2,3-b]pyrazin-7-yl]benzoic acid was reacted with benzhydrylamine as in General Procedure 10 to give the title compound. LCMS: m/z=502.95 (M+H$^+$); retention time=1.23 minutes.

Example 234

1-(2,5-Dichlorobenzyl)-1,2,3,4-tetrahydropyrido[2,3-b]pyrazine-7-carboxylic acid (pyridin-4-ylmethyl)amide

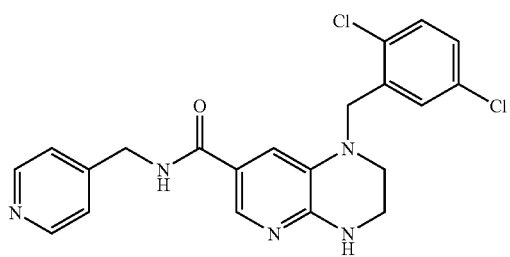

[1-(2,5-Dichlorobenzyl)-1,2,3,4-tetrahydropyrido[2,3-b]pyrazin-7-yl]benzoic acid was reacted with (4-pyridyl)methylamine as in General Procedure 10 to give the title compound. LCMS: m/z=427.98 (M+H$^+$); retention time=0.73 minutes.

Example 235

1-(2,5-Dichlorobenzyl)-1,2,3,4-tetrahydropyrido[2,3-b]pyrazine-7-carboxylic acid (pyridin-3-ylmethyl)amide

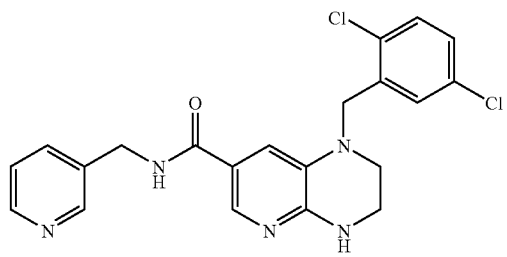

[1-(2,5-Dichlorobenzyl)-1,2,3,4-tetrahydropyrido[2,3-b]pyrazin-7-yl]benzoic acid was reacted with (3-pyridyl)methylamine as in General Procedure 10 to give the title compound. LCMS: m/z=427.98 (M+H$^+$); retention time=0.76 minutes.

Example 236

2-{4-[1-(2,5-Dichlorobenzyl)-1,2,3,4-tetrahydropyrido[2,3-b]pyrazine-7-carbonyl]piperazin-1-yl}-N-isopropylacetamide

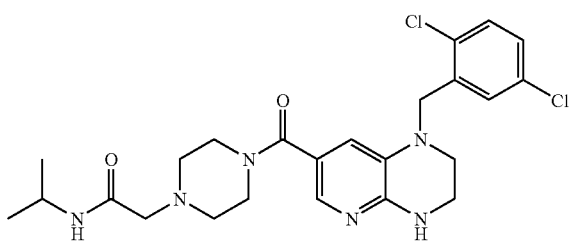

[1-(2,5-Dichlorobenzyl)-1,2,3,4-tetrahydropyrido[2,3-b]pyrazin-7-yl]benzoic acid was reacted with N-isopropyl-1-piperazineacetamide as in General Procedure 10 to give the title compound. LCMS: m/z=504.97 (M+H$^+$); retention time=0.78 minutes.

Example 237

[1-(2,5-Dichlorobenzyl)-1,2,3,4-tetrahydropyrido[2,3-b]pyrazin-7-yl]-[4-(2-methylquinolin-4-yl)piperazin-1-yl]methanone

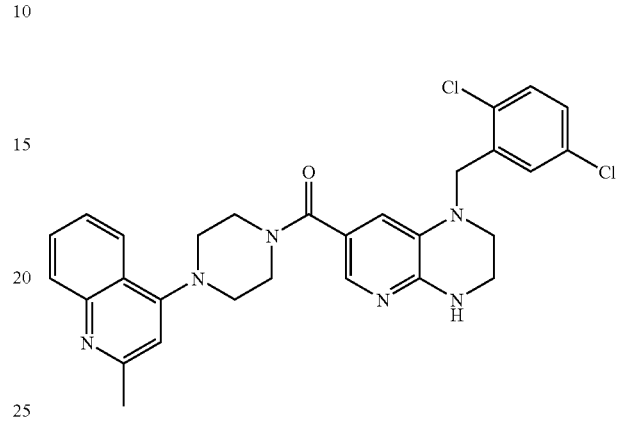

[1-(2,5-Dichlorobenzyl)-1,2,3,4-tetrahydropyrido[2,3-b]pyrazin-7-yl]benzoic acid was reacted with 1-(2-methylquinolin-4-yl)piperazine as in General Procedure 10 to give the title compound. LCMS: m/z=546.97 (M+H$^+$); retention time=0.8 minutes.

Example 238

[1-(2,5-Dichlorobenzyl)-1,2,3,4-tetrahydropyrido[2,3-b]pyrazin-7-yl]-((S)-2-pyrrolidin-1-ylmethyl-pyrrolidin-1-yl)methanone

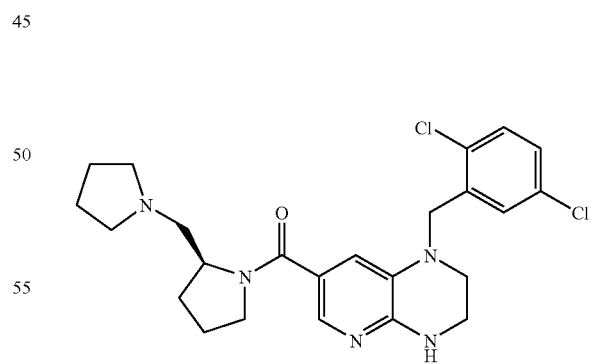

[1-(2,5-Dichlorobenzyl)-1,2,3,4-tetrahydropyrido[2,3-b]pyrazin-7-yl]benzoic acid was reacted with (S)-1-(2-pyrrolidinylmethyl)pyrrolidine as in General Procedure 10 to give the title compound. LCMS: m/z=474.04 (M+H$^+$); retention time=0.76 minutes.

Example 239

1-(2,5-Dichlorobenzyl)-1,2,3,4-tetrahydropyrido[2,3-b]pyrazine-7-carboxylic acid 3,5-bis-(trifluoromethyl)benzylamide

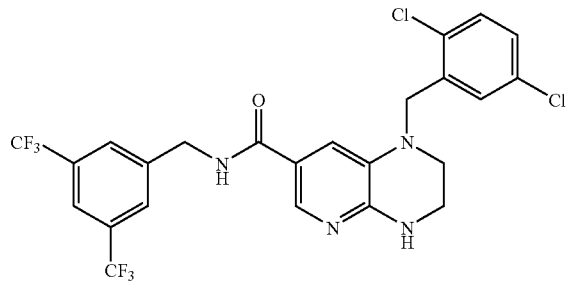

[1-(2,5-Dichlorobenzyl)-1,2,3,4-tetrahydropyrido[2,3-b]pyrazin-7-yl]benzoic acid was reacted with 3,5-bis(trifluoromethyl)benzylamine as in General Procedure 10 to give the title compound. LCMS: m/z=562.86 (M+H+); retention time=1.32 minutes.

Example 240

1-(2,5-Dichlorobenzyl)-1,2,3,4-tetrahydropyrido[2,3-b]pyrazine-7-carboxylic acid [2-(4-sulfamoylphenyl)ethyl]amide

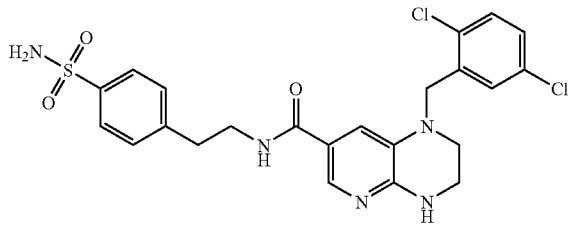

[1-(2,5-Dichlorobenzyl)-1,2,3,4-tetrahydropyrido[2,3-b]pyrazin-7-yl]benzoic acid was reacted with 2-(4-sulfamoylphenyl)ethylamine as in General Procedure 10 to give the title compound. LCMS: m/z=519.88 (M+H+); retention time=0.94 minutes.

Example 241

[1-(2,5-Dichlorobenzyl)-1,2,3,4-tetrahydropyrido[2,3-b]pyrazin-7-yl]-(2,3,5,6-tetrahydro-[1,2']bipyrazinyl-4-yl)methanone

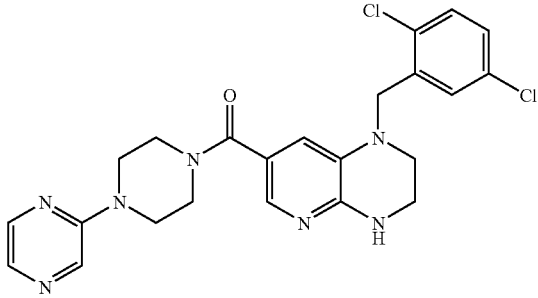

[1-(2,5-Dichlorobenzyl)-1,2,3,4-tetrahydropyrido[2,3-b]pyrazin-7-yl]benzoic acid was reacted with 2,3,5,6-tetrahydro-[1,2']bipyrazine as in General Procedure 10 to give the title compound. LCMS: m/z=483.94 (M+H+); retention time=0.94 minutes.

Example 242

1-(2,5-Dichlorobenzyl)-1,2,3,4-tetrahydropyrido[2,3-b]pyrazine-7-carboxylic acid (2-phenylthiazol-4-yl-methyl)amide

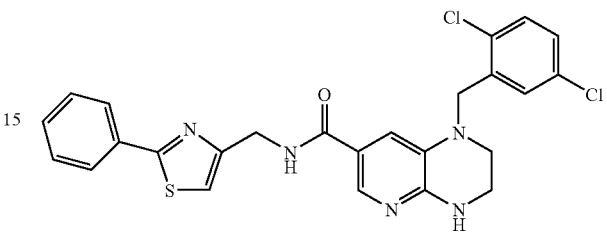

[1-(2,5-Dichlorobenzyl)-1,2,3,4-tetrahydropyrido[2,3-b]pyrazin-7-yl]benzoic acid was reacted with 4-(aminomethyl)-2-phenylthiazole as in General Procedure 10 to give the title compound. LCMS: m/z=509.91 (M+H+); retention time=1.17 minutes.

Example 243

[1-(2,5-Dichlorobenzyl)-1,2,3,4-tetrahydropyrido[2,3-b]pyrazin-7-yl]morpholin-4-yl-methanone

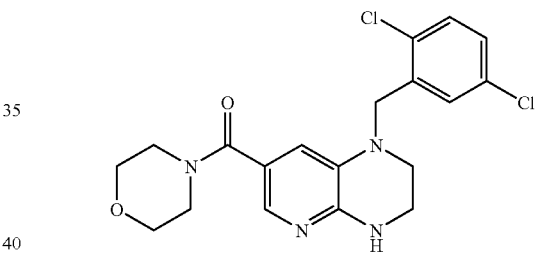

[1-(2,5-Dichlorobenzyl)-1,2,3,4-tetrahydropyrido[2,3-b]pyrazin-7-yl]benzoic acid was reacted with morpholine as in General Procedure 10 to give the title compound. LCMS: m/z=407.01 (M+H+); retention time=0.9 minutes.

Example 244

1-(2,5-Dichlorobenzyl)-1,2,3,4-tetrahydropyrido[2,3-b]pyrazine-7-carboxylic acid (naphthalen-1-yl-methyl)amide

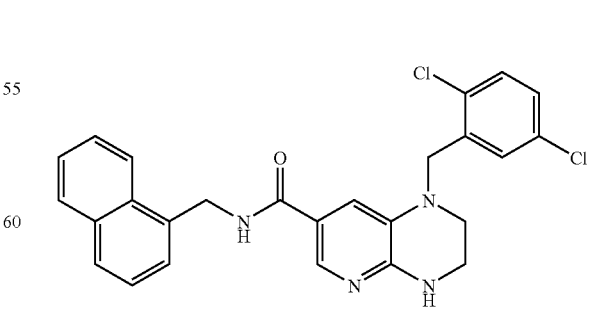

[1-(2,5-Dichlorobenzyl)-1,2,3,4-tetrahydropyrido[2,3-b]pyrazin-7-yl]benzoic acid was reacted with 1-(aminomethyl)

naphthalene as in General Procedure 10 to give the title compound. LCMS: m/z=476.96 (M+H$^+$); retention time=1.17 minutes.

Example 245

1-(2,5-Dichlorobenzyl)-1,2,3,4-tetrahydropyrido[2,3-b]pyrazine-7-carboxylic acid indan-1-ylamide

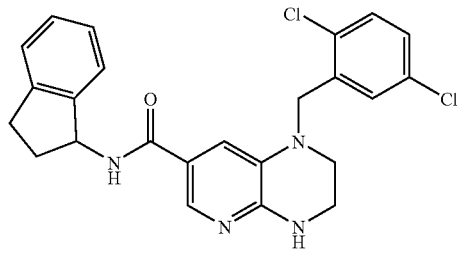

[1-(2,5-Dichlorobenzyl)-1,2,3,4-tetrahydropyrido[2,3-b]pyrazin-7-yl]benzoic acid was reacted with 1-aminoindan as in General Procedure 10 to give the title compound. LCMS: m/z=452.99 (M+H$^+$); retention time=1.14 minutes.

Example 246

1-(2,5-Dichlorobenzyl)-1,2,3,4-tetrahydropyrido[2,3-b]pyrazine-7-carboxylic acid benzylamide

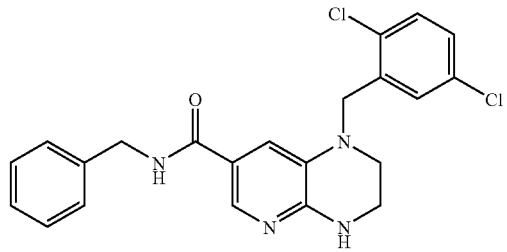

[1-(2,5-Dichlorobenzyl)-1,2,3,4-tetrahydropyrido[2,3-b]pyrazin-7-yl]benzoic acid was reacted with benzylamine as in General Procedure 10 to give the title compound. LCMS: m/z=427.01 (M+H$^+$); retention time=1.07 minutes.

Example 247

[1-(2,5-Dichlorobenzyl)-1,2,3,4-tetrahydropyrido[2,3-b]pyrazin-7-yl]-[4-(4-methoxyphenyl)piperazin-1-yl]methanone

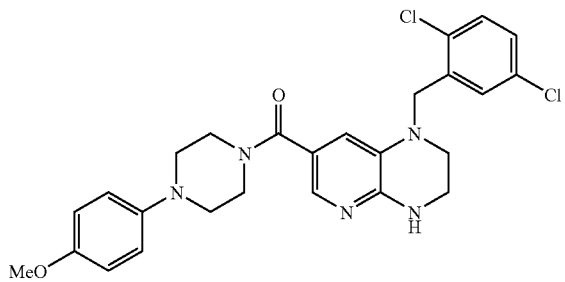

[1-(2,5-Dichlorobenzyl)-1,2,3,4-tetrahydropyrido[2,3-b]pyrazin-7-yl]benzoic acid was reacted with 1-(4-methoxyphenyl)piperazine as in General Procedure 10 to give the title compound. LCMS: m/z=511.94 (M+H$^+$); retention time=1.07 minutes.

Example 248

1-(2,5-Dichlorobenzyl)-1,2,3,4-tetrahydropyrido[2,3-b]pyrazine-7-carboxylic acid cyclohexylamide

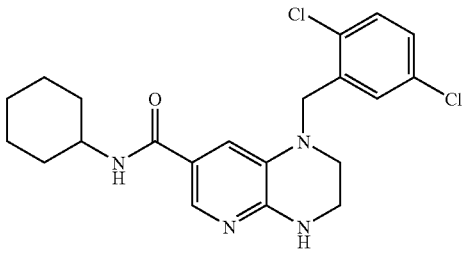

[1-(2,5-Dichlorobenzyl)-1,2,3,4-tetrahydropyrido[2,3-b]pyrazin-7-yl]benzoic acid was reacted with cyclohexylamine as in General Procedure 10 to give the title compound. LCMS: m/z=419.07 (M+H$^+$); retention time=1.11 minutes.

Example 249

1-(2,5-Dichlorobenzyl)-1,2,3,4-tetrahydropyrido[2,3-b]pyrazine-7-carboxylic acid (biphenyl-4-ylmethyl)amide

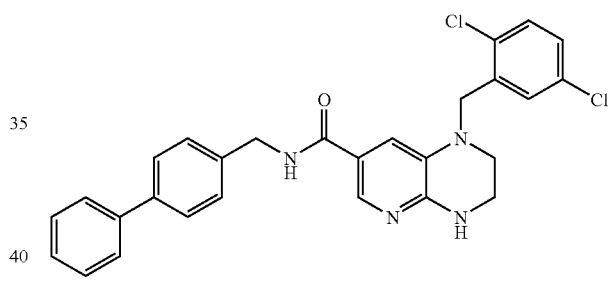

[1-(2,5-Dichlorobenzyl)-1,2,3,4-tetrahydropyrido[2,3-b]pyrazin-7-yl]benzoic acid was reacted with 4-phenylbenzylamine as in General Procedure 10 to give the title compound. LCMS: m/z=502.95 (M+H$^+$); retention time=1.25 minutes.

Example 250

[4-(4-Chlorophenyl)piperazin-1-yl]-[1-(2,5-dichlorobenzyl)-1,2,3,4-tetrahydropyrido[2,3-b]pyrazin-7-yl]methanone

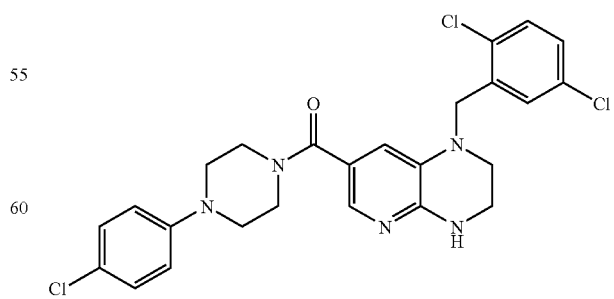

[1-(2,5-Dichlorobenzyl)-1,2,3,4-tetrahydropyrido[2,3-b]pyrazin-7-yl]benzoic acid was reacted with 1-(4-chlorophenyl)piperazine as in General Procedure 10 to give the title compound. LCMS: m/z=515.91 (M+H⁺); retention time=1.21 minutes.

Example 251

1-(2,5-Dichlorobenzyl)-1,2,3,4-tetrahydropyrido[2,3-b]pyrazine-7-carboxylic acid (2-phenoxyethyl)amide

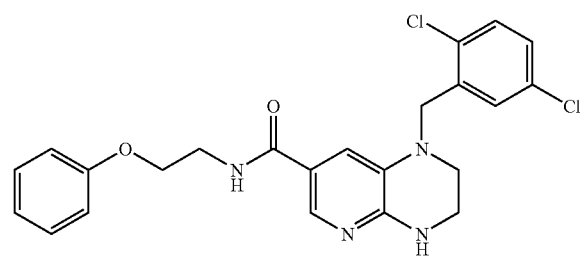

[1-(2,5-Dichlorobenzyl)-1,2,3,4-tetrahydropyrido[2,3-b]pyrazin-7-yl]benzoic acid was reacted with 2-phenoxyethylamine as in General Procedure 10 to give the title compound. LCMS: m/z=456.96 (M+H⁺); retention time=1.11 minutes.

Example 252

[1-(2,5-Dichlorobenzyl)-1,2,3,4-tetrahydropyrido[2,3-b]pyrazin-7-yl]-[4-(tetrahydrofuran-2-carbonyl)piperazin-1-yl]methanone

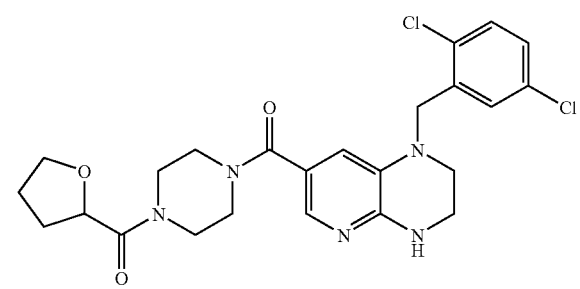

[1-(2,5-Dichlorobenzyl)-1,2,3,4-tetrahydropyrido[2,3-b]pyrazin-7-yl]benzoic acid was reacted with 4-(2-tetrahydrofuranylcarbonyl)piperazine as in General Procedure 10 to give the title compound. LCMS: m/z=503.96 (M+H⁺); retention time=0.88 minutes.

Example 253

1-(2,5-Dichlorobenzyl)-1,2,3,4-tetrahydropyrido[2,3-b]pyrazine-7-carboxylic acid phenethyl-amide

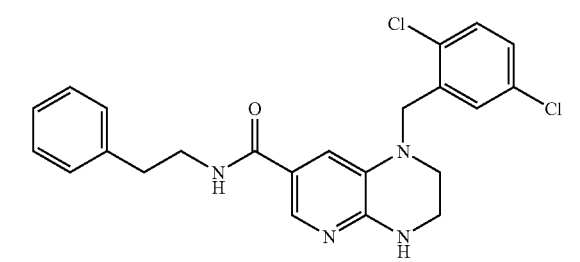

[1-(2,5-Dichlorobenzyl)-1,2,3,4-tetrahydropyrido[2,3-b]pyrazin-7-yl]benzoic acid was reacted with phenethylamine as in General Procedure 10 to give the title compound. LCMS: ln/z=441.01 (M+H⁺); retention time=1.111 minutes.

Example 254

1-(2,5-Dichlorobenzyl)-1,2,3,4-tetrahydropyrido[2,3-b]pyrazine-7-carboxylic acid (tetrahydrofuran-2-yl-methyl)amide

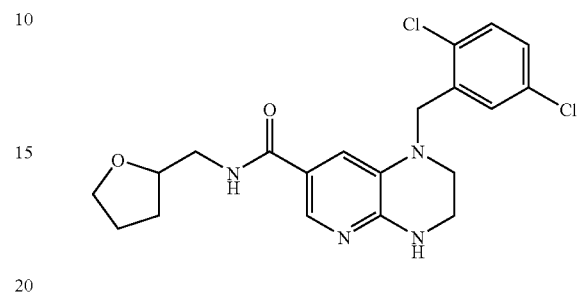

[1-(2,5-Dichlorobenzyl)-1,2,3,4-tetrahydropyrido[2,3-b]pyrazin-7-yl]benzoic acid was reacted with 2-tetrahydrofuranylmethylamine as in General Procedure 10 to give the title compound. LCMS: m/z=421.02 (M+H⁺); retention time=0.95 minutes.

Example 255

[4-(4-Chlorobenzyl)piperazin-1-yl]-[1-(2,5-dichlorobenzyl)-1,2,3,4-tetrahydropyrido[2,3-b]pyrazin-7-yl]methanone

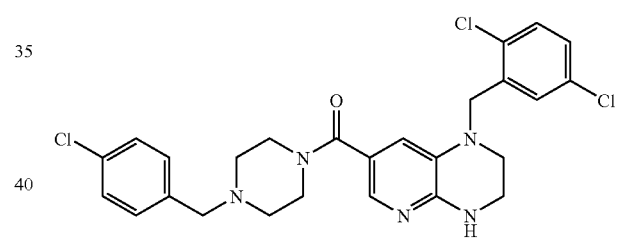

[1-(2,5-Dichlorobenzyl)-1,2,3,4-tetrahydropyrido[2,3-b]pyrazin-7-yl]benzoic acid was reacted with 1-(4-chlorobenzyl)piperazine as in General Procedure 10 to give the title compound. LCMS: m/z=529.92 (M+H⁺); retention time=0.9 minutes.

Example 256

1-(2,5-Dichlorobenzyl)-1,2,3,4-tetrahydropyrido[2,3-b]pyrazine-7-carboxylic acid 2-chloro-benzylamide

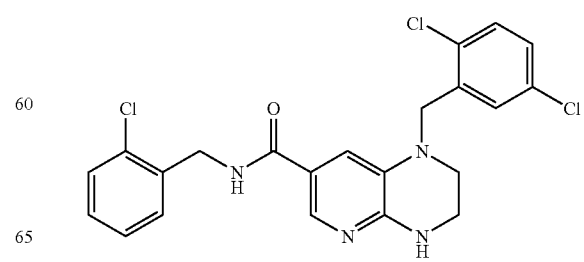

[1-(2,5-Dichlorobenzyl)-1,2,3,4-tetrahydropyrido[2,3-b]pyrazin-7-yl]benzoic acid was reacted with 2-chlorobenzylamine as in General Procedure 10 to give the title compound. LCMS: m/z=460.93 (M+H$^+$); retention time=1.14 minutes.

Example 257

[1-(2,5-Dichlorobenzyl)-1,2,3,4-tetrahydropyrido[2,3-b]pyrazin-7-yl]-[4-(2-(trifluoromethyl)phenyl)piperazin-1-yl]methanone

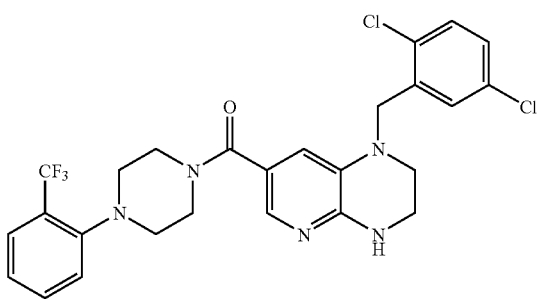

[1-(2,5-Dichlorobenzyl)-1,2,3,4-tetrahydropyrido[2,3-b]pyrazin-7-yl]benzoic acid was reacted with 1-(2-(trifluoromethyl)phenyl)piperazine as in General Procedure 10 to give the title compound. LCMS: m/z=549.92 (M+H$^+$); retention time=1.24 minutes.

Example 258

1-(2,5-Dichlorobenzyl)-1,2,3,4-tetrahydropyrido[2,3-b]pyrazine-7-carboxylic acid 4-methoxybenzylamide

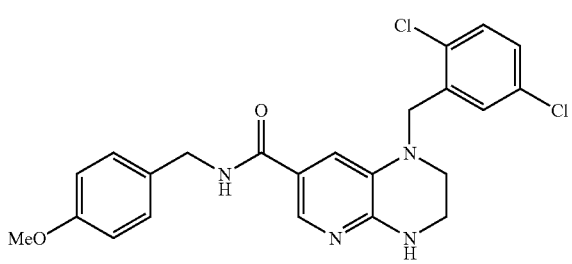

[1-(2,5-Dichlorobenzyl)-1,2,3,4-tetrahydropyrido[2,3-b]pyrazin-7-yl]benzoic acid was reacted with 4-methoxybenzylamine as in General Procedure 10 to give the title compound. LCMS: m/z=456.96 (M+H$^+$); retention time=1.08 minutes.

Example 259

1-(2,5-Dichlorobenzyl)-1,2,3,4-tetrahydropyrido[2,3-b]pyrazine-7-carboxylic acid indan-2-ylamide

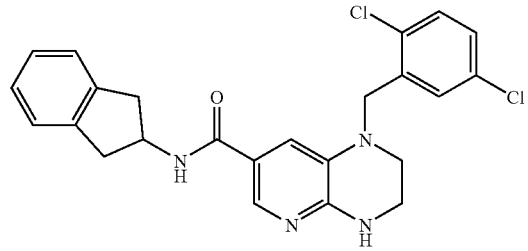

[1-(2,5-Dichlorobenzyl)-1,2,3,4-tetrahydropyrido[2,3-b]pyrazin-7-yl]benzoic acid was reacted with 2-aminoindan as in General Procedure 10 to give the title compound. LCMS: m/z=452.99 (M+H$^+$); retention time=1.13 minutes.

Example 260

[1-(2,5-Dichlorobenzyl)-1,2,3,4-tetrahydropyrido[2,3-b]pyrazin-7-yl]-(4-phenethyl-piperazin-1-yl)methanone

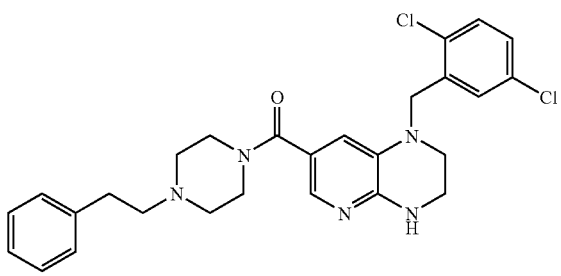

[1-(2,5-Dichlorobenzyl)-1,2,3,4-tetrahydropyrido[2,3-b]pyrazin-7-yl]benzoic acid was reacted with 1-(2-phenethyl)piperazine as in General Procedure 10 to give the title compound. LCMS: m/z=509.99 (M+H$^+$); retention time=0.84 minutes.

Example 261

[4-(2-Chlorophenyl)piperazin-1-yl]-[1-(2,5-dichlorobenzyl)-1,2,3,4-tetrahydropyrido[2,3-b]pyrazin-7-yl]methanone

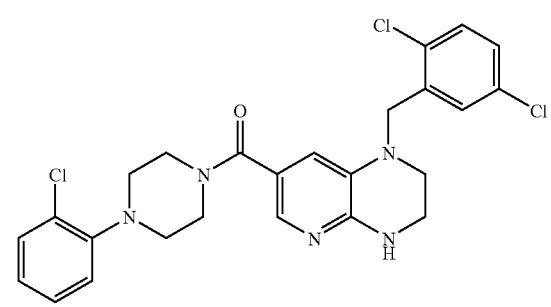

[1-(2,5-Dichlorobenzyl)-1,2,3,4-tetrahydropyrido[2,3-b]pyrazin-7-yl]benzoic acid was reacted with 1-(2-chlorophenyl)piperazine as in General Procedure 10 to give the title compound. LCMS: m/z=515.91 (M+H⁺); retention time=1.21 minutes.

Example 262

[(4-Cyclohexylmethyl)piperazin-1-yl]-[1-(2,5-dichlorobenzyl)-1,2,3,4-tetrahydropyrido[2,3-b]pyrazin-7-yl]methanone

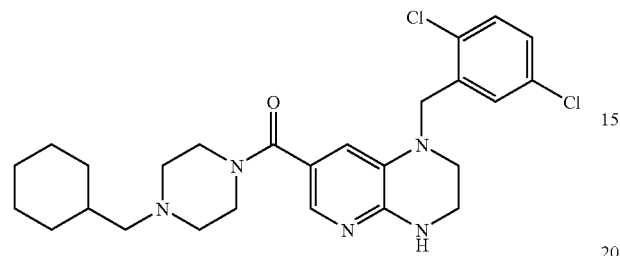

[1-(2,5-Dichlorobenzyl)-1,2,3,4-tetrahydropyrido[2,3-b]pyrazin-7-yl]benzoic acid was reacted with 1-(cyclohexylmethyl)piperazine as in General Procedure 10 to give the title compound. LCMS: m/z=502.04 (M+H⁺); retention time=0.85 minutes.

Example 263

1-(2,5-Dichlorobenzyl)-1,2,3,4-tetrahydropyrido[2,3-b]pyrazine-7-carboxylic acid 4-sulfamoyl-benzylamide

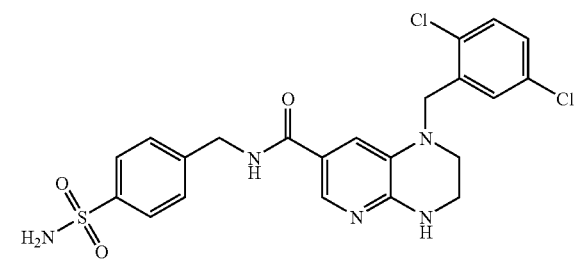

[1-(2,5-Dichlorobenzyl)-1,2,3,4-tetrahydropyrido[2,3-b]pyrazin-7-yl]benzoic acid was reacted with 4-sulfamoylbenzylamine as in General Procedure 10 to give the title compound. LCMS: m/z=505.87 (M+H⁺); retention time=0.93 minutes.

Example 264

[1-(2,5-Dichlorobenzyl)-1,2,3,4-tetrahydropyrido[2,3-b]pyrazin-7-yl]-(2-pyridin-3-yl-pyrrolidin-1-yl)methanone

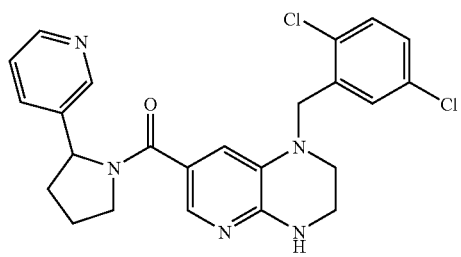

[1-(2,5-Dichlorobenzyl)-1,2,3,4-tetrahydropyrido[2,3-b]pyrazin-7-yl]benzoic acid was reacted with 2-(3-pyridinyl) pyrrolidine as in General Procedure 10 to give the title compound. LCMS: m/z=467.97 (M+H⁺); retention time=0.82 minutes.

Example 265

3-(6-bromo-pyridin-2-ylamino)propionic acid

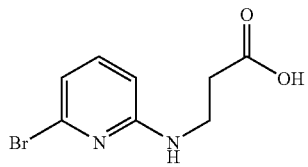

2-Amino-6-bromopyridine (25.0 g) was added to a mixture of ethyl acrylate (17.39 g) (1.2 eq) and acetic acid (4.55 g, 0.52 eq). The reaction mixture was heated at 130° C. for 70 hours and then cooled to room temperature. An aqueous NaOH solution (6N, 60 mL, 2.50 eq) was added and the resulting mixture was heated at reflux for one (1) hour and then cooled to room temperature. The solution was washed twice with ether and then acidified to pH 4-5 with concentrated HCl. The precipitate was collected by filtration to give the title compound as a tan solid (68% yield). M.p. 108-109° C., LCMS: m/z=245.06 (M+H⁺), ¹H-NMR (DMSO-d₆, 400 MHz) δ 3.33-3.40 (m, 4H), 6.46 (d, J=8.2 Hz, 1H), 6.63 (d, J=7.3 Hz, 1H), 7.02 (t, J=5.4 Hz, 1H), 7.27 (dd, J=8.2 and 7.3 Hz, 1H), 12.22 (bs, 1H).

Example 266

7-bromo-2,3-dihydro-1H-[1,8]naphthyridin-4-one

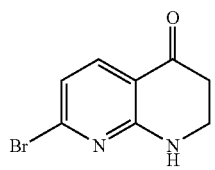

3-(6-Bromo-pyridin-2-ylamino)propionic acid (5.0 g) was combined with Eaton's reagent (100 mL) in a ratio of 5 g 3-(6-bromo-pyridin-2-ylamino)propionic acid per 100 mL Eaton's reagent. The resulting mixture was heated at 75° C. for 2.5 hours. Ice cold water (50 mL) was added to the reaction mixture, followed by aqueous NaOH (50% w/w) to pH 12. The mixture was then extracted twice with ethyl acetate (200 mL) and the combined organic phases were dried over sodium sulfate, filtered, and concentrated under reduced pressure. The mixture was purified by silica gel chromatography using a gradient of 0-80% ethyl acetate/hexane as the eluting solvent to give the title compound as a yellow solid (34% yield). M.p. 196-197° C., LCMS: m/z=227.26 (M+H⁺), ¹H-NMR (DMSO-d₆, 400 MHz) δ 2.57 (t, J=7.2 Hz, 2H), 3.34-3.49 (m, 2H), 6.80 (d, J=8.0 Hz, 1H), 7.74 (d, J=8.0 Hz, 1H), 7.96 (bs, 1H).

Example 267

7-bromo-1,2,3,4-tetrahydro-[1,8]naphthyridin-4-ol

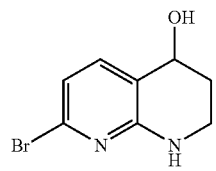

7-Bromo-2,3-dihydro-1H-[1,8]naphthyridin-4-one (1.459 g) was placed in methanol (25 mL) and sodium borohydride (437 mg, 1.84 eq) was added portionwise over five (5) minutes. The reaction was stirred at room temperature for 15 minutes and then quenched with acetic acid (3 mL). The reaction mixture was concentrated under reduced pressure and the residue was taken up in toluene (100 mL). Silica gel was added and the mixture was concentrated under reduced pressure. Purification by silica gel chromatography using dry loading and a gradient of 0-80% ethyl acetate/hexane as the eluting solvent gave the title compound as a pale yellow solid (78% yield). M.p. 130-131° C., LCMS: m/z=230.71 (M+H$^+$), $^1$H-NMR (MeOH-d$_4$, 400 MHz) δ 1.80-1.94 (m, 2H), 3.33-3.48 (m, 2H), 4.66 (t, J=4.4 Hz, 1H), 6.66 (d, J=7.6 Hz, 1H), 7.31 (d, J=7.6 Hz, 1H).

Example 268

6-bromo-1,2,3,4-tetrahydro-[1,8]naphthyridin-4-ol

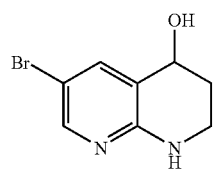

7-Bromo-1,2,3,4-tetrahydro-[1,8]naphthyridin-4-ol (460 mg) was dissolved in anhydrous tetrahydrofuran (25 mL) and cooled to −78° C. A solution of n-butyllithium in tetrahydrofuran was added (1.6 M, 8.5 mL) (5-7 equiv.) and the reaction was warmed slowly to room temperature. After 2-5 hours, methanol (2 mL) was added and the contents were concentrated to dryness. The residue was dissolved in a mixture of dichloromethane and acetic acid (1:1, v/v, 20 mL) and N-bromosuccinimide (450 mg) (1.2 equiv.) were added. After 45 minutes, the mixture was concentrated to dryness onto silica gel, and purified by silica gel chromatography to give the title compound as yellow solids (25-65% yield). M.p. 125-128° C., LCMS: m/z=229 (M+H$^+$), $^1$H-NMR (DMSO-d$_6$, 400 MHz) δ 1.72 (m, 2H), 3.25 (m, 2H), 4.56 (m, 1H), 5.33 (d, J=5.0 Hz, 1H), 6.8 (bs, 1H), 7.47 (d, J=2.5 Hz, 1H), 7.87 (d, J=2.5 Hz, 1H).

Example 269

6-[6-(4-Methyl-piperazin-1-yl)pyridin-3-yl]-1,2,3,4-tetrahydro-[1,8]naphthyridin-4-ol

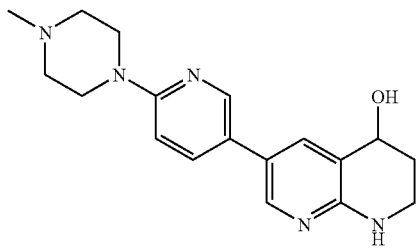

6-Bromo-1,2,3,4-tetrahydro-[1,8]naphthyridin-4-ol (89 mg) was reacted with 1-methyl-4-[5-(4,4,5,5-tetramethyl-[1,3,2]dioxaborolan-2-yl)-pyridin-2-yl]-piperazine (125 mg) as in General Procedure 13. Silica gel chromatography using a gradient of 0-10% (5% NH$_4$OH in methanol)/methylene chloride as the eluting solvent gave the title compound as brown solids (22% yield). M.p. 124-128° C., LCMS: m/z=326 (M+H$^+$), $^1$H-NMR (CDCl$_3$, 400 MHz) δ 2.00 (m, 1H), 2.08 (s, 1H), 2.62 (t, J=5.0 Hz, 4H), 3.49 (m, 2H), 3.58 (m, 2H), 3.63 (t, J=5.0 Hz, 4H), 4.85 (t, J=4.0 Hz, 1H), 6.68 (s, 1H), 6.71 (s, 1H), 7.59 (dd, J=2.6, 8.8 Hz, 1H), 7.66 (d, J=2.2 Hz, 1H), 8.01 (d, J=2.3 Hz, 1H), 8.32 (d, J=2.5 Hz, 1H).

Example 270

[4-(5-Hydroxy-5,6,7,8-tetrahydro-[1,8]naphthyridin-3-yl)phenyl]-(4-methyl-piperazin-1-yl)methanone

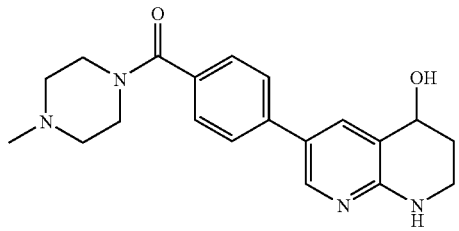

6-Bromo-1,2,3,4-tetrahydro-[1,8]naphthyridin-4-ol (300 mg) was reacted with (4-methyl-piperazin-1-yl)-[4-(4,4,5,5-tetramethyl-[1,3,2]dioxaborolan-2-yl)-phenyl]methanone (450 mg) as in General Procedure 13. Basic alumina chromatography using a gradient of 0-10% methanol/ethyl acetate as the eluting solvent gave the title compound as a white foam (49% yield). LCMS: m/z=353 (M+H$^+$), $^1$H-NMR (DMSO-d$_6$, 400 MHz) δ 1.78 (m, 1H), 2.19 (s, 3H), 2.32 (bs, 4H), 3.27 (m, 1H), 3.36 (m, 1H), 3.50 (bs, 4H), 4.65 (m, 1H), 5.27 (d, J=4.8 Hz, 1H), 6.81 (s, 1H), 7.41 (d, J=8.3 Hz, 2H), 7.62 (d, J=8.3 Hz, 2H), 7.71 (d, J=2.2 Hz, 1H), 8.22 (d, J=2.2 Hz, 1H).

Example 271

6-Bromo-4-(3-chlorophenoxy)-1,2,3,4-tetrahydro-[1,8]naphthyridine

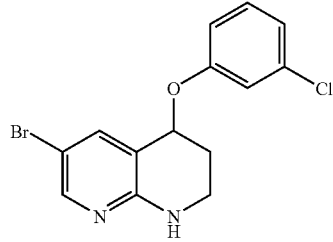

6-Bromo-1,2,3,4-tetrahydro-[1,8]naphthyridin-4-ol (225 mg) was reacted with 3-chlorophenol (0.30 mL) as in General Procedure 12. Basic alumina chromatography using a gradient of 0-1% methanol/methylene chloride as the eluting solvent gave the title compound as a white film (60% yield). LCMS: m/z=339 (M+H$^+$), $^1$H-NMR (CDCl$_3$, 400 MHz) δ 2.00 (m, 1H), 2.21 (m, 1H), 3.40 (m, 1H), 3.51 (m, 1H), 5.04 (s, 1H), 5.27 (t, J=3.9 Hz, 1H), 6.87 (d, J=8.3 Hz, 1H), 7.00 (m, 2H), 7.24 (m, 1H), 7.48 (d, J=2.1 Hz, 1H), 8.06 (d, J=2.1 Hz, 1H).

Example 272

{4-[5-(2,5-Dichlorophenoxy)-5,6,7,8-tetrahydro-[1,8]naphthyridin-3-yl]phenyl}-(4-methyl-piperazin-1-yl)methanone

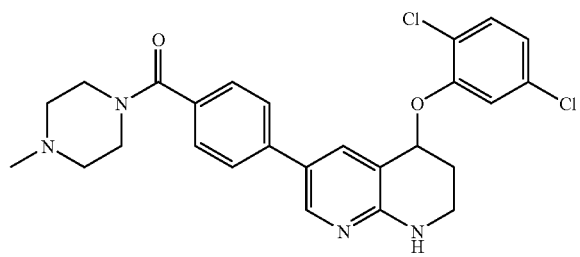

[4-(5-Hydroxy-5,6,7,8-tetrahydro-[1,8]naphthyridin-3-yl)phenyl]-(4-methylpiperazin-1-yl)methanone (26 mg) was reacted with 2,5-chlorophenol (22 mg) as in General Procedure 12. Silica gel chromatography using a gradient of 0-10% methanol/CH$_2$Cl$_2$ as the eluting solvent gave the title compound as an off-white film (33% yield). LCMS: m/z=497 (M+H$^+$), $^1$H-NMR (CDCl$_3$, 400 MHz) δ 2.12 (m, 1H), 2.37 (m, 1H), 2.71 (s, 3H), 2.98 (bs, 4H), 3.59 (m, 1H), 3.79 (m, 1H), 3.97 (bs, 4H), 4.95 (m, 1H), 5.36 (s, 1H), 7.03 (d, J=8.3 Hz, 1H), 7.11 (s, 1H) 7.34 (d, J=8.3 Hz, 1H), 7.43 (d, J=8.1 Hz, 2H), 7.48 (d, J=8.1 Hz, 2H), 7.67 (s, 1H), 8.14 (s, 1H).

Example 273

4-(2-Chloro-3,6-difluorophenoxy)-6-[6-(4-methylpiperazin-1-yl)pyridin-3-yl]-1,2,3,4-tetrahydro-[1,8]naphthyridine

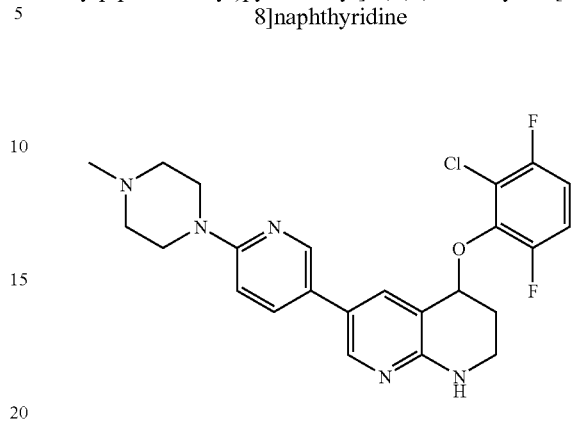

6-[6-(4-Methylpiperazin-1-yl)pyridin-3-yl]-1,2,3,4-tetrahydro-[1,8]naphthyridin-4-ol (85 mg) was reacted with 2-chloro-3,6-difluorophenol (50 mg) as in General Procedure 12. Silica gel chromatography using a gradient of 0-10% methanol/CH$_2$Cl$_2$ as the eluting solvent gave the title compound as a yellow foam (54% yield). LCMS: m/z=472 (M+H$^+$), $^1$H-NMR (DMSO-d$_6$, 400 MHz) δ 1.89 (m, 1H), 2.21 (s, 3H), 2.24 (m, 1H), 2.39 (t, J=4.8 Hz, 4H), 3.40 (m, 1H), 3.47 (t, J=4.8 Hz, 4H), 3.63 (m, 1H), 6.82 (d, J=8.8 Hz, 1H), 7.03 (d, J=2.3 Hz, 1H), 7.17 (d, J=2.3 Hz, 1H) 7.25 (m, 1H), 7.39 (m, 1H), 7.52 (dd, J=2.5, 8.8 Hz, 1H), 8.08 (d, J=2.5 Hz, 1H), 8.19 (d, J=2.5 Hz, 1H).

Example 274

{4-[5-(3-Chlorophenoxy)-5,6,7,8-tetrahydro-[1,8]naphthyridin-3-yl]-phenyl}-(4-methylpiperazin-1-yl)methanone

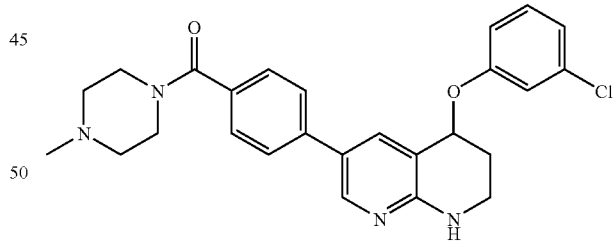

[4-(5-Hydroxy-5,6,7,8-tetrahydro-[1,8]naphthyridin-3-yl)phenyl]-(4-methylpiperazin-1-yl)methanone (20 mg) was reacted with 3-chlorophenol (21.8 mg) as in General Procedure 12. Silica gel chromatography using a gradient of 0-15% methanol/CH$_2$Cl$_2$ as the eluting solvent gave the title compound as a yellow foam (50% yield). LCMS: m/z=463.12 (M+H$^+$), $^1$H-NMR (CDCl$_3$, 400 MHz) δ 2.00-2.12 (m, 1H), 2.27-2.33 (m, 1H), 2.33 (s, 3H), 2.34-2.6 (m, 4H), 3.4-3.7 (m, 4H), 3.7-3.9 (m, 2H), 5.18 (bs, 1H), 5.38 (t, J=3.6 Hz, 1H), 6.91 (dd, J=1.6 and 8.3 Hz, 1H), 6.99-7.04 (m, 2H), 7.23-7.27 (m, 1H), 7.43-7.50 (m, 4H), 7.61 (d, J=2.0 Hz), 8.30 (d, J=2.2 Hz).

Example 275

{4-[5-(3,5-Dichlorophenoxy)-5,6,7,8-tetrahydro-[1,8]naphthyridin-3-yl]phenyl}-(4-methylpiperazin-1-yl)methanone

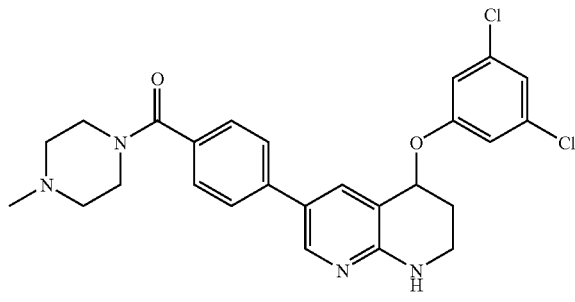

[4-(5-Hydroxy-5,6,7,8-tetrahydro-[1,8]naphthyridin-3-yl)phenyl]-(4-methylpiperazin-1-yl)methanone (20 mg) was reacted with 3,5-dichlorophenol (27.7 mg) as in General Procedure 12. Silica gel chromatography using a gradient of 0-15% methanol/$CH_2Cl_2$ as the eluting solvent gave the title compound as a yellow foam (82% yield). LCMS: m/z=497.12 (M+H$^+$), $^1$H-NMR (CDCl$_3$, 400 MHz) δ 2.02-2.13 (m, 1H), 2.24-2.35 (m, 1H), 2.33 (s, 3H), 2.35-2.60 (m, 4H), 3.40-3.66 (m, 4H), 3.70-3.92 (m, 2H), 5.30 (bs, 1H), 5.37 (t, J=3.3 Hz, 1H), 6.93 (d, J=1.6 Hz, 2H), 7.02 (dd, J=1.6 and 1.6 Hz, 1H), 7.44-7.51 (m, 4H), 7.60 (d, J=2.1 Hz, 1H), 8.31 (d, J=2.1 Hz, 1H).

Example 276

(4-Methylpiperazin-1-yl)-{4-[5-(pyridine-3-yloxy)-5,6,7,8-tetrahydro-[1,8]naphthyridin-3-yl]phenyl}methanone

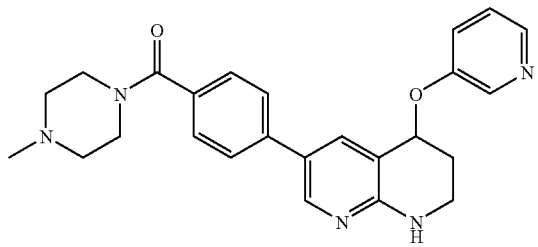

[4-(5-Hydroxy-5,6,7,8-tetrahydro-[1,8]naphthyridin-3-yl)phenyl]-(4-methylpiperazin-1-yl)methanone (20 mg) was reacted with 3-hydroxypyridine (16.2 mg) as in General Procedure 12. Silica gel chromatography using a gradient of 0-15% methanol/$CH_2Cl_2$ as the eluting solvent gave the title compound as a yellow foam (20% yield). LCMS: m/z=430.17 (M+H$^+$), $^1$H-NMR (CDCl$_3$, 400 MHz) δ 2.02-2.12 (m, 1H), 2.30-2.34 (m, 1H), 2.33 (s, 3H), 2.34-2.56 (m, 4H), 3.40-3.70 (m, 4H), 3.70-3.90 (m, 2H), 5.24 (bs, 1H), 5.44 (t, J=3.5 Hz, 1H), 7.26-7.29 (m, 1H), 7.31-7.37 (m, 1H), 7.41-7.50 (m, 4H), 7.58 (d, J=2.0 Hz, 1H), 8.28-8.33 (m, 2H), 8.43 (d, J=2.5 Hz, 1H).

Example 277

1-(4-Fluoro-2-{6-[4-(4-methylpiperazine-1-carbonyl)phenyl]-1,2,3,4-tetrahydro-[1,8]naphthyridin-4-yloxy}phenyl)ethanone

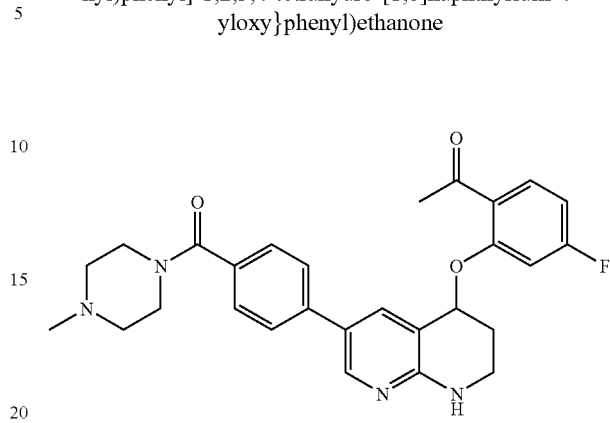

[4-(5-Hydroxy-5,6,7,8-tetrahydro-[1,8]naphthyridin-3-yl)phenyl]-4-methylpiperazin-1-yl)methanone (30 mg) was reacted with 1-(4-fluoro-2-hydroxyphenyl)ethanone (39.4 mg) as in General Procedure 12. Silica gel chromatography using a gradient of 0-15% methanol/$CH_2Cl_2$ as the eluting solvent gave the title compound as a yellow foam (53% yield). LCMS: m/z=489.14 (M+H$^+$), $^1$H-NMR (CDCl$_3$, 400 MHz) δ 2.11-2.25 (m, 2H), 2.32 (s, 3H), 2.32-2.58 (m, 4H), 2.45 (s, 3H), 3.40-3.68 (m, 4H), 3.70-3.90 (m, 2H), 5.31 (bs, 1H), 5.51 (t, J=3.3 Hz, 1H), 6.75-6.82 (m, 1H), 6.89 (dd, J=2.1 and 10.7 Hz, 1H), 7.41-7.51 (m, 4H), 7.57-7.61 (m, 1H), 7.80 (dd, J=7.1 and 8.6 Hz, 1H), 8.33 (bs, 1H).

Example 278

4-(3-Chlorophenoxy)-6-[2-(4-methylpiperazin-1-yl)pyridin-4-yl]-1,2,3,4-tetrahydro-[1,8]naphthyridine

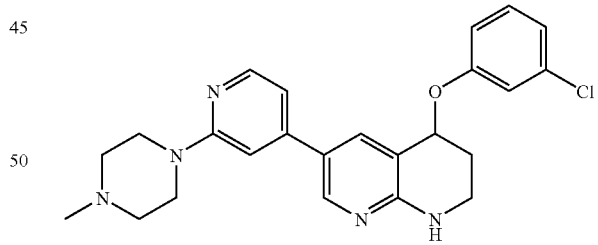

6-Bromo-4-(3-chlorophenoxy)-1,2,3,4-tetrahydro-[1,8]naphthyridine (20 mg) was reacted with 1-methyl-4-[4-(4,4,5,5-tetramethyl-[1,3,2]dioxaborolan-2-yl)pyridin-2-yl]piperazine (25 mg) as in General Procedure 13. Silica gel chromatography using a gradient of 0-100% ethyl acetate/hexane as the eluting solvent gave the title compound as a white foam (36% yield). LCMS: m/z=436.06 (M+H$^+$), $^1$H-NMR (CDCl$_3$, 400 MHz) δ 2.0-2.11 (m, 1H), 2.24-2.40 (m, 1H), 2.35 (s, 3H), 2.54 (t, J=4.9 Hz, 4H), 3.4-3.51 (m, 1H), 3.57-3.68 (m, 5H), 5.27 (bs, 1H), 5.38 (t, J=3.4 Hz, 1H), 6.64 (s, 1H), 6.73 (dd, J=1.0 and 5.2 Hz, 1H), 6.90 (dd, J=2.2 and 8.3 Hz, 1H), 6.95-7.03 (m, 1H), 7.04-7.08 (m, 1H), 7.22-7.28 (m, 1H), 7.57 (d, J=1.9 Hz, 1H), 8.17 (d, J=5.2 Hz, 1H), 8.31 (d, J=2.2 Hz).

Example 279

4-(3-Chlorophenoxy)-6-(3-morpholin-4-yl-phenyl)-1,2,3,4-tetrahydro-[1,8]naphthyridine

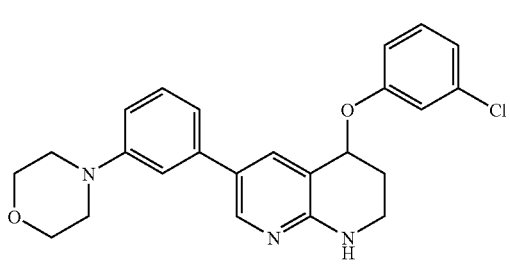

6-Bromo-4-(3-chlorophenoxy)-1,2,3,4-tetrahydro-[1,8] naphthyridine (20 mg) was reacted with 4-[3-(4,4,5,5-tetramethyl-[1,3,2]dioxaborolan-2-yl)phenyl]morpholine (23.9 mg) as in General Procedure 13. Silica gel chromatography using a gradient of 0-100% ethyl acetate/hexane as the eluting solvent gave the title compound as a yellow foam (49% yield). LCMS: m/z=422.18 (M+H+), $^1$H-NMR (CDCl$_3$, 400 MHz) δ 2.00-2.11 (m, 1H), 2.22-2.26 (m, 1H), 3.19 (t, J=4.8 Hz, 4H), 3.40-3.45 (m, 1H), 3.58-3.64 (m, 1H), 3.88 (t, J=4.8 Hz, 4H), 5.14 (bs, 1H), 5.37 (t, J=1.0 Hz, 1H), 6.82-6.92 (m, 2H), 6.92 (s, 1H), 6.95-7.02 (m, 2H), 7.03-7.08 (m, 1H), 7.20-7.33 (m, 2H), 7.55 (d, J=1.9 Hz, 1H), 8.27 (d, J=2.1 Hz, 1H).

Example 280

4-(3-Chlorophenoxy)-6-(4-morpholin-4-yl-phenyl)-1,2,3,4-tetrahydro-[1,8]naphthyridine

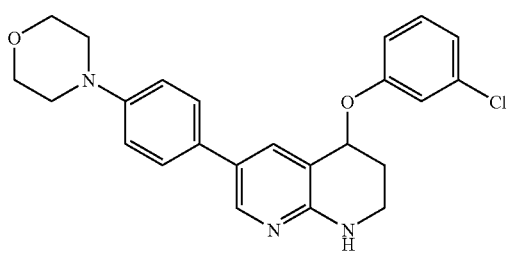

6-Bromo-4-(3-chlorophenoxy)-1,2,3,4-tetrahydro-[1,8] naphthyridine (20 mg) was reacted with 4-morpholinophenylboronic acid (20.7 mg) as in General Procedure 13. Silica gel chromatography using a gradient of 0-100% ethyl acetate/hexane as the eluting solvent gave the title compound as a yellow solid (73% yield). M.p. 124-126° C., LCMS: m/z=422.28 (M+H+), $^1$H-NMR (CDCl$_3$, 400 MHz) δ 2.0-2.11 (m, 1H), 2.22-2.5 (m, 1H), 3.17 (t, J=4.7 Hz, 4H), 3.38-3.48 (m, 1H), 3.54-3.67 (m, 1H), 3.87 (t, J=4.7 Hz, 4H), 5.10 (s, 1H), 5.37 (t, J=1.0 Hz, 1H), 6.88-7.02 (m, 4H), 7.03-7.07 (m, 1H), 7.21-7.26 (m, 1H), 7.37 (d, J=8.6 Hz, 2H), 7.56 (d, J=1.9 Hz, 1H), 8.25 (d, J=1.9 Hz, 1H).

Example 281

4-(3-Chlorophenoxy)-6-[6-(4-methylpiperazin-1-yl) pyridin-3-yl]-1,2,3,4-tetrahydro-[1,8]naphthyridine

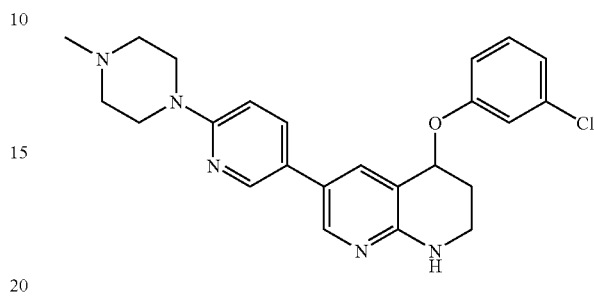

6-Bromo-4-(3-chlorophenoxy)-1,2,3,4-tetrahydro-[1,8] naphthyridine (20 mg) was reacted with 1-methyl-4-[5-(4,4,5,5-tetramethyl-[1,3,2]dioxaborolan-2-yl)pyridin-2-yl]piperazine (25.0 mg) as in General Procedure 13. Silica gel chromatography using a gradient of 0-20% methanol/CH$_2$Cl$_2$ as the eluting solvent gave the title compound as an orange foam (55% yield). LCMS: m/z=436.12 (M+H+), $^1$H-NMR (CDCl$_3$, 400 MHz) δ 2.0-2.11 (m, 1H), 2.21-2.32 (m, 1H), 2.36 (s, 3H), 2.54 (t, J=5.0 Hz, 4H), 3.39-3.49 (m, 1H), 3.53-3.68 (m, 1H), 3.59 (t, J=5.0 Hz, 4H), 5.10 (s, 1H), 5.37 (t, J=3.5 Hz, 1H), 6.68 (d, J=8.8 Hz, 1H), 6.90 (dd, J=2.3 and 8.3 Hz, 1H), 6.98-7.07 (m, 2H), 7.20-7.27 (m, 1H), 7.50 (d, J=2.1 Hz, 1H), 7.56 (dd, J=2.5 and 8.8 Hz, 1H), 8.20 (d, J=2.2 Hz, 1H), 8.29 (d, J=2.4 Hz, 1H).

Example 282

7-Bromo-4-[1-iodomethylidene]-1,2,3,4-tetrahydro-[1,8]naphthyridine

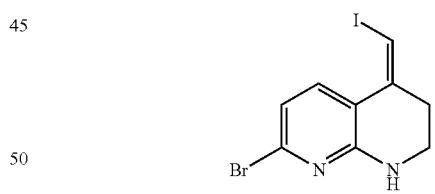

To a suspension of 7-bromo-2,3-dihydro-1H-[1,8]naphthyridin-4-one (1.5 g) in anhydrous tetrahydrofuran (195 mL) was added a solution of CrCl$_2$ (6.79 g, 8.35 eq) and CHI$_3$ (5.55 g, 2.13 eq) in anhydrous tetrahydrofuran (66 mL). The reaction was stirred at room temperature for 16 hours, diluted with methylene chloride (300 mL), and then washed with saturated NaHCO$_3$ (300 mL). The aqueous phase was extracted twice with methylene chloride (100 mL) and the combined organic layers were washed with brine and then dried over Na$_2$SO$_4$. The solution was filtered and concentrated under reduced pressure. Silica gel chromatography using a gradient of 0-30% ethyl acetate/hexane as the eluting solvent gave the title compound as a yellow solid (27% yield). Alkene geometry was determined by nOe. LCMS: m/z=352 (M+H+), $^1$H-NMR (CDCl$_3$, 400 MHz) δ 2.69 (t, J=6.0 Hz, 2H), 3.43-3.51 (m, 2H), 5.25 (bs, 1H), 6.23 (s, 1H), 6.74 (d, J=8.0 Hz, 1H), 8.19 (d, J=8.0 Hz, 1H).

Example 283

7-Bromo-4-[1-(2,5-difluorophenyl)methylidene]-1,2,3,4-tetrahydro-[1,8]naphthyridine

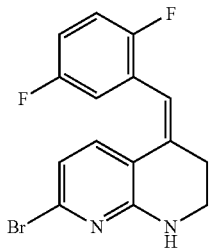

Na$_2$CO$_3$ (2N, 3.46 mL, 10.0 eq) was added to a mixture of 7-bromo-4-[1-iodomethylidene]-1,2,3,4-tetrahydro-[1,8]naphthyridine (607 mg), 2,5-difluorophenylboronic acid (328 mg, 1.2 eq), and Pd(PPh$_3$)$_4$ (150 mg, 0.075 eq) in toluene/ethanol (4:1 v/v). The reaction was heated at 85° C. for five (5) hours, Celite was added, and the mixture was then concentrated under reduced pressure. The dry powder was then dry loaded onto a silica gel column and a gradient of 0-20% ethyl acetate/hexane as the eluting solvent gave the title compound as a yellow solid (70% yield). M.p. 178-179° C., LCMS: m/z=337 (M+H$^+$), $^1$H-NMR (CDCl$_3$, 400 MHz) δ 2.62 (t, J=5.8 Hz, 2H), 3.55-3.62 (m, 2H), 5.25 (bs, 1H), 6.26 (s, 1H), 6.45 (d, J=7.9 Hz, 1H), 6.85-6.95 (m, 1H), 6.96-7.12 (m, 3H).

Example 284

4-(2,5-Difluorobenzyl)-1,2,3,4-tetrahydro-[1,8]naphthyridine

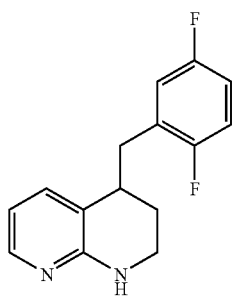

7-Bromo-4-[1-(2,5-difluorophenyl)methylidene]-1,2,3,4-tetrahydro-[1,8]naphthyridine (200 mg) was dissolved in methanol (20 mL) and Pd/C (20 mg) was added. The reaction was hydrogenated at atmospheric pressure for 1.5 hours, filtered through Celite, and then concentrated under reduced pressure to give the title compound as a clear colorless oil (near quantitative yield). LCMS: m/z=261.11 (M+H$^+$), $^1$H-NMR (MeOH-d$_4$, 400 MHz) δ 1.68-1.86 (m, 2H), 2.80 (dd, J=9.0 and 13.3, 1H), 2.96 (dd, J=10.0 and 13.3 Hz, 1H), 3.02-3.12 (m, 1H), 3.34-3.41 (m, 1H), 3.46-3.55 (m, 1H), 6.44 (dd, J=5.2 and 7.2 Hz, 1H), 6.93-7.03 (m, 2H), 7.03-7.11 (m, 2H), 7.72 (dd, J=1.0 and 5.0 Hz, 1H).

Example 285

6-Bromo-4-(2,5-difluorobenzyl)-1,2,3,4-tetrahydro-[1,8]naphthyridine

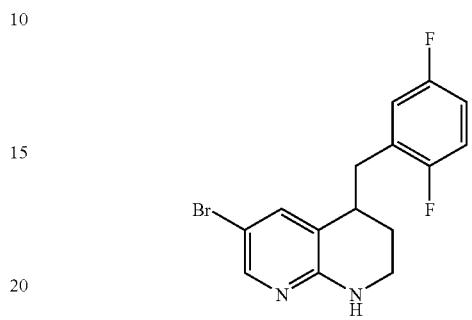

To a solution of 4-(2,5-difluorobenzyl)-1,2,3,4-tetrahydro-[1,8]naphthyridine (23 mg) in CH$_2$Cl$_2$/acetic acid (5.5 mL, 10:1, v/v) was added N-bromosuccinimide (18.8 mg, 1.2 eq). The reaction was stirred at room temperature for one (1) hour, concentrated under reduced pressure, and purified by silica gel chromatography using a gradient of 0-60% ethyl acetate/hexane as the eluting solvent to give the title compound as a clear, colorless oil (30% yield). LCMS: m/z=339 (M+H$^+$), $^1$H-NMR (CDCl$_3$, 400 MHz) δ 1.66-1.75 (m, 1H), 1.75-1.86 (m, 1H), 2.73 (dd, J=9.6 and 13.4 Hz, 1H), 2.95 (dd, J=6.0 and 13.4 Hz, 1H), 2.99-3.08 (m, 1H), 3.34-3.43 (m, 1H), 3.45-3.55 (m, 1H), 5.22 (bs, 1H), 6.80-6.86 (m, 1H), 6.88-6.96 (m, 1H), 6.98-7.05 (m, 1H), 7.16 (d, J=1.9 Hz, 1H), 7.91 (d, J=1.9 Hz, 1H).

Example 286

4-(2,5-Difluorobenzyl)-6-[6-(4-methylpiperazin-1-yl)pyridin-3-yl]-1,2,3,4-tetrahydro-[1,8]naphthyridine

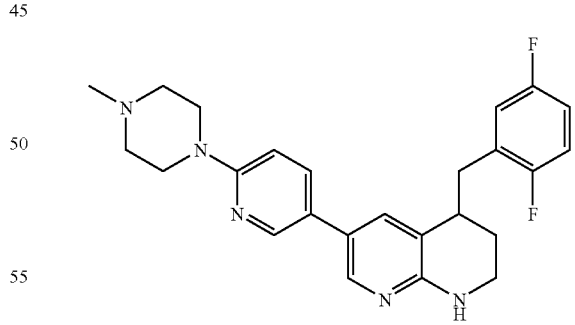

Na$_2$CO$_3$ (2N, 53 μL) (4.0 eq) was added to a mixture of 6-bromo-4-(2,5-difluorobenzyl)-1,2,3,4-tetrahydro-[1,8]naphthyridine (9.0 mg) (1 eq), 1-methyl-4-[5-(4,4,5,5-tetramethyl-[1,3,2]dioxaborolan-2-yl)pyridin-2-yl]piperazine (11.3 mg) (1.4 eq), and Pd(PPh$_3$)$_4$ (3.0 mg, 0.1 eq) in toluene/ethanol (4:1, v/v, 2 mL). The reaction was heated at 90° C. for six (6) hours. The reaction mixture was then concentrated under reduced pressure and the residue was taken up in CH$_2$Cl$_2$ (15 mL) and washed with water (15 mL). The organic phase was dried over Na₂SO₄, filtered, concentrated under reduced pressure, and purified by silica gel chromatography using a gradient of 0-20% methanol/CH₂Cl₂ as the eluting solvent to give the title compound as a yellow foam (26% yield). LCMS: m/z=436 (M+H⁺), ¹H-NMR (CDCl₃, 400 MHz) δ 1.7-2.0 (m, 2H), 2.37 (s, 3H), 2.55-2.60 (m, 4H), 2.81 (dd, J=9.1 and 13.3 Hz, 1H), 2.98 (dd, J=6.4 and 13.3H, 1H), 3.08-3.18 (m, 1H), 3.40-3.50 (m, 1H), 3.53-3.70 (m, 5H), 5.18 (bs, 1H), 6.68 (d, J=8.8 Hz, 1H), 6.81-6.87 (m, 1H), 6.89-6.96 (m, 1H), 6.98-7.06 (m, 1H), 7.16 (d, J=1 Hz, 1H), 7.50 (dd, J=2.5 and 8.8 Hz, 1H), 8.05 (d, J=1 Hz, 1H), 8.24 (d, J=2.5 Hz, 1H).

Example 287

(4-{1-[5-Chloro-2-(trifluoromethyl)benzyl]-1,2,3,4-tetrahydropyrido[2,3-b]pyrazin-7-yl}phenyl)-(4-morpholin-4-yl-piperidin-1-yl)methanone

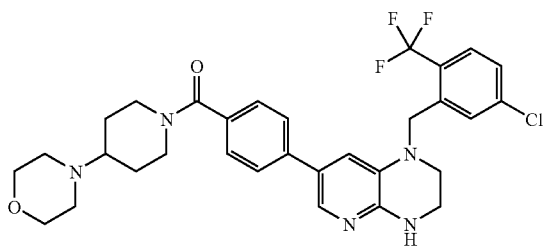

4-{1-[5-Chloro-2-(trifluoromethyl)benzyl]-1,2,3,4-tetrahydro-pyrido[2,3-b]pyrazin-7-yl}benzoic acid (70 mg) was reacted with 4-piperidin-4-yl-morpholine as in General Procedure 8 to give the title compound as a light yellow foam (43% yield). M.p. (foam), LCMS: m/z=600.14 (M+H⁺), ¹H-NMR (CDCl₃, 400 MHz) δ 1.42-1.58 (m, 2H), 1.72-1.94 (m, 2H), 2.35-2.45 (m, 1H), 2.52-2.58 (m, 4H), 2.86-3.03 (m, 2H), 3.47-3.53 (m, 2H), 3.63-3.74 (m, 6H), 3.88-3.96 (m, 1H), 4.58 (s, 2H), 5.12 (s, 1H), 6.59 (d, J=8.3 Hz, 1H), 7.32-7.49 (m, 5H), 7.64 (d, J=8.3 Hz, 1H), 7.74 (d, J=1.76 Hz, 1H).

Example 288

(4-{1-[5-Chloro-2-(trifluoromethyl)benzyl]-1,2,3,4-tetrahydropyrido[2,3-b]pyrazin-7-yl}phenyl)-(4-thiazol-2-yl-piperazin-1-yl)methanone

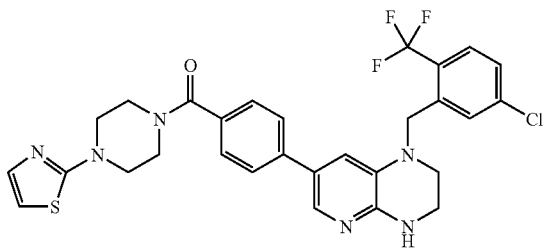

4-{1-[5-Chloro-2-(trifluoromethyl)benzyl]-1,2,3,4-tetrahydro-pyrido[2,3-b]pyrazin-7-yl}benzoic acid (70 mg) was reacted with 1-thiazol-2-yl-piperazine as in General Procedure 8 to give the title compound as a yellow solid (61% yield). M.p. 243-244, LCMS: m/z=598.92 (M+H⁺), ¹H-NMR (CDCl₃, 400 MHz) δ 3.49-3.92 (m, 12H), 4.63 (s, 2H), 5.06 (bs, 1H), 6.57-6.64 (m, 2H), 7.21 (d, J=3.52 Hz, 1H), 7.35-7.43 (m, 5H), 7.51 (s, 1H), 7.65 (d, J=8.4 Hz, 1H), 7.76 (s, 1H).

Example 289

3,6-Difluoro-2-[7-(6-morpholin-4-yl-pyridin-3-yl)-3,4-dihydro-2H-pyrido[2,3-b]pyrazin-1-ylmethyl]benzonitrile

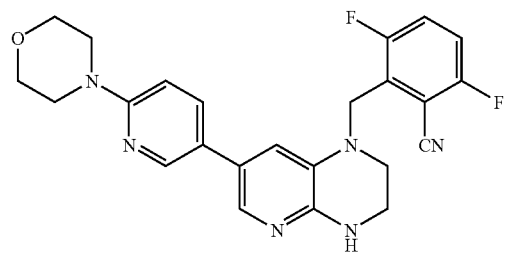

1-(2-Chloro-3,6-difluorobenzyl)-7-(6-morpholin-4-yl-pyridin-3-yl)-1,2,3,4-tetrahydropyrido[2,3-b]pyrazine (300 mg) was dissolved in anhydrous DMF. CuCN (5.0 eq) was added and the resulting mixture was heated to 150° C. in a microwave for 30 minutes. The reaction mixture was concentrated, taken up in CH₂Cl₂, washed three (3) times with an aqueous solution of NH₄OH (10%), and the organic phase was dried, filtered, and concentrated. The residue was purified via silica gel chromatography (0-100% ethyl acetate in hexanes followed by 5% methanol in ethyl acetate) to give the title compound (37% yield). M.p 188-190° C., LCMS: m/z=449.05 (M+H⁺), ¹H-NMR (CDCl₃, 400 MHz) δ 3.24-3.31 (m, 2H), 3.48-3.56 (m, 6H), 3.80-3.88 (m, 4H), 4.51 (s, 2H), 4.86 (bs, 1H), 6.65-6.73 (m, 1H), 6.98-7.06 (m, 2H), 7.09-7.19 (m, 2H), 7.59-7.64 (m, 2H), 8.36 (s, 1H).

Example 290

7-Iodo-1-[5-(trifluoromethyl)furan-2-ylmethyl]-3,4-dihydro-1H-pyrido[2,3-b]pyrazin-2-one

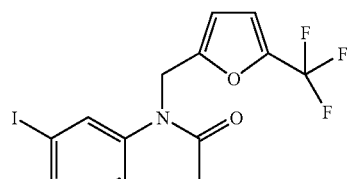

7-Iodo-3,4-dihydro-1H-pyrido[2,3-b]pyrazin-2-one (659 mg) was reacted with 2-(chloromethyl)-5-(trifluoromethyl) furan as in General Procedure 1 to give the title compound as a beige solid (87% yield). M.p. 189-191° C., LCMS: m/z=424.20 (M+H⁺), ¹H-NMR (CDCl₃, 400 MHz) δ 4.21 (s, 2H), 4.95 (bs, 1H), 5.05 (s, 2H), 6.39 (s, 1H), 6.75 (s, 1H), 7.50 (s, 1H), 7.96 (s, 1H).

Example 291

7-Iodo-1-[5-(trifluoromethyl)furan-2-ylmethyl]-1,2,3,4-tetrahydropyrido[2,3-b]pyrazine

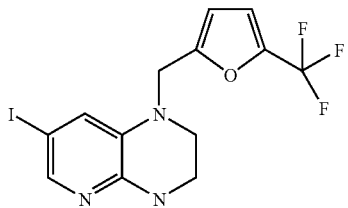

7-Iodo-1-[5-(trifluoromethyl)furan-2-ylmethyl]-3,4-dihydro-1H-pyrido[2,3-b]pyrazin-2-one (860 mg) was reduced as in General Procedure 3 to give the title compound as a white solid (18% yield). M.p. 153-154° C., LCMS: m/z=409.89 (M+H$^+$), $^1$H-NMR (CDCl$_3$, 400 MHz) δ 3.33-3.40 (m, 2H), 3.47-3.59 (m, 2H), 4.38 (s, 2H), 5.10 (bs, 1H), 6.28 (s, 1H), 6.73 (s, 1H), 6.90 (s, 1H), 7.61 (s, 1H).

Example 292

7-(6-Morpholin-4-yl-pyridin-3-yl)-1-[5-(trifluoromethyl)furan-2-ylmethyl]-1,2,3,4-tetrahydropyrido[2,3-b]pyrazine

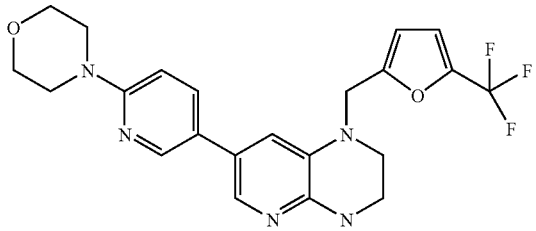

7-Iodo-1-[5-(trifluoromethyl)furan-2-ylmethyl]-1,2,3,4-tetrahydropyrido[2,3-b]pyrazine (60 mg) was reacted with 4-[5-(4,4,5,5-tetramethyl-[1,3,2]dioxaborolan-2-yl)pyridin-2-yl]morpholine as in General Procedure 4A to give the title compound as an orange foam (30% yield). M.p. (foam), LCMS: m/z=446.13 (M+H$^+$), $^1$H-NMR (CDCl$_3$, 400 MHz) δ 3.42-3.47 (m, 2H), 3.48-3.54 (m, 4H), 3.58-3.67 (m, 2H), 3.80-3.89 (m, 4H), 4.47 (s, 1H), 5.02 (bs, 1H), 6.30 (s, 1H), 6.67 (d, J=5.2 Hz, 1H), 6.72 (s, 1H), 6.85 (s, 1H), 7.55-7.62 (m, 2H), 8.31 (s, 1H).

Example 293

7-[2-(4-Methylpiperazin-1-yl)pyridin-4-yl]-1-[5-(trifluoromethyl)furan-2-ylmethyl]-1,2,3,4-tetrahydropyrido[2,3-b]pyrazine

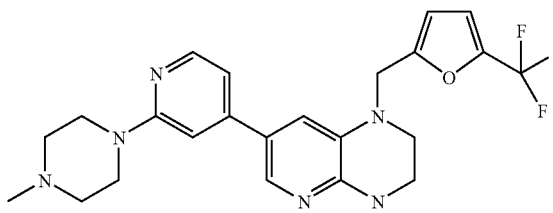

7-Iodo-1-[5-(trifluoromethyl)furan-2-ylmethyl]-1,2,3,4-tetrahydropyrido[2,3-b]pyrazine (60 mg) was reacted with 1-methyl-4-[4-(4,4,5,5-tetramethyl-[1,3,2]dioxaborolan-2-yl)pyridin-2-yl]piperazine as in General Procedure 4A to give the title compound as a beige foam (30% yield). M.p. (foam), $^1$H-NMR (CDCl$_3$, 400 MHz) δ 2.31-3.36 (m, 4H), 2.38-2.53 (m, 4H), 3.42-3.48 (m, 2H), 3.48-3.58 (m, 1H), 3.61-3.66 (m, 2H), 3.74-3.84 (m, 2H), 5.02 (bs, 1H), 6.31 (s, 1H), 6.74 (s, 1H), 6.93 (s, 1H), 7.41-7.50 (m, 3H), 7.73 (s, 1H).

Example 294

7-Iodo-1-[2-(trifluoromethoxy)benzyl]-3,4-dihydro-1H-pyrido[2,3-b]pyrazin-2-one

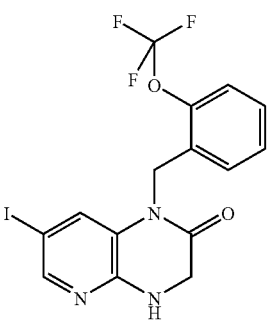

7-Iodo-3,4-dihydro-1H-pyrido[2,3-b]pyrazin-2-one (942 mg) was reacted with 2-(trifluoromethoxy)benzyl bromide as in General Procedure 1 to give the title compound as a light yellow solid (61% yield). m.p.=235° C., LCMS: m/z=449.92 (M+H$^+$), $^1$H-NMR (CDCl$_3$, 400 MHz) δ 4.29 (2H, s), 4.89 (1H, s), 5.16 (2H, s), 7.09 (2H, m), 7.24 (1H, m), 7.34 (2H, m), 7.92 (1H, s).

Example 295

1-[5-Chloro-2-(trifluoromethyl)benzyl]-1,2,3,4-tetrahydropyrido[2,3-b]pyrazine-7-carboxylic acid [4-(dimethylamino)butyl]amide

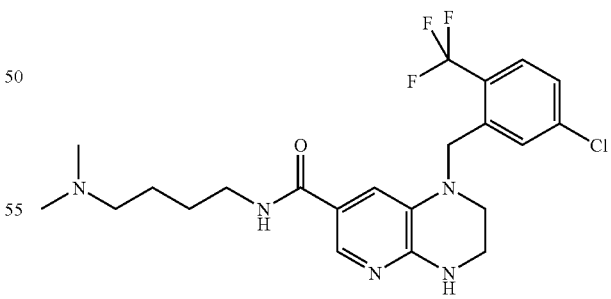

4-{1-[5-Chloro-2-(trifluoromethyl)benzyl]-1,2,3,4-tetrahydro-pyrido[2,3-b]pyrazin-7-yl}benzoic acid (84 mg) was reacted with 4-(dimethylamino)butylamine as in General Procedure 8 to give the title compound as a yellow solid (45% yield). m.p.=182° C., LCMS: m/z=545.86 (M+H$^+$), $^1$H-NMR (CDCl$_3$, 400 MHz) δ 1.60 (2H, m), 1.69 (2H, m), 2.20 (6H, s), 2.31 (2H, m), 3.43 (2H, m), 3.49 (2H, m), 3.69 (2H, m), 4.62

(2H, s), 5.27 (1H, bs), 6.61 (1H, s), 7.35 (1H, d, J=8.3 Hz), 7.39 (2H, d, J=7.8 Hz), 7.51 (1H, s), 7.63 (1H, d, J=8.3 Hz), 7.70 (1H, m), 7.75 (3H, m).

Example 296

7-Iodo-1-[2-(trifluoromethoxy)benzyl]-1,2,3,4-tetrahydropyrido[2,3-b]pyrazine

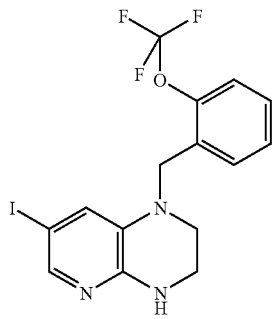

7-Iodo-1-[2-(trifluoromethoxy)benzyl]-3,4-dihydro-1H-pyrido[2,3-b]pyrazin-2-one (940 mg) was reduced as in General Procedure 3 to give the title compound as a brown sticky solid. LCMS: m/z=435.82 (M+H$^+$), $^1$H-NMR (CDCl$_3$, 400 MHz) δ 3.38 (2H, m), 3.55 (2H, m), 4.44 (2H, s), 4.95 (1H, s), 6.71 (1H, s), 7.30 (4H, m), 7.59 (1H, s).

Example 297

4-{1-[2-(Trifluoromethoxy)benzyl]-1,2,3,4-tetrahydropyrido[2,3-b]pyrazin-7-yl}benzoic acid ethyl ester

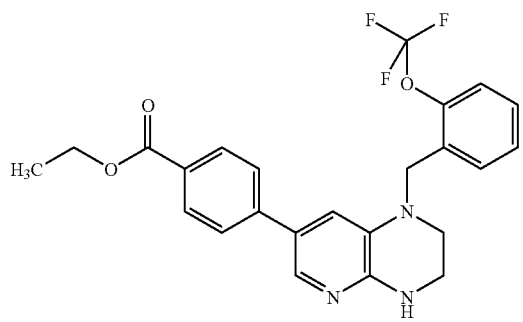

7-Iodo-1-[2-(trifluoromethoxy)benzyl]-1,2,3,4-tetrahydropyrido[2,3-b]pyrazine (699 mg) was reacted with (4-ethoxycarbonylphenyl)boronic acid as in General Procedure 4B to give the title compound as a yellow solid. m.p.=153° C., LCMS: m/z=458.00 (M+H$^+$), $^1$H-NMR (CDCl$_3$, 400 MHz) δ 1.38 (3H, t, J=7.1 Hz), 3.47 (2H, m), 3.64 (2H, m), 4.36 (2H, quartet, J=7.1 Hz), 4.56 (2H, s), 5.22 (1H, bs), 6.73 (1H, s), 7.25 (1H, m), 7.31 (2H, m), 7.37 (1H, d, J=7.3 Hz), 7.42 (2H, d, J=7.8. Hz), 7.75 (1H, s), 8.00 (2H, d, J=8.1 Hz).

Example 298

4-{1-[2-(Trifluoromethoxy)benzyl]-1,2,3,4-tetrahydropyrido[2,3-b]pyrazin-7-yl}benzoic acid

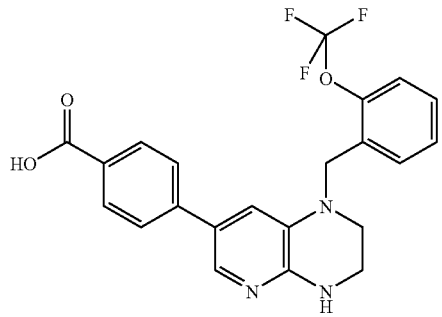

4-{1-[2-(Trifluoromethoxy)benzyl]-1,2,3,4-tetrahydropyrido[2,3-b]pyrazin-7-yl}benzoic acid ethyl ester (356 mg) was saponified as in General Procedure 7 to give the title compound as an orange solid (76% yield). m.p.=250° C., LCMS: m/z=430.14 (M+H$^+$), $^1$H-NMR (DMSO-d$_6$, 400 MHz) δ 3.55 (2H, s), 4.70 (2H, s), 7.03 (1H, s), 7.43 (4H, m), 7.61 (2H, d, J=8.1 Hz), 7.72 (1H, s), 7.93 (2H, d, J=8.1 Hz).

Example 299

1-(2-Chloropyridin-3-ylmethyl)-7-iodo-3,4-dihydro-1H-pyrido[2,3-b]pyrazin-2-one

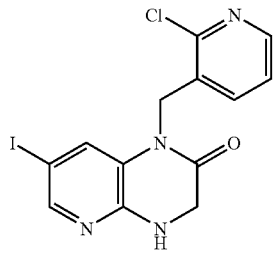

7-Iodo-3,4-dihydro-1H-pyrido[2,3-b]pyrazin-2-one (1.189 g) was reacted with 3-(bromomethyl)-2-chloropyridine as in General Procedure 1 to give the title compound as an orange solid (58% yield). m.p.=249° C., LCMS: m/z=401.18 (M+H$^+$), $^1$H-NMR (CDCl$_3$, 400 MHz) δ 4.29 (2H, s), 5.16 (2H, s), 7.04 (1H, s), 7.26 (1H, m), 7.36 (1H, d, J=7.6 Hz), 7.91 (1H, s), 8.34 (1H, d, J=4.3 Hz).

Example 300

1-(2-Chloropyridin-3-ylmethyl)-7-iodo-1,2,3,4-tetrahydropyrido[2,3-b]pyrazine

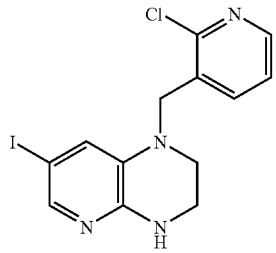

1-(2-Chloropyridin-3-ylmethyl)-7-iodo-3,4-dihydro-1H-pyrido[2,3-b]pyrazin-2-one (1.005 g) was reduced as in General Procedure 3 to give the title compound as a brown sticky solid. LCMS: m/z=387.16 (M+H$^+$).

Example 301

4-[1-(2-Chloropyridin-3-ylmethyl)-1,2,3,4-tetrahydropyrido[2,3-b]pyrazin-7-yl]benzoic acid ethyl ester

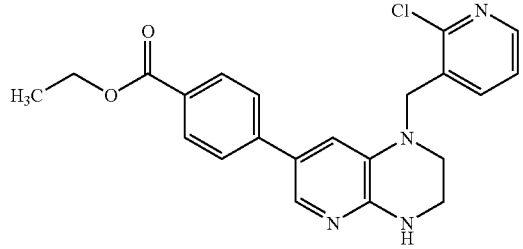

1-(2-Chloropyridin-3-ylmethyl)-7-iodo-1,2,3,4-tetrahydropyrido[2,3-b]pyrazine (389 mg) was reacted with (4-ethoxycarbonylphenyl) boronic acid as in General Procedure 4B to give the title compound as a yellow solid. LCMS: m/z=409.34 (M+H$^+$).

Example 302

4-[1-(2-Chloropyridin-3-ylmethyl)-1,2,3,4-tetrahydropyrido[2,3-b]pyrazin-7-yl]benzoic acid

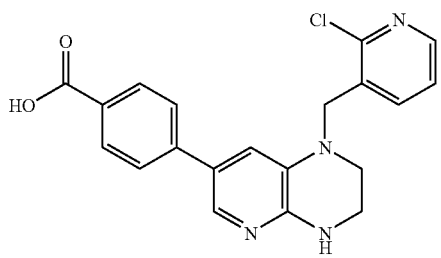

4-[1-(2-Chloropyridin-3-ylmethyl)-1,2,3,4-tetrahydropyrido[2,3-b]pyrazin-7-yl]benzoic acid ethyl ester (51 mg) was saponified as in General Procedure 7 to give the title compound as a yellow solid (82% yield). LCMS: m/z=381.29 (M+H$^+$), $^1$H-NMR (DMSO-d$_6$, 400 MHz) δ 4.64 (2H, s), 6.87 (1H, s), 7.40 (1H, m), 7.60 (2H, d, J=8.3 Hz), 7.74 (2H, m), 7.90 (2H, d, J=8.3 Hz), 8.34 (1H, m).

Example 303

{4-[1-(2-Chloropyridin-3-ylmethyl)-1,2,3,4-tetrahydropyrido[2,3-b]pyrazin-7-yl]phenyl}-(4-pyrrolidin-1-yl-piperidin-1-yl)methanone

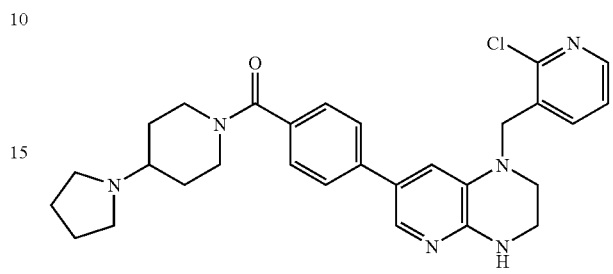

4-[1-(2-Chloropyridin-3-ylmethyl)-1,2,3,4-tetrahydropyrido[2,3-b]pyrazin-7-yl]benzoic acid (38 mg) was reacted with 4-(1-pyrrolidinyl)piperidine as in General Procedure 8 to give the title compound as a yellow solid (20% yield). LCMS: m/z=516.89 (M+H$^+$), $^1$H-NMR (CDCl$_3$, 400 MHz) δ 1.50 (1H, m), 1.80 (5H, m), 1.97 (2H, m), 2.27 (1H, m), 2.58 (4H, m), 3.01 (2H, m), 3.50 (2H, m), 3.67 (2H, m), 3.79 (1H, m), 4.54 (2H, s), 4.95 (1H, bs), 6.58 (1H, d, J=1.5 Hz), 7.23 (1H, m), 7.36 (4H, m), 7.62 (1H, dd, J=7.6, 1.8 Hz), 7.73 (1H, d, J=1.8 Hz), 8.34 (1H, dd, J=4.8, 1.8 Hz).

Example 304

N-(4-{1-[5-Chloro-2-(trifluoromethyl)benzyl]-1,2,3,4-tetrahydropyrido[2,3-b]pyrazin-7-yl}phenyl)acetamide

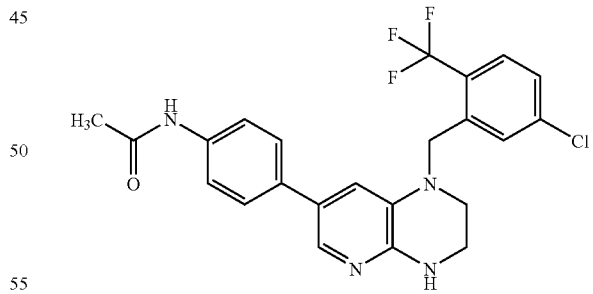

1-[5-Chloro-2-(trifluoromethyl)benzyl]-7-iodo-1,2,3,4-tetrahydropyrido[2,3-b]pyrazine (90 mg) was reacted with 4-acetamidophenylboronic acid as in General Procedure 4B to give the title compound as a light gray solid (42% yield). m.p.=244° C., LCMS: m/z=461.24 (M+H$^+$), $^1$H-NMR (CDCl$_3$, 400 MHz) δ 2.13 (3H, s), 3.49 (2H, m), 3.65 (2H, m), 3.82 (2H, s), 4.61 (2H, s), 6.58 (1H, s), 7.28 (2H, d, J=8.1 Hz), 7.36 (1H, d, J=7.3 Hz), 7.51 (3H, m), 7.60 (1H, s), 7.65 (1H, d, J=8.6 Hz).

Example 305

(4-Pyrrolidin-1-yl-piperidin-1-yl)-(4-{1-[2-(trifluoromethoxy)benzyl]-1,2,3,4-tetrahydropyrido[2,3-b]pyrazin-7-yl}phenyl)methanone

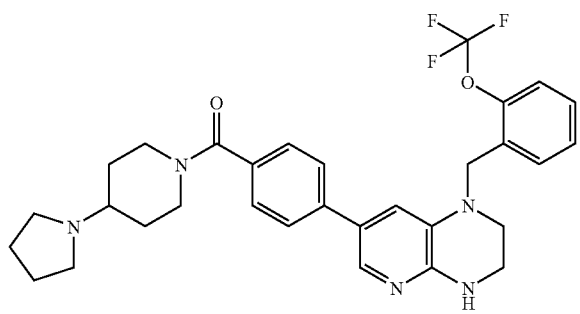

4-{1-[2-(Trifluoromethoxy)benzyl]-1,2,3,4-tetrahydropyrido[2,3-b]pyrazin-7-yl}benzoic acid (98 mg) was reacted with 4-(1-pyrrolidinyl)piperidine as in General Procedure 8 to give the title compound as a yellow solid (65% yield). LCMS: m/z=565.98 (M+H$^+$), $^1$H-NMR (CDCl$_3$, 400 MHz) δ 1.53 (2H, bs), 2.88 (7H, m), 2.27 (1H, m), 2.57 (4H, s), 2.98 (2H, m), 3.46 (2H, m), 3.63 (2H, m), 3.81 (1H, bs), 4.55 (2H, s), 5.21 (1H, s), 6.71 (1H, s), 7.33 (8H, m), 7.71 (1H, s).

Example 306

(3-{1-[5-Chloro-2-(trifluoromethyl)benzyl]-1,2,3,4-tetrahydropyrido[2,3-b]pyrazin-7-yl}phenyl)-(4-phenylpiperazin-1-yl)methanone

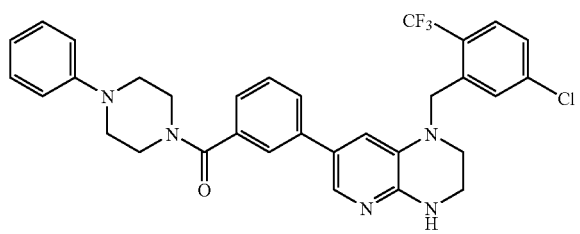

3-{1-[5-chloro-2-(trifluoromethyl)benzyl]-1,2,3,4-tetrahydropyrido[2,3-b]pyrazin-7-yl}benzoic acid was reacted with 1-phenylpiperazine as in General Procedure 10 to give the title compound. LCMS: m/z=591.97 (M+H$^+$); retention time=0.97 minutes.

Example 307

(3-{1-[5-Chloro-2-(trifluoromethyl)benzyl]-1,2,3,4-tetrahydropyrido[2,3-b]pyrazin-7-yl}phenyl)-(4-pyrimidin-2-ylpiperazin-1-yl)methanone

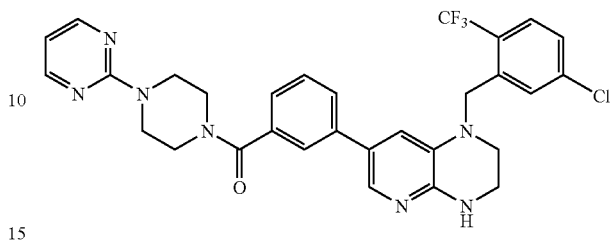

3-{1-[5-chloro-2-(trifluoromethyl)benzyl]-1,2,3,4-tetrahydropyrido[2,3-b]pyrazin-7-yl}benzoic acid was reacted with 1-(2-pyrimidinyl)piperazine as in General Procedure 10 to give the title compound. LCMS: m/z=593.97 (M+H$^+$); retention time=0.84 minutes.

Example 308

[4-(4-Chlorophenyl)-piperazin-1-yl]-(3-{1-[5-Chloro-2-(trifluoromethyl)benzyl]-1,2,3,4-tetrahydropyrido[2,3-b]pyrazin-7-yl}phenyl)methanone

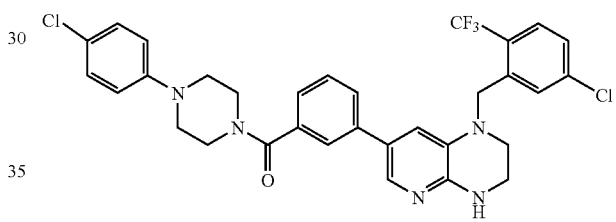

3-{1-[5-chloro-2-(trifluoromethyl)benzyl]-1,2,3,4-tetrahydropyrido[2,3-b]pyrazin-7-yl}benzoic acid was reacted with 1-(4-chlorophenyl)piperazine as in General Procedure 10 to give the title compound. LCMS: m/z=625.95 (M+H$^+$); retention time=1.05 minutes.

Example 309

[4-(4-Chlorophenyl)-4-hydroxypiperidin-1-yl]-(3-{1-[5-Chloro-2-(trifluoromethyl)benzyl]-1,2,3,4-tetrahydropyrido[2,3-b]pyrazin-7-yl}phenyl)methanone

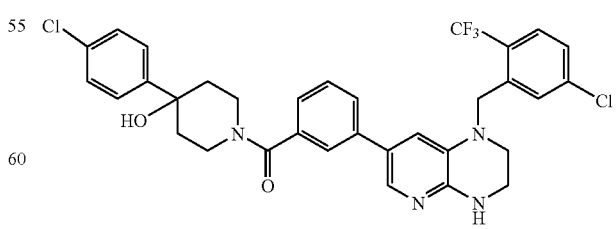

3-{1-[5-chloro-2-(trifluoromethyl)benzyl]-1,2,3,4-tetrahydropyrido[2,3-b]pyrazin-7-yl}benzoic acid was reacted with 4-(4-chlorophenyl)-4-hydroxypiperidine as in General Pro-

Example 310

1-[1-(3-{1-[5-Chloro-2-(trifluoromethyl)benzyl]-1,2,3,4-tetrahydropyrido[2,3-b]pyrazin-7-yl}benzoyl)piperidin-4-yl]-1,3-dihydrobenzoimidazol-2-one

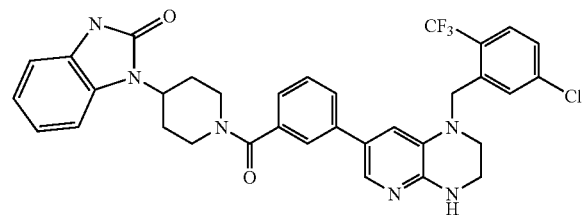

3-{1-[5-chloro-2-(trifluoromethyl)benzyl]-1,2,3,4-tetrahydropyrido[2,3-b]pyrazin-7-yl}benzoic acid was reacted with 1,3-dihydro-1-(4-piperidinyl)benzoimidazol-2-one as in General Procedure 10 to give the title compound. LCMS: m/z=647.02 (M+H$^+$); retention time=0.83 minutes.

Example 311

(3-{1-[5-Chloro-2-(trifluoromethyl)benzyl]-1,2,3,4-tetrahydropyrido[2,3-b]pyrazin-7-yl}phenyl)-[4-(2-methoxyphenyl)piperazin-1-yl]methanone

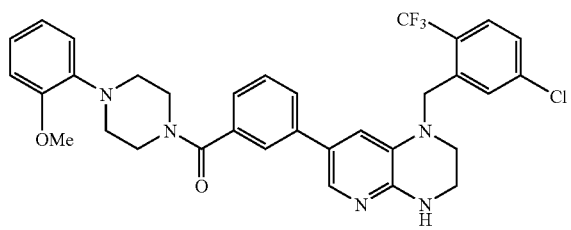

3-{1-[5-chloro-2-(trifluoromethyl)benzyl]-1,2,3,4-tetrahydropyrido[2,3-b]pyrazin-7-yl}benzoic acid was reacted with 1-(2-methoxyphenyl)piperazine as in General Procedure 10 to give the title compound. LCMS: m/z=621.97 (M+H$^+$); retention time=0.95 minutes.

Example 312

(3-{1-[5-Chloro-2-(trifluoromethyl)benzyl]-1,2,3,4-tetrahydropyrido[2,3-b]pyrazin-7-yl}phenyl)-{4-[3-(trifluoromethyl)phenyl]piperazin-1-yl}methanone

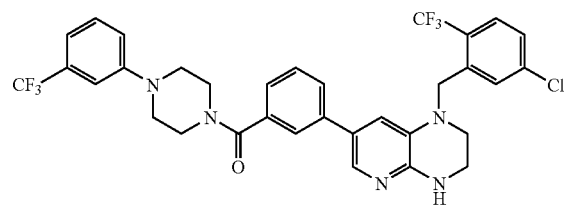

3-{1-[5-chloro-2-(trifluoromethyl)benzyl]-1,2,3,4-tetrahydropyrido[2,3-b]pyrazin-7-yl}benzoic acid was reacted with 1-[3-(trifluoromethyl)phenyl]piperazine as in General Procedure 10 to give the title compound. LCMS: m/z=640.96 (M+H$^+$); retention time=0.95 minutes.

Example 313

(3-{1-[5-Chloro-2-(trifluoromethyl)benzyl]-1,2,3,4-tetrahydropyrido[2,3-b]pyrazin-7-yl}phenyl)-(4-phenylpiperidin-1-yl)methanone

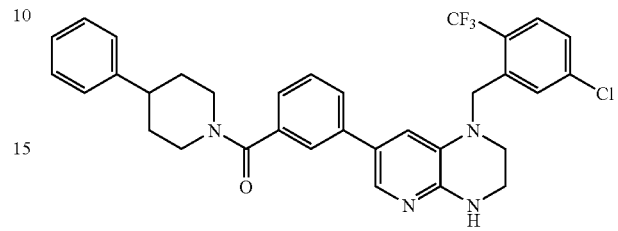

3-{1-[5-chloro-2-(trifluoromethyl)benzyl]-1,2,3,4-tetrahydropyrido[2,3-b]pyrazin-7-yl}benzoic acid was reacted with 4-phenylpiperidine as in General Procedure 10 to give the title compound. LCMS: m/z=590.98 (M+H$^+$); retention time=1.03 minutes.

Example 314

(3-{1-[5-Chloro-2-(trifluoromethyl)benzyl]-1,2,3,4-tetrahydropyrido[2,3-b]pyrazin-7-yl}phenyl)-[4-(1H-indol-3-yl)piperidin-1-yl]methanone

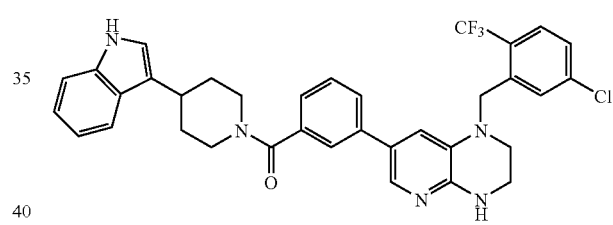

3-{1-[5-chloro-2-(trifluoromethyl)benzyl]-1,2,3,4-tetrahydropyrido[2,3-b]pyrazin-7-yl}benzoic acid was reacted with 4-(1H-indol-3-yl)piperidine as in General Procedure 10 to give the title compound. LCMS: m/z=630.02 (M+H$^+$); retention time=0.98 minutes.

Example 315

(4-Benzhydrylpiperazin-1-yl)-(3-{1-[5-Chloro-2-(trifluoromethyl)benzyl]-1,2,3,4-tetrahydropyrido[2,3-b]pyrazin-7-yl}phenyl)methanone

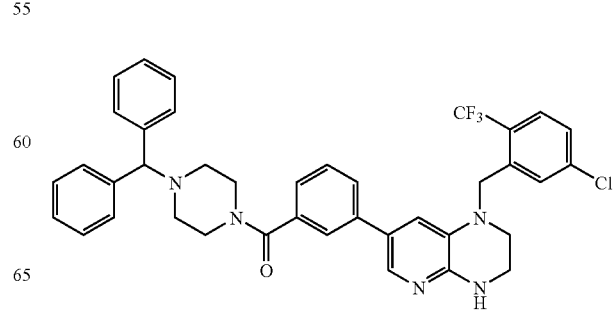

dure 10 to give the title compound. LCMS: m/z=659.98 (M+H$^+$); retention time=1.07 minutes.

3-{1-[5-chloro-2-(trifluoromethyl)benzyl]-1,2,3,4-tetrahydropyrido[2,3-b]pyrazin-7-yl}benzoic acid was reacted with 1-benzhydrylpiperazine as in General Procedure 10 to give the title compound. LCMS: m/z=680.97 (M+H$^+$); retention time=1.03 minutes.

Example 316

(4-Benzylpiperidin-1-yl)-(3-{1-[5-Chloro-2-(trifluoromethyl)benzyl]-1,2,3,4-tetrahydropyrido[2,3-b]pyrazin-7-yl}phenyl)methanone

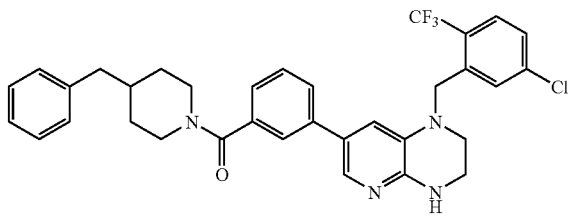

3-{1-[5-chloro-2-(trifluoromethyl)benzyl]-1,2,3,4-tetrahydropyrido[2,3-b]pyrazin-7-yl}benzoic acid was reacted with 4-benzylpiperidine as in General Procedure 10 to give the title compound. LCMS: m/z=605.01 (M+H$^+$); retention time=1.09 minutes.

Example 317

(3-{1-[5-Chloro-2-(trifluoromethyl)benzyl]-1,2,3,4-tetrahydropyrido[2,3-b]pyrazin-7-yl}phenyl)-[4-(3,4-dichlorophenyl)piperazin-1-yl]methanone

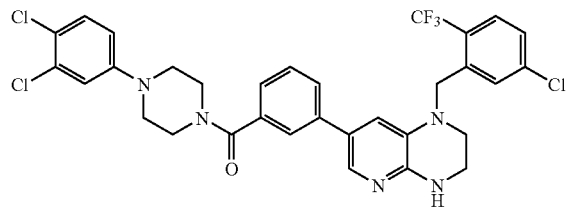

3-{1-[5-chloro-2-(trifluoromethyl)benzyl]-1,2,3,4-tetrahydropyrido[2,3-b]pyrazin-7-yl}benzoic acid was reacted with 1-(3,4-dichlorophenyl)piperazine as in General Procedure 10 to give the title compound. LCMS: m/z=661.88 (M+H$^+$); retention time=1.11 minutes.

Example 318

8-(3-{1-[5-Chloro-2-(trifluoromethyl)benzyl]-1,2,3,4-tetrahydropyrido[2,3-b]pyrazin-7-yl}benzoyl)-1-phenyl-1,3,8-triaza-spiro[4.5]decan-4-one

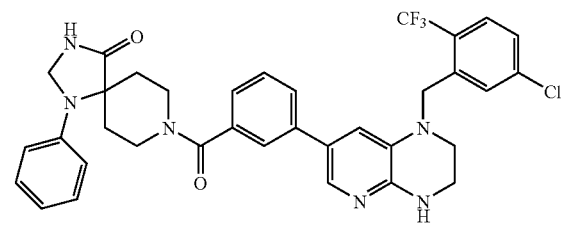

3-{1-[5-chloro-2-(trifluoromethyl)benzyl]-1,2,3,4-tetrahydropyrido[2,3-b]pyrazin-7-yl}benzoic acid was reacted with 1-phenyl-1,3,8-triaza-spiro[4.5]decan-4-one as in General Procedure 10 to give the title compound. LCMS: m/z=661.00 (M+H$^+$); retention time=0.87 minutes.

Example 319

(3-{1-[5-Chloro-2-(trifluoromethyl)benzyl]-1,2,3,4-tetrahydropyrido[2,3-b]pyrazin-7-yl}phenyl)-{4-[2-(trifluoromethyl)phenyl]piperazin-1-yl}methanone

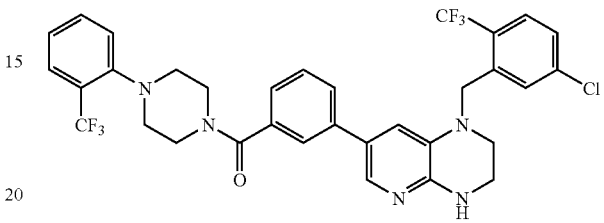

3-{1-[5-chloro-2-(trifluoromethyl)benzyl]-1,2,3,4-tetrahydropyrido[2,3-b]pyrazin-7-yl}benzoic acid was reacted with 1-[2-(trifluoromethyl)phenyl]piperazine as in General Procedure 10 to give the title compound. LCMS: m/z=659.99 (M+H$^+$); retention time=1.1 minutes.

Example 320

(3-{1-[5-Chloro-2-(trifluoromethyl)benzyl]-1,2,3,4-tetrahydropyrido[2,3-b]pyrazin-7-yl}phenyl)-(4-thieno[3,2-d]pyrimidin-4-ylpiperazin-1-yl)methanone

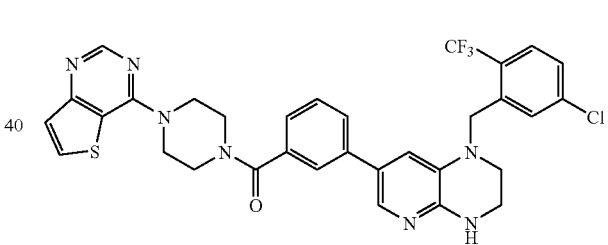

3-{1-[5-chloro-2-(trifluoromethyl)benzyl]-1,2,3,4-tetrahydropyrido[2,3-b]pyrazin-7-yl}benzoic acid was reacted with 1-(4-thieno[3,2-d]pyrimidinyl)piperazine as in General Procedure 10 to give the title compound. LCMS: m/z=649.98 (M+H$^+$); retention time=0.65 minutes.

Example 321

[4-(4-Chlorobenzyl)piperazin-1-yl]-(3-{1-[5-Chloro-2-(trifluoromethyl)benzyl]-1,2,3,4-tetrahydropyrido[2,3-b]pyrazin-7-yl}phenyl)methanone

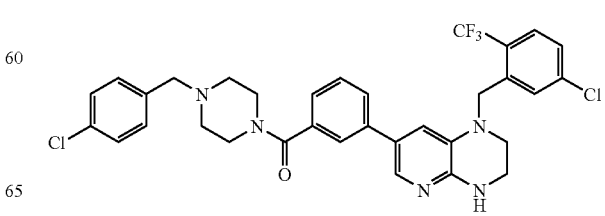

3-{1-[5-chloro-2-(trifluoromethyl)benzyl]-1,2,3,4-tetrahydropyrido[2,3-b]pyrazin-7-yl}benzoic acid was reacted with 1-(4-chlorobenzyl)piperazine as in General Procedure 10 to give the title compound. LCMS: m/z=639.99 (M+H⁺); retention time=0.7 minutes.

Example 322

(3-{1-[5-Chloro-2-(trifluoromethyl)benzyl]-1,2,3,4-tetrahydropyrido[2,3-b]pyrazin-7-yl}phenyl)-[4-(4-methoxybenzyl)piperazin-1-yl]methanone

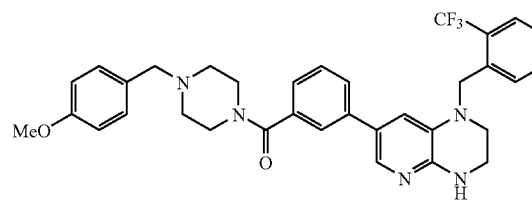

3-{1-[5-chloro-2-(trifluoromethyl)benzyl]-1,2,3,4-tetrahydropyrido[2,3-b]pyrazin-7-yl}benzoic acid was reacted with 1-(4-methoxybenzyl)piperazine as in General Procedure 10 to give the title compound. LCMS: m/z=636.01 (M+H⁺); retention time=0.62 minutes.

Example 323

(4-Benzoylpiperazin-1-yl)-(3-{1-[5-Chloro-2-(trifluoromethyl)benzyl]-1,2,3,4-tetrahydropyrido[2,3-b]pyrazin-7-yl}phenyl)methanone

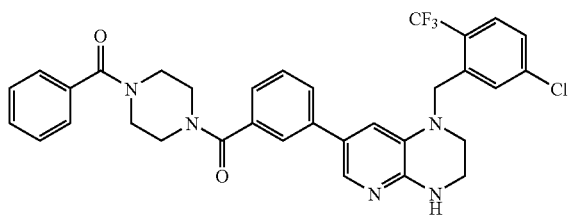

3-{1-[5-chloro-2-(trifluoromethyl)benzyl]-1,2,3,4-tetrahydropyrido[2,3-b]pyrazin-7-yl}benzoic acid was reacted with 1-benzoylpiperazine as in General Procedure 10 to give the title compound. LCMS: m/z=619.98 (M+H⁺); retention time=0.82 minutes.

Example 324

(3-{1-[5-Chloro-2-(trifluoromethyl)benzyl]-1,2,3,4-tetrahydropyrido[2,3-b]pyrazin-7-yl}phenyl)-(4-furo[3,2-c]pyridin-4-ylpiperazin-1-yl)methanone

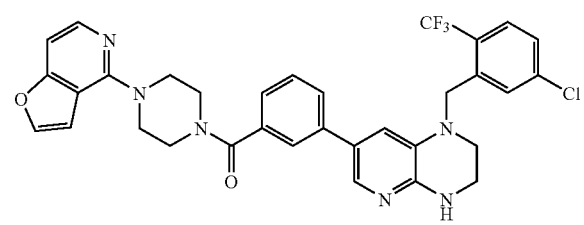

3-{1-[5-chloro-2-(trifluoromethyl)benzyl]-1,2,3,4-tetrahydropyrido[2,3-b]pyrazin-7-yl}benzoic acid was reacted with 1-(4-furo[3,2-c]pyridinyl)piperazine as in General Procedure 10 to give the title compound. LCMS: m/z=633.99 (M+H⁺); retention time=0.64 minutes.

Example 325

(3-{1-[5-Chloro-2-(trifluoromethyl)benzyl]-1,2,3,4-tetrahydropyrido[2,3-b]pyrazin-7-yl}phenyl)-[4-(6-fluorobenzo[d]isoxazol-3-yl)piperidin-1-yl]methanone

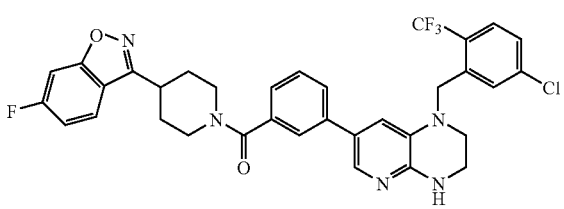

3-{1-[5-chloro-2-(trifluoromethyl)benzyl]-1,2,3,4-tetrahydropyrido[2,3-b]pyrazin-7-yl}benzoic acid was reacted with 4-(6-fluorobenzo[d]isoxazol-3-yl)piperidine as in General Procedure 10 to give the title compound. LCMS: m/z=649.95 (M+H⁺); retention time=1.00 minutes.

Example 326

4-(3-{1-[5-Chloro-2-(trifluoromethyl)benzyl]-1,2,3,4-tetrahydropyrido[2,3-b]pyrazin-7-yl}benzoylamino)piperidine-1-carboxylic acid ethyl ester

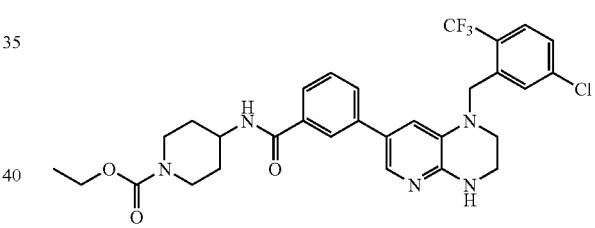

3-{1-[5-chloro-2-(trifluoromethyl)benzyl]-1,2,3,4-tetrahydropyrido[2,3-b]pyrazin-7-yl}benzoic acid was reacted with 4-aminopiperidine-1-carboxylic acid ethyl ester as in General Procedure 10 to give the title compound. LCMS: m/z=601.99 (M+H⁺); retention time=0.86 minutes.

Example 327

N-(1-Benzylpiperidin-4-yl)-3-{1-[5-chloro-2-(trifluoromethyl)benzyl]-1,2,3,4-tetrahydropyrido[2,3-b]pyrazin-7-yl}benzamide

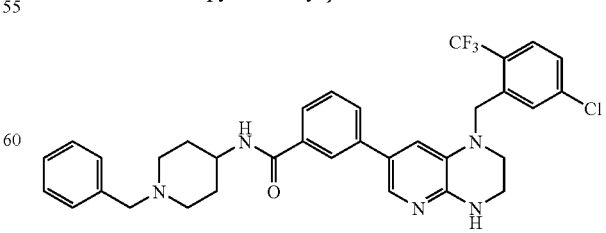

3-{1-[5-chloro-2-(trifluoromethyl)benzyl]-1,2,3,4-tetrahydropyrido[2,3-b]pyrazin-7-yl}benzoic acid was reacted with 4-amino-1-benzylpiperidine as in General Procedure 10 to give the title compound. LCMS: m/z=619.96 (M+H⁺); retention time=0.62 minutes.

Example 328

3-{1-[5-Chloro-2-(trifluoromethyl)benzyl]-1,2,3,4-tetrahydropyrido[2,3-b]pyrazin-7-yl}-N-(2,2-diphenylethyl)benzamide

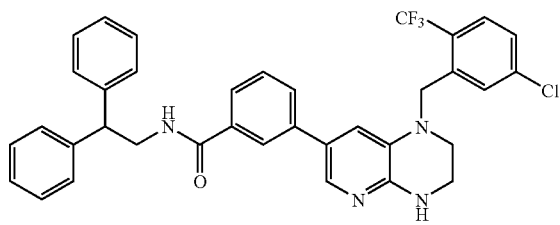

3-{1-[5-chloro-2-(trifluoromethyl)benzyl]-1,2,3,4-tetrahydropyrido[2,3-b]pyrazin-7-yl}benzoic acid was reacted with 2,2-diphenylethylamine as in General Procedure 10 to give the title compound. LCMS: m/z=626.96 (M+H⁺); retention time=1.06 minutes.

Example 329

3-{1-[5-Chloro-2-(trifluoromethyl)benzyl]-1,2,3,4-tetrahydropyrido[2,3-b]pyrazin-7-yl}-N-(1-methylpiperidin-4-yl)benzamide

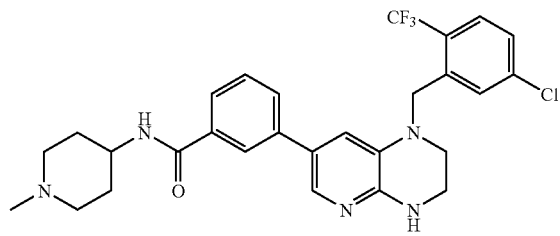

3-{1-[5-chloro-2-(trifluoromethyl)benzyl]-1,2,3,4-tetrahydropyrido[2,3-b]pyrazin-7-yl}benzoic acid was reacted with 4-amino-1-methylpiperidine as in General Procedure 10 to give the title compound. LCMS: m/z=543.99 (M+H⁺); retention time=0.53 minutes.

Example 330

(3-{1-[5-Chloro-2-(trifluoromethyl)benzyl]-1,2,3,4-tetrahydropyrido[2,3-b]pyrazin-7-yl}phenyl)-[4-(2-pyridin-2-yl-ethyl)piperazin-1-yl]methanone

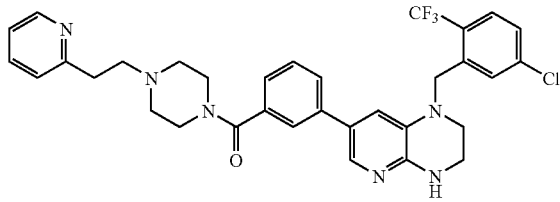

3-{1-[5-chloro-2-(trifluoromethyl)benzyl]-1,2,3,4-tetrahydropyrido[2,3-b]pyrazin-7-yl}benzoic acid was reacted with 1-piperazinyl-2-(2-pyridinyl)ethane as in General Procedure 10 to give the title compound. LCMS: m/z=620.99 (M+H⁺); retention time=0.55 minutes.

Example 331

3-{1-[5-Chloro-2-(trifluoromethyl)benzyl]-1,2,3,4-tetrahydropyrido[2,3-b]pyrazin-7-yl}-N-[4-(trifluoromethoxy)benzyl]benzamide

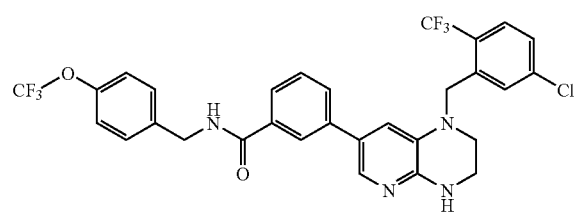

3-{1-[5-chloro-2-(trifluoromethyl)benzyl]-1,2,3,4-tetrahydropyrido[2,3-b]pyrazin-7-yl}benzoic acid was reacted with 4-(trifluoromethoxy)benzylamine as in General Procedure 10 to give the title compound. LCMS: m/z=620.94 (M+H⁺); retention time=1.04 minutes.

Example 332

N-[3,5-Bis(trifluoromethyl)benzyl]-3-{1-[5-chloro-2-(trifluoromethyl)benzyl]-1,2,3,4-tetrahydropyrido[2,3-b]pyrazin-7-yl}benzamide

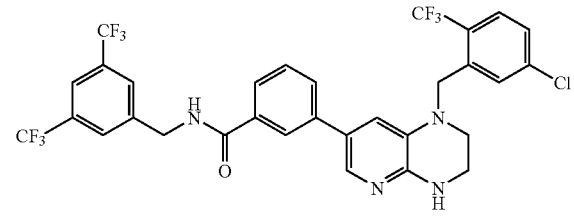

3-{1-[5-chloro-2-(trifluoromethyl)benzyl]-1,2,3,4-tetrahydropyrido[2,3-b]pyrazin-7-yl}benzoic acid was reacted with 3,5-bis(trifluoromethyl)benzylamine as in General Procedure 10 to give the title compound. LCMS: m/z=672.88 (M+H⁺); retention time=1.11 minutes.

Example 333

N-Benzhydryl-3-{1-[5-chloro-2-(trifluoromethyl)benzyl]-1,2,3,4-tetrahydropyrido[2,3-b]pyrazin-7-yl}benzamide

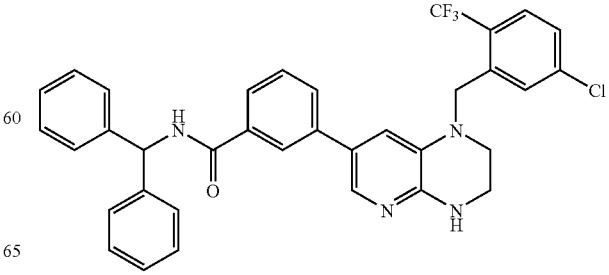

3-{1-[5-chloro-2-(trifluoromethyl)benzyl]-1,2,3,4-tetrahydropyrido[2,3-b]pyrazin-7-yl}benzoic acid was reacted with benzhydrylamine as in General Procedure 10 to give the title compound. LCMS: m/z=612.98 (M+H$^+$); retention time=1.06 minutes.

Example 334

3-{1-[5-Chloro-2-(trifluoromethyl)benzyl]-1,2,3,4-tetrahydropyrido[2,3-b]pyrazin-7-yl}-N-pyridin-4-ylmethylbenzamide

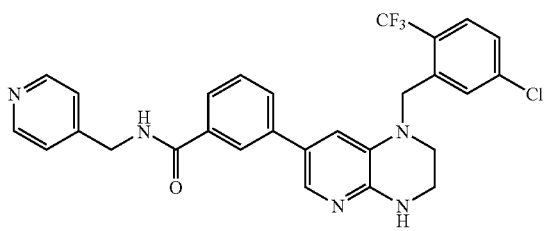

3-{1-[5-chloro-2-(trifluoromethyl)benzyl]-1,2,3,4-tetrahydropyrido[2,3-b]pyrazin-7-yl}benzoic acid was reacted with 4-(aminomethyl)pyridine as in General Procedure 10 to give the title compound. LCMS: m/z=537.96 (M+H$^+$); retention time=0.56 minutes.

Example 335

3-{1-[5-Chloro-2-(trifluoromethyl)benzyl]-1,2,3,4-tetrahydropyrido[2,3-b]pyrazin-7-yl}-N-pyridin-3-ylmethylbenzamide

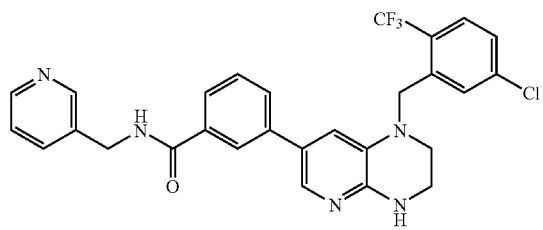

3-{1-[5-chloro-2-(trifluoromethyl)benzyl]-1,2,3,4-tetrahydropyrido[2,3-b]pyrazin-7-yl}benzoic acid was reacted with 3-(aminomethyl)pyridine as in General Procedure 10 to give the title compound. LCMS: m/z=538 (M+H$^+$); retention time=0.59 minutes.

Example 336

2-[4-(3-{1-[5-Chloro-2-(trifluoromethyl)benzyl]-1,2,3,4-tetrahydropyrido[2,3-b]pyrazin-7-yl}benzoyl)piperazin-1-yl]-N-isopropylacetamide

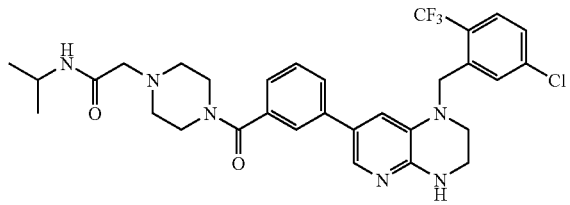

3-{1-[5-chloro-2-(trifluoromethyl)benzyl]-1,2,3,4-tetrahydropyrido[2,3-b]pyrazin-7-yl}benzoic acid was reacted with 2-piperazinyl-N-isopropylacetamide as in General Procedure 10 to give the title compound. LCMS: m/z=615.01 (M+H$^+$); retention time=0.61 minutes.

Example 337

(3-{1-[5-Chloro-2-(trifluoromethyl)benzyl]-1,2,3,4-tetrahydropyrido[2,3-b]pyrazin-7-yl}phenyl)-[4-(2-methylquinolin-4-yl)piperazin-1-yl]methanone

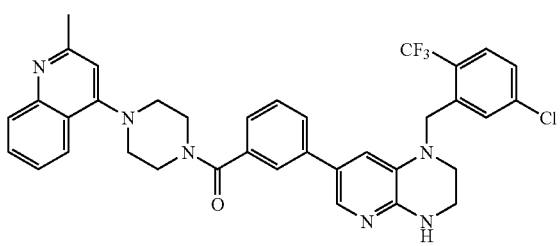

3-{1-[5-chloro-2-(trifluoromethyl)benzyl]-1,2,3,4-tetrahydropyrido[2,3-b]pyrazin-7-yl}benzoic acid was reacted with 2-methyl-4-(1-piperazinyl)quinoline as in General Procedure 10 to give the title compound. LCMS: m/z=656.99 (M+H$^+$); retention time=0.61 minutes.

Example 338

3-{1-[5-Chloro-2-(trifluoromethyl)benzyl]-1,2,3,4-tetrahydropyrido[2,3-b]pyrazin-7-yl}-N-[2-(4-sulfamoylphenyl)ethyl]benzamide

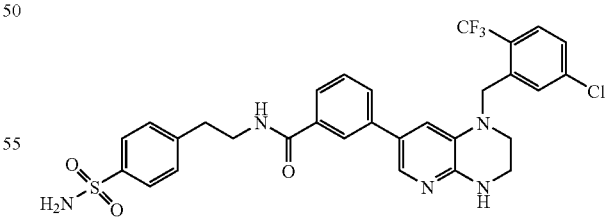

3-{1-[5-chloro-2-(trifluoromethyl)benzyl]-1,2,3,4-tetrahydropyrido[2,3-b]pyrazin-7-yl}benzoic acid was reacted with 2-(4-sulfamoylphenyl)ethylamine as in General Procedure 10 to give the title compound. LCMS: m/z=629.94 (M+H$^+$); retention time=0.77 minutes.

Example 339

(3-{1-[5-Chloro-2-(trifluoromethyl)benzyl]-1,2,3,4-tetrahydropyrido[2,3-b]pyrazin-7-yl}phenyl)-(2,3,5,6-tetrahydro-[1,2']bipyrazinyl-4-yl)methanone

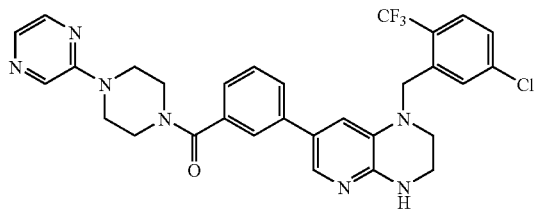

3-{1-[5-chloro-2-(trifluoromethyl)benzyl]-1,2,3,4-tetrahydropyrido[2,3-b]pyrazin-7-yl}benzoic acid was reacted with 2-(1-piperazinyl)pyrazine as in General Procedure 10 to give the title compound. LCMS: m/z=593.97 (M+H$^+$); retention time=0.78 minutes.

Example 340

3-{1-[5-Chloro-2-(trifluoromethyl)benzyl]-1,2,3,4-tetrahydropyrido[2,3-b]pyrazin-7-yl}-N-(2-phenylthiazol-4-ylmethyl)benzamide

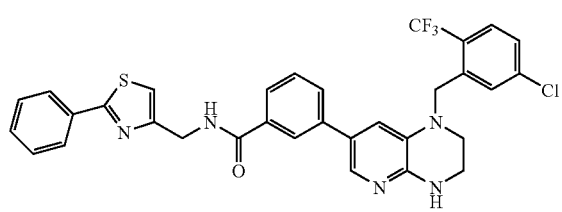

3-{1-[5-chloro-2-(trifluoromethyl)benzyl]-1,2,3,4-tetrahydropyrido[2,3-b]pyrazin-7-yl}benzoic acid was reacted with 2-phenyl-4-(aminomethyl)thiazole as in General Procedure 10 to give the title compound. LCMS: m/z=619.9 (M+H$^+$); retention time=0.99 minutes.

Example 341

(3-{1-[5-Chloro-2-(trifluoromethyl)benzyl]-1,2,3,4-tetrahydropyrido[2,3-b]pyrazin-7-yl}phenyl)morpholin-4-ylmethanone

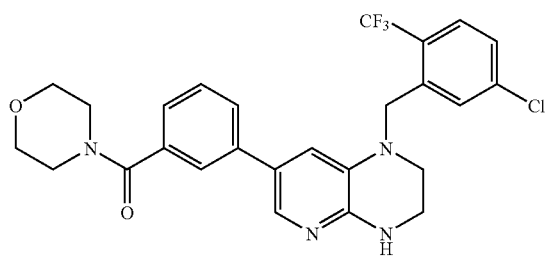

3-{1-[5-chloro-2-(trifluoromethyl)benzyl]-1,2,3,4-tetrahydropyrido[2,3-b]pyrazin-7-yl}benzoic acid was reacted with morpholine as in General Procedure 10 to give the title compound. LCMS: m/z=516.96 (M+H$^+$); retention time=0.76 minutes.

Example 342

3-{1-[5-Chloro-2-(trifluoromethyl)benzyl]-1,2,3,4-tetrahydropyrido[2,3-b]pyrazin-7-yl}-N-naphthalen-1-ylmethylbenzamide

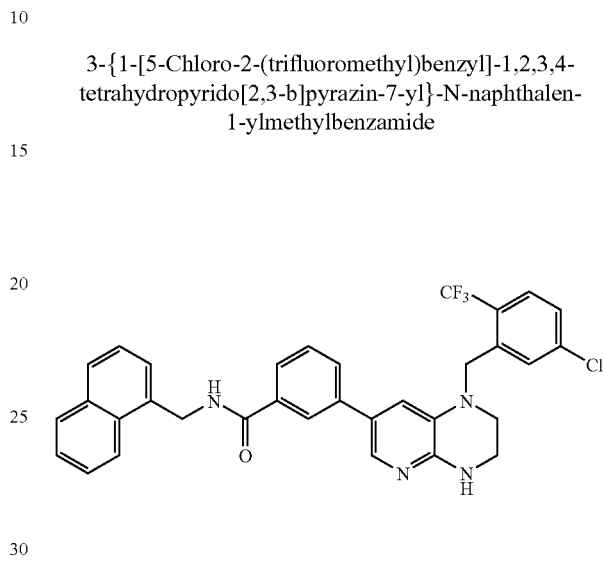

3-{1-[5-chloro-2-(trifluoromethyl)benzyl]-1,2,3,4-tetrahydropyrido[2,3-b]pyrazin-7-yl}benzoic acid was reacted with 1-(aminomethyl)naphthalene as in General Procedure 10 to give the title compound. LCMS: m/z=586.96 (M+H$^+$); retention time=1.02 minutes.

Example 343

3-{1-[5-Chloro-2-(trifluoromethyl)benzyl]-1,2,3,4-tetrahydropyrido[2,3-b]pyrazin-7-yl}-N-indan-1-ylbenzamide

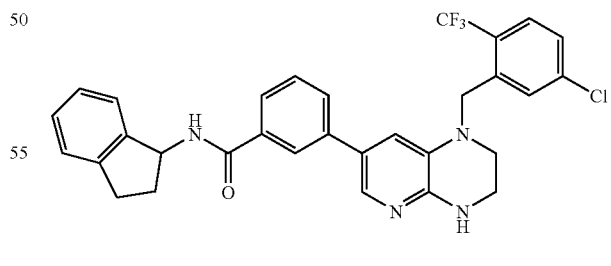

3-{1-[5-chloro-2-(trifluoromethyl)benzyl]-1,2,3,4-tetrahydropyrido[2,3-b]pyrazin-7-yl}benzoic acid was reacted with 1-aminoindan as in General Procedure 10 to give the title compound. LCMS: m/z=562.95 (M+H$^+$); retention time=0.99 minutes.

Example 344

(3-{1-[5-Chloro-2-(trifluoromethyl)benzyl]-1,2,3,4-tetrahydropyrido[2,3-b]pyrazin-7-yl}phenyl)-[4-(3-methoxyphenyl)piperazin-1-yl]methanone

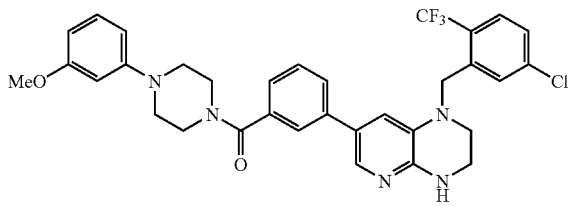

3-{1-[5-chloro-2-(trifluoromethyl)benzyl]-1,2,3,4-tetrahydropyrido[2,3-b]pyrazin-7-yl}benzoic acid was reacted with 1-(3-methoxyphenyl)piperazine as in General Procedure 10 to give the title compound. LCMS: m/z=622.01 (M+H$^+$); retention time=0.97 minutes.

Example 345

(3-{1-[5-Chloro-2-(trifluoromethyl)benzyl]-1,2,3,4-tetrahydropyrido[2,3-b]pyrazin-7-yl}phenyl)-[4-(4-methoxyphenyl)piperazin-1-yl]methanone

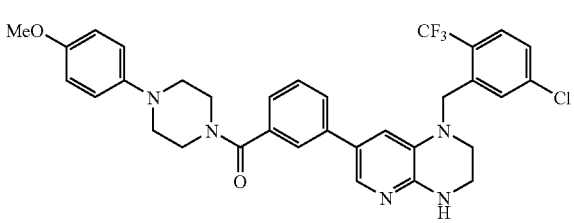

3-{1-[5-chloro-2-(trifluoromethyl)benzyl]-1,2,3,4-tetrahydropyrido[2,3-b]pyrazin-7-yl}benzoic acid was reacted with 1-(4-methoxyphenyl)piperazine as in General Procedure 10 to give the title compound. LCMS: m/z=621.98 (M+H$^+$); retention time=0.92 minutes.

Example 346

3-{1-[5-Chloro-2-(trifluoromethyl)benzyl]-1,2,3,4-tetrahydropyrido[2,3-b]pyrazin-7-yl}-N-cyclohexyl-benzamide

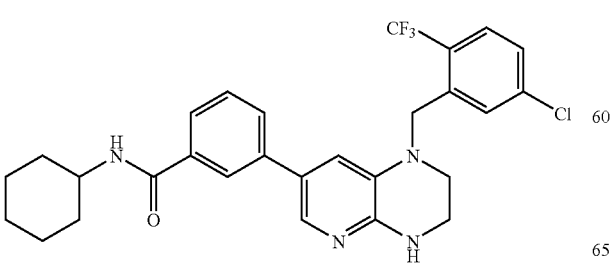

3-{1-[5-chloro-2-(trifluoromethyl)benzyl]-1,2,3,4-tetrahydropyrido[2,3-b]pyrazin-7-yl}benzoic acid was reacted with cyclohexylamine as in General Procedure 10 to give the title compound. LCMS: m/z=529.01 (M+H$^+$); retention time=0.96 minutes.

Example 347

3-{1-[5-Chloro-2-(trifluoromethyl)benzyl]-1,2,3,4-tetrahydropyrido[2,3-b]pyrazin-7-yl}-N-(4-methanesulfonylbenzyl)benzamide

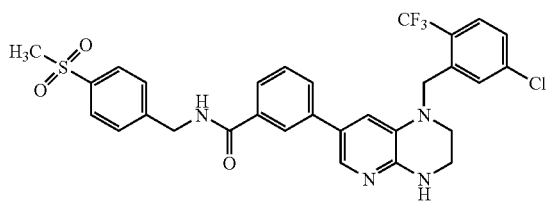

3-{1-[5-chloro-2-(trifluoromethyl)benzyl]-1,2,3,4-tetrahydropyrido[2,3-b]pyrazin-7-yl}benzoic acid was reacted with 4-methanesulfonylbenzylamine as in General Procedure 10 to give the title compound. LCMS: m/z=614.91 (M+H$^+$); retention time=0.81 minutes.

Example 348

N-(2-Chlorobenzyl)-3-{1-[5-Chloro-2-(trifluoromethyl)benzyl]-1,2,3,4-tetrahydropyrido[2,3-b]pyrazin-7-yl}benzamide

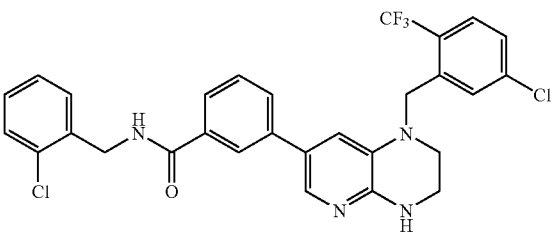

3-{1-[5-chloro-2-(trifluoromethyl)benzyl]-1,2,3,4-tetrahydropyrido[2,3-b]pyrazin-7-yl}benzoic acid was reacted with 2-chlorobenzylamine as in General Procedure 10 to give the title compound. LCMS: m/z=570.9 (M+H$^+$); retention time=0.98 minutes.

Example 349

N-(4-Chlorobenzyl)-3-{1-[5-Chloro-2-(trifluoromethyl)benzyl]-1,2,3,4-tetrahydropyrido[2,3-b]pyrazin-7-yl}benzamide

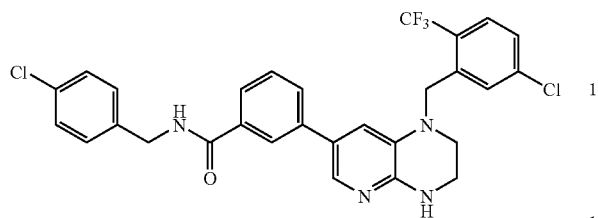

3-{1-[5-chloro-2-(trifluoromethyl)benzyl]-1,2,3,4-tetrahydropyrido[2,3-b]pyrazin-7-yl}benzoic acid was reacted with 4-chlorobenzylamine as in General Procedure 10 to give the title compound. LCMS: m/z=570.9 (M+H$^+$); retention time=0.99 minutes.

Example 350

N-(3-Chlorobenzyl)-3-{1-[5-Chloro-2-(trifluoromethyl)benzyl]-1,2,3,4-tetrahydropyrido[2,3-b]pyrazin-7-yl}benzamide

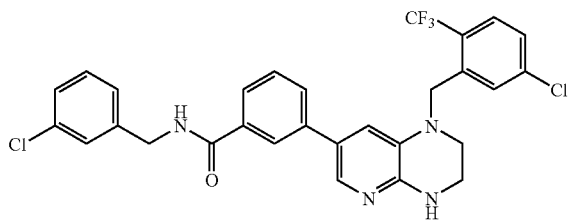

3-{1-[5-chloro-2-(trifluoromethyl)benzyl]-1,2,3,4-tetrahydropyrido[2,3-b]pyrazin-7-yl}benzoic acid was reacted with 3-chlorobenzylamine as in General Procedure 10 to give the title compound. LCMS: m/z=570.99 (M+H$^+$); retention time=0.99 minutes.

Example 351

(3-{1-[5-Chloro-2-(trifluoromethyl)benzyl]-1,2,3,4-tetrahydropyrido[2,3-b]pyrazin-7-yl}phenyl)-[4-(tetrahydrofuran-2-carbonyl)piperazin-1-yl]methanone

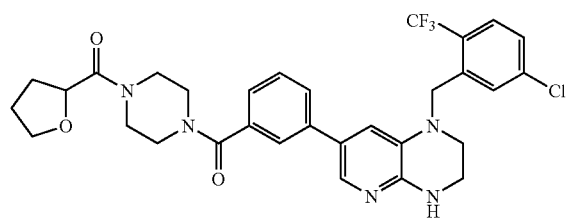

3-{1-[5-chloro-2-(trifluoromethyl)benzyl]-1,2,3,4-tetrahydropyrido[2,3-b]pyrazin-7-yl}benzoic acid was reacted with 1-(tetrahydrofuran-2-carbonyl)piperazine as in General Procedure 10 to give the title compound. LCMS: m/z=613.98 (M+H$^+$); retention time=0.73 minutes.

Example 352

3-{1-[5-Chloro-2-(trifluoromethyl)benzyl]-1,2,3,4-tetrahydropyrido[2,3-b]pyrazin-7-yl}-N-(tetrahydrofuran-2-ylmethyl)benzamide

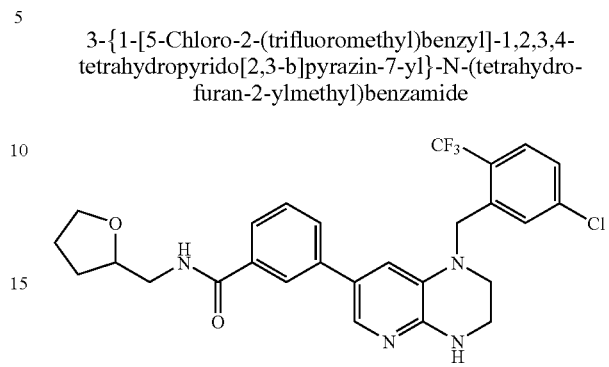

3-{1-[5-chloro-2-(trifluoromethyl)benzyl]-1,2,3,4-tetrahydropyrido[2,3-b]pyrazin-7-yl}benzoic acid was reacted with 2-(aminomethyl)tetrahydrofuran as in General Procedure 10 to give the title compound. LCMS: m/z=530.97 (M+H$^+$); retention time=0.81 minutes.

Example 353

3-{1-[5-Chloro-2-(trifluoromethyl)benzyl]-1,2,3,4-tetrahydropyrido[2,3-b]pyrazin-7-yl}-N-(3-methoxybenzyl)benzamide

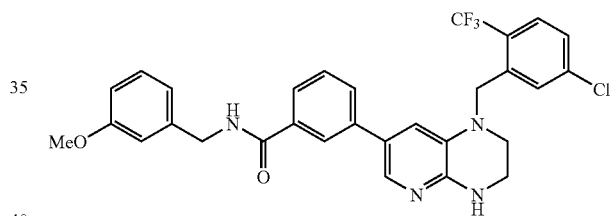

3-{1-[5-chloro-2-(trifluoromethyl)benzyl]-1,2,3,4-tetrahydropyrido[2,3-b]pyrazin-7-yl}benzoic acid was reacted with 3-methoxybenzylamine as in General Procedure 10 to give the title compound. LCMS: m/z=566.99 (M+H$^+$); retention time=0.93 minutes.

Example 354

3-{1-[5-Chloro-2-(trifluoromethyl)benzyl]-1,2,3,4-tetrahydropyrido[2,3-b]pyrazin-7-yl}-N-(4-methoxybenzyl)benzamide

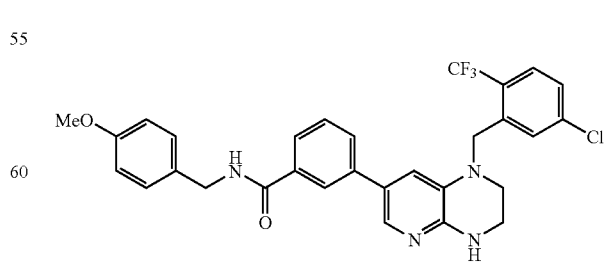

3-{1-[5-chloro-2-(trifluoromethyl)benzyl]-1,2,3,4-tetrahydropyrido[2,3-b]pyrazin-7-yl}benzoic acid was reacted with 4-methoxybenzylamine as in General Procedure 10 to give the title compound. LCMS: m/z=566.93 (M+H$^+$); retention time=0.91 minutes.

Example 355

3-{1-[5-Chloro-2-(trifluoromethyl)benzyl]-1,2,3,4-tetrahydropyrido[2,3-b]pyrazin-7-yl}-N-(2-phenoxyethyl)benzamide

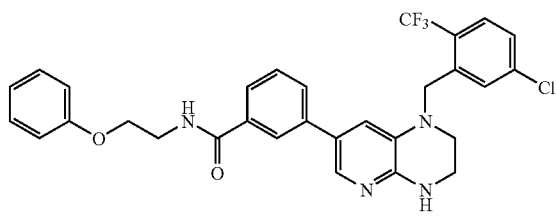

3-{1-[5-chloro-2-(trifluoromethyl)benzyl]-1,2,3,4-tetrahydropyrido[2,3-b]pyrazin-7-yl}benzoic acid was reacted with 2-phenoxyethylamine as in General Procedure 10 to give the title compound. LCMS: m/z=566.93 (M+H$^+$); retention time=0.94 minutes.

Example 356

N-Benzyl-3-{1-[5-Chloro-2-(trifluoromethyl)benzyl]-1,2,3,4-tetrahydropyrido[2,3-b]pyrazin-7-yl}benzamide

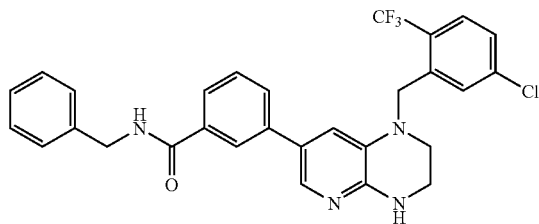

3-{1-[5-chloro-2-(trifluoromethyl)benzyl]-1,2,3,4-tetrahydropyrido[2,3-b]pyrazin-7-yl}benzoic acid was reacted with benzylamine as in General Procedure 10 to give the title compound. LCMS: m/z=536.96 (M+H$^+$); retention time=0.92 minutes.

Example 357

[4-(3-Chlorophenyl)piperazin-1-yl]-(3-{1-[5-chloro-2-(trifluoromethyl)benzyl]-1,2,3,4-tetrahydropyrido[2,3-b]pyrazin-7-yl}phenyl)methanone

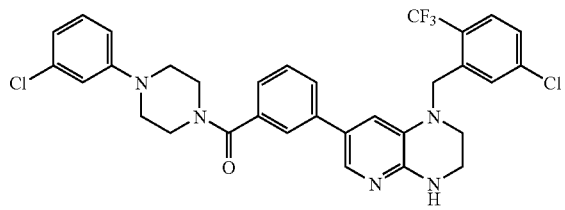

3-{1-[5-chloro-2-(trifluoromethyl)benzyl]-1,2,3,4-tetrahydropyrido[2,3-b]pyrazin-7-yl}benzoic acid was reacted with 1-(3-chlorophenyl)piperazine as in General Procedure 10 to give the title compound. LCMS: m/z=625.97 (M+H$^+$); retention time=1.05 minutes.

Example 358

3-{1-[5-Chloro-2-(trifluoromethyl)benzyl]-1,2,3,4-tetrahydropyrido[2,3-b]pyrazin-7-yl}-N-indan-2-ylbenzamide

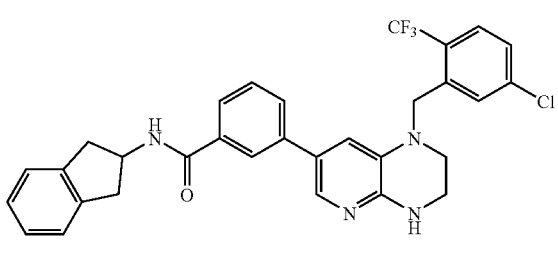

3-{1-[5-chloro-2-(trifluoromethyl)benzyl]-1,2,3,4-tetrahydropyrido[2,3-b]pyrazin-7-yl}benzoic acid was reacted with 2-aminoindan as in General Procedure 10 to give the title compound. LCMS: m/z=562.95 (M+H$^+$); retention time=0.98 minutes.

Example 359

(3-{1-[5-Chloro-2-(trifluoromethyl)benzyl]-1,2,3,4-tetrahydropyrido[2,3-b]pyrazin-7-yl}phenyl)-(4-phenethylpiperazin-1-yl)methanone

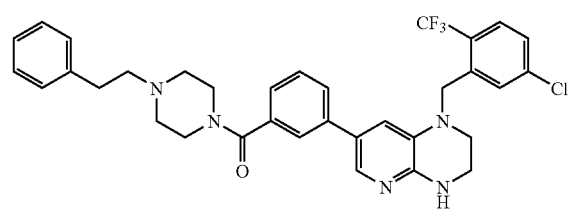

3-{1-[5-chloro-2-(trifluoromethyl)benzyl]-1,2,3,4-tetrahydropyrido[2,3-b]pyrazin-7-yl}benzoic acid was reacted with 1-phenethylpiperazine as in General Procedure 10 to give the title compound. LCMS: m/z=618.98 (M+H$^+$); retention time=0.64 minutes.

Example 360

[4-(2-Chlorophenyl)piperazin-1-yl]-(3-{1-[5-chloro-2-(trifluoromethyl)benzyl]-1,2,3,4-tetrahydropyrido[2,3-b]pyrazin-7-yl}phenyl)methanone

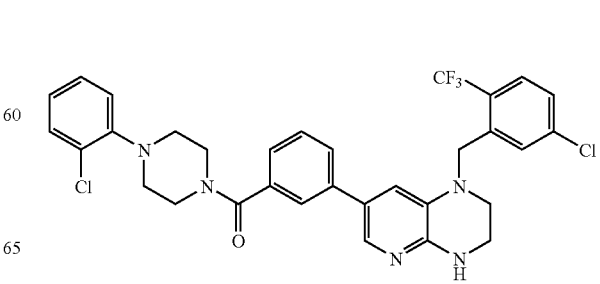

3-{1-[5-chloro-2-(trifluoromethyl)benzyl]-1,2,3,4-tetrahydropyrido[2,3-b]pyrazin-7-yl}benzoic acid was reacted with 1-(2-chlorophenyl)piperazine as in General Procedure 10 to give the title compound. LCMS: m/z=625.96 (M+H+); retention time=1.05 minutes.

Example 361

N-(1-Benzylpyrrolidin-3-yl)-3-{1-[5-chloro-2-(trifluoromethyl)benzyl]-1,2,3,4-tetrahydropyrido[2,3-b]pyrazin-7-yl}benzamide

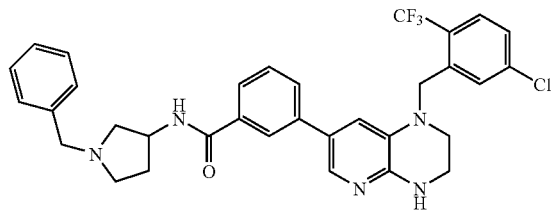

3-{1-[5-chloro-2-(trifluoromethyl)benzyl]-1,2,3,4-tetrahydropyrido[2,3-b]pyrazin-7-yl}benzoic acid was reacted with 3-amino-1-benzylpyrrolidine as in General Procedure 10 to give the title compound. LCMS: m/z=604.99 (M+H+); retention time=0.63 minutes.

Example 362

(3-{1-[5-Chloro-2-(trifluoromethyl)benzyl]-1,2,3,4-tetrahydropyrido[2,3-b]pyrazin-7-yl}phenyl)-[4-(cyclohexylmethyl)piperazin-1-yl]methanone

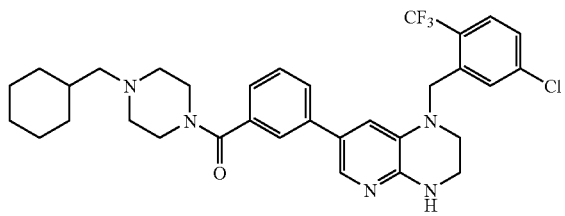

3-{1-[5-chloro-2-(trifluoromethyl)benzyl]-1,2,3,4-tetrahydropyrido[2,3-b]pyrazin-7-yl}benzoic acid was reacted with 1-(cyclohexylmethyl)piperazine as in General Procedure 10 to give the title compound. LCMS: m/z=611.96 (M+H+); retention time=0.65 minutes.

Example 363

3-{1-[5-Chloro-2-(trifluoromethyl)benzyl]-1,2,3,4-tetrahydropyrido[2,3-b]pyrazin-7-yl}-N-(4-sulfamoylbenzyl)benzamide

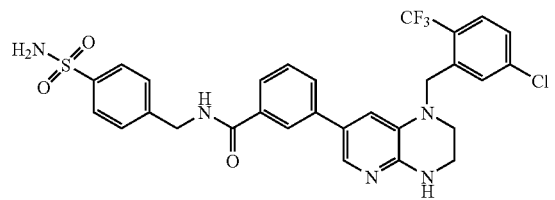

3-{1-[5-chloro-2-(trifluoromethyl)benzyl]-1,2,3,4-tetrahydropyrido[2,3-b]pyrazin-7-yl}benzoic acid was reacted with 4-sulfamoylbenzylamine as in General Procedure 10 to give the title compound. LCMS: In/z=615.9 (M+H+); retention time=0.77 minutes.

Example 364

(3-{1-[5-Chloro-2-(trifluoromethyl)benzyl]-1,2,3,4-tetrahydropyrido[2,3-b]pyrazin-7-yl}phenyl)-(4-morpholin-4-ylpiperidin-1-yl)methanone

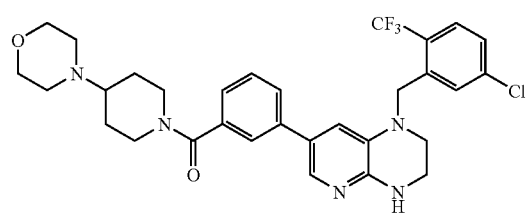

3-{1-[5-chloro-2-(trifluoromethyl)benzyl]-1,2,3,4-tetrahydropyrido[2,3-b]pyrazin-7-yl}benzoic acid was reacted with 4-(4-morpholinyl)piperidine as in General Procedure 10 to give the title compound. LCMS: m/z=598.99 (M+H+); retention time=0.52 minutes.

Example 365

(3-{1-[5-Chloro-2-(trifluoromethyl)benzyl]-1,2,3,4-tetrahydropyrido[2,3-b]pyrazin-7-yl}phenyl)-((S)-2-pyrrolidin-1-ylmethylpyrrolidin-1-yl)methanone

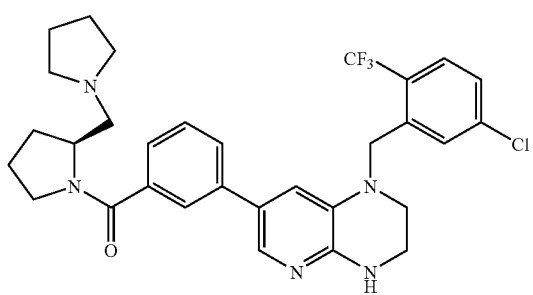

3-{1-[5-chloro-2-(trifluoromethyl)benzyl]-1,2,3,4-tetrahydropyrido[2,3-b]pyrazin-7-yl}benzoic acid was reacted with (S)-2-(1-pyrrolidinylmethyl)pyrrolidine as in General Procedure 10 to give the title compound. LCMS: m/z=583.96 (M+H+); retention time=0.58 minutes.

Example 366

(3-{1-[5-Chloro-2-(trifluoromethyl)benzyl]-1,2,3,4-tetrahydropyrido[2,3-b]pyrazin-7-yl}phenyl)-(2-pyridin-3-ylpyrrolidin-1-yl)methanone

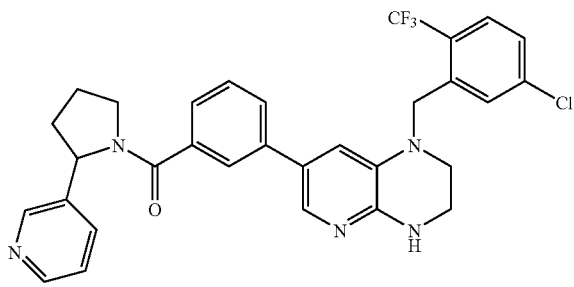

3-{1-[5-chloro-2-(trifluoromethyl)benzyl]-1,2,3,4-tetrahydropyrido[2,3-b]pyrazin-7-yl}benzoic acid was reacted with 2-(3-pyridinyl)pyrrolidine as in General Procedure 10 to give the title compound. LCMS: m/z=577.95 (M+H$^+$); retention time=0.65 minutes.

Example 367

3-{1-[5-Chloro-2-(trifluoromethyl)benzyl]-1,2,3,4-tetrahydropyrido[2,3-b]pyrazin-7-yl}-N-(2-methoxybenzyl)-N-methylbenzamide

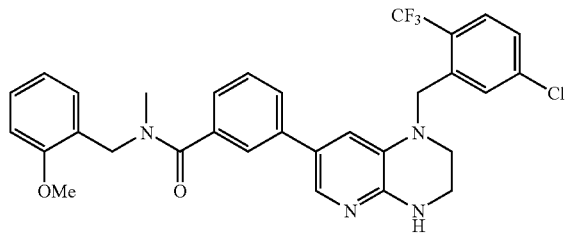

3-{1-[5-chloro-2-(trifluoromethyl)benzyl]-1,2,3,4-tetrahydropyrido[2,3-b]pyrazin-7-yl}benzoic acid was reacted with N-methyl-2-methoxybenzylamine as in General Procedure 10 to give the title compound. LCMS: m/z=580.94 (M+H$^+$); retention time=0.96 minutes.

Example 368

(4-{1-[5-Chloro-2-(trifluoromethyl)benzyl]-1,2,3,4-tetrahydropyrido[2,3-b]pyrazin-7-yl}phenyl)-(4-phenylpiperazin-1-yl)methanone

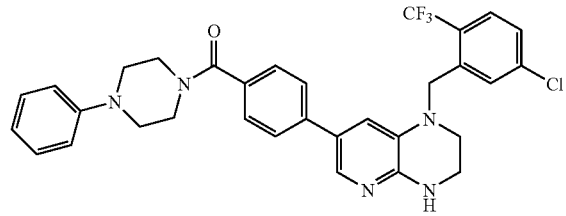

4-{1-[5-chloro-2-(trifluoromethyl)benzyl]-1,2,3,4-tetrahydropyrido[2,3-b]pyrazin-7-yl}benzoic acid was reacted with 1-phenylpiperazine as in General Procedure 10 to give the title compound. LCMS: m/z=592.00 (M+H$^+$); retention time=0.98 minutes.

Example 369

(4-{1-[5-Chloro-2-(trifluoromethyl)benzyl]-1,2,3,4-tetrahydropyrido[2,3-b]pyrazin-7-yl}phenyl)-(4-pyrimidin-2-ylpiperazin-1-yl)methanone

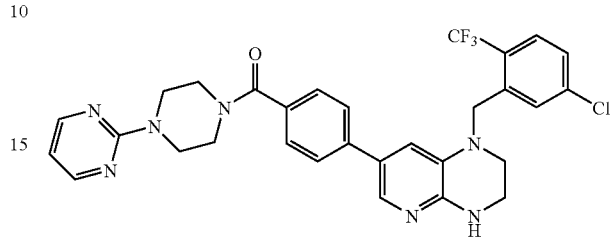

4-{1-[5-chloro-2-(trifluoromethyl)benzyl]-1,2,3,4-tetrahydropyrido[2,3-b]pyrazin-7-yl}benzoic acid was reacted with 1-(2-pyrimidinyl)piperazine as in General Procedure 10 to give the title compound. LCMS: m/z=593.98 (M+H$^+$); retention time=0.84 minutes.

Example 370

[4-(4-Chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone

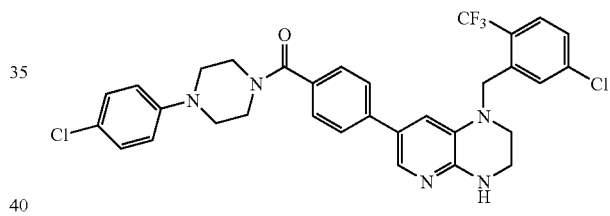

4-{1-[5-chloro-2-(trifluoromethyl)benzyl]-1,2,3,4-tetrahydropyrido[2,3-b]pyrazin-7-yl}benzoic acid was reacted with 1-(4-chlorophenyl)piperazine as in General Procedure 10 to give the title compound. LCMS: m/z=625.96 (M+H$^+$); retention time=1.06 minutes.

Example 371

[4-(4-Chlorophenyl)-4-hydroxypiperidin-1-yl]-(4-{1-[5-chloro-2-(trifluoromethyl)benzyl]-1,2,3,4-tetrahydropyrido[2,3-b]pyrazin-7-yl}phenyl)methanone

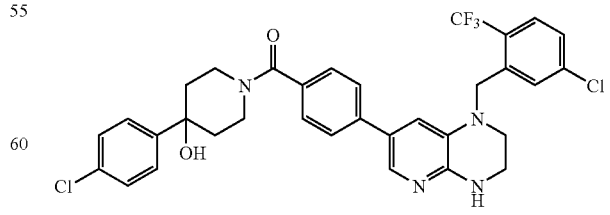

4-{1-[5-chloro-2-(trifluoromethyl)benzyl]-1,2,3,4-tetrahydropyrido[2,3-b]pyrazin-7-yl}benzoic acid was reacted with 4-(4-chlorophenyl)-4-hydroxypiperidine as in General Procedure 10 to give the title compound. LCMS: m/z=640.96 (M+H⁺); retention time=0.94 minutes.

Example 372

1-[1-(4-{1-[5-Chloro-2-(trifluoromethyl)benzyl]-1,2,3,4-tetrahydropyrido[2,3-b]pyrazin-7-yl}benzoyl)piperidin-4-yl]-1,3-dihydrobenzoimidazol-2-one

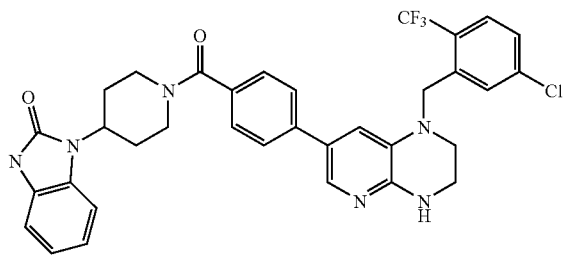

4-{1-[5-chloro-2-(trifluoromethyl)benzyl]-1,2,3,4-tetrahydropyrido[2,3-b]pyrazin-7-yl}benzoic acid was reacted with 1,3-dihydro-1-(4-piperidinyl)benzoimidazol-2-one as in General Procedure 10 to give the title compound. LCMS: m/z=647.03 (M+H⁺); retention time=0.81 minutes.

Example 373

(4-{1-[5-Chloro-2-(trifluoromethyl)benzyl]-1,2,3,4-tetrahydropyrido[2,3-b]pyrazin-7-yl}phenyl)-[4-(2-methoxyphenyl)piperazin-1-yl]methanone

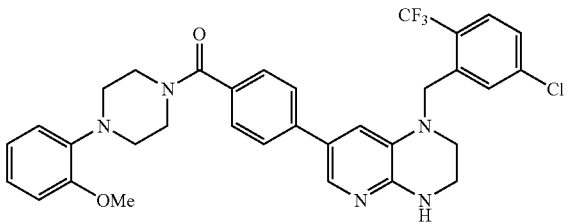

4-{1-[5-chloro-2-(trifluoromethyl)benzyl]-1,2,3,4-tetrahydropyrido[2,3-b]pyrazin-7-yl}benzoic acid was reacted with 1-(2-methoxyphenyl)piperazine as in General Procedure 10 to give the title compound. LCMS: m/z=621.98 (M+H⁺); retention time=0.95 minutes.

Example 374

(4-{1-[5-Chloro-2-(trifluoromethyl)benzyl]-1,2,3,4-tetrahydropyrido[2,3-b]pyrazin-7-yl}phenyl)-{4-[3-(trifluoromethyl)phenyl]piperazin-1-yl}methanone

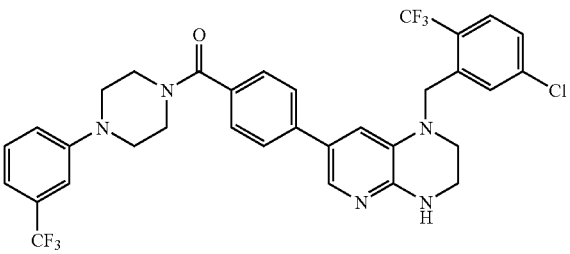

4-{1-[5-chloro-2-(trifluoromethyl)benzyl]-1,2,3,4-tetrahydropyrido[2,3-b]pyrazin-7-yl}benzoic acid was reacted with 1-[3-(trifluoromethyl)phenyl]piperazine as in General Procedure 10 to give the title compound. LCMS: m/z=659.99 (M+H⁺); retention time=1.08 minutes.

Example 375

(4-{1-[5-Chloro-2-(trifluoromethyl)benzyl]-1,2,3,4-tetrahydropyrido[2,3-b]pyrazin-7-yl}phenyl)-(4-phenylpiperidin-1-yl)methanone

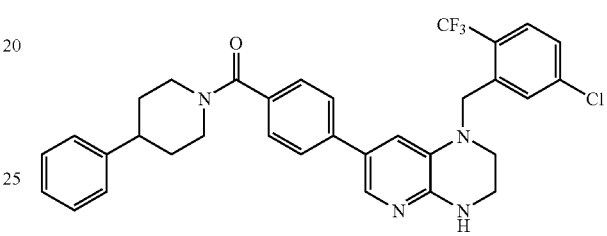

4-{1-[5-chloro-2-(trifluoromethyl)benzyl]-1,2,3,4-tetrahydropyrido[2,3-b]pyrazin-7-yl}benzoic acid was reacted with 4-phenylpiperidine as in General Procedure 10 to give the title compound. LCMS: m/z=590.99 (M+H⁺); retention time=1.04 minutes.

Example 376

(4-{1-[5-Chloro-2-(trifluoromethyl)benzyl]-1,2,3,4-tetrahydropyrido[2,3-b]pyrazin-7-yl}phenyl)-[4-(1H-indol-3-yl)piperidin-1-yl]methanone

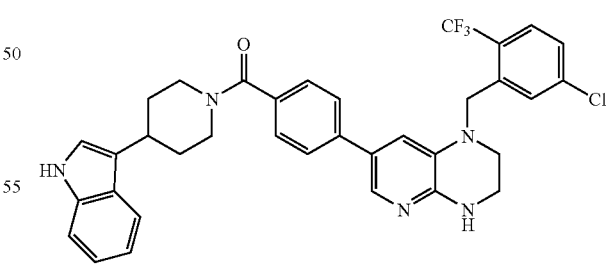

4-{1-[5-chloro-2-(trifluoromethyl)benzyl]-1,2,3,4-tetrahydropyrido[2,3-b]pyrazin-7-yl}benzoic acid was reacted with 4-(1H-indol-3-yl)piperidine as in General Procedure 10 to give the title compound. LCMS: m/z=630.92 (M+H⁺); retention time=0.99 minutes.

Example 377

(4-Benzhydrylpiperazin-1-yl)-(4-{1-[5-chloro-2-(trifluoromethyl)benzyl]-1,2,3,4-tetrahydropyrido[2,3-b]pyrazin-7-yl}phenyl)methanone

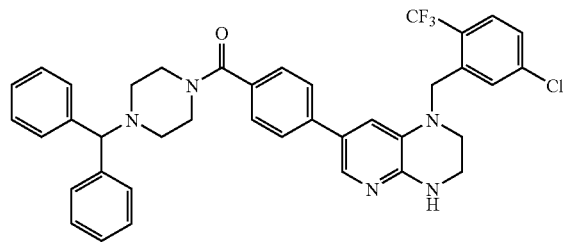

4-{1-[5-chloro-2-(trifluoromethyl)benzyl]-1,2,3,4-tetrahydropyrido[2,3-b]pyrazin-7-yl}benzoic acid was reacted with 1-benzhydrylpiperazine as in General Procedure 10 to give the title compound. LCMS: m/z=680.99 (M+H$^+$); retention time=1.00 minutes.

Example 378

(4-Benzylpiperidin-1-yl)-(4-{1-[5-chloro-2-(trifluoromethyl)benzyl]-1,2,3,4-tetrahydropyrido[2,3-b]pyrazin-7-yl}phenyl)methanone

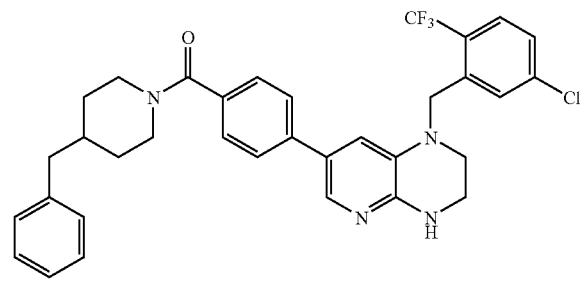

4-{1-[5-chloro-2-(trifluoromethyl)benzyl]-1,2,3,4-tetrahydropyrido[2,3-b]pyrazin-7-yl}benzoic acid was reacted with 4-benzylpiperidine as in General Procedure 10 to give the title compound. LCMS: m/z=605.00 (M+H$^+$); retention time=1.09 minutes.

Example 379

(4-{1-[5-Chloro-2-(trifluoromethyl)benzyl]-1,2,3,4-tetrahydropyrido[2,3-b]pyrazin-7-yl}phenyl)-[4-(3,4-dichlorophenyl)piperazin-1-yl]methanone

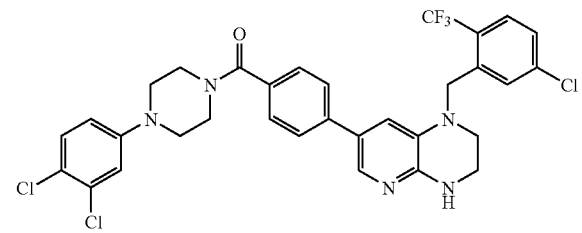

4-{1-[5-chloro-2-(trifluoromethyl)benzyl]-1,2,3,4-tetrahydropyrido[2,3-b]pyrazin-7-yl}benzoic acid was reacted with 1-(3,4-dichlorophenyl)piperazine as in General Procedure 10 to give the title compound. LCMS: m/z=659.92 (M+H$^+$); retention time=1.12 minutes.

Example 380

8-(4-{1-[5-Chloro-2-(trifluoromethyl)benzyl]-1,2,3,4-tetrahydropyrido[2,3-b]pyrazin-7-yl}benzoyl)-1-phenyl-1,3,8-triaza-spiro[4.5]decan-4-one

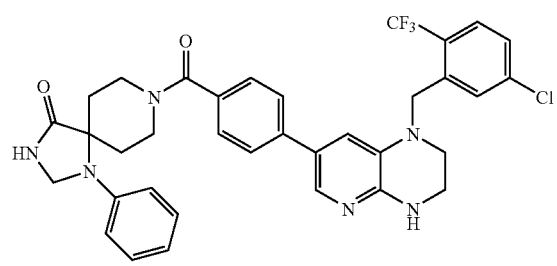

4-{1-[5-chloro-2-(trifluoromethyl)benzyl]-1,2,3,4-tetrahydropyrido[2,3-b]pyrazin-7-yl}benzoic acid was reacted with 1-phenyl-1,3,8-triaza-spiro[4.5]decan-4-one as in General Procedure 10 to give the title compound. LCMS: m/z=661.03 (M+H$^+$); retention time=0.86 minutes.

Example 381

(4-{1-[5-Chloro-2-(trifluoromethyl)benzyl]-1,2,3,4-tetrahydropyrido[2,3-b]pyrazin-7-yl}phenyl)-{4-[2-(trifluoromethyl)phenyl]piperazin-1-yl}methanone

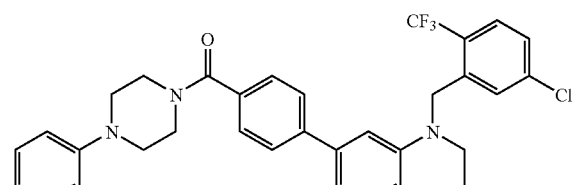

4-{1-[5-chloro-2-(trifluoromethyl)benzyl]-1,2,3,4-tetrahydropyrido[2,3-b]pyrazin-7-yl}benzoic acid was reacted with 1-[2-(trifluoromethyl)phenyl]piperazine as in General Procedure 10 to give the title compound. LCMS: m/z=659.99 (M+H$^+$); retention time=1.10 minutes.

Example 382

(4-{1-[5-Chloro-2-(trifluoromethyl)benzyl]-1,2,3,4-tetrahydropyrido[2,3-b]pyrazin-7-yl}phenyl)-(4-thieno[3,2-d]pyrimidin-4-yl-piperazin-1-yl)methanone

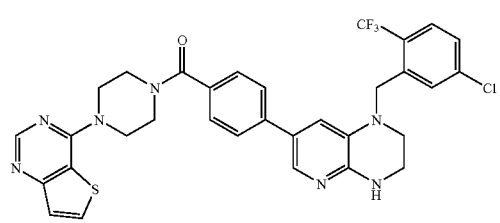

4-{1-[5-chloro-2-(trifluoromethyl)benzyl]-1,2,3,4-tetrahydropyrido[2,3-b]pyrazin-7-yl}benzoic acid was reacted with 1-(4-thieno[3,2-d]pyrimidinyl)piperazine as in General Procedure 10 to give the title compound. LCMS: m/z=648.99 (M+H$^+$); retention time=0.64 minutes.

Example 383

[4-(4-Chlorobenzyl)piperazin-1-yl]-(4-{1-[5-chloro-2-(trifluoromethyl)benzyl]-1,2,3,4-tetrahydropyrido[2,3-b]pyrazin-7-yl}phenyl)methanone

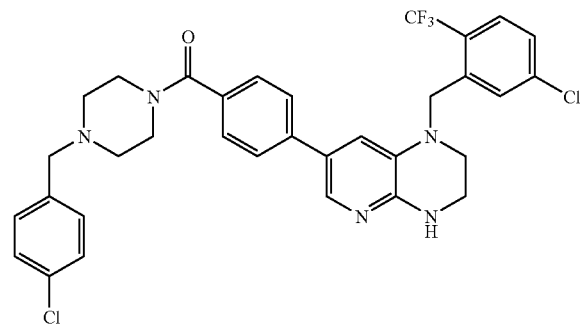

4-{1-[5-chloro-2-(trifluoromethyl)benzyl]-1,2,3,4-tetrahydropyrido[2,3-b]pyrazin-7-yl}benzoic acid was reacted with 1-(4-chlorobenzyl)piperazine as in General Procedure 10 to give the title compound. LCMS: m/z=639.99 (M+H$^+$); retention time=0.69 minutes.

Example 384

(4-{1-[5-Chloro-2-(trifluoromethyl)benzyl]-1,2,3,4-tetrahydropyrido[2,3-b]pyrazin-7-yl}phenyl)-[4-(4-methoxybenzyl)piperazin-1-yl]methanone

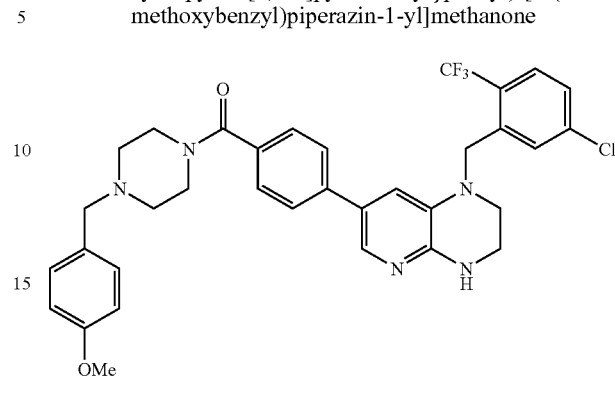

4-{1-[5-chloro-2-(trifluoromethyl)benzyl]-1,2,3,4-tetrahydropyrido[2,3-b]pyrazin-7-yl}benzoic acid was reacted with 1-(4-methoxybenzyl)piperazine as in General Procedure 10 to give the title compound. LCMS: m/z=636.02 (M+H$^+$); retention time=0.61 minutes.

Example 385

(4-Benzoylpiperazin-1-yl)-(4-{1-[5-chloro-2-(trifluoromethyl)benzyl]-1,2,3,4-tetrahydropyrido[2,3-b]pyrazin-7-yl}phenyl)methanone

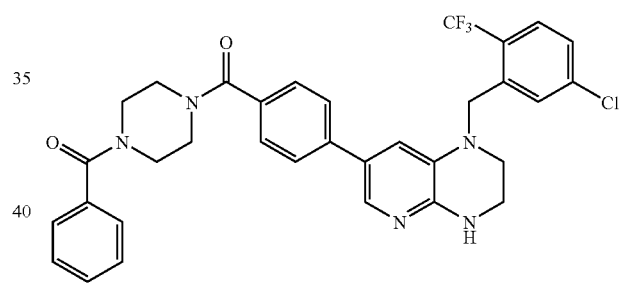

4-{1-[5-chloro-2-(trifluoromethyl)benzyl]-1,2,3,4-tetrahydropyrido[2,3-b]pyrazin-7-yl}benzoic acid was reacted with 1-benzoylpiperazine as in General Procedure 10 to give the title compound. LCMS: m/z=619.98 (M+H$^+$); retention time=0.82 minutes.

Example 386

(4-{1-[5-Chloro-2-(trifluoromethyl)benzyl]-1,2,3,4-tetrahydropyrido[2,3-b]pyrazin-7-yl}phenyl)-(4-furo[3,2-c]pyridin-4-ylpiperazin-1-yl)methanone

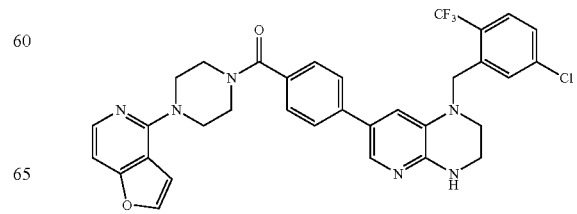

4-{1-[5-chloro-2-(trifluoromethyl)benzyl]-1,2,3,4-tetrahydropyrido[2,3-b]pyrazin-7-yl}benzoic acid was reacted with 1-(4-furo[3,2-c]pyridinyl)piperazine as in General Procedure 10 to give the title compound. LCMS: m/z=633.03 (M+H$^+$); retention time=0.63 minutes.

Example 387

(4-{1-[5-Chloro-2-(trifluoromethyl)benzyl]-1,2,3,4-tetrahydropyrido[2,3-b]pyrazin-7-yl}phenyl)-[4-(6-fluorobenzo[d]isoxazol-3-yl)-piperidin-1-yl]methanone

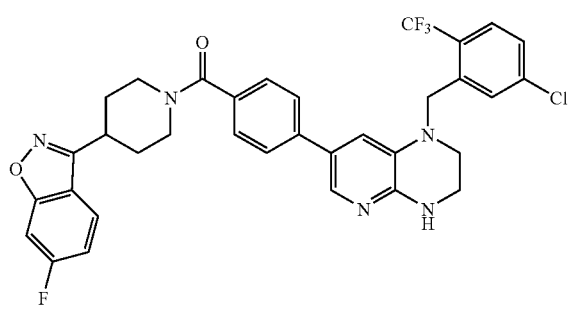

4-{1-[5-chloro-2-(trifluoromethyl)benzyl]-1,2,3,4-tetrahydropyrido[2,3-b]pyrazin-7-yl}benzoic acid was reacted with 4-(6-fluorobenzo[d]isoxazol-3-yl)piperidine as in General Procedure 10 to give the title compound. LCMS: m/z=649.96 (M+H$^+$); retention time=1.00 minutes.

Example 388

4-{1-[5-Chloro-2-(trifluoromethyl)benzyl]-1,2,3,4-tetrahydropyrido[2,3-b]pyrazin-7-yl}-N-(2-pyridin-2-yl-ethyl)benzamide

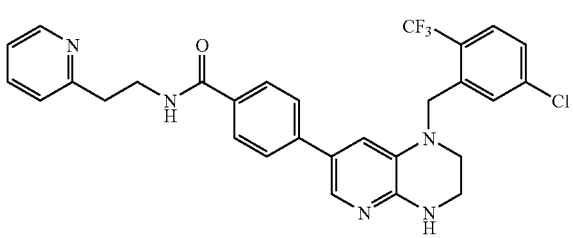

4-{1-[5-chloro-2-(trifluoromethyl)benzyl]-1,2,3,4-tetrahydropyrido[2,3-b]pyrazin-7-yl}benzoic acid was reacted with 2-(2-pyridinyl)ethylamine as in General Procedure 10 to give the title compound. LCMS: m/z=551.01 (M+H$^+$); retention time=0.56 minutes.

Example 389

4-(4-{1-[5-Chloro-2-(trifluoromethyl)benzyl]-1,2,3,4-tetrahydropyrido[2,3-b]pyrazin-7-yl}benzoylamino)piperidine-1-carboxylic acid ethyl ester

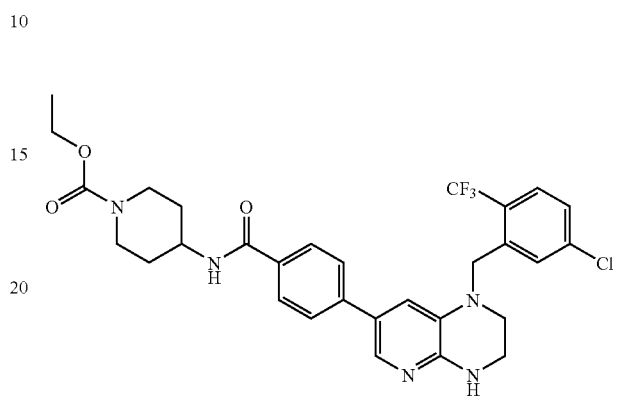

4-{1-[5-chloro-2-(trifluoromethyl)benzyl]-1,2,3,4-tetrahydropyrido[2,3-b]pyrazin-7-yl}benzoic acid was reacted with 4-aminopiperidine-1-carboxylic acid ethyl ester as in General Procedure 10 to give the title compound. LCMS: m/z=601.99 (M+H$^+$); retention time=0.85 minutes.

Example 390

N-(1-Benzylpiperidin-4-yl)-4-{1-[5-chloro-2-(trifluoromethyl)benzyl]-1,2,3,4-tetrahydropyrido[2,3-b]pyrazin-7-yl}benzamide

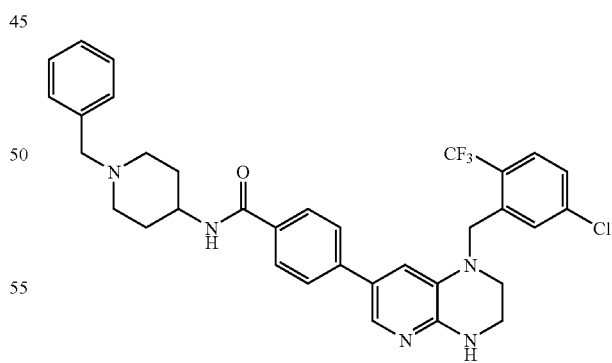

4-{1-[5-chloro-2-(trifluoromethyl)benzyl]-1,2,3,4-tetrahydropyrido[2,3-b]pyrazin-7-yl}benzoic acid was reacted with 4-amino-1-benzylpiperidine as in General Procedure 10 to give the title compound. LCMS: m/z=619.99 (M+H$^+$); retention time=0.61 minutes.

Example 391

4-{1-[5-Chloro-2-(trifluoromethyl)benzyl]-1,2,3,4-tetrahydropyrido[2,3-b]pyrazin-7-yl}-N-(2,2-diphenylethyl)benzamide

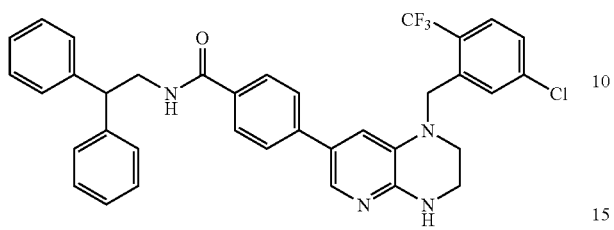

4-{1-[5-chloro-2-(trifluoromethyl)benzyl]-1,2,3,4-tetrahydropyrido[2,3-b]pyrazin-7-yl}benzoic acid was reacted with 2,2-diphenylethylamine as in General Procedure 10 to give the title compound. LCMS: m/z=626.99 (M+H$^+$); retention time=1.06 minutes.

Example 392

1-[4-(4-{1-[5-Chloro-2-(trifluoromethyl)benzyl]-1,2,3,4-tetrahydropyrido[2,3-b]pyrazin-7-yl}benzoyl)piperazin-1-yl]ethanone

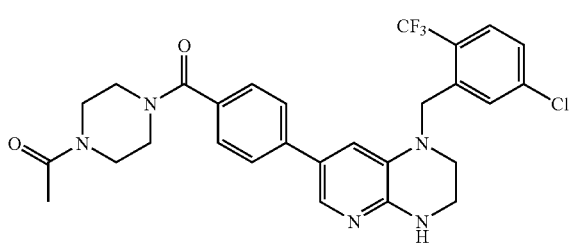

4-{1-[5-chloro-2-(trifluoromethyl)benzyl]-1,2,3,4-tetrahydropyrido[2,3-b]pyrazin-7-yl}benzoic acid was reacted with 1-acetylpiperazine as in General Procedure 10 to give the title compound. LCMS: m/z=557.97 (M+H$^+$); retention time=0.68 minutes.

Example 393

4-{1-[5-Chloro-2-(trifluoromethyl)benzyl]-1,2,3,4-tetrahydropyrido[2,3-b]pyrazin-7-yl}-N-(1-methylpiperidin-4-yl)benzamide

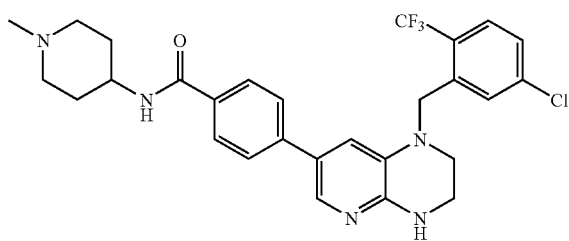

4-{1-[5-chloro-2-(trifluoromethyl)benzyl]-1,2,3,4-tetrahydropyrido[2,3-b]pyrazin-7-yl}benzoic acid was reacted with 4-amino-1-methylpiperidine as in General Procedure 10 to give the title compound. LCMS: m/z=543.96 (M+H$^+$); retention time=0.51 minutes.

Example 394

(4-{1-[5-Chloro-2-(trifluoromethyl)benzyl]-1,2,3,4-tetrahydropyrido[2,3-b]pyrazin-7-yl}phenyl)-[4-(2-pyridin-2-yl-ethyl)piperazin-1-yl]methanone

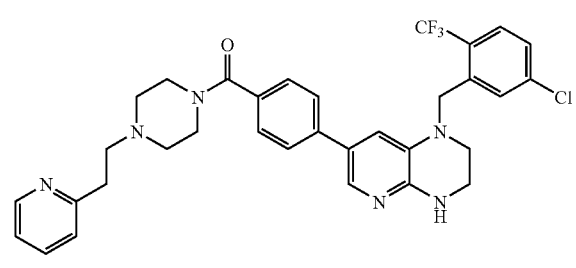

4-{1-[5-chloro-2-(trifluoromethyl)benzyl]-1,2,3,4-tetrahydropyrido[2,3-b]pyrazin-7-yl}benzoic acid was reacted with 1-piperazinyl-2-(2-pyridinyl)ethane as in General Procedure 10 to give the title compound. LCMS: m/z=620.98 (M+H$^+$); retention time=0.53 minutes.

Example 395

4-{1-[5-Chloro-2-(trifluoromethyl)benzyl]-1,2,3,4-tetrahydropyrido[2,3-b]pyrazin-7-yl}-N-[4-(trifluoromethoxy)benzyl]benzamide

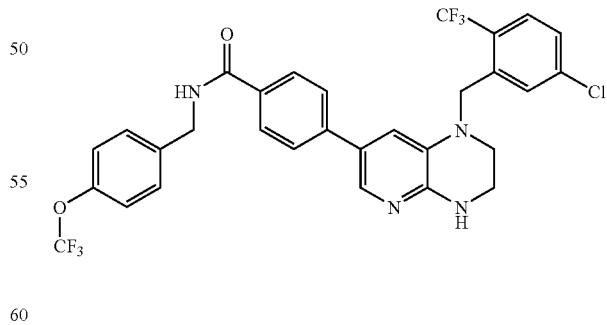

4-{1-[5-chloro-2-(trifluoromethyl)benzyl]-1,2,3,4-tetrahydropyrido[2,3-b]pyrazin-7-yl}benzoic acid was reacted with 4-(trifluoromethoxy)benzylamine as in General Procedure 10 to give the title compound. LCMS: m/z=620.95 (M+H$^+$); retention time=1.03 minutes.

Example 396

4-{1-[5-Chloro-2-(trifluoromethyl)benzyl]-1,2,3,4-tetrahydropyrido[2,3-b]pyrazin-7-yl}-N-[4-(trifluoromethyl)benzyl]benzamide

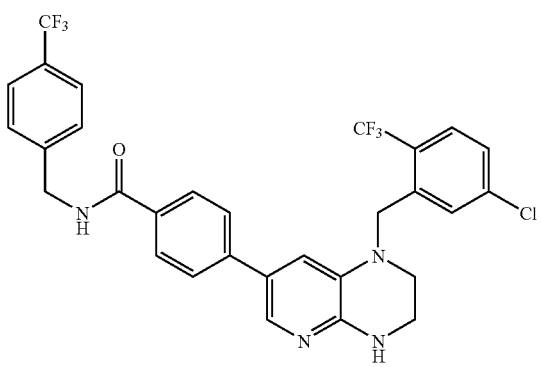

4-{1-[5-chloro-2-(trifluoromethyl)benzyl]-1,2,3,4-tetrahydropyrido[2,3-b]pyrazin-7-yl}benzoic acid was reacted with 4-(trifluoromethyl)benzylamine as in General Procedure 10 to give the title compound. LCMS: m/z=604.92 (M+H$^+$); retention time=1.01 minutes.

Example 397

N-[3,5-Bis(trifluoromethyl)benzyl]-4-{1-[5-Chloro-2-(trifluoromethyl)benzyl]-1,2,3,4-tetrahydropyrido[2,3-b]pyrazin-7-yl}benzamide

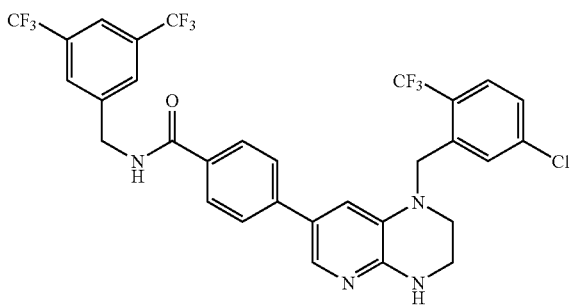

4-{1-[5-chloro-2-(trifluoromethyl)benzyl]-1,2,3,4-tetrahydropyrido[2,3-b]pyrazin-7-yl}benzoic acid was reacted with 3,5-bis(trifluoromethyl)benzylamine as in General Procedure 10 to give the title compound. LCMS: m/z=672.90 (M+H$^+$); retention time=1.11 minutes.

Example 398

4-{1-[5-Chloro-2-(trifluoromethyl)benzyl]-1,2,3,4-tetrahydropyrido[2,3-b]pyrazin-7-yl}-N-(2-thiophen-2-yl-ethyl)benzamide

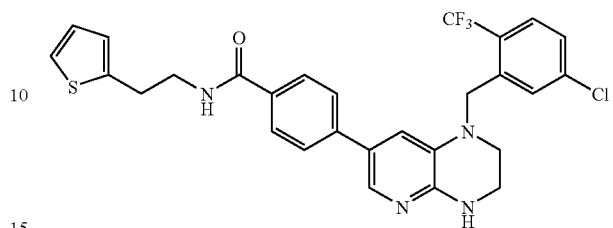

4-{1-[5-chloro-2-(trifluoromethyl)benzyl]-1,2,3,4-tetrahydropyrido[2,3-b]pyrazin-7-yl}benzoic acid was reacted with 2-(2-aminoethyl)thiophene as in General Procedure 10 to give the title compound. LCMS: m/z=556.91 (M+H$^+$); retention time=0.92 minutes.

Example 399

N-Benzhydryl-4-{1-[5-chloro-2-(trifluoromethyl)benzyl]-1,2,3,4-tetrahydropyrido[2,3-b]pyrazin-7-yl}benzamide

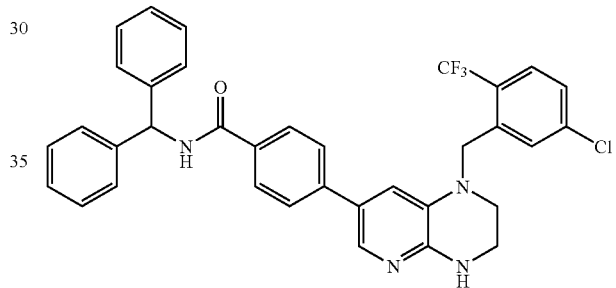

4-{1-[5-chloro-2-(trifluoromethyl)benzyl]-1,2,3,4-tetrahydropyrido[2,3-b]pyrazin-7-yl}benzoic acid was reacted with benzhydrylamine as in General Procedure 10 to give the title compound. LCMS: m/z=613.00 (M+H$^+$); retention time=1.06 minutes.

Example 400

4-{1-[5-Chloro-2-(trifluoromethyl)benzyl]-1,2,3,4-tetrahydropyrido[2,3-b]pyrazin-7-yl}-N-pyridin-4-ylmethylbenzamide

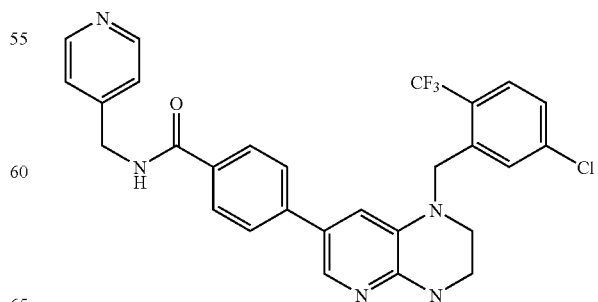

4-{1-[5-chloro-2-(trifluoromethyl)benzyl]-1,2,3,4-tetrahydropyrido[2,3-b]pyrazin-7-yl}benzoic acid was reacted with 4-(aminomethyl)pyridine as in General Procedure 10 to give the title compound. LCMS: m/z=537.98 (M+H⁺); retention time=0.54 minutes.

Example 401

4-{1-[5-Chloro-2-(trifluoromethyl)benzyl]-1,2,3,4-tetrahydropyrido[2,3-b]pyrazin-7-yl}-N-pyridin-3-ylmethylbenzamide

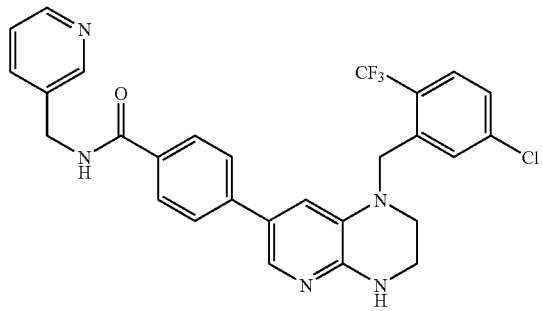

4-{1-[5-chloro-2-(trifluoromethyl)benzyl]-1,2,3,4-tetrahydropyrido[2,3-b]pyrazin-7-yl}benzoic acid was reacted with 3-(aminomethyl)pyridine as in General Procedure 10 to give the title compound. LCMS: m/z=537.95 (M+H⁺); retention time=0.57 minutes.

Example 402

2-[4-(4-{1-[5-Chloro-2-(trifluoromethyl)benzyl]-1,2,3,4-tetrahydropyrido[2,3-b]pyrazin-7-yl}benzoyl)piperazin-1-yl]-N-isopropylacetamide

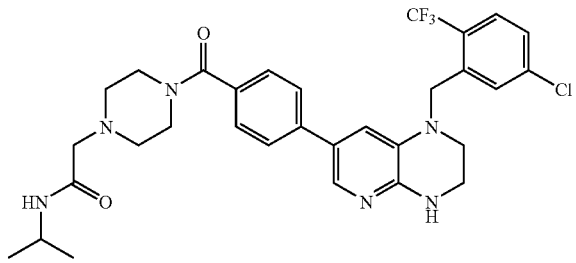

4-{1-[5-chloro-2-(trifluoromethyl)benzyl]-1,2,3,4-tetrahydropyrido[2,3-b]pyrazin-7-yl}benzoic acid was reacted with 2-piperazinyl-N-isopropylacetamide as in General Procedure 10 to give the title compound. LCMS: m/z=615.03 (M+H⁺); retention time=0.58 minutes.

Example 403

(4-{1-[5-Chloro-2-(trifluoromethyl)benzyl]-1,2,3,4-tetrahydropyrido[2,3-b]pyrazin-7-yl}phenyl)-[4-(2-methylquinolin-4-yl)piperazin-1-yl]methanone

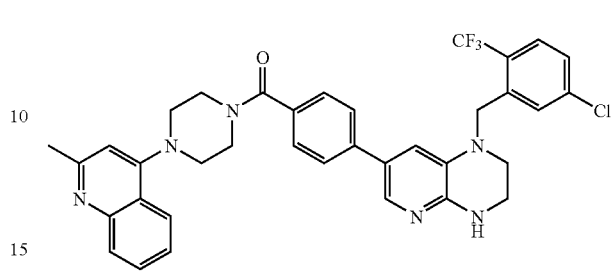

4-{1-[5-chloro-2-(trifluoromethyl)benzyl]-1,2,3,4-tetrahydropyrido[2,3-b]pyrazin-7-yl}benzoic acid was reacted with 2-methyl-4-(1-piperazinyl)quinoline as in General Procedure 10 to give the title compound. LCMS: m/z=656.96 (M+H⁺); retention time=0.62 minutes.

Example 404

4-{1-[5-Chloro-2-(trifluoromethyl)benzyl]-1,2,3,4-tetrahydropyrido[2,3-b]pyrazin-7-yl}-N-(2-methoxyethyl)benzamide

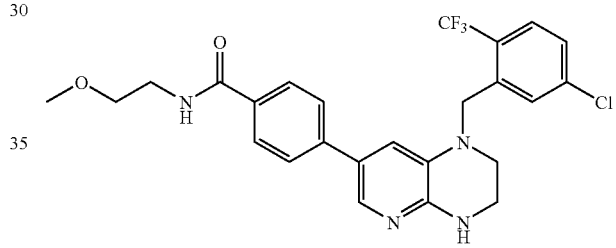

4-{1-[5-chloro-2-(trifluoromethyl)benzyl]-1,2,3,4-tetrahydropyrido[2,3-b]pyrazin-7-yl}benzoic acid was reacted with 2-methoxyethylamine as in General Procedure 10 to give the title compound. LCMS: m/z=504.97 (M+H⁺); retention time=0.74 minutes.

Example 405

4-{1-[5-Chloro-2-(trifluoromethyl)benzyl]-1,2,3,4-tetrahydropyrido[2,3-b]pyrazin-7-yl}-N-[2-(4-sulfamoylphenyl)ethyl]benzamide

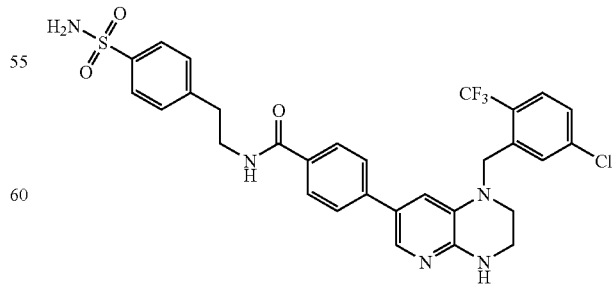

4-{1-[5-chloro-2-(trifluoromethyl)benzyl]-1,2,3,4-tetrahydropyrido[2,3-b]pyrazin-7-yl}benzoic acid was reacted with

Example 406

(4-{1-[5-Chloro-2-(trifluoromethyl)benzyl]-1,2,3,4-tetrahydropyrido[2,3-b]pyrazin-7-yl}phenyl)-(2,3,5,6-tetrahydro[1,2']bipyrazinyl-4-yl)methanone

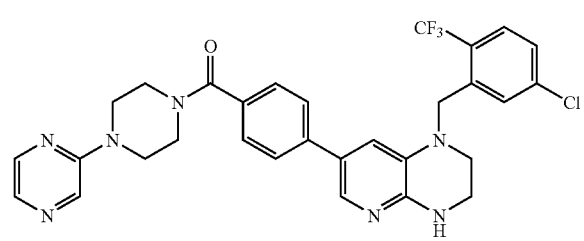

4-{1-[5-chloro-2-(trifluoromethyl)benzyl]-1,2,3,4-tetrahydropyrido[2,3-b]pyrazin-7-yl}benzoic acid was reacted with 2-(1-piperazinyl)pyrazine as in General Procedure 10 to give the title compound. LCMS: m/z=593.98 (M+H$^+$); retention time=0.79 minutes.

Example 407

4-{1-[5-Chloro-2-(trifluoromethyl)benzyl]-1,2,3,4-tetrahydropyrido[2,3-b]pyrazin-7-yl}-N-(2-phenylthiazol-4-ylmethyl)benzamide

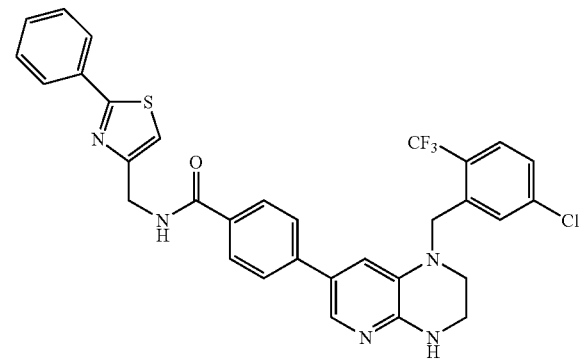

4-{1-[5-chloro-2-(trifluoromethyl)benzyl]-1,2,3,4-tetrahydropyrido[2,3-b]pyrazin-7-yl}benzoic acid was reacted with 2-phenyl-4-(aminomethyl)thiazole as in General Procedure 10 to give the title compound. LCMS: m/z=619.90 (M+H$^+$); retention time=0.98 minutes.

Example 408

(4-{1-[5-Chloro-2-(trifluoromethyl)benzyl]-1,2,3,4-tetrahydropyrido[2,3-b]pyrazin-7-yl}phenyl)morpholin-4-ylmethanone

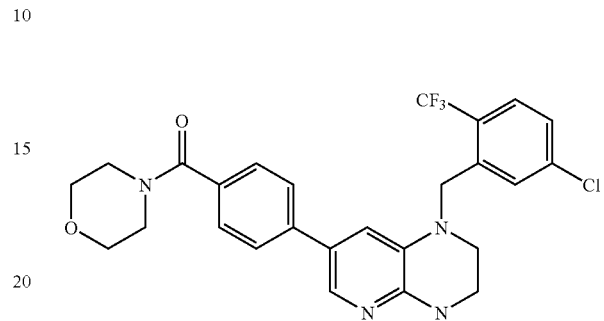

4-{1-[5-chloro-2-(trifluoromethyl)benzyl]-1,2,3,4-tetrahydropyrido[2,3-b]pyrazin-7-yl}benzoic acid was reacted with morpholine as in General Procedure 10 to give the title compound. LCMS: m/z=516.96 (M+H$^+$); retention time=0.74 minutes.

Example 409

4-{1-[5-Chloro-2-(trifluoromethyl)benzyl]-1,2,3,4-tetrahydropyrido[2,3-b]pyrazin-7-yl}-N-naphthalen-1-ylmethylbenzamide

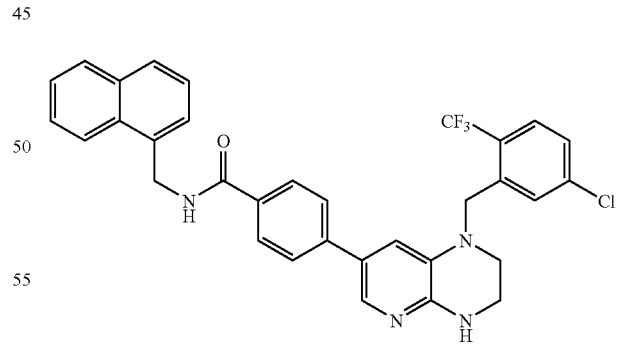

4-{1-[5-chloro-2-(trifluoromethyl)benzyl]-1,2,3,4-tetrahydropyrido[2,3-b]pyrazin-7-yl}benzoic acid was reacted with 1-(aminomethyl)naphthalene as in General Procedure 10 to give the title compound. LCMS: m/z=586.95 (M+H$^+$); retention time=1.01 minutes.

Example 410

4-{1-[5-Chloro-2-(trifluoromethyl)benzyl]-1,2,3,4-tetrahydropyrido[2,3-b]pyrazin-7-yl}-N-indan-1-ylbenzamide

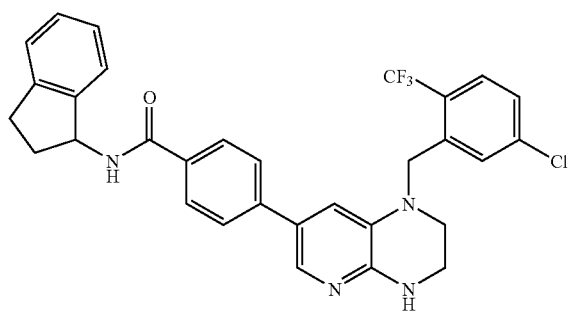

4-{1-[5-chloro-2-(trifluoromethyl)benzyl]-1,2,3,4-tetrahydropyrido[2,3-b]pyrazin-7-yl}benzoic acid was reacted with 1-aminoindan as in General Procedure 10 to give the title compound. LCMS: m/z=562.95 (M+H$^+$); retention time=0.98 minutes.

Example 411

(4-{1-[5-Chloro-2-(trifluoromethyl)benzyl]-1,2,3,4-tetrahydropyrido[2,3-b]pyrazin-7-yl}phenyl)-[4-(4-methoxyphenyl)piperazin-1-yl]methanone

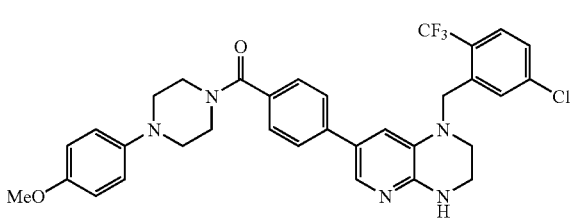

4-{1-[5-chloro-2-(trifluoromethyl)benzyl]-1,2,3,4-tetrahydropyrido[2,3-b]pyrazin-7-yl}benzoic acid was reacted with 1-(4-methoxyphenyl)piperazine as in General Procedure 10 to give the title compound. LCMS: m/z=622.01 (M+H$^+$); retention time=0.92 minutes.

Example 412

N-(2-Chlorobenzyl)-4-{1-[5-chloro-2-(trifluoromethyl)benzyl]-1,2,3,4-tetrahydropyrido[2,3-b]pyrazin-7-yl}benzamide

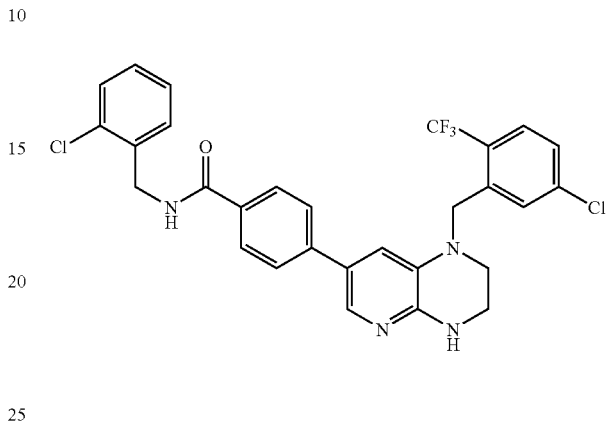

4-{1-[5-chloro-2-(trifluoromethyl)benzyl]-1,2,3,4-tetrahydropyrido[2,3-b]pyrazin-7-yl}benzoic acid was reacted with 2-chlorobenzylamine as in General Procedure 10 to give the title compound. LCMS: m/z=570.90 (M+H$^+$); retention time=0.98 minutes.

Example 413

N-(4-Chlorobenzyl)-4-{1-[5-chloro-2-(trifluoromethyl)benzyl]-1,2,3,4-tetrahydropyrido[2,3-b]pyrazin-7-yl}benzamide

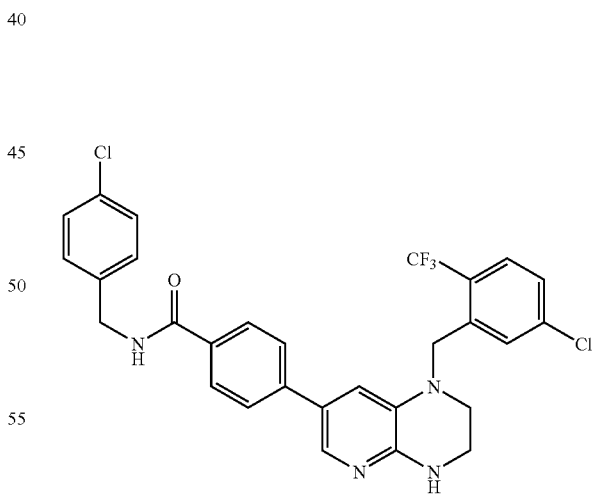

4-{1-[5-chloro-2-(trifluoromethyl)benzyl]-1,2,3,4-tetrahydropyrido[2,3-b]pyrazin-7-yl}benzoic acid was reacted with 4-chlorobenzylamine as in General Procedure 10 to give the title compound. LCMS: m/z=570.90 (M+H$^+$); retention time=0.98 minutes.

Example 414

N-(3-Chloro-benzyl)-4-{1-[5-chloro-2-(trifluoromethyl)benzyl]-1,2,3,4-tetrahydropyrido[2,3-b]pyrazin-7-yl}benzamide

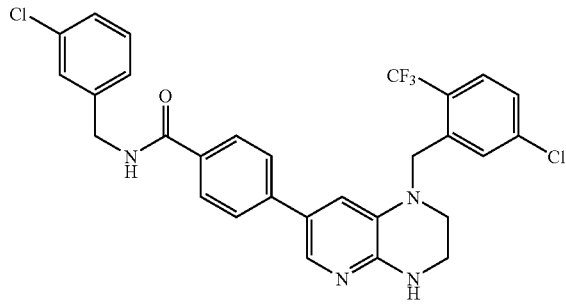

4-{1-[5-chloro-2-(trifluoromethyl)benzyl]-1,2,3,4-tetrahydropyrido[2,3-b]pyrazin-7-yl}benzoic acid was reacted with 3-chlorobenzylamine as in General Procedure 10 to give the title compound. LCMS: m/z=570.90 (M+H$^+$); retention time=0.98 minutes.

Example 415

(4-{1-[5-Chloro-2-(trifluoromethyl)benzyl]-1,2,3,4-tetrahydropyrido[2,3-b]pyrazin-7-yl}phenyl)-[4-(tetrahydrofuran-2-carbonyl)piperazin-1-yl]methanone

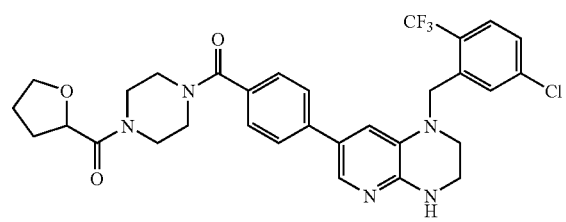

4-{1-[5-chloro-2-(trifluoromethyl)benzyl]-1,2,3,4-tetrahydropyrido[2,3-b]pyrazin-7-yl}benzoic acid was reacted with 1-(tetrahydrofuran-2-carbonyl)piperazine as in General Procedure 10 to give the title compound. LCMS: m/z=613.98 (M+H$^+$); retention time=0.72 minutes.

Example 416

4-{1-[5-Chloro-2-(trifluoromethyl)benzyl]-1,2,3,4-tetrahydropyrido[2,3-b]pyrazin-7-yl}-N-phenethylbenzamide

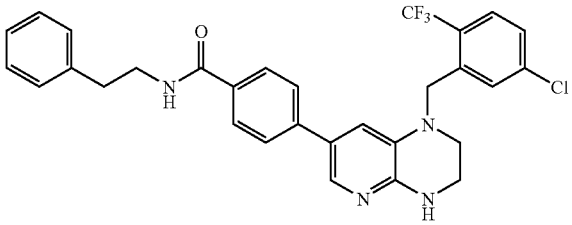

4-{1-[5-chloro-2-(trifluoromethyl)benzyl]-1,2,3,4-tetrahydropyrido[2,3-b]pyrazin-7-yl}benzoic acid was reacted with phenethylamine as in General Procedure 10 to give the title compound. LCMS: m/z=550.96 (M+H$^+$); retention time=0.94 minutes.

Example 417

4-{1-[5-Chloro-2-(trifluoromethyl)benzyl]-1,2,3,4-tetrahydropyrido[2,3-b]pyrazin-7-yl}-N-(tetrahydrofuran-2-ylmethyl)benzamide

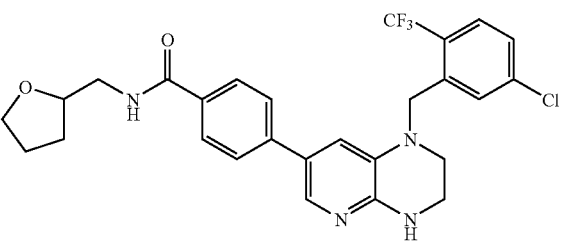

4-{1-[5-chloro-2-(trifluoromethyl)benzyl]-1,2,3,4-tetrahydropyrido[2,3-b]pyrazin-7-yl}benzoic acid was reacted with 2-(aminomethyl)tetrahydrofuran as in General Procedure 10 to give the title compound. LCMS: m/z=530.96 (M+H$^+$); retention time=0.78 minutes.

Example 418

4-{1-[5-Chloro-2-(trifluoromethyl)benzyl]-1,2,3,4-tetrahydropyrido[2,3-b]pyrazin-7-yl}-N-(3-methoxybenzyl)benzamide

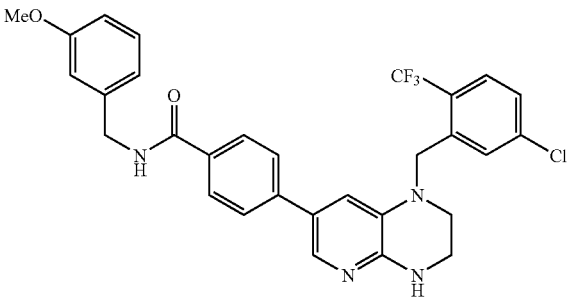

4-{1-[5-chloro-2-(trifluoromethyl)benzyl]-1,2,3,4-tetrahydropyrido[2,3-b]pyrazin-7-yl}benzoic acid was reacted with 3-methoxybenzylamine as in General Procedure 10 to give the title compound. LCMS: m/z=566.97 (M+H$^+$); retention time=0.91 minutes.

Example 419

4-{1-[5-Chloro-2-(trifluoromethyl)benzyl]-1,2,3,4-tetrahydropyrido[2,3-b]pyrazin-7-yl}-N-(4-methoxybenzyl)benzamide

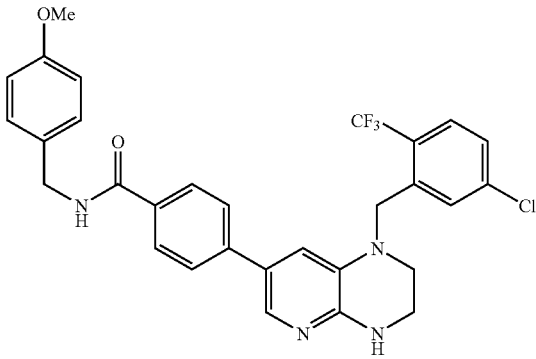

4-{1-[5-chloro-2-(trifluoromethyl)benzyl]-1,2,3,4-tetrahydropyrido[2,3-b]pyrazin-7-yl}benzoic acid was reacted with 4-methoxybenzylamine as in General Procedure 10 to give the title compound. LCMS: m/z=566.97 (M+H$^+$); retention time=0.90 minutes.

Example 420

4-{1-[5-Chloro-2-(trifluoromethyl)benzyl]-1,2,3,4-tetrahydropyrido[2,3-b]pyrazin-7-yl}-N-(2-phenoxyethyl)benzamide

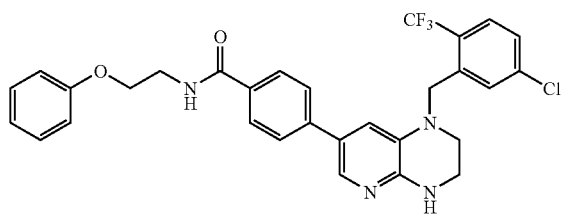

4-{1-[5-chloro-2-(trifluoromethyl)benzyl]-1,2,3,4-tetrahydropyrido[2,3-b]pyrazin-7-yl}benzoic acid was reacted with 2-phenoxyethylamine as in General Procedure 10 to give the title compound. LCMS: m/z=566.93 (M+H$^+$); retention time=0.93 minutes.

Example 421

N-Benzyl-4-{1-[5-chloro-2-(trifluoromethyl)benzyl]-1,2,3,4-tetrahydropyrido[2,3-b]pyrazin-7-yl}benzamide

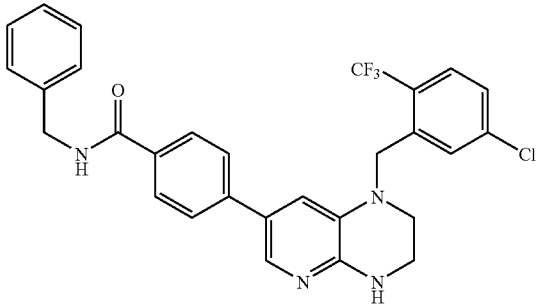

4-{1-[5-chloro-2-(trifluoromethyl)benzyl]-1,2,3,4-tetrahydropyrido[2,3-b]pyrazin-7-yl}benzoic acid was reacted with benzylamine as in General Procedure 10 to give the title compound. LCMS: m/z=536.96 (M+H$^+$); retention time=0.91 minutes.

Example 422

[4-(3-Chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone

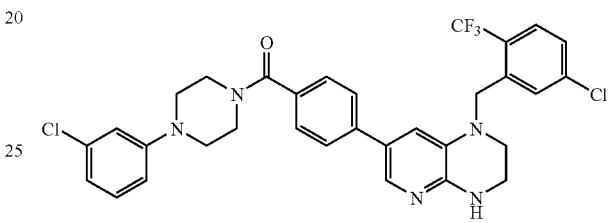

4-{1-[5-chloro-2-(trifluoromethyl)benzyl]-1,2,3,4-tetrahydropyrido[2,3-b]pyrazin-7-yl}benzoic acid was reacted with 1-(3-chlorophenyl)piperazine as in General Procedure 10 to give the title compound. LCMS: m/z=625.96 (M+H$^+$); retention time=1.06 minutes.

Example 423

4-{1-[5-Chloro-2-(trifluoromethyl)benzyl]-1,2,3,4-tetrahydropyrido[2,3-b]pyrazin-7-yl}-N-indan-2-ylbenzamide

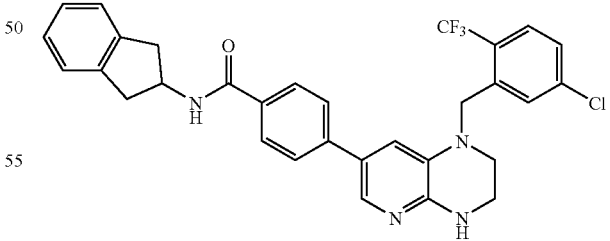

4-{1-[5-chloro-2-(trifluoromethyl)benzyl]-1,2,3,4-tetrahydropyrido[2,3-b]pyrazin-7-yl}benzoic acid was reacted with 2-aminoindan as in General Procedure 10 to give the title compound. LCMS: m/z=562.96 (M+H$^+$); retention time=0.98 minutes.

Example 424

(4-{1-[5-Chloro-2-(trifluoromethyl)benzyl]-1,2,3,4-tetrahydropyrido[2,3-b]pyrazin-7-yl}phenyl)-(4-phenethylpiperazin-1-yl)methanone

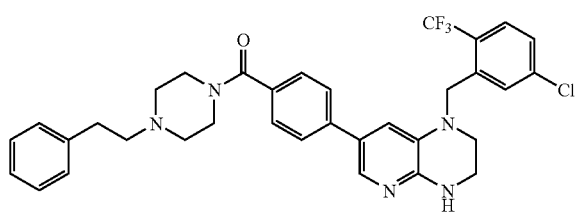

4-{1-[5-chloro-2-(trifluoromethyl)benzyl]-1,2,3,4-tetrahydropyrido[2,3-b]pyrazin-7-yl}benzoic acid was reacted with 1-phenethylpiperazine as in General Procedure 10 to give the title compound. LCMS: m/z=620.02 (M+H$^+$); retention time=0.63 minutes.

Example 425

N-Biphenyl-4-ylmethyl-4-{1-[5-Chloro-2-(trifluoromethyl)benzyl]-1,2,3,4-tetrahydropyrido[2,3-b]pyrazin-7-yl}benzamide

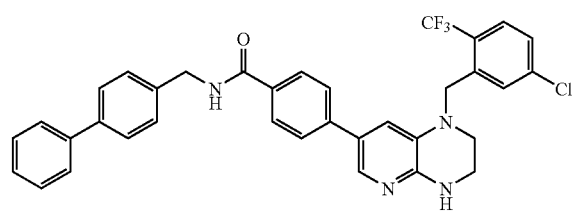

4-{1-[5-chloro-2-(trifluoromethyl)benzyl]-1,2,3,4-tetrahydropyrido[2,3-b]pyrazin-7-yl}benzoic acid was reacted with 4-(aminomethyl)biphenyl as in General Procedure 10 to give the title compound. LCMS: m/z=613.00 (M+H$^+$); retention time=1.07 minutes.

Example 426

[4-(2-Chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone

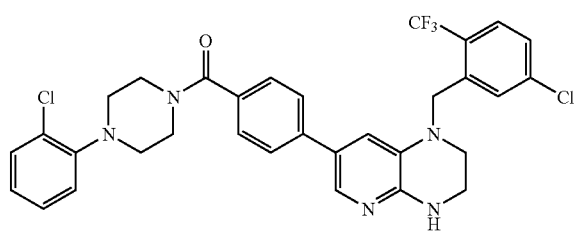

4-{1-[5-chloro-2-(trifluoromethyl)benzyl]-1,2,3,4-tetrahydropyrido[2,3-b]pyrazin-7-yl}benzoic acid was reacted with 1-(2-chlorophenyl)piperazine as in General Procedure 10 to give the title compound. LCMS: m/z=625.96 (M+H$^+$); retention time=1.07 minutes.

Example 427

N-(1-Benzylpyrrolidin-3-yl)-4-{1-[5-chloro-2-(trifluoromethyl)benzyl]-1,2,3,4-tetrahydropyrido[2,3-b]pyrazin-7-yl}benzamide

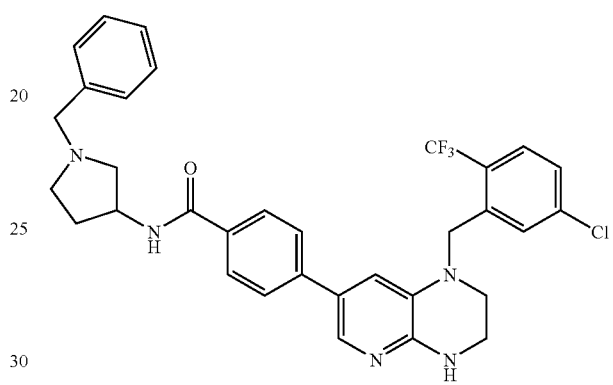

4-{1-[5-chloro-2-(trifluoromethyl)benzyl]-1,2,3,4-tetrahydropyrido[2,3-b]pyrazin-7-yl}benzoic acid was reacted with 3-amino-1-benzylpyrrolidine as in General Procedure 10 to give the title compound. LCMS: m/z=605.96 (M+H$^+$); retention time=0.62 minutes.

Example 428

(4-{1-[5-Chloro-2-(trifluoromethyl)benzyl]-1,2,3,4-tetrahydropyrido[2,3-b]pyrazin-7-yl}phenyl)-[4-(cyclohexylmethyl)piperazin-1-yl]methanone

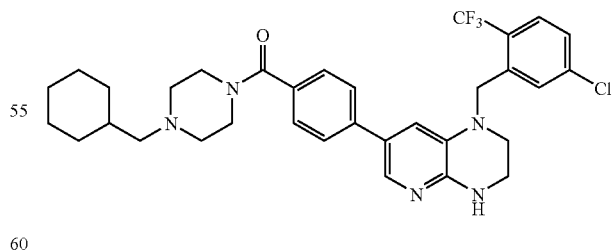

4-{1-[5-chloro-2-(trifluoromethyl)benzyl]-1,2,3,4-tetrahydropyrido[2,3-b]pyrazin-7-yl}benzoic acid was reacted with 1-(cyclohexylmethyl)piperazine as in General Procedure 10 to give the title compound. LCMS: m/z=611.96 (M+H$^+$); retention time=0.64 minutes.

Example 429

4-{1-[5-Chloro-2-(trifluoromethyl)benzyl]-1,2,3,4-tetrahydropyrido[2,3-b]pyrazin-7-yl}-N-(4-sulfamoylbenzyl)benzamide

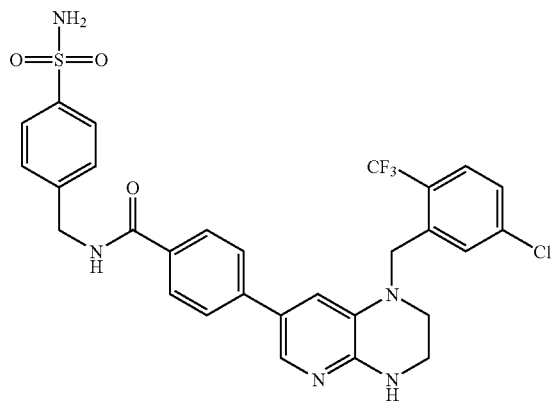

4-{1-[5-chloro-2-(trifluoromethyl)benzyl]-1,2,3,4-tetrahydropyrido[2,3-b]pyrazin-7-yl}benzoic acid was reacted with 4-sulfamoylbenzylamine as in General Procedure 10 to give the title compound. LCMS: m/z=615.91 (M+H$^+$); retention time=0.75 minutes.

Example 430

(4-{1-[5-Chloro-2-(trifluoromethyl)benzyl]-1,2,3,4-tetrahydropyrido[2,3-b]pyrazin-7-yl}phenyl)-((S)-2-pyrrolidin-1-ylmethylpyrrolidin-1-yl)methanone

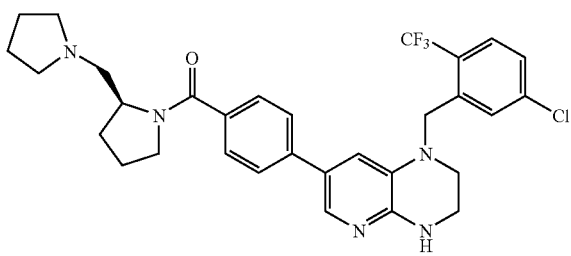

4-{1-[5-chloro-2-(trifluoromethyl)benzyl]-1,2,3,4-tetrahydropyrido[2,3-b]pyrazin-7-yl}benzoic acid was reacted with (S)-2-(1-pyrrolidinylmethyl)pyrrolidine as in General Procedure 10 to give the title compound. LCMS: m/z=583.95 (M+H$^+$); retention time=0.58 minutes.

Example 431

(4-{1-[5-Chloro-2-(trifluoromethyl)benzyl]-1,2,3,4-tetrahydropyrido[2,3-b]pyrazin-7-yl}phenyl)-(2-pyridin-3-yl-pyrrolidin-1-yl)methanone

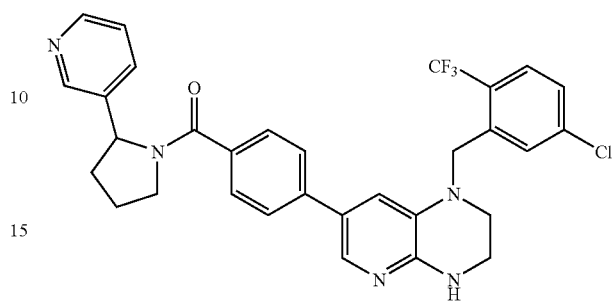

4-{1-[5-chloro-2-(trifluoromethyl)benzyl]-1,2,3,4-tetrahydropyrido[2,3-b]pyrazin-7-yl}benzoic acid was reacted with 2-(3-pyridinyl)pyrrolidine as in General Procedure 10 to give the title compound. LCMS: m/z=577.97 (M+H$^+$); retention time=0.63 minutes.

Example 432

4-{1-[5-Chloro-2-(trifluoromethyl)benzyl]-1,2,3,4-tetrahydropyrido[2,3-b]pyrazin-7-yl}-N-(2-methoxybenzyl)-N-methylbenzamide

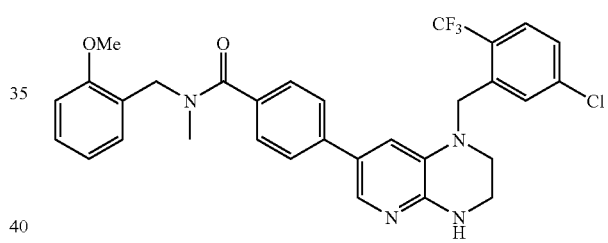

4-{1-[5-chloro-2-(trifluoromethyl)benzyl]-1,2,3,4-tetrahydropyrido[2,3-b]pyrazin-7-yl}benzoic acid was reacted with N-methyl-2-methoxybenzylamine as in General Procedure 10 to give the title compound. LCMS: m/z=580.98 (M+H$^+$); retention time=0.96 minutes.

Example 433

(4-{1-[5-Chloro-2-(trifluoromethyl)benzyl]-1,2,3,4-tetrahydropyrido[2,3-b]pyrazin-7-yl}phenyl)-(1,3-dihydroisoindol-2-yl)methanone

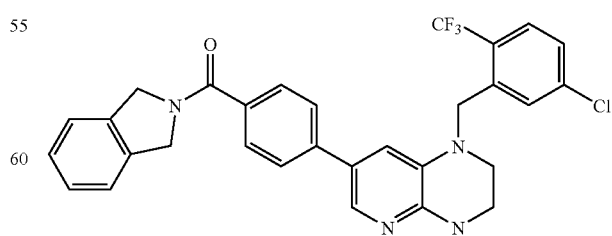

4-{1-[5-chloro-2-(trifluoromethyl)benzyl]-1,2,3,4-tetrahydropyrido[2,3-b]pyrazin-7-yl}benzoic acid was reacted with 1,3-dihydroisoindole as in General Procedure 10 to give the title compound. LCMS: m/z=548.94 (M+H⁺); retention time=0.94 minutes.

Example 434

{4-[1-(5-Chloro-2-trifluoromethyl-benzyl)-1,2,3,4-tetrahydropyrido[2,3-b]pyrazin-7-yl]-phenyl}-(spiro[isobenzofuran-1(3H), 4'-piperidine]-1-yl)methanone

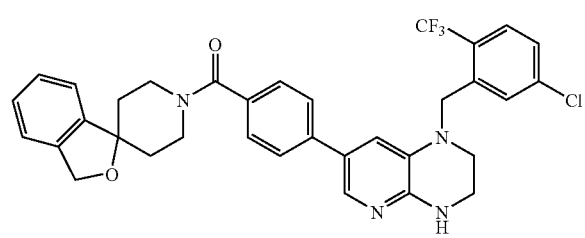

4-{1-[5-chloro-2-(trifluoromethyl)benzyl]-1,2,3,4-tetrahydropyrido[2,3-b]pyrazin-7-yl}benzoic acid was reacted with spiro(isobenzofuran-1(3H), 4'-piperidine) as in General Procedure 10 to give the title compound. LCMS: m/z=618.98 (M+H⁺); retention time=1.00 minutes.

Example 435

6-Bromo-3,4-dihydro-1H-quinoxalin-2-one

5-bromo-2,3-diaminopyridine (2.0 g, 10.6 mmol) and glyoxylic acid monohydrate (1.23 g, 13.4 mmol) were combined in water (55 mL), sonicated for 10 minutes and stirred overnight. The product was filtered, washed with water (5×100 mL) and dried under vacuum to afford 2.214 g of crude product. To a suspension of this material in methanol (100 mL) was added NaBH₄ (1.0 g, 26.3 mmol) with periodic cooling in an ice water bath to maintain reaction temperature below 35° C. After stirring for 4 hours, the reaction was quenched with 6N HCl (20 mL) and the resulting mixture stirred overnight. The mixture was warmed to 50° C. for 0.5 hour before removing volatile solvents by rotary evaporation. After adjusting the pH of the aqueous reside to 8 by the addition of 10N NaOH, the product was removed by filtration and washed with water (5×50 mL) to give the title compound (1.985 g, 82%). m.p. 265° C. (dec), ¹H-NMR (DMSO-d₆, 400 MHz) δ 10.47 (s, 1H), 7.65 (d, J=2.1 Hz, 1H), 7.01-6.99 (m, 2H), 3.94 (s, 2H).

Example 436

7-Bromo-1-(2-chloro-3,6-difluorobenzyl)-1,4-dihydro-2H-pyrido[2,3-b]pyrazin-3-one

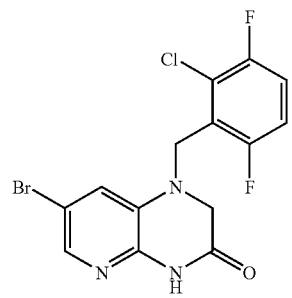

To a solution of 6-bromo-3,4-dihydro-1H-quinoxalin-2-one (228 mg, 1.00 mmol) in DMF (10 mL) was added NaH (40 mg of a 60% dispersion in mineral oil, 1.00 mmol) and the resulting mixture sonicated for 5 minutes. After stirring at room temperature for 20 minutes, 2-chloro-3,6-difluorobenzylbromide (242 mg, 1.00 mmol) was added and the mixture was stirred for 20 minutes. Solvent was reduced ~90% and the residue was triturated with ether (3×1 mL) and water (2×2 mL) to give the title compound (275 mg, 71%). m.p. 214-216° C. (dec); LCMS: m/z=388/390/392 (M+H⁺); ¹H-NMR (DMSO-d₆, 400 MHz) δ 7.73 (s, 1H), 7.47-7.42 (m, 1H), 7.35 (s, 1H), 7.32-7.26 (m, 1H), 7.11 (s, 1H), 5.24, (s, 2H), 4.01 (s, 2H).

Example 437

1-(2-Chloro-3,6-difluorobenzyl)-7-[6-(4-methylpiperazin-1-yl)pyridin-3-yl]-1,4-dihydro-2H-pyrido[2,3-b]pyrazin-3-one

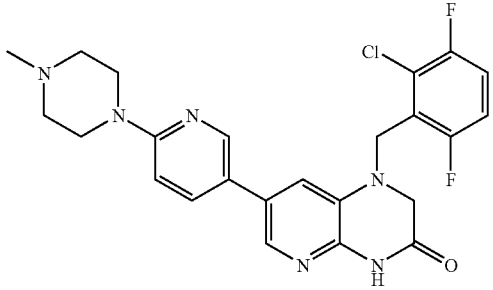

A mixture of 7-bromo-1-(2-chloro-3,6-difluorobenzyl)-1,4-dihydro-2H-pyrido[2,3-b]pyrazin-3-one (42 mg, 0.11 mmol), 1-methyl-4-[5-(4,4,5,5-tetramethyl-[1,3,2]dioxaborolan-2-yl)pyridin-2-yl]piperazine (40 mg, 0.13 mmol), palladium (II) acetate (4 mg) and triphenylphosphine (14 mg) in n-propanol (1.0 mL) was degassed with argon while adding a 1.26 M aqueous solution of Na₂CO₃ (0.12 mL) followed by water (0.38 mL). This mixture was heated in a microwave for 10 minutes at 130° C., cooled to room temperature and extracted into CH₂Cl₂. The organic phase was passed through a plug of Na₂SO₄, absorbed onto florisil and evaporated to dryness. This material was purified by silica gel chromatography by eluting with increasing amounts of 5% NH₄OH/methanol in dichloromethane. The isolated material was recrystallized from methanol to give the title compound (15.4 mg, 29%). m.p. 235-236° C. (dec); LCMS: m/z=485/487 (M+H⁺); ¹H-NMR (CDCl3-d₆, 400 MHz) δ 8.22 (d, J=2.4 Hz, 1H), 7.89 (d, J=2.4 Hz, 1H), 7.49-7.46 (m, 1H), 7.16 (s, 1H), 7.15-7.06 (m, 1H), 7.05-6.93 (m, 1H), 6.69 (d, J=8.8, 1H), 5.43, (s, 2H), 4.81 (s, 1H), 4.24 (s, 2H), 3.61-3.59 (m, 4H), 2.55-2.52 (m, 4H), 2.36 (s, 3H).

It is understood that the examples and embodiments described herein are for illustrative purposes only and that various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A compound of Formula I

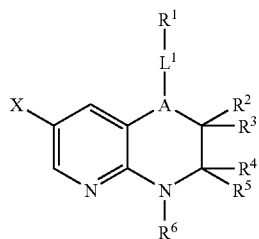

I or a pharmaceutically acceptable salt form thereof,
wherein:
A is N;
X is chosen from -L²G¹L³G²L⁴R⁷ and R⁸;
L¹ is —C₀₋₃-alkyl-C(=O)—C₀₋₃-alkyl-, —C₀₋₃-alkyl-S(=O)₂—C₀₋₃-alkyl-, or —C₁₋₆-alkyl-;
R¹ is an optionally mono- or polysubstituted group chosen from aryl and heteroaryl,
    wherein the substituents may be identical or different and are chosen from halogen, —NO₂, —OR²⁰, —C(=O)R²⁰, —C(=O)OR²⁰, —C(=O)NR²⁰R²¹, —NR²⁰R²¹, C₁₋₃-alkyl, C₁₋₃-haloalkyl, aryl, heteroaryl, C₃₋₁₀-cycloalkyl, heterocycloalkyl, pseudohalogen, —S(=O)ₙR²⁰, —S(=O)₂NR²⁰R²¹, —OCH₂F, —OCHF₂, —OCF₃, —NHOH, —OC(=O)R²⁰, —OC(=O)NR²⁰R²¹, —NR²⁰C(=O)R²¹, —NR²⁰C(=O)OR²¹, and —SCF₃;
R² and R³ are independently chosen from H, OH, and C₁₋₆-alkyl, or R² and R³ together form a carbonyl group;
R⁴ and R⁵ are independently chosen from H and C₁₋₆-alkyl, or R⁴ and R⁵ together form a carbonyl group;
R⁶ is chosen from H and C₁₋₆-alkyl;
L² is a bond, —C₀₋₃-alkyl-C(=O)—C₀₋₃-alkyl-, —C₀₋₃-alkyl-S(=O), —C₀₋₃-alkyl-, —C₀₋₃-alkyl-C(=O)NR³⁰—C₀₋₃-alkyl-, —C₀₋₃-alkyl-S(=O)₂NR³⁰—C₀₋₃-alkyl-, —C₀₋₃-alkyl-C(=O)O—C₀₋₃-alkyl-, —C₀₋₃-alkyl-OC(=O)NR³⁰—C₀₋₃-alkyl-, —C₀₋₃-alkyl-NR³⁰—C₀₋₃-alkyl-, —C₀₋₃-alkyl-O—C₀₋₃-alkyl-, —C₁₋₃-alkyl-, —C₂₋₃-alkenyl-, or —C₂₋₃-alkynyl-;
G¹ is a bond, or an optionally mono- or polysubstituted group chosen from aryl, C₃₋₁₀-cycloalkyl, heterocycloalkyl, and heteroaryl,
    wherein the substituents may be identical or different and are chosen from halogen, —NO₂, —OR⁴⁰, —C(=O)R⁴⁰, —C(=O)OR⁴⁰, —C(=O)NR⁴⁰R⁴¹, —NR⁴⁰R⁴¹, C₁₋₃-alkyl, C₁₋₃-haloalkyl, aryl, heteroaryl, C₃₋₁₀-cycloalkyl, heterocycloalkyl, pseudohalogen, —S(=O)ₙR⁴⁰, —S(=O)₂NR⁴⁰R⁴¹, —OCH₂F, —OCHF₂, —OCF₃, —NHOH, —OC(=O)R⁴⁰, —OC(=O)NR⁴⁰R⁴¹, —NR⁴⁰C(=O)R⁴¹, —NR⁴⁰C(=O)OR⁴¹, and —SCF₃;
L³ is a bond, —C₀₋₃-alkyl-C(=O)—C₀₋₃-alkyl-, —C₀₋₃-alkyl-S(=O)ₙ—C₀₋₃-alkyl-, —C₀₋₃-alkyl-C(=O)NR⁵⁰—C₀₋₃-alkyl-, —C₀₋₃-alkyl-S(=O)₂NR⁵⁰—C₀₋₃-alkyl-, —C₀₋₃-alkyl-C(=O)O—C₀₋₃-alkyl-, —C₀₋₃-alkyl-OC(=O)NR⁵⁰—C₀₋₃-alkyl-, —C₀₋₃-alkyl-NR⁵⁰—C₀₋₃-alkyl-, —C₀₋₃-alkyl-O—C₀₋₃-alkyl-, —C₁₋₃-alkyl-, —C₂₋₃-alkenyl-, or —C₂₋₃-alkynyl-;
G² is a bond, or an optionally mono- or polysubstituted group chosen from aryl, C₃₋₁₀-cycloalkyl, heterocycloalkyl, and heteroaryl,
    wherein the substituents may be identical or different and are chosen from halogen, —NO₂, —OR⁶⁰, —C(=O)R⁶⁰, —C(=O)OR⁶⁰, —C(=O)NR⁶⁰R⁶¹, —NR⁶⁰R⁶¹, C₁₋₃-alkyl, C₁₋₃-haloalkyl, aryl, heteroaryl, C₃₋₁₀-cycloalkyl, heterocycloalkyl, pseudohalogen, —S(=O)ₙR⁶⁰, —S(=O)₂NR⁶⁰R⁶¹, —OCH₂F, —OCHF₂, —OCF₃, —NHOH, —OC(=O)R⁶⁰, —OC(=O)NR⁶⁰R⁶¹, —NR⁶⁰C(=O)R⁶¹, —NR⁶⁰C(=O)OR⁶¹, and —SCF₃;
L⁴ is a bond, —C₀₋₃-alkyl-C(=O)—C₀₋₃-alkyl-, —C₀₋₃-alkyl-S(=O)ₙ—C₀₋₃-alkyl-, —C₀₋₃-alkyl-C(=O)NR⁷⁰—C₀₋₃-alkyl-, —C₀₋₃-alkyl-S(=O)₂NR⁷⁰—C₀₋₃-alkyl-, —C₀₋₃-alkyl-C(=O)O—C₀₋₃-alkyl-, —C₀₋₃-alkyl-OC(=O)NR⁷⁰—C₀₋₃-alkyl-, —C₀₋₃-alkyl-NR⁷⁰—C₀₋₃-alkyl-, —C₀₋₃-alkyl-O—C₀₋₃-alkyl-, —C₁₋₃-alkyl-, —C₂₋₃-alkenyl-, or —C₂₋₃-alkynyl-;
R⁷ is an optionally mono- or polysubstituted group chosen from C₁₋₆-alkyl, C₂₋₆-alkenyl, C₂₋₆-alkynyl, aryl, C₃₋₁₀-cycloalkyl, heterocycloalkyl, and heteroaryl,
    wherein the substituents may be identical or different and are chosen from halogen, —NO₂, —OR⁸⁰, —C(=O)R⁸⁰, —C(=O)OR⁸⁰, —C(=O)NR⁸⁰R⁸¹, —NR⁸⁰R⁸¹, C₁₋₆-alkyl, C₁₋₆-haloalkyl, aryl, heteroaryl, C₃₋₁₀-cycloalkyl, heterocycloalkyl, pseudohalogen, —S(=O)ₙR⁸⁰, —S(=O)₂NR⁸⁰R⁸¹, —OCH₂F, —OCHF₂, —OCF₃, —NHOH, —OC(=O)R⁸⁰, —OC(=O)NR⁸⁰R⁸¹, —NR⁸⁰C(=O)R⁸¹, —NR⁸⁰C(=O)OR⁸¹, —SiR⁸⁰R⁸¹R⁸² and —SCF₃;
R⁸ is chosen from H, halogen, CN, and C(=O)OH;
R¹⁰, R²⁰, R²¹, R³⁰, R⁴⁰, R⁴¹, R⁵⁰, R⁶⁰, R⁶¹, R⁷⁰, R⁸⁰, R⁸¹, and R⁸² at each occurrence are independently chosen from H, C₁₋₆-alkyl, C₁₋₆-haloalkyl, aryl, heteroaryl, C₃₋₁₀-cycloalkyl, and heterocycloalkyl; and
n is 0, 1, or 2;
provided that when L¹ is —C(=O)— and R¹ is phenyl, R⁸ is not or Br.

2. A compound as defined in claim 1, wherein L¹ is —C₀₋₃-alkyl-C(=O)—C₀₋₃-alkyl-, or —C₀₋₃-alkyl-S(=O)₂—C₀₋₃alkyl-.

3. A compound as defined in claim 1, wherein L¹ is —C₁₋₆-alkyl-.

4. A compound as defined in claim 1, wherein each R¹ substituent is independently chosen from halogen, —C(=O)—C₁₋₆-alkyl, C₁₋₃-haloalkyl, cyano, and —OCF₃.

5. A compound as defined in claim 1, wherein R² and R³ are independently chosen from H and C₁₋₆-alkyl, or R² and R³ together form a carbonyl group.

6. A compound as defined in claim 1, wherein R⁴ and R⁵ are H.

7. A compound as defined in claim 1, wherein R⁶ is H.

8. A compound as defined in claim 1, wherein X is -L²G¹L³G²L⁴R⁷.

9. A compound as defined in claim 8, wherein L² is a bond, —$C_{0-3}$-alkyl-C(=O)—$C_{0-3}$-alkyl-, —S(=O)$_n$—$C_{0-3}$-alkyl-, —C(=O)NR³⁰—$C_{0-3}$-alkyl-, —S(=O)$_2$NR³⁰—$C_{0-3}$-alkyl-, —C(=O)O—$C_{0-3}$-alkyl-, —CH$_2$—OC(=O)NR³⁰—$C_{0-3}$-alkyl-, —$C_{0-3}$-alkyl-OC(=O)NR³⁰—CH$_2$—, —CH$_2$—NR³⁰—$C_{0-3}$-alkyl-, —CH$_2$—O—$C_{0-3}$-alkyl-, —CH$_2$—OC(=O)—$C_{0-3}$-alkyl-, —CH$_2$—NR¹⁰C(=O)—$C_{0-3}$-alkyl-, —CH$_2$—NR¹⁰S(=O)$_2$—$C_{0-3}$-alkyl-, —$C_{1-3}$-alkyl-, —$C_{2-3}$-alkenyl-, or —$C_{2-3}$-alkynyl-.

10. A compound as defined in claim 9, wherein L² is a bond, —$C_{0-3}$-alkyl-C(=O)—$C_{0-3}$-alkyl-, —C(=O)NR³⁰—$C_{0-3}$-alkyl-, —C(=O)O—$C_{0-3}$-alkyl-, or —$C_{2-3}$-alkynyl-.

11. A compound as defined in 8, wherein G¹ is a bond, or an optionally mono- or polysubstituted group chosen from aryl, heterocycloalkyl, and heteroaryl.

12. A compound as defined in claim 8, wherein L³ is a bond, —$C_{0-3}$-alkyl-C(=O)—$C_{0-3}$-alkyl-, —$C_{0-3}$-alkyl-C(=O)NR⁵⁰—$C_{0-3}$-alkyl-, —$C_{0-3}$-alkyl-S(=O)$_2$NR⁵⁰—$C_{0-3}$-alkyl-, —$C_{0-3}$-alkyl-C(=O)O—$C_{0-3}$-alkyl-, —$C_{0-3}$-alkyl-OC(=O)NR⁵⁰—$C_{0-3}$-alkyl-, —$C_{0-3}$-alkyl-NR⁵⁰—$C_{0-3}$-alkyl-, —$C_{0-3}$-alkyl-O—$C_{0-3}$-alkyl-, or —$C_{1-3}$-alkyl-.

13. A compound as defined in claim 8, wherein G² is a bond, or an optionally mono- or polysubstituted group chosen from aryl, heterocycloalkyl, and heteroaryl.

14. A compound as defined in claim 8, wherein L⁴ is a bond, —$C_{0-3}$-alkyl-C(=O)—$C_{0-3}$-alkyl-, —$C_{0-3}$-alkyl-C(=O)NR⁷⁰—$C_{0-3}$-alkyl-, —$C_{0-3}$-alkyl-C(=O)O—$C_{0-3}$-alkyl-, or —$C_{1-3}$-alkyl-.

15. A compound as defined in claim 8, wherein R⁷ is an optionally mono- or polysubstituted group chosen from $C_{1-6}$-alkyl, aryl, $C_{3-10}$-cycloalkyl, heterocycloalkyl, and heteroaryl.

16. A compound as defined in claim 15, wherein each R⁷ substituent is independently chosen from halogen, —OR⁸⁰, —C(=O)R⁸⁰, —C(=O)OR⁸⁰, —C(=O)NR⁸⁰R⁸¹, —NR⁸⁰R⁸¹, $C_{1-6}$-alkyl, $C_{1-6}$-haloalkyl, aryl, heteroaryl, $C_{3-10}$-cycloalkyl, heterocycloalkyl, cyano, —S(=O)$_n$R⁸⁰, —S(=O)$_2$NR⁸⁰R⁸¹, —OCF$_3$, and —SiR⁸⁰R⁸¹R⁸².

17. A compound as defined in claim 8, wherein at least one of G¹ and R⁷ is an optionally mono- or polysubstituted group chosen from aryl, $C_{3-10}$-cycloalkyl, heterocycloalkyl, and heteroaryl.

18. A compound as defined in claim 1, wherein said compound is 1-(2-chloro-3,6-difluorobenzyl)-7-pyridin-3-yl-3,4-dihydro-1H-pyrido[2,3-b]pyrazin-2-one;
4-[1-(2-chloro-3,6-difluorobenzyl)-2-oxo-1,2,3,4-tetrahydropyrido[2,3-b]pyrazin-7-yl]benzoic acid ethyl ester;
4-[1-(2-chloro-3,6-difluorobenzyl)-2-oxo-1,2,3,4-tetrahydropyrido[2,3-b]pyrazin-7-yl]benzoic acid;
1-(2-chloro-3,6-difluorobenzyl)-7-[4-(4-methylpiperazine-1-carbonyl)phenyl]-3,4-dihydro-1H-pyrido[2,3-b]pyrazin-2-one;
4-(1-benzyl-2-oxo-1,2,3,4-tetrahydropyrido[2,3-b]pyrazin-7-yl)benzoic acid ethyl ester;
4-(1-benzyl-2-oxo-1,2,3,4-tetrahydropyrido[2,3-b]pyrazin-7-yl)benzoic acid;
1-benzyl-7-pyridin-3-yl-3,4-dihydro-1H-pyrido[2,3-b]pyrazin-2-one;
4-(1-benzyl-2-oxo-1,2,3,4-tetrahydropyrido[2,3-b]pyrazin-7-yl)-N-(2-pyrrolidin-1-yl-ethyl)benzamide;
S-1-benzyl-7-[4-(2-[(pyrrolidin-1-yl)methyl]pyrrolidine-1-carbonyl)phenyl]-3,4-dihydro-1H-pyrido[2,3-b]pyrazin-2-one;
4-(1-benzyl-2-oxo-1,2,3,4-tetrahydropyrido[2,3-b]pyrazin-7-yl)-N-(3-morpholin-4-yl-propyl)benzamide;
4-(1-benzyl-2-oxo-1,2,3,4-tetrahydropyrido[2,3-b]pyrazin-7-yl)-N-(4-dimethylaminobutyl)benzamide;
4-(1-benzyl-2-oxo-1,2,3,4-tetrahydropyrido[2,3-b]pyrazin-7-yl)-N-(6-dimethylaminohexyl)benzamide;
S-1-benzyl-7-[3-(2[-(pyrrolidin-1-yl)methyl]pyrrolidine-1-carbonyl)phenyl]-3,4-dihydro-1H-pyrido[2,3-b]pyrazin-2-one;
3-(1-benzyl-2-oxo-1,2,3,4-tetrahydropyrido[2,3-b]pyrazin-7-yl)-N-(2-dimethylamino-ethyl)benzamide;
1-benzyl-7-[3-(pyrrolidine-1-carbonyl)phenyl]-3,4-dihydro-1H-pyrido[2,3-b]pyrazin-2-one;
7-(4-acetylphenyl)-1-benzyl-3,4-dihydro-1H-pyrido[2,3-b]pyrazin-2-one;
3-(1-benzyl-2-oxo-1,2,3,4-tetrahydropyrido[2,3-b]pyrazin-7-yl)-N-ethyl-benzamide;
4-(1-benzyl-2-oxo-1,2,3,4-tetrahydropyrido[2,3-b]pyrazin-7-yl)benzamide;
1-benzyl-7-(4-methanesulfonyl-phenyl)-3,4-dihydro-1H-pyrido[2,3-b]pyrazin-2-one;
1-benzyl-7-[4-(4-methylpiperazine-1-carbonyl)phenyl]-3,4-dihydro-1H-pyrido[2,3-b]pyrazin-2-one;
1-benzyl-7-[4-(4-(pyrrolidin-1-yl)piperidine-1-carbonyl)phenyl]-3,4-dihydro-1H-pyrido[2,3-b]pyrazin-2-one;
4-(1-benzyl-2-oxo-1,2,3,4-tetrahydropyrido[2,3-b]pyrazin-7-yl)-N-ethyl-benzamide;
5-(1-benzyl-2-oxo-1,2,3,4-tetrahydropyrido[2,3-b]pyrazin-7-yl)pyridine-2-carbonitrile;
5-(1-benzyl-2-oxo-1,2,3,4-tetrahydropyrido[2,3-b]pyrazin-7-yl)pyridine-2-carboxylic acid ethyl ester;
3-(1-benzyl-2-oxo-1,2,3,4-tetrahydropyrido[2,3-b]pyrazin-7-yl)benzoic acid methyl ester;
3-(1-benzyl-2-oxo-1,2,3,4-tetrahydropyrido[2,3-b]pyrazin-7-yl)benzoic acid;
1-benzyl-7-pyridin-3-yl-1,2,3,4-tetrahydropyrido[2,3-b]pyrazine;
4-(1-benzyl-1,2,3,4-tetrahydropyrido[2,3-b]pyrazin-7-yl)benzoic acid ethyl ester;
4-(1-benzyl-1,2,3,4-tetrahydropyrido[2,3-b]pyrazin-7-yl)benzoic acid;
[4-(1-benzyl-1,2,3,4-tetrahydropyrido[2,3-b]pyrazin-7-yl)phenyl]-(4-methylpiperazin-1-yl)methanone;
[4-(1-benzyl-1,2,3,4-tetrahydropyrido[2,3-b]pyrazin-7-yl)phenyl]-((S)-2-pyrrolidinylmethylpyrrolidin-1-yl)methanone;
[4-(1-benzyl-1,2,3,4-tetrahydropyrido[2,3-b]pyrazin-7-yl)phenyl]-(4-(pyrrolidin-1-yl)piperidin-1-yl)methanone;
phenyl-(7-pyridin-3-yl-3,4-dihydro-2H-pyrido[2,3-b]pyrazin-1-yl)methanone;
4-(1-benzoyl-1,2,3,4-tetrahydropyrido[2,3-b]pyrazin-7-yl)benzoic acid ethyl ester;
2-pyrrolidin-1-yl-ethanesulfonic acid[4-(1-benzyl-2-oxo-1,2,3,4-tetrahydropyrido[2,3-b]pyrazin-7-yl)phenyl]amide;
2-pyrrolidin-1-yl-ethanesulfonic acid[4-(1-benzoyl-1,2,3,4-tetrahydropyrido[2,3-b]pyrazin-7-yl)phenyl]amide;
2-(4-methylpiperazin-1-yl)-ethanesulfonic acid[4-(1-benzoyl-1,2,3,4-tetrahydropyrido[2,3-b]pyrazin-7-yl)phenyl]amide;
2-pyrrolidin-1-yl-ethanesulfonic acid{4-[1-(2,5-difluorobenzyl)-2-oxo-1,2,3,4-tetrahydropyrido[2,3-b]pyrazin-7-yl]phenyl}-amide;

2-[ethyl-((S)-1-pyrrolidin-1-ylmethyl-propyl)-amino]-ethanesulfonic acid{4-[1-(2,5-difluorobenzyl)-2-oxo-1,2,3,4-tetrahydropyrido[2,3-b]pyrazin-7-yl]phenyl}-amide;

2-morpholin-4-yl-ethanesulfonic acid{4-[1-(2,5-difluorobenzyl)-2-oxo-1,2,3,4-tetrahydropyrido[2,3-b]pyrazin-7-yl]phenyl}-amide;

2-pyrrolidin-1-yl-ethanesulfonic acid{4-[1-(2,5-difluorobenzyl)-1,2,3,4-tetrahydropyrido[2,3-b]pyrazin-7-yl]phenyl}-amide;

4-(1-benzoyl-1,2,3,4-tetrahydropyrido[2,3-b]pyrazin-7-yl)-N-(2-dimethylamino-ethyl)benzamide;

4-(1-benzoyl-1,2,3,4-tetrahydropyrido[2,3-b]pyrazin-7-yl)-N-(3-dimethylamino-propyl)benzamide;

{7-[4-(4-methylpiperazine-1-carbonyl)phenyl]-3,4-dihydro-2H-pyrido[2,3-b]pyrazin-1-yl}phenylmethanone;

4-[1-(2,5-difluorobenzyl)-2-oxo-1,2,3,4-tetrahydropyrido[2,3-b]pyrazin-7-yl]benzoic acid ethyl ester;

4-[1-(2,5-difluorobenzyl)-2-oxo-1,2,3,4-tetrahydropyrido[2,3-b]pyrazin-7-yl]benzoic acid;

1-(2,5-difluorobenzyl)-7-[4-((S)-2-[(pyrrolidin-1-yl)methyl]pyrrolidine-1-carbonyl)phenyl]-3,4-dihydro-1H-pyrido[2,3-b]pyrazin-2-one;

4-[1-(2,5-difluorobenzyl)-2-oxo-1,2,3,4-tetrahydropyrido[2,3-b]pyrazin-7-yl]-N-(2-pyrrolidin-1-yl-ethyl)benzamide;

1-(2,5-difluorobenzyl)-7-[4-(4-methylpiperazine-1-carbonyl)phenyl]-3,4-dihydro-1H-pyrido[2,3-b]pyrazin-2-one;

1-(2,5-difluorobenzyl)-7-[4-(4-(pyrrolidin-1-yl)piperidine-1-carbonyl)phenyl]-3,4-dihydro-1H-pyrido[2,3-b]pyrazin-2-one;

(S)-2-[(pyrrolidin-1-yl)methyl]pyrrolidine-1-carboxylic acid{4-[1-(2,5-difluorobenzyl)-2-oxo-1,2,3,4-tetrahydropyrido[2,3-b]pyrazin-7-yl]phenyl}-amide;

4-[1-(2,5-difluorobenzyl)-1,2,3,4-tetrahydropyrido[2,3-b]pyrazin-7-yl]benzoic acid ethyl ester;

4-[1-(2,5-difluorobenzyl)-1,2,3,4-tetrahydropyrido[2,3-b]pyrazin-7-yl]benzoic acid;

{4-[1-(2,5-difluorobenzyl)-1,2,3,4-tetrahydropyrido[2,3-b]pyrazin-7-yl]phenyl}-((S)-2-((pyrrolidin-1-yl)methyl)pyrrolidin-1-yl)methanone;

{4-[1-(2,5-difluorobenzyl)-1,2,3,4-tetrahydropyrido[2,3-b]pyrazin-7-yl]phenyl}-(4-(pyrrolidin-1-yl)piperidin-1-yl)methanone;

{4-[1-(2,5-difluorobenzyl)-1,2,3,4-tetrahydropyrido[2,3-b]pyrazin-7-yl]phenyl}-(4-methylpiperazin-1-yl)methanone;

{4-[1-(2,5-difluorobenzyl)-1,2,3,4-tetrahydropyrido[2,3-b]pyrazin-7-yl]phenyl}-morpholin-4-yl-methanone;

1-(2,5-difluorobenzyl)-7-[6-(4-methylpiperazin-1-yl)pyridin-3-yl]-1,2,3,4-tetrahydropyrido[2,3-b]pyrazine;

1-(2,5-difluorobenzyl)-7-(6-morpholin-4-yl-pyridin-3-yl)-1,2,3,4-tetrahydropyrido[2,3-b]pyrazine;

5-[1-(2,5-difluorobenzyl)-1,2,3,4-tetrahydropyrido[2,3-b]pyrazin-7-yl]-pyridine-2-carbonitrile;

5-[1-(2,5-difluorobenzyl)-1,2,3,4-tetrahydropyrido[2,3-b]pyrazin-7-yl]-pyridine-2-carboxylic acid;

5-[1-(2,5-difluorobenzyl)-1,2,3,4-tetrahydropyrido[2,3-b]pyrazin-7-yl]-nicotinic acid ethyl ester;

5-[1-(2,5-difluorobenzyl)-1,2,3,4-tetrahydropyrido[2,3-b]pyrazin-7-yl]-nicotinic acid;

1-(2,5-difluorobenzyl)-1,2,3,4-tetrahydropyrido[2,3-b]pyrazine-7-carboxylic acid ethyl ester;

{5-[1-(2,5-difluorobenzyl)-1,2,3,4-tetrahydropyrido[2,3-b]pyrazin-7-yl]-pyridin-2-yl}morpholin-4-yl-methanone;

[1-(2,5-difluorobenzyl)-1,2,3,4-tetrahydropyrido[2,3-b]pyrazin-7-yl]-(4-methylpiperazin-1-yl)methanone;

1-(2,5-difluorobenzyl)-1,2,3,4-tetrahydropyrido[2,3-b]pyrazine-7-carboxylic acid[2(4-methylpiperazin-1-yl)ethyl]amide;

7-[4-((S)-2-[(pyrrolidin-1-yl)methyl]pyrrolidine-1-carbonyl)phenyl]-1-(2,4,5-trifluorobenzyl)-3,4-dihydro-1H-pyrido[2,3-b]pyrazin-2-one;

((S)-2-((pyrrolidin-1-yl)methyl)pyrrolidin-1-yl)-{4-[1-(2,4,5-trifluorobenzyl)-1,2,3,4-tetrahydropyrido[2,3-b]pyrazin-7-yl]phenyl}-methanone;

7-[4-(4-methylpiperazine-1-carbonyl)phenyl]-1-(2,4,5-trifluorobenzyl)-3,4-dihydro-1H-pyrido[2,3-b]pyrazin-2-one;

(4-methylpiperazin-1-yl)-{4-[1-(2,4,5-trifluorobenzyl)-1,2,3,4-tetrahydropyrido[2,3-b]pyrazin-7-yl]phenyl}-methanone;

(2,5-difluorophenyl)-{7-[4-(4-methylpiperazine-1-carbonyl)phenyl]-3,4-dihydro-2H-pyrido[2,3-b]pyrazin-1-yl}-methanone;

(2,5-difluorophenyl)-{7-[4-((S)-2-[(pyrrolidin-1-yl)methyl]pyrrolidine-1-carbonyl)phenyl]-3,4-dihydro-2H-pyrido[2,3-b]pyrazin-1-yl}-methanone;

1-(2,5-difluorobenzyl)-3,3-dimethyl-7-[4-((S)-2-[(pyrrolidin-1-yl)methyl]pyrrolidine-1-carbonyl)phenyl]-3,4-dihydro-1H-pyrido[2,3-b]pyrazin-2-one;

1-(2,5-difluorobenzyl)-3,3-dimethyl-7-[4-(4-methylpiperazine-1-carbonyl)phenyl]-3,4-dihydro-1H-pyrido[2,3-b]pyrazin-2-one;

{4-[1-(2,5-difluorobenzyl)-3,3-dimethyl-1,2,3,4-tetrahydropyrido[2,3-b]pyrazin-7-yl]phenyl}-((S)-2-((pyrrolidin-1-yl)methyl)pyrrolidin-1-yl)methanone;

{4-[1-(2,5-difluorobenzyl)-3,3-dimethyl-1,2,3,4-tetrahydropyrido[2,3-b]pyrazin-7-yl]phenyl}-(4-methylpiperazin-1-yl)methanone;

{4-[1-(2-chloro-3,6-difluorobenzyl)-1,2,3,4-tetrahydropyrido[2,3-b]pyrazin-7-yl]phenyl}-(4-(pyrrolidin-1-yl)piperidin-1-yl)methanone;

{4-[1-(2-chloro-3,6-difluorobenzyl)-1,2,3,4-tetrahydropyrido[2,3-b]pyrazin-7-yl]phenyl}-((S)-2-((pyrrolidin-1-yl)methyl)pyrrolidin-1-yl)methanone;

1-(2-chloro-3,6-difluorobenzyl)-7-(3-chloro-2-morpholin-4-yl-pyridin-4-yl)-1,2,3,4-tetrahydropyrido[2,3-b]pyrazine;

1-(2-chloro-3,6-difluorobenzyl)-7-(3-fluoro-2-morpholin-4-yl-pyridin-4-yl)-1,2,3,4-tetrahydropyrido[2,3-b]pyrazine;

1-(2-chloro-3,6-difluorobenzyl)-7-(3,5-dimethyl-isoxazol-4-yl)-1,2,3,4-tetrahydropyrido[2,3-b]pyrazine;

{4-[1-(2-chloro-3,6-difluorobenzyl)-1,2,3,4-tetrahydropyrido[2,3-b]pyrazin-7-yl]phenyl}-(4-methylpiperazin-1-yl)methanone;

1-(2-chloro-3,6-difluorobenzyl)-7-(6-morpholin-4-yl-pyridin-3-yl)-1,2,3,4-tetrahydropyrido[2,3-b]pyrazine;

1-(2-chloro-3,6-difluorobenzyl)-7-[2-(4-methylpiperazin-1-yl)-pyrimidin-5-yl]-1,2,3,4-tetrahydropyrido[2,3-b]pyrazine;

1-(2-chloro-3,6-difluorobenzyl)-7-(2-morpholin-4-yl-pyrimidin-5-yl)-1,2,3,4-tetrahydropyrido[2,3-b]pyrazine;

1-(2-chloro-3,6-difluorobenzyl)-7-(4-morpholin-4-yl-phenyl)-1,2,3,4-tetrahydropyrido[2,3-b]pyrazine;

2-phenyl-1-{7-[4-(4-(pyrrolidin-1-yl)piperidine-1-carbonyl)phenyl]-3,4-dihydro-2H-pyrido[2,3-b]pyrazin-1-yl}-ethanone;

2-(2,5-difluorophenyl)-1-{7-[2-(4-methylpiperazin-1-yl)pyridin-4-yl]-3,4-dihydro-2H-pyrido[2,3-b]pyrazin-1-yl}ethanone;

2-(2,5-difluorophenyl)-1-{7-[4-(4-(pyrrolidin-1-yl)piperidine-1-carbonyl)phenyl]-3,4-dihydro-2H-pyrido[2,3-b]pyrazin-1-yl}ethanone;

{4-[1-(5-chloro-2-trifluoromethylbenzyl)-1,2,3,4-tetrahydropyrido[2,3-b]pyrazin-7-yl]phenyl}-(4-(pyrrolidin-1-yl)piperidin-1-yl)methanone;

1-(5-chloro-2-trifluoromethylbenzyl)-7-[6-(4-methylpiperazin-1-yl)pyridin-3-yl]-1,2,3,4-tetrahydropyrido[2,3-b]pyrazine;

1-(2-chloro-5-trifluoromethylbenzyl)-7-[6-(4-methylpiperazin-1-yl)pyridin-3-yl]-1,2,3,4-tetrahydropyrido[2,3-b]pyrazine;

1-(2,5-difluorobenzenesulfonyl)-7-[6-(4-methylpiperazin-1-yl)pyridin-3-yl]-1,2,3,4-tetrahydropyrido[2,3-b]pyrazine;

1-benzenesulfonyl-7-[6-(4-methylpiperazin-1-yl)pyridin-3-yl]-1,2,3,4-tetrahydropyrido[2,3-b]pyrazine;

1-(2-chlorobenzenesulfonyl)-7-[6-(4-methylpiperazin-1-yl)pyridin-3-yl]-1,2,3,4 tetrahydropyrido[2,3-b]pyrazine;

1-(2,5-dichlorobenzyl)-7-(2-methoxypyrimidin-5-yl)-1,2,3,4-tetrahydropyrido[2,3-b]pyrazine;

4-[1-(2,5-dichlorobenzyl)-1,2,3,4-tetrahydropyrido[2,3-b]pyrazin-7-yl]-3,6-dihydro-2H-pyridine-1-carboxylic acid tert-butyl ester;

1-(2,5-dichlorobenzyl)-7-(1,2,3,6-tetrahydropyridin-4-yl)-1,2,3,4-tetrahydropyrido[2,3-b]pyrazine, {4-[1-(2,5-dichlorobenzyl)-1,2,3,4-tetrahydropyrido[2,3-b]pyrazin-7-yl]phenyl}-(4-methylpiperazin-1-yl)methanone;

1-(2,6-dichlorobenzyl)-7-pyridin-3-yl-3,4-dihydro-1H-pyrido[2,3-b]pyrazin-2-one;

1-(2,6-dichlorobenzyl)-7-pyridin-3-yl-1,2,3,4-tetrahydropyrido[2,3-b]pyrazine;

4-[1-(2,6-dichlorobenzyl)-2-oxo-1,2,3,4-tetrahydropyrido[2,3-b]pyrazin-7-yl]benzoic acid ethyl ester;

4-[1-(2,6-dichlorobenzyl)-2-oxo-1,2,3,4-tetrahydropyrido[2,3-b]pyrazin-7-yl]benzoic acid;

S-1-(2,6-dichlorobenzyl)-7-[4-((2-pyrrolidin-1-yl)methylpyrrolidine-1-carbonyl)phenyl]-3,4-dihydro-1H-pyrido[2,3-b]pyrazin-2-one;

4-[1-(2,6-dichlorobenzyl)-2-oxo-1,2,3,4-tetrahydropyrido[2,3-b]pyrazin-7-yl]-N-(2-pyrrolidin-1-yl-ethyl)benzamide;

4-[1-(2,6-dichlorobenzyl)-2-oxo-1,2,3,4-tetrahydropyrido[2,3-b]pyrazin-7-yl]-N-(6-dimethylaminohexyl)benzamide;

4-[1-(2,6-dichlorobenzyl)-2-oxo-1,2,3,4-tetrahydropyrido[2,3-b]pyrazin-7-yl]-N-(4-dimethylaminobutyl)benzamide;

7-[4-(4-methylpiperazine-1-carbonyl)phenyl]-1-[1-(2,4,5-trifluorophenyl)ethyl]-3,4-dihydro-1H-pyrido[2,3-b]pyrazin-2-one;

S-{2-[(pyrrolidin-1-yl)methyl]pyrrolidin-1-yl}-(4-{1-[1-(2,4,5-trifluorophenyl)ethyl]-1,2,3,4-tetrahydropyrido[2,3-b]pyrazin-7-yl}phenyl)methanone;

(4-methylpiperazin-1-yl)-(4-{1-[1-(2,4,5-trifluorophenyl)ethyl]-1,2,3,4-tetrahydropyrido[2,3-b]pyrazin-7-yl}phenyl)methanone;

S-(4-{1-[1-(2,5-difluorophenyl)ethyl]-1,2,3,4-tetrahydropyrido[2,3-b]pyrazin-7-yl}phenyl)-{2-[(pyrrolidin-1-yl)methyl]pyrrolidin-1-yl}methanone;

1-[1-(2,5-difluorophenyl)ethyl]-7-[4-(4-methylpiperazine-1-carbonyl)phenyl]-3,4-dihydro-1H-pyrido[2,3-b]pyrazin-2-one;

S-(4-{1-[1-(2,5-difluorophenyl)ethyl]-1,2,3,4-tetrahydropyrido[2,3-b]pyrazin-7-yl}phenyl)-{2-[(pyrrolidin-1-yl)methyl]pyrrolidin-1-yl}methanone;

1-(2,5-dichlorobenzyl)-7-[4-(4-(pyrrolidin-1-yl)piperidine-1-carbonyl)phenyl]-3,4-dihydro-1H-pyrido[2,3-b]pyrazin-2-one;

S-1-(2,5-dichlorobenzyl)-7-[4-(2-[(pyrrolidin-1-yl)methyl]pyrrolidine-1-carbonyl)phenyl]-3,4-dihydro-1H-pyrido[2,3-b]pyrazin-2-one;

S-{4-[1-(2,5-dichlorobenzyl)-1,2,3,4-tetrahydropyrido[2,3-b]pyrazin-7-yl]phenyl}-{2-[(pyrrolidin-1-yl)methyl]pyrrolidin-1-yl}methanone;

{4-[1-(2,5-dichlorobenzyl)-1,2,3,4-tetrahydropyrido[2,3-b]pyrazin-7-yl]phenyl}-(4-(pyrrolidin-1-yl)piperidin-1-yl)methanone;

1-(2,6-dichlorobenzyl)-7-[4-(4-(pyrrolidin-1-yl)piperidine-1-carbonyl)phenyl]-3,4-dihydro-1H-pyrido[2,3-b]pyrazin-2-one;

{4-[1-(2,6-dichlorobenzyl)-1,2,3,4-tetrahydropyrido[2,3-b]pyrazin-7-yl]phenyl}-(4-(pyrrolidin-1-yl)piperidin-1-yl)methanone;

{4-[1-(2,6-dichlorobenzyl)-1,2,3,4-tetrahydropyrido[2,3-b]pyrazin-7-yl]phenyl}-{2-[(pyrrolidin-1-yl)methyl]pyrrolidin-1-yl}methanone;

7-(6-chloropyridin-3-yl)-1-(2,5-dichlorobenzyl)-1,2,3,4-tetrahydropyrido[2,3-b]pyrazine;

1-(2,5-dichlorobenzyl)-7-(6-pyrrolidin-1-yl-pyridin-3-yl)-1,2,3,4-tetrahydropyrido[2,3-b]pyrazine;

7-(2-chloropyridin-4-yl)-1-(2,6-dichlorobenzyl)-1,2,3,4-tetrahydropyrido[2,3-b]pyrazine;

{3-[1-(2,5-dichlorobenzyl)-1,2,3,4-tetrahydropyrido[2,3-b]pyrazin-7-yl]prop-2-ynyl}carbamic acid tert-butyl ester;

3-[1-(2,5-dichlorobenzyl)-1,2,3,4-tetrahydropyrido[2,3-b]pyrazin-7-yl]prop-2-ynylamine;

{3-[1-(2,6-dichlorobenzyl)-1,2,3,4-tetrahydropyrido[2,3-b]pyrazin-7-yl]prop-2-ynyl}carbamic acid tert-butyl ester;

3-[1-(2,6-dichlorobenzyl)-1,2,3,4-tetrahydropyrido[2,3-b]pyrazin-7-yl]prop-2-ynylamine;

N-{3-[1-(2,6-dichlorobenzyl)-1,2,3,4-tetrahydropyrido[2,3-b]pyrazin-7-yl]prop-2-ynyl}-2-dimethylamino-acetamide;

{3-[1-(2,5-dichlorobenzyl)-1,2,3,4-tetrahydropyrido[2,3-b]pyrazin-7-yl]prop-2-ynyl}-dimethylamine;

1-(2,5-dichlorobenzyl)-7-[3-(1,1-dioxo-1$\lambda^6$-thiomorpholin-4-yl)prop-1-ynyl]-1,2,3,4-tetrahydropyrido[2,3-b]pyrazine;

1-[1-(2-chloro-3,6-difluorophenyl)ethyl]-7-[6-(4-methylpiperazin-1-yl)pyridin-3-yl]-1,2,3,4-tetrahydropyrido[2,3-b]pyrazine;

1-(2,5-dichlorobenzyl)-7-[6-(4-methylpiperazin-1-yl)pyridin-3-yl]-1,2,3,4-tetrahydropyrido[2,3-b]pyrazine;

1-[3-fluoro-2-(trifluoromethyl)benzyl]-7-[6-(4-methylpiperazin-1-yl)pyridin-3-yl]-1,2,3,4-tetrahydropyrido[2,3-b]pyrazine;

1-(2-chloro-3,6-difluorobenzyl)-7-(2-chloropyridin-4-yl)-1,2,3,4-tetrahydropyrido[2,3-b]pyrazine;

1-(2-chloro-3,6-difluorobenzyl)-7-(2-pyrrolidin-1-yl-pyridin-4-yl)-1,2,3,4-tetrahydropyrido[2,3-b]pyrazine;

5-[1-(2-chloro-3,6-difluorobenzyl)-1,2,3,4-tetrahydropyrido[2,3-b]pyrazin-7-yl]-pyridin-2-ylamine;

1-(2-chloro-3,6-difluorobenzyl)-7-[6-(4-methylpiperazin-1-yl)pyridin-3-yl]-1,2,3,4-tetrahydropyrido[2,3-b]pyrazine;

1-(2-chloro-3,6-difluorobenzyl)-7-(2-morpholin-4-yl-pyridin-4-yl)-1,2,3,4-tetrahydropyrido[2,3-b]pyrazine;

1-(2,5-dichlorobenzyl)-4-methyl-7-[6-(4-methylpiperazin-1-yl)pyridin-3-yl]-1,2,3,4-tetrahydropyrido[2,3-b]pyrazine;
1-(2-chloro-3,6-difluorobenzyl)-7-(3-morpholin-4-yl-phenyl)-1,2,3,4-tetrahydropyrido[2,3-b]pyrazine;
1-(2-chloro-3,6-difluorobenzyl)-7-[2-(4-methylpiperazin-1-yl)pyridin-4-yl]-1,2,3,4-tetrahydropyrido[2,3-b]pyrazine;
1-(2-chloro-3,6-difluorobenzyl)-7-[1-(3-methylbutyl)-1H-pyrazol-4-yl]-1,2,3,4-tetrahydropyrido[2,3-b]pyrazine;
1-(2-chloro-3,6-difluorobenzyl)-7-(1H-pyrazol-4-yl)-1,2,3,4-tetrahydropyrido[2,3-b]pyrazine;
4-{1-[5-chloro-2-(trifluoromethyl)benzyl]-1,2,3,4-tetrahydropyrido[2,3-b]pyrazin-7-yl}benzoic acid ethyl ester;
3-{1-[5-chloro-2-(trifluoromethyl)benzyl]-1,2,3,4-tetrahydropyrido[2,3-b]pyrazin-7-yl}benzoic acid ethyl ester;
4-{1-[5-chloro-2-(trifluoromethyl)benzyl]-1,2,3,4-tetrahydropyrido[2,3-b]pyrazin-7-yl}benzoic acid;
3-{1-[5-chloro-2-(trifluoromethyl)benzyl]-1,2,3,4-tetrahydropyrido[2,3-b]pyrazin-7-yl}benzoic acid;
(2-{4-[1-(2-chloro-3,6-difluorobenzyl)-1,2,3,4-tetrahydropyrido[2,3-b]pyrazin-7-yl]-pyrazol-1-yl}ethyl)dimethylamine;
1-[5-chloro-2-(trifluoromethyl)benzyl]-7-(2-piperazin-1-yl-pyridin-4-yl)-1,2,3,4-tetrahydro-pyrido[2,3-b]pyrazine;
1-[4-(4-{1-[5-chloro-2-(trifluoromethyl)benzyl]-1,2,3,4-tetrahydro-pyrido[2,3-b]pyrazin-7-yl}pyridin-2-yl)piperazin-1-yl]ethanone;
1-[5-chloro-2-(trifluoromethyl)benzyl]-7-(1H-pyrazol-4-yl)-1,2,3,4-tetrahydro-pyrido[2,3-b]pyrazine;
1-[5-chloro-2-(trifluoromethyl)benzyl]-7-(1-triisopropylsilanyl-1H-pyrrol-3-yl)-1,2,3,4-tetrahydropyrido[2,3-b]pyrazine;
1-[5-chloro-2-(trifluoromethyl)benzyl]-7-(1H-pyrrol-3-yl)-1,2,3,4-tetrahydro-pyrido[2,3-b]pyrazine;
1-[5-chloro-2-(trifluoromethyl)benzyl]-7-(1-methyl-1H-pyrazol-4-yl)-1,2,3,4-tetrahydropyrido[2,3-b]pyrazine;
{1-[(5-chloro-2-trifluoromethyl)benzyl]-1,2,3,4-tetrahydro-pyrido[2,3-b]pyrazin-7-yl}piperidin-1-yl-methanone;
{1-[(5-chloro-2-trifluoromethyl)benzyl]-1,2,3,4-tetrahydropyrido[2,3-b]pyrazin-7-yl}-(4-methoxy-piperidin-1-yl)methanone;
[1-(2,5-dichlorobenzyl)-1,2,3,4-tetrahydropyrido[2,3-b]pyrazin-7-yl]-(4-phenylpiperazin-1-yl)-methanone;
[1-(2,5-dichlorobenzyl)-1,2,3,4-tetrahydropyrido[2,3-b]pyrazin-7-yl]-(4-pyrimidin-2-yl-piperazin-1-yl)-methanone;
[4-(4-chlorophenyl)-4-hydroxypiperidin-1-yl]-[1-(2,5-dichlorobenzyl)-1,2,3,4-tetrahydropyrido[2,3-b]pyrazin-7-yl]methanone;
1-{1-[1-(2,5-dichlorobenzyl)-1,2,3,4-tetrahydropyrido[2,3-b]pyrazine-7-carbonyl]piperidin-4-yl}-1,3-dihydrobenzoimidazol-2-one;
[1-(2,5-dichlorobenzyl)-1,2,3,4-tetrahydropyrido[2,3-b]pyrazin-7-yl]-[4-(2-methoxyphenyl)piperazin-1-yl]methanone;
[1-(2,5-dichlorobenzyl)-1,2,3,4-tetrahydropyrido[2,3-b]pyrazin-7-yl]-{4-[3-(trifluoromethyl)phenyl]piperazin-1-yl}methanone;
[1-(2,5-dichlorobenzyl)-1,2,3,4-tetrahydropyrido[2,3-b]pyrazin-7-yl]-(4-phenylpiperidin-1-yl)methanone;
[1-(2,5-dichlorobenzyl)-1,2,3,4-tetrahydropyrido[2,3-b]pyrazin-7-yl]-[4-(3,4-dichlorophenyl)-piperazin-1-yl]methanone;
(4-benzhydrylpiperazin-1-yl)-[1-(2,5-dichlorobenzyl)-1,2,3,4-tetrahydropyrido[2,3-b]pyrazin-7-yl]methanone;
(4-benzylpiperidin-1-yl)-[1-(2,5-dichlorobenzyl)-1,2,3,4-tetrahydropyrido[2,3-b]pyrazin-7-yl]methanone;
8-[1-(2,5-dichlorobenzyl)-1,2,3,4-tetrahydropyrido[2,3-b]pyrazine-7-carbonyl]-1-phenyl-1,3,8-triaza-spiro[4.5]decan-4-one;
[1-(2,5-dichlorobenzyl)-1,2,3,4-tetrahydropyrido[2,3-b]pyrazin-7-yl]-(4-thieno[3,2-d]pyrimidin-4-yl-piperazin-1-yl)methanone;
[1-(2,5-dichlorobenzyl)-1,2,3,4-tetrahydropyrido[2,3-b]pyrazin-7-yl]-[4-(4-methoxybenzyl)piperazin-1-yl]methanone;
(4-benzoylpiperazin-1-yl)-[1-(2,5-dichlorobenzyl)-1,2,3,4-tetrahydropyrido[2,3-b]pyrazin-7-yl]methanone;
[1-(2,5-dichlorobenzyl)-1,2,3,4-tetrahydropyrido[2,3-b]pyrazin-7-yl]-(4-furo[3,2-c]pyridin-4-yl-piperazin-1-yl)methanone;
[1-(2,5-dichlorobenzyl)-1,2,3,4-tetrahydropyrido[2,3-b]pyrazin-7-yl]-[4-(6-fluorobenzo[d]isoxazol-3-yl)piperidin-1-yl]methanone;
[4-(3-chlorophenyl)piperazin-1-yl]-[1-(2,5-dichlorobenzyl)-1,2,3,4-tetrahydropyrido[2,3-b]pyrazin-7-yl]methanone;
1-(2,5-dichlorobenzyl)-1,2,3,4-tetrahydropyrido[2,3-b]pyrazine-7-carboxylic acid (2-pyridin-2-yl-ethyl)amide;
4-{[1-(2,5-dichlorobenzyl)-1,2,3,4-tetrahydropyrido[2,3-b]pyrazine-7-carbonyl]amino}piperidine-1-carboxylic acid ethyl ester;
1-(2,5-dichlorobenzyl)-1,2,3,4-tetrahydropyrido[2,3-b]pyrazine-7-carboxylic acid (1-benzyl-piperidin-4-yl)amide;
1-(2,5-dichlorobenzyl)-1,2,3,4-tetrahydropyrido[2,3-b]pyrazine-7-carboxylic acid (2,2-diphenylethyl)amide;
1-{4-[1-(2,5-dichlorobenzyl)-1,2,3,4-tetrahydropyrido[2,3-b]pyrazine-7-carbonyl]piperazin-1-yl}ethanone;
1-(2,5-dichlorobenzyl)-1,2,3,4-tetrahydropyrido[2,3-b]pyrazine-7-carboxylic acid 3-chlorobenzylamide;
[1-(2,5-dichlorobenzyl)-1,2,3,4-tetrahydropyrido[2,3-b]pyrazin-7-yl]-[4-(2-pyridin-2-yl-ethyl)piperazin-1-yl]methanone;
1-(2,5-dichlorobenzyl)-1,2,3,4-tetrahydropyrido[2,3-b]pyrazine-7-carboxylic acid 4-(trifluoromethoxy)benzylamide;
[1-(2,5-dichlorobenzyl)-1,2,3,4-tetrahydropyrido[2,3-b]pyrazin-7-yl]-(4-morpholin-4-yl-piperidin-1-yl)methanone;
1-(2,5-dichlorobenzyl)-1,2,3,4-tetrahydropyrido[2,3-b]pyrazine-7-carboxylic acid (2-thiophen-2-yl-ethyl)amide;
1-(2,5-dichlorobenzyl)-1,2,3,4-tetrahydropyrido[2,3-b]pyrazine-7-carboxylic acid benzhydrylamide;
1-(2,5-dichlorobenzyl)-1,2,3,4-tetrahydropyrido[2,3-b]pyrazine-7-carboxylic acid (pyridin-4-ylmethyl)amide;
1-(2,5-dichlorobenzyl)-1,2,3,4-tetrahydropyrido[2,3-b]pyrazine-7-carboxylic acid (pyridin-3-ylmethyl)amide;
2-{4-[1-(2,5-dichlorobenzyl)-1,2,3,4-tetrahydropyrido[2,3-b]pyrazine-7-carbonyl]piperazin-1-yl}-N-isopropylacetamide;
[1-(2,5-dichlorobenzyl)-1,2,3,4-tetrahydropyrido[2,3-b]pyrazin-7-yl]-[4-(2-methylquinolin-4-yl)piperazin-1-yl]methanone;

[1-(2,5-dichlorobenzyl)-1,2,3,4-tetrahydropyrido[2,3-b]
pyrazin-7-yl]-((S)-2-pyrrolidin-1-ylmethyl-pyrrolidin-
1-yl)methanone;
1-(2,5-dichlorobenzyl)-1,2,3,4-tetrahydropyrido[2,3-b]
pyrazine-7-carboxylic acid 3,5-bis-(trifluoromethyl)
benzylamide;
1-(2,5-dichlorobenzyl)-1,2,3,4-tetrahydropyrido[2,3-b]
pyrazine-7-carboxylic acid[2-(4-sulfamoylphenyl)
ethyl]amide;
[1-(2,5-dichlorobenzyl)-1,2,3,4-tetrahydropyrido[2,3-b]
pyrazin-7-yl]-(2,3,5,6-tetrahydro-[1,2']bipyrazinyl-4-
yl)methanone;
1-(2,5-dichlorobenzyl)-1,2,3,4-tetrahydropyrido[2,3-b]
pyrazine-7-carboxylic acid (2-phenylthiazol-4-yl-me-
thyl)amide;
[1-(2,5-dichlorobenzyl)-1,2,3,4-tetrahydropyrido[2,3-b]
pyrazin-7-yl]morpholin-4-yl-methanone;
1-(2,5-dichlorobenzyl)-1,2,3,4-tetrahydropyrido[2,3-b]
pyrazine-7-carboxylic acid (naphthalen-1-yl-methyl)
amide;
1-(2,5-dichlorobenzyl)-1,2,3,4-tetrahydropyrido[2,3-b]
pyrazine-7-carboxylic acid indan-1-ylamide;
1-(2,5-dichlorobenzyl)-1,2,3,4-tetrahydropyrido[2,3-b]
pyrazine-7-carboxylic acid benzylamide;
[1-(2,5-dichlorobenzyl)-1,2,3,4-tetrahydropyrido[2,3-b]
pyrazin-7-yl]-[4-(4-methoxyphenyl)piperazin-1-yl]
methanone;
1-(2,5-dichlorobenzyl)-1,2,3,4-tetrahydropyrido[2,3-b]
pyrazine-7-carboxylic acid cyclohexylamide;
1-(2,5-dichlorobenzyl)-1,2,3,4-tetrahydropyrido[2,3-b]
pyrazine-7-carboxylic acid (biphenyl-4-ylmethyl)
amide;
[4-(4-chlorophenyl)piperazin-1-yl]-[1-(2,5-dichloroben-
zyl)-1,2,3,4-tetrahydropyrido[2,3-b]pyrazin-7-yl]
methanone;
1-(2,5-dichlorobenzyl)-1,2,3,4-tetrahydropyrido[2,3-b]
pyrazine-7-carboxylic acid (2-phenoxyethyl)amide;
[1-(2,5-dichlorobenzyl)-1,2,3,4-tetrahydropyrido[2,3-b]
pyrazin-7-yl]-[4-(tetrahydrofuran-2-carbonyl)piper-
azin-1-yl]methanone;
1-(2,5-dichlorobenzyl)-1,2,3,4-tetrahydropyrido[2,3-b]
pyrazine-7-carboxylic acid phenethyl-amide;
1-(2,5-dichlorobenzyl)-1,2,3,4-tetrahydropyrido[2,3-b]
pyrazine-7-carboxylic acid (tetrahydrofuran-2-yl-me-
thyl)amide;
[4-(4-chlorobenzyl)piperazin-1-yl]-[1-(2,5-dichloroben-
zyl)-1,2,3,4-tetrahydropyrido[2,3-b]pyrazin-7-yl]
methanone;
1-(2,5-dichlorobenzyl)-1,2,3,4-tetrahydropyrido[2,3-b]
pyrazine-7-carboxylic acid 2-chloro-benzylamide;
[1-(2,5-dichlorobenzyl)-1,2,3,4-tetrahydropyrido[2,3-b]
pyrazin-7-yl]-[4-(2-(trifluoromethyl)phenyl)piperazin-
1-yl]methanone;
1-(2,5-dichlorobenzyl)-1,2,3,4-tetrahydropyrido[2,3-b]
pyrazine-7-carboxylic acid 4-methoxybenzylamide;
1-(2,5-dichlorobenzyl)-1,2,3,4-tetrahydropyrido[2,3-b]
pyrazine-7-carboxylic acid indan-2-ylamide;
[1-(2,5-dichlorobenzyl)-1,2,3,4-tetrahydropyrido[2,3-b]
pyrazin-7-yl]-(4-phenethyl-piperazin-1-yl)methanone;
[4-(2-chlorophenyl)piperazin-1-yl]-[1-(2,5-dichloroben-
zyl)-1,2,3,4-tetrahydropyrido[2,3-b]pyrazin-7-yl]
methanone;
[(4-cyclohexylmethyl)piperazin-1-yl]-[1-(2,5-dichlo-
robenzyl)-1,2,3,4-tetrahydropyrido[2,3-b]pyrazin-7-yl]
methanone;
1-(2,5-dichlorobenzyl)-1,2,3,4-tetrahydropyrido[2,3-b]
pyrazine-7-carboxylic acid 4-sulfamoyl-benzylamide;

[1-(2,5-dichlorobenzyl)-1,2,3,4-tetrahydropyrido[2,3-b]
pyrazin-7-yl]-(2-pyridin-3-yl-pyrrolidin-1-yl)metha-
none;
(4-{1-[5-chloro-2-(trifluoromethyl)benzyl]-1,2,3,4-tet-
rahydropyrido[2,3-b]pyrazin-7-yl}phenyl)-(4-morpho-
lin-4-yl-piperidin-1-yl)methatone;
(4-{1-[5-chloro-2-(trifluoromethyl)benzyl]-1,2,3,4-tet-
rahydropyrido[2,3-b]pyrazin-7-yl}phenyl)-(4-thiazol-
2-yl-piperazin-1-yl)methatone;
3,6-difluoro-2-[7-(6-morpholin-4-yl-pyridin-3-yl)-3,4-di-
hydro-2H-pyrido[2,3-b]pyrazin-1-ylmethyl]benzoni-
trile;
7-(6-morpholin-4-yl-pyridin-3-yl)-1-[5-(trifluoromethyl)
furan-2-ylmethyl]-1,2,3,4-tetrahydropyrido[2,3-b]
pyrazine;
7-[2-(4-methylpiperazin-1-yl)pyridin-4-yl]-1-[5-(trifluo-
romethyl)furan-2-ylmethyl]-1,2,3,4-tetrahydropyrido
[2,3-b]pyrazine;
1-[5-chloro-2-(trifluoromethyl)benzyl]-1,2,3,4-tetrahy-
dropyrido[2,3-b]pyrazine-7-carboxylic acid[4-(dim-
ethylamino)butyl]amide;
4-{1-[2-(trifluoromethoxy)benzyl]-1,2,3,4-tetrahydropy-
rido[2,3-b]pyrazin-7-yl}benzoic acid ethyl ester;
4-{1-[2-(trifluoromethoxy)benzyl]-1,2,3,4-tetrahydropy-
rido[2,3-b]pyrazin-7-yl}benzoic acid;
4-[1-(2-chloropyridin-3-ylmethyl)-1,2,3,4-tetrahydropy-
rido[2,3-b]pyrazin-7-yl]benzoic acid ethyl ester;
4-[1-(2-chloropyridin-3-ylmethyl)-1,2,3,4-tetrahydropy-
rido[2,3-b]pyrazin-7-yl]benzoic acid;
{4-[1-(2-chloropyridin-3-ylmethyl)-1,2,3,4-tetrahydropy-
rido[2,3-b]pyrazin-7-yl]phenyl}-(4-pyrrolidin-1-yl-pi-
peridin-1-yl)methanone;
N-(4-{1-[5-chloro-2-(trifluoromethyl)benzyl]-1,2,3,4-tet-
rahydropyrido[2,3-b]pyrazin-7-yl}phenyl)acetamide;
(4-pyrrolidin-1-yl-piperidin-1-yl)-(4-{1-[2-(trifluo-
romethoxy)benzyl]-1,2,3,4-tetrahydropyrido[2,3-b]
pyrazin-7-yl}phenyl)methanone;
(3-{1-[5-chloro-2-(trifluoromethyl)benzyl]-1,2,3,4-tet-
rahydropyrido[2,3-b]pyrazin-7-yl}phenyl)-(4-phe-
nylpiperazin-1-yl)methanone;
(3-{1-[5-chloro-2-(trifluoromethyl)benzyl]-1,2,3,4-tet-
rahydropyrido[2,3-b]pyrazin-7-yl}phenyl)-(4-pyrimi-
din-2-ylpiperazin-1-yl)methanone;
[4-(4-chlorophenyl)-piperazin-1-yl]-(3-{1-[5-chloro-2-
(trifluoromethyl)benzyl]-1,2,3,4-tetrahydropyrido[2,3-
b]pyrazin-7-yl}phenyl)methanone;
[4-(4-chlorophenyl)-4-hydroxypiperidin-1-yl]-(3-{1-[5-
chloro-2-(trifluoromethyl)benzyl]-1,2,3,4-tetrahydro-
pyrido[2,3-b]pyrazin-7-yl}phenyl)methanone;
1-[1-(3-{1-[5-chloro-2-(trifluoromethyl)benzyl]-1,2,3,4-
tetrahydropyrido[2,3-b]pyrazin-7-yl}benzoyl)piperi-
din-4-yl]-1,3-dihydrobenzoimidazol-2-one;
(3-{1-[5-chloro-2-(trifluoromethyl)benzyl]-1,2,3,4-tet-
rahydropyrido[2,3-b]pyrazin-7-yl}phenyl)-[4-(2-meth-
oxyphenyl)piperazin-1-yl]methanone;
(3-{1-[5-chloro-2-(trifluoromethyl)benzyl]-1,2,3,4-tet-
rahydropyrido[2,3-b]pyrazin-7-yl}phenyl)-{4-[3-(trif-
luoromethyl)phenyl]piperazin-1-yl}methanone;
(3-{1-[5-chloro-2-(trifluoromethyl)benzyl]-1,2,3,4-tet-
rahydropyrido[2,3-b]pyrazin-7-yl}phenyl)-(4-phe-
nylpiperidin-1-yl)methanone;
(3-{1-[5-chloro-2-(trifluoromethyl)benzyl]-1,2,3,4-tet-
rahydropyrido[2,3-b]pyrazin-7-yl}phenyl)-[4-(1H-in-
dol-3-yl)piperidin-1-yl]methanone;
(4-benzhydrylpiperazin-1-yl)-(3-{1-[5-chloro-2-(trifluo-
romethyl)benzyl]-1,2,3,4-tetrahydropyrido[2,3-b]
pyrazin-7-yl}phenyl)methanone;

(4-benzylpiperidin-1-yl)-(3-{1-[5-chloro-2-(trifluoromethyl)benzyl]-1,2,3,4-tetrahydropyrido[2,3-b]pyrazin-7-yl}phenyl)methanone;

(3-{1-[5-chloro-2-(trifluoromethyl)benzyl]-1,2,3,4-tetrahydropyrido[2,3-b]pyrazin-7-yl}phenyl)-[4-(3,4-dichlorophenyl)piperazin-1-yl]methanone;

8-(3-{1-[5-chloro-2-(trifluoromethyl)benzyl]-1,2,3,4-tetrahydropyrido[2,3-b]pyrazin-7-yl}benzoyl)-1-phenyl-1,3,8-triaza-spiro[4.5]decan-4-one;

(3-{1-[5-chloro-2-(trifluoromethyl)benzyl]-1,2,3,4-tetrahydropyrido[2,3-b]pyrazin-7-yl}phenyl)-{4-[2-(trifluoromethyl)phenyl]piperazin-1-yl}methanone;

(3-{1-[5-chloro-2-(trifluoromethyl)benzyl]-1,2,3,4-tetrahydropyrido[2,3-b]pyrazin-7-yl}phenyl)-(4-thieno[3,2-d]pyrimidin-4-ylpiperazin-1-yl)methanone;

[4-(4-chlorobenzyl)piperazin-1-yl]-(3-{1-[5-chloro-2-(trifluoromethyl)benzyl]-1,2,3,4-tetrahydropyrido[2,3-b]pyrazin-7-yl}phenyl)methanone;

(3-{1-[5-chloro-2-(trifluoromethyl)benzyl]-1,2,3,4-tetrahydropyrido[2,3-b]pyrazin-7-yl}phenyl)-[4-(4-methoxybenzyl)piperazin-1-yl]methanone;

(4-benzoylpiperazin-1-yl)-(3-{1-[5-chloro-2-(trifluoromethyl)benzyl]-1,2,3,4-tetrahydropyrido[2,3-b]pyrazin-7-yl}phenyl)methanone;

(3-{1-[5-chloro-2-(trifluoromethyl)benzyl]-1,2,3,4-tetrahydropyrido[2,3-b]pyrazin-7-yl}phenyl)-(4-furo[3,2-c]pyridin-4-ylpiperazin-1-yl)methanone;

(3-{1-[5-chloro-2-(trifluoromethyl)benzyl]-1,2,3,4-tetrahydropyrido[2,3-b]pyrazin-7-yl}phenyl)-[4-(6-fluorobenzo[d]isoxazol-3-yl)piperidin-1-yl]methanone;

4-(3-{1-[5-chloro-2-(trifluoromethyl)benzyl]-1,2,3,4-tetrahydropyrido[2,3-b]pyrazin-7-yl}benzoylamino)piperidine-1-carboxylic acid ethyl ester;

N-(1-benzylpiperidin-4-yl)-3-{1-[5-chloro-2-(trifluoromethyl)benzyl]-1,2,3,4-tetrahydropyrido[2,3-b]pyrazin-7-yl}benzamide;

3-{1-[5-chloro-2-(trifluoromethyl)benzyl]-1,2,3,4-tetrahydropyrido[2,3-b]pyrazin-7-yl}-N-(2,2-diphenylethyl)benzamide;

3-{1-[5-chloro-2-(trifluoromethyl)benzyl]-1,2,3,4-tetrahydropyrido[2,3-b]pyrazin-7-yl}-N-(1-methylpiperidin-4-yl)benzamide;

(3-{1-[5-chloro-2-(trifluoromethyl)benzyl]-1,2,3,4-tetrahydropyrido[2,3-b]pyrazin-7-yl}phenyl)-[4-(2-pyridin-2-yl-ethyl)piperazin-1-yl]methanone;

3-{1-[5-chloro-2-(trifluoromethyl)benzyl]-1,2,3,4-tetrahydropyrido[2,3-b]pyrazin-7-yl}-N-[4-(trifluoromethoxy)benzyl]benzamide;

N-[3,5-bis(trifluoromethyl)benzyl]-3-{1-[5-chloro-2-(trifluoromethyl)benzyl]-1,2,3,4-tetrahydropyrido[2,3-b]pyrazin-7-yl}benzamide;

N-benzhydryl-3-{1-[5-chloro-2-(trifluoromethyl)benzyl]-1,2,3,4-tetrahydropyrido[2,3-b]pyrazin-7-yl}benzamide;

3-{1-[5-chloro-2-(trifluoromethyl)benzyl]-1,2,3,4-tetrahydropyrido[2,3-b]pyrazin-7-yl}-N-pyridin-4-ylmethylbenzamide;

3-{1-[5-chloro-2-(trifluoromethyl)benzyl]-1,2,3,4-tetrahydropyrido[2,3-b]pyrazin-7-yl}-N-pyridin-3-ylmethylbenzamide;

2-[4-(3-{1-[5-chloro-2-(trifluoromethyl)benzyl]-1,2,3,4-tetrahydropyrido[2,3-b]pyrazin-7-yl}benzoyl)piperazin-1-yl]-N-isopropylacetamide;

(3-{1-[5-chloro-2-(trifluoromethyl)benzyl]-1,2,3,4-tetrahydropyrido[2,3-b]pyrazin-7-yl}phenyl)-[4-(2-methylquinolin-4-yl)piperazin-1-yl]methanone;

3-{1-[5-chloro-2-(trifluoromethyl)benzyl]-1,2,3,4-tetrahydropyrido[2,3-b]pyrazin-7-yl}-N-[2-(4-sulfamoylphenyl)ethyl]benzamide;

(3-{1-[5-chloro-2-(trifluoromethyl)benzyl]-1,2,3,4-tetrahydropyrido[2,3-b]pyrazin-7-yl}phenyl)-(2,3,5,6-tetrahydro-[1,2']bipyrazinyl-4-yl)methanone;

3-{1-[5-chloro-2-(trifluoromethyl)benzyl]-1,2,3,4-tetrahydropyrido[2,3-b]pyrazin-7-yl}-N-(2-phenylthiazol-4-ylmethyl)benzamide;

(3-{1-[5-chloro-2-(trifluoromethyl)benzyl]-1,2,3,4-tetrahydropyrido[2,3-b]pyrazin-7-yl}phenyl)morpholin-4-ylmethanone;

3-{1-[5-chloro-2-(trifluoromethyl)benzyl]-1,2,3,4-tetrahydropyrido[2,3-b]pyrazin-7-yl}-N-naphthalen-1-ylmethylbenzamide;

3-{1-[5-chloro-2-(trifluoromethyl)benzyl]-1,2,3,4-tetrahydropyrido[2,3-b]pyrazin-7-yl}-N-indan-1-ylbenzamide;

(3-{1-[5-chloro-2-(trifluoromethyl)benzyl]-1,2,3,4-tetrahydropyrido[2,3-b]pyrazin-7-yl}phenyl)-[4-(3-methoxyphenyl)piperazin-1-yl]methanone;

(3-{1-[5-chloro-2-(trifluoromethyl)benzyl]-1,2,3,4-tetrahydropyrido[2,3-b]pyrazin-7-yl}phenyl)-[4-(4-methoxyphenyl)piperazin-1-yl]methanone;

3-{1-[5-chloro-2-(trifluoromethyl)benzyl]-1,2,3,4-tetrahydropyrido[2,3-b]pyrazin-7-yl}-N-cyclohexylbenzamide;

3-{1-[5-chloro-2-(trifluoromethyl)benzyl]-1,2,3,4-tetrahydropyrido[2,3-b]pyrazin-7-yl}-N-(4-methanesulfonylbenzyl)benzamide;

N-(2-chlorobenzyl)-3-{1-[5-chloro-2-(trifluoromethyl)benzyl]-1,2,3,4-tetrahydropyrido[2,3-b]pyrazin-7-yl}benzamide;

N-(4-chlorobenzyl)-3-{1-[5-chloro-2-(trifluoromethyl)benzyl]-1,2,3,4-tetrahydropyrido[2,3-b]pyrazin-7-yl}benzamide;

N-(3-chlorobenzyl)-3-{1-[5-chloro-2-(trifluoromethyl)benzyl]-1,2,3,4-tetrahydropyrido[2,3-b]pyrazin-7-yl}benzamide;

(3-{1-[5-chloro-2-(trifluoromethyl)benzyl]-1,2,3,4-tetrahydropyrido[2,3-b]pyrazin-7-yl}phenyl)-[4-(tetrahydrofuran-2-carbonyl)piperazin-1-yl]methanone;

3-{1-[5-chloro-2-(trifluoromethyl)benzyl]-1,2,3,4-tetrahydropyrido[2,3-b]pyrazin-7-yl}-N-(tetrahydrofuran-2-ylmethyl)benzamide;

3-{1-[5-chloro-2-(trifluoromethyl)benzyl]-1,2,3,4-tetrahydropyrido[2,3-b]pyrazin-7-yl}-N-(3-methoxybenzyl)benzamide;

3-{1-[5-chloro-2-(trifluoromethyl)benzyl]-1,2,3,4-tetrahydropyrido[2,3-b]pyrazin-7-yl}-N-(4-methoxybenzyl)benzamide;

3-{1-[5-chloro-2-(trifluoromethyl)benzyl]-1,2,3,4-tetrahydropyrido[2,3-b]pyrazin-7-yl}-N-(2-phenoxyethyl)benzamide;

N-benzyl-3-{1-[5-chloro-2-(trifluoromethyl)benzyl]-1,2,3,4-tetrahydropyrido[2,3-b]pyrazin-7-yl}benzamide;

[4-(3-chlorophenyl)piperazin-1-yl]-(3-{1-[5-chloro-2-(trifluoromethyl)benzyl]-1,2,3,4-tetrahydropyrido[2,3-b]pyrazin-7-yl}phenyl)methanone;

3-{1-[5-chloro-2-(trifluoromethyl)benzyl]-1,2,3,4-tetrahydropyrido[2,3-b]pyrazin-7-yl}-N-indan-2-ylbenzamide;

(3-{1-[5-chloro-2-(trifluoromethyl)benzyl]-1,2,3,4-tetrahydropyrido[2,3-b]pyrazin-7-yl}phenyl)-(4-phenethylpiperazin-1-yl)methanone;

[4-(2-chlorophenyl)piperazin-1-yl]-(3-{1-[5-chloro-2-(trifluoromethyl)benzyl]-1,2,3,4-tetrahydropyrido[2,3-b]pyrazin-7-yl}phenyl)methanone;

N-(1-benzylpyrrolidin-3-yl)-3-{1-[5-chloro-2-(trifluoromethyl)benzyl]-1,2,3,4-tetrahydropyrido[2,3-b]pyrazin-7-yl}benzamide;

(3-{1-[5-chloro-2-(trifluoromethyl)benzyl]-1,2,3,4-tetrahydropyrido[2,3-b]pyrazin-7-yl}phenyl)-[4-(cyclohexylmethyl)piperazin-1-yl]methanone;

3-{1-[5-chloro-2-(trifluoromethyl)benzyl]-1,2,3,4-tetrahydropyrido[2,3-b]pyrazin-7-yl}-N-(4-sulfamoylbenzyl)benzamide;

(3-{1-[5-chloro-2-(trifluoromethyl)benzyl]-1,2,3,4-tetrahydropyrido[2,3-b]pyrazin-7-yl}phenyl)-(4-morpholin-4-ylpiperidin-1-yl)methanone;

(3-{1-[5-chloro-2-(trifluoromethyl)benzyl]-1,2,3,4-tetrahydropyrido[2,3-b]pyrazin-7-yl}phenyl)-((S)-2-pyrrolidin-1-ylmethylpyrrolidin-1-yl)methanone;

(3-{1-[5-chloro-2-(trifluoromethyl)benzyl]-1,2,3,4-tetrahydropyrido[2,3-b]pyrazin-7-yl}phenyl)-(2-pyridin-3-ylpyrrolidin-1-yl)methanone;

3-{1-[5-chloro-2-(trifluoromethyl)benzyl]-1,2,3,4-tetrahydropyrido[2,3-b]pyrazin-7-yl}-N-(2-methoxybenzyl)-N-methylbenzamide;

(4-{1-[5-chloro-2-(trifluoromethyl)benzyl]-1,2,3,4-tetrahydropyrido[2,3-b]pyrazin-7-yl}phenyl)-(4-phenylpiperazin-1-yl)methanone;

(4-{1-[5-chloro-2-(trifluoromethyl)benzyl]-1,2,3,4-tetrahydropyrido[2,3-b]pyrazin-7-yl}phenyl)-(4-pyrimidin-2-ylpiperazin-1-yl)methanone;

[4-(4-chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone;

[4-(4-chlorophenyl)-4-hydroxypiperidin-1-yl]-(4-{1-[5-chloro-2-(trifluoromethyl)benzyl]-1,2,3,4-tetrahydropyrido[2,3-b]pyrazin-7-yl}phenyl)methanone;

1-[1-(4-{1-[5-chloro-2-(trifluoromethyl)benzyl]-1,2,3,4-tetrahydropyrido[2,3-b]pyrazin-7-yl}benzoyl)piperidin-4-yl]-1,3-dihydrobenzoimidazol-2-one;

(4-{1-[5-chloro-2-(trifluoromethyl)benzyl]-1,2,3,4-tetrahydropyrido[2,3-b]pyrazin-7-yl}phenyl)-[4-(2-methoxyphenyl)piperazin-1-yl]methanone;

(4-{1-[5-chloro-2-(trifluoromethyl)benzyl]-1,2,3,4-tetrahydropyrido[2,3-b]pyrazin-7-yl}phenyl)-{4-[3-(trifluoromethyl)phenyl]piperazin-1-yl}methanone;

(4-{1-[5-chloro-2-(trifluoromethyl)benzyl]-1,2,3,4-tetrahydropyrido[2,3-b]pyrazin-7-yl}phenyl)-(4-phenylpiperidin-1-yl)methanone;

(4-{1-[5-chloro-2-(trifluoromethyl)benzyl]-1,2,3,4-tetrahydropyrido[2,3-b]pyrazin-7-yl}phenyl)-[4-(1H-indol-3-yl)piperidin-1-yl]methanone;

(4-benzhydrylpiperazin-1-yl)-(4-{1-[5-chloro-2-(trifluoromethyl)benzyl]-1,2,3,4-tetrahydropyrido[2,3-b]pyrazin-7-yl}phenyl)methanone;

(4-benzylpiperidin-1-yl)-(4-{1-[5-chloro-2-(trifluoromethyl)benzyl]-1,2,3,4-tetrahydropyrido[2,3-b]pyrazin-7-yl}phenyl)methanone;

(4-{1-[5-chloro-2-(trifluoromethyl)benzyl]-1,2,3,4-tetrahydropyrido[2,3-b]pyrazin-7-yl}phenyl)-[4-(3,4-dichlorophenyl)piperazin-1-yl]methanone;

8-(4-{1-[5-chloro-2-(trifluoromethyl)benzyl]-1,2,3,4-tetrahydropyrido[2,3-b]pyrazin-7-yl}benzoyl)-1-phenyl-1,3,8-triaza-spiro[4.5]decan-4-one;

(4-{1-[5-chloro-2-(trifluoromethyl)benzyl]-1,2,3,4-tetrahydropyrido[2,3-b]pyrazin-7-yl}phenyl)-{4-[2-(trifluoromethyl)phenyl]piperazin-1-yl}methanone;

(4-{1-[5-chloro-2-(trifluoromethyl)benzyl]-1,2,3,4-tetrahydropyrido[2,3-b]pyrazin-7-yl}phenyl)-(4-thieno[3,2-d]pyrimidin-4-yl-piperazin-1-yl)methanone;

[4-(4-chlorobenzyl)piperazin-1-yl]-(4-{1-[5-chloro-2-(trifluoromethyl)benzyl]-1,2,3,4-tetrahydropyrido[2,3-b]pyrazin-7-yl}phenyl)methanone;

(4-{1-[5-chloro-2-(trifluoromethyl)benzyl]-1,2,3,4-tetrahydropyrido[2,3-b]pyrazin-7-yl}phenyl)-[4-(4-methoxybenzyl)piperazin-1-yl]methanone;

(4-benzoylpiperazin-1-yl)-(4-{1-[5-chloro-2-(trifluoromethyl)benzyl]-1,2,3,4-tetrahydropyrido[2,3-b]pyrazin-7-yl}phenyl)methanone;

(4-{1-[5-chloro-2-(trifluoromethyl)benzyl]-1,2,3,4-tetrahydropyrido[2,3-b]pyrazin-7-yl}phenyl)-(4-furo[3,2-c]pyridin-4-ylpiperazin-1-yl)methanone;

(4-{1-[5-chloro-2-(trifluoromethyl)benzyl]-1,2,3,4-tetrahydropyrido[2,3-b]pyrazin-7-yl}phenyl)-[4-(6-fluorobenzo[d]isoxazol-3-yl)-piperidin-1-yl]methanone;

4-{1-[5-chloro-2-(trifluoromethyl)benzyl]-1,2,3,4-tetrahydropyrido[2,3-b]pyrazin-7-yl}-N-(2-pyridin-2-ylethyl)benzamide;

4-(4-{1-[5-chloro-2-(trifluoromethyl)benzyl]-1,2,3,4-tetrahydropyrido[2,3-b]pyrazin-7-yl}benzoylamino)piperidine-1-carboxylic acid ethyl ester;

N-(1-benzylpiperidin-4-yl)-4-{1-[5-chloro-2-(trifluoromethyl)benzyl]-1,2,3,4-tetrahydropyrido[2,3-b]pyrazin-7-yl}benzamide;

4-{1-[5-chloro-2-(trifluoromethyl)benzyl]-1,2,3,4-tetrahydropyrido[2,3-b]pyrazin-7-yl}-N-(2,2-diphenylethyl)benzamide;

1-[4-(4-{1-[5-chloro-2-(trifluoromethyl)benzyl]-1,2,3,4-tetrahydropyrido[2,3-b]pyrazin-7-yl}benzoyl)piperazin-1-yl]ethanone;

4-{1-[5-chloro-2-(trifluoromethyl)benzyl]-1,2,3,4-tetrahydropyrido[2,3-b]pyrazin-7-yl}-N-(1-methylpiperidin-4-yl)benzamide;

(4-{1-[5-chloro-2-(trifluoromethyl)benzyl]-1,2,3,4-tetrahydropyrido[2,3-b]pyrazin-7-yl}phenyl)-[4-(2-pyridin-2-yl-ethyl)piperazin-1-yl]methanone;

4-{1-[5-chloro-2-(trifluoromethyl)benzyl]-1,2,3,4-tetrahydropyrido[2,3-b]pyrazin-7-yl}-N-[4-(trifluoromethoxy)benzyl]benzamide;

4-{1-[5-chloro-2-(trifluoromethyl)benzyl]-1,2,3,4-tetrahydropyrido[2,3-b]pyrazin-7-yl}-N-[4-(trifluoromethyl)benzyl]benzamide;

N-[3,5-bis(trifluoromethyl)benzyl]-4-{1-[5-chloro-2-(trifluoromethyl)benzyl]-1,2,3,4-tetrahydropyrido[2,3-b]pyrazin-7-yl}benzamide;

4-{1-[5-chloro-2-(trifluoromethyl)benzyl]-1,2,3,4-tetrahydropyrido[2,3-b]pyrazin-7-yl}-N-(2-thiophen-2-yl-ethyl)benzamide;

N-benzhydryl-4-{1-[5-chloro-2-(trifluoromethyl)benzyl]-1,2,3,4-tetrahydropyrido[2,3-b]pyrazin-7-yl}benzamide;

4-{1-[5-chloro-2-(trifluoromethyl)benzyl]-1,2,3,4-tetrahydropyrido[2,3-b]pyrazin-7-yl}-N-pyridin-4-ylmethylbenzamide;

4-{1-[5-chloro-2-(trifluoromethyl)benzyl]-1,2,3,4-tetrahydropyrido[2,3-b]pyrazin-7-yl}-N-pyridin-3-ylmethylbenzamide;

2-[4-(4-{1-[5-chloro-2-(trifluoromethyl)benzyl]-1,2,3,4-tetrahydropyrido[2,3-b]pyrazin-7-yl}benzoyl)piperazin-1-yl]-N-isopropylacetamide;

(4-{1-[5-chloro-2-(trifluoromethyl)benzyl]-1,2,3,4-tetrahydropyrido[2,3-b]pyrazin-7-yl}phenyl)-[4-(2-methylquinolin-4-yl)piperazin-1-yl]methanone;

4-{1-[5-chloro-2-(trifluoromethyl)benzyl]-1,2,3,4-tetrahydropyrido[2,3-b]pyrazin-7-yl}-N-(2-methoxyethyl)benzamide;

4-{1-[5-chloro-2-(trifluoromethyl)benzyl]-1,2,3,4-tetrahydropyrido[2,3-b]pyrazin-7-yl}-N-[2-(4-sulfamoylphenyl)ethyl]benzamide;

(4-{1-[5-chloro-2-(trifluoromethyl)benzyl]-1,2,3,4-tetrahydropyrido[2,3-b]pyrazin-7-yl}phenyl)-(2,3,5,6-tetrahydro[1,2']bipyrazinyl-4-yl)methanone;

4-{1-[5-chloro-2-(trifluoromethyl)benzyl]-1,2,3,4-tetrahydropyrido[2,3-b]pyrazin-7-yl}-N-(2-phenylthiazol-4-ylmethyl)benzamide;

(4-{1-[5-chloro-2-(trifluoromethyl)benzyl]-1,2,3,4-tetrahydropyrido[2,3-b]pyrazin-7-yl}phenyl)morpholin-4-ylmethanone;

4-{1-[5-chloro-2-(trifluoromethyl)benzyl]-1,2,3,4-tetrahydropyrido[2,3-b]pyrazin-7-yl}-N-naphthalen-1-ylmethylbenzamide;

4-{1-[5-chloro-2-(trifluoromethyl)benzyl]-1,2,3,4-tetrahydropyrido[2,3-b]pyrazin-7-yl}-N-indan-1-ylbenzamide;

(4-{1-[5-chloro-2-(trifluoromethyl)benzyl]-1,2,3,4-tetrahydropyrido[2,3-b]pyrazin-7-yl}phenyl)-[4-(4-methoxyphenyl)piperazin-1-yl]methanone;

N-(2-chlorobenzyl)-4-{1-[5-chloro-2-(trifluoromethyl)benzyl]-1,2,3,4-tetrahydropyrido[2,3-b]pyrazin-7-yl}benzamide;

N-(4-chlorobenzyl)-4-{1-[5-chloro-2-(trifluoromethyl)benzyl]-1,2,3,4-tetrahydropyrido[2,3-b]pyrazin-7-yl}benzamide;

N-(3-chloro-benzyl)-4-{1-[5-chloro-2-(trifluoromethyl)benzyl]-1,2,3,4-tetrahydropyrido[2,3-b]pyrazin-7-yl}benzamide;

(4-{1-[5-chloro-2-(trifluoromethyl)benzyl]-1,2,3,4-tetrahydropyrido[2,3-b]pyrazin-7-yl}phenyl)-[4-(tetrahydrofuran-2-carbonyl)piperazin-1-yl]methanone;

4-{1-[5-chloro-2-(trifluoromethyl)benzyl]-1,2,3,4-tetrahydropyrido[2,3-b]pyrazin-7-yl}-N-phenethylbenzamide;

4-{1-[5-chloro-2-(trifluoromethyl)benzyl]-1,2,3,4-tetrahydropyrido[2,3-b]pyrazin-7-yl}-N-(tetrahydrofuran-2-ylmethyl)benzamide;

4-{1-[5-chloro-2-(trifluoromethyl)benzyl]-1,2,3,4-tetrahydropyrido[2,3-b]pyrazin-7-yl}-N-(3-methoxybenzyl)benzamide;

4-{1-[5-chloro-2-(trifluoromethyl)benzyl]-1,2,3,4-tetrahydropyrido[2,3-b]pyrazin-7-yl}-N-(4-methoxybenzyl)benzamide;

4-{1-[5-chloro-2-(trifluoromethyl)benzyl]-1,2,3,4-tetrahydropyrido[2,3-b]pyrazin-7-yl}-N-(2-phenoxyethyl)benzamide;

N-benzyl-4-{1-[5-chloro-2-(trifluoromethyl)benzyl]-1,2,3,4-tetrahydropyrido[2,3-b]pyrazin-7-yl}benzamide;

[4-(3-chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone;

4-{1-[5-chloro-2-(trifluoromethyl)benzyl]-1,2,3,4-tetrahydropyrido[2,3-b]pyrazin-7-yl}-N-indan-2-ylbenzamide;

(4-{1-[5-chloro-2-(trifluoromethyl)benzyl]-1,2,3,4-tetrahydropyrido[2,3-b]pyrazin-7-yl}phenyl)-(4-phenethylpiperazin-1-yl)methanone;

N-biphenyl-4-ylmethyl-4-{1-[5-chloro-2-(trifluoromethyl)benzyl]-1,2,3,4-tetrahydropyrido[2,3-b]pyrazin-7-yl}benzamide;

[4-(2-chlorophenyl)piperazin-1-yl]-(4-{1-[5-chloro-2-(trifluoromethyl)benzyl]-1,2,3,4-tetrahydropyrido[2,3-b]pyrazin-7-yl}phenyl)methanone;

N-(1-benzylpyrrolidin-3-yl)-4-{1-[5-chloro-2-(trifluoromethyl)benzyl]-1,2,3,4-tetrahydropyrido[2,3-b]pyrazin-7-yl}benzamide;

(4-{1-[5-chloro-2-(trifluoromethyl)benzyl]-1,2,3,4-tetrahydropyrido[2,3-b]pyrazin-7-yl}phenyl)-[4-(cyclohexylmethyl)piperazin-1-yl]methanone;

4-{1-[5-chloro-2-(trifluoromethyl)benzyl]-1,2,3,4-tetrahydropyrido[2,3-b]pyrazin-7-yl}-N-(4-sulfamoylbenzyl)benzamide;

(4-{1-[5-chloro-2-(trifluoromethyl)benzyl]-1,2,3,4-tetrahydropyrido[2,3-b]pyrazin-7-yl}phenyl)-((S)-2-pyrrolidin-1-ylmethylpyrrolidin-1-yl)methanone;

(4-{1-[5-chloro-2-(trifluoromethyl)benzyl]-1,2,3,4-tetrahydropyrido[2,3-b]pyrazin-7-yl}phenyl)-(2-pyridin-3-yl-pyrrolidin-1-yl)methanone;

4-{1-[5-chloro-2-(trifluoromethyl)benzyl]-1,2,3,4-tetrahydropyrido[2,3-b]pyrazin-7-yl}-N-(2-methoxybenzyl)-N-methylbenzamide;

(4-{1-[5-chloro-2-(trifluoromethyl)benzyl]-1,2,3,4-tetrahydropyrido[2,3-b]pyrazin-7-yl}phenyl)-(1,3-dihydroisoindol-2-yl)methanone;

{4-[1-(5-chloro-2-trifluoromethyl-benzyl)-1,2,3,4-tetrahydropyrido[2,3-b]pyrazin-7-yl]-phenyl}-(spiro[isobenzofuran-1(3H), 4'-piperidine]-1-yl)methanone; or 1-(2-chloro-3,6-difluorobenzyl)-7-[6-(4-methylpiperazin-1-yl)pyridin-3-yl]-1,4-dihydro-2H-pyrido[2,3-b]pyrazin-3-one;

or a pharmaceutically acceptable salt form thereof.

19. A pharmaceutical composition comprising a compound as defined in claim 1 and a pharmaceutical acceptable carrier, diluent, or excipient.

* * * * *